(12) United States Patent
Manoharan et al.

(10) Patent No.: US 11,597,932 B2
(45) Date of Patent: Mar. 7, 2023

(54) CHIRALLY-ENRICHED DOUBLE-STRANDED RNA AGENTS

(71) Applicant: ALNYLAM PHARMACEUTICALS, INC., Cambridge, MA (US)

(72) Inventors: Muthiah Manoharan, Cambridge, MA (US); Nate Taneja, Cambridge, MA (US); Hartmut Ingo Jahns, Cambridge, MA (US); Shigeo Matsuda, Cambridge, MA (US); Klaus Charisse, Cambridge, MA (US); Guo He, Cambridge, MA (US); Jayaprakash K. Nair, Cambridge, MA (US); Christopher Brown, Cambridge, MA (US); Mark K. Schlegel, Cambridge, MA (US); Vasant Jadhav, Cambridge, MA (US); Martin Maier, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 30 days.

(21) Appl. No.: 16/956,271

(22) PCT Filed: Dec. 21, 2018

(86) PCT No.: PCT/US2018/067103
§ 371 (c)(1),
(2) Date: Jun. 19, 2020

(87) PCT Pub. No.: WO2019/126651
PCT Pub. Date: Jun. 27, 2019

(65) Prior Publication Data
US 2021/0207144 A1  Jul. 8, 2021

Related U.S. Application Data

(60) Provisional application No. 62/609,093, filed on Dec. 21, 2017.

(51) Int. Cl.
*C12N 15/113*  (2010.01)

(52) U.S. Cl.
CPC ...... *C12N 15/1136* (2013.01); *C12N 2310/14* (2013.01); *C12N 2310/315* (2013.01); *C12N 2310/344* (2013.01); *C12N 2320/51* (2013.01)

(58) Field of Classification Search
CPC ............ C12N 15/1136; C12N 2310/14; C12N 2310/315; C12N 2310/344; C12N 2320/51
See application file for complete search history.

(56) References Cited

U.S. PATENT DOCUMENTS

2005/0256069 A1  11/2005  Manoharan et al.

FOREIGN PATENT DOCUMENTS

| WO | 2005/004794 A2 | 1/2005 |
|---|---|---|
| WO | 2012/018881 A2 | 2/2012 |
| WO | 2015/107425 A2 | 7/2015 |
| WO | 2016/028649 A1 | 2/2016 |
| WO | 2017/062862 A2 | 4/2017 |

OTHER PUBLICATIONS

Choung et al., "Chemical modification of siRNAs to improve serum stability without loss of efficacy," Biochemical and Biophysical Research Communications 342: 919-927 (2006).
Leuschner et al., Cleavage of the siRNA passenger strand during RISC assembly in human cells, EMBO Reports 7: 314-320 (2006).
Wan et al., "Synthesis, biophysical properties and biological activity of second generation antisense oligonucleotides containing chiral phosphorothioate linkages," Nucleic Acids Research 42: 13456-13468.
Wolfrum et al., "Mechanisms and optimization of in vivo delivery of lipophilic siRNAs," Nature Biotechnology 25: 1149-1157.

*Primary Examiner* — J. E. Angell
(74) *Attorney, Agent, or Firm* — Jeffrey N. Townes; Cozen O'Connor

(57) ABSTRACT

The present invention relates to a chirally-modified dsRNA agent capable of inhibiting the expression of a target gene. The sense and antisense strands of chirally-modified dsRNA agent independently or in combination comprises one or more site specific-site specific/position specific, chirally-modified internucleotide linkages.

24 Claims, 73 Drawing Sheets

F12 ELF Duration Study in Rat

| Group | Duplex | Motif | Rats/Group (Female) | Dose and Bleeds |
|---|---|---|---|---|
| 1 | AD-85392 | 6PS Mix | 3 | |
| 2 | AD-218932 | 3PS Mix | 3 | |
| 3 | AD-218933 | R/R-S | 3 | |
| 4 | AD-218934 | S/R-S | 3 | 0.5 mg/kg |
| 5 | AD-218935 | R/R-SS | 3 | Pre-dose, D3, D7, D14, D21, D32, D50 |
| 6 | AD-218936 | R/RR-SS | 3 | |
| 7 | AD-218937 | R/RS-SS | 3 | |
| 8 | AD-218938 | mix-mix/RR-SS | 3 | |

*27 animals (including PBS control)

Figure 104A

F12 ELF Isomers for Rat Duration Study

| Duplex | Oligo ID# | S/AS | Sequence (5'-3') | Configuration Motif |
|---|---|---|---|---|
| AD-85392 6PS Mixture | 170173 170420 | S AS | gsgsaacuCfaAfUfAfaagugcuuuaL96 usAfsaagCfaCfUfuuauUfgAfguuccsusg | mix-mix — L96 / mix-mix — mix-mix |
| AD-218932.1 3PS Mixture | 401932 401933 | S AS | gsgaacuCfaAfUfAfaagugcuuuaL96 usAfaagCfaCfUfuuauUfgAfguuccusg | mix — L96 / mix — mix |
| AD-218933.1 R/R-S | 401934 401940 | S AS | (gRs)gaacuCfaAfUfAfaagugcuuuaL96 (uRs)AfaagCfaCfUfuuauUfgAfguucc(uSs)g | S — L96 / S — S |
| AD-218934.1 S/R-S | 401935 401940 | S AS | (gSs)gaacuCfaAfUfAfaagugcuuuaL96 (uRs)AfaagCfaCfUfuuauUfgAfguucc(uSs)g | S — L96 / S — S |
| AD-218935.1 R/R-SS | 401934 401941 | S AS | (gRs)gaacuCfaAfUfAfaagugcuuuaL96 (uRs)AfaagCfaCfUfuuauUfgAfguuc(cSs)(uSs)g | S — L96 / S — S |
| AD-218936.1 R/RR-SS | 401934 401942 | S AS | (gRs)gaacuCfaAfUfAfaagugcuuuaL96 (uRs)(AfRs)aagCfaCfUfuuauUfgAfguuc(cSs)(uSs)g | S — L96 / S-S — S-S |
| AD-218937.1 R/RS-SS | 401934 401943 | S AS | (gRs)gaacuCfaAfUfAfaagugcuuuaL96 (uRs)(AfSs)aagCfaCfUfuuauUfgAfguuc(cSs)(uSs)g | S — L96 / S-S — S-S |
| AD-218938.1 mix-mix/RR-SS | 170173 401942 | S AS | gsgsaacuCfaAfUfAfaagugcuuuaL96 (uRs)(AfRs)aagCfaCfUfuuauUfgAfguuc(cSs)(uSs)g | mix-mix — L96 / S-S — S-S |

Figure 104B

F12 ELF Sense Strand Isomers for Rat Duration Study

| Duplex | Oligo ID# | S/AS | Sequence (5'–3') | Configuration Motif |
|---|---|---|---|---|
| AD-218945 4PS Mixture | 170173 401933 | S AS | gsgsaacuCfaAfUfAfaagugcuuuaL96 usAfaagCfaCfUfuuauUfgAfguuccusg | mix-mix————L96 mix————mix |
| AD-218939 MixMix/R-S | 170173 401940 | S AS | gsgsaacuCfaAfUfAfaagugcuuuaL96 (uRs)AfaagCfaCfUfuuauUfgAfguuccu(uSs)g | mix-mix————L96 S————S |
| AD-218940 RR/R-S | 401936 401940 | S AS | (gRs)(gRs)aacuCfaAfUfAfaagugcuuuaL96 (uRs)AfaagCfaCfUfuuauUfgAfguuccu(uSs)g | S-S————L96 S————S |
| AD-218941 RS/R-S | 401937 401940 | S AS | (gRs)(gSs)aacuCfaAfUfAfaagugcuuuaL96 (uRs)AfaagCfaCfUfuuauUfgAfguuccu(uSs)g | S-S————L96 S————S |
| AD-218942 SR/R-S | 401938 401940 | S AS | (gSs)(gRs)aacuCfaAfUfAfaagugcuuuaL96 (uRs)AfaagCfaCfUfuuauUfgAfguuccu(uSs)g | S-S————L96 S————S |
| AD-218943 SS/R-S | 401939 401940 | S AS | (gSs)(gSs)aacuCfaAfUfAfaagugcuuuaL96 (uRs)AfaagCfaCfUfuuauUfgAfguuccu(uSs)g | S-S————L96 S————S |
| AD-227932.1 Mix/R-S | 401932 401940 | S AS | gsgaacuCfaAfUfAfaagugcuuuaL96 (uRs)AfaagCfaCfUfuuauUfgAfguuccu(uSs)g | mix————L96 S————S |
| AD-218933 R/R-S | 401934 401940 | S AS | (gRs)gaacuCfaAfUfAfaagugcuuuaL96 (uRs)AfaagCfaCfUfuuauUfgAfguuccu(uSs)g | S————L96 S————S |
| AD-218934 S/R-S | 401935 401940 | S AS | (gSs)gaacuCfaAfUfAfaagugcuuuaL96 (uRs)AfaagCfaCfUfuuauUfgAfguuccu(uSs)g | S————L96 S————S |

30 animals (including PBS control group)

Figure 105B

F12 ELF Sense Strand Isomers to Day 28

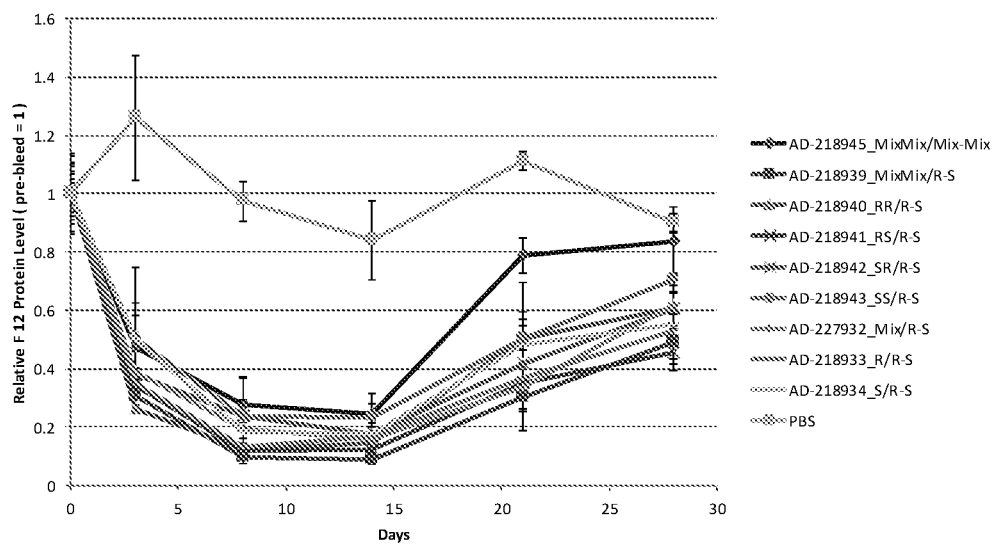

Figure 105C

In Vivo Study of AD-85392 and the Chiral PS Version in Mouse

| Group | Variants Tested | Duplex | PS Motif | Dose (Target ED70) | Bleeds |
|---|---|---|---|---|---|
| 1 | ELF10 Mismatch at N20 | AD-85392 | 6PS Mix | 0.3 mg/kg | Pre-dose, D3, D7, D14, D21, D28, D35 |
| 2 | | AD-353044 | Mix/R-SS | | |
| 3 | | AD-218938 | MixMix/RR-SS | | |
| 4 | ELF8 Perfect Match | AD-74210 | 6PS Mix | | |
| 5 | | AD-353041 | Mix/R-SS | | |
| 6 | | AD-353040 | MixMix/RR-SS | | |
| 7 | ELF10 Perfect Match | AD-73598 | 6PS Mix | | |
| 8 | | AD-353043 | Mix/R-SS | | |
| 9 | | AD-353042 | MixMix/RR-SS | | |

*30 animals (including PBS control group)

Figure 106A

F12 ELF Duplexes

| Duplex | Oligo ID# | S/AS | Sequence (5'- 3') | Configuration Motif |
|---|---|---|---|---|
| AD-85392 6PS Mix | 170173 | S | gsgsaacuCfaAfUfAfaagugcuuuaL96 | mix-mix — L96 |
| | 170420 | AS | usAfsaagCfaCfUfuuauUfgAfguuucsusg | mix-mix — mix-mix |
| AD-353044 Mix/R-SS | 401932 | S | gsgaacuCfaAfUfAfaagugcuuuaL96 | mix — L96 |
| | 401941 | AS | (uRs)AfaagCfaCfUfuuauUfgAfguuc(cSs)(uSs)g | S-S — S |
| AD-218938 MixMix/RR-SS | 170173 | S | gsgsaacuCfaAfUfAfaagugcuuuaL96 | mix-mix — L96 |
| | 401942 | AS | (uRs)(AfRs)aagCfaCfUfuuauUfgAfguuc(cSs)(uSs)g | S-S — S |
| AD-74210 6PS Mixture | 147454 | S | gsasaacuCfaAfUfAfaagugcuuuaL96 | mix-mix — L96 |
| | 148543 | AS | usAfsaagCfacuuuauUfgAfguuucsusg | mix-mix — mix-mix |
| AD-353041 Mix/R-SS | 455686 | S | gsaaacuCfaAfUfAfaagugcuuuaL96 | mix — L96 |
| | 455687 | AS | (uRs)AfaagCfacuuuauUfgAfguuu(cSs)(uSs)g | S-S — S |
| AD-353040 MixMix/RR-SS | 147454 | S | gsasaacuCfaAfUfAfaagugcuuuaL96 | mix-mix — L96 |
| | 455688 | AS | (uRs)(AfRs)aagCfacuuuauUfgAfguuu(cSs)(uSs)g | S-S — S |
| AD-73598 6PS Mixture | 147454 | S | gsasaacuCfaAfUfAfaagugcuuuaL96 | mix-mix — L96 |
| | 147455 | AS | usAfsaagCfaCfUfuuauUfgAfguuucsusg | mix-mix — mix-mix |
| AD-353043 Mix/R-SS | 455686 | S | gsaaacuCfaAfUfAfaagugcuuuaL96 | mix — L96 |
| | 555738 | AS | (uRs)AfaagCfaCfUfuuauUfgAfguuu(cSs)(uSs)g | S-S — S |
| AD-353042 MixMix/RR-SS | 147454 | S | gsasaacuCfaAfUfAfaagugcuuuaL96 | mix-mix — L96 |
| | 555739 | AS | (uRs)(AfRs)aagCfaCfUfuuauUfgAfguuu(cSs)(uSs)g | S-S — S |

Figure 106B

Evaluation in NHP

| Group | Duplex | Motif | Animals/Group | Dose (mg/kg) |
|---|---|---|---|---|
| 1 | AD-85392 | 6PS Mix | 3 | 0.5 |
| 2 | AD-85392 | 6PS Mix | 3 | 1.5 |
| 3 | AD-413741 | MM/MM-SS | 3 | 0.5 |
| 4 | AD-413742 | MM/RR-MM | 3 | 0.5 |
| 5 | AD-218938 | MM/RR-SS | 3 | 0.5 |
| 6 | AD-413744 | MM/R-SS | 3 | 0.5 |
| 7 | AD-413743 | MM/VP-SS | 3 | 0.5 |
| 8 | AD-85531 | 6PS Mix | 3 | 1 |
| 9 | AD-413745 | RR/R-SS | 3 | 1 |
| 10 | AD-87038 | 6PS Mix | 3 | 3 |
| 11 | AD-413740 | RR/R-SS | 3 | 3 |

Figure 111A

F12 and ANG Chiral PS siRNA Duplexes for NHP Study

| Duplex | Target | Oligo ID# | S/AS | Sequence (5'-3') | Configuration Motif |
|---|---|---|---|---|---|
| AD-85392.11 6PS Mixture | | 170173 170420 | S AS | gsgsaacuCfaAfUfAfaagugcuuuaL96 usAfsaagCfaCfUfuuauUfgAfguuccsusg | mix-mix — L96 mix-mix — mix-mix |
| AD-413741.2 MM/MM-SS | | 170173 780201 | S AS | gsgsaacuCfaAfUfAfaagugcuuuaL96 usAfsaagCfaCfUfuuauUfgAfguuc(cSs)(uSs)g | mix-mix — L96 S-S — mix-mix |
| AD-413742.2 MM/RR-MM | F12 Sequence 1 | 170173 780202 | S AS | gsgsaacuCfaAfUfAfaagugcuuuaL96 (uRs)(AfRs)aagCfaCfUfuuauUfgAfguuccsusg | mix-mix — L96 mix-mix — mix-mix |
| AD-218938.6 MM/RR-SS | | 170173 401942 | S AS | gsgsaacuCfaAfUfAfaagugcuuuaL96 (uRs)(AfRs)aagCfaCfUfuuauUfgAfguuc(cSs)(uSs)g | mix-mix — L96 S-S — S-S |
| AD-413744.2 MM/R-SS | | 170173 401941 | S AS | gsgsaacuCfaAfUfAfaagugcuuuaL96 (uRs)AfaagCfaCfUfuuauUfgAfguuc(cSs)(uSs)g | mix-mix — L96 S-S — S-S |
| AD-413743.2 MM/VP-SS | | 170173 780203 | S AS | gsgsaacuCfaAfUfAfaagugcuuuaL96 VPuAfaagCfaCfUfuuauUfgAfguuc(cSs)(uSs)g | mix-mix — L96 S-S — VP |
| AD-85531.14 6PS Mixture | F12 Sequence 2 | 170178 170179 | S AS | uscsaauaAfaGfUfGfcuuugaaaauL96 asUfsuuucaaagcacUfuUfauugasgsu | mix-mix — L96 mix-mix — mix-mix |
| AD-413745.2 RR/R-SS | | 780204 515650 | S AS | (uRs)(cRs)aauaAfaGfUfGfcuuugaaaauL96 (aRs)UfuuucaaagcacUfuUfauug(aSs)(gSs)u | R-R — L96 S-S — S-S |
| AD-87038.14 6PS Mixture | Angptl3 Sequence 3 | 149774 172416 | S AS | cscsagaaGfuAfAfCfuucacuuaaaL96 usUfsuaag(Tgn)gaaguuAfcUfucuggsgsu | mix-mix — L96 mix-mix — mix-mix |
| AD-413740.2 RR/R-SS | | 780205 780206 | S AS | (cRs)(cRs)agaaGfuAfAfCfuucacuuaaaL96 (uRs)Ufuaag(Tgn)gaaguuAfcUfucug(gSs)(gSs)u | R-R — L96 S-S — S-S |

Figure 111B

CHIRALLY-ENRICHED DOUBLE-STRANDED RNA AGENTS

CROSS-REFERENCE TO RELATED APPLICATIONS

This application is a 371 National-Stage application of International PCT Application No. PCT/US2018/067103, filed Dec. 21, 2018, and claims priority to U.S. Provisional Patent Application No. 62/609,093, filed Dec. 21, 2017, both of which are incorporated herein by reference in their entirety.

FIELD OF THE INVENTION

The invention relates to chirally-modified dsRNA agents having site specific (e.g., terminal), chirally-modified internucleotide linkages that are advantaqueous for inhibition of target gene expression, as well as dsRNA compositions suitable for therapeutic use. Additionally, the invention provides methods of inhibiting the expression of target genes of interest by administering these chirally-modified dsRNA agents, e.g., for the treatment of various diseases.

BACKGROUND

RNA interference or "RNAi" is a term initially coined by Fire and co-workers to describe the observation that short double-stranded RNA (dsRNA) can block gene expression (Fire et al. (1998) Nature 391, 806-811; Elbashir et al. (2001) Genes Dev. 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 17-25 nucleotides) derived from the double-stranded RNA trigger, and the protein component that cleaves the target RNA is Argonaute 2 (Ago2), A RISC associated endonuclease.

Double-stranded RNA (dsRNA) molecules with good gene-silencing properties are needed for drug development based on RNA interference (RNAi). An initial step in RNAi is the activation of the RNA induced silencing complex (RISC), which requires removal of the sense strand of the dsRNA duplex. Sense strand was known to act as the first RISC substrate that is cleaved by Argonaute 2 in the middle of the duplex region. Immediately after the cleaved 5'-end and 3'-end fragments of the sense strand are removed for the RISC to become activated by the antisense strand (Rand et al. (2005) Cell 123, 621).

It was believed that when the cleavage and removal of the sense strand is inhibited, the endonucleolytic cleavage of target mRNA is impaired (Leuschner et al. (2006) EMBO Rep., 7, 314; Rand et al. (2005) Cell 123, 621; Schwarz et al. (2004) Curr. Biol. 14, 787). Leuschner et al. showed that incorporation of a 2'-O-Me ribose to the Ago2 cleavage site in the sense strand inhibits RNAi in HeLa cells (Leuschner et al. (2006) EMBO Rep., 7, 314). A similar effect was observed with phosphorothioate modifications, showing that cleavage of the sense strand was required for efficient RNAi also in mammals.

It was also believed that an effective means of protecting siRNAs against nuclease activity is to exchange their phosphodiester linkage for phosphorothioate (PS). An epimeric mixture of PS-modified siRNAs may typically be used to protect against nuclease activity in vivo. However, the stability of the siRNAs to nucleases can be affected by the absolute stereochemical configurations of the chiral phosphorus atoms.

There is thus an ongoing need for dsRNA agents to improve the gene silencing efficacy of siRNA gene therapeutics. This invention is directed to that need.

SUMMARY

This invention provides effective stereochemical solution for dsRNA agents optionally conjugated to at least one ligand, which are advantaqueous for inhibition of target gene expression, as well as RNAi compositions suitable for therapeutic use. The inventors have discovered that by selecting the chirality of phosphorus atom of phosphorothioate linkage(s) at the termini of a modified dsRNA, the number of internucleotide phosphorothioate backbone modifications within each strand of dsRNA agent may be reduced while simultaneously maintaining or improving the in vivo pharmacological properties, such as the stability of dsRNA agents against nucleases and gene silencing potency (RISC loading).

In one aspect, the invention relates to a chirally-modified double-stranded RNA (dsRNA) agent capable of inhibiting the expression of a target gene. The chirally-modified dsRNA agent comprises a sense strand and an antisense strand, each strand having 14 to 40 nucleotides.

The chirally-modified dsRNA agent comprises three or more chirally-modified internucleotide linkages (e.g., at terminal). The chirally-modified dsRNA agent may comprise four or more chirally-modified internucleotide linkages (e.g., at terminal). The chirally-modified dsRNA agent may comprise five or more chirally-modified internucleotide linkages (e.g., at terminal). The chirally-modified dsRNA agent may comprise six or more chirally-modified internucleotide linkages (e.g., at terminal). The chirally-modified dsRNA agent may comprise seven or more chirally-modified internucleotide linkages (e.g., at terminal). The chirally-modified dsRNA agent may comprise eight or more chirally-modified internucleotide linkages (e.g., at terminal). A terminal, chiral modification to the internucleotide linkage may occur at the 5' end, 3' end, or both the 5' end and 3' end.

The chirally-modified internucleotide linkages may be site-specific, e.g., at terminal of a strand.

The chirally-modified dsRNA agent comprises three or more site specific (e.g., terminal), chirally-modified internucleotide linkages at position(s) 1, 2, 3, or combinations thereof from the 5'-end and/or 3'-end of the antisense strand or the 5'-end of the sense strand, or of said position(s) of both strands of the dsRNA. The chirally-modified dsRNA agent may comprise four or more site specific (e.g., terminal), chirally-modified internucleotide linkages at position(s) 1, 2, 3, 4, or combinations thereof from the 5'-end and/or 3'-end of the antisense strand or the 5'-end of the sense strand, or of said position(s) of both strand of the dsRNA. The chirally-modified dsRNA agent may comprise five or more site specific (e.g., terminal), chirally-modified internucleotide linkages at position(s) 1, 2, 3, 4, 5, or combinations thereof from the 5'-end and/or 3'-end of the antisense strand or the 5'-end of the sense strand, or of said position(s) of both strand of the dsRNA. The chirally-modified dsRNA agent may comprise six or more site specific (e.g., terminal), chirally-modified internucleotide linkages at position(s) 1, 2, 3, 4, 5, 6, or combinations thereof from the 5'-end and/or 3'-end of the antisense strand or the 5'-end of the sense strand, or of said position(s) of both strand of the dsRNA.

The chirally-modified dsRNA agent may comprise seven or more site specific (e.g., terminal), chirally-modified internucleotide linkages at position(s) 1, 2, 3, 4, 5, 6, 7, or combinations thereof from the 5'-end and/or 3'-end of the antisense strand or the 5'-end of the sense strand, or of said position(s) of both strand of the dsRNA. The chirally-modified dsRNA agent may comprise eight or more site specific (e.g., terminal), chirally-modified internucleotide linkages at position(s) 1, 2, 3, 4, 5, 6, 7, 8, or combinations thereof from the 5'-end and/or 3'-end of the antisense strand or the 5'-end of the sense strand, or of said position(s) of both strand of the dsRNA.

A site specific, chiral modification to the internucleotide linkage may occur at the 5' end, 3' end, or both the 5' end and 3' end. In one embodiment, site specific chiral modification(s) to the internucleotide linkage may occur at internal positions other than terminal ends. In another embodiment, site specific (e.g., terminal) chiral modification(s) to the internucleotide linkage may occur at internal, at internal and at the 5'-end, at internal and at the 3'-end, and combinations thereof. A chiral modification to the internucleotide linkage may occur on the sense strand, antisense strand, or both the sense strand and antisense strand. Each of the chiral pure phosphorus atoms may be in either Rp configuration or Sp configuration, and combination thereof.

In an given strand, either sense or antisense, of the dsRNA when multiple of chirally pure phosphorothioate linkages are present, the combined chiral configuration of phosphorous atom are all $R_P$ or all $S_P$ or all site specific combinations of $R_P$ and $S_P$. An all $R_P$ sense strand is paired with an achiral, all $R_P$, all $S_P$, or all possible site specific combination of $R_p$ and $S_P$ antisense strand depends on the total number chirally-modified internucleotide linkage on each strand and vice versa. Similarly, an all $S_P$ sense strand is paired with paired with an achiral, all $R_P$, all $S_P$, or all possible site specific combination of $R_p$ and $S_P$ antisense strand depends on the total number chirally-modified internucleotide linkage on each strand and vice versa. As sense strand carrying site specific combinations of $R_P$ and $S_p$ chirally pure internucleotide linkage is paired with an achiral, all $R_P$, all $S_P$, or all possible site specific combination of $R_p$ and $S_P$ antisense strand depends on the total number chirally-modified internucleotide linkage on each strand and vice versa.

In some embodiments, the sense strand comprises one or more chirally-modified internucleotide linkages (e.g., at terminal) at the 5' end.

In one embodiment, a chiral modification occurs at the first internucleotide linkage from the 5' end of the sense strand, and the linkage phosphorus atom is in Rp configuration. In one embodiment, a chiral modification occurs at the first internucleotide linkage from the 5' end of the sense strand, and the linkage phosphorus atom is in Sp configuration.

In one embodiment, a chiral modification occurs at the second internucleotide linkage from the 5' end of the sense strand, and the linkage phosphorus atom is in Rp configuration. In one embodiment, a chiral modification occurs at the second internucleotide linkage from the 5' end of the sense strand, and the linkage phosphorus atom is in Sp configuration.

In one embodiment, a chiral modification occurs at the third internucleotide linkage from the 5' end of the sense strand, and the linkage phosphorus atom is in Rp configuration. In one embodiment, a chiral modification occurs at the third internucleotide linkage from the 5' end of the sense strand, and the linkage phosphorus atom is in Sp configuration.

In one embodiment, a chiral modification occurs at the $n^{th}$ internucleotide linkage from the 5' end of the sense strand, and the linkage phosphorus atom is in Rp configuration. In one embodiment, a chiral modification occurs at the $n^{th}$ internucleotide linkage from the 5' end of the sense strand, and the linkage phosphorus atom is in Sp configuration.

In some embodiments, the sense strand comprises two or more chirally-modified internucleotide linkages (e.g., at terminal) at the 5' end. In one embodiment, chiral modifications occur at the first and second internucleotide linkages from the 5' end of the sense strand, and the linkage phosphorus atom is in Rp configuration. In one embodiment, chiral modifications occur at the first and second internucleotide linkages from the 5' end of the sense strand, and the linkage phosphorus atom is in Sp configuration. In another embodiment, chiral modifications occur at the first and second internucleotide linkages from the 5' end of the sense strand, and the linkage phosphorus atom configuration is in combination of $R_P$ and $S_P$, viz. $S_PR_P$ or $SpS_P$ configuration.

In one embodiment, chiral modifications occur at the first and $n^{th}$ internucleotide linkages from the 5' end of the sense strand, and the linkage phosphorus atom is in Rp configuration. In one embodiment, chiral modifications occur at the first and $n^{th}$ internucleotide linkages from the 5' end of the sense strand, and the linkage phosphorus atom is in Sp configuration. In another embodiment, chiral modifications occur at the first and $n^{th}$ internucleotide linkages from the 5' end of the sense strand, and the linkage phosphorus atom configuration is in combination of $R_P$ and $S_P$, viz. $S_PR_P$ or $SpS_P$ configuration.

In one embodiment, chiral modifications occur at the second and $n^{th}$ internucleotide linkages from the 5' end of the sense strand, and the linkage phosphorus atom is in Rp configuration. In one embodiment, chiral modifications occur at the second and $n^{th}$ internucleotide linkages from the 5' end of the sense strand, and the linkage phosphorus atom is in Sp configuration. In another embodiment, chiral modifications occur at the second and $n^{th}$ internucleotide linkages from the 5' end of the sense strand, and the linkage phosphorus atom configuration is in combination of $R_P$ and $S_P$, viz. $S_PR_P$ or $SpS_P$ configuration.

In some embodiments, the sense strand comprises three or more chirally-modified internucleotide linkages (e.g., at terminal) at the 5' end. In one embodiment, chiral modifications occur at the first, second and third internucleotide linkages from the 5' end of the sense strand, and the linkage phosphorus atom is in Rp configuration. In one embodiment, chiral modifications occur at the first, second and third internucleotide linkages from the 5' end of the sense strand, and the linkage phosphorus atom is in Sp configuration. In another embodiment, chiral modifications occur at the first, second and third internucleotide linkages from the 5' end of the sense strand, and the linkage phosphorus configuration is in combination of $R_P$ and $S_P$, viz. $R_PR_PR_P$, $R_PS_PR_P$, $S_PR_PR_P$, $S_PS_PR_P$, $S_PR_PS_P$ $R_PS_PS_P$ or $SpS_PSp$ configuration.

In one embodiment, chiral modifications occur at the first, second and $n^{th}$ internucleotide linkages from the 5' end of the sense strand, and the linkage phosphorus atom is in Rp configuration. In one embodiment, chiral modifications occur at the first, second and $n^{th}$ internucleotide linkages from the 5' end of the sense strand, and the linkage phosphorus atom is in Sp configuration. In another embodiment, chiral modifications occur at the first, second and $n^{th}$ internucleotide linkages from the 5' end of the sense strand, and the linkage phosphorus configuration is in combination of $R_P$ and $S_P$, viz. $R_PR_PS_P$, $R_PS_PR_P$, $S_PR_PR_P$, $S_PS_PR_P$, $S_PR_PS_P$ $R_PS_PS_P$ or $SpS_PSp$ configuration.

In one embodiment, chiral modifications occur at the second, third and $n^{th}$ internucleotide linkages from the 5' end of the sense strand, and the linkage phosphorus atom is in Rp configuration. In one embodiment, chiral modifications occur at the second, third and $n^{th}$ internucleotide linkages from the 5' end of the sense strand, and the linkage phosphorus atom is in Sp configuration. In another embodiment, chiral modifications occur at the second, third and $n^{th}$ internucleotide linkages from the 5' end of the sense strand, and the linkage phosphorus configuration is in combination of $R_P$ and $S_P$, viz. $R_PR_PR_P$, $R_PS_PR_P$, $S_PR_PR_P$, $S_PS_PR_P$, $S_PR_PS_P$ $R_PS_PS_P$ or $SpS_PSp$ configuration.

In some embodiments, the antisense strand comprises one or more chirally-modified internucleotide linkages (e.g., at terminal) at the 5' end.

In one embodiment, a chiral modification occurs at the first internucleotide linkage from the 5' end of the antisense strand, and the linkage phosphorus atom is in Rp configuration. In one embodiment, a chiral modification occurs at the first internucleotide linkage from the 5' end of the antisense strand, and the linkage phosphorus atom is in Sp configuration.

In one embodiment, a chiral modification occurs at the second internucleotide linkage from the 5' end of the antisense strand, and the linkage phosphorus atom is in Rp configuration. In one embodiment, a chiral modification occurs at the second internucleotide linkage from the 5' end of the antisense strand, and the linkage phosphorus atom is in Sp configuration.

In one embodiment, a chiral modification occurs at the third internucleotide linkage from the 5' end of the antisense strand, and the linkage phosphorus atom is in Rp configuration. In one embodiment, a chiral modification occurs at the third internucleotide linkage from the 5' end of the antisense strand, and the linkage phosphorus atom is in Sp configuration.

In one embodiment, a chiral modification occurs at the $n^{th}$ internucleotide linkage from the 5' end of the antisense strand, and the linkage phosphorus atom is in Rp configuration. In one embodiment, a chiral modification occurs at the $n^{th}$ internucleotide linkage from the 5' end of the antisense strand, and the linkage phosphorus atom is in Sp configuration.

In some embodiments, the antisense strand comprises two or more chirally-modified internucleotide linkages (e.g., at terminal) at the 5' end.

In one embodiment, chiral modifications occur at the first and second internucleotide linkages from the 5' end of the antisense strand, and the linkage phosphorus atom is in Rp configuration. In one embodiment, chiral modifications occur at the first and second internucleotide linkages from the 5' end of the antisense strand, and the linkage phosphorus atom is in Sp configuration. In another embodiment, chiral modifications occur at the first and second internucleotide linkages from the 5' end of the antisense strand, and the linkage phosphorus atom configuration is in combination of $R_P$ and $S_P$, viz. $S_PR_P$ or $SpS_P$ configuration.

In one embodiment, chiral modifications occur at the first and $n^{th}$ internucleotide linkages from the 5' end of the antisense strand, and the linkage phosphorus atom is in Rp configuration. In one embodiment, chiral modifications occur at the first and $n^{th}$ internucleotide linkages from the 5' end of the antisense strand, and the linkage phosphorus atom is in Sp configuration. In another embodiment, chiral modifications occur at the first and $n^{th}$ internucleotide linkages from the 5' end of the antisense strand, and the linkage phosphorus atom configuration is in combination of $R_P$ and $S_P$, viz. $S_PR_P$ or $SpS_P$ configuration.

In one embodiment, chiral modifications occur at the second and $n^{th}$ internucleotide linkages from the 5' end of the antisense strand, and the linkage phosphorus atom is in Rp configuration. In one embodiment, chiral modifications occur at the second and $n^{th}$ internucleotide linkages from the 5' end of the antisense strand, and the linkage phosphorus atom is in Sp configuration. In another embodiment, chiral modifications occur at the second and $n^{th}$ internucleotide linkages from the 5' end of the antisense strand, and the linkage phosphorus atom configuration is in combination of $R_P$ and $S_P$, viz. RpRp, $S_PR_P$ or $SpS_P$ configuration.

In some embodiments, the antisense strand comprises three or more chirally-modified internucleotide linkages (e.g., at terminal) at the 5' end.

In one embodiment, chiral modifications occur at the first, second and third internucleotide linkages from the 5' end of the antisense strand, and the linkage phosphorus atom is in Rp configuration. In one embodiment, chiral modifications occur at the first, second and third internucleotide linkages from the 5' end of the antisense strand, and the linkage phosphorus atom is in Sp configuration. In another embodiment, chiral modifications occur at the first, second and third internucleotide linkages from the 5' end of the antisense strand, and the linkage phosphorus configuration is in combination of $R_P$ and $S_P$, viz. $R_PR_PR_P$, $R_PS_PR_P$, $S_PR_PR_P$, $S_PS_PR_P$, $S_PR_PS_P$, $R_PS_PS_P$ or $SpS_PSp$ configuration.

In one embodiment, chiral modifications occur at the first, second and $n^{th}$ internucleotide linkages from the 5' end of the antisense strand, and the linkage phosphorus atom is in Rp configuration. In one embodiment, chiral modifications occur at the first, second and $n^{th}$ internucleotide linkages from the 5' end of the antisense strand, and the linkage phosphorus atom is in Sp configuration. In another embodiment, chiral modifications occur at the first, second and $n^{th}$ internucleotide linkages from the 5' end of the antisense strand, and the linkage phosphorus configuration is in combination of $R_P$ and $S_P$, viz. $R_PR_PR_P$, $R_PS_PR_P$, $S_PR_PR_P$, $S_PS_PR_P$, $S_PR_PS_P$ $R_PS_PS_P$ or $SpS_PSp$ configuration.

In one embodiment, chiral modifications occur at the second, third and $n^{th}$ internucleotide linkages from the 5' end of the antisense strand, and the linkage phosphorus atom is in Rp configuration. In one embodiment, chiral modifications occur at the second, third and $n^{th}$ internucleotide linkages from the 5' end of the antisense strand, and the linkage phosphorus atom is in Sp configuration. In another embodiment, chiral modifications occur at the second, third and $n^{th}$ internucleotide linkages from the 5' end of the antisense strand, and the linkage phosphorus configuration is in combination of $R_P$ and $S_P$, viz. $R_PR_PR_P$, $R_PS_PR_P$, $S_PR_P$ $R_P$, $S_PS_PR_P$, $S_PR_PS_P$ $R_PS_PS_P$ or $SpS_PSp$ configuration.

In some embodiments, the antisense strand comprises one or more chirally-modified internucleotide linkages (e.g., at terminal) at the 3' end.

In one embodiment, a chiral modification occurs at the first internucleotide linkage from the 3' end of the antisense strand, and the linkage phosphorus atom is in Rp configuration. In one embodiment, a chiral modification occurs at the first internucleotide linkage from the 3' end of the antisense strand, and the linkage phosphorus atom is in Sp configuration.

In one embodiment, a chiral modification occurs at the second internucleotide linkage from the 3' end of the antisense strand, and the linkage phosphorus atom is in Rp configuration. In one embodiment, a chiral modification occurs at the second internucleotide linkage from the 3' end of the antisense strand, and the linkage phosphorus atom is in Sp configuration.

In one embodiment, a chiral modification occurs at the third internucleotide linkage from the 3' end of the antisense strand, and the linkage phosphorus atom is in Rp configuration. In one embodiment, a chiral modification occurs at the third internucleotide linkage from the 3' end of the antisense strand, and the linkage phosphorus atom is in Sp configuration.

In one embodiment, a chiral modification occurs at the $n^{th}$ internucleotide linkage from the 3' end of the antisense strand, and the linkage phosphorus atom is in Rp configuration. In one embodiment, a chiral modification occurs at the $n^{th}$ internucleotide linkage from the 3' end of the antisense strand, and the linkage phosphorus atom is in Sp configuration.

In some embodiments, the antisense strand comprises two or more chirally-modified internucleotide linkages (e.g., at terminal) at the 3' end.

In one embodiment, chiral modifications occur at the first and second internucleotide linkages from the 3' end of the antisense strand, and the linkage phosphorus atom is in Rp configuration. In one embodiment, chiral modifications occur at the first and second internucleotide linkages from the 3' end of the antisense strand, and the linkage phosphorus atom is in Sp configuration. In another embodiment, chiral modifications occur at the first and second internucleotide linkages from the 3' end of the antisense strand, and the linkage phosphorus atom configuration is in combination of $R_P$ and $S_P$, viz. RpRp, $S_P R_P$ or $SpS_P$ configuration.

In one embodiment, chiral modifications occur at the first and $n^{th}$ internucleotide linkages from the 3' end of the antisense strand, and the linkage phosphorus atom is in Rp configuration. In one embodiment, chiral modifications occur at the first and $n^{th}$ internucleotide linkages from the 3' end of the antisense strand, and the linkage phosphorus atom is in Sp configuration. In another embodiment, chiral modifications occur at the first and $n^{th}$ internucleotide linkages from the 3' end of the antisense strand, and the linkage phosphorus atom configuration is in combination of $R_P$ and $S_P$, viz. RpRp, $S_P R_P$ or $SpS_P$ configuration.

In one embodiment, chiral modifications occur at the second and $n^{th}$ internucleotide linkages from the 3' end of the antisense strand, and the linkage phosphorus atom is in Rp configuration. In one embodiment, chiral modifications occur at the second and $n^{th}$ internucleotide linkages from the 3' end of the antisense strand, and the linkage phosphorus atom is in Sp configuration. In another embodiment, chiral modifications occur at the second and $n^{th}$ internucleotide linkages from the 3' end of the antisense strand, and the linkage phosphorus atom configuration is in combination of $R_P$ and $S_P$, viz. RpRp, $S_P R_P$ or $SpS_P$ configuration.

In some embodiments, the antisense strand comprises three or more chirally-modified internucleotide linkages (e.g., at terminal) at the 3' end.

In one embodiment, chiral modifications occur at the first, second and third internucleotide linkages from the 3' end of the antisense strand, and the linkage phosphorus atom is in Rp configuration. In one embodiment, chiral modifications occur at the first, second and third internucleotide linkages from the 3' end of the antisense strand, and the linkage phosphorus atom is in Sp configuration. In another embodiment, chiral modifications occur at the first, second and third internucleotide linkages from the 3' end of the antisense strand, and the linkage phosphorus configuration is in combination of $R_P$ and $S_P$, viz. $R_P R_P R_P$, $R_P S_P R_P$, $S_P R_P R_P$, $S_P S_P R_P$, $S_P R_P S_P$ $R_P S_P S_P$ or $SpS_P Sp$ configuration.

In one embodiment, chiral modifications occur at the first, second and $n^{th}$ internucleotide linkages from the 3' end of the antisense strand, and the linkage phosphorus atom is in Rp configuration. In one embodiment, chiral modifications occur at the first, second and $n^{th}$ internucleotide linkages from the 3' end of the antisense strand, and the linkage phosphorus atom is in Sp configuration. In another embodiment, chiral modifications occur at the first, second and $n^{th}$ internucleotide linkages from the 3' end of the antisense strand, and the linkage phosphorus configuration is in combination of $R_P$ and $S_P$, viz. $R_P R_P R_P$, $R_P S_P R_P$, $S_P R_P R_P$, $S_P S_P R_P$, $S_P R_P S_P$ $R_P S_P S_P$ or $SpS_P Sp$ configuration.

In one embodiment, chiral modifications occur at the second, third and $n^{th}$ internucleotide linkages from the 3' end of the antisense strand, and the linkage phosphorus atom is in Rp configuration. In one embodiment, chiral modifications occur at the second, third and $n^{th}$ internucleotide linkages from the 3' end of the antisense strand, and the linkage phosphorus atom is in Sp configuration. In another embodiment, chiral modifications occur at the second, third and $n^{th}$ internucleotide linkages from the 3' end of the antisense strand, and the linkage phosphorus configuration is in combination of $R_P$ and $S_P$, viz. $R_P R_P S_P$, $R_P S_P R_P$, $S_P R_P$ $R_P$, $S_P S_P R_P$, $S_P R_P S_P$ $R_P S_P S_P$ or $SpS_P Sp$ configuration.

In some embodiments, the chirally-modified dsRNA agent comprises: a chiral modification occurs at the first internucleotide linkage from the 3' end of the antisense strand and a chiral modification at the first internucleotide linkage from the 5'-end of the same antisense strand. In one embodiment, the chiral modifications at both ends of the antisense strand have the linkage phosphorus atom in Sp configuration. In another embodiment, the terminal chiral modifications at both ends of the antisense strand have the linkage phosphorus atom in $R_P$ configuration. In another embodiment, the terminal chiral modifications at both ends of the antisense strand have the linkage phosphorus atom in either $R_P S_P$ or $S_P R_P$ configurations.

In some embodiments, the chirally-modified dsRNA agent comprises: a chiral modification occurs at the second internucleotide linkage from the 3' end of the antisense strand and a second chiral modification at the first internucleotide linkage from the 5'-end of the same antisense strand. In one embodiment, the chiral modifications at both ends of the antisense strand have the linkage phosphorus atom in Sp configuration. In another embodiment, the terminal chiral modifications at both ends of the antisense strand have the linkage phosphorus atom in $R_P$ configuration. In another embodiment, the terminal chiral modifications at both ends of the antisense strand have the linkage phosphorus atom in either $R_P S_P$ or $S_P R_P$ configurations.

In some embodiments, the chirally-modified dsRNA agent comprises: a chiral modification occurs at the third internucleotide linkage from the 3' end of the antisense strand and a second chiral modification at the first internucleotide linkage from the 5'-end of the same antisense strand. In one embodiment, the chiral modifications at both ends of the antisense strand have the linkage phosphorus atom in Sp configuration. In another embodiment, the terminal chiral modifications at both ends of the antisense strand have the linkage phosphorus atom in $R_P$ configuration. In another embodiment, the terminal chiral modifications at both ends of the antisense strand have the linkage phosphorus atom in either $R_P S_P$ or $S_P R_P$ configurations.

In some embodiments, the chirally-modified dsRNA agent comprises: a chiral modification occurs at the first internucleotide linkage from the 3' end of the antisense strand and a second chiral modification at the second internucleotide linkage from the 5'-end of the same antisense strand. In one embodiment, the chiral modifications at both ends of the antisense strand have the linkage phosphorus atom in Sp configuration. In another embodiment, the terminal chiral modifications at both ends of the antisense strand have the linkage phosphorus atom in $R_P$ configuration. In another embodiment, the terminal chiral modifications at both ends of the antisense strand have the linkage phosphorus atom in either $R_PS_P$ or $S_PR_P$ configurations.

In some embodiments, the chirally-modified dsRNA agent comprises: a chiral modification occurs at the second internucleotide linkage from the 3' end of the antisense strand and a second chiral modification at the second internucleotide linkage from the 5'-end of the same antisense strand. In one embodiment, the chiral modifications at both ends of the antisense strand have the linkage phosphorus atom in Sp configuration. In another embodiment, the terminal chiral modifications at both ends of the antisense strand have the linkage phosphorus atom in $R_P$ configuration. In another embodiment, the terminal chiral modifications at both ends of the antisense strand have the linkage phosphorus atom in either $R_PS_P$ or $S_PR_P$ configurations.

In some embodiments, the chirally-modified dsRNA agent comprises: a chiral modification occurs at the third internucleotide linkage from the 3' end of the antisense strand and a second chiral modification at the second internucleotide linkage from the 5'-end of the same antisense strand. In one embodiment, the chiral modifications at both ends of the antisense strand have the linkage phosphorus atom in Sp configuration. In another embodiment, the terminal chiral modifications at both ends of the antisense strand have the linkage phosphorus atom in $R_P$ configuration. In another embodiment, the terminal chiral modifications at both ends of the antisense strand have the linkage phosphorus atom in either $R_PS_P$ or $S_PR_P$ configurations.

Any of the above embodiments discussing that the sense strand comprises one or more, two or more, or three or more chirally-modified internucleotide linkages (e.g., at terminal) at the 5' end can be combined with any of the above embodiments discussing that the antisense strand comprises one or more, two or more, or three or more chirally-modified internucleotide linkages (e.g., at terminal) at the 5' end and/or at the 3' end, to produce various embodiments of a chirally-modified dsRNA agent comprising multiple (e.g., three or more, four or more, five or more, six or more, seven or more, or eight or more) chirally-modified internucleotide linkages chirally-modified internucleotide linkages.

For instance, in some embodiments, the chirally-modified dsRNA agent comprises: a terminal, chiral modification occurring at the first internucleotide linkage from the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp configuration or Sp configuration.

In some embodiments, the chirally-modified dsRNA agent comprises: terminal, chiral modifications occurring at the first and second internucleotide linkages at the 3' end of the antisense strand, having the linkage phosphorus atom in Sp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp configuration.

In some embodiments, the chirally-modified dsRNA agent comprises: terminal, chiral modifications occurring at the first, second, and third internucleotide linkages at the 3' end of the antisense strand, having the linkage phosphorus atom in Sp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp configuration.

In some embodiments, the chirally-modified dsRNA agent comprises: terminal, chiral modifications occurring at the first and second internucleotide linkages at the 3' end of the antisense strand, having the linkage phosphorus atom in Sp configuration; a terminal, chiral modification occurring at the third internucleotide linkage at the 3' end of the antisense strand, having the linkage phosphorus atom in Rp configuration; a terminal, chiral modification occurring at the first internucleotide linkage at the 5' end of the antisense strand, having the linkage phosphorus atom in Rp configuration; and a terminal, chiral modification occurring at the first internucleotide linkage at the 5' end of the sense strand, having the linkage phosphorus atom in either Rp configuration.

In some embodiments, the chirally-modified dsRNA agent comprises: terminal, chiral modifications occurring at the first and second internucleotide linkages at the 3' end of the antisense strand, having the linkage phosphorus atom in Sp configuration; terminal, chiral modifications occurring at the first and second internucleotide linkages at the 5' end of the antisense strand, having the linkage phosphorus atom in Rp configuration; and a terminal, chiral modification occurring at the first internucleotide linkage at the 5' end of the sense strand, having the linkage phosphorus atom in either Rp configuration.

The chiral purity with respect to the chiral linkage phosphorus atom for each terminal, chirally-modified internucleotide linkage is at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

A chirally pure (or substantially chirally pure) diastereoisomeric form of the chirally-modified RNA agent may refer to a particular diastereoisomeric form of the chirally-modified RNA agent having a chiral purity of at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In some embodiments, one or more site specific (e.g., terminal), chirally-modified internucleotide linkages independently have the structure of Formula A:

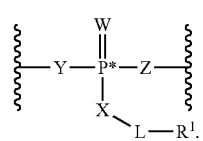

In formula A, P* is an asymmetric phosphorus atom and is either Rp or Sp. W is O, S or Se. Each of X, Y and Z is independently —O—, —S—, —N(-L-R¹)—, —C(R''')(R''')— or L. In some embodiments, in at least one chirally-modified internucleotide linkage, X is —S—.

In some embodiments L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R)C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, -Cy- is an optionally substituted bivalent ring selected from phenylene, carbocyclylene, arylene, heteroarylene, or heterocyclylene.

In some embodiments -L-R represent a negative charge or a positive associated with X.

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

Each R' is independently —R, —C(O)R, —CO$_2$R, or —SO$_2$R; or two R' on the same nitrogen are taken together with their intervening atoms to form an optionally substituted heterocyclic or heteroaryl ring; or two R' on the same carbon are taken together with their intervening atoms to form an optionally substituted aryl, carbocyclic, heterocyclic, or heteroaryl ring. Each R is independently hydrogen, or an optionally substituted group selected from $C_1$-$C_6$ aliphatic, phenyl, carbocyclyl, aryl, heteroaryl, or heterocyclyl.

Each ∼∼∼ independently represents a connection to a nucleoside. In some embodiments the connection to a nucleoside is through 3'- and the second nucleoside connection is through 5'-carbon and vice versa. In another embodiment the first nucleoside is connected through 3'-carbon and the second nucleoside is through 3'-carbon. In another embodiment the first nucleoside connection is through 5'-carbon and the second nucleoside connection is through 5'-carbon. In another embodiment the first nucleoside connection is through the 2'-carbon and the second nucleoside connection is through 5'-carbon and vice versa. In another embodiment the first nucleoside connection is through the 2'-carbon and the second nucleoside connection is through 3'-carbon and vice versa. In another embodiment the first nucleoside connection is through the 2'-carbon and the second nucleoside connection is through 2'-carbon.

In some embodiments, one or more terminal, chirally-modified internucleotide linkage of Formula A has the structure of Formula A-1:

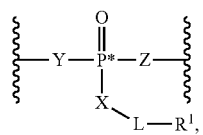

wherein each variable is as defined above.

In some embodiments, one or more terminal, chirally-modified internucleotide linkage of Formula A has the structure of Formula A-2:

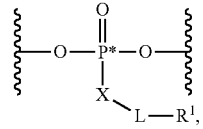

wherein each variable is as defined above.

In some embodiments, one or more terminal, chirally-modified internucleotide linkage of Formula A has the structure of Formula A-3:

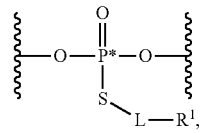

wherein each variable is as defined above. Exemplary terminal, chirally-modified internucleotide linkages of Formula A-3 are:

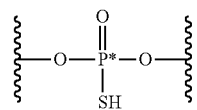

(a phosphorothioate linkage),

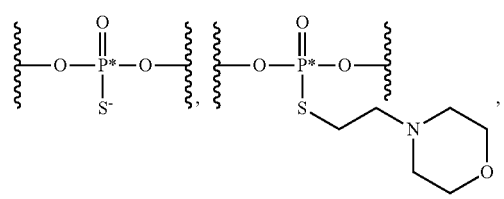

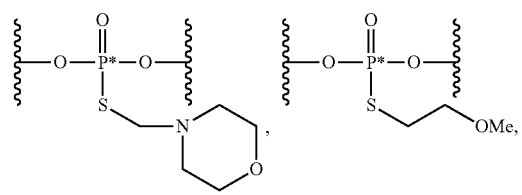

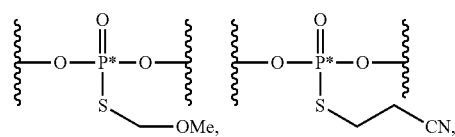

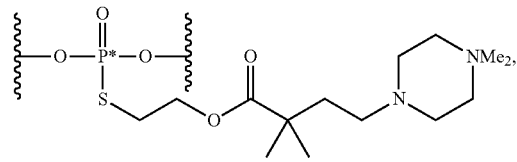

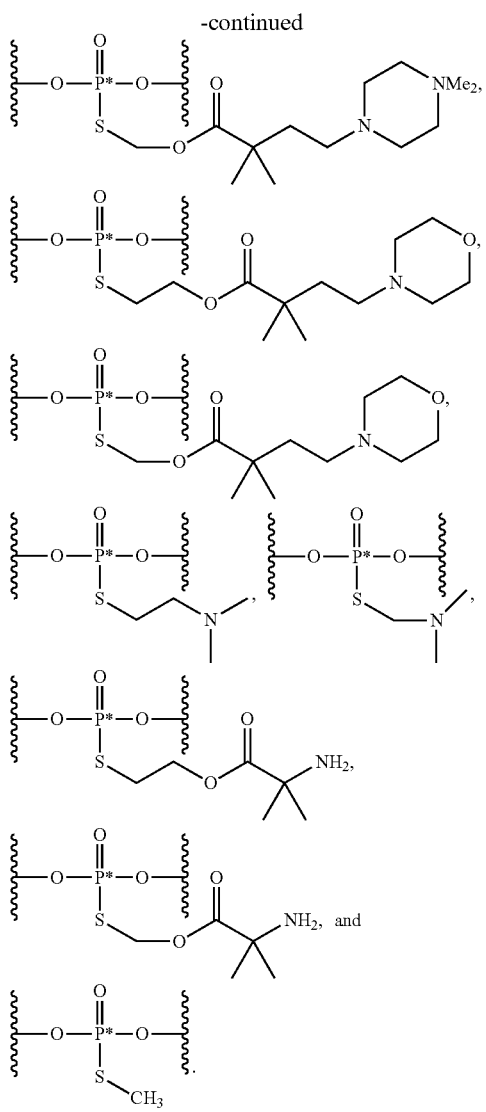

In some embodiments, one or more terminal, chirally-modified internucleotide linkage of Formula A has the structure of Formula A-4:

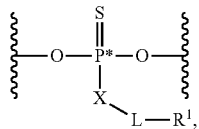

wherein each variable is as defined above.

In some embodiments, one or more terminal, chirally-modified internucleotide linkage of Formula A has the structure of Formula A-5:

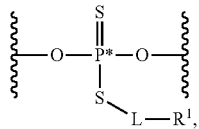

wherein each variable is as defined above.

The chirally-modified internucleotide linkage may be a phosphorothioate linkage. In one embodiment, each site specific (e.g., terminal), chirally-modified internucleotide linkage is a phosphorothioate linkage.

In the chirally-modified dsRNA agent, an internucleotide linkage connects two nucleotides to form a dinucleotide. Each nucleotide of a dinucleotide connected by the site specific (e.g., terminal), chirally-modified internucleotide linkage may be independently modified with a modification selected from the group consisting of acyclic nucleotides, LNA, HNA, CeNA, 2'-O-methoxyalkyl (e.g., 2'-O-methoxymethyl, 2'-O-methoxyethyl, or 2'-O-2-methoxypropanyl), 2'-O-methyl, 2'-O-allyl, 2'-C-allyl, 2'-deoxy, 2'-fluoro, 2'-O—N-methylacetamido (2'-O-NMA), 2'-O-dimethylaminoethoxyethyl (2'-O-DMAEOE), 2'-O-aminopropyl (2'-O-AP), 2'-ara-F, L-nucleoside modification (such as 2'-modified L-nucleosides, e.g., 2'-deoxy-L-nucleoside), BNA abasic sugar, abasic cyclic and open-chain alkyl.

In some embodiments, each of the sense and antisense strands of the chirally-modified dsRNA agent is independently modified with a modification selected from the group consisting of acyclic nucleotides, LNA, HNA, CeNA, 2'-O-methoxyalkyl (e.g., 2'-O-methoxymethyl, 2'-O-methoxyethyl, or 2'-O-2-methoxypropanyl), 2'-O-methyl, 2'-O-allyl, 2'-C-allyl, 2'-deoxy, 2'-fluoro, 2'-O—N-methylacetamido (2'-O-NMA), 2'-O-dimethylaminoethoxyethyl (2'-O-DMAEOE), 2'-O-aminopropyl (2'-O-AP), 2'-ara-F, L-nucleoside modification (such as 2'-modified L-nucleoside, e.g., 2'-deoxy-L-nucleoside), BNA abasic sugar, abasic cyclic and open-chain alkyl.

In one embodiment, each of the sense and antisense strands of the chirally-modified dsRNA agent contains at least two different modifications as described above.

In one embodiment, 100%, 95%, 90%, 85%, 80%, 75%, 70%, 65%, 60%, 55%, 50%, 45%, 40%, 35% or 30% of the chirally-modified dsRNA agent is modified. For example, when 50% of chirally-modified dsRNA agent is modified, 50% of all nucleotides present in chirally-modified dsRNA agent contain a modification as described above.

In some embodiments, each of the sense and antisense strands of the chirally-modified dsRNA agent has 12-40 nucleotides in length. For instance, each strand can independently have 14-40 nucleotides, 17-37 nucleotides, 25-37 nucleotides, 15-30 nucleotides, 27-30 nucleotides, 17-23 nucleotides, 17-21 nucleotides, 17-19 nucleotides, 19-35 nucleotides, 19-25 nucleotides, 19-23 nucleotides, 19-21 nucleotides, 21-25 nucleotides, or 21-23 nucleotides. In one embodiment, each strand has 19-35 nucleotides. In one embodiment, each strand has 18-23 nucleotides. In one embodiment, the sense strand has 19-22 nucleotides, and the antisense strand has 19-25 nucleotides. In one example, the sense strand has 21 nucleotides, and the antisense strand has 23 nucleotides.

In some embodiments, the duplex region of the chirally-modified dsRNA agent ranges from 10 to 30 nucleotide pairs in length, for instance, from 17 to 25 nucleotide pairs, from 17 to 23 nucleotide pairs, from 19 to 25 nucleotide pairs, from 19 to 23 nucleotide pairs, or from 19 to 22 nucleotide pairs in length.

In some embodiments, the chirally-modified dsRNA agent further comprises 3' and/or 5' overhang(s) of 1-10 nucleotides in length, for instance, an overhang of 1, 2, 3, 4, 5, or 6 nucleotides. In some embodiments, the chirally-modified dsRNA agent may also have a blunt end, located at the 5'-end of the antisense strand (or the 3'-end of the sense strand), or vice versa.

In one embodiment, the chirally-modified dsRNA agent comprises a 3' overhang at the 3'-end of the antisense strand, and optionally a blunt end at the 5'-end of the antisense strand. In one embodiment, the chirally-modified dsRNA agent has a 5' overhang at the 5'-end of the sense strand, and optionally a blunt end at the 5'-end of the antisense strand. In one embodiment, the chirally-modified dsRNA agent has two blunt ends at both ends of the dsRNA duplex.

In one embodiment, the dsRNA agent of the invention does not contain any 2'-F modification.

In some embodiments, the nucleotide at position 1 of the 5'-end of the antisense strand in the chirally-modified dsRNA agent is selected from the group consisting of A, dA, dU, U, and dT. In one embodiment, at least one of the first, second, and third base pairs from the 5'-end of the antisense strand is an AU base pair. In one embodiment, the antisense strand of the dsRNA agent of the invention is 100% complementary to a target RNA to hybridize thereto and inhibits its expression through RNA interference. In another embodiment, the antisense strand of the dsRNA agent of the invention is at least 95%, at least 90%, at least 85%, at least 80%, at least 75%, at least 70%, at least 65%, at least 60%, at least 55%, or at least 50% complementary to a target RNA.

In some embodiments, the chirally-modified dsRNA agent further comprises at least one ASGPR ligand. The ASGPR ligand may be attached to the chirally-modified dsRNA agent through one or more linkers, as described infra in this disclosure. In one embodiment, the ASGPR ligand may be attached to the chirally-modified dsRNA agent through one or more cleavable linkers, as described infra in this disclosure. For example, the ASGPR ligand is one or more GalNAc derivatives attached through a monovalent, bivalent or trivalent branched linker, such as:

In one embodiment, the ASGPR ligand is attached to the 3' end of the antisense strand. In one embodiment, the ASGPR ligand is attached to the 5' end of the antisense strand. In one embodiment, the ASGPR ligands are attached to both 3' and 5' end of the antisense strand. In one embodiment, the ASGPR ligand is attached to any position on the antisense strand. In one embodiment, the linkage between the ASGPR ligand and the antisense strand is chiral linkage involving P-atom chirality in either $R_P$ or $S_P$ configuration.

This invention also provides effective nucleotide or chemical motifs for the chirally-modified dsRNA agents described above by introducing the chemical motifs described below into the chirally-modified dsRNA agents described above.

Accordingly, one aspect of the invention relates to a chirally-modified double-stranded RNA (dsRNA) agent for inhibiting the expression of a target gene. The chirally-modified dsRNA agent comprises a sense strand and an antisense strand, each strand having 14 to 40 nucleotides. The chirally-modified dsRNA agent comprises three or more site specific (e.g., terminal), chirally-modified internucleotide linkages as described above. The sense strand comprises one or more site specific (e.g., terminal), chirally-modified internucleotide linkages towards the 5' end. The antisense strand comprises one or more site specific (e.g., terminal), chirally-modified internucleotide linkages towards the 5' end and one or more site specific (e.g., terminal), chirally-modified internucleotide linkages towards the 3' end of the strand.

Each of the embodiments described above in the first aspect of the chirally-modified dsRNA agent relating to the

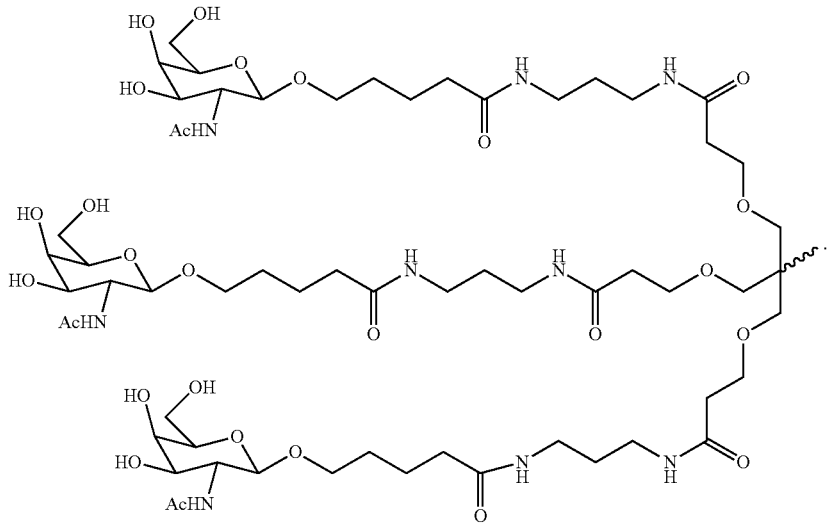 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the ASGPR ligand is attached to the 3' end of the sense strand. In one embodiment, the ASGPR ligand is attached to the 5' end of the sense strand. In one embodiment, the ASGPR ligands are attached to both 3' and 5' end of the sense strand. In one embodiment, the ASGPR ligand is attached to any position on the sense strand. In one embodiment, the linkage between the ASGPR ligand and the sense strand is chiral linkage involving P-atom chirality in either $R_P$ or $S_P$ configuration.

site specific chirally-modified internucleotide linkages applies to this aspect of the invention.

In some embodiments, the chirally-modified dsRNA agent has at least two phosphorothioate internucleotide linkages at the first five nucleotides on the antisense strand (counting from the 5' end).

In some embodiments, the antisense strand comprises two blocks of one, two or three phosphorothioate internucleotide linkages separated by 1, 2, 3, 4, 5, 6, 7, 8, 9, 10, 11, 12, 13, 14, 15, 16, 17, or 18 phosphate internucleotide linkages.

In some embodiments, the chirally-modified dsRNA agent has one or more lipophilic moieties conjugated to one or more positions on at least one strand. Examples of lipophilic moieties include, but not limited to, lipid (a saturated or unsaturated $C_4$-$C_3$ hydrocarbon chain, and an optional functional group selected from the group consisting of hydroxyl, amine, carboxylic acid, sulfonate, phosphate, thiol, azide, and alkyne), cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. In one embodiment, the lipophilic moiety is a saturated or unsaturated $C_6$-$C_{18}$ hydrocarbon chain. In one example, the lipohilic moiety is docosahexaenoic acid.

In certain embodiments, the lipophilic moiety is a $C_6$-$C_{30}$ acid (e.g., hexanoic acid, heptanoic acid, octanoic acid, nonanoic acid, decanoic acid, undecanoic acid, dodcanoic acid, tridecanoic acid, tetradecanoic acid, pentadecanoic acid, hexadecanoic acid, heptadecanoic acid, octadecanoic acid, oleic acid, linoleic acid, arachidonic acid, cis-4,7,10, 13,16,19-docosahexanoic acid, vitamin A, vitamin E, cholesterol etc.) or a $C_6$-$C_{30}$ alcohol (e.g., hexanol, heptanol, octanol, nonanol, decanol, undecanol, dodcanol, tridecanol, tetradecanol, pentadecanol, hexadecanol, heptadecanol, octadecanol, oleyl alcohol, linoleyl alcohol, arachidonic alcohol, cis-4,7,10,13,16,19-docosahexanol, retinol, vitamin E, cholesterol etc.).

In some embodiments, the chirally-modified dsRNA agent has less than 20%, less than 15%, less than 10%, less than 5% non-natural nucleotide, or substantially no non-natural nucleotide. Examples of non-natural nucleotide include acyclic nucleotides, LNA, HNA, CeNA, 2'-O-methoxyalkyl (e.g., 2'-O-methoxymethyl, 2'-O-methoxyethyl, or 2'-O-2-methoxypropanyl), 2'-O-allyl, 2'-C-allyl, 2'-fluoro, 2'-O—N-methylacetamido (2'-O-NMA), a 2'-0-dimethylaminoethoxyethyl (2'-O-DMAEOE), 2'-O-aminopropyl (2'-O-AP), 2'-ara-F, L-nucleoside modification (such as 2'-modified L-nucleoside, e.g., 2'-deoxy-L-nucleoside), BNA abasic sugar, abasic cyclic and open-chain alkyl.

In some embodiments, the chirally-modified dsRNA agent has greater than 80%, greater than 85%, greater than 90%, greater than 95%, or virtually 100% natural nucleotides. For the purpose of these embodiments, natural nucleotides can include those having 2'-OH, 2'-deoxy, and 2'-OMe.

In one embodiment, the chirally-modified dsRNA agent comprises a sense strand and antisense strand each having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the chirally-modified dsRNA agent has one or more lipophilic moieties conjugated to one or more positions on at least one strand; and wherein the chirally-modified dsRNA agent has less than 20%, less than 15%, less than 10%, less than 5% non-natural nucleotide, or substantially no non-natural nucleotide.

In one embodiment, the chirally-modified dsRNA agent comprises a sense strand and antisense strand each having a length of 15-30 nucleotides; at least two phosphorothioate internucleotide linkages at the first five nucleotides on the antisense strand (counting from the 5' end); wherein the duplex region is between 19 to 25 base pairs (preferably 19, 20, 21 or 22); wherein the chirally-modified dsRNA agent has one or more lipophilic moieties conjugated to one or more positions on at least one strand; and wherein the chirally-modified dsRNA agent has greater than 80%, greater than 85%, greater than 95%, or virtually 100% natural nucleotides, such as those having 2'-OH, 2'-deoxy, or 2'-OMe.

In some embodiments, the chirally-modified dsRNA agent has less than 12, less than 10, less than 8, less than 6, less than 4, less than 2, or no 2'-F modifications on the sense strand. In some embodiments, the chirally-modified dsRNA agent has less than 12, less than 10, less than 8, less than 6, less than 4, less than 2, or no 2'-F modifications on the antisense strand.

In some embodiments, the chirally-modified dsRNA agent has one or more 2'-F modifications on any position of the sense strand or antisense strand.

In one embodiment, the sense strand sequence of the chirally-modified dsRNA agent is represented by formula (I):

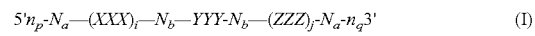

$$5'n_p\text{-}N_a\text{—}(XXX)_i\text{—}N_b\text{—}YYY\text{-}N_b\text{—}(ZZZ)_j\text{-}N_a\text{-}n_q 3' \qquad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 1, 2, 3, 4, 5, or 6 modified nucleotides;

each $n_p$ and $n_q$ independently represent an overhang nucleotide;

wherein $N_b$ and Y do not have the same modification;

wherein XXX, YYY and ZZZ each independently represent one motif of three identical modifications on three consecutive nucleotides.

In some embodiments, the sense strand of the chirally-modified dsRNA agent contains at least one motif of three identical modifications on three consecutive nucleotides, where one of the motifs occurs at the cleavage site in the sense strand. For instance, the sense strand can contain at least one motif of three 2'-F modifications on three consecutive nucleotides within 7-15 positions from the 5'end.

In some embodiments, the antisense strand of the chirally-modified dsRNA agent contains at least one motif of three identical modifications on three consecutive nucleotides, where one of the motifs occurs at or near the cleavage site in the antisense strand. For instance, the antisense strand can contain at least one motif of three 2'-O-methyl modifications on three consecutive nucleotides within 9-15 positions from the 5'end.

For a dsRNA agent having a duplex region of 17-23 nt in length, the cleavage site of the antisense strand is typically around the 10-12 positions from the 5'-end. Thus the motifs of three identical modifications may occur at the 9-11 positions; 10-12 positions; 11-13 positions; 12-14 positions; or 13-15 positions of the antisense strand, the count starting from the 1' nucleotide from the 5'-end of the antisense strand, or, the count starting from the 1 paired nucleotide within the duplex region from the 5'-end of the antisense strand. The cleavage site in the antisense strand may also change according to the length of the duplex region from the 5'-end.

In some embodiments, the chirally-modified dsRNA agent comprises a sense strand and antisense strand each having 14 to 30 nucleotides, wherein the sense strand contains at least two motifs of three identical modifications on three consecutive nucleotides, where at least one of the motifs occurs at or near the cleavage site within the strand and at least one of the motifs occurs at another portion of the strand that is separated from the motif at the cleavage site by at least one nucleotide. In one embodiment, the antisense strand also contains at least one motif of three identical modifications on three consecutive nucleotides, where at least one of the motifs occurs at or near the cleavage site within the strand. The modification in the motif occurring at or near the cleavage site in the sense strand is different than the modification in the motif occurring at or near the cleavage site in the antisense strand.

In some embodiments, the chirally-modified dsRNA agent comprises a sense strand and antisense strand each having 14 to 30 nucleotides, wherein the sense strand contains at least one motif of three 2'-F modifications on three consecutive nucleotides, where at least one of the motifs occurs at or near the cleavage site in the strand. In one embodiment, the antisense strand also contains at least one motif of three 2'-O-methyl modifications on three consecutive nucleotides at or near the cleavage site.

In some embodiments, the chirally-modified dsRNA agent comprises a sense strand and antisense strand each having 14 to 30 nucleotides, wherein the sense strand contains at least one motif of three 2'-F modifications on three consecutive nucleotides at positions 9,10,11 from the 5'end, and wherein the antisense strand contains at least one motif of three 2'-O-methyl modifications on three consecutive nucleotides at positions 11,12,13 from the 5'end.

In some embodiments, the chirally-modified dsRNA agent further comprises the following features:
(a) a sense strand having:
 (i) a length of 18-23 nucleotides;
 (ii) three consecutive 2'-F modifications at positions 7-15; and
(b) an antisense strand having:
 (i) a length of 18-23 nucleotides;
 (ii) at least 2'-F modifications anywhere on the strand; and
 (iii) at least two phosphorothioate internucleotide linkages at the first five nucleotides (counting from the 5' end);
wherein the chirally-modified dsRNA agent has one or more lipophilic moieties conjugated to one or more positions on at least one strand; and
wherein the chirally-modified dsRNA agent has either two nucleotides overhang at the 3'-end of the antisense strand and a blunt end at the 5'-end of the antisense strand, or two blunt ends at both ends of the duplex.

In some embodiments, the chirally-modified dsRNA agent further comprises the following features:
(a) a sense strand having:
 (i) a length of 18-23 nucleotides;
 (ii) less than four 2'-F modifications;
(b) an antisense strand having:
 (i) a length of 18-23 nucleotides;
 (ii) less than twelve 2'-F modfication; and
 (iii) at least two phosphorothioate internucleotide linkages at the first five nucleotides (counting from the 5' end);
wherein the chirally-modified dsRNA agent has one or more lipophilic moieties conjugated to one or more positions on at least one strand; and
wherein the chirally-modified dsRNA agent has either two nucleotides overhang at the 3'-end of the antisense strand and a blunt end at the 5'-end of the antisense strand, or two blunt ends at both ends of the duplex.

In some embodiments, the chirally-modified dsRNA agent further comprises the following features:
(a) a sense strand having:
 (i) a length of 19-35 nucleotides;
 (ii) less than four 2'-F modifications;
(b) an antisense strand having:
 (i) a length of 19-35 nucleotides;
 (ii) less than twelve 2'-F modfication; and
 (iii) at least two phosphorothioate internucleotide linkages at the first five nucleotides (counting from the 5' end);
wherein the duplex region is between 19 to 25 base pairs (preferably 19, 20, 21 or 22);
wherein the chirally-modified dsRNA agent has one or more lipophilic moieties conjugated to one or more positions on at least one strand; and
wherein the chirally-modified dsRNA agent has either two nucleotides overhang at the 3'-end of the antisense strand and a blunt end at the 5'-end of the antisense strand, or two blunt ends at both ends of the duplex.

In a particular embodiment, the chirally-modified dsRNA agents comprise:
(a) a sense strand having:
 (i) a length of 21 nucleotides;
 (ii) an ASGPR ligand attached to the 3'-end, wherein said ASGPR ligand comprises three GalNAc derivatives attached through a trivalent branched linker;
 (iii) 2'-F modifications at positions 3, 5, 7, 9 to 11, 13, 17, 19, and 21, and 2'-OMe modifications at positions 2, 4, 6, 8, 12, 14 to 16, 18, and 20 (counting from the 5' end), with position 1 modified with either 2'-F or 2'-OMe; and
 (iv) a phosphorothioate internucleotide linkage at the first internucleotide linkage at the 5'end, having the linkage phosphorus atom in either Rp configuration or Sp configuration;
and
(b) an antisense strand having:
 (i) a length of 23 nucleotides;
 (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
 (iii) a phosphorothioate internucleotide linkages at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;
wherein the chirally-modified dsRNA agents have a two nucleotide overhang at the 3'-end of the antisense strand, and a blunt end at the 5'-end of the antisense strand.

In another particular embodiment, the chirally-modified dsRNA agents of the present invention comprise:
(a) a sense strand having:
 (i) a length of 21 nucleotides;
 (ii) an ASGPR ligand attached to the 3'-end, wherein said ASGPR ligand comprises three GalNAc derivatives attached through a trivalent branched linker;
 (iii) 2'-F modifications at positions 3, 5, 7, 9 to 11, 13, 15, 17, 19, and 21, and 2'-OMe modifications at positions 2, 4, 6, 8, 12, 14, 16, 18, and 20 (counting from the 5' end), with position 1 modified with either 2'-F or 2'-OMe; and
 (iv) a phosphorothioate internucleotide linkage at the first internucleotide linkage at the 5'end, having the linkage phosphorus atom in either Rp configuration or Sp configuration or racemic;
and
(b) an antisense strand having:
(i) a length of 23 nucleotides;
(ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and
(iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, and 12 to 21, 2'-F modifications at positions 7, and 9, and a desoxy-nucleotide (e.g. dT) at position 11 (counting from the 5' end); and
(iv) a phosphorothioate internucleotide linkage at the first internucleotide linkage at the 5'end, having the linkage phosphorus atom in either Rp configuration or Sp configuration or racemic;
and
(b) an antisense strand having:
(i) a length of 23 nucleotides;
(ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
(iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, 12, 14, and 16 to 21, and 2'-F modifications at positions 7, 9, 11, 13, and 15; and
(iv) a phosphorothioate internucleotide linkage at the first internucleotide linkage at the 5'end, having the linkage phosphorus atom in either Rp configuration or Sp configuration or racemic;
and
(b) an antisense strand having:
(i) a length of 23 nucleotides;
(ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
(iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 9, and 12 to 21, and 2'-F modifications at positions 10, and 11; and
(iv) a phosphorothioate internucleotide linkage at the first internucleotide linkage at the 5'end, having the linkage phosphorus atom in either Rp configuration or Sp configuration or racemic;
and
(b) an antisense strand having:
(i) a length of 23 nucleotides;
(ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
(iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 3, 5, 7, 9 to 11, and 13, and 2'-OMe modifications at positions 2, 4, 6, 8, 12, and 14 to 21, with position 1 modified with either 2'-F or 2'-OMe; and
(iv) a phosphorothioate internucleotide linkage at the first internucleotide linkage at the 5'end, having the linkage phosphorus atom in either Rp configuration or Sp configuration or racemic;
and
(b) an antisense strand having:
(i) a length of 23 nucleotides;
(ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
(iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and
  (iv) a phosphorothioate internucleotide linkage at the first internucleotide linkage at the 5'end, having the linkage phosphorus atom in either Rp configuration or Sp configuration or racemic;
and
(b) an antisense strand having:
  (i) a length of 25 nucleotides;
  (ii) 2'-OMe modifications at positions 1, 4, 6, 7, 9, 11 to 13, 15, 17, and 19 to 23, 2'-F modifications at positions 2, 3, 5, 8, 10, 14, 16, and 18, and desoxy-nucleotides (e.g. dT) at positions 24 and 25 (counting from the 5' end); and
  (iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a four nucleotide overhang at the 3'-end of the antisense strand, and a blunt end at the 5'-end of the antisense strand.

In another particular embodiment, the chirally-modified dsRNA agents comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, and 12 to 21, and 2'-F modifications at positions 7, and 9 to 11; and
  (iv) a phosphorothioate internucleotide linkage at the first internucleotide linkage at the 5'end, having the linkage phosphorus atom in either Rp configuration or Sp configuration or racemic;
and
(b) an antisense strand having:
  (i) a length of 23 nucleotides;
  (ii) 2'-OMe modifications at positions 1, 3 to 5, 7, 8, 10 to 13, 15, and 17 to 23, and 2'-F modifications at positions 2, 6, 9, 14, and 16 (counting from the 5' end); and
  (iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 6, 8, and 12 to 21, and 2'-F modifications at positions 7, and 9 to 11; and
  (iv) a phosphorothioate internucleotide linkage at the first internucleotide linkage at the 5'end, having the linkage phosphorus atom in either Rp configuration or Sp configuration or racemic;
and
(b) an antisense strand having:
  (i) a length of 23 nucleotides;
  (ii) 2'-OMe modifications at positions 1, 3 to 5, 7, 10 to 13, 15, and 17 to 23, and 2'-F modifications at positions 2, 6, 8, 9, 14, and 16 (counting from the 5' end); and (iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In another particular embodiment, the chirally-modified dsRNA agents comprise:
(a) a sense strand having:
  (i) a length of 19 nucleotides;
  (ii) an ASGPR ligand attached to the 3'-end, wherein said ASGPR ligand comprises three GalNAc derivatives attached through a trivalent branched linker;
  (iii) 2'-OMe modifications at positions 1 to 4, 6, and 10 to 19, and 2'-F modifications at positions 5, and 7 to 9; and
  (iv) a phosphorothioate internucleotide linkage at the first internucleotide linkage at the 5'end, having the linkage phosphorus atom in either Rp configuration or Sp configuration or racemic;
and
(b) an antisense strand having:
  (i) a length of 21 nucleotides;
  (ii) 2'-OMe modifications at positions 1, 3 to 5, 7, 10 to 13, 15, and 17 to 21, and 2'-F modifications at positions 2, 6, 8, 9, 14, and 16 (counting from the 5' end); and
  (iii) a phosphorothioate internucleotide linkage at the first internucleotide linkage at the 5'end, having the linkage phosphorus atom in Rp configuration, and a phosphorothioate internucleotide linkage at the first internucleotide linkage at the 3'end, having the linkage phosphorus atom in Sp configuration;

wherein the chirally-modified dsRNA agents have a two nucleotide overhang at the 3'-end of the antisense strand, and a blunt end at the 5'-end of the antisense strand.

In one embodiment, the chirally-modified dsRNA agents described herein further comprise at least one, at least two, or at least three thermally destabilizing modifications in the dsRNA duplex. In one embodiment, at least one thermally destabilizing modification is on the seed region of the antisense strand.

In some embodiments, the chirally-modified dsRNA agents described herein include one or more of the following criteria:
1. A low GC content, preferably between about 30-52%.
2. At least 2, preferably at least 3 A or U bases at positions 15-19 of the dsRNA on the antisense strand.

3. An A base at position 19 of the sense strand.

4. An A base at position 3 the sense strand.

5. A U base at position 10 of the sense strand.

6. An A base at position 14 of the sense strand.

7. A base other than C at position 19 of the sense strand.

8. A base other than G at position 13 of the sense strand.

9. A Tm, which refers to the character of the internal repeat that results in inter- or intramolecular structures for one strand of the dsRNA duplex, that may not be stable at greater than 50° C., at greater than 37° C., at greater than 30° C., or at greater than 20° C.

10. A base other than U at position 5 of the sense strand.

11. A base other than A at position 11 of the sense strand.

In one embodiment, the chirally-modified dsRNA agent includes at least two, at least three, at least four, at least five, at least six, at least seven, at least eight, at least nine, at least ten, or all of the above criteria.

Another aspect of the invention relates to a chirally-modified dsRNA agent capable of inhibiting the expression of a target gene. The chirally-modified dsRNA agent comprises a sense strand and an antisense strand, each strand having 14 to 40 nucleotides. The chirally-modified dsRNA agent comprises three or more site specific (e.g., terminal), chirally-modified internucleotide linkages as described above. The sense strand comprises one or more site specific (e.g., terminal), chirally-modified internucleotide linkages towards the 5' end. The antisense strand comprises one or more site specific (e.g., terminal), chirally-modified internucleotide linkages towards the 5' end and one or more site specific (e.g., terminal), chirally-modified internucleotide linkages towards the 3' end. The sense strand and the antisense strand comprises one or more chirally-modified internucleotide linkages in the interior position(s) other than the chiral linkage towards 5'- and 3'-terminals or combination thereof.

Each of the embodiments described above in the first aspect of the chirally-modified dsRNA agent relating to the site specific (e.g., terminal), chirally-modified internucleotide linkages applies to this aspect of the invention.

In one embodiment, the sense strand of the chirally-modified dsRNA agent further comprises an endonuclease susceptible modified nucleotide at the cleavage site of the sense strand. In one example, the endonuclease susceptible modified nucleotide is at position 11 from the 5' end of the sense strand.

In one embodiment, the antisense strand of the chirally-modified dsRNA agent further comprises a third modified nucleotide that provides the nucleotide a steric bulk that is less or equal to the steric bulk of a 2'-OMe modification, and the third modified nucleotide is at positions 6-10 from the 5' end of the antisense strand. For example, the third modified nucleotide is at position 10 from the 5' end of the antisense strand.

The invention further relates to the use of the chirally-modified dsRNA agent as defined herein for inhibiting expression of a target gene. In one embodiment, the chirally-modified dsRNA agent as defined herein is used for inhibiting expression of a target gene in vitro.

The invention further relates to the chirally-modified dsRNA agent as defined herein for use in inhibiting expression of a target gene in a subject in vivo. The subject may be any animal, preferably a mammal, more preferably a mouse, a rat, a sheep, a cattle, a dog, a cat, or a human.

In one aspect, the invention relates to a pharmaceutical composition comprising the chirally-modified dsRNA agent as defined herein, and a pharmaceutically acceptable carrier or excipient.

In another aspect, the invention provides a method for inhibiting the expression of a target gene in a subject, comprising the step of administering the chirally-modified dsRNA agent as defined herein to the subject in an amount sufficient to inhibit expression of the target gene. The chirally-modified dsRNA agent may be administered through subcutaneous or intravenous administration.

Another aspect of the invention provides a method for delivering the dsRNA agents to a specific target in a subject by subcutaneous or intravenous administration.

BRIEF DESCRIPTION OF THE DRAWINGS

FIG. 104. Duration study for the F12 ELF and its chiral PS siRNA versions in rats. FIG. 104A shows the study design for the duration study, including the configuration motifs for the F12 PS chirally-modified siRNAs used, animals and dosage used, and the durations of the study. FIG. 104B lists the F12 ELF isomers used for the duration study in rats.

FIG. 105. In vivo relative protein expression levels of the F12 ELF siRNA and its sense strand chiral PS isomers in rats. FIG. 105B lists the F12 ELF sense strand isomers used for the duration study in rats. FIG. 105C shows the results of the F12 ELF sense strand isomers duration study to Day 28.

FIG. 106. In vivo relative plasma expression levels of the F12 ELF siRNA and its chiral PS siRNA versions in mice. FIG. 106A shows the study design, including the sequence variables and configuration motifs for the F12 PS chirally-modified siRNAs used, dosage used, and the durations of the study. FIG. 106B lists the F12 ELF isomers used.

FIG. 107. In vitro free uptake and transfection IC50 results of the F12 ELF siRNA and its chiral PS siRNA versions in primary mice hepatocytes and primary cyno hepatocytes.

FIG. 108. Evaluation of the F12 ELF siRNA and its chiral PS siRNA versions in NHP.

FIG. 109. In vitro free uptake IC50 results of the C5, F12, hAGT siRNAs and their chiral PS siRNA versions in primary mice hepatocytes and primary cyno hepatocytes.

FIG. 110. In vivo activity of the C5, F12, hAGT siRNAs and their chiral PS siRNA versions in mice.

FIG. 111. Evaluation of the F12 and Angptl3 (ANG) siRNAs and their chiral PS siRNA versions in NHP. FIG. 111A lists the configuration motifs for the chirally-modified siRNAs used and the animal and dosage used. FIG. 111B lists all the sequences used.

Figure 1:
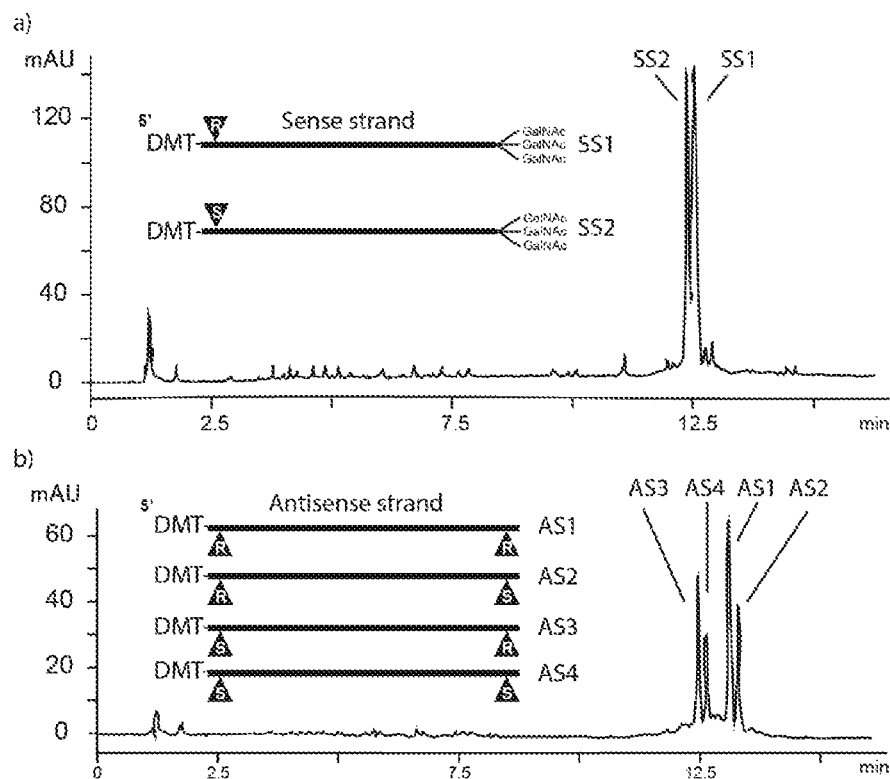
FIG. 1. Separation of PS diastereomers DMT-on sense and antisense strand on analytical IEX chromatography: a) Rp/Sp in 1PS sense strand and b) all four diastereomers of a 2PS antisense strand.

In al the figures, the labels "R" and "S" in all the figures denote Rp and Sp configuration of the linkage phosphorus atom, and the label "mix" denotes racemic mixture of the configurations.

DETAILED DESCRIPTION

This invention provides effective stereochemical solution for dsRNA agents optionally conjugated to at least one ligand, which are advantaqueous for inhibition of target gene expression, as well as RNAi compositions suitable for therapeutic use. The inventors discovered new chemical entities that are particular stereoisomers of oligonucleotides of interest. That is, this invention provides substantially pure preparations of a dsRNA agent comprising a specific pattern of backbone chiral centers (i.e., a specific pattern of chiral linkage phosphorus stereochemistry (Rp/Sp)).

The embodiments of the invention demonstrate that individual stereoisomers of a chirally-modified dsRNA agent can show different stability and/or activity from each other. For instance, the stability improvements achieved through inclusion of chirally-modified internucleotide linkages at site specific (e.g., terminal) location(s) of an oligonucleotide (e.g., a dsRNA agent) can be comparable to, or even better than those achieved through use of modified backbone linkages, bases, and/or sugars (e.g., through use of certain types of modified phosphates, 2'-modifications, base modifications, etc.). Also, the activity improvements achieved through inclusion dsRNA agent can be comparable to, or even better than those achieved through use of modified backbone linkages, bases, and/or sugars (e.g., through use of certain types of modified phosphates, 2'-modifications, base modifications, etc.).

The dsRNA agent is chirally modified, i.e., the dsRNA agent comprises site specific (e.g., terminal), chirally-modified internucleotide linkage(s). The chirally-modified dsRNA agent has chirally-modified internucleotide linkages at the terminal region of an oligonucleotide, e.g., the first one, two, three, or four, or five internucleotide linkages (i.e., the internucleotide linkages between the dinucleotides at positions 1 and 2, the internucleotide linkages between the dinucleotides at positions 2 and 3, the internucleotide linkages between the dinucleotides at positions 3 and 4, the internucleotide linkages between the dinucleotides at positions 4 and 5, or the internucleotide linkages between the dinucleotides at positions 5 and 6, respectively). A terminal chiral modification to the internucleotide linkage may occur at the 5' end, 3' end, or both the 5' end and 3' end. A terminal chiral modification to the internucleotide linkage may occur on the sense strand, antisense strand, or both the sense strand and antisense strand. Each of the chiral linkage phosphorus atoms in the site specific (e.g., terminal), chirally modified internucleotide linkage(s) may be in either Rp configuration or Sp configuration.

In some embodiments, chiral modifications to the internucleotide linkage occur at the first one or two internucleotide linkages at the 5' end and/or 3' end of the sense strand and/or antisense strand. Typically, both the sense strand and the antisense strand contain site specific (e.g., terminal), chirally-modified internucleotide linkage(s).

In one embodiment, the sense strand comprises site specific (e.g., terminal), racemic internucleotide linkage(s) and the antisense strand comprises site specific (e.g., terminal), chirally-modified internucleotide linkage(s). In another embodiment, the sense strand comprises only natural phosphodiester internucleotide linkage(s) and the antisense strand comprises site specific (e.g., terminal), chirally-modified internucleotide linkage(s).

The invention provides substantially chirally pure preparations of individual stereoisomers of the chirally-modified dsRNA agents. The phrase "chirally pure" is used to describe a chirally controlled oligonucleotide (e.g., a chirally-modified dsRNA agent) that exists in a single diastereomeric form with respect to a chiral center (e.g., the chiral linkage phosphorus atom(s) of site specific (e.g., terminal), chirally-modified internucleotide linkage(s)). The chiral purity of the chirally controlled oligonucleotide (e.g., a chirally-modified dsRNA agent) may be measured by ds-purity (diastereoselectivity), i.e., the percentage of the major diastereomer in a diastereomeric mixture. For instance, the chiral purity of a chirally-modified dsRNA agent with respect to the chiral linkage phosphorus atom(s) may be measured by ds-purity (diastereoselectivity) with respect to the chiral linkage phosphorus atom(s).

One way of characterizing the chiral purity of the chirally controlled oligonucleotide is at the oligonucleotide level. For instance, a chirally-modified dsRNA agent may have three site specific (e.g., terminal), chirally-modified internucleotide linkages: i) one site specific (e.g., terminal), chirally-modified internucleotide linkage towards the 5' end of the sense strand; ii) one site specific (e.g., terminal), chirally-modified internucleotide linkage towards the 5' end of the antisense strand, and iii) one site specific (e.g., terminal), chirally-modified internucleotide linkage towards the 3' end of the antisense strand. The sense strand of this dsRNA thus has two diastereomeric forms: R or S (R represents for the Rp configuration and S represents for the Sp configuration), each designating a single diastereomeric form with respect to the chiral linkage phosphorus atom of the chirally-modified internucleotide linkage. If a R diastereoisomer of the sense strand has a ds-purity of 95%, for instance, this means the percentage of the R diastereoisomer in this chirally-modified sense strand is 95%. The antisense strand of this dsRNA thus has four diastereomeric forms: R-R, R-S, S-R, or S-S, each designating a single diastereomeric form with respect to the chiral linkage phosphorus atoms of the chirally-modified internucleotide linkages. If a R-R diastereoisomer of the antisense strand has a ds-purity of 95%, for instance, this means the percentage of the R-R diastereoisomer in this chirally-modified antisense strand is 95%.

The chiral purity of the chirally controlled dsRNA agent may also be characterized at the dsRNA level. For instance, a chirally-modified dsRNA agent that has the same three site specific (e.g., terminal), chirally-modified internucleotide linkages as discussed above has eight diastereomeric forms: R/R-R, R/R-S, R/S-R, R/S-S, S/R-R, S/R-S, S/S-R, or S/S-S, each designating a single diastereomeric form with respect to the chiral linkage phosphorus atoms of the chirally-modified internucleotide linkages. In this case, a R/R-S diastereoisomer with a ds-purity of 95%, for instance, means the percentage of the R/R-S diastereoisomer in this chirally-modified dsRNA agent is 95%.

Alternatively, the chiral purity of the chirally controlled oligonucleotide may be characterized at the dinucleotide level. For instance, a chirally-modified dsRNA agent that has the same three site specific (e.g., terminal), chirally-modified internucleotide linkages as discussed above can be considered as having a dinucleotide building block containing a chirally-modified internucleotide linkage at each of the three terminal positions. Each of the three dinucleotide building blocks thus has two diastereomeric forms: R or S, each designating a single diastereomeric form with respect to the chiral linkage phosphorus atom of the chirally-modified internucleotide linkage. If a R diastereoisomer for a dinucleotide building block has a ds-purity of 95%, for instance, this means the percentage of the R diastereoisomer in the dinucleotide building block is 95%.

In some embodiments, the chiral purity of a chirally controlled oligonucleotide (e.g., a chirally-modified dsRNA agent) can be controlled by stereoselectivity of each coupling step in its preparation process. For instance, if a coupling step has a stereoselectivity (e.g., diastereoselectivity) of 60% (60% of the new internucleotide linkage formed from the coupling step has the intended stereochemistry), the new internucleotide linkage formed after such a coupling step may be referred to as having a 60% chiral purity. In some embodiments, each coupling step has a stereoselectivity of at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or at least 99.5%. In some embodiments, each coupling step has a stereoselectivity of virtually 100%, for instance, virtually all detectable product from the coupling step by an analytical method (e.g., NMR, HPLC, etc.) has the intended stereoselectivity.

In some embodiments, the chirally-modified dsRNA agent comprises three site specific (e.g., terminal), chirally-modified internucleotide linkages: i) a chirally-modified internucleotide linkage (e.g., a phosphorothioate internucleotide linkage) at the first internucleotide linkage at the 5'end of the sense strand; ii) a chirally-modified internucleotide linkage (e.g., a phosphorothioate internucleotide linkage) at the first internucleotide linkage at the 5'end of the antisense strand, and iii) a chirally-modified internucleotide linkage (e.g., a phosphorothioate internucleotide linkage) at the first internucleotide linkage at the 3'end of the antisense strand. The chirally-modified dsRNA agent having these three site specific (e.g., terminal), chirally-modified internucleotide linkages has eight diastereomeric forms: R/R-R, R/R-S, R/S-R, R/S-S, S/R-R, S/R-S, S/S-R, or S/S-S, each designating a single diastereomeric form with respect to the chiral linkage phosphorus atoms of the chirally-modified internucleotide linkages.

For instance, S/R-S represents a diastereomeric form having i) a chirally-modified internucleotide linkage (e.g., a phosphorothioate internucleotide linkage) at the first internucleotide linkage at the 5'end of the sense strand, where the linkage phosphorus atom is in Sp configuration, ii) a chirally-modified internucleotide linkage (e.g., a phosphorothioate internucleotide linkage) at the first internucleotide linkage at the 5'end of the antisense strand, where the linkage phosphorus atom is in Rp configuration, and iii) a chirally-modified internucleotide linkage (e.g., a phosphorothioate internucleotide linkage) at the first internucleotide linkage at the 3'end of the antisense strand, where the linkage phosphorus atom is in Sp configuration.

In one embodiment, provided is the chirally-modified dsRNA agent in a R/R-R diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a R/R-S diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a R/S-R diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a R/S-S diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a S/R-R diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a S/R-S diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a S/S-R diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In one embodiment, provided is the chirally-modified dsRNA agent in a S/S-S diastereomeric form, with the chiral purity of at least 50%, for instance, at least 60%, at least 70%, at least 80%, at least 85%, at least 90%, at least 91%, at least 92%, at least 93%, at least 94%, at least 95%, at least 96%, at least 97%, at least 98%, at least 99%, at least 99.5%, or virtually 100%.

In some embodiments, the chirally-modified dsRNA agent comprises four terminal, chirally-modified internucleotide linkages. In one embodiment, chiral modifications (e.g., phosphorothioate modifications) to the internucleotide linkage occur at the first internucleotide linkage at both the 5' end and 3' end of the sense strand and antisense strand. In one embodiment, the chirally-modified dsRNA agent has i) a chirally-modified internucleotide linkage (e.g., a phosphorothioate internucleotide linkage) at the first internucleotide linkage at the 5'end of the sense strand; ii) a chirally-modified internucleotide linkage (e.g., a phosphorothioate internucleotide linkage) at the first internucleotide linkage at the 5'end of the antisense strand, iii) a chirally-modified internucleotide linkage (e.g., a phosphorothioate internucleotide linkage) at the first internucleotide linkage at the 3'end of the antisense strand; and iv) a chirally-modified internucleotide linkage (e.g., a phosphorothioate internucleotide linkage) at the second internucleotide linkage at one of the 5' end of the sense strand, the 5' end of the antisense strand, and the 3' end of the antisense strand.

In these embodiments for the chirally-modified dsRNA agent comprising four site specific (e.g., terminal), chirally-modified internucleotide linkages, each of the chiral linkage phosphorus atom may be in either Rp configuration or Sp configuration. In one embodiment, the linkage phosphorus atom at the first internucleotide linkage at the 3' end of the antisense strand has Sp configuration; the linkage phosphorus atom at the first internucleotide linkage at the 5' end of the antisense strand has Rp configuration; and the linkage phosphorus atom at the first internucleotide linkage at the 5' end of the sense strand has either Rp configuration or Sp configuration.

In some embodiments, the chirally-modified dsRNA agent comprises five site specific (e.g., terminal), chirally-modified internucleotide linkages. In one embodiment, the chirally-modified dsRNA agent has i) chiral modifications (e.g., phosphorothioate modifications) to the internucleotide linkage occurring at the first internucleotide linkage at both the 5' end and 3' end of the sense strand and antisense strand; and ii) a chirally-modified internucleotide linkage (e.g., a phosphorothioate internucleotide linkage) at the second internucleotide linkage at one of the 5' end of the sense strand, the 5' end of the antisense strand, and the 3' end of the antisense strand.

In one embodiment, the chirally-modified dsRNA agent has i) a chirally-modified internucleotide linkage (e.g., a phosphorothioate internucleotide linkage) at the first internucleotide linkage at the 5'end of the sense strand; ii) a chirally-modified internucleotide linkage (e.g., a phosphorothioate internucleotide linkage) at the first internucleotide linkage at the 5'end of the antisense strand, iii) a chirally-modified internucleotide linkage (e.g., a phosphorothioate internucleotide linkage) at the first internucleotide linkage at the 3'end of the antisense strand; and iv) two chirally-modified internucleotide linkages (e.g., phosphorothioate internucleotide linkages) at the second internucleotide linkage at two of the 5' end of the sense strand, the 5' end of the antisense strand, and the 3' end of the antisense strand.

In these embodiments for the chirally-modified dsRNA agent comprising five site specific (e.g., terminal), chirally-modified internucleotide linkages, each of the chiral linkage phosphorus atom may be in either Rp configuration or Sp configuration. In one embodiment, the linkage phosphorus atom at the first internucleotide linkage at the 3' end of the antisense strand has Sp configuration; the linkage phosphorus atom at the first internucleotide linkage at the 5' end of the antisense strand has Rp configuration; and the linkage phosphorus atom at the first internucleotide linkage at the 5' end of the sense strand has either Rp configuration or Sp configuration.

In some embodiments, the chirally-modified dsRNA agent comprises six site specific (e.g., terminal), chirally-modified internucleotide linkages. In one embodiment, the chirally-modified dsRNA agent has i) two chirally-modified internucleotide linkages (e.g., phosphorothioate internucleotide linkages) at the first and second internucleotide linkages at the 5'end of the sense strand; ii) two chirally-modified internucleotide linkages (e.g., phosphorothioate internucleotide linkages) at the first and second internucleotide linkages at the 5'end of the antisense strand, and iii) two chirally-modified internucleotide linkages (e.g., phosphorothioate internucleotide linkages) at the first and second internucleotide linkages at the 3'end of the antisense strand.

In these embodiments for the chirally-modified dsRNA agent comprising six site specific (e.g., terminal), chirally-modified internucleotide linkages, each of the chiral linkage phosphorus atom may be in either Rp configuration or Sp configuration. In one embodiment, the linkage phosphorus atom at the first internucleotide linkage at the 3' end of the antisense strand has Sp configuration; the linkage phosphorus atom at the first internucleotide linkage at the 5' end of the antisense strand has Rp configuration; and the linkage phosphorus atom at the first internucleotide linkage at the 5' end of the sense strand has either Rp configuration or Sp configuration.

In some embodiments, the chirally-modified dsRNA agent comprises seven site specific (e.g., terminal), chirally-modified internucleotide linkages.

In some embodiments, the chirally-modified dsRNA agent comprises eight site specific (e.g., terminal), chirally-modified internucleotide linkages.

Oligonucleotide synthesis general references: The nucleotides in the chirally-modified dsRNA agent may be made using the general methods for preparing an oligoribonucleotide with solid phase synthesis, see, e.g., "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedon*, 1992, 48, 2223-2311 and Beaucage, S. L. and Iyer, R. P., *Tetrahedon*, 1993, 49, 6123-6194, or references referred to therein. Chemical modifications on oligonucleotides are described in WO 00/44895, WO01/75164, and WO02/44321, which are incorporated herein by reference in their entirety. Additional synthetic methods of oligonucleotides and their chemical modifications may be found in U.S. Pat. No. 8,106,022, which is incorporated herein by reference in its entirety.

Phosphate group synthesis references: The preparation of phosphinate oligoribonucleotides is described in U.S. Pat. No. 5,508,270, which is incorporated herein by reference in its entirety. The preparation of alkyl phosphonate oligoribonucleotides is described in U.S. Pat. No. 4,469,863, which is incorporated herein by reference in its entirety. The preparation of phosphoramidite oligoribonucleotides is described in U.S. Pat. Nos. 5,256,775 and 5,366,878, which are incorporated herein by reference in their entirety. The preparation of phosphotriester oligoribonucleotides is described in U.S. Pat. No. 5,023,243, which is incorporated herein by reference in its entirety. The preparation of borano phosphate oligoribonucleotide is described in U.S. Pat. Nos. 5,130,302 and 5,177,198, which are incorporated herein by reference in their entirety. The preparation of 3'-Deoxy-3'-amino phosphoramidate oligoribonucleotides is described in U.S. Pat. No. 5,476,925, which is incorporated herein by reference in its entirety. 3'-Deoxy-3'-methylenephosphonate oligoribonucleotides is described in An, H, et al. *J. Org. Chem.* 2001, 66, 2789-2801, which is incorporated herein by reference in its entirety. Preparation of sulfur bridged nucleotides is described in Sproat et al. *Nucleosides Nucleotides* 1988, 7,651 and Crosstick et al. *Tetrahedron Lett.* 1989, 30, 4693, which are incorporated herein by reference in their entirety.

Sugar group synthesis references: Modifications to the 2' modifications can be found in Verma, S. et al. *Annu. Rev. Biochem.* 1998, 67, 99-134, which is incorporated herein by reference in its entirety. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310), which are incorporated herein by reference in their entirety.

Terminal modification references: Terminal modifications are described in Manoharan, M. et al. *Antisense and Nucleic Acid Drug Development* 12, 103-128 (2002), which is incorporated herein by reference in its entirety.

Base synthesis references: N-2 substituted purine nucleoside amidites can be prepared as is described in U.S. Pat. No. 5,459,255, which is incorporated herein by reference in its entirety. 3-Deaza purine nucleoside amidites can be prepared as is described in U.S. Pat. No. 5,457,191, which is incorporated herein by reference in its entirety. 5,6-Substituted pyrimidine nucleoside amidites can be prepared as is described in U.S. Pat. No. 5,614,617, which is incorporated herein by reference in its entirety. 5-Propynyl pyrimidine nucleoside amidites can be prepared as is described in U.S. Pat. No. 5,484,908, which is incorporated herein by reference in its entirety.

A general method of preparing a chirally pure (or substantially chirally pure) diastereoisomeric form of a chirally controlled oligonucleotide may be found in U.S. Patent Application Publication No. 2017/0037399, which is incorporated by reference in its entirety.

The chirally-modified dsRNA agent in a single diastereomeric form can be prepared on the oligonucleotide level or by coupling the diastereomeric form of dinucleotide building blocks.

When preparing the single diastereomeric form of the chirally-modified dsRNA agent on the oligonucleotide level, each of the sense strand and antisense strand may be synthesized according to the general oligonucleotide synthesis method as discussed above, with incorporating the chirally modified internucleotide linkage(s) (e.g., phosphorothioate internucleotide linkage(s) at the desired locations, e.g., based on the phosphate group synthesis method as discussed above. The resulting epimeric mixture may be separated into individual diastereomers by methods known to one skilled in the art. A chirally pure (or substantially chirally pure) diastereoisomeric form of the chirally-modified RNA agent may then be prepared by annealing a single diastereoisomeric form of the chirally-modified sense strand with a single diastereoisomeric form of the chirally-modified antisense strand.

When preparing the single diastereomeric form of the chirally-modified dsRNA agent on the dinucleotide building block level, the dsRNA agent may be synthesized according to the general oligonucleotide synthesis method as discussed above, Each of the desirable site specific (e.g., terminal), chirally-modified internucleotide linkages (e.g., phosphorothioate internucleotide linkages) may be introduced to the dsRNA agent by coupling the corresponding dinucleotide building block containing a chirally-modified internucleotide linkage. Each of the dinucleotide building blocks may be synthesized with incorporating the chirally modified internucleotide linkage (e.g., phosphorothioate internucleotide linkage) between the dinucleotide, e.g., based on the phosphate group synthesis method as discussed above. The resulting epimeric mixture may be separated into individual diastereomers by methods known to one skilled in the art. A chirally pure (or substantially chirally pure) diastereoisomeric form of the chirally-modified RNA agent may then then be prepared by coupling a single diastereoisomeric form of each of the dinucleotide building blocks to the desired locations of the dsRNA agent.

Additional details for preparing a chirally pure (or substantially chirally pure) diastereoisomeric form of the chirally-modified RNA agent may be found in the Examples.

The inventors also found that having 2'-OMe modifications at nucleotide positions 2 and 14 from the 5'-end of the antisense strand dampened the gene silencing activity of a dsRNA agent. By introducing chemical modifications at the 2' position or equivalent positions in a non-ribose, acyclic or backbone that provide less steric bulk than a 2'-OMe modification at certain positions in antisense and/or sense strand, the dsRNA agents were able to regain the gene silencing activity. The inventors also determined that introducing a thermally destabilizing nucleotide on the sense strand at a site opposite to the seed region of the antisense strand (i.e. at position 2-8 of the 5'-end of the antisense strand) provides better gene silencing activity.

The sense strand and antisense strand of the chirally-modified dsRNA agent may be completely modified. The chirally-modified dsRNA agent optionally conjugates with an asialoglycoprotein receptor (ASGPR) ligand, for instance on the sense strand. The resulting chirally-modified dsRNA agents present effective in vivo gene silencing activity.

Accordingly, the invention provides a chirally-modified double-stranded RNAi (dsRNA) agent capable of inhibiting the expression of a target gene. The chirally-modified dsRNA agent comprises a sense strand and an antisense strand. Each strand can range from 12-40 nucleotides in length. For example, each strand can be between 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex dsRNA. The duplex region may be 12-40 nucleotide pairs in length. For example, the duplex region can be between 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In one embodiment, the chirally-modified dsRNA agent comprises one or more overhang regions and/or capping groups at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In one embodiment, the nucleotides in the overhang region of the chirally-modified dsRNA agent can each independently be a modified or unmodified nucleotide including, but not limited to 2'-sugar modified, such as, 2-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the chirally-modified dsRNA agent may be phosphorylated. In some embodiments, the overhang region contains two nucleotides having a phosphorothioate between the two nucleotides, where the two nucleotides can be the same or different. In one embodiment, the overhang is present at the 3'-end of the sense strand, antisense strand or both strands. In one embodiment, this 3'-overhang is present in the antisense strand. In one embodiment, this 3'-overhang is present in the sense strand.

The chirally-modified dsRNA agent may comprise only a single overhang, which can strengthen the interference activity of the chirally-modified dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length.

In one embodiment, the chirally-modified dsRNA agent may also have two blunt ends, at both ends of the dsRNA duplex.

In one embodiment, the chirally-modified dsRNA agent is a double ended bluntmer of 19 nt in length, wherein the sense strand contains at least one thermally destabilizing nucleotide, where at least one thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand. The antisense strand contains at least two modified nucleic acids that is smaller than a sterically demanding 2'-OMe; preferably, the two modified nucleic acids that is smaller than a sterically demanding 2'-OMe are at positions 2 and 14 of the 5'end of the antisense strand.

In one embodiment, the chirally-modified dsRNA agent is a double ended bluntmer of 20 nt in length, wherein the sense strand contains at least one thermally destabilizing nucleotide, where at least one thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand. The antisense strand contains at least two modified nucleic acids that is smaller than a sterically demanding 2'-OMe; preferably, the two modified nucleic acids that is smaller than a sterically demanding 2'-OMe are at positions 2 and 14 of the 5'end of the antisense strand.

In one embodiment, the chirally-modified dsRNA agent is a double ended bluntmer of 21 nt in length, wherein the sense strand contains at least one thermally destabilizing nucleotide, where at least one thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand. The antisense strand contains at least two modified nucleic acids that is smaller than a sterically demanding 2'-OMe; preferably, the two modified nucleic acids that is smaller than a sterically demanding 2'-OMe are at positions 2 and 14 of the 5'end of the antisense strand.

In one embodiment, the chirally-modified dsRNA agent comprises a 21 nucleotides (nt) sense strand and a 23 nucleotides (nt) antisense, wherein the sense strand contains at least one thermally destabilizing nucleotide, where at least one thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand when the sense strand is 21 nucleotides in length. The antisense strand contains at least two modified nucleic acids that is smaller than a sterically demanding 2'-OMe; preferably, the two modified nucleic acids that is smaller than a sterically demanding 2'-OMe are at positions 2 and 14 of the 5'end of the antisense strand, wherein one end of the dsRNA is blunt, while the other end is comprises a 2 nt overhang. Preferably, the 2 nt overhang is at the 3'-end of the antisense. Optionally, the dsRNA further comprises a ligand (preferably a receptor ligand i.e. ASGPR ligand).

In one embodiment, the chirally-modified dsRNA agent comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the sense strand contains at least one thermally destabilizing nucleotide, where at least one thermally destabilizing nucleotide occurs at or near the site that is opposite to the seed region of the antisense strand (i.e. at position 2-8 of the 5'-end of the antisense strand), For example, the thermally destabilizing nucleotide occurs between positions 14-17 of the 5'-end of the sense strand. The antisense strand contains at least two modified nucleic acids that are smaller than a sterically demanding 2'-OMe; preferably, the two modified nucleic acids that are smaller than a sterically demanding 2'-OMe are at positions 2 and 14 of the 5'end of the antisense strand.

In one embodiment, the chirally-modified dsRNA agent comprises a sense and antisense strands, wherein said chirally-modified dsRNA agent comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end. The antisense strand comprises two modified nucleic acids that are smaller than a sterically demanding 2'-OMe are at positions 2 and 14 of the 5'end of the antisense strand; wherein said 3' end of said sense strand and said 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said chirally-modified dsRNA agent is introduced into a mammalian cell, and wherein dicer cleavage of said chirally-modified dsRNA preferentially results in an siRNA comprising said 3' end of said antisense strand, thereby reducing expression of the target gene in the mammal. Optionally, the chirally-modified dsRNA agent further comprises a ligand.

In one embodiment, the sense strand comprises a modified nucleotide that is susceptible to enzymatic degradation at position 11 from the 5'end. The antisense strand comprises two modified nucleic acids that are smaller than a sterically demanding 2'-OMe are at positions 2 and 14 of the 5'end of the antisense strand.

In one embodiment, the antisense strand comprises two modified nucleic acids that are smaller than a sterically demanding 2'-OMe are at positions 2 and 14 of the 5'end of the antisense strand.

In one embodiment, every nucleotide in the sense strand and antisense strand of the chirally-modified dsRNA agent may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with acyclic nucleotides, L-nucleotides, 2'-modified L-nucleotides, LNA, HNA, CeNA, 2'-O-methoxyalkyl (e.g., 2'-O-methoxymethyl, 2'-O-methoxyethyl, or 2'-O-2-methoxypropanyl), 2'-O-methyl, 2'-O-allyl, 2'-C-allyl, 2'-deoxy, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-deoxy, 2'-O-methyl or 2'-fluoro modifications, acyclic nucleotides or others.

In one embodiment, the sense strand and antisense strand each comprises two differently modified nucleotides selected from 2'-O-methyl or 2'-deoxy.

In one embodiment, each residue of the sense strand and antisense strand is independently modified with 2'-O-methyl nucleotide, 2'-deoxy nucleotide, 2'-deoxyfluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide.

In one embodiment the said nucleotide modifications including unmodified nucleotides on each strand of site-specifically chirally-modified dsRNA are placed/arranged in any random order, unspecified pattern, stretches of one more pattern(s) in any order strating from the 5'-end of each strand. The site specific, chirally-modified linkage(s) in such nucleotide pattern(s), stretches and/or stretches of pattern(s) modulate potency of the dsRNA in in vitro, ex vivo and in vivo, in all experimental cell cultures and in all animals. The said dsRNAs constitute a pharmaceutical composition to treat intended diseases indication(s) in human and in other animals of interest.

In one embodiment, the chirally-modified dsRNA agent comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine).

Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the chirally-modified dsRNA agent comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

The inventors found that introducing 4'-modified and/or 5'-modified nucleotide to the 3'-end of a phosphodiester (PO), phosphorothioate (PS), and/or phosphorodithioate (PS2) linkage of a dinucleotide at any position of single stranded or double stranded oligonucleotide can exert steric effect to the internucleotide linkage and, hence, protecting or stabilizing it against nucleases.

In one embodiment, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In one embodiment, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In one embodiment, 5'-alkylated nucleoside is introduced at any position on the sense strand or antisense strand of a chirally-modified dsRNA, and such modification maintains or improves potency of the chirally-modified dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In one embodiment, 4'-alkylated nucleoside is introduced at any position on the sense strand or antisense strand of a chirally-modified dsRNA, and such modification maintains or improves potency of the chirally-modified dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In one embodiment, 4'-O-alkylated nucleoside is introduced at any position on the sense strand or antisense strand of a chirally-modified dsRNA, and such modification maintains or improves potency of the chirally-modified dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In one embodiment, the chirally-modified dsRNA agent can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the chirally-modified dsRNA agent can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

The chirally-modified dsRNA agent that contains conjugations of one or more carbohydrate moieties to a dsRNA agent can optimize one or more properties of the chirally-modified dsRNA agent. In many cases, the carbohydrate moiety will be attached to a modified subunit of the chirally-modified dsRNA agent. E.g., the ribose sugar of one or more ribonucleotide subunits of a chirally-modified dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the chirally-modified dsRNA agent is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The chirally-modified dsRNA agent may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In one embodiment, the chirally-modified dsRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), (OH)$_2$(O)P-5'-CH2-), 5'-alkyletherphosphonates (R=alkylether=methoxymethyl (MeOCH$_2$—), ethoxymethyl, etc., e.g. RP(OH)(O)—O-5'-). In one example, the modification can in placed in the antisense strand of a chirally-modified dsRNA agent.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972, which is incorporated by reference in its entirety), the EALA peptide (Vogel et al., J. Am. Chem. Soc., 1996, 118: 1581-1586, which is incorporated by reference in its entirety), and their derivatives (Turk et al., Biochem. Biophys. Acta, 2002, 1559: 56-68, which is incorporated by reference in its entirety). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyamino acids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases or a chelator (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNF-alpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP. An RFGF analogue (e.g., amino acid sequence AALLPVLLAAP) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) and the Drosophila Antennapedia protein (RQIKIWFQNRRMKWKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991, which is incorporated by reference in its entirety). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002, which is incorporated by reference in its entirety). An RGD peptide can facilitate targeting of an iRNA agent to tumors of a variety of other tissues, including the lung, kidney, spleen, or liver (Aoki et al., Cancer Gene Therapy 8:783-787, 2001, which is incorporated by reference in its entirety). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001, which is incorporated by reference in its entirety). Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003, which is incorporated by reference in its entirety).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; a, p, or 7 peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a monovalent, bivalent or trivalent branched linker.

In one embodiment, the chirally-modified dsRNA is conjugated to a bivalent and trivalent branched linkers include the structures shown in any of formula (IV)-(VII):

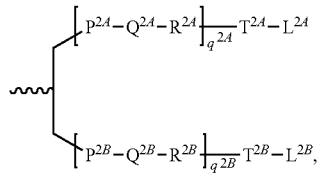
Formula (IV)

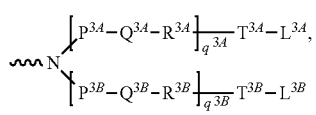
Formula (V)

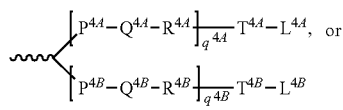
Formula (VI), or

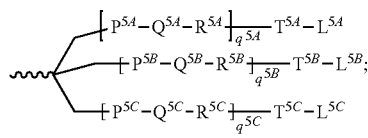
Formula (VII)

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$p^{2A}$, $p^{2B}$, $p^{3A}$, $p^{3B}$, $p^{4A}$, $p^{4B}$, $p^{5A}$, $p^{5B}$, $p^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

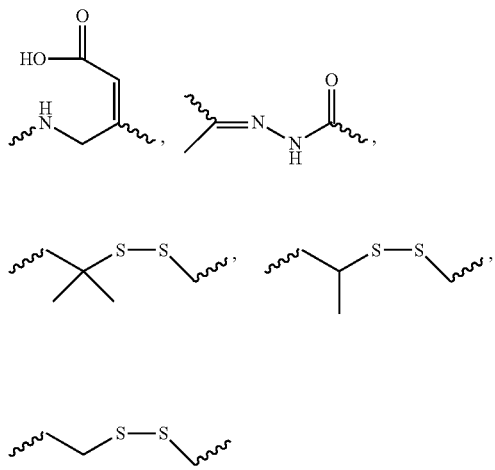

heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

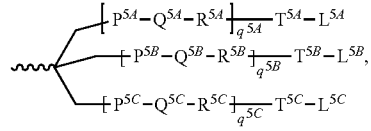
Formula (VII)

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include but are not limited to the following compounds:

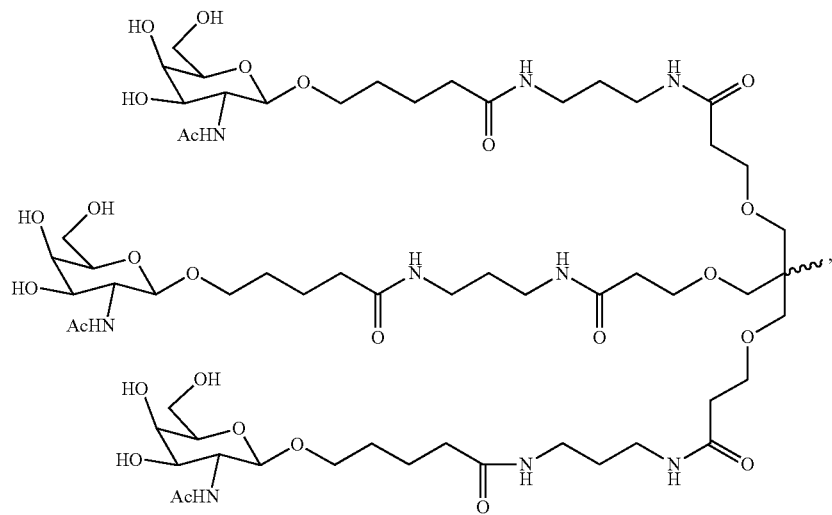
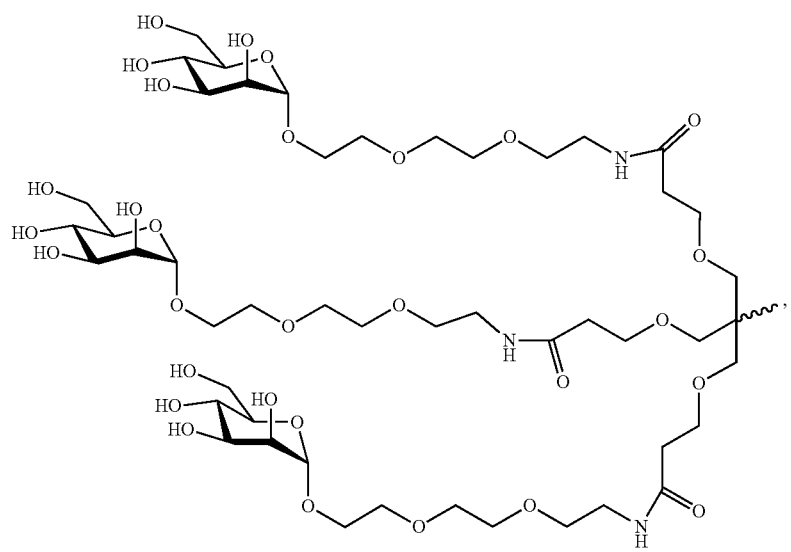
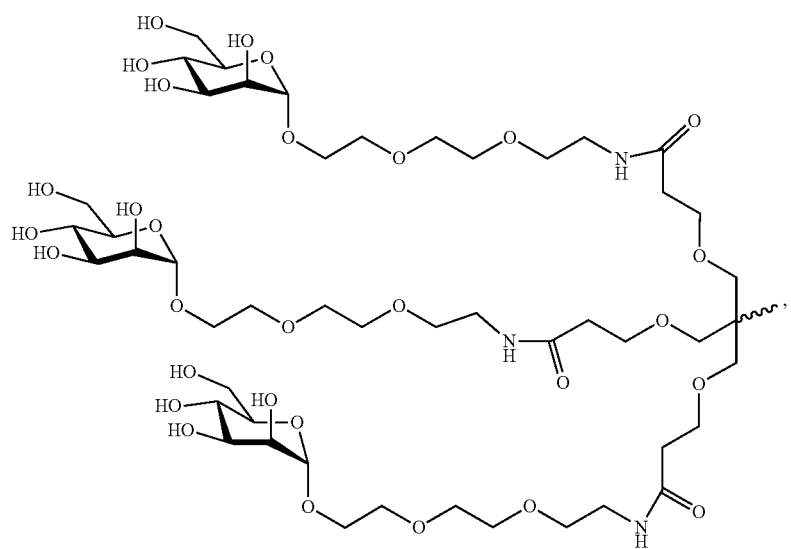

-continued
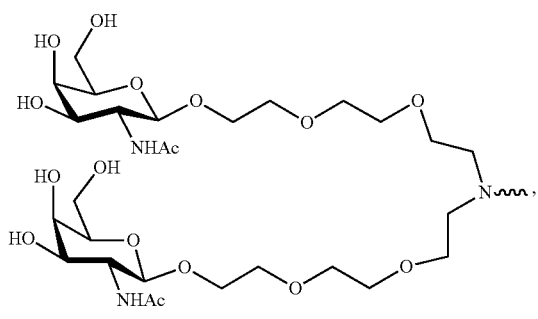
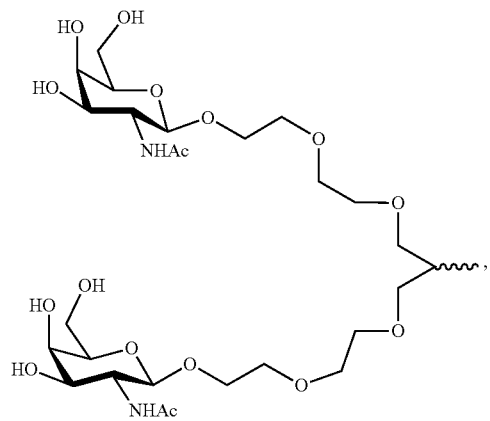
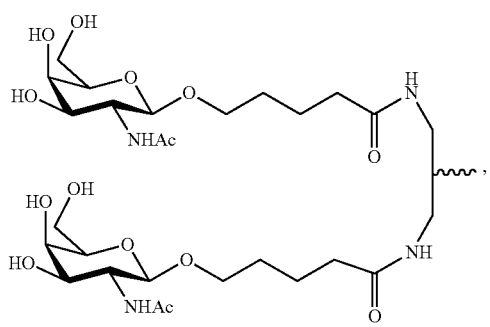
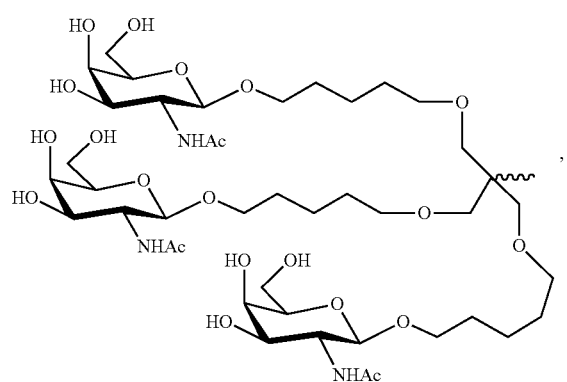
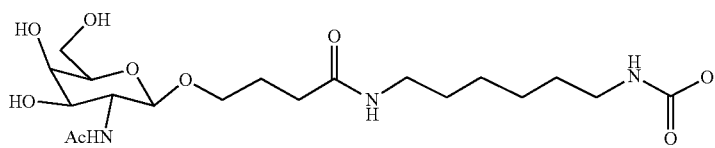
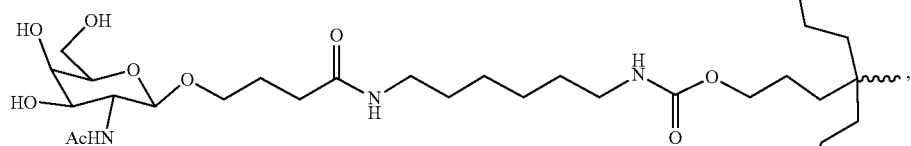
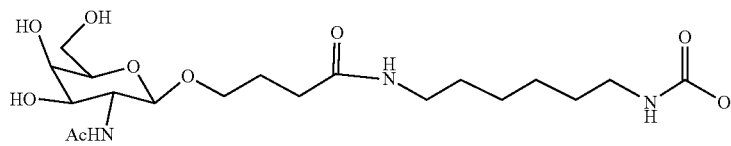

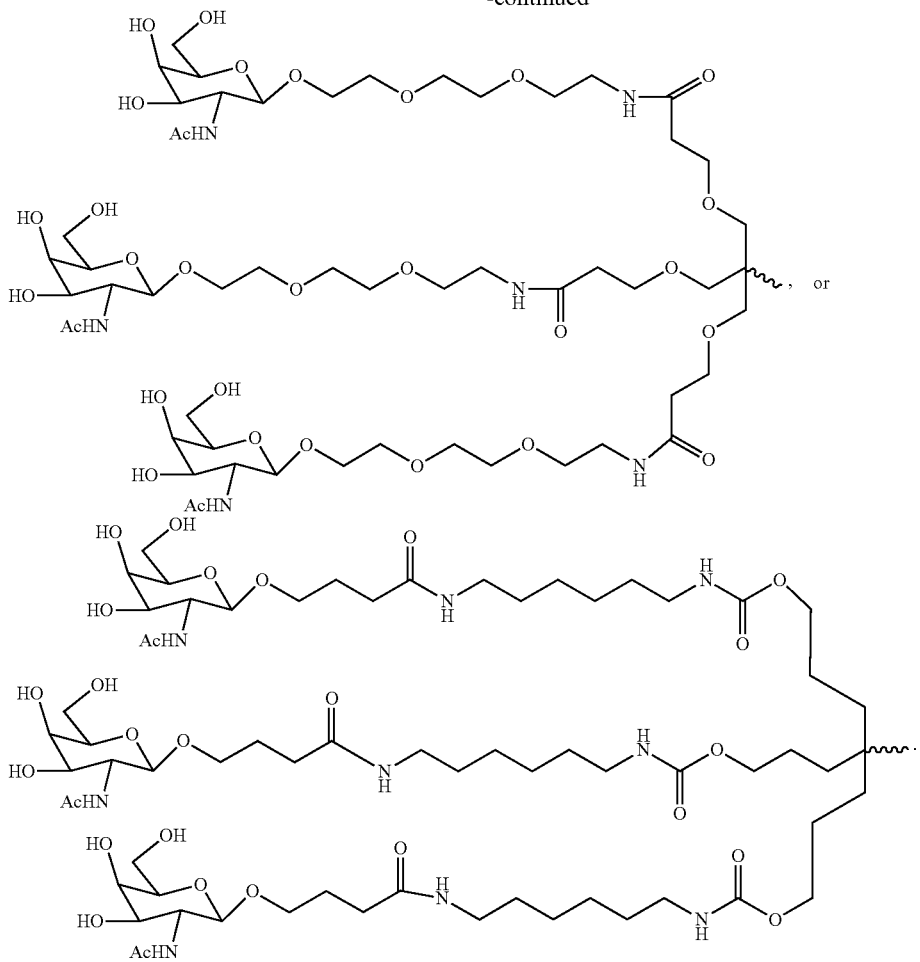

Definitions

As used herein, the terms "dsRNA agent", "siRNA", and "iRNA agent" are used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences typically differ by at least 5 nucleotides.

In one embodiment, a dsRNA agent of the invention is "sufficiently complementary" to a target RNA, e.g., a target mRNA, such that the dsRNA agent silences production of protein encoded by the target mRNA. In another embodiment, the dsRNA agent of the invention is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA agent of the invention specifically discriminates a single-nucleotide difference. In this case, the dsRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

The phrase "stereochemically isomeric forms," as used herein, refers to different compounds made up of the same atoms bonded by the same sequence of bonds but having different three-dimensional structures which are not interchangeable. In some embodiments of the invention, provided chemical compositions may be or include pure preparations of individual stereochemically isomeric forms of a compound; in some embodiments, provided chemical compositions may be or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition may contain all diastereomers and/or enantiomers of the compound. In some embodiments, a chemical composition may contain less than all diastereomers and/or enantiomers of a compound. In some embodiments, if a particular enantiomer of a compound of the present invention is desired, it may be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization.

The phrase "linkage phosphorus" is used to indicate the phosphorus atom present in the internucleotide linkage, corresponding to the phosphorus atom of a phosphodiester of an internucleotide linkage as occurring in naturally occurring DNA and RNA. In some embodiments, a linkage phosphorus atom is in a modified internucleotide linkage (e.g., a modified phosphate linkage), wherein each oxygen atom of a phosphodiester linkage is optionally and independently replaced by an organic or inorganic moiety. In some embodiments, a linkage phosphorus atom in one or more chirally-modified internucleotide linkages is chiral, designated by the P* atom in Formula A. In some embodiments, a linkage phosphorus atom in one or more internucleotide linkages is achiral or racemic.

The term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-R$^1$ wherein each of X, L and R$^1$ is independently as defined and described herein.

The term 'BNA' refers to bridged nucleic acid, and is often referred as constrained or inaccessible RNA. BNA can contain a 5-, 6-membered, or even a 7-membered bridged structure with a "fixed" C$_3$'-endo sugar puckering. The bridge is typically incorporated at the 2'-, 4'-position of the ribose to afford a 2', 4'-BNA nucleotide (e.g., LNA, or ENA). Examples of BNA nucleotides include the following nucleosides:

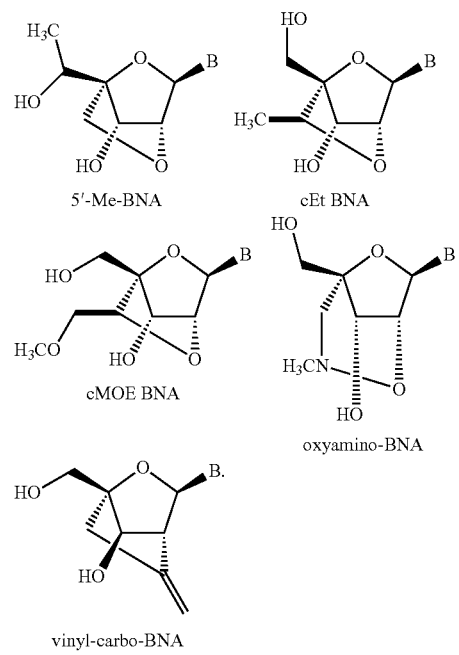

The term 'LNA' refers to locked nucleic acid, and is often referred as constrained or inaccessible RNA. LNA is a modified RNA nucleotide. The ribose moiety of an LNA nucleotide is modified with an extra bridge (e.g., a methylene bridge or an ethylene bridge) connecting the 2' hydroxyl to the 4' carbon of the same ribose sugar. For instance, the bridge can "lock" the ribose in the 3'-endo North) conformation:

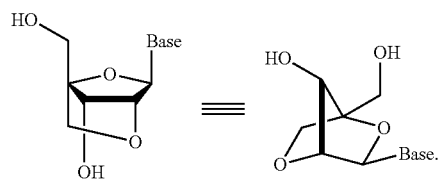

The term 'ENA' refers to ethylene-bridged nucleic acid, and is often referred as constrained or inaccessible RNA.

The "cleavage site" herein means the backbone linkage in the target gene or the sense strand that is cleaved by the RISC mechanism by utilizing the iRNA agent. And the target cleavage site region comprises at least one or at least two nucleotides on both side of the cleavage site. For the sense strand, the cleavage site is the backbone linkage in the sense strand that would get cleaved if the sense strand itself was the target to be cleaved by the RNAi mechanism. The cleavage site can be determined using methods known in the art, for example the 5'-RACE assay as detailed in Soutschek et al., Nature (2004) 432, 173-178, which is incorporated by reference in its entirety. As is well understood in the art, the cleavage site region for a conical double stranded RNAi agent comprising two 21-nucleotides long strands (wherein the strands form a double stranded region of 19 consecutive base pairs having 2-nucleotide single stranded overhangs at the 3'-ends), the cleavage site region corresponds to positions 9-12 from the 5'-end of the sense strand.

The term "halo" refers to any radical of fluorine, chlorine, bromine or iodine. The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S— alkyl radical.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In some embodiments, aliphatic groups contain 1-50 aliphatic carbon atoms, for instance, 1-10 aliphatic carbon atoms, 1-6 aliphatic carbon atoms, 1-5 aliphatic carbon atoms, 1-4 aliphatic carbon atoms, 1-3 aliphatic carbon atoms, or 1-2 aliphatic carbon atoms. In some embodiments, "cycloaliphatic" (or "carbocycle" or "cycloalkyl") refers to a monocyclic or bicyclic $C_3$-$C_{10}$ hydrocarbon (e.g., a monocyclic $C_3$-$C_6$ hydrocarbon) that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below.

The term "alkenylene" refers to a bivalent alkenyl group. A substituted alkenylene chain is a polymethylene group containing at least one double bond in which one or more hydrogen atoms are replaced with a substituent. Suitable substituents include those described below.

The term "aryl" refers to a 6-carbon monocyclic or 10-carbon bicyclic aromatic ring system wherein 0, 1, 2, 3, or 4 atoms of each ring may be substituted by a substituent. The term "aryl" may be used interchangeably with the term "aryl ring." Examples of aryl groups include phenyl, biphenyl, naphthyl, anthracyl, and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" or "heteroar-" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. The term also include groups in which a heteroaromatic ring is fused to one or more aryl, cycloaliphatic, or heterocyclyl rings, where the radical or point of attachment is on the heteroaromatic ring. Examples of heteroaryl groups include pyrrolyl, pyridyl, pyridazinyl, pyrazolyl, triazolyl, tetrazolyl, oxazolyl, isoxazolyl, oxadiazolyl, furyl or furanyl, imidazolyl, benzimidazolyl, pyrimidinyl, pyrazinyl, indolizinyl, thiophenyl or thienyl, quinolinyl, indolyl, thiazolyl, isothiazolyl, thiadiazolyl, purinyl, naphthyridinyl, pteridinyl, isoindolyl, benzothienyl, benzofuranyl, dibenzofuranyl, indazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl," "heterocycle," "heterocyclic radical," or "heterocyclic ring" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). Examples of heterocyclyl groups include trizolyl, tetrazolyl, piperazinyl, pyrrolidinyl, dioxanyl, dioxolanyl, diazepinyl, oxazepinyl, thiazepinyl, morpholinyl, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, quinuclidinyl, and the like. The term "heterocyclylalkyl" refers to an alkyl group substituted by a heterocyclyl, wherein the alkyl and heterocyclyl portions independently are optionally substituted.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_1$ aliphatic which may be substituted as defined below, or an unsubstituted 5-6-membered saturated, partially unsaturated, or aryl ring having 0-4 heteroatoms independently selected from nitrogen, oxygen, or sulfur.

The terms "nucleoside(s)" and "nucleotide(s)" are used interchangeably to refer nucleoside(s) and nucleotide(s); to represent modified or unmodified nucleotide(s) present in the sense strand or in the antisense strand, or both, or free/non-incorporated modified or unmodified nucleoside(s)/nucleotide(s).

The term "site specific" refers to a specific position or location within a sense strand or antisense strand or both strands with respect to 5'-end or 3'-end of either the sense strand or antisense strand of the dsRNA. For example, a site specific chirally-modified internucleotide linkage implies the placement of the chirally-modified internucleotide linkage at the n$^{th}$ position from the 5'-end or 3'-end of a given strand, for example, the n$^{th}$ internucleotide linkage position from the 5'-end of the antisense strand or sense strand. Site specific positions refers to two or more defined positions from the 5'-end or from the 3'-end of the sense strand or antisense strand.

A site specific, chiral modification to the internucleotide linkage may occur at the 5' end, 3' end, or both the 5' end and 3' end of a strand. This is being referred to herein as a "terminal" chiral modification. The terminal modification may occur at a 3' or 5' terminal position in a terminal region, e.g., at a position on a terminal nucleotide or within the last 2, 3, 4, 5, 6, 7, 8, 9 or 10 nucleotides of a strand.

In one embodiment, the term "n$^{th}$ position" refers to: (i) one, two, three, four, five, six, seven, or eight site specific internucleotide location(s) anywhere between the 1 nucleotide and 8$^{th}$ nucleotide, and combinations thereof from the 5'-end of the antisense strand; (ii) one, two, three, four, five, six, seven, or eight site specific internucleotide location(s) anywhere between the 1$^{st}$ nucleotide and 8$^{th}$ nucleotide, and combinations thereof from the 3'-end of the antisense strand; (iii) one, two, three, four, five, six, seven, or eight site specific internucleotide location(s) anywhere between the 1$^{st}$ nucleotide and 8$^{th}$ nucleotide, and combinations thereof from the both 5'-end and 3'-end of the antisense strand; (iv) one, two, three, four, five, six, seven, or eight site specific internucleotide location(s) anywhere between the 1$^{st}$ nucleotide and 8$^{th}$ nucleotide, and combinations thereof from the 5'-end of the sense strand; (v) a combined one, two, three, four, five, six, seven, or eight site specific internucleotide location(s) anywhere between the 1$^{st}$ nucleotide and 8$^{th}$ nucleotide, and combinations thereof from the 3'-end and/or 5'-end of the antisense strand and 5'-end of sense strand.

Alternatively, a site specific chiral modification to the internucleotide linkage may occur at internal positions, other than the terminal regions of a strand. For instance, a site specific chiral modification to the internucleotide linkage may occur near the dicer cleavage site of the sense and/or antisense strand. The term "dicer cleavage site" has been described herein. In one embodiment, the chirally-modified dsRNA agent is a dicer substrate that is cleavable by a dicer in vivo to result in a 17-23 nucleotide long siRNA duplex, which then contains terminal chirally-modified internucleotide linkages (1, 2, 3, 4, 5, 6, 7, or 8 or more terminal chirally-modified internucleotide linkages) at the 3'-end and/or 5'-end of a strand.

While not bound by theory, the inventors believe that the in vivo stability benefit of stereopure PS linkages is more enhanced on the dsRNA duplexes that do not contain dominant internal cleavage sites. Accordingly, in one embodiment, the chirally-modified dsRNA duplexes comprise less than 5%, less than 10%, less than 15%, less than 20%, less than 25%, less than 30%, less than 35%, less than 40%, less than 45%, or less than 50% internal nucleotides cleavage of the dsRNA duplex.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred p, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups is redox cleavable linking groups, which may be used in the chirally-modified dsRNA agents that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based cleavable linking groups, which may be used in the chirally-modified dsRNA agent, are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups, which may be used in the chirally-modified dsRNA agent, are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups, which may be used in the chirally-modified dsRNA agent, are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups, which may be used in the chirally-modified dsRNA agent, are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula—NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom.

Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The invention further relates to the use of the chirally-modified dsRNA agent as defined herein for inhibiting expression of a target gene. In one embodiment, the chirally-modified dsRNA agent as defined herein is used for inhibiting expression of a target gene in vitro. The invention further relates to the chirally-modified dsRNA agent as defined herein for use in inhibiting expression of a target gene in a subject in vivo. The subject may be any animal, such as a mammal, e.g., a mouse, a rat, a sheep, a cattle, a dog, a cat, or a human.

In one embodiment, the chirally-modified dsRNA agent is administered in buffer.

In one embodiment, the chirally-modified dsRNA agent (e.g., an siRNA) described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 10% water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A siRNA preparation can be formulated in combination with another agent, e.g., another therapeutic agent or an agent that stabilizes a siRNA, e.g., a protein that complexes with siRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the siRNA preparation includes another siRNA compound, e.g., a second siRNA that can mediate RNAi with respect to a second gene, or with respect to the same gene. Still other preparation can include at least 3, 5, ten, twenty, fifty, or a hundred or more different siRNA species. Such siRNAs can mediate RNAi with respect to a similar number of different genes.

In one embodiment, the siRNA preparation includes at least a second therapeutic agent (e.g., an agent other than a RNA or a DNA). For example, a siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Exemplary formulations which can be used for administering the chirally-modified dsRNA agent are discussed below.

Liposomes. For ease of exposition the formulations, compositions and methods in this section are discussed largely with regard to unmodified siRNA compounds. It may be understood, however, that these formulations, compositions and methods can be practiced with other siRNA/dsRNAs compounds, e.g., modified siRNAs, and such practice is within the invention. An siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the siRNA are delivered into the cell where the siRNA can specifically bind to a target RNA and can mediate RNAi. In some cases the liposomes are also specifically targeted, e.g., to direct the siRNA to particular cell types.

A liposome containing a siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The siRNA preparation is then added to the micelles that include the lipid component. The cationic groups on the lipid interact with the siRNA and condense around the siRNA to form a liposome. After condensation, the detergent is removed, e.g., by dialysis, to yield a liposomal preparation of siRNA.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Nal. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984, which are incorporated by reference in their entirety. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986, which is incorporated by reference in its entirety). Microfluidization can be used when consistently small (50 to 200 nm) and relatively uniform aggregates are desired (Mayhew, et al. *Biochim. Biophys. Acta* 775:169, 1984, which is incorporated by reference in its entirety). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274, which is incorporated by reference in its entirety).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and include U.S. Pat. Nos. 5,283,185; 5,171, 678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Felgner, P. L. et al., *Proc. Natl. Acad. Sci., USA* 8:7413-7417, 1987 and U.S. Pat. No. 4,897,355 for a description of DOTMA and its use with DNA, which are incorporated by reference in their entirety).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991, which is incorporated by reference in its entirety). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987, which are incorporated by reference in their entirety).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with siRNA are useful for treating a dermatological disorder.

Liposomes that include siRNA can be made highly deformable. Such deformability can enable the liposomes to penetrate through pore that are smaller than the average radius of the liposome. For example, transfersomes are a type of deformable liposomes. Transfersomes can be made by adding surface edge activators, usually surfactants, to a standard liposomal composition. Transfersomes that include siRNA can be delivered, for example, subcutaneously by infection in order to deliver siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants. For ease of exposition the formulations, compositions and methods in this section are discussed largely with regard to unmodified siRNA compounds. It may be understood, however, that these formulations, compositions and methods can be practiced with other siRNA compounds, e.g., modified siRNA compounds, and such practice is within the scope of the invention. Surfactants find wide application in formulations such as emulsions (including microemulsions) and liposomes (see above). siRNA (or a precursor, e.g., a larger dsiRNA which can be processed into a siRNA, or a DNA which encodes a siRNA or precursor) compositions can include a surfactant. In one embodiment, the siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

Micelles and other Membranous Formulations. For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles. For ease of exposition the particles, formulations, compositions and methods in this section are discussed largely with regard to modified siRNA compounds. It may be understood, however, that these particles, formulations, compositions and methods can be practiced with other siRNA compounds, e.g., unmodified siRNA compounds, and such practice is within the invention. In another embodiment, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The chirally-modified dsRNA agents may be formulated for pharmaceutical use. The present invention further relates to a pharmaceutical composition comprising the chirally-modified dsRNA agent as defined herein. Pharmaceutically acceptable compositions comprise a therapeutically-effective amount of one or more of the chirally-modified dsRNA agents in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantaqueous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

iRNA agent preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need, including primates, in particular humans, and other mammals such as equines, cattle, swine and sheep; and poultry and pets in general.

Double-stranded RNAi agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470, which is incorporated by reference in its entirety), or by stereotactic injection (see, e.g., Chen et al. (1994) Proc. Natl. Acad. Sci. USA 91:3054-3057, which is incorporated by reference in its entirety). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA agent and one that produces a transcript that includes the bottom strand of a dsRNA agent. When the templates are transcribed, the dsRNA agent is produced, and processed into siRNA agent fragments that mediate gene silencing.

Routes of Delivery

The chirally-modified dsRNA agent as defined herein or a pharmaceutical composition comprising a chirally-modified dsRNA agent as defined herein can be administered to a subject using different routes of delivery. A composition that includes an iRNA can be delivered to a subject by a variety of routes. Exemplary routes include: intravenous, intramuscular, intrathecal, intraperitoneal, intraventricular, subcutaneous, topical, rectal, anal, vaginal, nasal, pulmonary, ocular and transdermal; and intravenous, intramuscular, intrathecal, subcutaneous and ocular infusion The iRNA molecules and/or the chirally-modified dsRNA agent of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering a chirally-modified dsRNA agent as defined herein, e.g., a siRNA agent, to a subject (e.g., a human subject). In another aspect, the present invention relates to a chirally-modified dsRNA agent as defined herein for use in inhibiting expression of a target gene in a subject. The method or the medical use includes administering a unit dose of the chirally-modified dsRNA agent, e.g., a siRNA agent, e.g., double stranded siRNA agent that (a) the double-stranded part is 14-40 nucleotides (nt) long, for example, 21-23 nt, (b) is complementary to a target RNA (e.g., an endogenous or pathogen target RNA), and, optionally, (c) includes at least one 3' overhang 1-5 nucleotide long. In one embodiment, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4\times10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than a dsRNA agent, e.g., other than a siRNA agent. In another embodiment, the subject has atherosclerosis and the effective dose of a dsRNA agent, e.g., a siRNA agent, is administered in combination with, e.g., after surgical intervention, e.g., angioplasty.

In one embodiment, a subject is administered an initial dose and one or more maintenance doses of a chirally-modified dsRNA agent, e.g., a siRNA agent, (e.g., a precursor, e.g., a larger dsRNA agent which can be processed into a siRNA agent, or a DNA which encodes a chirally-modified dsRNA agent, e.g., a siRNA agent, or precursor thereof). The maintenance dose or doses can be the same or lower than the initial dose, e.g., one-half less of the initial dose.

A maintenance regimen can include treating the subject with a dose or doses ranging from 0.01 µg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the composition includes a plurality of chirally-modified dsRNA agent species. In another embodiment, the chirally-modified dsRNA agent species has sequences that are non-overlapping and non-adjacent to another species with respect to a naturally occurring target sequence. In another embodiment, the plurality of chirally-modified dsRNA agent species is specific for different naturally occurring target genes. In another embodiment, the chirally-modified dsRNA agent is allele specific.

The chirally-modified dsRNA agents described herein can be administered to mammals, particularly large mammals such as nonhuman primates or humans in a number of ways.

In one embodiment, the administration of the chirally-modified dsRNA agent, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of chirally-modified dsRNA agents described herein In particular embodiments, the present invention relates to the chirally-modified dsRNA agents for use in the methods described above.

Methods of Inhibiting Expression of the Target Gene

Embodiments of the invention also relate to methods for inhibiting the expression of a target gene. The method comprises the step of administering the chirally-modified dsRNA agents in any of the preceding embodiments, in an amount sufficient to inhibit expression of the target gene. The present invention further relates to a use of a chirally-modified dsRNA agent as defined herein for inhibiting expression of a target gene in a target cell. In a preferred embodiment, the present invention further relates to a use of a chirally-modified dsRNA agent for inhibiting expression of a target gene in a target cell in vitro.

Another aspect the invention relates to a method of modulating the expression of a target gene in a cell, comprising providing to said cell a chirally-modified dsRNA agent of this invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA (p21) gene, MYB gene, JUN gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In particular embodiments, the present invention relates to the chirally-modified dsRNA agents of the present invention for use in the methods described above.

The invention is further illustrated by the following examples, which should not be construed as further limiting. The contents of all references, pending patent applications and published patents, cited throughout this application are hereby expressly incorporated by reference.

EXAMPLES

Example 1. Position Dependent Effect of Chirally Pure PS Linkages on Nuclease Stability, RISC Loading, and Overall In Vivo Activity of siRNAs An effective means of protecting siRNAs against nuclease activity is to exchange their phosphodiester linkage for phosphorothioate (PS), which is chiral at the phosphorous (Rp/Sp centers). This example demonstrates an efficient method to introduce chirally pure internucleotide phosphorothioate linkages into siRNA agents, and the resulting chirally pure, terminal PS-modified siRNAs maintained or improved pharmacological properties in vivo while having reduced numbers of PS linkages.

Approaches to Synthesize Chirally Pure 3PS, 4PS, 5PS and 6PS siRNAs.

Different protocols can be used to yield chirally pure PS linkages in oligonucleotides: such as H-phosphonate method, separation of the PS diastereoisomers on the oligonucleotide level, chiral pure dinucleotide building blocks of phosphoramidite method or the oxazaphospholidine approach.

This example demonstrates three approaches: Approach 1, separation of the PS diastereomers on the oligonucleotide level, Approach 2, using chirally pure dinucleotide building blocks, and Approach 3, using oxazaphospholidine (OAP) monomers. In this example, all possible dinucleotides connected by a phosphothioate linkage (PS) containing 2'-OMe modification and/or 2'-F modification were synthesized and analyzed (see Jahns et al., "Stereochemical bias introduced during RNA synthesis modulates the activity of phosphorothioate siRNAs," *Nature Communications* 6: 6317 (2015), which is incorporated herein by reference in its entirety).

Approach 1: separation of the PS diastereomers on the oligonucleotide level. The full-length oligonucleotides were synthesized on an ABI using standard 2'-OMe-, 2'-F-phosphoramidite conditions and 5-Ethylthio-1H-Tetrazole (ETT) as the activator. The final DMT group was kept on to facilitate separation of the PS diastereoisomers. The diastereomeric mixtures of the 21mer 5'-1PS sense strand (SS1 and SS2; the sequence and chirality of the siRNA are shown in Table 1) and the 23mer 3', 5'-2PS antisense strand (AS1, AS2, AS3, AS4; the sequence and chirality of the siRNA are shown in Table 1) of the C5 target sequence, respectively, were synthesized. The diastereomers were separated by ion exchange purification (IEX). FIG. 1 shows the results of the separation on analytical IEX chromatography of the Rp/Sp PS diastereomers of the 5'-1PS sense strand with the DMT protection group (DMT-on) and all four PS diastereomers of the 3', 5'-2PS antisense strand with DMT-on. The DMT-on oligonucleotides with a Sp stereochemistry on the 5'end typically elutes on the RP-HPLC before the Rp diastereomer (see Wan et al., "Synthesis, biophysical properties and biological activity of second generation antisense oligonucleotides containing chiral phosphorothioate linkages," *Nucleic Acids Research* 42(22): 13456-13468 (2014), which is incorporated herein by reference in its entirety), and the same trend was observed for the diastereomers separated by IEX. The 5'end Rp diasteromer was faster migrating than the Sp diastereomer when the DMT-group was removed. Some diastereomers in an oligonucleotide did not resolve without the DMT-group present at the 5'end. All diastereoisomers were separated with a purity of >90%, except the compound AS2 and AS4, which had a purity of ~80% (FIG. 1).

After the PS diastereomers of the single stranded, 3PS-modified C5 sequences were separated, the diastereomers of the 5'-1PS sense strand (SS1, SS2) and the 3', 5'-2PS antisense strand (AS1-AS4) were then assembled to eight chirally pure diastereomers of a 3PS-modified siRNA (see si4, si6, si8, si10, si12, si14, si16 and si18 in Table 3).

TABLE 1

The sequence and chirality of the siRNA

| SINGLE STRAND | TARGET | PS-CHIRALITY | SEQUENCE AND CHIRALITY OF siRNA* |
|---|---|---|---|
| SS1 SS4 | CC5 mrTTR | MIX | |
| SS2 SS5 | CC5 mrTTR | 5'Rp | |
| SS3 SS6 | CC5 mrTTR | 3'Sp | |
| AS1 AS6 | CC5 mrTTR | MIX | |
| AS2 AS7 | CC5 mrTTR | 5'Rp-3'Rp | |
| AS3 AS8 | CC5 mrTTR | 5'Rp-3'Sp | |
| AS4 AS9 | CC5 mrTTR | 5'Sp-3'Rp | |
| AS5 AS10 | CC5 mrTTR | 5'Sp-3'Sp | |

Figure 2:
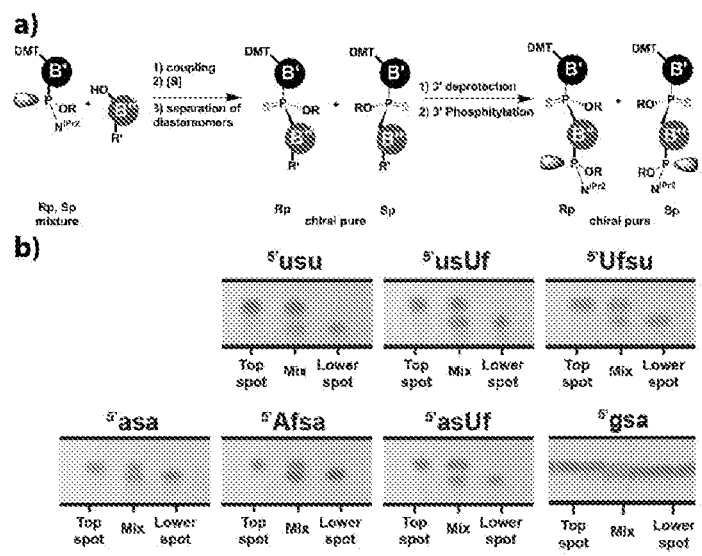
FIG. 2. Synthesis and separation of phosphorothioate (PS) dinucleotide diastereomer: (a) Phosphoramidite coupling, sulfurization to PS-linkage, separation of phosphorothioate dinucleotide diastereomers and synthesis of chiral pure PS-dinucleotide phosphoramidite building block (b) Thin layer chromatogram of dinucleotides after separation of diastereomers: top spot=fast eluting diastereomer, mix=co-spot of top and lower spot, lower spot=slower eluting diastereomer (small letter u,a,g=2'OMe nucleoside, small s=PS-linkage, capital+f=2'F-nucleoside).

Approach 2: using chirally pure dinucleotide building blocks. The synthesis of the chirally pure dinucleotide building blocks for C5 and mrTTR sequence (shown in Table 3) in a four step reaction, including coupling/sulfurization, 3'TBDMS-deprotection and 3'-phosphitylation (FIG. 2a). The mixture of the PS dinucleotide diastereoisomers were effectively separated, after sulfurization, by thin layer chromatography (TLC) into a faster-migrating diastereoisomer (top spot) and a slower-migrating diastereoisomer (lower spot) (FIG. 2b). The separation yielded more than 99% purity and good overall yield for all compounds.

The chemical shift of the $^{31}$P-NMR signal of the PS diastereomers was used to assign the Rp/Sp stereochemistry and the diastereoisomeric product ratio. The downfield shifted (by $^{31}$P-NMR spectra) diastereomer was assigned as the Rp diastereoisomers, whereas the upfield shifted (by $^{31}$P-NMR spectra) diastereomer was assigned as the Sp diastereoisomer (Table 2) (see Bartlett et al., "Stereochemical course of polymerization catalyzed by avian myeloblastosis virus reverse transcriptase." *Journal of Biological Chemistry* 257(15): 8879-8884 (1982); Connolly et al., "Synthesis and characterization of an octanucleotide containing the EcoRI recognition sequence with a phosphorothioate group at the cleavage site," *Biochemistry* 23(15): 3443-3453 (1984), both of which are incorporated herein by reference in their entirety).

The diastereomeric dinucleotide product ratio was affected by the 2' sugar modification as well as the nucleobases, whereas the diastereomeric product ratio from batch to batch in each dinucleotide was consistent. Using ETT as an activator resulted in a bias toward specific diastereomeric forms. The diastereomeric ratio of Rp/Sp in some dinucleotides yielded an epimeric mixture (e.g., csUf), a bias toward the Rp diastereoisomer (e.g., Rp/Sp=70/30 in usc), or a bias towards the Sp diastereoisomer (e.g., Rp/Sp=28/72 in Gfsg) (see Jahns et al., "Stereochemical bias introduced during RNA synthesis modulates the activity of phosphorothioate siRNAs," *Nature Communications* 6: 6317 (2015), which is incorporated herein by reference in its entirety).

To assign the stereochemistry of the fully deprotected stereochemically pure PS dinucleotide, the compounds were incubated with snake venom phosphodiesterase (SVPDE) and phosphodiesterase II (PDII). The top spot diastereomer was assigned as the Rp diastereomer, based on the $^{31}$P-NMR chemical shift and the fact that SVPDE degrades selectively the Rp PS diastereomer (see Potter et al., "Synthesis and configurational analysis of a dinucleoside phosphate isotopically chiral at phosphorus. Stereochemical course of Penicillium citrinum nuclease P1 reaction," *Biochemistry* 22(6): 1369-1377 (1983), which is incorporated herein by reference in its entirety). PDII showed selectivity for degradation of the Sp PS diastereomer throughout the six dinucleotides. The (gsa) dinucleotide was an exception, in which the top spot was assigned as the Sp diastereomer, based on the $^{31}$P-NMR and the nuclease degradation rules (see Table 2). The results of the stereochemistry assignment of the stereochemically pure PS dinucleotides are shown in Table 2.

TABLE 2

Properties of chirally pure phosphorothioate dinucleotides

| PS dinucleotide | TLC top spot | | | | TLC lower spot | | | |
|---|---|---|---|---|---|---|---|---|
| | HRMS | $^{31}$P-NMR | SVPDE/ Config. | PDE II | HRMS | $^{31}$P-NMR | SVPDE/ Config. | PDE II |
| usu | 617.0908[1] | 56.74 | deg./Rp | — | 617.0917[1] | 55.55 | no deg./Sp | — |
| usUf | 605.0718[1] | 56.78 | deg./Rp | — | 605.0742[1] | 55.68 | no deg./Sp | — |
| Ufsu | 605.0727[1] | 56.82 | deg./Rp | no deg. | 605.0737[1] | 55.97 | no deg./Sp | deg. |
| asa | 641.1668[2] | 57.51 | deg./Rp | no deg. | 641.1655[2] | 56.27 | no deg./Sp | deg. |
| Afsa | 629.1449[2] | 57.21 | deg./Rp | no deg. | 629.1452[2] | 55.40 | no deg./Sp | deg. |
| asUf | 606.1171[2] | 57.83 | deg./Rp | no deg. | 606.1183[2] | 56.63 | no deg./Sp | deg. |
| gsa | 657.1580[2] | 56.07 | no deg./Sp | deg. | 657.1583[2] | 57.53 | deg./Rp | no deg |

TLC top spot: diastereoisomer with higher Rf value of the two diastereisomers;
TLC lower spot: diastereoisomer with lower Rf value of the two diastereisomers;
HRMS (High Resolution Mass Spectrometry): [1](M + Na), [2](M + H);
$^{31}$P-NMR in (D$_2$O), ppm
SVPDE (Snake Venom Phosphodiesterase degradation): 48-hour time point.
deg.: degradation overtime; no deg.: no degradation overtime.
Config.: PS diastereomer configuration.
PDE II (Phosphodiesterase II): 48-hour time point.

The chirally pure 3PS C5 sequence and 3PS mrTTR sequence oligonucleotides were then synthesized using the dinucleotide Approach 2, yielding eight diastereomer oligonucleotides for the preparation of each target siRNAs, si3-si18, as shown in Table 3. For the sense strands of these siRNAs, a precursor 19-mer carrying the 3'GalNAc was synthesized on an automated oligonucleotide synthesizer. To introduce the chirally pure PS linkages at the 5' termini of the sense strand, the corresponding dinucleotide building block was manually coupled and oxidized to the precursor. For the antisense strand, two chirally pure PS linkages were incorporated, at both the 3' and 5' termini. The chirally pure dinucleotide building block yielding the 3' termini PS chirality was manually coupled to the controlled pore glass (CPG) followed by the next 19-nucleotide couplings containing phosphodiester internucleotide linkages, on the oligonucleotide synthesizer. The chirally pure linkages at the 5' termini of the antisense strand were incorporated by a manual coupling step leading to the desired chirally pure 2PS antisense strand (Approach 2, FIG. 2a). All oligonucleotides were synthesized with DMT-on to confirm the stereochemical purity in the oligonucleotides (as shown FIG. 1).

The stereochemistry of the C5 compounds made by the two different approaches (Approach 1 and Approach 2) were confirmed with the DMT-on and off flip on RP-HPLC and $^{31}$P-NMR (Table 2). Both the separation of the diastereomers on the oligonucleotide level (Approach 1) and by using the chirally pure dinucleotide building blocks (Approach 2) yielded in stereochemically pure oligonucleotides. The latter approach, however, yielded in a higher purity on a larger scale.

All other oligonucleotides, containing two or more consecutive chirally pure PS linkages (2PS, 3PS, 4PS) were synthesized using coupling of OAP monomer building blocks (Approach 3).

The hybridization ability of the epimeric mixture was compared with the chirally pure 3PS compounds by measuring the melting temperatures ($T_m$s) (Table 3). The PS chirality at the 3' and 5' terminal linkages had only a minor effect (1° C.) on the hybridization of the mrTTR siRNAs.

Table 3. Sequence and chirality of the 3PS-modified siRNAs:

TABLE 3

Sequence and chirality of the 3PS-modified siRNAs:

| siRNA | TARGET | PS-CHIRALITY | SEQUENCE AND CHIRALITY OF SiRNA* | Tm (° C.) |
|---|---|---|---|---|
| si1 | mrTTR | MIX |  | 74.3 |
| si2 | CC5 | MIX |  | nd |
| si3<br>si4 | mrTTR<br>CC5 | R/R-R |  | 74.3<br>nd |
| si5<br>si6 | mrTTR<br>CC5 | R/R-S |  | 74.4<br>nd |
| si7<br>si8 | mrTTR<br>CC5 | R/S-R |  | 74.4<br>nd |
| si9<br>si10 | mrTTR<br>CC5 | R/S-S |  | 73.8<br>nd |
| si11<br>si12 | mrTTR<br>CC5 | S/R-R | 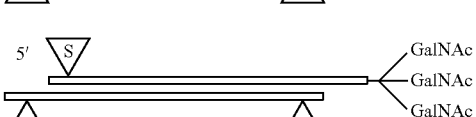 | 74.8<br>nd |
| si13<br>si14 | mrTTR<br>CC5 | S/R-S |  | 74.3<br>nd |
| si15<br>si16 | mrTTR<br>CC5 | S/S-R | 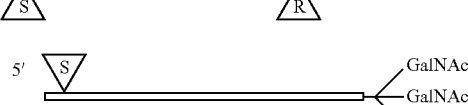 | 73.4<br>nd |
| si17<br>si18 | mrTTR<br>CC5 | S/S-S | 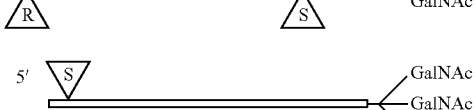 | 73.1<br>nd |

Tm: MELTING TEMPERATURE,
MIX = EPIMERIC MIXTURE,
X/X-X = 5' END CHIRALITY OF SENSE STRAND/5' END CHIRALITY OF ANTISENSE STRAND-3' END CHIRALITY OF ANTISENSE STRAND,
*UPPER SEQUENCE: 3'GalNAc-SENSE STRAND; LOWER SEQUENCE: ANTISENSE STRAND;
ND: NOT DETERMINED

Sp Diastereoisomer at the 3'-AS Strand Yield in Higher In Vitro Activity.

Figure 3:
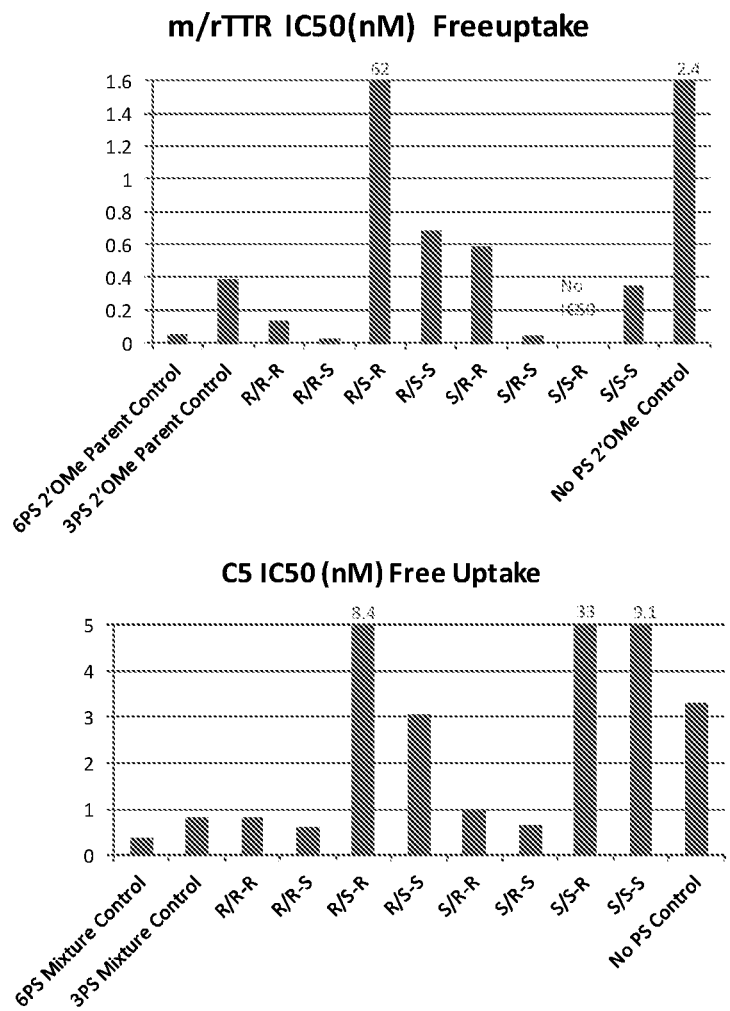
FIG. 3. The IC50 values for in vitro free uptake in mrTTR and C5.

To assess the biological consequences of different diastereoisomers at the terminal positions of a siRNA, (i.e. the 5'-1PS of a sense strand, the 5'-1PS and the 3'-1PS of an antisense strand), the eight chirally pure siRNAs isomers and their epimeric mixtures (si1-si18, as shown in Table 3) were tested within an in vitro free uptake experiment in primary mouse hepatocytes. All siRNAs were tested at a graded concentration for their inhibition of target mRNA expression and their $IC_{50}$ values are shown in FIG. 3. The epimeric 3PS mixture (si1 in mrTTR and si2 in C5) showed strong knockdown with $IC_{50}$ values of 0.38 nM and 0.82 nM, respectively. In both targets, two chirally pure 3PS compounds, R/R-S (si5/si6) and S/R-S (si13/si14) resulted in a significant higher activity compared to the epimeric 3PS mixture. In a direct comparison of the eight chirally pure siRNAs isomers, with a change of one chiral PS center (e.g., R/R-R vs. R/S-R), the siRNAs with a Rp diastereomer at the 5'-1PS antisense strand yielded in a higher in vitro activity in all cases (si3, si5, si1, si13>si7, si9, si15, si17 for mrTTR; and si4, si6, si12, si14>si8, si10, si16, si18 for C5). On the other hand, the Sp diastereomer at the 3'-1PS antisense strand improved the activity (si3, si7, si1, si15<si5, si9, si13, si17 for mrTTR; and si4<si6, si8<si10, si12<si14, si16<si18 for C5). The Rp diastereomer at the 5'-1PS sense strand improved the activity, with the exception of the R/S-S to S/S-S (si9, si10>si17, si18) compounds.

Two important pharmacological properties of an siRNA are its stability against nucleases and its inherent RNAi silencing potency. The evaluation of the nuclease stability of a PS-containing oligonucleotide is typically measured using the 3'exonuclease SVPDE, which has a preference to degrade the Rp diastereoisomers. In this example, the incubation of the chirally pure dinucleotides with the 5'exonuclease, phosphodiesterase II (PD II), displayed higher stability for the Rp diastereoisomers compared to the Sp diastereomers. A phosphorothioate linkage is in general more stable than a phosphodiester, whereas the stability difference of Rp vs.

Sp may depend on the nucleases that the compounds are incubated with. The nuclease stability of the dinucleotides and the in vitro experiments indicate that the 5'-1PS Rp diastereomer and the 3'-1PS Sp diastereomer were beneficial for the siRNA nuclease stability and activity.

Factors affecting the potency of siRNAs may include duplex stability (see Khvorova et al., "Functional siRNAs and miRNAs Exhibit Strand Bias," *Cell* 115(2): 209-16 (2003); Addepalli et al., "Modulation of thermal stability can enhance the potency of siRNA." *Nucleic Acids Research* 38(20): 7320-31 (2010), both of which are incorporated herein by reference in their entirety), the strand selection (see Schwarz et al., "Asymmetry in the Assembly of the RNAi Enzyme Complex," *Cell* 115(2): 199-208 (2003), which is incorporated herein by reference in its entirety), the presence of certain nucleotide motifs (see Huesken et al., "Design of a genome-wide siRNA library using an artificial neural network." *Nat Biotech* 23(8): 995-1001 (2005), which is incorporated herein by reference in its entirety), and chemical modification of guide and/or passenger strands (see Bramsen, et al., "A screen of chemical modifications identifies position-specific modification by UNA to most potently reduce siRNA off-target effects," *Nucleic Acids Research* 38(17): 5761-73 (2010), which is incorporated herein by reference in its entirety). From a pharmacodynamic perspective, the essential destination of therapeutic siRNA is the cellular Argonaute (Ago) 2 in targeted cells. In mammals, Ago2, which belongs to the Ago subfamily of Ago proteins (see Carmell et al., "The Argonaute family: tentacles that reach into RNAi, developmental control, stem cell maintenance, and tumorigenesis," *Genes & Development* 16(21): 2733-42 (2002)), is the protein within the RNA-induced silencing complex (RISC) that binds to the guide strand and catalyzes the cleavage of the target mRNA (see Liu et al., "Argonaute2 Is the Catalytic Engine of Mammalian RNAi," *Science* 305(5689): 1437-41 (2004); Meister et al., "Human Argonaute2 Mediates RNA Cleavage Targeted by miRNAs and siRNAs," *Molecular Cell* 15(2): 185-97 (2004), both of which are incorporated herein by reference in their entirety). Crystal structures of human Ago2 in complex with RNA guides show extensive hydrogen bonding contacts between Ago2 residues and the non-bridging oxygens of the PO linkages at the 3' end and 5' end of the antisense strand (see Elkayam et al., "The Structure of Human Argonaute-2 in Complex with miR-20a," *Cell* 150 (1): 100-110 (2012); Schirle et al., "The Crystal Structure of Human Argonaute2," *Science* 336 (6084): 1037-1040 (2012), both of which are incorporated herein by reference in their entirety).

Figure 4:
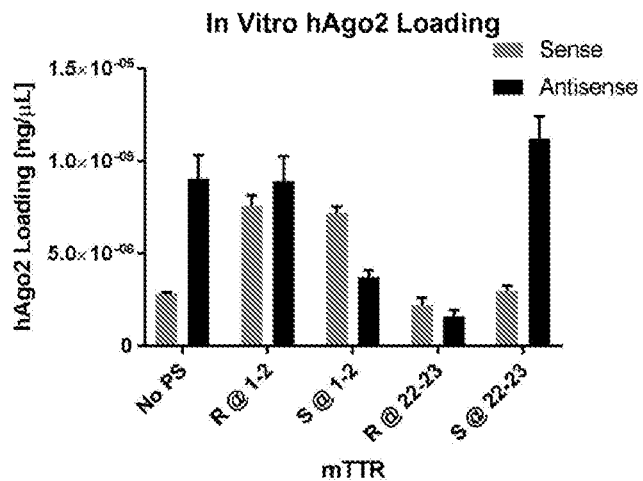
FIG. 4. The RISC loading data of the chirally pure 1PS compounds. No PS: si19; R@1-2: si20; S@1-2: si21; R@22-23: si22; S@22-23: si23.

To assess the effect of PS stereochemistry on Ago loading, which leads to different activities of the chirally pure 3PS siRNAs in vitro, the siRNA was first evaluated as a chirally pure 1PS compound. As shown in Table 4, siRNAs with a single, stereochemically pure PS (Rp/Sp) linkages at the 5' end of the antisense strand (si20/si21) and the 3' end of the antisense strand (si22/si23) were synthesized and compared to the non-PS siRNA (si19) and the 6PS stereomixture siRNAs (si24 and si25). With the chirally pure 1PS compounds (si20-23), the exclusive effect of Rp/Sp stereochemistry at the terminal ends of the antisense strand on Ago loading were explored. Ago2-associated siRNA was quantified by SL-RT QPCR in vitro using HEK293 cell lysates overexpressing FLAG-HA-tagged human Ago2 (Pei et al., "Quantitative evaluation of siRNA delivery in vivo," *RNA* 16(12): 2553-2563 (2010), which is incorporated herein by reference in its entirety). Superase-In, a nuclease inhibitor was used to eliminate undesirable degradation of the siRNAs. The antisense strand of the non-PS siRNA, si19, showed an expected preference in loading with 10 fg/μl. The antisense strands of si20 (with the 5'-Rp configuration) and si21 (with the 5'-Sp configuration) showed minor difference, with a slight Ago loading preference for the 5'-Rp configuration. Surprisingly, the stereochemistry at the 3' end of the antisense strand showed remarkable differences. The antisense strand of si23 (with the 3'-Sp configuration) yielded a five-fold higher Ago loading compared to that of si22 (with the 3'-Rp configuration at the same position). The results are shown in FIG. 4. This is a surprising demonstration in the first time that the Sp stereochemistry of a PS linkage substantially improved the Ago loading.

TABLE 4

Sequence and chirality of 1PS-modified siRNAs

| siRNA | TARGET | PS-CHIRALITY | SEQUENCE AND CHIRALITY OF siRNA* |
|---|---|---|---|
| si19 | mrTTR | no | 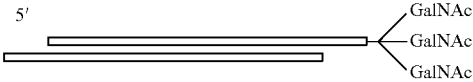 |
| si20 | mrTTR | 5'R | 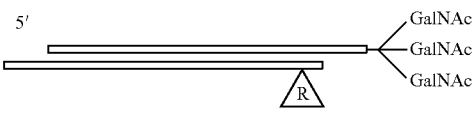 |
| si21 | mrTTR | 5'S | 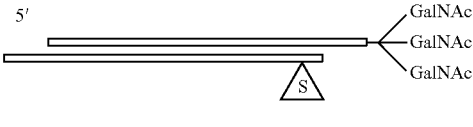 |
| si22 | mrTTR | 3'R | 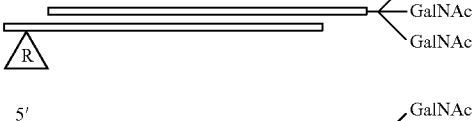 |
| si23 | mrTTR | 3'S |  |
| si24 | mrTTR | MIX | 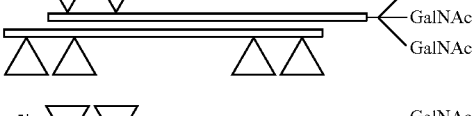 |
| si25 | CC5 | MIX | 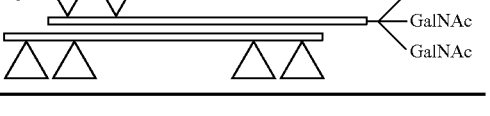 |

MIX = EPIMERIC MIXTURE;
5'X: 5' END CHIRALITY OF THE ANTISENSE STRAND;
3'X: 3' END CHIRALITY OF THE ANTISENSE STRAND;
*UPPER SEQUENCE: 3' END GalNAc CONJUGATED SENSE STRAND; LOWER SEQUENCE: ANTISENSE STRAND

Figure 5:
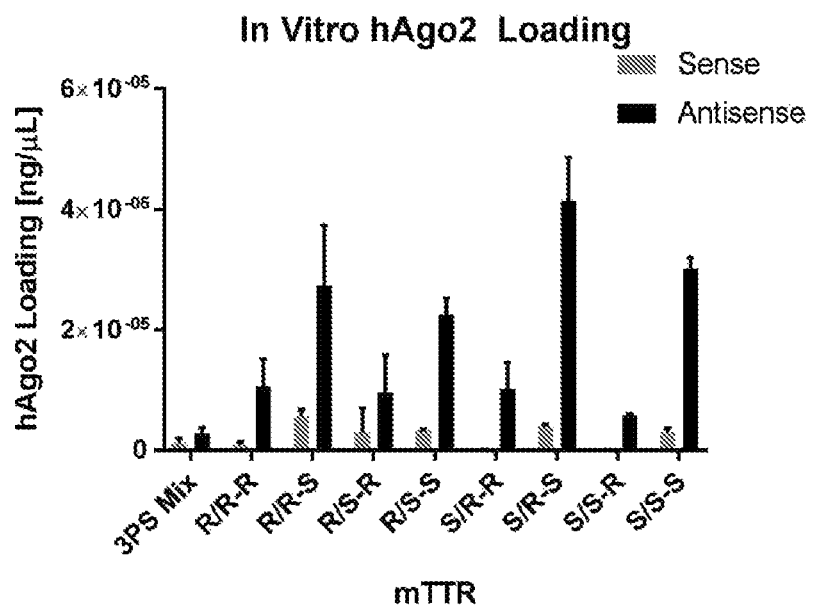
FIG. 5. The RISC loading data of the chirally pure 3PS-modified compounds.

The in vitro Ago loading abilities for all eight chirally pure 3PS mrTTR diastereomers were tested, to evaluate whether the effect of the improved Ago loading activity of the Sp stereochemistry at the 3'end of the antisense strand in the 1PS-modified siRNA translates to the chirally pure 3PS siRNAs. As shown in FIG. 5, all compounds showed good loading compared to the 3PS epimeric mixture. In a direct comparison of the eight compounds, with a change of one chiral PS center at the time (e.g., R/R-R vs. R/R-S), the siRNAs with a Sp diastereomer at the 3' end antisense strand yielded higher in vitro Ago loading activity in all cases (Table 3: si5, si9, si13, si17>si3, si7, si11, si15). The chirality of the 5' end antisense strand appeared to play a relative minor role (R/R-R vs. R/S-R). The two compounds with the R/R-S (si5) and S/R-S (si13) chirality pattern showed a five-fold higher Ago loading activity compared to the 3PS epimeric mixture. The chirality of the 5'end sense strand had no effect on the Ago loading activity in vitro.

Figure 6:
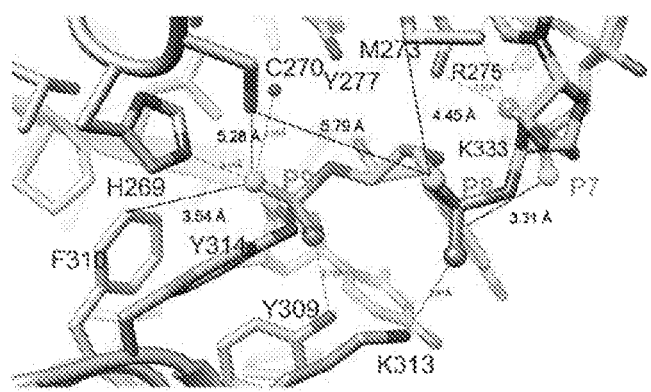
FIG. 6. the crystal structure of hAgo1 PAZ with a 9mer RNA sequence 5'-CGU GA$_5$C$_6$ U$_7$C$_8$U$_9$-3'.

The PAZ domain is a highly conserved RNA-binding module found in Ago, which represents a hydrophobic environment (see Ma et al., "Structural basis for overhang-specific small interfering RNA recognition by the PAZ domain," Nature 429(6989): 318-322 (2004), which is incorporated herein by reference in its entirety). To further analyze the 3'end antisense strand chirality, the crystal structure of hAgo1 PAZ with a 9-mer RNA sequence 5'-CGU $GA_5C_6$ $U_7C_8U_9$-3' was analyzed, to evaluate the contacts between the phosphate groups and PAZ residues. As shown in FIG. 6, the interactions of PAZ residues with phosphates between U9 and C8 (P9) and C8 and U7 (P8) were analyzed. The environments of the Sp and Rp "sulfurs" on P9 are significantly different. Thus, the environment of the Sp isomer is more hydrophobic (beneficial for sulfur), despite a direct contact to His-269 as well the vicinity of F310, compared to the Rp isomer with two H-bonds to Tyr-309 and Tyr-314 (beneficial for oxygen). The co-crystal structure of Ago with the 9-mer supports the experimental finding that the Sp diastereomer of the PS linkage at the 3'end of the antisense strand improved the Ago loading activity. The crystal structure indicated further, that at the P8 internucleotide linkage, the Sp diastereomer in a PS linkage could be beneficial to accommodate the antisense strand in Ago.

Figure 7:
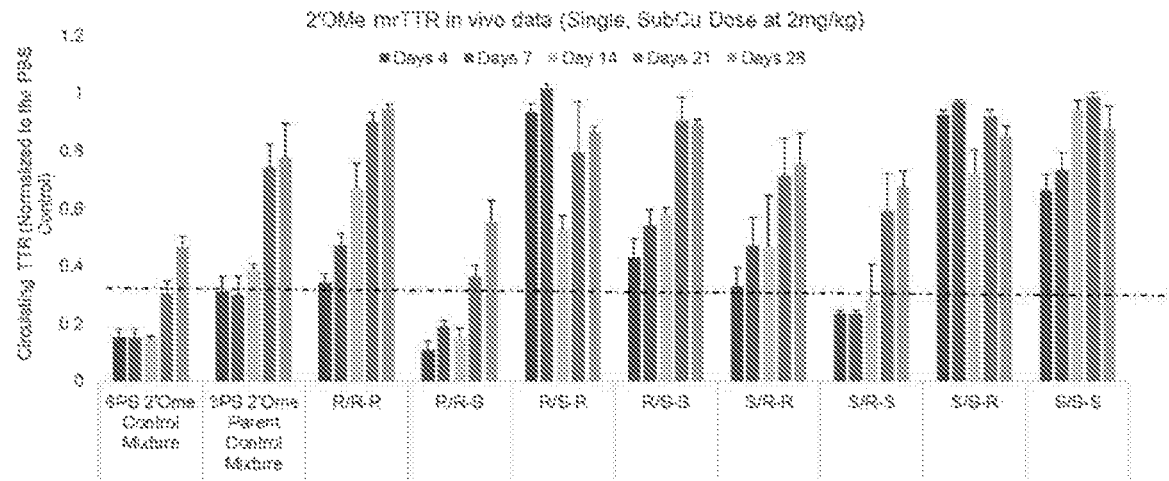
FIG. 7. The results of in vivo mrTTR silencing.

In Vivo Analysis Reveals a Positional Based Preference for Each PS Stereoisomer Configuration To understand whether the observed in vitro activity and Ago loading activity would translate into in vivo activities, each compound was screened in WT mice to determine the impact of the chirally pure 3PS-modified, 3'-GalNAc conjugated siRNAs on the efficacy/duration, and was compared to the 6PS-epimeric mixture siRNAs. Animals received a single, subcutaneous dose of each siTTR compound at the 6PS parent $ED_{80}$, 2 mg/kg. Circulating mouse TTR protein levels were measured at day 4, 7, 14, 21 and 28 days post dose with each sample normalized to the individual pre-dose for that particular animal. As shown in FIG. 7, the 6PS-modified epimeric mixture control achieved approximately 85% knockdown, and the 3PS-modified epimeric mixture showed reduced knockdown at day 4, 7 and 14 (approximately 70-60%) combined with a quicker recovery with TTR levels in the day 21/28 animals returning to baseline. The in vivo activity loss for the 3PS-modified epimeric mixture may be attributed to the reduced PS content causing the impact on the stability (see Zlatev et al., "5'-C-Malonyl RNA: Small Interfering RNAs Modified with 5'-Monophosphate Bioisostere Demonstrate Gene Silencing Activity," *ACS Chemical Biology* 11(4): 953-960 (2016), which is incorporated herein by reference in its entirety). The compounds with the 5'end antisense Sp stereoisomer, si7/si9/si15/si17 (Table 2), demonstrated a significant loss of activity, which we associated with the Sp PS diastereomer susceptibility of 5'exonucleases (as shown in the dinucleotide model with degradation by PDII). Consistent with the in vitro data, the diastereomers si5 (R/R-S) and si13 (S/R-S) showed better in vivo activities compared to other diastereomers, each showing an efficacy comparable to the epimeric 6PS-modified mixture, but significantly improved efficacy than the 3PS-modified epimeric mixture.

Figure 8:
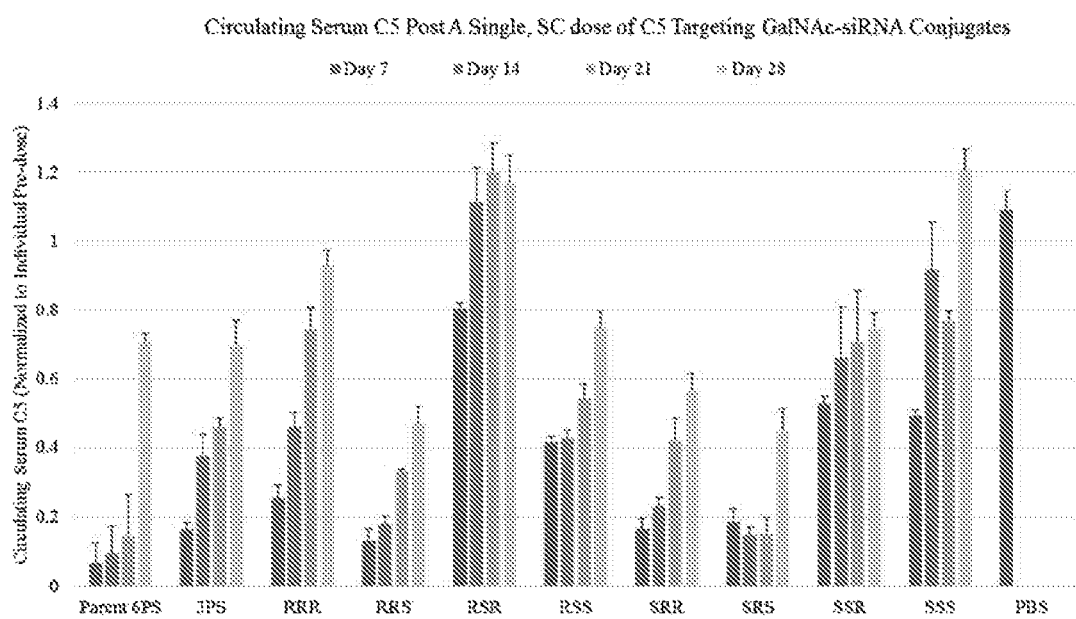
FIG. 8. The results of in vivo C5 silencing.

To confirm that the data generated with the GalNAc-siRNA-TTR, analyzed above, would translate to a second sequence, a similar experiment was carried out using the chirally pure 3PS GalNAc-siRNA-C5 sequence. Again, each compound was screened in WT mice. Each animal was dosed with a single, subcutaneous dose of 2.5 mg/kg and both efficacy and duration were measured by quantifying circulating C5 levels. As shown in FIG. 8, the 6PS-modified epimeric mixture control achieved approximately 93% knockdown, and the 3PS-modified epimeric mixture showed an activity loss to approximately 82%. C5 levels in the animals dosed with the 3PS-modified epimeric mixture recovered at a quicker rate when compared to the 6PS-modified epimeric mixture, with the Day 28 C5 activity showing levels at 80% when compared to the PBS control. The compounds with the Rp configuration on the 5'-end of the antisense strand, si4/si6/si12/si14, showed comparable activity to at least the 3 PS-modified epimeric mixture. Again, consistent with the in vitro data, the diastereomers si6 (R/R-S) and si14 (S/R-S) showed better in vivo activities compared to the other diastereomers, each showing an efficacy comparable to the epimeric 6 PS-modified mixture, but significantly improved efficacy relative to the 3PS-modified epimeric mixture.

Figure 9:
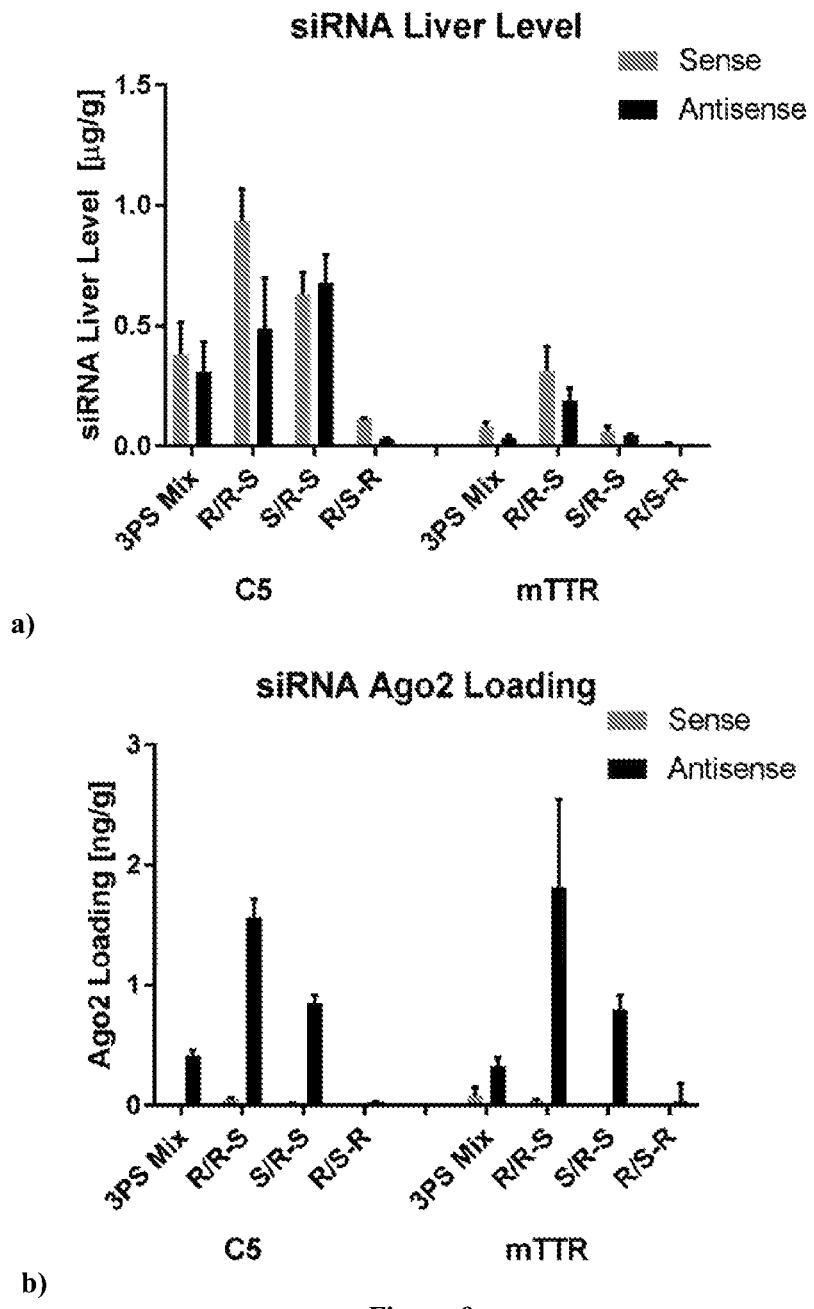
FIG. 9. SiRNA liver Level (a) and Ago2 Loading (b).
Figure 10:
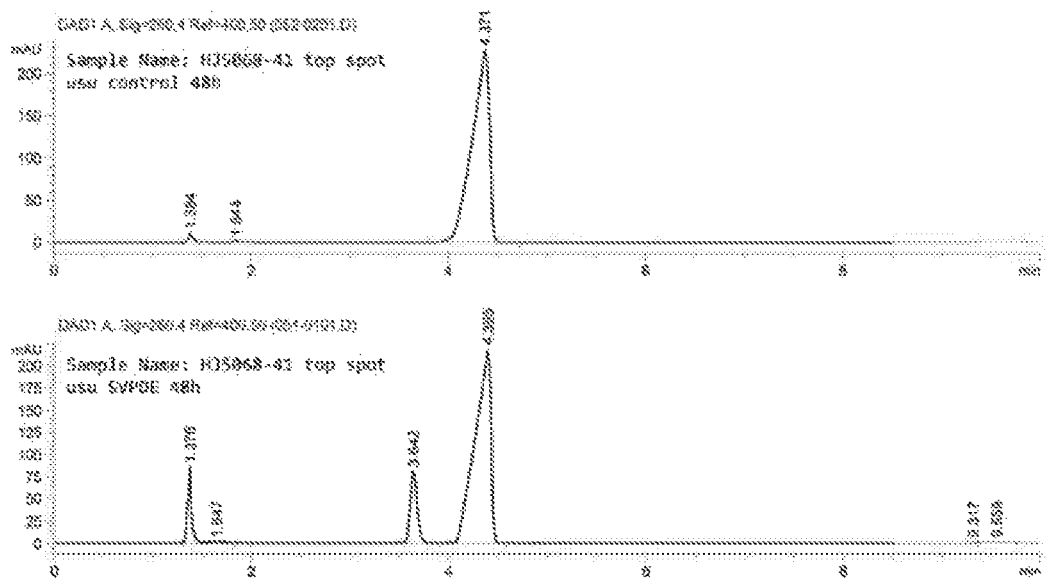
FIG. 10. RP-HPLC profiles of chiral pure phosphorothioate dinucleotide U$_{OMe}$ sU$_{OMe}$ (TLC top spot): top: control; bottom: 48 hours after incubation with SVPDE.
Figure 11:
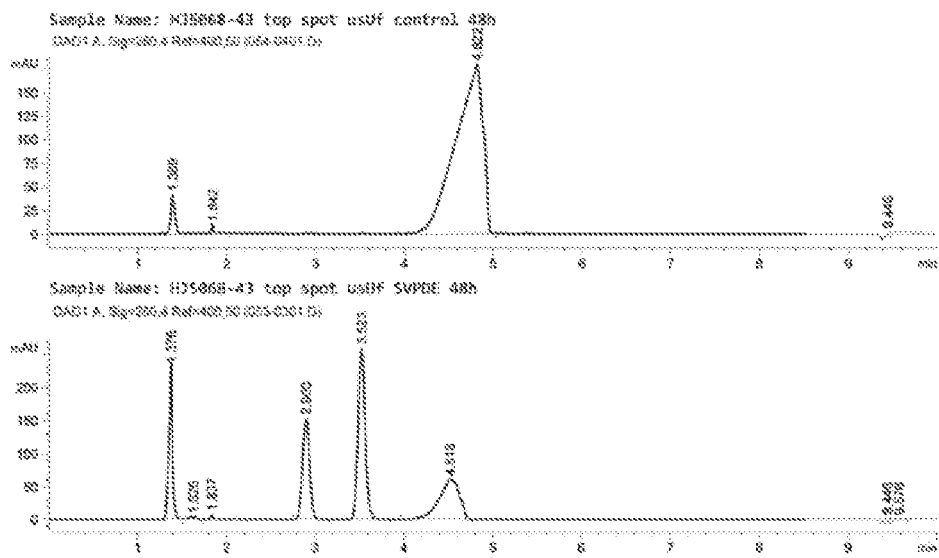
FIG. 11. RP-HPLC profiles of chiral pure phosphorothioate dinucleotide U$_{OMe}$ sU$_F$ (TLC top spot): top: control; bottom: 48 hours after incubation with SVPDE.
Figure 12:
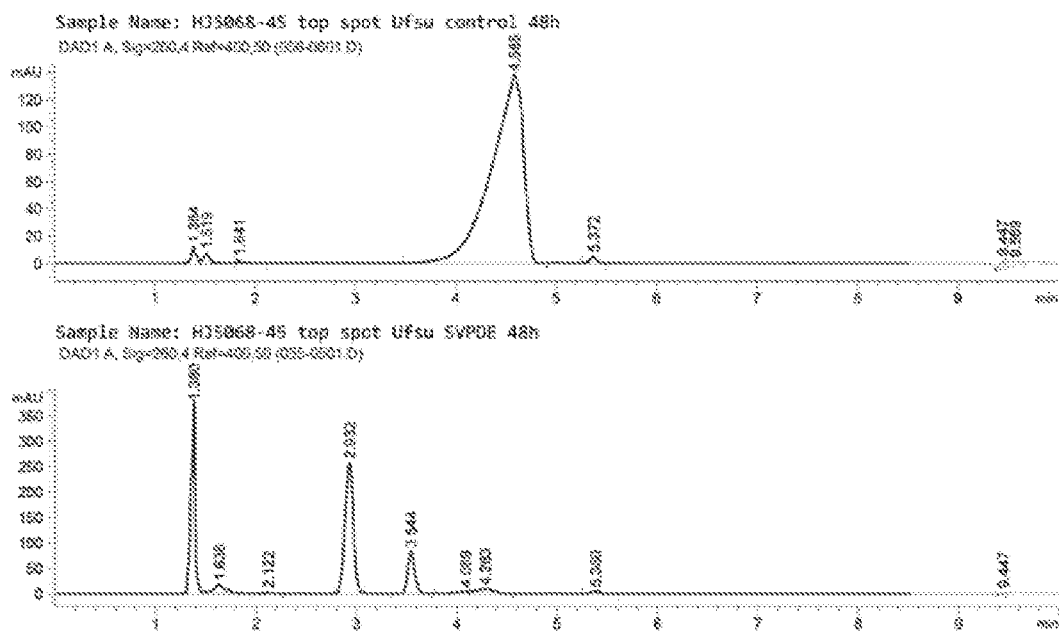
FIG. 12. RP-HPLC profiles of chiral pure phosphorothioate dinucleotide U$_F$ sU$_{OMe}$ (TLC top spot): top: control; bottom: 48 hours after incubation with SVPDE.
Figure 13:
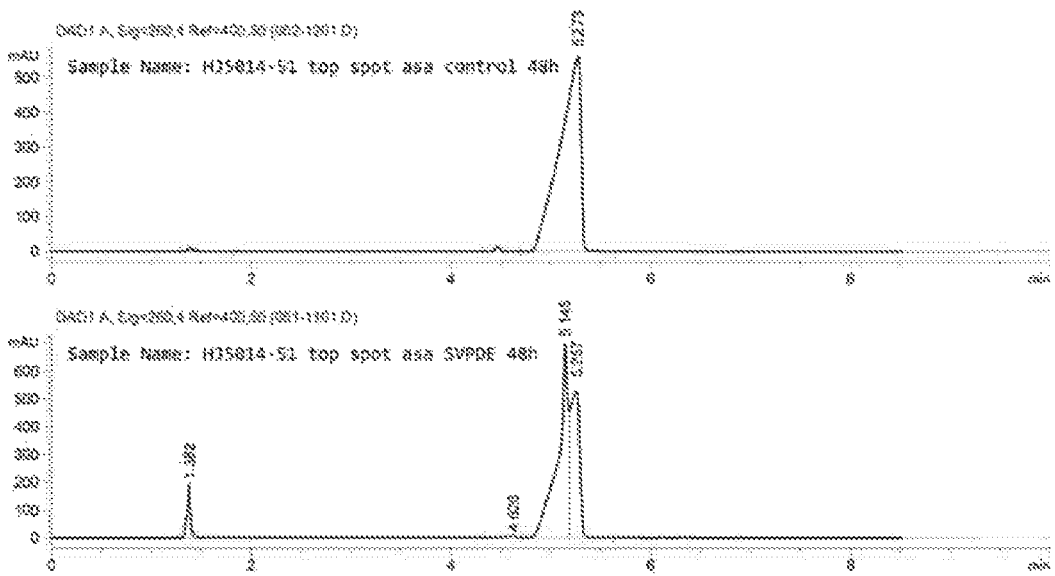
FIG. 13. RP-HPLC profiles of chiral pure phosphorothioate dinucleotide A$_{OMe}$ sA$_{OMe}$ (TLC top spot): top: control; bottom: 48 hours after incubation with SVPDE.
Figure 14:
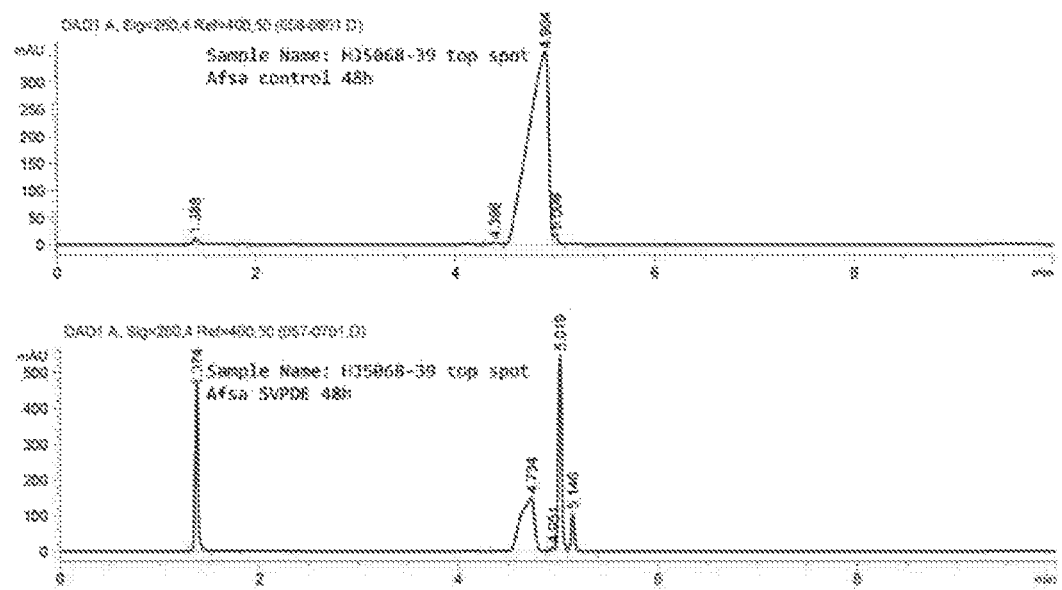
FIG. 14. RP-HPLC profiles of chiral pure phosphorothioate dinucleotide A$_F$ sA$_{OMe}$ (TLC top spot): top: control; bottom: 48 hours after incubation with SVPDE.
Figure 15:
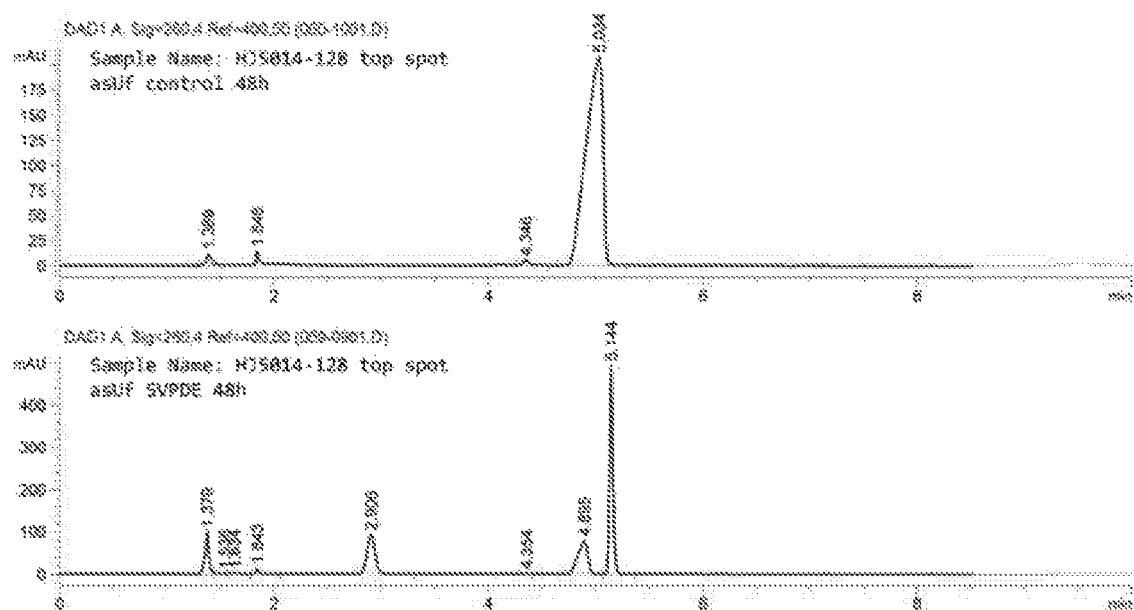
FIG. 15. RP-HPLC profiles of chiral pure phosphorothioate dinucleotide A$_{OMe}$ sU$_F$ (TLC top spot): top: control; bottom: 48 hours after incubation with SVPDE.
Figure 16:
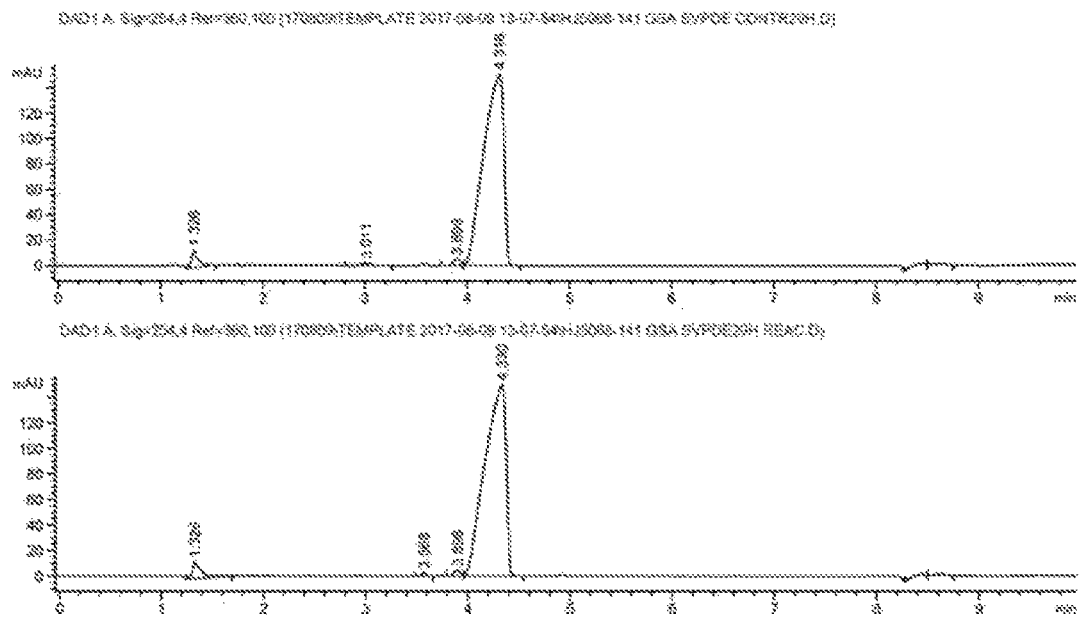
FIG. 16. RP-HPLC profiles of chiral pure phosphorothioate dinucleotide G$_{OMe}$ sA$_{OMe}$ (TLC top spot): top: control; bottom: 48 hours after incubation with SVPDE.
Figure 17:
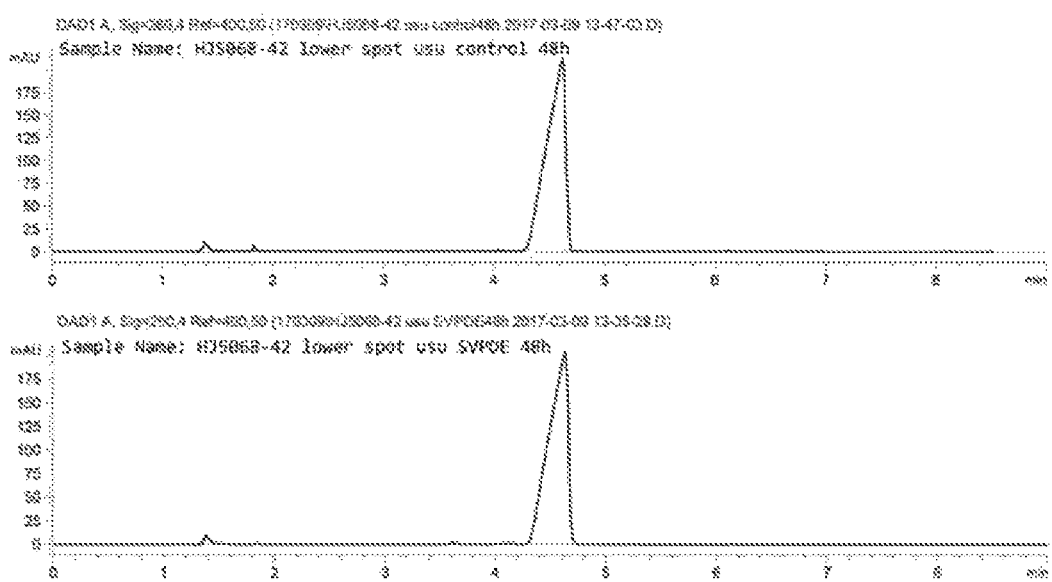
FIG. 17. RP-HPLC profiles of chiral pure phosphorothioate dinucleotide U$_{OMe}$ sU$_{OMe}$ (TLC lower spot): top: control; bottom: 48 hours after incubation with SVPDE.
Figure 18:
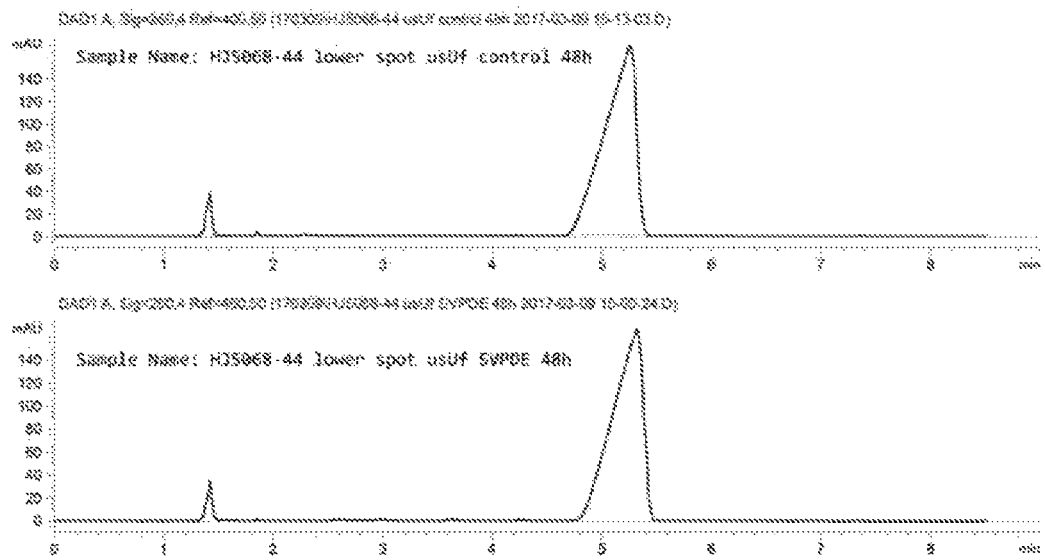
FIG. 18. RP-HPLC profiles of chiral pure phosphorothioate dinucleotide $U_{OMe}$ $sU_F$ (TLC lower spot): top: control; bottom: 48 hours after incubation with SVPDE.
Figure 19:
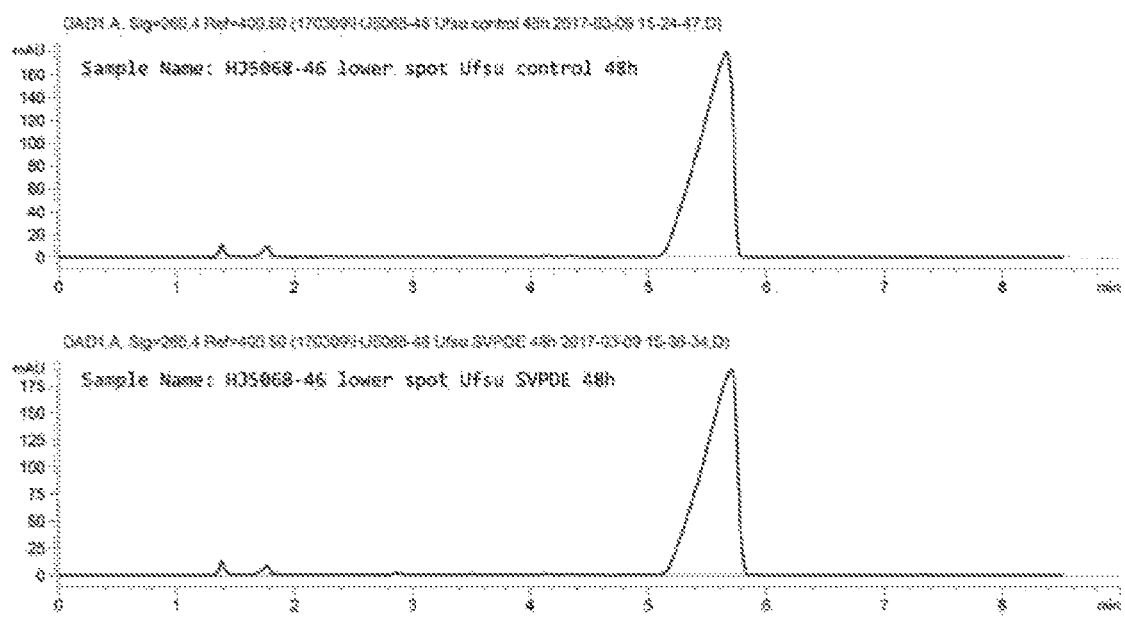
FIG. 19. RP-HPLC profiles of chiral pure phosphorothioate dinucleotide $U_F$ $sU_{OMe}$ (TLC lower spot): top: control; bottom: 48 hours after incubation with SVPDE.
Figure 20:
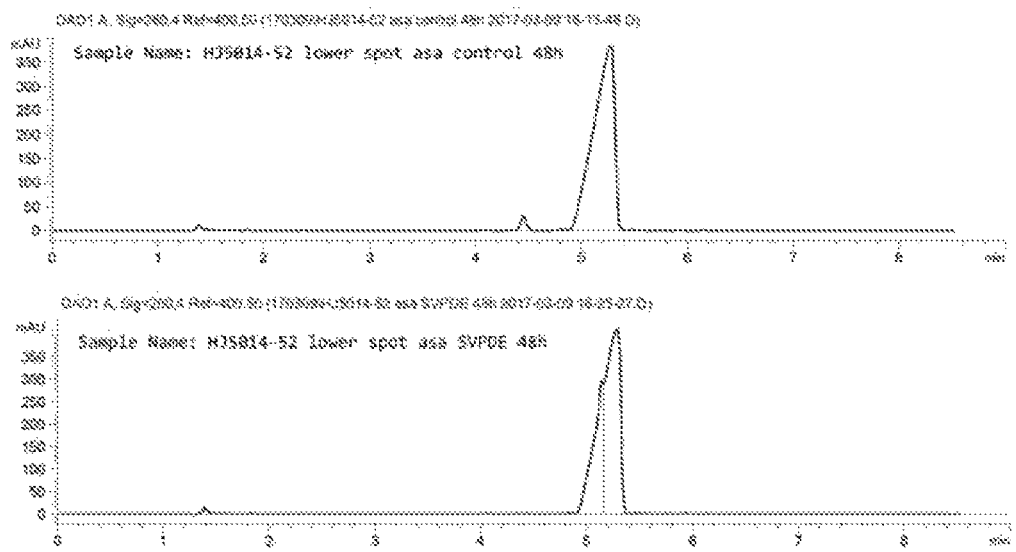
FIG. 20. RP-HPLC profiles of chiral pure phosphorothioate dinucleotide $A_{OMe}$ $sA_{OMe}$ (TLC lower spot): top: control; bottom: 48 hours after incubation with SVPDE.
Figure 21:
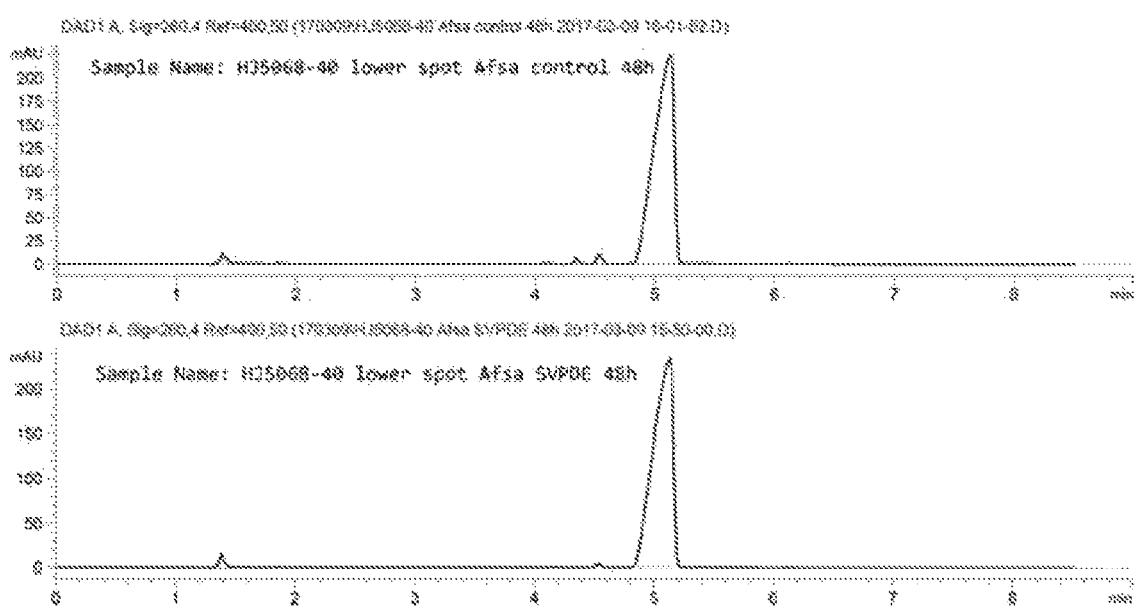
FIG. 21. RP-HPLC profiles of chiral pure phosphorothioate dinucleotide $U_F$ $sA_{OMe}$ (TLC lower spot): top: control; bottom: 48 hours after incubation with SVPDE.
Figure 22:
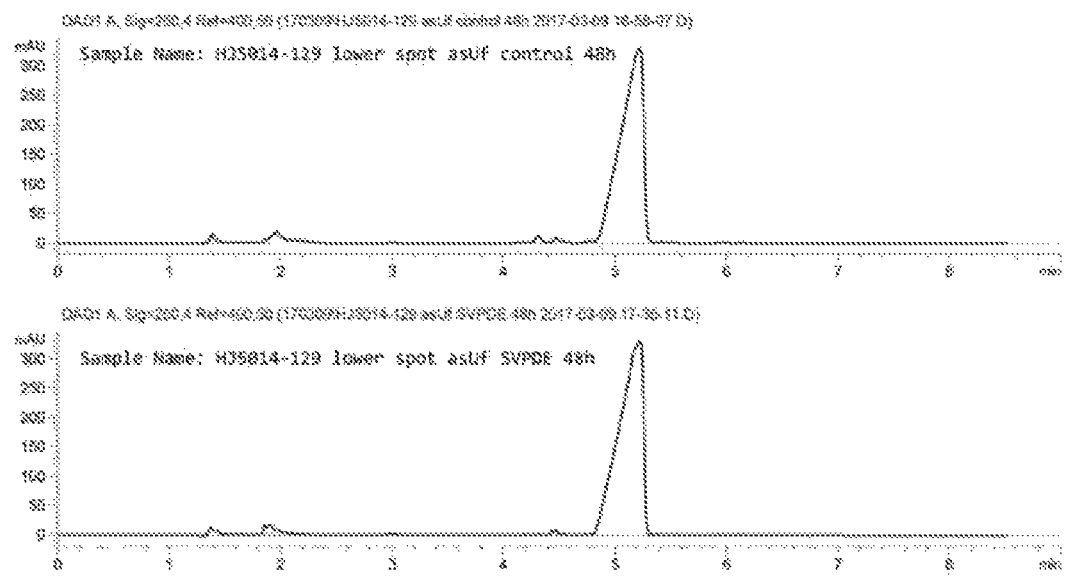
FIG. 22. RP-HPLC profiles of chiral pure phosphorothioate dinucleotide $A_{OMe}$ $sU_F$ (TLC lower spot): top: control; bottom: 48 hours after incubation with SVPDE.
Figure 23:
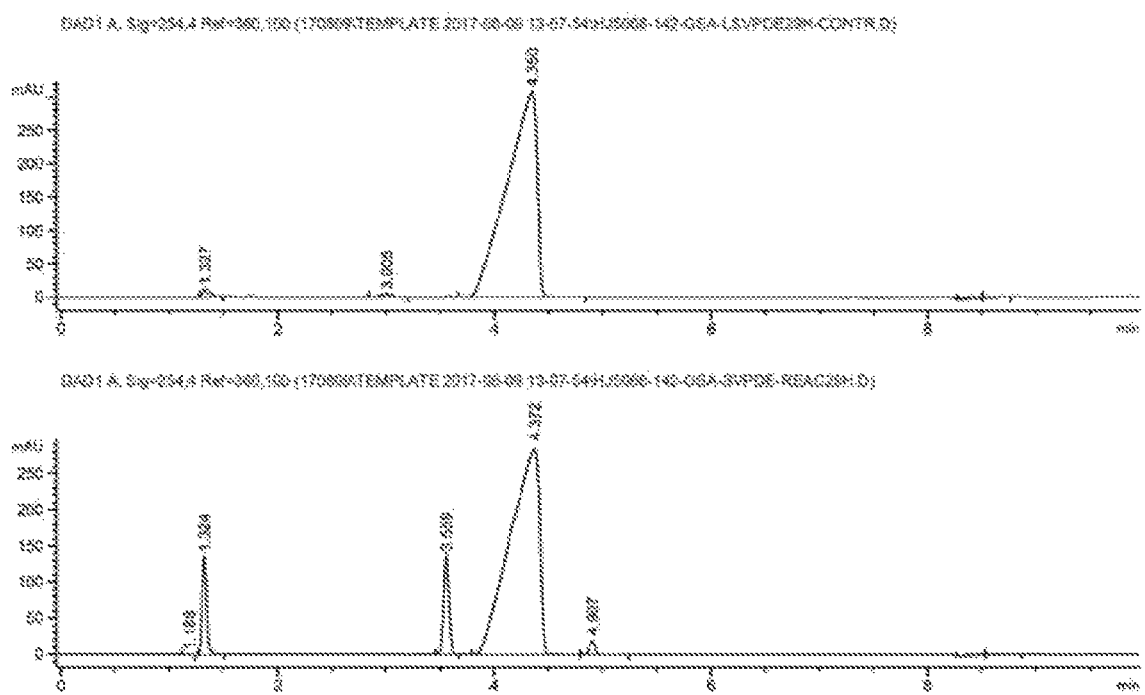
FIG. 23. RP-HPLC profiles of chiral pure phosphorothioate dinucleotide $G_{OMe}$ $sA_{OMe}$ (TLC lower spot): top: control; bottom: 48 hours after incubation with SVPDE.
Figure 24:
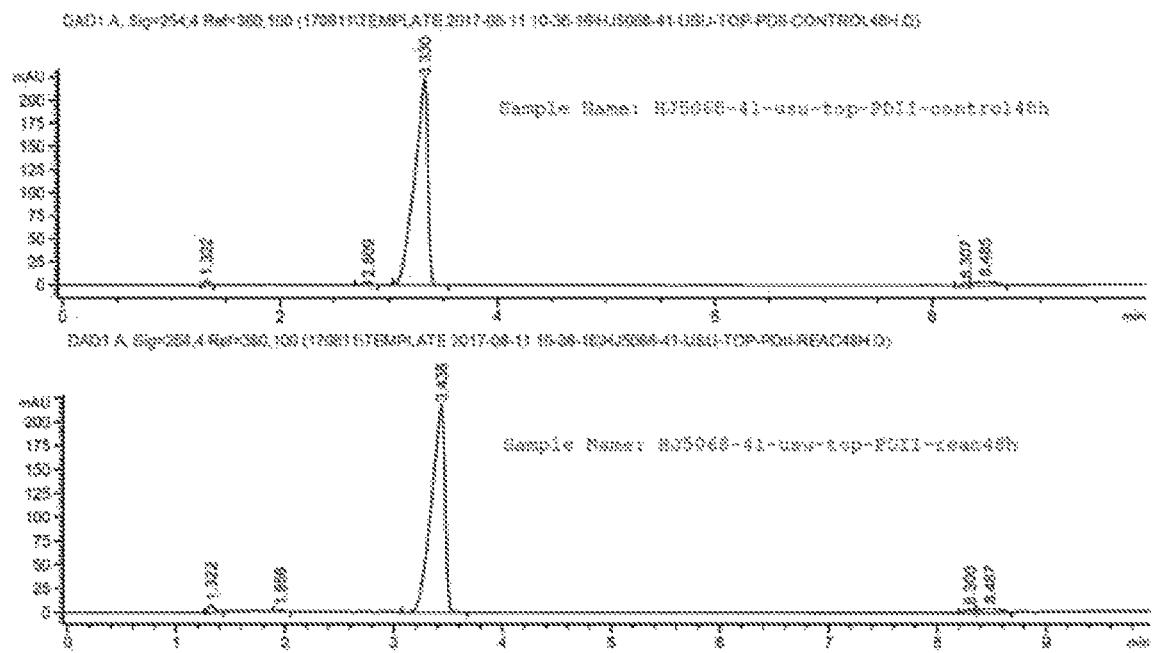
FIG. 24. RP-HPLC profiles of chiral pure phosphorothioate dinucleotide $U_{OMe}$ $sU_{OMe}$ (TLC top spot) after 48 hours reaction time: top: control; bottom: 48 hours after incubation with PDII.
Figure 25:
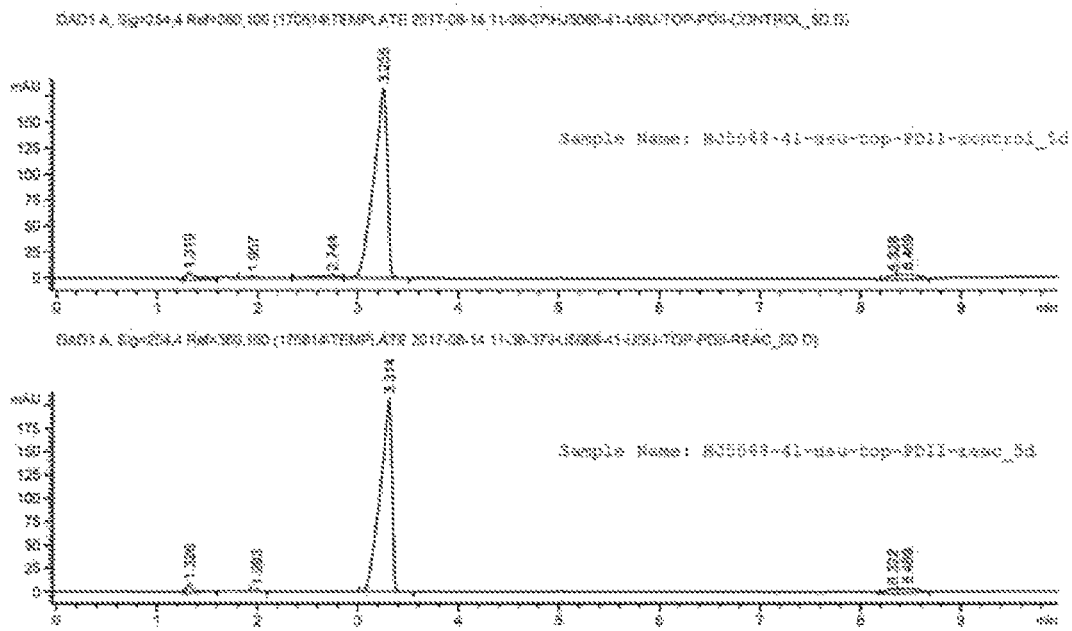
FIG. 25. RP-HPLC profiles of chiral pure phosphorothioate dinucleotide $U_{OMe}$ $sU_{OMe}$ (TLC top spot) after 5 days reaction time: top: control; bottom: 5 days after incubation with PDII.
Figure 26:
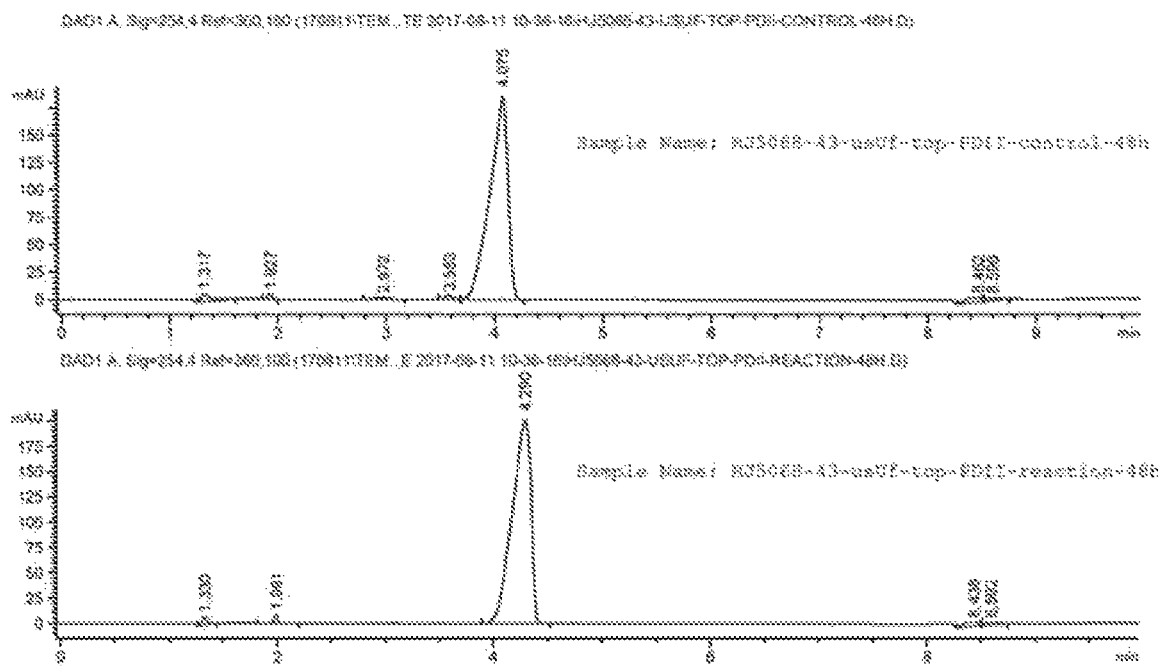
FIG. 26. RP-HPLC profiles of chiral pure phosphorothioate dinucleotide $U_{OMe}$ $sU_F$ (TLC top spot) after 48 hours reaction time: top: control; bottom: 48 hours after incubation with PDII.
Figure 27:
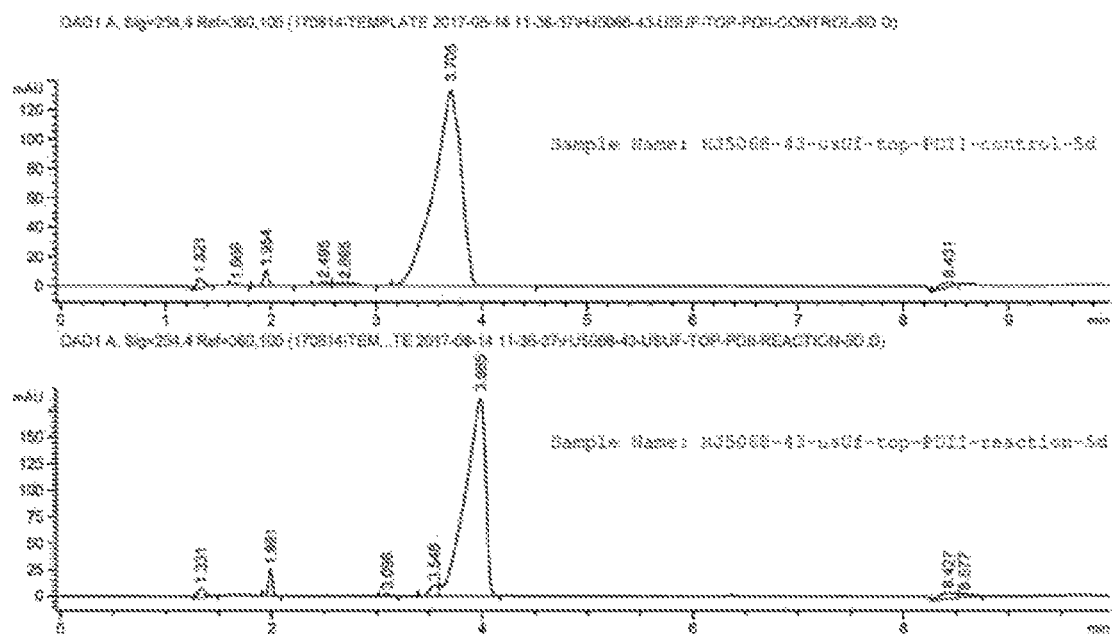
FIG. 27. RP-HPLC profiles of chiral pure phosphorothioate dinucleotide $U_{OMe}$ $sU_F$ (TLC top spot) after 5 days reaction time: top: control; bottom: 5 days after incubation with PDII.
Figure 28:
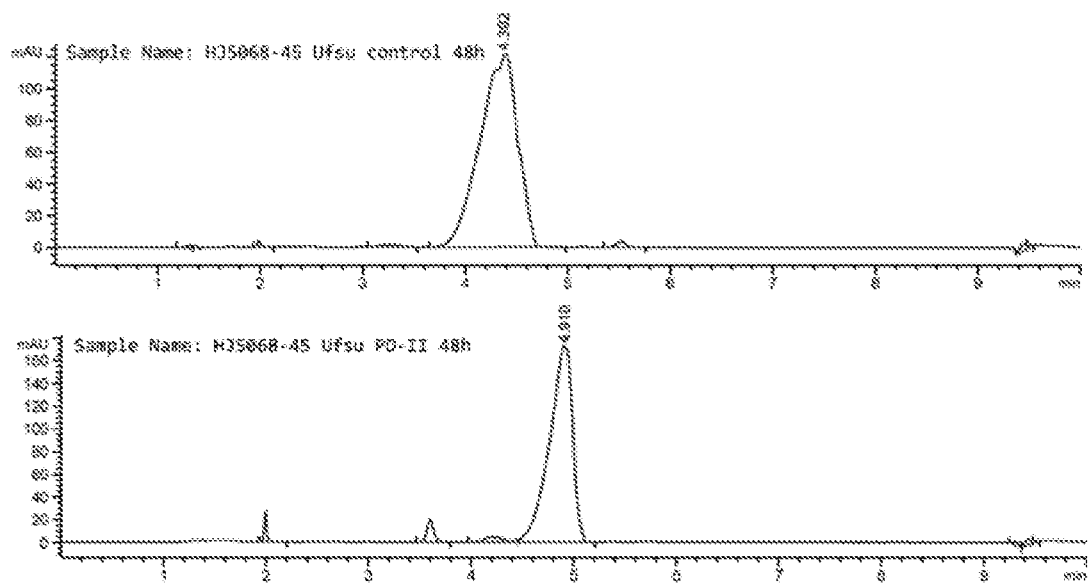
FIG. 28. RP-HPLC profiles of chiral pure phosphorothioate dinucleotide $U_F$ $sU_{OMe}$. (TLC top spot) after 48 hours reaction time: top: control; bottom: 48 hours after incubation with PDII.
Figure 29:
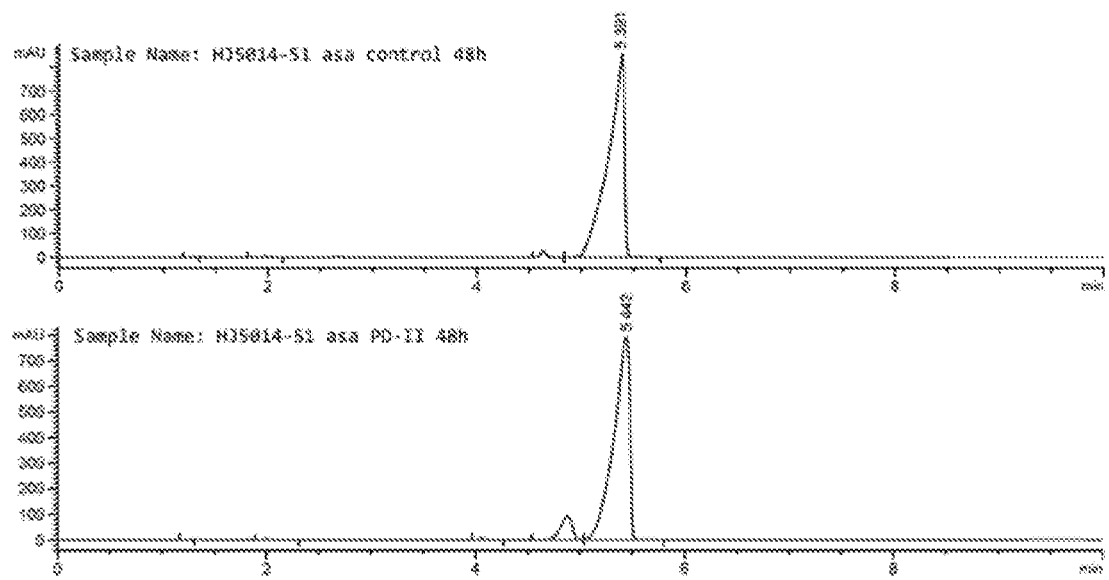
FIG. 29. RP-HPLC profiles of chiral pure phosphorothioate dinucleotide $A_{OMe}$ $sA_{OMe}$ (TLC top spot) after 48 hours reaction time: top: control; bottom: 48 hours after incubation with PDII.
Figure 30:
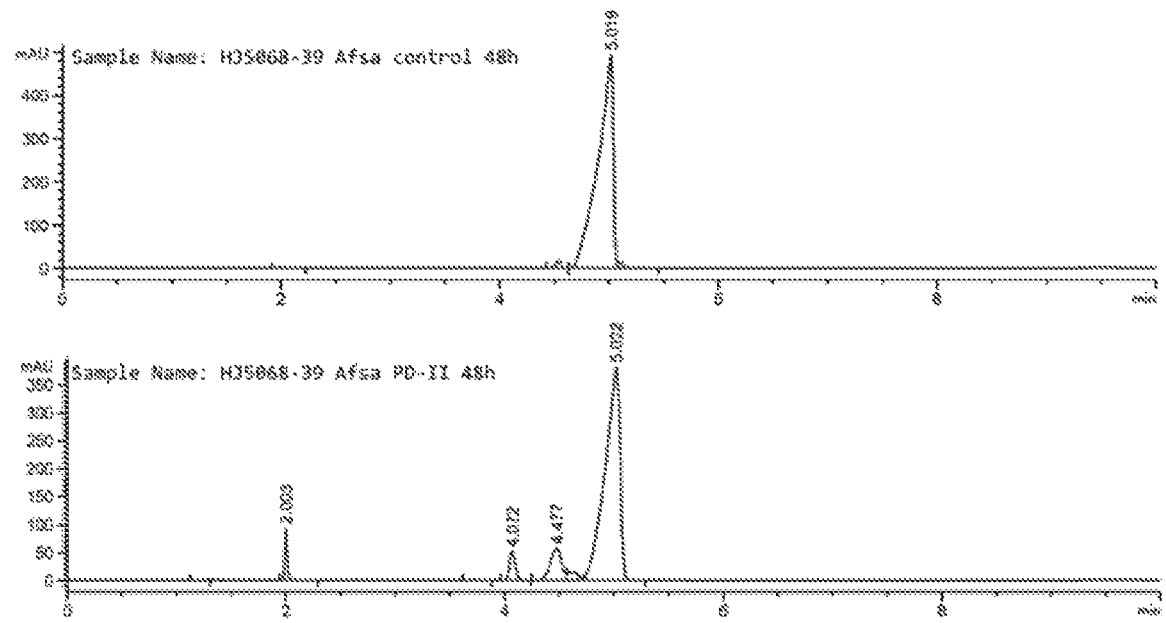
FIG. 30. RP-HPLC profiles of chiral pure phosphorothioate dinucleotide $A_F$ $sA_{OMe}$ (TLC top spot) after 48 hours reaction time: top: control; bottom: 48 hours after incubation with PDII.
Figure 31:
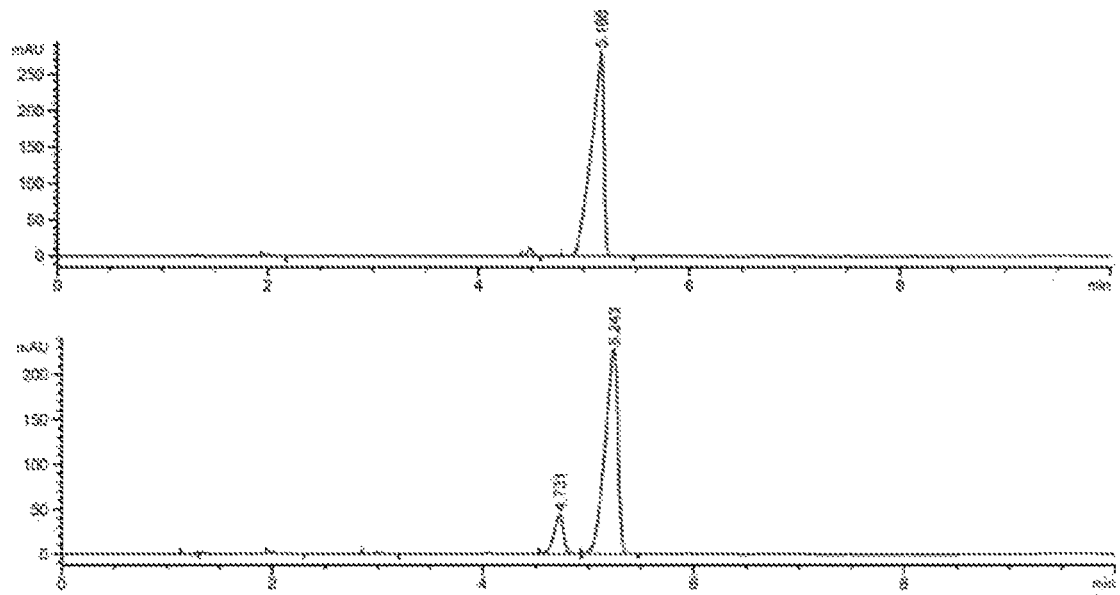
FIG. 31. RP-HPLC profiles of chiral pure phosphorothioate dinucleotide $A_{OMe}$ $sU_F$ (TLC top spot) after 48 hours reaction time: top: control; bottom: 48 hours after incubation with PDII.
Figure 32:
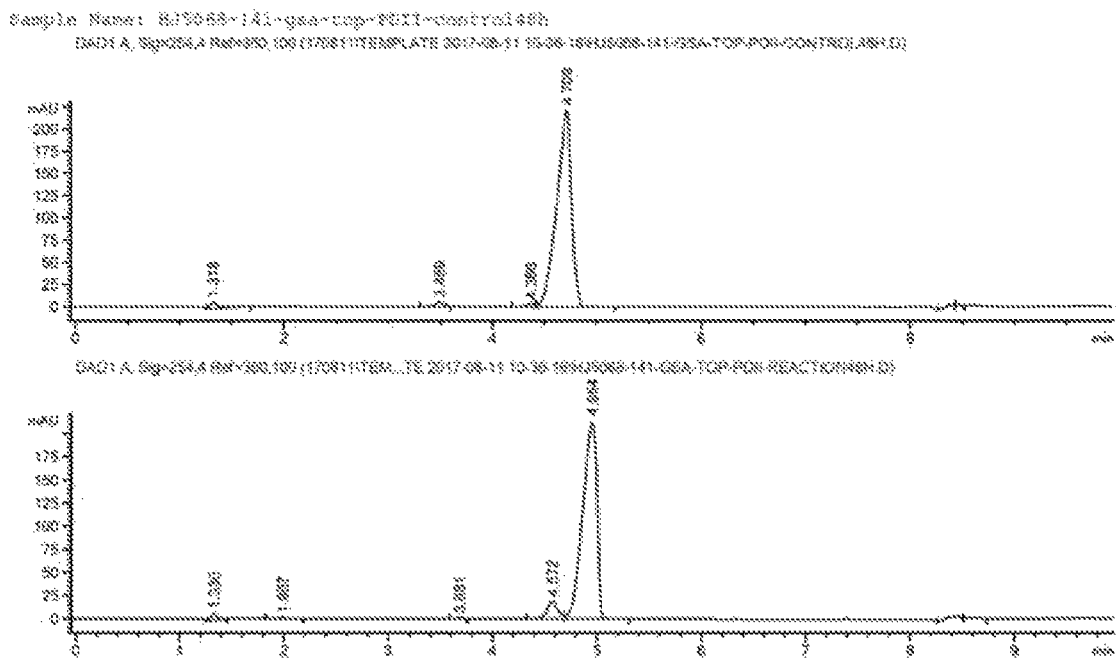
FIG. 32. RP-HPLC profiles of chiral pure phosphorothioate dinucleotide $G_{OMe}$ $sA_{OMe}$ (TLC top spot) after 48 hours reaction time: top: control; bottom: 48 hours after incubation with PDII.
Figure 33:
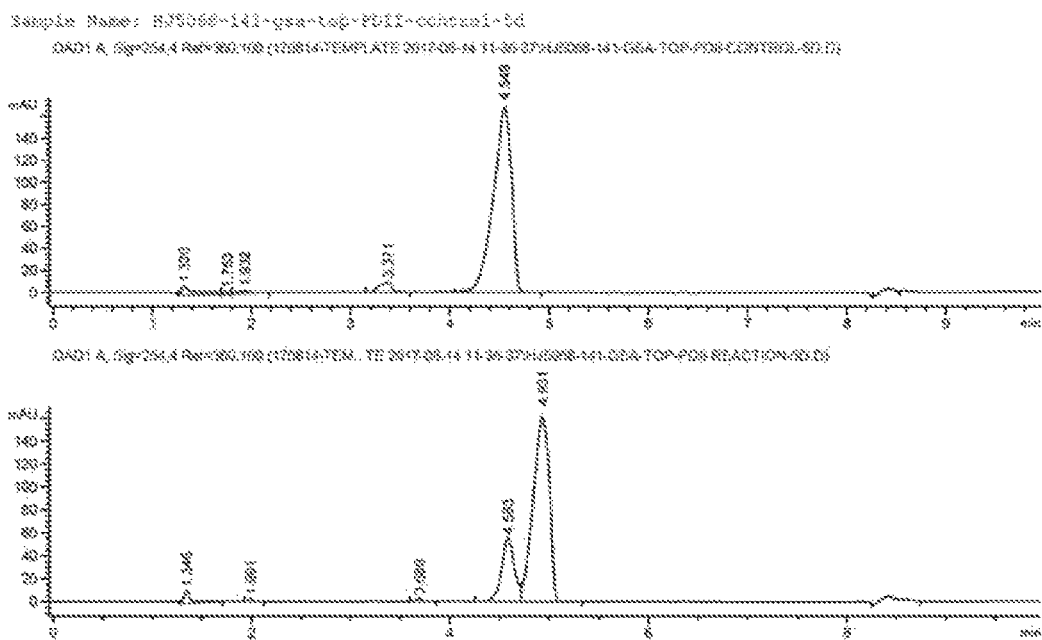
FIG. 33. RP-HPLC profiles of chiral pure phosphorothioate dinucleotide $G_{OMe}$ $sA_{OMe}$ (TLC top spot) after 5 days reaction time: top: control; bottom: 5 days after incubation with PDII.
Figure 34:
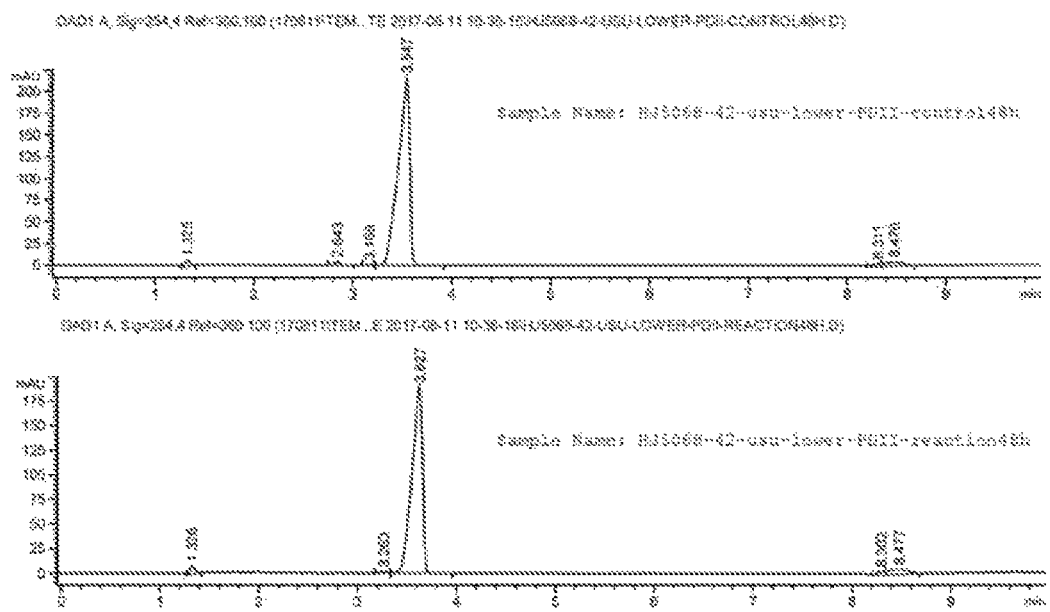
FIG. 34. RP-HPLC profiles of chiral pure phosphorothioate dinucleotide $U_{OMe}$ $sU_{OMe}$ (TLC lower spot) after 48 hours reaction time: top: control; bottom: 48 hours after incubation with PDII.
Figure 35:
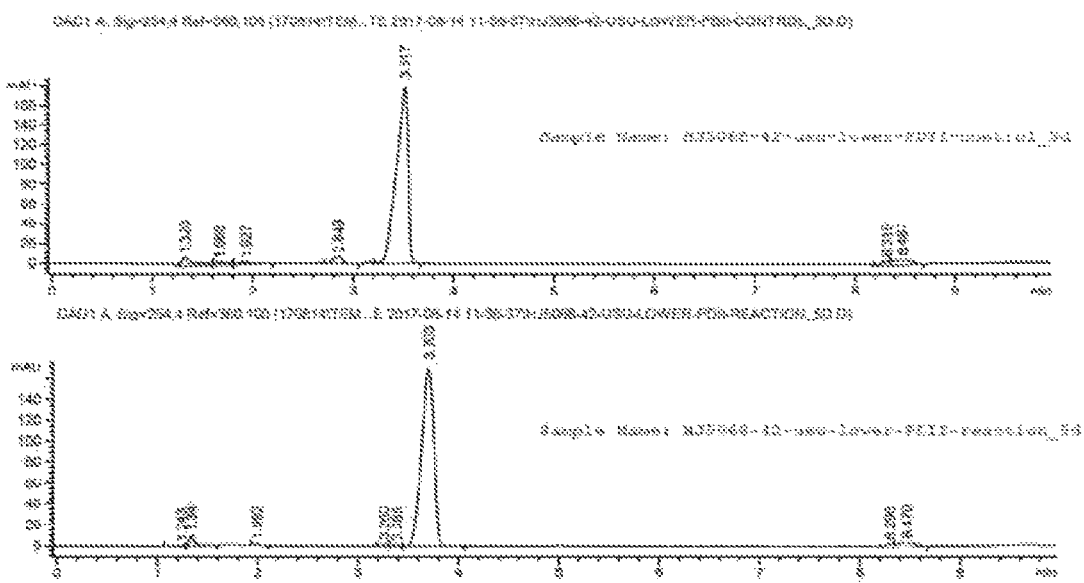
FIG. 35. RP-HPLC profiles of chiral pure phosphorothioate dinucleotide $U_{OMe}$ $sU_{OMe}$ (TLC lower spot) after 5 days reaction time: top: control; bottom: 5 days after incubation with PDII.
Figure 36:
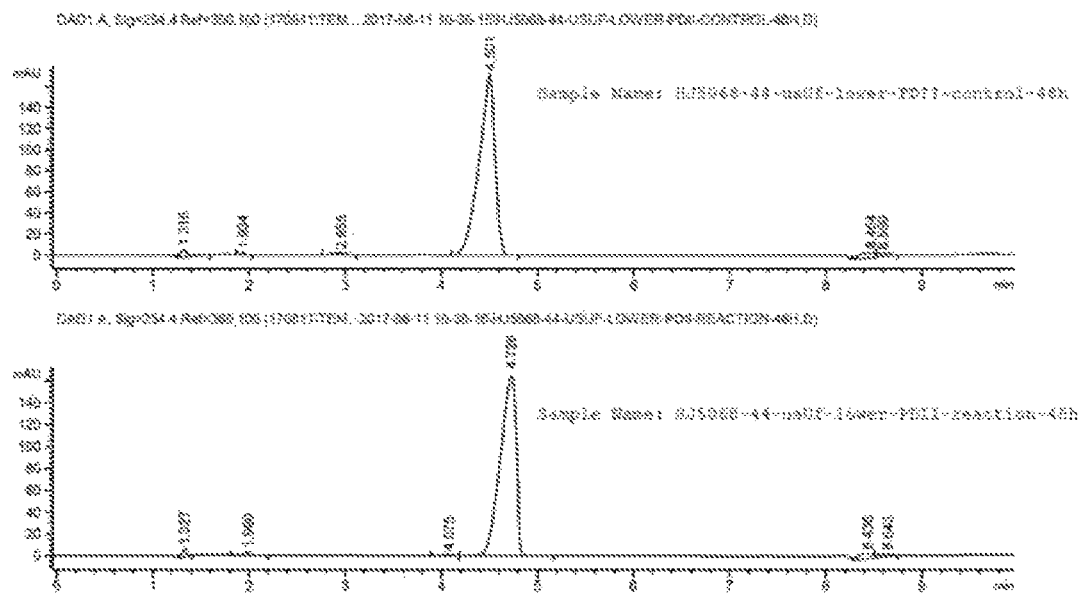
FIG. 36. RP-HPLC profiles of chiral pure phosphorothioate dinucleotide $U_{OMe}$ $sU_F$ (TLC lower spot) after 48 hours reaction time: top: control; bottom: 48 hours after incubation with PDII.
Figure 37:
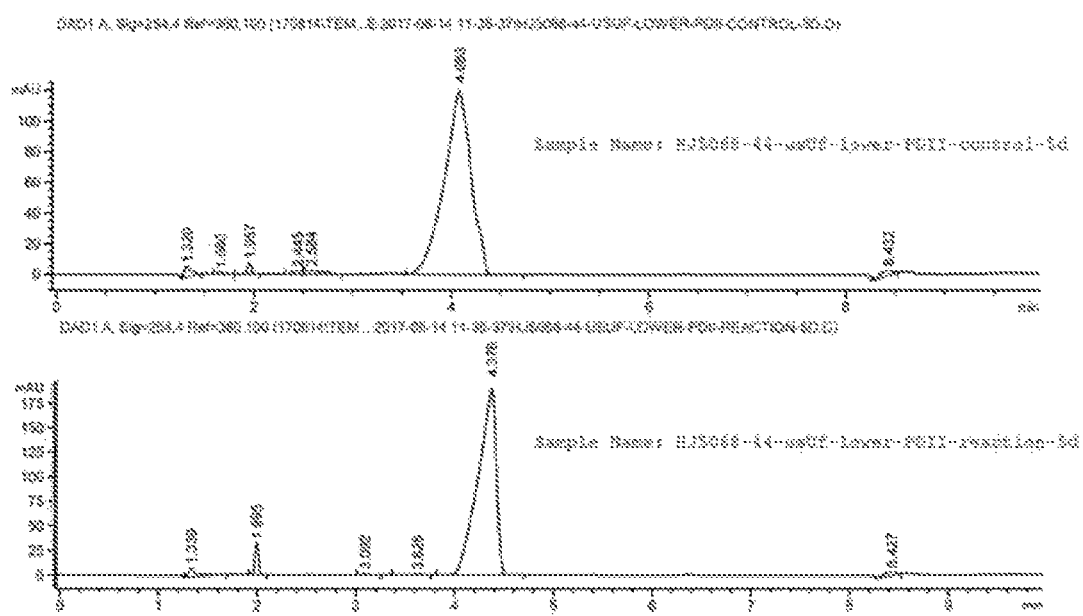
FIG. 37. RP-HPLC profiles of chiral pure phosphorothioate dinucleotide $U_{OMe}$ $sU_F$ (TLC lower spot) after 5 days reaction time: top: control; bottom: 5 days after incubation with PDII.
Figure 38:
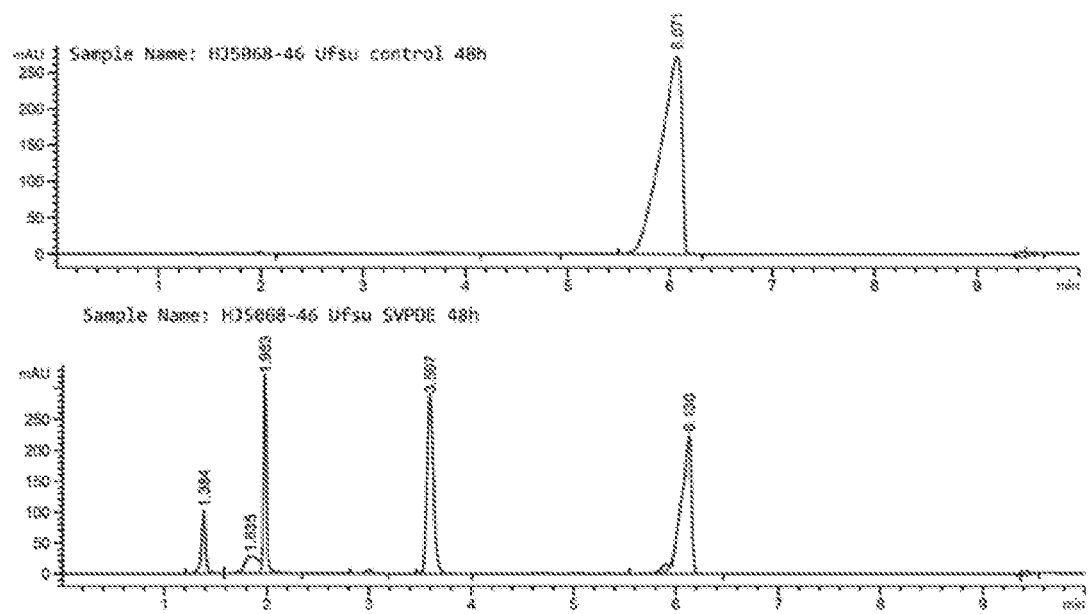
FIG. 38. RP-HPLC profiles of chiral pure phosphorothioate dinucleotide $U_F$ $sU_{OMe}$ (TLC lower spot) after 48 hours reaction time: top: control; bottom: 48 hours after incubation with PDII.
Figure 39:
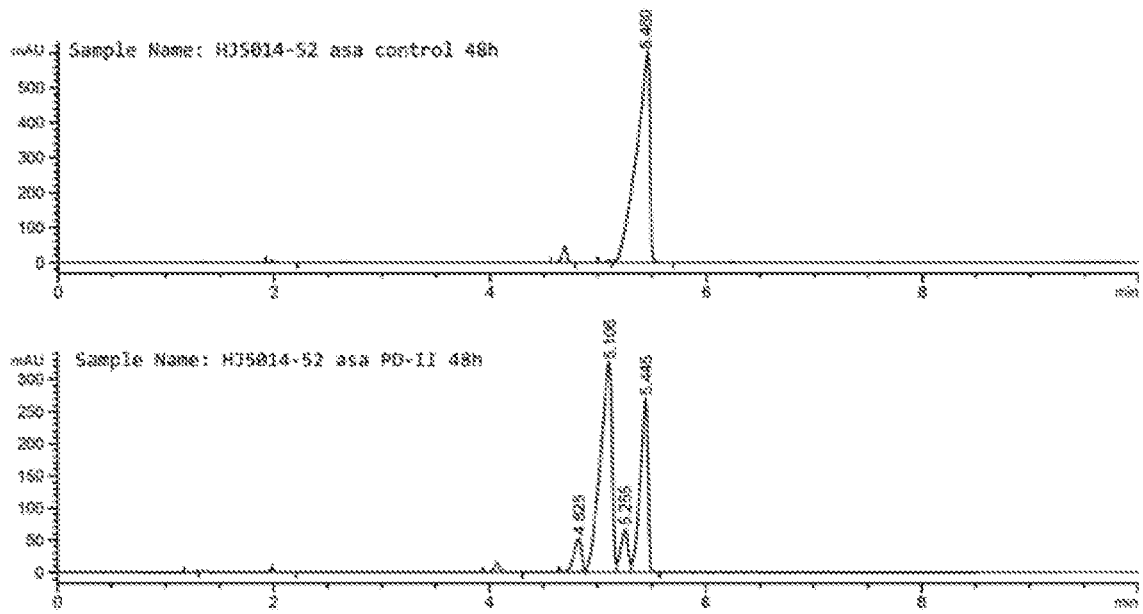
FIG. 39. RP-HPLC profiles of chiral pure phosphorothioate dinucleotide $A_{OMe}$ $sA_{OMe}$ (TLC lower spot) after 48 hours reaction time: top: control; bottom: 48 hours after incubation with PDII.
Figure 40:
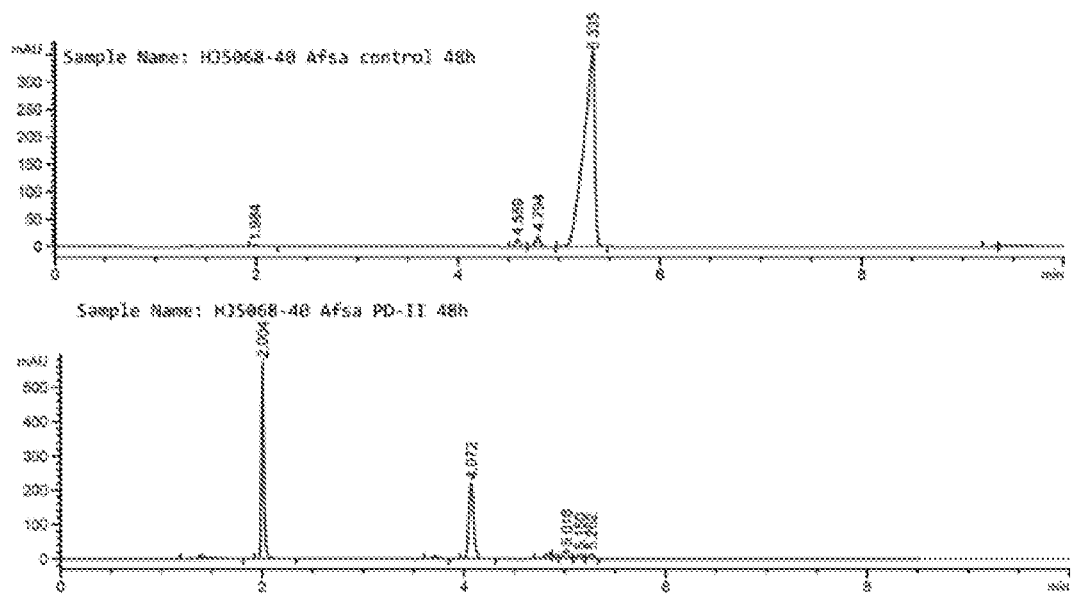
FIG. 40. RP-HPLC profiles of chiral pure phosphorothioate dinucleotide $A_F$ $sA_{OMe}$ (TLC lower spot) after 48 hours reaction time: top: control; bottom: 48 hours after incubation with PDII.
Figure 41:
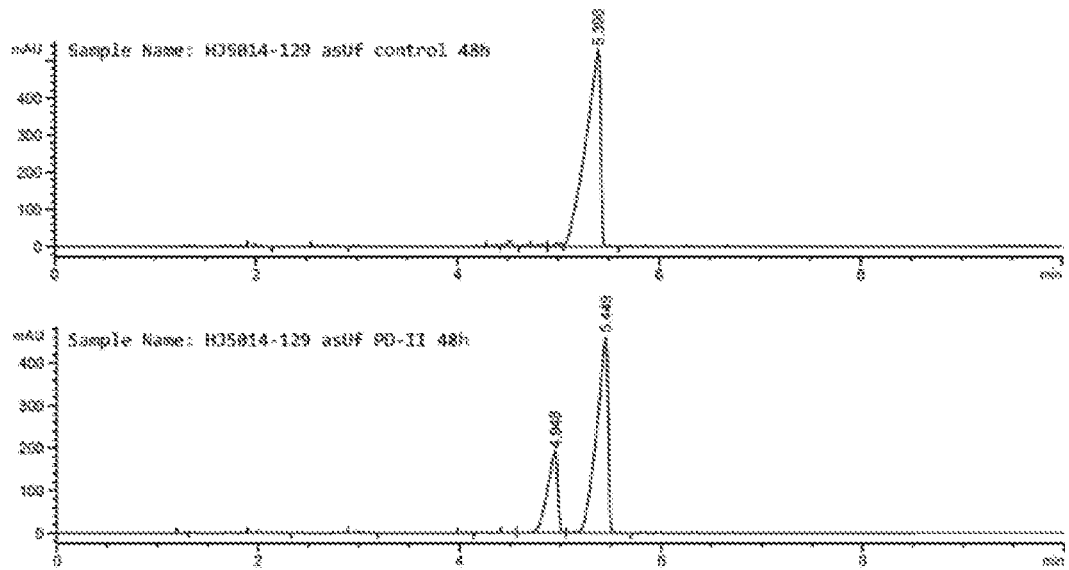
FIG. 41. RP-HPLC profiles of chiral pure phosphorothioate dinucleotide $A_{OMe}$ $sU_F$ (TLC lower spot) after 48 hours reaction time: top: control; bottom: 48 hours after incubation with PDII.
Figure 42:
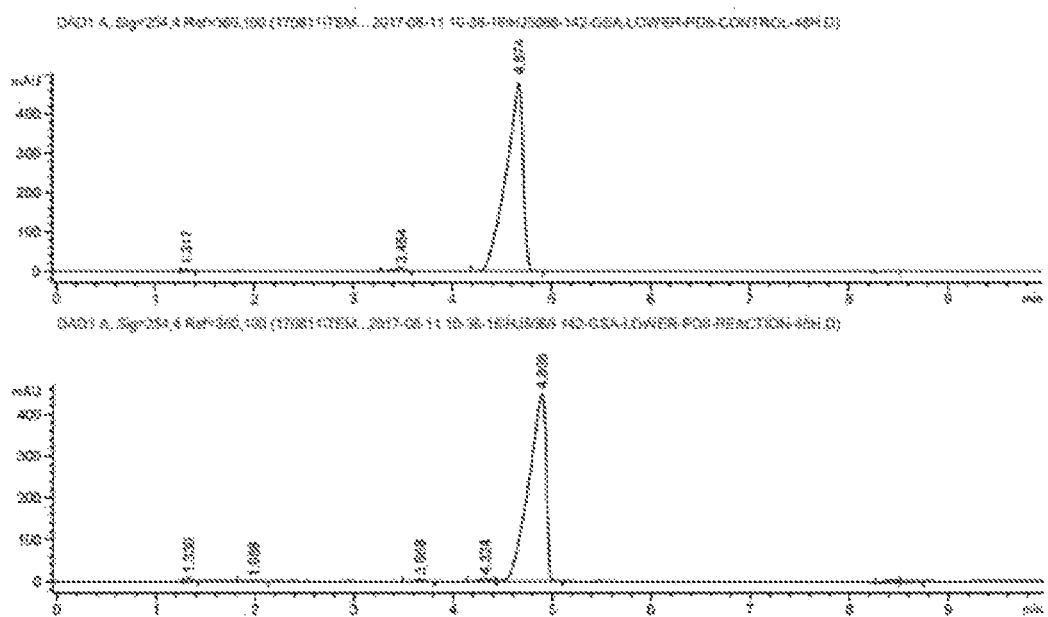
FIG. 42. RP-HPLC profiles of chiral pure phosphorothioate dinucleotide $G_{OMe}$ $sA_{OMe}$ (TLC lower spot) after 48 hours reaction time: top: control; bottom: 48 hours after incubation with PDII.
Figure 43:
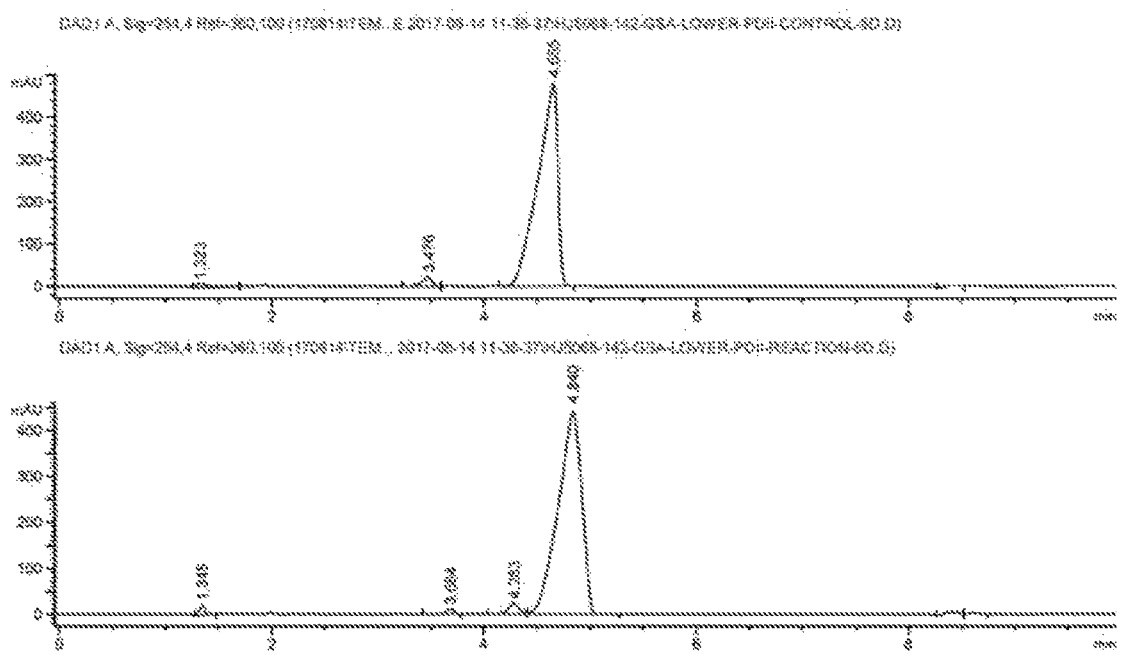
FIG. 43. RP-HPLC profiles of chiral pure phosphorothioate dinucleotide $G_{OMe}$ $sA_{OMe}$ (TLC lower spot) after 5 days reaction time: top: control; bottom: reaction with PDII.

To confirm the in vitro data indicating that the 5'-Rp chirality of the sense/antisense strand and the 3'-Sp chirality of the antisense strand was beneficial for the nuclease stability in vivo, the whole liver levels were examined, at day 4 in the case of the C5 target and at day 7 in the mrTTR target. The results in FIG. 9a illustrate that the R/R-S (si5 and si6) compounds had increased total liver levels, as compared to the 3PS-modified epimeric mixture, whereas the R/S-R compounds (si7 and si8) with the opposite chirality in the antisense strand yielded lower whole liver levels.

The Ago2 loading activities of the two high-activity compounds R/R-S (si5 and si6) and S/R-S (si13 and si14) were examined. The results in FIG. 9b illustrate that the si5 and si6 diastereomers showed up to 3-fold increased Ago2 loading activities, as compared to the 3PS-modified epimeric mixture. The Ago loading activities of si13 and si14 diastereomers showed up to 2-fold increased Ago2 loading activities, as compared to the 3PS-modified epimeric mixture.

These results suggest that the Rp PS stereochemistry at the 5'end and the Sp PS stereochemistry at the 3' end of antisense strand improved nuclease stability and resulted in a more potent siRNA, as compared to the 3PS epimeric mixture. In addition, evaluation of the in vitro and in vivo RISC loading experiments of the chirally pure 1PS-modified compounds and the chirally pure 3PS-modified compounds, in combination with the co-crystal structure analysis of hAgo2, indicated the preference of the Sp stereochemistry at the 3'end of antisense strand, which can be beneficial for RISC loading.

Example 2: Synthesis, Characterization, and Activity of Chirally Pure dsRNA Agents Having a Plurality of Chirally-Modified Phosphorothioate Linkages Chirally pure dsRNA agents having three chirally-modified phosphorothioate linkages (3PS) were synthesized using synthetic Approach 1 (DMT-On purification of chiral PS oligonucleotide approach) and/or Approach 2 and/or Approach 3.

Chirally pure dsRNA agents having 3, 4, 5, or 6 chirally-modified phosphorothioate linkages (e.g., 3PS, 4PS, 5PS, or 6PS) were synthesized using synthetic Approach 2 (chiral PS dinucleotide approach) and/or synthetic Approach 3 (Chiral OAP phosphoramidite building blocks).

Any oligonucleotide, containing two or more consecutive chirally pure PS linkages (e.g., 2PS, 3PS, or 4PS) were synthesized by coupling of OAP monomer building blocks (Approach 3).

Exemplary synthesis of the building blocks by Approach 2 and Approach 3 are described below.

A-1. Synthesis of Chirally Pure 2'-OMe Uridine-2'-OMe Uridine Phosphorothioate Dinucleotide ($U_{OMe}sU_{OMe}$)

Scheme A-1. Synthesis of chirally pure 2'-OMe uridine-2'-OMe uridine phosphorothioate dinucleotide ($U_{OMe}sU_{OMe}$) phosphoramidite building block (usu)

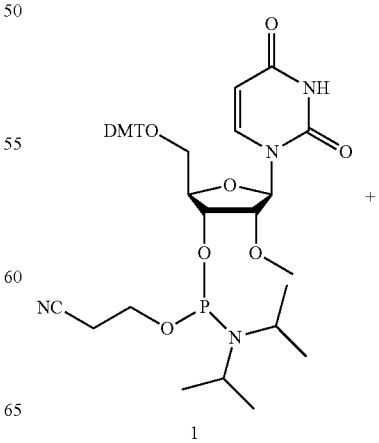

1

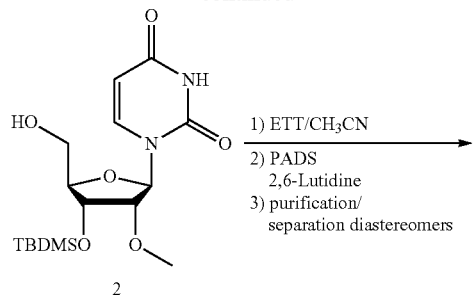

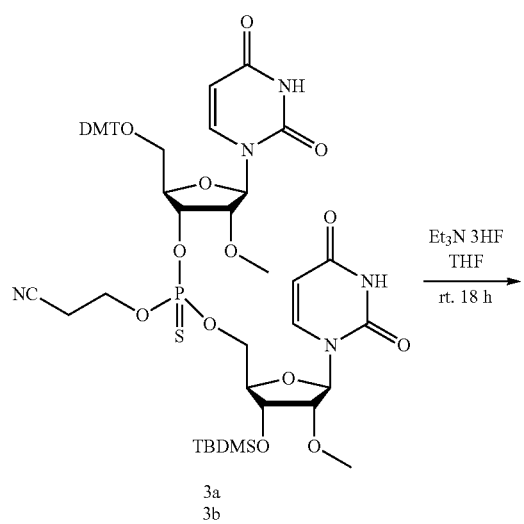

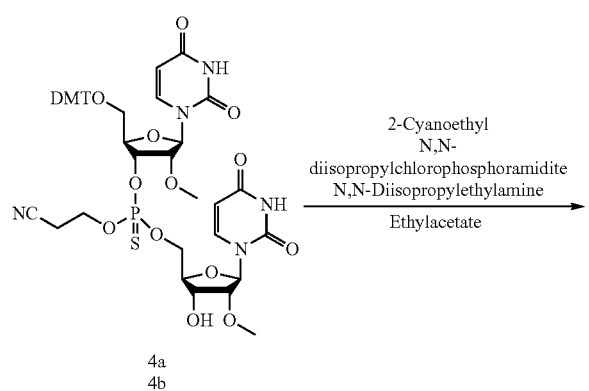

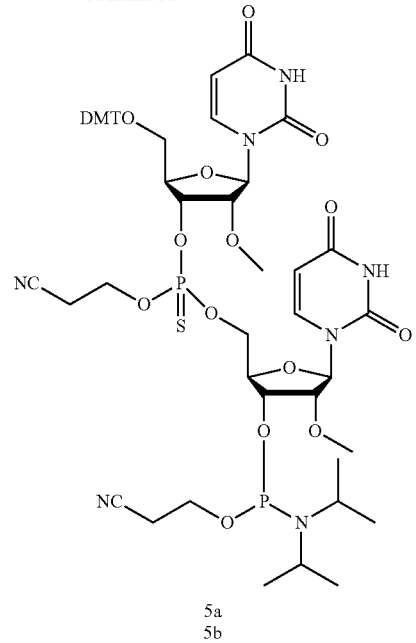

5a
5b

Compound 3: Compound 1 (11.18 g, 14.7 mmol) and compound 2 (5.73 g, 15.4 mmol, 1.05 eq.) were dried under high vacuum and dissolved in 150 ml dichloromethane (dry). To this solution 117 ml ETT (3.83 g, 29.4 mmol, 2 eq.) was added and the reaction mixture was stirred for 2.5 hours. PADS (6.35 g, 22.05 mmol, 1.5 eq.) and 2.52 ml 2.6-lutidine (2.36 g, 22.05 mmol, 1.5 eq.) were added, and the reaction mixture was stirred for 4 hours. The reaction mixture was diluted with 800 ml dichloromethane and washed with H$_2$O (300 ml) twice. The organic layer was dried over anhydrous Na$_2$SO$_4$ and concentrated. The diastereomers were separated on CombiFlash (330 g column, EtOAc: n-hexane (4:1), 3a R$_f$ (top spot)=0.45, 3b R$_f$ (lower spot)=0.24) to yield 3a (9.12 g, 56%) and 3b (6.7 g, 43%).

3a $^1$H NMR (500 MHz, acetonitrile-d$_3$) δ 9.17 (s, 2H), 7.65 (d, J=8.2 Hz, 1H), 7.59 (d, J=8.2 Hz, 1H), 7.46 (d, J=7.4 Hz, 2H), 7.40-7.27 (m, 8H), 6.92 (d, J=8.8 Hz, 4H), 5.94 (d, J=4.8 Hz, 1H), 5.85 (d, J=3.4 Hz, 1H), 5.66 (d, J=8.1 Hz, 1H), 5.35 (d, J=8.1 Hz, 1H), 5.25-5.16 (m, 1H), 4.51-4.40 (m, 1H), 4.36-4.10 (m, 7H), 3.80 (s, 6H), 3.48 (s, 3H), 3.46 (s, 3H), 3.45-3.43 (m, 2H), 2.75-2.70 (m, 2H), 0.93 (s, 9H), 0.14 (s, 6H). $^{13}$C NMR (126 MHz, CD$_3$CN) δ 163.95, 163.75, 159.91, 151.37, 151.34, 145.52, 141.03, 140.88, 136.38, 136.24, 131.22, 131.21, 130.46, 129.46, 129.18, 129.07, 128.18, 121.08, 114.29, 114.28, 103.23, 102.99, 89.11, 88.03, 87.83, 83.63, 82.95, 82.87, 82.71, 82.65, 82.31, 82.28, 76.06, 76.03, 70.88, 68.10, 68.05, 64.32, 64.29, 62.99, 59.23, 58.87, 56.04, 26.15, 20.16, 20.09, 18.75, 15.39, −4.36, −4.62. $^{31}$P NMR (162 MHz, CD$_3$CN) δ 68.77. Molecular weight for C$_{50}$H$_{62}$N$_5$O$_{15}$PSSi (M+Na): calculated 1086.3368, found 1086.3392.

3b $^1$H NMR (500 MHz, acetonitrile-d$_3$) δ 9.09 (s, 2H), 7.67 (d, J=8.2 Hz, 1H), 7.49 (dd, J=21.3, 7.8 Hz, 3H), 7.34 (d, J=8.9 Hz, 8H), 7.06 (d, J=7.7 Hz, 1H), 6.91 (d, J=8.9 Hz, 4H), 5.93 (d, J=4.7 Hz, 1H), 5.81 (d, J=3.2 Hz, 1H), 5.64 (d, J=8.1 Hz, 1H), 5.33 (d, J=8.1 Hz, 1H), 5.26-5.17 (m, 1H), 4.33-4.20 (m, 6H), 4.13-4.09 (m, 1H), 4.07-4.03 (m, 1H), 3.80 (s, 6H), 3.52 (s, 3H), 3.45 (s, 3H), 3.43 (d, J=3.0 Hz, 2H), 2.84 (t, J=5.8 Hz, 2H), 0.92 (s, 9H), 0.12 (s, 6H). $^{13}$C NMR (126 MHz, CD$_3$CN) δ 163.89, 163.73, 159.90, 159.89, 151.37, 151.28, 145.59, 141.00, 140.92, 138.31, 136.33, 136.20, 131.25, 131.23, 129.15, 129.05, 128.14, 121.34, 114.26, 114.26, 103.17, 102.98, 89.20, 88.01, 87.95, 83.59, 82.78, 82.71, 82.67, 82.62, 82.43, 82.40, 75.97, 75.93, 70.66, 67.77, 67.72, 64.57, 64.54, 62.87, 59.28, 58.83, 56.02, 26.16, 20.22, 20.15, 18.74, 15.39, −4.34, −4.61. $^{31}$P NMR (162 MHz, CD$_3$CN) δ 69.27. Molecular weight for C$_{50}$H$_{62}$N$_5$O$_{15}$PSSi (M+Na): calculated 1086.3368, found 1086.3392.

Compound 4: Compound 3 (3a top spot: 9.12 g, 8.6 mmol; 3b lower spot: 7.14 g, 6.7 mmol) was dissolved in dry THF (3a: 125 ml; 3b: 100 ml) and Et$_3$N 3HF (3a: 16.8 ml, 103.2 mmol, 12 eq.; 3b: 13.1 ml, 80.5 mmol, 12 eq.) was added. The reaction mixture was stirred for 14 hours. The reaction mixture was concentrated and purified by Combi-Flash column (DCM: 5% MeOH, R$_f$ (top spot)=0.23, Rr (lower spot)=0.24) to yield 4 (4a (top spot: 6.58 g, 80.2%), 4b (lower spot: 5.24 g, 82.4%)).

4a $^1$H NMR (500 MHz, DMSO-d$_6$) δ 11.45 (d, J=1.9 Hz, 1H), 11.38 (d, J=1.9 Hz, 1H), 7.66 (d, J=8.1 Hz, 1H), 7.59 (d, J=8.1 Hz, 1H), 7.37 (d, J=7.5 Hz, 2H), 7.32 (t, J=7.7 Hz, 2H), 7.25 (d, J=8.8 Hz, 5H), 6.90 (d, J=7.9 Hz, 4H), 5.85 (d, J=5.4 Hz, 1H), 5.82 (d, J=4.8 Hz, 1H), 5.62 (dd, J=8.1, 2.1 Hz, 1H), 5.43-5.37 (m, 2H), 5.14-5.08 (m, 1H), 4.31 (ddd, J=10.3, 6.8, 3.1 Hz, 1H), 4.27-4.22 (m, 1H), 4.22-4.17 (m, 2H), 4.17-4.01 (m, 4H), 3.73 (s, 6H), 3.38 (s, 3H), 3.35 (s, 3H), 3.33-3.28 (m, 3H), 2.88-2.81 (m, 2H). $^{13}$C NMR (126 MHz, DMSO) δ 162.88, 162.77, 158.17, 150.32, 150.29, 144.25, 140.17, 140.13, 135.05, 134.85, 129.75, 127.91, 127.72, 126.87, 120.00, 117.95, 113.26, 102.15, 102.14, 102.12, 102.09, 86.82, 86.79, 86.41, 86.24, 81.82, 81.75, 81.59, 81.16, 81.13, 79.90, 74.99, 74.97, 74.95, 68.39, 67.74, 67.69, 63.04, 63.00, 62.21, 58.02, 57.63, 55.04, 55.03, 18.79, 18.72. $^{31}$P NMR (202 MHz, DMSO) δ 67.74. Molecular weight for C$_{44}$H$_{48}$N5O$_{15}$PS (M+Na): calculated 972.2503, found 972.2500.

4b $^1$H NMR (400 MHz, acetonitrile-d$_3$) δ 9.09 (s, 2H), 7.63 (d, J=8.1 Hz, 1H), 7.49-7.41 (m, 3H), 7.37-7.21 (m, 7H), 6.92-6.83 (m, 4H), 5.90 (d, J=4.7 Hz, 1H), 5.78 (d, J=3.3 Hz, 1H), 5.60 (d, J=8.1 Hz, 1H), 5.32 (d, J=8.1 Hz, 1H), 5.23-5.13 (m, 1H), 4.32-4.18 (m, 5H), 4.15-4.05 (m, 2H), 4.03-3.94 (m, 1H), 3.77 (s, 7H), 3.49 (s, 3H), 3.46 (s, 3H), 3.40 (d, J=3.2 Hz, 2H), 3.32 (d, J=7.2 Hz, 1H), 2.85-2.77 (m, 2H). $^{13}$C NMR (101 MHz, CD$_3$CN) δ 163.89, 163.78, 159.90, 151.40, 151.30, 145.63, 141.06, 140.97, 136.35, 136.26, 131.26, 131.23, 129.16, 129.07, 128.15, 118.68, 114.28, 103.19, 103.04, 88.95, 87.99, 83.60, 82.83, 82.74, 82.68, 82.61, 82.42, 82.38, 75.92, 75.88, 69.70, 68.32, 68.27, 64.55, 64.51, 62.90, 59.28, 59.09, 56.03, 20.21, 20.12. $^{31}$P NMR (162 MHz, CD$_3$CN) δ 69.20. Molecular weight for C$_{44}$H$_{48}$N$_5$O$_{15}$PS (M+Na): calculated 972.2503, found 972.2500.

Compound 5: Compound 4 (4a top spot: 2 g, 2.1 mmol; 4b lower spot: 0.6 g, 0.63 mmol) was dried overnight under high vacuum and dissolved in dry ethyl acetate (4a: 25 ml; 4b: 5 ml). N,N-Diisopropylamine (4a: 915 μl, 679 mg, 5.25 mmol, 2.5 eq.; 4b: 274 μl, 204 mg, 4.58 mmol, 2.25 eq.) was added dropwise under rigorous stirring. Subsequently, 2-cyanoethyl N,N-diisopropylchlorophosphoramidite (4a: 937 μl, 994 mg, 4.2 mmol, 2 eq.; 4b: 281 μl, 298 mg, 1.26 mmol, 2.5 eq.) was added dropwise (over 1 minute), and the reaction mixture was stirred at room temperature for 1.5 hours. The reaction mixture was diluted with 200 ml EA, washed with 100 ml NaHCO$_3$ and 100 ml brine, dried over Na$_2$SO$_4$, and concentrated to dryness. The crude (white foam) was dissolved in 5 ml DCM and precipitated in 1 L cold n-hexane/diethyl ether (1:1) to yield 5a (top spot: 1.8 g, 74.5%), 5b (lower spot: 594.2 mg, 82%).

5a $^1$H NMR 58 (500 MHz, acetonitrile-d$_3$) δ 9.30 (s, 1H), 7.67-7.62 (m, 1H), 7.57 (d, J=8.2 Hz, 1H), 7.47-7.42 (m, 2H), 7.37-7.30 (m, 6H), 7.29-7.24 (m, 1H), 6.90 (d, J=8.8 Hz, 4H), 5.92 (d, J=4.7 Hz, 1H), 5.88 (dd, J=7.4, 4.3 Hz, 1H), 5.67-5.62 (m, 1H), 5.37-5.30 (m, 1H), 5.22-5.14 (m, 1H), 4.49-4.36 (m, 1H), 4.35-4.23 (m, 4H), 4.22-4.14 (m, 1H), 4.12-4.07 (m, 2H), 3.95-3.91 (m, 1H), 3.91-3.83 (m, 1H), 3.81-3.75 (m, 7H), 3.70-3.61 (m, 2H), 3.49-3.46 (m, 5H), 3.45-3.41 (m, 3H), 2.74-2.64 (m, 4H), 1.22-1.15 (m, 12H). $^{13}$C NMR (126 MHz, CD$_3$CN) δ 164.64, 164.59, 164.50, 160.46, 152.03, 151.97, 146.07, 146.06, 141.60, 141.57, 141.48, 136.94, 136.92, 136.78, 131.77, 129.74, 129.62, 128.74, 120.30, 120.24, 114.85, 103.79, 103.69, 89.82, 89.79, 89.24, 89.21, 88.59, 88.41, 88.38, 83.73, 83.29, 83.25, 83.21, 83.20, 83.16, 83.14, 82.87, 82.69, 82.62, 82.58, 76.55, 76.52, 76.49, 72.39, 72.28, 71.80, 71.66, 69.07, 69.01, 68.65, 64.88, 64.85, 63.45, 60.47, 60.32, 59.91, 59.81, 59.67, 59.66, 59.65, 59.41, 56.63, 56.61, 56.60, 56.58, 44.87, 44.82, 44.81, 44.77, 44.76, 44.72, 44.71, 25.72, 25.66, 25.57, 25.51, 25.46, 21.71, 21.65, 21.63, 21.57, 20.71, 20.64. $^{31}$P NMR (202 MHz, CD$_3$CN) δ 151.97, 151.56, 68.52. Molecular weight for C$_3$H$_{65}$N$_7$O$_{16}$P$_2$S (M+H): calculated 1150.3762, found 1150.3782.

5b $^1$H NMR 61 (500 MHz, acetonitrile-d$_3$) δ 9.09 (s, 2H), 7.65 (d, J=8.2 Hz, 1H), 7.51-7.43 (m, 3H), 7.37-7.30 (m, 6H), 7.29-7.24 (m, 1H), 6.89 (d, J=7.7 Hz, 4H), 5.92 (t, J=4.8 Hz, 1H), 5.83 (dd, J=7.7, 4.0 Hz, 1H), 5.64-5.60 (m, 1H), 5.34-5.30 (m, 1H), 5.24-5.17 (m, 1H), 4.42-4.15 (m, 8H), 3.94-3.81 (m, 2H), 3.78 (s, 6H), 3.72-3.61 (m, 2H), 3.50 (d, J=3.0 Hz, 3H), 3.47 (s, 2H), 3.45-3.40 (m, 4H), 2.86-2.79 (m, 2H), 2.71-2.63 (m, 2H), 1.21-1.15 (m, 12H). $^{13}$C NMR (126 MHz, CD$_3$CN) δ 163.87, 163.82, 163.76, 159.91, 151.40, 151.37, 151.32, 145.60, 145.59, 140.96, 140.92, 136.34, 136.20, 131.25, 131.23, 129.15, 129.06, 128.15, 114.28, 103.25, 103.19, 103.13, 89.41, 88.80, 88.04, 88.03, 87.91, 87.89, 83.20, 83.18, 82.70, 82.41, 81.95, 81.88, 81.83, 76.03, 75.99, 71.54, 71.42, 71.06, 70.92, 68.15, 68.11, 67.79, 67.75, 64.58, 64.54, 62.94, 62.91, 59.88, 59.73, 59.36, 59.30, 59.21, 59.13, 59.11, 58.86, 58.84, 56.03, 44.28, 44.25, 44.18, 44.15, 25.17, 25.11, 25.09, 25.03, 24.99, 24.96, 24.93, 24.91, 21.15, 21.08, 21.03, 20.22, 20.15. $^{31}$P NMR (202 MHz, CD$_3$CN) δ 151.68, 151.44, 68.80, 68.77. Molecular weight for C$_{53}$H$_{65}$N$_7$O$_{16}$P$_2$S (M+H): calculated 1150.3762, found 1150.3765.

A-2. Synthesis of Fully Deprotected, Chirally Pure U$_{OMe}$sU$_{OMe}$ (usu)

Scheme A-2. Synthesis of fully deprotected, chirally pure U$_{OMe}$sU$_{OMe}$ dinucleotide (usu)

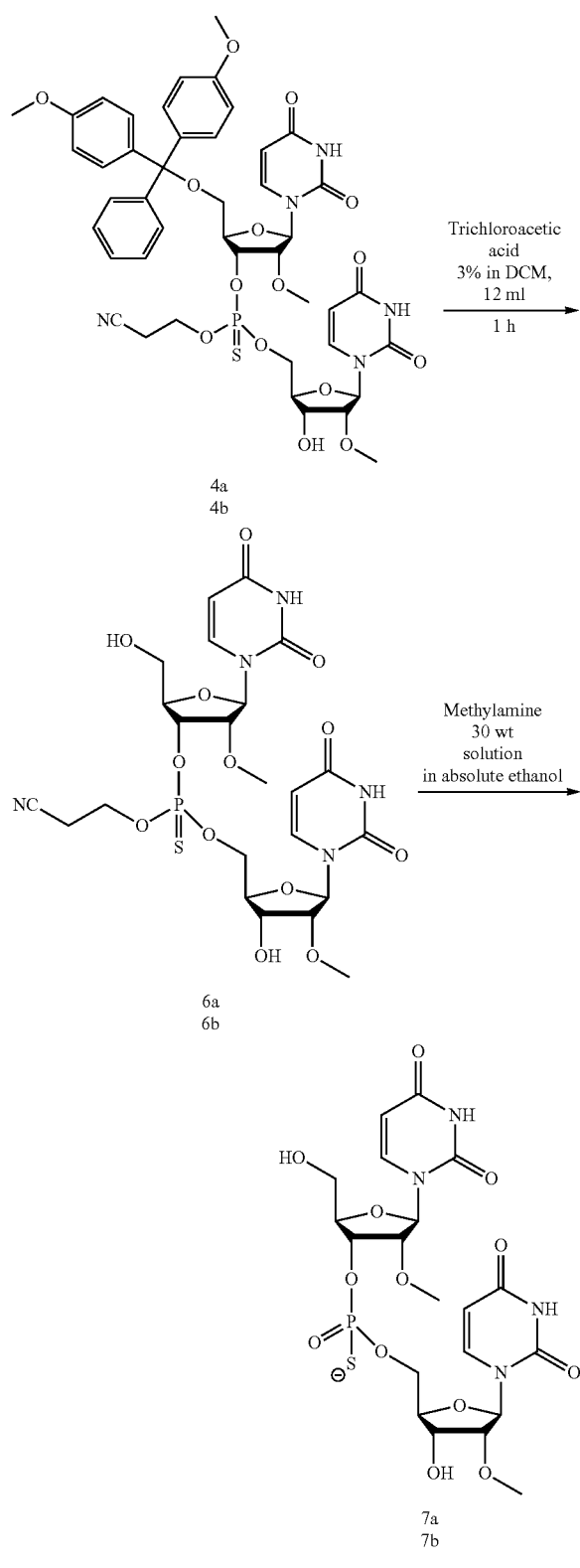

4a
4b 6a
6b 7a
7b

Compound 6: Compound 4 (4a top spot: 500 mg, 0.53 mmol; 4b lower spot: 500 mg, 0.53 mmol) was dissolved in 1.5 ml dichloromethane and 8 ml trichloroacetic acid (3% in DCM) was added. The reaction mixture was stirred at room temperature for 1 hour. The reaction mixture was concentrated and purified by CombiFlash column (40 g Gold column, 50 ml/min flow, 5% MeOH in DCM for 4 minutes, 10% MeOH in DCM for 5 minutes, 10% MeOH in DCM for 10 minutes) to yield 6a (Rf=0.27, 340 mg, 99%) and 6b (Rf=0.24, 561 mg, 90%).

6a $^1$H NMR (500 MHz, DMSO-d$_6$) δ 7.87 (d, J=8.2 Hz, 1H), 7.61 (d, J=8.1 Hz, 1H), 5.91 (d, J=7.1 Hz, 1H), 5.84 (d, J=5.0 Hz, 1H), 5.73-5.69 (m, 1H), 5.65 (d, J=8.1 Hz, 1H), 5.06 (ddd, J=10.4, 4.7, 1.8 Hz, 1H), 4.34-4.28 (m, 1H), 4.27-4.00 (m, 8H), 3.82 (t, J=5.1 Hz, 1H), 3.64-3.57 (m, 2H), 3.34 (s, 3H), 3.33 (s, 3H), 2.94 (t, J=5.8 Hz, 2H). $^{13}$C NMR (126 MHz, DMSO) δ 163.02, 162.94, 150.65, 150.43, 140.35, 140.23, 118.34, 102.75, 102.30, 86.88, 85.25, 83.81, 83.78, 82.02, 81.95, 81.67, 80.54, 80.50, 76.38, 76.34, 68.39, 67.82, 67.77, 63.32, 63.29, 60.59, 58.15, 57.77, 57.55, 54.96, 18.97, 18.90. $^{31}$P NMR (202 MHz, DMSO) δ 66.76. Molecular weight for C$_{23}$H$_{30}$N$_5$O$_3$PS (M+H): calculated 648.1377, found 648.1375.

6b $^1$H NMR (500 MHz, DMSO-d$_6$) δ 11.42 (d, J=2.0 Hz, 1H), 11.38 (d, J=1.8 Hz, 1H), 7.87 (d, J=8.2 Hz, 1H), 7.61 (d, J=8.1 Hz, 1H), 5.91 (d, J=6.9 Hz, 1H), 5.83 (d, J=4.7 Hz, 1H), 5.71 (dd, J=8.1, 2.1 Hz, 1H), 5.64 (dd, J=8.1, 2.2 Hz, 1H), 5.42-5.36 (m, 2H), 5.06 (ddd, J=10.6, 4.8, 2.1 Hz, 1H), 4.32-4.08 (m, 7H), 4.05-4.00 (m, 1H), 3.82 (t, J=5.0 Hz, 1H), 3.60 (s, 2H), 3.36 (s, 6H), 2.96 (t, J=5.8 Hz, 2H). $^{13}$C NMR (126 MHz, DMSO) δ 162.92, 162.85, 150.57, 150.35, 140.25, 140.07, 118.16, 102.58, 102.13, 86.90, 85.24, 83.69, 83.65, 81.79, 81.72, 81.57, 80.42, 80.38, 76.09, 76.06, 68.30, 67.56, 67.51, 63.31, 63.27, 60.51, 58.00, 57.68, 54.88, 18.80, 18.73. $^{31}$P NMR (202 MHz, DMSO) δ 66.87. Molecular weight for C$_{23}$H$_{30}$N$_5$O$_3$PS (M+Na): calculated 670.1196, found 670.1216.

Compound 7: Compound 6 (6a top spot: 340 mg, 0.38 mmol; 6b lower spot: 312 mg, 0.35 mmol) was dissolved in 12 ml methylamine (33 wt % solution in absolute ethanol) and stirred for 5 minutes at room temperature. The reaction mixture was concentrated and purified by CombiFlash column (24 g Gold column, 35 ml/min flow, ethyl acetate/MeOH (70:30) for 8 minutes, ethyl acetate/MeOH (60:40) for 5 minutes) to yield 7a (228 mg, 78%) and 7b (428 mg, 86%). In ethyl acetate/MeOH (2:1), 7a Rf=0.08 and 7b Rf=0.08.

7a $^1$H NMR (500 MHz, deuterium oxide) δ 8.12 (d, J=8.2 Hz, 6H), 8.02 (d, J=8.1 Hz, 1H), 6.04 (s, 1H), 5.97 (s, 1H), 5.90 (d, J=8.1 Hz, 1H), 5.85 (d, J=8.0 Hz, 1H), 4.91-4.83 (m, 1H), 4.47 (t, J=4.9 Hz, 1H), 4.35-4.24 (m, 3H), 4.24-4.12 (m, 2H), 4.10-3.95 (m, 2H), 3.95-3.84 (m, 1H), 3.60 (s, 3H), 3.56 (s, 3H). $^{13}$C NMR (126 MHz, d$_2$O) δ 165.84, 165.76, 151.22, 151.18, 141.32, 141.18, 102.30, 101.87, 87.44, 87.12, 82.93, 82.89, 82.85, 82.51, 82.43, 81.35, 81.32, 71.46, 71.42, 67.83, 63.72, 63.66, 59.45, 58.09, 57.76. $^{31}$P NMR (202 MHz, D$_2$O) δ 56.74. Molecular weight for C$_{20}$H$_{27}$N$_4$O$_{13}$PS (M+Na): calculated 617.0931, found 617.0908.

7b $^1$H NMR (500 MHz, deuterium oxide) δ 8.04 (d, J=8.1 Hz, 1H), 7.97 (d, J=8.1 Hz, 1H), 6.04 (d, J=3.3 Hz, 1H), 5.99 (d, J=3.5 Hz, 1H), 5.92-5.88 (m, 2H), 4.88-4.83 (m, 1H), 4.47 (t, J=5.4 Hz, 1H), 4.38-4.33 (m, 1H), 4.31-4.19 (m, 4H), 4.06 (t, J=4.0 Hz, 1H), 4.00-3.85 (m, 2H), 3.57 (s, 3H), 3.55 (s, 3H). $^{13}$C NMR (126 MHz, D$_2$O) δ 166.11, 166.02, 151.42, 141.34, 102.32, 102.14, 87.27, 87.15, 83.23, 83.19, 82.73, 82.70, 82.63, 81.31, 81.28, 71.42, 71.38, 67.96, 64.46, 64.41, 59.90, 58.09, 57.90. $^{31}$P NMR (202 MHz, $D_2O$) δ 55.55. Molecular weight for $C_{20}H_{27}N_4O_{13}PS$ (M+Na): calculated 617.0931, found 617.0917.

B-1. Synthesis of Chirally Pure 2'-OMe Uridine-2'F-Uridine Phosphorothioate Dinucleotide ($U_{OMe}$-$sU_F$) (usUf)

Scheme B-1. Synthesis of chirally pure 2'-OMe uridine-2'F-uridine phosphorothioate dinucleotide ($U_{OMe}sU_F$) phosphoramidite building block (usUf)

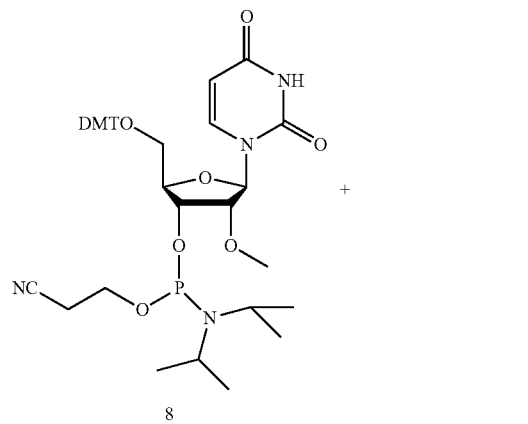

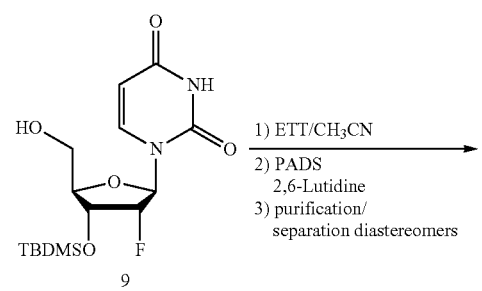

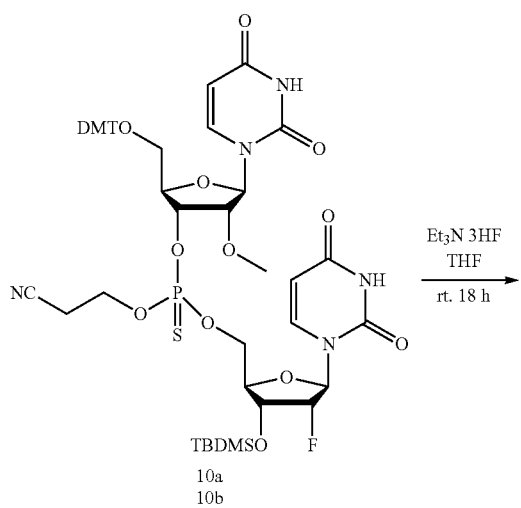

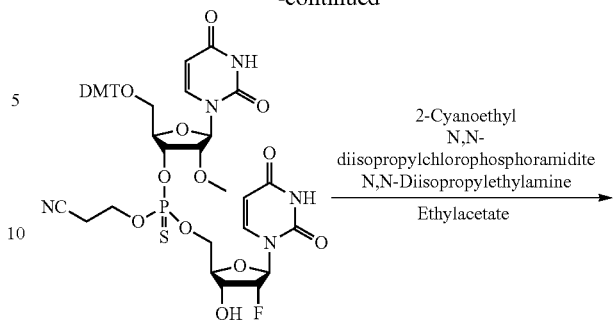

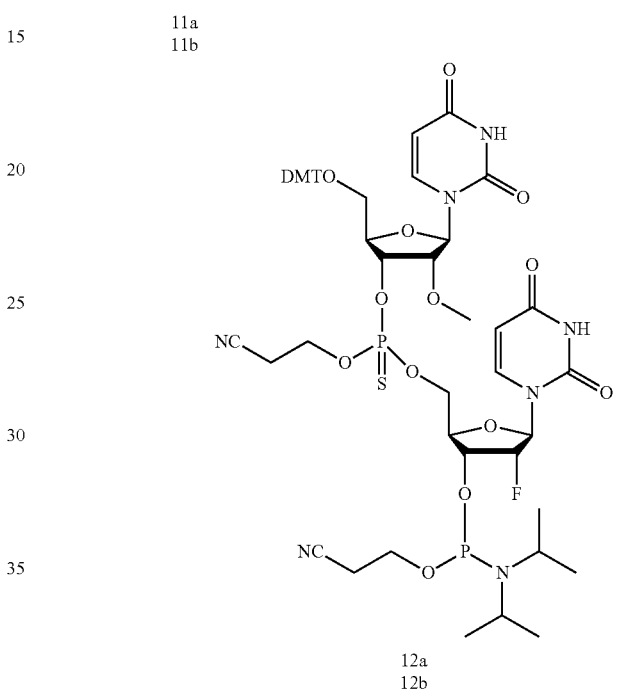

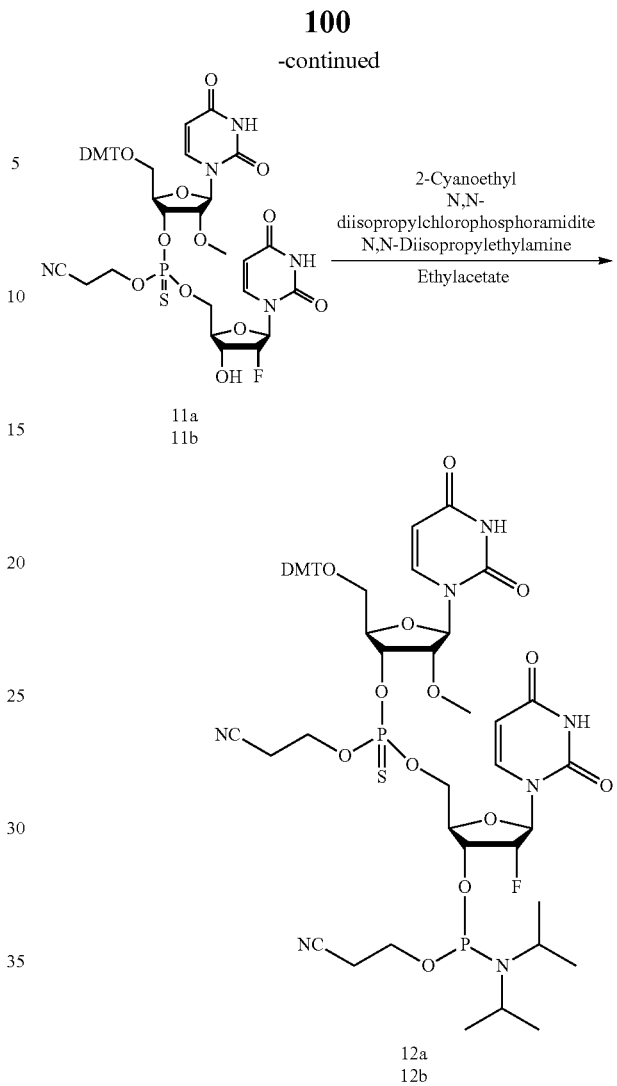

Compound 10: Compound 8 (11.18 g, 14.7 mmol) and compound 9 (5.55 g, 15.4 mmol, 1.05 eq.) were dried under high vacuum and dissolved in 350 ml dichloromethane (dry). To this solution was added 117 ml ETT (3.83 g, 29.4 mmol, 2 eq.), and the reaction mixture was stirred for 2.5 hours. PADS (6.35 g, 22.05 mmol, 1.5 eq.) and 2.52 ml 2.6-lutidine (2.36 g, 22.05 mmol, 1.5 eq.) were added, and the reaction mixture was stirred for 4 hours. The reaction mixture was diluted with 800 ml dichloromethane and washed with $H_2O$ (300 ml) twice. The organic layer was dried over anhydrous $Na_2SO_4$ and concentrated. The diastereomers were separated on CombiFlash column (330 g column, EtOAc: n-hexane (4:1)) to yield 10a (top spot: 3.37 g, 22%) and 10b (lower spot: 6.3 g, 41%). In EtOAc: n-hexane (4:1), 10a ($R_f$=0.5) and 10b (R=0.23).

10a $^1$H NMR (400 MHz, acetonitrile-$d_3$) δ 7.90 (d, J=8.1 Hz 1H), 7.61 (d, J=8.1 Hz, 1H), 7.43-7.38 (m, 2H), 7.35-7.22 (m, 7H), 6.91-6.84 (m, 4H), 5.96 (d, J=3.9 Hz, 1H), 5.85 (dd, J=19.3, 2.1 Hz, 1H), 5.65 (d, J=8.0 Hz, 1H), 5.27-5.19 (m, 2H), 5.10 (ddd, J=53.1, 4.8, 2.1 Hz, 1H), 4.53-4.40 (m, 2H), 4.34-4.22 (m, 2H), 4.18-4.10 (m, 3H), 4.06-3.98 (m, 1H), 3.78 (s, 6H), 3.58 (dd, J=11.2, 3.0 Hz, 1H), 3.51 (s, 3H), 3.48 (dd, J=11.1, 2.9 Hz, 1H), 2.71 (q, J=6.1 Hz, 2H), 0.91 (s, 9H), 0.14 (d, J=4.8 Hz, 6H). $^{13}$C NMR (126 MHz, $CD_3OD$) δ 166.07, 165.91, 160.01, 152.27, 151.88, 146.40, 143.10, 143.08, 142.11, 137.34, 131.21, 129.29, 128.67, 127.67, 124.20, 118.61, 113.98, 113.85, 103.30, 103.18, 94.14, 94.09, 92.62, 92.58, 91.62, 91.59, 91.34, 91.31, 87.83, 87.79, 87.70, 85.34, 85.30, 82.97, 82.87, 82.79, 77.47, 77.43, 77.39, 70.90, 70.77, 67.47, 67.42, 64.57, 64.53, 61.95, 59.28, 59.26, 55.71, 55.67, 26.16, 19.99, 19.92, 18.92, −4.61, −4.79. $^{31}$P NMR (162 MHz, CD$_3$CN) δ 67.12. $^{19}$F NMR (376 MHz, CD$_3$OD) δ −209.65, −209.70, −209.75, −209.80, −209.84, −209.89, −210.14, −210.18, −210.23, −210.28, −210.32, −210.37. Molecular weight for C$_{49}$H$_{59}$FN$_5$O$_4$PSSi (M+Na): calculated 1074.3168, found 1074.3146.

10b $^1$H NMR (400 MHz, acetonitrile-d$_3$) δ 7.93 (d, J=8.1 Hz, 1H), 7.49 (d, J=8.1 Hz, 1H), 7.41 (d, J=7.4 Hz, 2H), 7.32-7.22 (m, 7H), 6.87 (dd, J=9.0, 2.4 Hz, 4H), 5.94 (d, J=3.7 Hz, 1H), 5.73 (dd, J=20.3, 1.4 Hz, 1H), 5.61 (d, J=8.1 Hz, 1H), 5.30-5.17 (m, 2H), 5.16-4.98 (m, 1H), 4.52-4.40 (m, 1H), 4.35-4.23 (m, 3H), 4.19-4.08 (m, 4H), 4.01-3.94 (m, 1H), 3.77 (s, 6H), 3.54 (s, 4H), 2.88 (t, J=5.8 Hz, 2H), 0.91 (s, 9H), 0.13 (d, J=3.6 Hz, 6H). $^{13}$C NMR (126 MHz, CD$_3$OD) δ 165.98, 165.87, 160.41, 160.37, 151.95, 151.71, 145.68, 143.24, 141.78, 136.26, 131.67, 131.60, 131.23, 129.57, 129.31, 129.01, 128.67, 128.25, 118.62, 114.30, 114.29, 113.99, 103.10, 102.90, 94.22, 92.72, 92.28, 91.99, 88.61, 88.59, 83.16, 83.14, 82.78, 82.72, 82.36, 82.29, 75.76, 75.73, 70.56, 70.43, 67.12, 67.08, 64.68, 64.64, 62.40, 59.21, 55.77, 26.19, 20.85, 20.02, 19.96, 18.92, −4.57, −4.76. $^{31}$P NMR (202 MHz, CD$_3$CN) δ 67.90. $^{19}$F NMR (376 MHz, CD$_3$OD) δ −208.37, −208.43, −208.48, −208.52, −208.57, −208.62, −208.77, −208.82, −208.87, −208.91, −208.96, −209.01. Molecular weight for C$_{49}$H$_{59}$FN$_5$O$_{14}$PSSi (M+Na): calculated 1074.3168, found 1074.3157.

Compound 11: Compound 10 (10a top spot: 3.3 g, 3.1 mmol; 10b lower spot: 6.25 g, 6.6 mmol) was dissolved in dry THF (10a: 45 ml; 10b: 90 ml) and Et$_3$N 3HF (10a: 6.2 ml, 37.7 mmol, 12 eq.; 10b: 12.9 ml, 78.9 mmol, 12 eq.) was added. The reaction mixture was stirred for 14 hours. The reaction mixture was concentrated, co-evaporated three times with THF, and purified by CombiFlash column (5% MeOH in DCM) to yield 11a (top spot: 2.12 g, 73%) and 11b (lower spot: 1.52 g, 24.5%).

11a H NMR (500 MHz, DMSO-d$_6$) δ 11.45 (s, 1H), 11.41 (s, 1H), 7.67 (d, J=8.1 Hz, 1H), 7.58 (d, J=8.1 Hz, 1H), 7.37 (d, J=7.7 Hz, 2H), 7.32 (t, J=7.6 Hz, 2H), 7.25 (d, J=8.5 Hz, 5H), 6.90 (d, J=8.5 Hz, 4H), 5.90-5.79 (m, 3H), 5.74 (s, 1H), 5.59 (dd, J=8.0, 1.7 Hz, 1H), 5.39 (dd, J=8.0, 1.7 Hz, 1H), 5.20-5.04 (m, 2H), 4.44-4.36 (m, 1H), 4.28-4.00 (m, 8H), 3.73 (s, 6H), 3.38 (s, 3H), 2.84 (q, J=5.5 Hz, 2H). $^{13}$C NMR (126 MHz, DMSO) δ 163.02, 162.77, 158.16, 150.27, 150.08, 144.24, 140.87, 140.20, 135.04, 134.84, 129.74, 127.89, 127.72, 126.86, 117.91, 113.24, 102.12, 102.09, 101.86, 101.85, 93.47, 91.99, 88.94, 88.64, 86.54, 86.52, 86.23, 81.15, 81.10, 80.17, 80.10, 79.94, 79.91, 74.88, 68.09, 67.96, 67.34, 67.31, 63.02, 62.98, 62.15, 57.99, 55.02, 54.86, 18.76, 18.69. $^{31}$P NMR (202 MHz, DMSO) δ 67.99. $^{19}$F NMR (376 MHz, DMSO) δ −206.87, −206.92, −206.98, −207.01, −207.06, −207.12. Molecular weight for C$_{43}$H$_{43}$FN$_5$O$_{14}$PS (M+Na): calculated 960.2303, found 960.2320.

11b $^1$H NMR (400 MHz, DMSO-d$_6$) δ 11.45 (s, 1H), 11.40 (s, 1H), 7.70 (d, J=8.1 Hz, 1H), 7.54 (d, J=8.1 Hz, 1H), 7.41-7.35 (m, 2H), 7.31 (t, J=7.5 Hz, 2H), 7.25 (d, J=8.6 Hz, 5H), 6.89 (d, J=8.6 Hz, 4H), 5.88-5.73 (m, 3H), 5.57 (d, J=8.1 Hz, 1H), 5.36 (d, J=8.1 Hz, 1H), 5.19-5.02 (m, 2H), 4.27-4.16 (m, 7H), 4.02-3.96 (m, 1H), 3.73 (s, 6H), 3.41 (s, 3H), 2.94 (t, J=5.7 Hz, 2H). $^{13}$C NMR (126 MHz, DMSO) δ 164.57, 164.36, 159.70, 151.79, 151.61, 145.83, 142.34, 141.77, 136.60, 136.40, 131.30, 129.43, 129.27, 128.38, 119.65, 114.78, 103.58, 103.57, 103.38, 95.10, 95.08, 90.52, 90.50, 90.23, 88.21, 87.78, 82.58, 82.54, 81.62, 81.56, 76.16, 69.49, 69.36, 68.48, 68.45, 64.90, 64.87, 63.46, 59.57, 56.56, 20.35, 20.28. $^{31}$P NMR (162 MHz, DMSO) δ 68.27. $^{19}$F NMR (376 MHz, DMSO) δ −206.61, −206.67, −206.72, −206.75, −206.81, −206.87. Molecular weight for C$_{43}$H$_{43}$FN$_5$O$_{14}$PS (M+Na)$^−$ calculated 937.89, found 936.2.

Compound 12: Compound 11 (11a top spot: 2 g, 2.1 mmol; 11b lower spot: 0.6 g, 0.63 mmol) was dried overnight under high vacuum and dissolved in dry ethyl acetate (11a: 25 ml; 11b: 5 ml). N,N-Diisopropylamine (11a: 915 μl, 679 mg, 5.25 mmol, 2.5 eq.; 11b: 274 μl, 204 mg, 4.58 mmol, 2.25 eq.) was added dropwise under rigorous stirring. Subsequently, 2-cyanoethyl N,N-diisopropylchlorophosphoramidite (11a: 937 μl, 994 mg, 4.2 mmol, 2 eq.; 11b: 281 μl, 298 mg, 1.26 mmol, 2.5 eq.) was added dropwise (over 1 minute), and the reaction mixture was stirred at room temperature for 1.5 hours. The reaction mixture was diluted with 200 ml ethyl acetate, washed with 100 ml NaHCO$_3$ and 100 ml brine, dried over Na$_2$SO$_4$, and concentrated to dryness. The crude (white foam) was dissolved in 5 ml DCM and precipitated from 1 L cold n-hexane/diethyl ether (1:1) to yield 12a (top spot: 1.86 g, 78%) and 12b (lower spot: 609.6 mg, 85%).

12a $^1$H NMR 72 (500 MHz, acetonitrile-d$_3$) δ 9.14 (s, 2H), 7.66 (dd, J=8.1, 4.1 Hz, 1H), 7.48-7.44 (m, 2H), 7.38-7.28 (m, 8H), 6.92 (d, J=8.7 Hz, 4H), 5.93 (d, J=4.1 Hz, 1H), 5.89-5.82 (m, 1H), 5.63 (d, J=8.1 Hz, 1H), 5.34 (dd, J=8.1, 5.2 Hz, 1H), 5.28-5.12 (m, 2H), 4.60-4.48 (m, 2H), 4.37-4.24 (m, 4H), 4.19-4.07 (m, 3H), 3.90-3.83 (m, 1H), 3.80 (s, 6H), 3.72-3.61 (m, 2H), 3.49 (d, J=3.3 Hz, 3H), 3.44 (d, J=3.0 Hz, 2H), 2.75-2.65 (m, 4H), 1.23-1.18 (m, 12H). $^{13}$C NMR (126 MHz, CD$_3$CN) δ 163.89, 163.87, 163.71, 159.92, 159.91, 151.41, 151.39, 151.17, 151.13, 145.55, 142.09, 141.92, 140.90, 136.39, 136.39, 136.25, 131.24, 131.22, 129.19, 129.07, 128.18, 114.28, 103.23, 103.18, 103.11, 103.08, 94.30, 93.77, 92.81, 92.28, 91.41, 91.33, 91.13, 91.05, 88.03, 87.93, 87.90, 82.69, 82.33, 81.18, 80.81, 76.00, 75.96, 70.85, 70.73, 70.59, 67.84, 67.52, 64.31, 64.28, 63.00, 62.95, 60.00, 59.84, 59.81, 59.65, 59.28, 56.05, 56.04, 56.02, 44.39, 44.36, 44.29, 44.26, 25.17, 25.13, 24.98, 24.93, 21.14, 21.08, 21.02, 20.15, 20.08. $^{31}$P NMR (202 MHz, CD$_3$CN) δ 152.24, 152.21, 152.13, 152.08, 68.63, 68.60. $^{19}$F NMR (376 MHz, CD$_3$CN) δ −205.04, −205.07, −205.09, −205.12, −205.15, −205.17, −205.21, −205.23, −205.26, −205.29, −205.31, −205.64, −205.66, −205.69, −205.71, −205.75, −205.76, −205.78, −205.80, −205.83, −205.85, −205.89, −205.90. Molecular weight for C$_{52}$H$_{62}$FN$_7$O$_{15}$P$_2$S (M+H): calculated 1138.3562, found 1138.3549.

12b $^1$H NMR 73 (500 MHz, acetonitrile-d$_3$) δ 9.10 (s, 2H), 7.66 (d, J=8.2 Hz, 1H), 7.46 (d, J=8.2 Hz, 2H), 7.38-7.28 (m, 8H), 6.91 (d, J=8.7 Hz, 4H), 5.94-5.89 (m, 1H), 5.82-5.71 (m, 1H), 5.60-5.55 (m, 1H), 5.36-5.30 (m, 1H), 5.27-5.11 (m, 2H), 4.60-4.35 (m, 2H), 4.34-4.14 (m, 6H), 4.11 (q, J=4.6 Hz, 1H), 3.89-3.82 (m, 1H), 3.80 (s, 6H), 3.71-3.62 (m, 2H), 3.53-3.48 (m, 3H), 3.44-3.37 (m, 2H), 2.84 (q, J=6.0 Hz, 2H), 2.67 (t, J=6.0 Hz, 2H), 1.23-1.15 (m, 12H). $^{13}$C NMR (126 MHz, CD$_3$CN) δ 163.85, 163.83, 163.70, 159.91, 159.90, 151.46, 151.45, 151.08, 151.06, 145.60, 145.58, 142.29, 142.09, 140.87, 136.35, 136.21, 131.25, 131.23, 129.16, 129.07, 128.15, 114.29, 103.23, 103.20, 103.14, 103.10, 103.07, 103.04, 92.88, 92.37, 91.79, 91.50, 88.03, 87.79, 82.67, 82.42, 80.98, 80.64, 76.02, 70.36, 67.31, 67.02, 64.49, 62.89, 60.01, 59.85, 59.74, 59.60, 59.27, 56.04, 56.03, 47.22, 44.34, 44.24, 25.12, 24.97, 21.13, 21.07, 21.02, 20.21, 20.14. $^{31}$P NMR (202 MHz, CD$_3$CN) δ 152.08, 152.04, 68.79, 68.73. $^{19}$F NMR (376 MHz, CD$_3$CN) δ −204.19, −204.22, −204.25, −204.25, −204.27, −204.30, −204.33, −204.36, −204.39, −204.41, −204.44, −204.47, −204.62, −204.64, −204.67, −204.69, −204.73, −204.75, −204.76, −204.78, −204.82, −204.83, −204.83, −204.87, −204.89. Molecular weight for C$_{52}$H$_{62}$FN$_7$O$_{15}$P$_2$S (M+H): calculated 1138.3562, found 1138.3533.

B-2. Synthesis of Fully Deprotected, Chirally Pure U$_{OMe}$sU$_F$ (usUf)

Scheme B-2. Synthesis of fully deprotected, chirally pure U$_{OMe}$sU$_F$ dinucleotide (usUf)

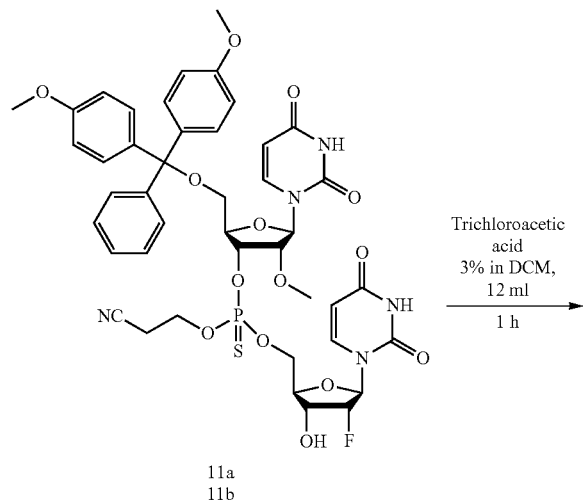

11a
11b

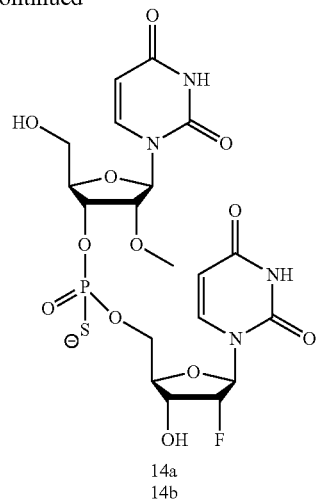

14a
14b

Compound 13: Compound 11 (11a top spot: 500 mg, 0.53 mmol; 11b lower spot: 500 mg, 0.53 mmol) was dissolved in 1.5 ml DCM, and 8 ml trichloroacetic acid (3% in DCM) was added. The reaction mixture was stirred at room temperature for 1 hour. The reaction mixture was concentrated and purified by Combiflash column (40 g Gold column, 50 ml/min flow, 5% MeOH in DCM for 4 minutes, 10% MeOH in DCM for 5 minutes, 10% MeOH in DCM for 10 minutes) to yield 13a quantitative and 13b (311 mg, 92%). 13a: Rf=0.21 and 13b: Rf=0.21.

13a $^1$H NMR (400 MHz, DMSO-d$_6$) δ 11.45 (dd, J=5.5, 2.0 Hz, 2H), 7.88 (d, J=8.2 Hz, 1H), 7.61 (d, J=8.1 Hz, 1H), 5.94-5.81 (m, 3H), 5.72 (dd, J=8.1, 2.1 Hz, 1H), 5.63 (dd, J=8.1, 2.1 Hz, 1H), 5.42 (t, J=4.3 Hz, 1H), 5.22-5.03 (m, 2H), 4.47-4.37 (m, 1H), 4.28-4.02 (m, 7H), 3.61 (s, 2H), 3.34 (s, 3H), 2.95 (t, J=5.8 Hz, 2H). $^{13}$C NMR (126 MHz, DMSO) δ 163.07, 162.84, 150.59, 150.13, 140.93, 140.07, 118.17, 102.61, 101.93, 93.48, 92.00, 88.90, 88.62, 85.20, 83.67, 80.41, 80.37, 80.21, 80.14, 76.15, 76.12, 68.07, 67.93, 67.25, 67.21, 63.17, 63.14, 60.56, 57.96, 54.88, 18.83, 18.76. $^{31}$P NMR (202 MHz, DMSO) δ 66.74. $^{19}$F NMR (376 MHz, DMSO) δ −206.85, −206.91, −206.96, −207.00, −207.05, −207.11. Molecular weight for C$_{22}$H$_{27}$FN$_5$O$_{12}$PS (M+H): calculated 636.1177, found 636.1168.

13b $^1$H NMR (400 MHz, DMSO-dd) δ 11.56-11.29 (m, 2H), 7.88 (d, J=8.2 Hz, 1H), 7.61 (d, J=8.1 Hz, 1H), 5.95-5.80 (m, 3H), 5.72 (dd, J=8.1, 2.1 Hz, 1H), 5.62 (dd, J=8.1, 2.1 Hz, 1H), 5.41 (t, J=4.8 Hz, 1H), 5.23-5.02 (m, 2H), 4.42-4.32 (m, 1H), 4.30-4.01 (m, 7H), 3.59 (s, 2H), 3.36 (s, 3H), 2.96 (t, J=5.8 Hz, 2H). $^{13}$C NMR (126 MHz, DMSO) δ 163.55, 163.33, 151.05, 150.58, 141.50, 140.54, 118.62, 103.07, 102.37, 94.01, 92.53, 89.56, 89.27, 85.68, 84.19, 84.16, 80.92, 80.88, 80.63, 80.56, 76.58, 76.54, 68.50, 68.37, 67.60, 67.56, 63.77, 63.74, 60.99, 58.47, 55.36, 19.27, 19.20. $^{31}$P NMR (202 MHz, DMSO) δ 66.85. $^{19}$F NMR (376 MHz, DMSO) δ −206.40, −206.46, −206.52, −206.55, −206.60, −206.66. Molecular weight for C$_{22}$H$_{27}$FN$_5$O$_{12}$PS (M+Na): calculated 658.0996, found 658.0997.

Compound 14: Compound 13 (13a top spot: 300 mg, 0.47 mmol; 13b lower spot: 292 mg, 0.46 mmol) was dissolved 12 ml methylamine (33 wt % solution in absolute ethanol) and stirred for 5 minutes at room temperature. The reaction mixture was concentrated and purified over CombiFlash column (24 g Gold column, 35 ml/min flow, ethyl acetate/ MeOH (70:30) for 8 minutes, ethyl acetate/MeOH (60:40) for 5 minutes) to yield 14a (254 mg, 92%) and 14b (250 mg, 93%). In ethyl acetate/MeOH (2:1), 14a: Rf=0.17 and 14b: Rf=0.17.

14a $^1$H NMR (500 MHz, deuterium oxide) δ 8.04-8.00 (m, 2H), 6.12 (d, J=17.7 Hz, 1H), 5.97 (m, 1H), 5.89-5.85 (m, 2H), 5.27-5.09 (m, 1H), 4.87-4.83 (m, 1H), 4.53-4.46 (m, 1H), 4.44-4.28 (m, 3H), 4.27-4.14 (m, 2H), 4.06-3.86 (m, 2H), 3.60 (s, 3H). $^{13}$C NMR (126 MHz, d$_2$o) δ 165.95, 151.27, 151.10, 141.38, 141.19, 102.19, 101.90, 94.13, 92.65, 88.40, 88.12, 87.41, 82.88, 82.83, 81.34, 80.84, 80.77, 71.48, 71.44, 67.51, 67.38, 63.00, 62.94, 59.48, 57.76. $^{31}$P NMR (202 MHz, D$_2$O) δ 56.78. $^{19}$F NMR (376 MHz, D$_2$O) δ −203.43, −203.48, −203.49, −203.54, −203.57, −203.62, −203.63, −203.68. Molecular weight for C$_{19}$H$_{24}$FN$_4$O$_{12}$PS (M+Na): calculated 605.0731, found 605.0718.

14b $^1$H NMR (500 MHz, deuterium oxide) δ 8.02-7.88 (m, 2H), 6.09 (d, J=18.4 Hz, 1H), 5.99 (d, J=3.8 Hz, 1H), 5.89 (d, J=8.1 Hz, 2H), 5.21 (dd, J=52.3, 4.1 Hz, 1H), 4.88-4.84 (m, 1H), 4.55-4.42 (m, 1H), 4.40-4.29 (m, 3H), 4.29-4.16 (m, 2H), 4.02-3.81 (m, 2H), 3.57 (s, 3H). $^{13}$C NMR (126 MHz, d$_2$o) δ 165.97, 151.34, 151.09, 141.75, 141.36, 102.16, 102.11, 94.01, 92.53, 88.82, 88.54, 87.21, 83.22, 83.18, 81.32, 81.28, 80.93, 80.85, 71.54, 71.49, 67.66, 67.53, 63.70, 63.66, 59.94, 57.89. $^{31}$P NMR (202 MHz, D$_2$O) δ 55.68. $^{19}$F NMR (376 MHz, D$_2$O) δ −202.94, −202.98, −202.99, −203.04, −203.07, −203.12, −203.13, −203.18. Molecular weight for C$_{19}$H$_{24}$FN$_4$O$_{12}$PS (M+Na): calculated 605.0731, found 605.0742.

C-1. Synthesis of Chirally Pure 2'-F Uridine-2'-OMe Uridine Phosphorothioate (U$_F$SU$_{OMe}$) Dinucleotide (Ufsu)

Scheme C-1. Synthesis of chirally pure 2'-F uridine-2'-OMe uridine phosphorothioate dinucleotide (U$_F$sU$_{OMe}$) phosphoramidite building block (Ufsu)

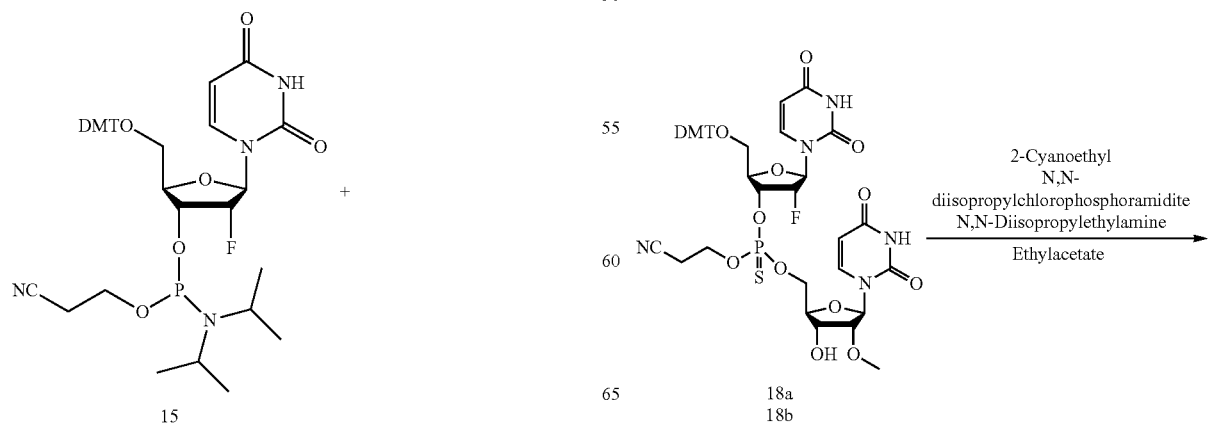

-continued

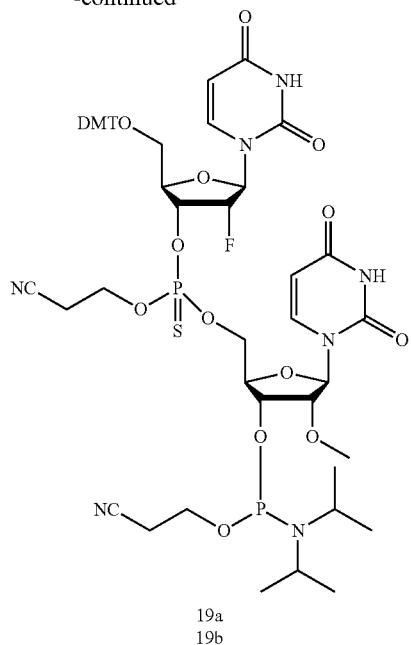

19a
19b

Compound 17: Compound 15 (11.01 g, 14.7 mmol) and compound 16 (5.74 g, 15.4 mmol, 1.05 eq.) were dried under high vacuum and dissolved in 100 ml dichloromethane (dry). To the solution was added 117 ml ETT (3.83 g, 29.4 mmol, 2 eq.), and the reaction mixture was stirred for 2.5 hours. PADS (6.35 g, 22.05 mmol, 1.5 eq.) and 2.52 ml 2.6-lutidine (2.36 g, 22.05 mmol, 1.5 eq.) were added, and the reaction mixture was stirred overnight. The reaction mixture was diluted with 800 ml dichloromethane and washed with $H_2O$ (300 ml) twice. The organic layer was dried over anhydrous $Na_2SO_4$ and concentrated. The diastereomers were separated over CombiFlash column (330 g column, EtOAc: n-hexane (4:1)) to yield 17a (top spot: 7.25 g 47%) and 17b (lower spot: 7.29 g, 47%)). In EtOAc: n-hexane (4:1), 17a $R_f$=0.23 and 17b $R_f$=0.18.

17a $^1$H NMR (400 MHz, DMSO-$d_6$) δ 11.43 (s, 1H), 11.33 (s, 1H), 7.77 (d, J=8.0 Hz, 1H), 7.57 (d, J=8.1 Hz, 1H), 7.42-7.36 (m, 2H), 7.33-7.20 (m, 7H), 6.91-6.84 (m, 4H), 5.92 (d, J=21.4 Hz, 1H), 5.81 (d, J=4.5 Hz, 1H), 5.63 (dd, J=8.1, 1.8 Hz, 1H), 5.60-5.42 (m, 2H), 5.36-5.24 (m, 1H), 4.34-4.21 (m, 3H), 4.21-4.06 (m, 2H), 4.03-3.93 (m, 2H), 3.86 (t, J=4.8 Hz, 1H), 3.73 (s, 6H), 3.38 (d, J=9.5 Hz, 1H), 3.34 (s, 3H), 3.29 (dd, J=11.0, 4.8 Hz, 1H), 2.83-2.73 (m, 2H), 0.87 (s, 9H), 0.08 (s, 5H). $^{13}$C NMR (126 MHz, DMSO) δ 163.11, 162.92, 158.13, 158.11, 150.31, 150.02, 144.31, 142.07, 140.13, 135.08, 135.03, 129.77, 129.72, 127.81, 127.76, 126.78, 120.26, 117.70, 113.15, 102.12, 101.73, 91.63, 90.05, 90.03, 89.75, 87.12, 85.97, 81.69, 81.62, 81.24, 79.61, 79.54, 73.12, 73.01, 69.64, 67.08, 67.06, 63.26, 63.23, 61.58, 57.61, 55.00, 25.54, 18.77, 18.70, 17.68, −4.88, −5.14. $^{31}$P NMR (202 MHz, DMSO) δ 68. $^{19}$. 19F NMR (376 MHz, DMSO) δ −203.64, −203.70, −203.75, −203.78, −203.83, −203.89. Molecular weight for $C_{49}H_{59}FN_5O_4PSSi$ (M+Na): calculated 1074.368, found 1074.3170.

17b $^1$H NMR (400 MHz, DMSO-$d_6$) δ 11.51-11.46 (m, 1H), 11.43-11.38 (m, 1H), 7.80 (d, J=8.1 Hz, 1H), 7.56 (d, J=8.2 Hz, 1H), 7.38 (d, J=7.5 Hz, 2H), 7.31-7.20 (m, 7H), 6.85 (dd, J=8.9, 2.1 Hz, 4H), 5.91 (d, J=21.8 Hz, 1H), 5.78 (d, J=4.0 Hz, 1H), 5.63-5.46 (m, 2H), 5.41 (dd, J=8.0, 2.0 Hz, 1H), 5.38-5.25 (m, 1H), 4.27-4.15 (m, 4H), 4.15-4.06 (m, 2H), 3.96-3.90 (m, 1H), 3.86-3.81 (m, 1H), 3.72 (s, 6H), 3.41-3.36 (m, 1H), 3.35 (s, 3H), 3.29-3.24 (m, 1H), 2.92 (t, J=5.8 Hz, 2H), 0.85 (s, 9H), 0.07 (s, 3H), 0.06 (s, 3H). $^{13}$C NMR (126 MHz, DMSO) δ 163.12, 162.94, 158.11, 156.61, 150.25, 150.00, 144.34, 142.06, 140.09, 137.28, 135.07, 135.00, 129.75, 129.73, 127.77, 127.75, 126.72, 120.32, 117.92, 113.11, 101.99, 101.69, 91.76, 90.27, 90.06, 89.78, 87.33, 85.98, 81.43, 81.40, 81.37, 79.48, 79.41, 72.88, 72.74, 69.40, 66.71, 63.59, 63.55, 61.33, 57.62, 54.95, 25.54, 18.84, 18.77, 17.67, −4.86, −5.13. $^{31}$P NMR (202 MHz, DMSO) δ 68.34. $^{19}$F NMR (376 MHz, DMSO) δ −203.36, −203.42, −203.47, −203.50, −203.56, −203.61. Molecular weight for $C_{49}H_9FN_5O_{14}PSSi$ (M+Na): calculated 1074.368, found 1074.3198.

Compound 18: Compound 17 (17a top spot: 6 g, 5.7 mmol; 17b lower spot: 6 g, 5.7 mmol) was dissolved in dry THF (17a: 80 ml; 17b: 80 ml), and $Et_3N$ 3HF (17a: 11.2 ml, 68.4 mmol, 12 eq.; 17b: 11.2 ml, 68.4 mmol, 12 eq.) was added. The reaction mixture was stirred for 14 hours. The reaction mixture was concentrated, co-evaporated three times with THF and purified by CombiFlash column (DCM to 5% MeOH in DCM) to yield 18a (top spot: 4.22 g, 78%) and 18b (lower spot: 4.09 g, 76%).

18a $^1$H NMR (500 MHz, DMSO-$d_6$) δ 11.48 (d, J=1.9 Hz, 1H), 11.38 (d, J=1.9 Hz, 1H), 7.80 (d, J=8.1 Hz, 1H), 7.54 (d, J=8.1 Hz, 1H), 7.42-7.36 (m, 2H), 7.30 (t, J=7.6 Hz, 2H), 7.28-7.20 (m, 5H), 6.87 (dd, J=9.0, 2.4 Hz, 4H), 5.91 (d, J=21.7 Hz, 1H), 5.84 (d, J=5.0 Hz, 1H), 5.63 (dd, J=8.1, 2.1 Hz, 1H), 5.54 (dd, J=53.1, 4.6 Hz, 1H), 5.42 (dd, J=8.0, 2.1 Hz, 1H), 5.40-5.36 (m, 1H), 5.36-5.25 (m, 1H), 4.28-4.21 (m, 2H), 4.21-4.14 (m, 1H), 4.14-4.06 (m, 2H), 4.05-4.00 (m, 1H), 4.00-3.93 (m, 1H), 3.78 (t, J=5.1 Hz, 1H), 3.73 (s, 6H), 3.34 (s, 4H), 3.27 (dd, J=11.1, 4.7 Hz, 1H), 2.83-2.76 (m, 2H). $^{13}$C NMR (126 MHz, DMSO) δ 163.14, 162.89, 158.13, 158.11, 150.34, 150.01, 144.31, 142.07, 139.97, 135.09, 135.02, 129.77, 129.72, 127.82, 127.77, 126.79, 117.77, 113.17, 102.14, 101.69, 91.75, 90.26, 90.10, 89.81, 86.59, 85.98, 81.84, 81.77, 81.61, 79.52, 79.45, 72.99, 72.87, 68.28, 67.78, 67.75, 63.21, 63.18, 61.47, 57.61, 55.01, 18.75, 18.68. $^{31}$P NMR (202 MHz, DMSO) δ 68.19. $^{19}$F NMR (376 MHz, DMSO) δ −207.61, −207.65, −207.66, −207.70, −207.75, −207.79, −207.80, −207.84. Molecular weight for $C_{43}H_{45}FN_5O_{14}PS$ (M+Na): calculated 960.2303, found 960.2311.

18b $^1$H NMR 54 (500 MHz, DMSO-$d_6$) δ 11.48 (d, J=2.3 Hz, 1H), 11.39 (d, J=2.3 Hz, 1H), 7.85-7.75 (m, 1H), 7.53 (dd, J=8.1, 1.0 Hz, 1H), 7.42-7.34 (m, 2H), 7.31-7.27 (m, 2H), 7.27-7.18 (m, 5H), 6.90-6.83 (m, 4H), 5.91 (d, J=21.9 Hz, 1H), 5.81 (d, J=4.6 Hz, 1H), 5.61-5.56 (m, 1H), 5.51-5.46 (m, 1H), 5.44-5.35 (m, 2H), 5.35-5.24 (m, 1H), 4.24-4.11 (m, 4H), 4.11-4.03 (m, 2H), 3.96-3.91 (m, 1H), 3.77 (t, J=5.0 Hz, 1H), 3.72 (s, 6H), 3.39-3.33 (m, 4H), 3.29-3.23 (m, 1H), 2.91 (t, J=5.9 Hz, 2H). $^{13}$C NMR (126 MHz, DMSO) δ 163.12, 162.88, 158.11, 158.08, 150.28, 149.99, 144.32, 142.08, 140.01, 135.06, 135.03, 129.76, 129.71, 127.79, 127.75, 126.73, 117.95, 113.14, 102.01, 101.67, 91.77, 90.30, 90.08, 89.80, 86.84, 86.82, 85.98, 81.69, 81.61, 81.54, 79.47, 79.38, 72.82, 72.69, 68.19, 67.55, 67.51, 63.49, 63.46, 61.36, 57.65, 54.97, 18.79, 18.72. $^{31}$P NMR (202 MHz, DMSO) δ 68.26. $^{19}$F NMR (376 MHz, DMSO) δ −207.39, −207.43, −207.44, −207.48, −207.53, −207.57, −207.58, −207.62. Molecular weight for $C_{43}H_{45}FN_5O_{14}PS$ (M+Na): calculated 960.2303, found 960.2313.

Compound 19: Compound 18 (18a top spot: 300 mg, 0.32 mmol; 18b lower spot: 300 mg, 0.32 mmol) was dried overnight under high vacuum, dissolved in 3 ml dry DCM for 18a and 3 ml dry ethyl acetate for 18b and cooled to 0° C. N,N-Diisopropylamine (18a: 84 μl, 62 mg, 0.48 mmol, 1.5 eq.; 18b: 84 μl, 62 mg, 0.48 mmol, 1.5 eq.) was added dropwise under rigorous stirring. Subsequently, 2-cyanoethyl N,N-diisopropylchlorophosphoramidite (18a 107 μl, 114 mg, 0.48 mmol, 1.5 eq.; 18b 107 μl, 114 mg, 0.48 mmol, 1.5 eq.) was added dropwise (over 1 minute), and the reaction mixture was stirred at 0° C. for 10 minutes and at room temperature for 60 minutes. The reaction mixture was diluted with 200 ml DCM or ethyl acetate for 18a and 18b, respectively, washed with 100 ml NaHCO₃ and 100 ml brine, dried over Na₂SO₄, and concentrated to dryness. The crude (white foam) was dissolved in 5 ml DCM and precipitated from 1 L cold n-hexane/diethyl ether (1:1) to yield 19a (top spot: 318 mg, 87%) and 19b (lower spot: 305 mg, 84%).

19a $^{31}$P NMR 70 (202 MHz, CD₃CN) δ 152.01, 151.47, 68.80, 68.74. $^{19}$F NMR (376 MHz, DMSO) δ −204.73, −204.78, −204.82, −204.87, −204.92, −204.96, −205.01, −205.85, −205.90, −205.96, −206.00, −206.04, −206.10. Molecular weight for $C_{52}H_{62}FN_7O_{15}P_2S$ (M+Na): calculated 1137.3484, found 1138.2.

19b $^{31}$P NMR 71 (202 MHz, CD₃CN) δ 151.78, 151.53, 68.77. $^{19}$F NMR (376 MHz, CD₃CN) δ −205.53, −205.58, −205.63, −205.66, −205.71, −205.76, −205.77, −205.80, −205.84, −205.90. Molecular weight for $C_{52}H_{62}FN_7O_{15}P_2S$ (M+H): calculated 1138.3562, found 1138.3595.

C-2. Synthesis of Fully Deprotected, Chirally Pure $U_FsU_{OMe}$ (Ufsu)

Scheme C-2. Synthesis of fully deprotected, chirally pure $U_FsU_{OME}$ dinucleotide (Ufsu)

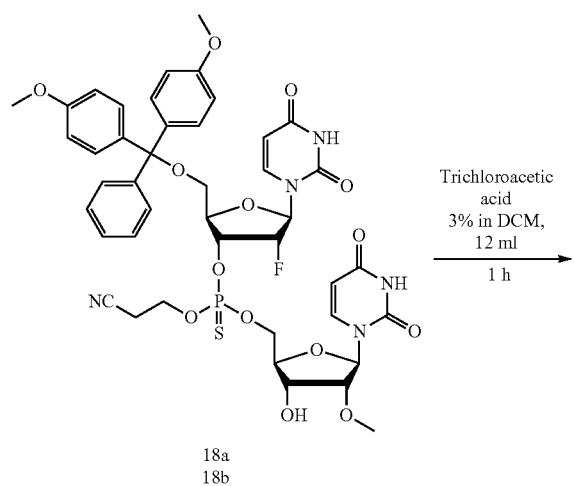

18a
18b

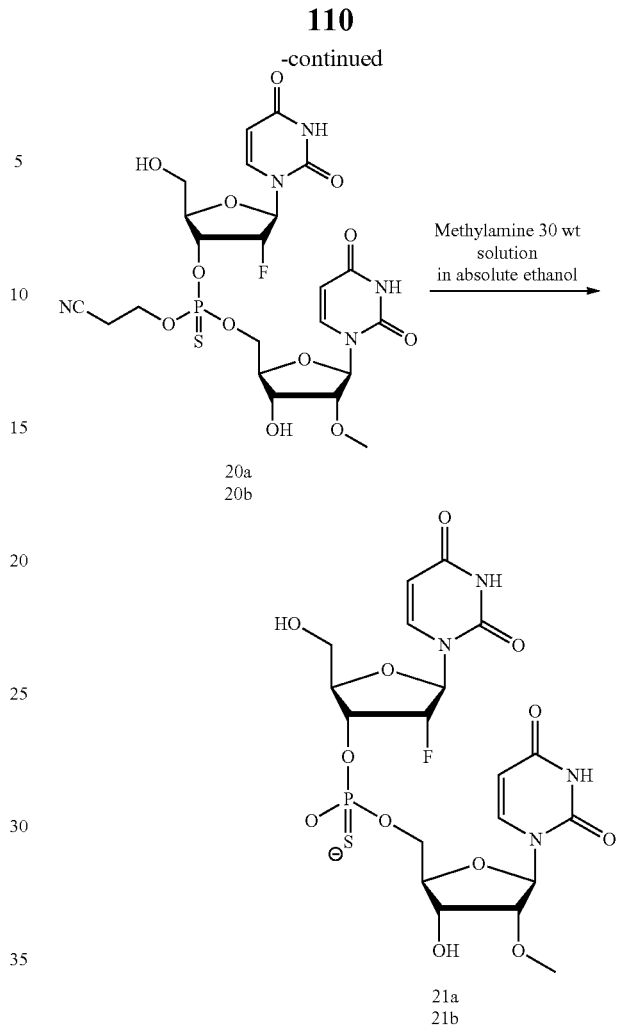

20a
20b 21a
21b

Compound 20: Compound 18 (18a top spot: 500 mg, 0.53 mmol; 18b lower spot: 500 mg, 0.53 mmol) was dissolved in 1.5 ml DCM, and 8 ml trichloroacetic acid (3% in DCM) was added. The reaction mixture was stirred at room temperature for 1 hour. The reaction mixture was concentrated and purified over CombiFlash column (40 g Gold column, 50 ml/min flow, 5% MeOH in DCM for 4 minutes, 10% MeOH in DCM in 5 minutes, 10% MeOH in DCM for 10 minutes) to yield 20a (306 mg, 90%) and 20b (327 mg, 96%). In 5% MeOH in DCM, 20a: Rf=0.24 and 20b Rf=0.28.

20a $^1$H NMR (400 MHz, DMSO-d₆) δ 11.48 (s, 1H), 11.41 (s, 1H), 7.84 (d, J=8.1 Hz, 1H), 7.58 (d, J=8.1 Hz, 1H), 5.96 (dd, J=18.8, 3.0 Hz, 1H), 5.85 (d, J=5.0 Hz, 1H), 5.67 (ddd, J=7.8, 5.5, 2.1 Hz, 2H), 5.53-5.29 (m, 3H), 5.17-5.03 (m, 1H), 4.34-4.08 (m, 6H), 4.06-3.99 (m, 1H), 3.80 (t, J=5.1 Hz, 1H), 3.76-3.66 (m, 1H), 3.60 (dt, J=12.1, 4.0 Hz, 1H), 3.34 (s, 3H), 2.96 (t, J=5.8 Hz, 2H). $^{13}$C NMR (126 MHz, DMSO) δ 163.07, 162.93, 150.38, 150.26, 141.21, 140.08, 118.12, 102.19, 102.12, 91.45, 91.44, 89.94, 89.93, 88.05, 87.78, 86.62, 81.94, 81.91, 81.88, 81.84, 81.58, 73.80, 73.77, 73.69, 73.66, 68.29, 67.74, 67.70, 63.42, 63.39, 59.60, 57.63, 54.89, 18.85, 18.78. $^{31}$P NMR (202 MHz, DMSO) δ 66.79. $^{19}$F NMR (376 MHz, DMSO) δ −207.63, −207.67, −207.68, −207.72, −207.77, −207.81, −207.82, −207.86. Molecular weight for $C_{22}H_{27}FN_5O_{12}PS$ (M+Na): calculated 658.0996, found 658.0989.

20b $^1$H NMR (400 MHz, DMSO-d₆) δ 11.48 (s, 1H), 11.41 (s, 1H), 7.85 (d, J=8.1 Hz, 1H), 7.61 (d, J=8.1 Hz, 1H), 5.95 (dd, J=18.9, 2.9 Hz, 1H), 5.84 (d, J=4.8 Hz, 1H), 5.66 (ddd, J=14.1, 8.1, 2.1 Hz, 2H), 5.52-5.29 (m, 3H), 5.16-5.01

(m, 1H), 4.34-4.17 (m, 4H), 4.17-4.08 (m, 2H), 4.08-3.99 (m, 1H), 3.82 (t, J=5.0 Hz, 1H), 3.76-3.67 (m, 1H), 3.58 (dt, J=12.3, 4.3 Hz, 1H), 3.36 (s, 3H), 2.95 (t, J=5.8 Hz, 2H). $^{13}$C NMR (126 MHz, DMSO) δ 163.07, 162.93, 150.35, 150.25, 141.22, 140.23, 118.06, 102.11, 102.09, 91.48, 91.46, 89.96, 89.94, 88.13, 87.86, 86.85, 81.88, 81.82, 81.79, 81.72, 81.58, 73.58, 73.54, 73.46, 73.43, 68.27, 67.76, 67.72, 63.47, 63.44, 59.52, 57.67, 54.88, 18.81, 18.75. $^{31}$P NMR (202 MHz, DMSO) δ 66.83. $^{19}$F NMR (376 MHz, DMSO) δ −207.48, −207.52, −207.53, −207.57, −207.62, −207.66, −207.67, −207.71. Molecular weight for $C_{22}H_{27}FN_5O_{12}PS$ (M+Na): calculated 658.0996, found 658.0984.

Compound 21: Compound 20 (20a top spot: 286 mg, 0.45 mmol; 20b lower spot: 307 mg, 0.48 mmol) was dissolved in 12 ml methylamine (33 wt % solution in absolute ethanol) and was stirred for 5 minutes at room temperature. The reaction mixture was concentrated and purified by Combi-Flash column (24 g Gold column, 35 ml/min flow, ethyl acetate/MeOH (70:30) for 8 minutes, ethyl acetate/MeOH (60:40) for 5 minutes) to yield 21a (229 mg, 87%) and 21b (242 mg, 86%). In ethyl acetate/MeOH (2:1), 21a: Rf=0.15 and 21b: Rf=0.14.

21a $^1$H NMR (500 MHz, deuterium oxide) δ 8.08 (d, J=8.1 Hz, 1H), 7.93 (d, J=8.1 Hz, 1H), 6.04 (s, 1H), 5.98 (d, J=18.3 Hz, 1H), 5.92 (d, J=8.1 Hz, 1H), 5.85 (d, J=8.1 Hz, 1H), 5.47-5.21 (m, 1H), 5.00-4.86 (m, 1H), 4.47 (t, J=5.3 Hz, 1H), 4.36-4.24 (m, 4H), 4.23-4.14 (m, 1H), 4.12-3.99 (m, 2H), 3.92-3.89 (m, 1H), 3.55 (s, 4H). $^{13}$C NMR (126 MHz, d$_2$o) δ 165.96, 165.81, 151.24, 150.95, 141.86, 141.31, 102.37, 101.81, 92.52, 92.50, 91.02, 89.60, 89.32, 87.01, 82.83, 82.66, 82.59, 81.63, 81.56, 70.94, 70.90, 70.82, 70.78, 67.85, 63.76, 63.71, 58.93, 58.09. $^{31}$P NMR (202 MHz, D$_2$O) δ 56.82. $^{19}$F NMR (376 MHz, D$_2$O) δ −200.17, −200.21, −200.22, −200.27, −200.30, −200.35, −200.36, −200.41. Molecular weight for $C_{19}H_{24}FN_4O_{12}PS$ (M+Na): calculated 605.0731, found 605.0727.

21b $^1$H NMR (400 MHz, DMSO-d$_6$) δ 11.29 (s, 1H), 11.26 (s, 1H), 8.76 (s, 1H), 8.73 (s, 1H), 8.69 (s, 1H), 8.65 (s, 1H), 8.03 (d, J=7.3 Hz, 4H), 7.69-7.59 (m, 2H), 7.59-7.48 (m, 4H), 6.47 (dd, J=16.7, 3.6 Hz, 1H), 6.23-6.15 (m, 1H), 5.93 (dt, J=51.4, 4.0 Hz, 1H), 5.65-5.57 (m, 1H), 5.54-5.42 (m, 1H), 5.34 (t, J=5.5 Hz, 1H), 4.55-4.18 (m, 8H), 3.78-3.58 (m, 2H), 3.36 (s, 3H), 2.97 (t, J=5.8 Hz, 2H). $^{13}$C NMR (126 MHz, d$_2$o) δ 166.11, 165.94, 151.37, 151.04, 142.23, 141.30, 102.37, 101.94, 92.44, 92.42, 90.94, 90.92, 89.76, 89.47, 86.99, 82.80, 82.72, 82.70, 81.73, 81.67, 70.40, 70.35, 70.27, 70.23, 67.90, 64.59, 64.54, 59.21, 58.09. $^{31}$P NMR (202 MHz, D$_2$O) δ 55.97. $^{19}$F NMR (376 MHz, D$_2$O) δ −200.30, −200.35, −200.40, −200.43, −200.49, −200.54. Molecular weight for $C_{19}H_{24}FN_4O_{12}PS$ (M+Na): calculated 605.0731, found 605.0737.

D-1. Synthesis of Chirally Pure 2'-F Adenosine-2'-OMe Adenosine Phosphorothioate Dinucleotide ($A_FSA_{OMe}$)(Afsa)

Scheme D-1. Synthesis of chirally pure 2'-F adenosine-2'-OMe adenosine phosphorothioate dinucleotide ($A_FsA_{OMe}$) phosphoramidite building block (Afsa)

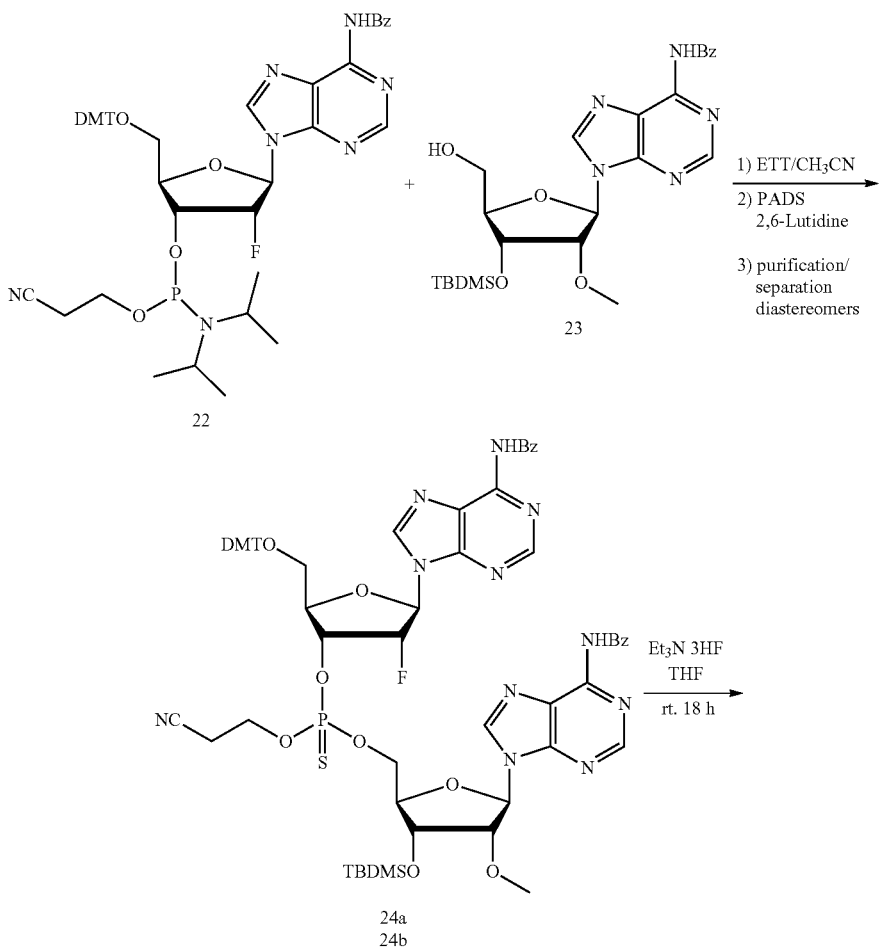

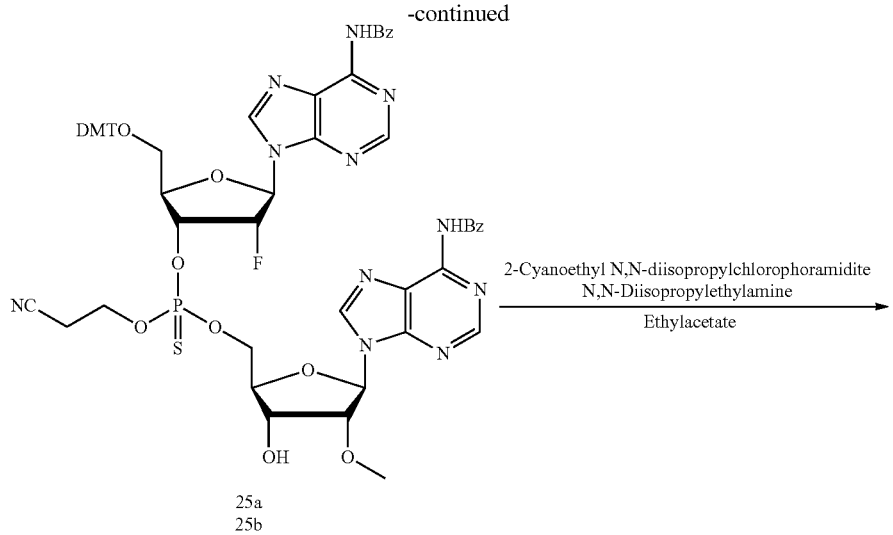

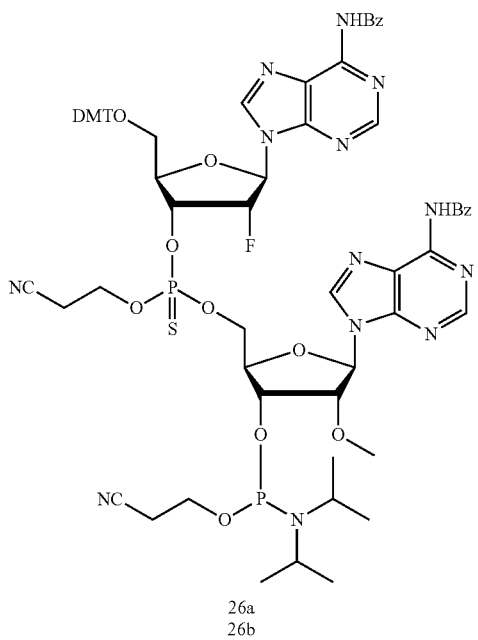

25a
25b 26a
26b

Compound 24: Compound 22 (12.87 g, 14.7 mmol) and compound 23 (7.71 g, 15.4 mmol, 1.05 eq.) were dried under high vacuum and dissolved in 110 ml dichloromethane (dry). To this solution was added 117 ml ETT (3.83 g, 29.4 mmol, 2 eq.), and the reaction mixture was stirred for 1.5 hours. PADS (6.35 g, 22.05 mmol, 1.5 eq.) and 2.52 ml 2.6-lutidine (2.36 g, 22.05 mmol, 1.5 eq.) were added, and the reaction mixture was stirred overnight. The reaction mixture was diluted with 1000 ml dichloromethane and washed twice with $H_2O$ (400 ml). The organic layer was dried over anhydrous $Na_2SO_4$, and concentrated. The diastereomers were separated on CombiFlash column (crude 30 g, EtOAc: n-hexane (1:1+2.5% MeOH)), to yield 24a (top spot: 8.48 g, 44%) and 24b (lower spot: 7.8 g, 41%). In EtOAc: n-hexane (1:1+2. % MeOH), 24a $R_f$=0.15 and 24b $R_f$=0.09).

24a $^1H$ NMR (500 MHz, acetonitrile-$d_3$) δ 9.45 (s, 2H), 8.60 (s, 1H), 8.53 (s, 1H), 8.30 (d, J=8.1 Hz, 2H), 8.09-7.97 (m, 4H), 7.69-7.59 (m, 2H), 7.58-7.47 (m, 4H), 7.39-7.31 (m, 2H), 7.26-7.15 (m, 7H), 6.77 (d, J=8.9 Hz, 4H), 6.36- 6.26 (m, 1H), 6.12 (d, J=3.8 Hz, 1H), 5.97-5.80 (m, 2H), 4.72 (t, J=5.2 Hz, 1H), 4.51-4.44 (m, 1H), 4.44-4.34 (m, 3H), 4.30-4.23 (m, 1H), 4.23-4.13 (m, 1H), 4.11-4.06 (m, 1H), 3.73 (s, 6H), 3.49 (dd, J=11.3, 2.5 Hz, 1H), 3.44 (s, 3H), 3.28 (dd, J=11.3, 4.2 Hz, 1H), 2.69 (q, J=6.6 Hz, 2H), 0.96 (s, 9H), 0.17 (d, J=1.9 Hz, 6H). $^{13}C$ NMR (126 MHz, $CD_3CN$) δ 159.70, 152.98, 152.77, 152.37, 151.17, 151.02, 145.79, 144.20, 143.36, 136.66, 133.61, 131.05, 129.71, 129.68, 129.28, 129.06, 128.81, 127.90, 125.76, 114.03, 92.97, 91.45, 88.39, 88.12, 88.02, 87.25, 83.68, 83.62, 81.43, 74.58, 74.57, 71.51, 68.82, 64.39, 62.38, 59.04, 55.96, 26.20, 20.12, 20.05, 18.78, −4.33, −4.53. $^{31}P$ NMR (202 MHz, $CD_3CN$) δ 68.98. $^{19}F$ NMR (376 MHz, $CD_3CN$) δ −207.65, −207.70, −207.75, −207.79, −207.84, −207.89. Molecular weight for $C_{65}H_{69}FN_{11}O_{12}PSSi$ (M+Na): calculated 1328.4237, found 1328.4243.

24b $^1H$ NMR (500 MHz, acetonitrile-$d_3$) δ 9.38 (s, 1H), 8.68 (s, 1H), 8.62 (s, 1H), 8.31 (s, 1H), 8.28 (s, 1H), 8.00 (d, J=7.7 Hz, 4H), 7.71-7.60 (m, 2H), 7.60-7.47 (m, 4H), 7.38-7.31 (m, 2H), 7.26-7.15 (m, 7H), 6.83-6.68 (m, 4H), 6.39-6.26 (m, 1H), 6.12 (d, J=3.6 Hz, 1H), 6.07-5.87 (m, 2H), 4.74 (t, J=5.3 Hz, 1H), 4.53-4.16 (m, 8H), 3.78-3.67 (m, 6H), 3.47 (s, 3H), 3.32-3.26 (m, 1H), 2.77 (t, J=5.8 Hz, 2H), 0.97 (s, 9H), 0.18 (s, 6H). $^{13}$C NMR (126 MHz, CD$_3$CN) δ 159.66, 152.82, 152.49, 151.20, 151.05, 145.84, 144.25, 143.35, 136.64, 136.54, 134.93, 134.84, 133.70, 133.63, 131.06, 131.04, 129.73, 129.70, 129.23, 129.02, 127.84, 125.81, 125.77, 114.01, 92.92, 91.41, 88.36, 88.09, 87.25, 83.59, 83.50, 81.54, 81.48, 74.77, 74.66, 74.63, 71.33, 68.33, 68.29, 64.65, 62.29, 59.04, 26.22, 20.20, 20.13, 18.79, −4.30, −4.47. $^{31}$P NMR (202 MHz, CD$_3$CN) δ 68.84. $^{19}$F NMR (376 MHz, CD$_3$CN) δ −208.52, −208.57, −208.62, −208.66, −208.71, −208.76. Molecular weight for C$_{65}$H$_{69}$FN$_{11}$O$_{12}$PSSi (M+Na): calculated 1328.4238, found 1328.4236.

Compound 25: Compound 24 (24a top spot: 5.67 g, 4.3 mmol; 24b lower spot: 4.9 g, 3.8 mmol) was dissolved in dry THF (24a: 80 ml; 24b: 70 ml), and Et$_3$N 3HF (24a: 8.5 ml, 52 mmol, 12 eq.; 24b: 7.4 ml, 45 mmol, 12 eq.) was added. The reaction mixture was stirred for 14 hours. The reaction mixture was concentrated, co-evaporated three times with THF and purified by Combiflash column (DCM to 5% MeOH in DCM) to yield 25a (top spot: 4.68 g, 90%) and 25b (lower spot: 3.27 g, 73%).

25a $^1$H NMR (500 MHz, DMSO-d$_6$) δ 11.24 (s, 1H), 11.20 (s, 1H), 8.72 (s, 1H), 8.64 (s, 1H), 8.63 (s, 1H), 8.60 (s, 1H), 8.04-8.01 (m, 4H), 7.63 (t, J=7.3 Hz, 2H), 7.53 (t, J=7.6 Hz, 4H), 7.29 (d, J=7.4 Hz, 2H), 7.20-7.14 (m, 7H), 6.76 (dd, J=8.9, 2.0 Hz, 4H), 6.55-6.45 (m, 1H), 6.16 (d, J=4.2 Hz, 1H), 6.14-5.99 (m, 1H), 5.94-5.83 (m, 1H), 5.60-5.52 (m, 1H), 4.48-4.45 (m, 2H), 4.44-4.35 (m, 2H), 4.34-4.26 (m, 1H), 4.23-4.10 (m, 2H), 4.08-4.00 (m, 1H), 3.68 (s, 6H), 3.39 (d, J=10.4 Hz, 1H), 3.35 (s, 3H), 3.23 (dd, J=11.1, 4.5 Hz, 1H), 2.84-2.80 (m, 2H). $^{13}$C NMR (126 MHz, DMSO) δ 165.60, 165.55, 158.00, 151.92, 151.77, 151.65, 151.42, 150.61, 150.47, 144.45, 143.82, 142.78, 135.20, 133.25, 133.22, 132.46, 132.44, 129.63, 129.59, 128.47, 128.42, 127.65, 127.63, 126.61, 125.78, 125.73, 117.82, 113.02, 91.42, 89.91, 86.49, 86.22, 85.78, 85.61, 82.69, 82.62, 81.73, 79.85, 79.78, 73.47, 73.44, 73.36, 73.33, 68.70, 68.04, 68.00, 63.24, 63.20, 61.39, 57.72, 54.95, 18.76, 18.69. $^{31}$P NMR (202 MHz, DMSO) δ 66.93. $^{19}$F NMR (376 MHz, cd3cn) δ −208.25, −208.30, −208.35, −208.39, −208.44, −208.49. Molecular weight for C$_{59}$H$_{55}$FN$_{11}$O$_{12}$PS (M+Na): calculated 1214.3372, found 1214.3378.

25b $^1$H NMR (500 MHz, DMSO-d$_6$) δ 11.25 (s, 1H), 11.21 (s, 1H), 8.74 (s, 1H), 8.68 (s, 1H), 8.62 (s, 1H), 8.60 (s, 1H), 8.06-8.00 (m, 4H), 7.63 (t, J=7.4 Hz, 2H), 7.53 (t, J=7.6 Hz, 4H), 7.28 (d, J=8.3 Hz, 2H), 7.19-7.11 (m, 7H), 6.74 (dd, J=9.0, 2.5 Hz, 4H), 6.49 (dd, J=20.0, 2.3 Hz, 1H), 6.17 (d, J=4.8 Hz, 1H), 6.15-6.00 (m, 1H), 5.95-5.84 (m, 1H), 5.56 (d, J=5.6 Hz, 1H), 4.49-4.42 (m, 2H), 4.35-4.25 (m, 3H), 4.22-4.13 (m, 3H), 3.67 (s, 6H), 3.38 (s, 4H), 3.22 (dd, J=11.3, 4.6 Hz, 1H), 2.87 (t, J=5.9 Hz, 2H). $^{13}$C NMR δ (126 MHz, DMSO) δ 165.59, 165.56, 157.96, 151.92, 151.79, 151.69, 151.42, 150.63, 150.48, 144.47, 143.83, 142.80, 135.21, 133.26, 133.22, 132.46, 132.43, 129.62, 129.58, 128.47, 128.42, 127.62, 127.62, 126.56, 125.79, 125.75, 117.93, 112.99, 91.45, 89.93, 86.50, 86.22, 85.87, 85.59, 82.66, 82.59, 81.76, 79.80, 79.72, 73.15, 73.12, 68.62, 67.99, 67.95, 63.49, 63.45, 61.21, 57.75, 54.92, 18.77, 18.70, −1.21. $^{31}$P NMR (202 MHz, DMSO) δ 66.98. $^{19}$F NMR (376 MHz, cd3cn) δ −208.15, −208.20, −208.25, −208.29, −208.34, −208.39. Molecular weight for C$_9$H$_{55}$FN$_{11}$O$_{12}$PS (M+Na): calculated 1214.3372, found 1214.3363.

Compound 26: Compound 25 (25a top spot: 1 g, 0.84 mmol; 25b lower spot: 1 g, 0.84 mmol) was dried overnight under high vacuum and dissolved in dry ethyl acetate (25a: 13 ml, 25b: 17 ml). N,N-Diisopropylamine (25a: 366 µl, 271 mg, 2.1 mmol, 2.5 eq.; 25b: 366 µl, 271 mg, 2.1 mmol, 2.5 eq.) was added dropwise under rigorous stirring. Subsequently, 2-cyanoethyl N,N-diisopropylchlorophosphoramidite (25a: 379 µl, 402 mg, 1.7 mmol, 2 eq.; 25b: 379 µl, 402 mg, 1.7 mmol, 2 eq.) was added dropwise (over 1 minute), and the reaction mixture was stirred at room temperature for 1.5 hours. The reaction mixture was diluted with 200 ml EA, washed with 100 ml NaHCO$_3$ and 100 ml brine, dried over Na$_2$SO$_4$, and concentrated to dryness. The crude (white foam) was dissolved in 5 ml DCM and precipitated from 1 L cold n-hexane/diethyl ether (1:1) to yield 26a (top spot: 1 g, 86%) and 26b (lower spot: 1.1 g, 90%).

26a $^1$H NMR (500 MHz, acetonitrile-d$_3$) δ 8.57 (s, 1H), 8.52 (d, J=2.7 Hz, 1H), 8.31-8.23 (m, 2H), 8.05-7.96 (m, 4H), 7.67-7.56 (m, 2H), 7.56-7.43 (m, 4H), 7.35-7.28 (m, 2H), 7.23-7.11 (m, 7H), 6.80-6.70 (m, 4H), 6.32-6.24 (m, 1H), 6.10 (dd, J=9.1, 4.3 Hz, 1H), 5.97-5.74 (m, 2H), 4.85-4.69 (m, 1H), 4.58-4.32 (m, 4H), 4.22-4.11 (m, 1H), 4.11-3.97 (m, 1H), 3.91-3.80 (m, 1H), 3.71 (s, 8H), 3.47 (s, 3H), 3.41 (s, 3H), 3.33-3.19 (m, 1H), 2.73-2.61 (m, 3H), 1.24-1.16 (m, 12H). $^{13}$C NMR (126 MHz, CD$_3$CN) δ 159.70, 152.92, 152.86, 152.34, 151.19, 151.07, 145.79, 144.21, 144.16, 143.40, 143.30, 136.65, 136.58, 134.94, 134.83, 133.70, 133.62, 131.06, 129.71, 129.69, 129.28, 129.06, 128.80, 127.89, 125.78, 114.02, 93.05, 93.04, 91.61, 91.54, 88.43, 88.41, 88.13, 88.02, 87.23, 83.29, 83.13, 82.98, 82.86, 82.76, 81.42, 81.34, 74.64, 74.52, 72.29, 72.17, 71.71, 71.57, 69.13, 68.76, 64.41, 64.38, 62.33, 62.29, 60.01, 59.87, 59.49, 59.33, 59.23, 59.02, 55.95, 46.09, 46.04, 44.32, 44.26, 44.22, 44.16, 25.14, 25.08, 25.04, 24.98, 23.43, 23.25, 23.18, 21.20, 21.12, 21.07, 20.11, 20.05. $^{31}$P NMR (202 MHz, CD$_3$CN) δ 151.95, 151.22, 69.01. $^{19}$F NMR (376 MHz, CD$_3$CN) δ −207.19, −207.24, −207.30, −207.35, −207.38, −207.44, −207.49, −207.54. Molecular weight for C$_{68}$H$_{72}$FN$_{13}$O$_{13}$P$_2$S (M+H): calculated 1392.4631, found 1392.4681.

26b $^1$H NMR (500 MHz, acetonitrile-d$_3$) δ 9.33 (s, 1H), 8.64 (s, 1H), 8.60 (d, J=2.2 Hz, 1H), 8.28 (d, J=1.7 Hz, 1H), 8.24 (d, J=5.4 Hz, 1H), 8.02-7.94 (m, 4H), 7.66-7.58 (m, 2H), 7.56-7.48 (m, 4H), 7.34-7.27 (m, 2H), 7.24-7.09 (m, 7H), 6.76-6.69 (m, 4H), 6.34-6.26 (m, 1H), 6.12-6.07 (m, 1H), 6.04-5.80 (m, 2H), 4.86-4.73 (m, 1H), 4.55 (dt, J=25.9, 4.6 Hz, 1H), 4.45-4.16 (m, 6H), 3.96-3.73 (m, 2H), 3.70 (s, 7H), 3.50 (s, 2H), 3.47-3.38 (m, 3H), 3.28-3.19 (m, 1H), 2.75 (q, J=5.9, 5.2 Hz, 2H), 2.72-2.63 (m, 2H), 1.25-1.18 (m, 12H). $^{13}$C NMR (126 MHz, CD$_3$CN) δ 159.66, 152.93, 152.51, 151.22, 151.08, 145.86, 145.84, 144.23, 144.22, 143.42, 143.27, 136.63, 136.54, 134.95, 134.87, 133.70, 133.62, 131.06, 131.04, 129.73, 129.70, 129.24, 129.02, 128.79, 127.84, 125.85, 125.80, 125.72, 114.01, 92.91, 91.42, 88.49, 88.32, 88.06, 87.98, 87.25, 83.23, 83.08, 82.92, 82.64, 81.56, 81.51, 74.75, 72.10, 71.97, 71.59, 71.45, 68.63, 68.29, 64.65, 64.61, 62.29, 60.02, 59.87, 59.50, 59.34, 59.27, 59.02, 55.95, 46.09, 46.04, 44.34, 44.28, 44.24, 44.18, 25.20, 25.16, 25.10, 25.00, 23.25, 23.18, 21.21, 21.15, 21.09, 20.19, 20.13. $^{31}$P NMR (202 MHz, CD$_3$CN) δ 151.89, 151.30, 68.73. $^{19}$F NMR (376 MHz, CD$_3$CN) δ −208.53, −208.58, −208.63, −208.67, −208.72, −208.76, −208.81, −208.85, −208.90, −208.95. Molecular weight for C$_{68}$H$_{72}$FN$_{13}$O$_{13}$P$_2$S (M+H): calculated 1392.4631, found 1392.4669.

D-2. Synthesis of Fully Deprotected, Chirally Pure $A_FsA_{OMe}$

Scheme D-2. Synthesis of fully deprotected, chirally pure $A_FsA_{OMe}$ dinucleotide (Afsa)

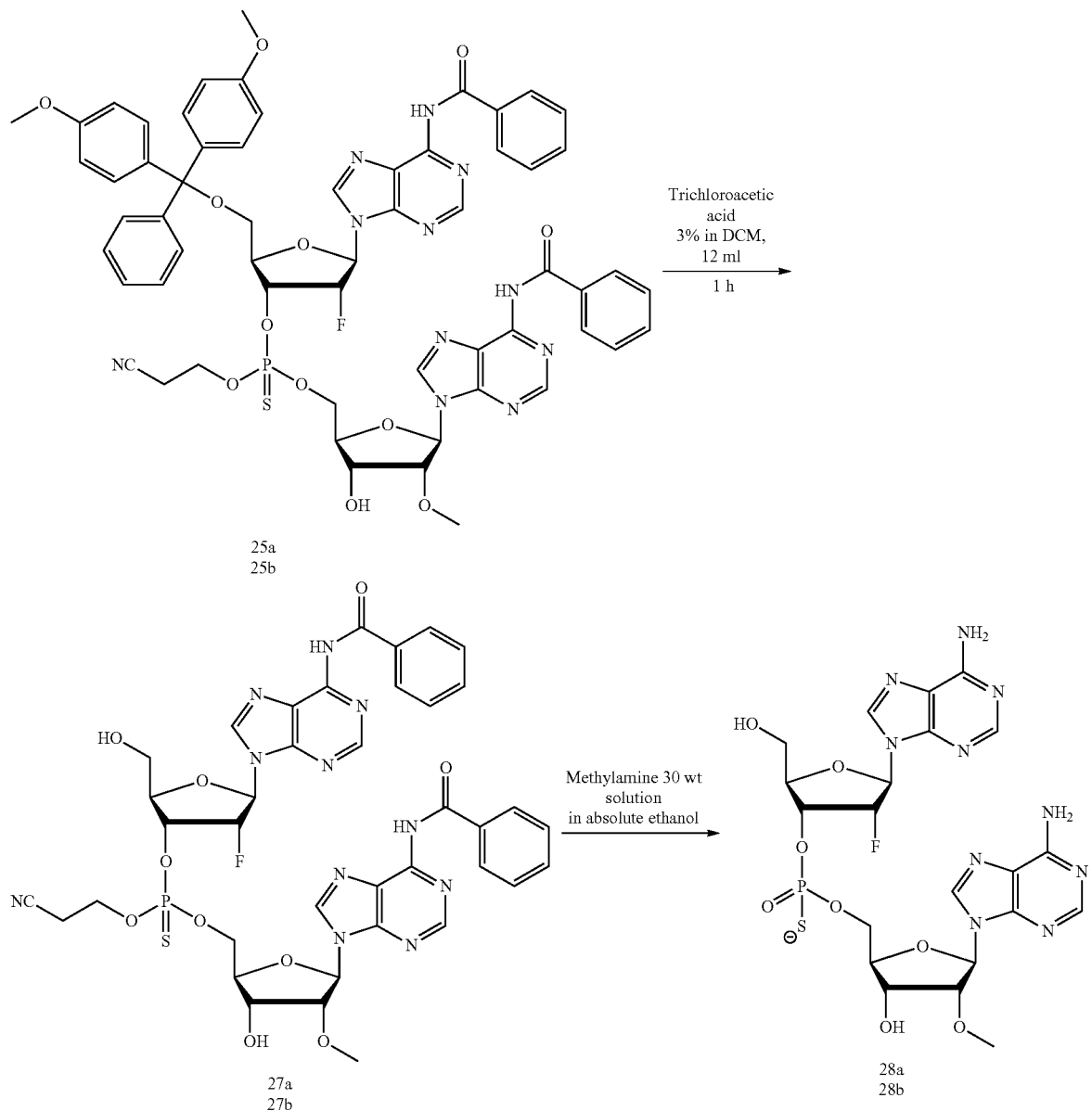

Compound 27: Compound 25 (25a top spot: 500 mg, 0.42 mmol; 25b lower spot: 500 mg, 0.42 mmol) was dissolved in 1.5 ml DCM, and 8 ml trichloroacetic acid (3% in DCM) was added. The reaction mixture was stirred at room temperature for 1 hour. The reaction mixture was concentrated and purified by CombiFlash column (40 g Gold column, 50 ml/min flow, DCM to 5% MeOH in DCM for 8 minutes, 5% MeOH in DCM for 15 minutes) to yield 27a (355 mg, 95%) and 27b (327 mg, 88%). In 5% MeOH in DCM, 27a: Rf=0.16 and 27b: Rf=0.16.

27a $^1$H NMR (400 MHz, DMSO-d$_6$) δ 11.29 (s, 1H), 11.26 (s, 1H), 8.76 (s, 1H), 8.73 (s, 1H), 8.69 (s, 1H), 8.65 (s, 1H), 8.03 (d, J=7.3 Hz, 4H), 7.69-7.59 (m, 2H), 7.59-7.48 (m, 4H), 6.47 (dd, J=16.7, 3.6 Hz, 1H), 6.23-6.15 (m, 1H), 5.93 (dt, J=51.4, 4.0 Hz, 1H), 5.65-5.57 (m, 1H), 5.54-5.42 (m, 1H), 5.34 (t, J=5.5 Hz, 1H), 4.55-4.18 (m, 8H), 3.78-3.58 (m, 2H), 3.36 (s, 3H), 2.97 (t, J=5.8 Hz, 2H). $^{13}$C NMR (126 MHz, DMSO) δ 165.62, 165.59, 151.97, 151.82, 151.80, 151.72, 150.58, 150.49, 142.98, 142.87, 133.25, 133.20, 132.49, 132.45, 128.48, 128.45, 128.44, 125.76, 125.74, 118.10, 91.51, 91.49, 89.96, 85.82, 85.72, 85.46, 82.80, 82.73, 82.67, 81.73, 74.36, 74.33, 74.25, 74.22, 68.67, 68.03, 67.99, 63.42, 63.39, 59.89, 57.73, 54.88, 18.84, 18.77. $^{31}$P NMR (202 MHz, DMSO) δ 66.78. $^{19}$F NMR (376 MHz, DMSO) δ −210.64, −210.67, −210.68, −210.72, −210.78, −210.81, −210.82, −210.85. Molecular weight for $C_{38}H_{37}FN_{11}O_{10}PS$ (M+Na): calculated 912.2065, found 912.2079.

27b $^1$H NMR (400 MHz, DMSO-d$_6$) δ 11.27 (d, J=13.1 Hz, 2H), 8.77 (d, J=5.5 Hz, 1H), 8.68 (d, J=8.1 Hz, 2H), 8.03 (d, J=8.0 Hz, 4H), 7.68-7.49 (m, 6H), 6.47 (dd, J=16.9, 3.5 Hz, 1H), 6.21 (d, J=4.4 Hz, 1H), 5.93 (dt, J=51.5, 3.9 Hz,

1H), 5.62 (d, J=5.3 Hz, 1H), 5.54-5.43 (m, 1H), 5.32 (t, J=5.5 Hz, 1H), 4.55-4.48 (m, 2H), 4.48-4.33 (m, 2H), 4.31-4.18 (m, 4H), 3.78-3.56 (m, 2H), 3.39 (s, 3H), 2.93 (t, J=5.8 Hz, 2H). $^{13}$C NMR (126 MHz, DMSO) δ 165.61, 165.59, 151.96, 151.83, 151.82, 151.71, 150.59, 150.51, 143.00, 142.97, 133.25, 133.20, 132.49, 132.45, 128.48, 128.45, 125.79, 125.76, 118.03, 91.53, 91.51, 90.00, 89.98, 85.92, 85.78, 85.51, 82.76, 82.70, 82.65, 82.60, 81.71, 74.16, 74.13, 68.68, 68.13, 68.09, 63.46, 63.42, 59.81, 57.77, 54.89, 18.79, 18.72. $^{31}$P NMR (202 MHz, DMSO) δ 66.88. $^{19}$F NMR (376 MHz, DMSO) δ −210.45, −210.48, −210.49, −210.53, −210.58, −210.62, −210.63, −210.66. Molecular weight for $C_{38}H_{37}FN_{11}O_{10}PS$ (M+Na): calculated 912.2065, found 912.2053.

Compound 28: Compound 27 (27a top spot: 340 mg, 0.38 mmol; 27b lower spot: 312 mg, 0.35 mmol) was dissolved 12 ml methylamine (33 wt % solution in absolute ethanol) and stirred for 2 hours at room temperature. The reaction mixture was concentrated and purified over CombiFlash column (24 g Gold column, 35 ml/min flow, ethyl acetate/MeOH (70:30) for 8 minutes, ethyl acetate/MeOH (60:40) for 5 minutes) to yield 28a (205 mg, 85%) and 28b (186 mg, 85%). In ethyl acetate/MeOH (2:1), 28a: Rf=0.16 and 28b: Rf=0.13.

28a $^{1}$H NMR (500 MHz, deuterium oxide) δ 8.39 (s, 1H), 8.23 (s, 1H), 8.14 (s, 1H), 7.83 (s, 1H), 6.15 (d, J=16.1 Hz, 1H), 6.00 (d, J=3.6 Hz, 1H), 5.41 (dd, 1H), 5.14-5.01 (m, 1H), 4.61 (t, J=5.1 Hz, 1H), 4.46-4.40 (m, 1H), 4.40-4.32 (m, 2H), 4.24-4.19 (m, 2H), 4.14 (d, J=13.1 Hz, 1H), 4.11-4.05 (m, 1H), 3.96 (dd, J=13.2, 3.6 Hz, 1H), 3.48 (s, 3H). $^{13}$C NMR (126 MHz, d$_2$o) δ 154.90, 154.50, 152.67, 151.81, 147.56, 146.83, 138.86, 138.69, 118.31, 117.86, 92.36, 90.86, 87.70, 87.44, 85.89, 83.97, 82.90, 82.82, 81.63, 81.56, 71.31, 71.27, 71.19, 71.15, 68.23, 63.34, 63.29, 59.01, 58.33. $^{31}$P NMR (202 MHz, D$_2$O) δ 57.21. $^{19}$F NMR (376 MHz, D$_2$O) δ −200.83, −200.87, −200.89, −200.93, −200.96, −201.01, −201.03, −201.07. Molecular weight for $C_{21}H_{26}FN_{10}O_8PS$ (M+H): calculated 629.1456, found 629.1449.

28b $^{1}$H NMR (500 MHz, deuterium oxide) δ 8.28 (s, 2H), 8.22 (s, 1H), 8.13 (s, 13H), 7.86 (s, 1H), 6.14 (d, J=15.9 Hz, 1H), 6.06-5.98 (m, 1H), 5.46 (d, J=52.3 Hz, 1H), 5.00 (dtd, J=18.9, 9.1, 4.1 Hz, 1H), 4.63 (t, J=4.7 Hz, 1H), 4.41-4.34 (m, 2H), 4.28 (s, 2H), 4.18 (s, 1H), 4.07-4.01 (m, 1H), 3.94-3.88 (m, 1H), 3.48 (s, 4H). $^{13}$C NMR (126 MHz, d$_2$o) δ 154.97, 154.67, 152.67, 151.92, 147.82, 147.11, 139.16, 138.56, 118.38, 117.96, 92.16, 90.64, 87.31, 87.04, 85.65, 83.56, 83.12, 83.04, 82.12, 82.06, 70.37, 70.31, 70.25, 70.19, 68.23, 64.81, 64.80, 64.77, 59.24, 58.25. $^{31}$P NMR (202 MHz, D$_2$O) δ 55.40. $^{19}$F NMR (376 MHz, D$_2$O) δ −202.19, −202.23, −202.24, −202.28, −202.32, −202.37, −202.38, −202.42. Molecular weight for $C_{21}H_{26}FN_{10}O_8PS$ (M+H): calculated 629.1456, found 629.1452.

E-1. Synthesis of Chirally Pure 2'-OMe Adenosine-2'-F Uridine Phosphorothioate Dinucleotide (A$_{OMe}$-SU$_F$) (asUf)

Scheme E-1. Synthesis of chirally pure 2'-OMe adenosine-2'-F uridine phosphorothioate dinucleotide (A$_{OMe}$sA$_F$) phosphoramidite building block (asUf)

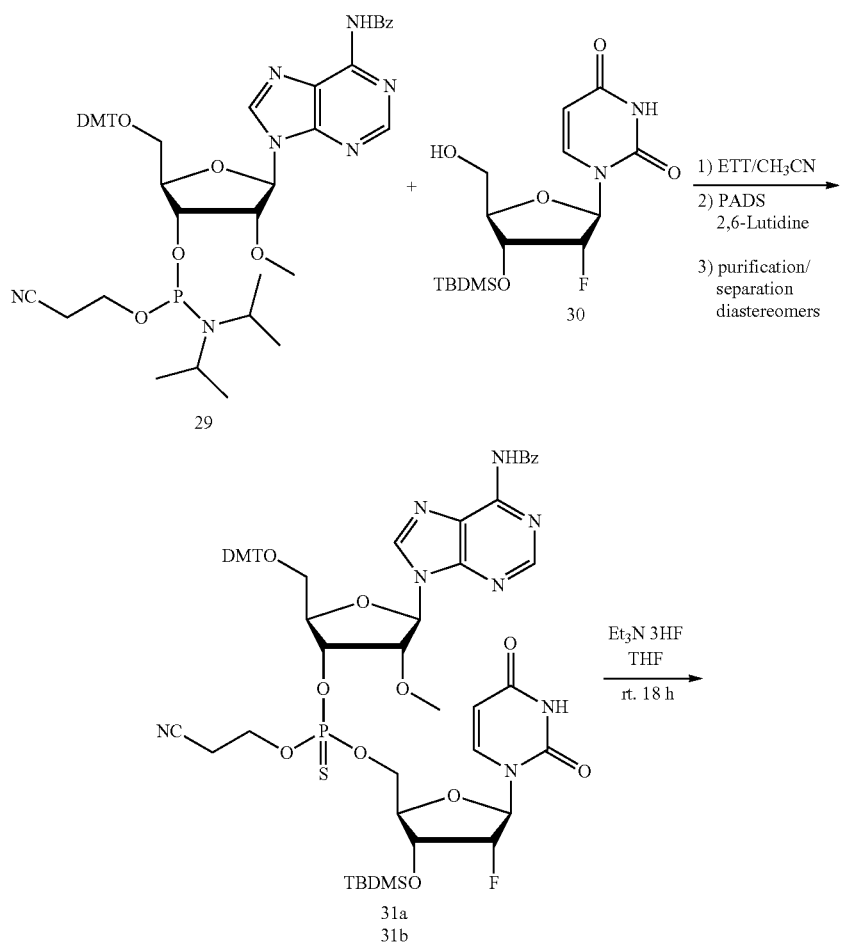

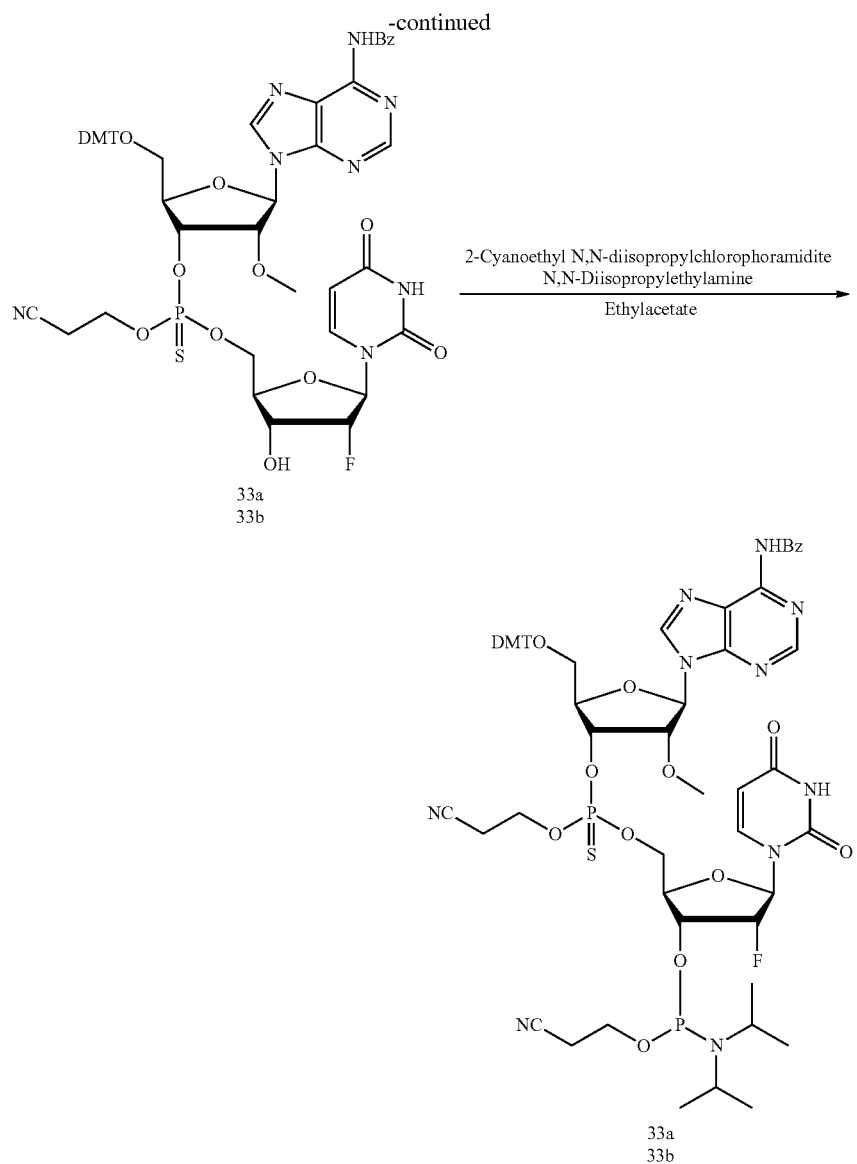

Compound 31: Compound 29 (13.1 g, 14.7 mmol) and compound 30 (5.6 g, 15.4 mmol, 1.05 eq.) were dried under high vacuum and dissolved in 110 ml dichloromethane (dry). To this solution was added 117 ml ETT (3.83 g, 29.4 mmol, 2 eq.), and the reaction mixture was stirred for 2 hours. PADS (6.35 g, 22.05 mmol, 1.5 eq.) and 2.52 ml 2.6-lutidine (2.36 g, 22.05 mmol, 1.5 eq.) were added, and the reaction mixture was stirred overnight. The reaction mixture was diluted with 1000 ml dichloromethane and washed with $H_2O$ (400 ml) twice. The organic layer was dried over anhydrous $Na_2SO_4$, and concentrated. The diastereomers were separated by CombiFlash column (crude 30 g, EtOAc: n-hexane (1:1+2.5% MeOH) to yield 31a (top spot: 9.44 g, 55%) and 31b (lower spot: 6.41 g, 37%). In EtOAc: n-hexane (1:1+2.5% MeOH), 31a $R_f$=0.23, 31b $R_f$=0.19.

31a $^1$H NMR 77a (500 MHz, DMSO-$d_6$) δ 11.43 (d, J=1.7 Hz, 1H), 11.25 (s, 1H), 8.60 (d, J=6.9 Hz, 2H), 8.04 (d, J=7.5 Hz, 2H), 7.67-7.60 (m, 2H), 7.57-7.52 (m, 2H), 7.39 (d, J=7.6 Hz, 2H), 7.29-7.23 (m, 6H), 7.23-7.17 (m, 1H), 6.84 (dd, J=8.9, 2.5 Hz, 4H), 6.18 (d, J=6.9 Hz, 1H), 5.90-5.84 (m, 1H), 5.63 (dd, J=8.0, 2.0 Hz, 1H), 5.41-5.35 (m, 1H), 5.22 (dd, J=52.9, 4.0 Hz, 1H), 5.07-5.01 (m, 1H), 4.49-4.40 (m, 2H), 4.40-4.33 (m, 1H), 4.27-4.14 (m, 3H), 4.11-4.06 (m, 1H), 3.72 (s, 6H), 3.37 (dd, J=10.7, 4.6 Hz, 1H), 3.34 (s, 4H), 2.92-2.87 (m, 2H), 0.85 (s, 9H), 0.13-0.07 (m, 6H). $^{13}$C NMR (126 MHz, DMSO) δ 165.58, 163.09, 158.09, 151.96, 151.61, 150.65, 150.12, 144.50, 143.47, 141.20, 135.26, 135.20, 133.20, 132.46, 129.68, 129.67, 128.46, 128.42, 127.75, 127.66, 126.72, 125.93, 117.93, 113.14, 101.89, 92.63, 92.61, 91.13, 91.10, 89.35, 89.09, 85.87, 85.24, 82.19, 80.32, 80.23, 78.96, 75.87, 69.18, 69.05, 66.63, 63.15, 63.11, 62.73, 59.70, 58.08, 54.98, 25.45, 18.86, 18.79, 17.62, −4.97, −5.28. $^{31}$P NMR (202 MHz, DMSO) δ 68.15. $^{19}$F NMR (162 MHz, DMSO) δ −214.77, −214.90, −215.02, −215.10, −215.23, −215.35. Molecular weight for $C_7H_{64}FN_8O_{13}PSSi$ (M+H): calculated 1179.3883, found 1179.3904.

31b $^1$H NMR (500 MHz, DMSO-$d_6$) δ 11.43 (d, J=1.8 Hz, 2H), 11.24 (s, 1H), 8.60 (d, J=12.5 Hz, 2H), 8.03 (d, J=7.4 Hz, 2H), 7.67-7.59 (m, 2H), 7.57-7.52 (m, 2H), 7.38 (d,

J=7.6 Hz, 2H), 7.27-7.22 (m, 6H), 7.22-7.16 (m, 1H), 6.86-6.80 (m, 4H), 6.16 (d, J=6.6 Hz, 1H), 5.88 (d, J=20.9 Hz, 1H), 5.63 (dd, J=8.0, 2.1 Hz, 1H), 5.43-5.37 (m, 1H), 5.22 (dd, J=53.3, 4.7 Hz, 1H), 5.08-5.02 (m, 1H), 4.46-4.39 (m, 1H), 4.39-4.35 (m, 1H), 4.33-4.20 (m, 4H), 4.08-4.03 (m, 1H), 3.71 (s, 6H), 3.42-3.37 (m, 1H), 3.36 (s, 3H), 3.31-3.27 (m, 1H), 2.95 (t, J=5.8 Hz, 2H), 0.87 (s, 9H), 0.12 (s, 3H), 0.11 (s, 3H). $^{13}$C NMR (126 MHz, DMSO) δ 165.58, 163.10, 158.07, 151.87, 151.56, 150.64, 150.11, 144.52, 143.71, 141.19, 135.25, 135.19, 133.21, 132.45, 129.67, 128.46, 128.42, 127.71, 127.64, 126.67, 126.00, 118.05, 113.10, 101.88, 92.69, 91.22, 89.46, 89.15, 85.81, 85.52, 82.20, 80.20, 80.13, 78.90, 75.76, 68.98, 68.86, 66.13, 63.41, 62.57, 58.11, 54.96, 25.49, 18.88, 18.81, 17.63, −4.94, −5.21. $^{31}$P NMR (202 MHz, DMSO) δ 68.36. $^{19}$F NMR (376 MHz, DMSO) δ −206.39, −206.44, −206.49, −206.53, −206.58, −206.64. Molecular weight for $C_7H_{64}FN_8O_{13}PSSi$ (M+H): calculated 1179.3883, found 1179.3907.

Compound 32: Compound 31 (31a top spot: 9.44 g, 8 mmol; 31b lower spot: 6.41 g, 5.4 mmol) was dissolved in dry THF (31a: 160 ml; 31b: 90 ml), and Et$_3$N 3HF (31a: 15.6 ml, 96 mmol, 12 eq.; 31b: 10.6 ml, 64.8 mmol, 12 eq.) was added. The reaction mixture was stirred for 14 hours. The reaction mixture was concentrated, co-evaporated three times with THF and purified by CombiFlash column (330 g Gold column, 150 ml/min flow, DCM to 5% MeOH in DCM) to yield 32a (top spot: 4.13 g, 49%) and 32b (lower spot: 2.23 g, 39%). In 5% MeOH in DCM, 32a: $R_f$=0.26, 32b: $R_f$=1.1.

32a $^1$H NMR (400 MHz, DMSO-d$_6$) δ 11.47-11.40 (m, 1H), 11.27 (s, 1H), 8.61 (d, J=7.0 Hz, 2H), 8.04 (d, J=7.6 Hz, 2H), 7.68-7.58 (m, 2H), 7.58-7.51 (m, 2H), 7.43-7.36 (m, 2H), 7.26 (d, J=8.6 Hz, 6H), 7.23-7.17 (m, 1H), 6.85 (dd, J=8.8, 2.1 Hz, 4H), 6.19 (d, J=6.8 Hz, 1H), 5.92-5.80 (m, 2H), 5.62 (dd, J=8.0, 1.9 Hz, 1H), 5.43-5.34 (m, 1H), 5.23-5.00 (m, 2H), 4.51-4.40 (m, 2H), 4.32-4.13 (m, 4H), 4.12-4.04 (m, 1H), 3.72 (s, 6H), 3.41-3.36 (m, 1H), 3.34 (s, 3H), 3.33-3.28 (m, 1H), 2.92 (q, J=5.4 Hz, 2H). $^{13}$C NMR (126 MHz, DMSO) δ 165.60, 163.05, 158.09, 151.91, 151.63, 150.66, 150.10, 144.52, 143.65, 140.87, 135.28, 135.20, 133.21, 132.47, 129.70, 128.48, 128.44, 127.77, 127.67, 126.73, 125.98, 120.35, 118.01, 113.15, 101.89, 93.50, 92.03, 88.97, 88.68, 85.86, 85.59, 82.20, 82.17, 80.23, 80.15, 78.96, 78.92, 75.80, 75.76, 68.09, 67.96, 67.32, 67.28, 63.11, 63.07, 62.68, 58.08, 54.99, 18.84, 18.77. $^{31}$P NMR (202 MHz, DMSO) δ 66.88. $^{19}$F NMR (376 MHz, DMSO) δ −206.83, −206.88, −206.94, −206.97, −207.02, −207.08. Molecular weight for $C_{51}H_{50}FN_8O_{13}PS$ (M+H): calculated 1065.3018, found 1065.3024.

32b $^1$H NMR (400 MHz, DMSO-d$_6$) δ 11.45 (d, J=1.7 Hz, 1H), 11.27 (s, 1H), 8.61 (d, J=9.3 Hz, 2H), 8.04 (d, J=7.3 Hz, 2H), 7.68-7.58 (m, 2H), 7.58-7.50 (m, 2H), 7.39 (d, J=7.4 Hz, 2H), 7.31-7.15 (m, 7H), 6.84 (dd, J=8.9, 2.9 Hz, 4H), 6.17 (d, J=6.7 Hz, 1H), 5.95-5.83 (m, 2H), 5.62 (dd, J=8.1, 2.1 Hz, 1H), 5.44-5.36 (m, 1H), 5.24-5.00 (m, 2H), 4.43-4.33 (m, 2H), 4.31-4.19 (m, 4H), 4.11-3.98 (m, 1H), 3.71 (s, 6H), 3.41-3.37 (m, 1H), 3.36 (s, 3H), 3.33-3.28 (m, 1H), 2.96 (t, J=5.8 Hz, 2H). $^{13}$C NMR (126 MHz, DMSO) δ 165.61, 163.07, 158.08, 152.05, 151.89, 151.72, 151.61, 150.66, 150.44, 150.11, 144.54, 143.75, 142.92, 140.86, 135.30, 135.23, 133.27, 133.22, 132.48, 132.44, 129.69, 128.48, 128.44, 127.76, 127.67, 126.71, 126.02, 118.14, 113.14, 101.92, 93.59, 92.09, 89.03, 88.74, 86.26, 85.85, 85.52, 82.58, 82.24, 82.21, 80.16, 80.09, 78.91, 78.88, 75.71, 75.67, 68.62, 67.99, 67.85, 66.96, 66.92, 63.38, 63.34, 62.62, 61.12, 58.10, 57.53, 54.98, 18.86, 18.79. $^{31}$P NMR (202 MHz, DMSO) δ 67.00. $^{19}$F NMR (376 MHz, DMSO) δ −206.44, −206.50, −206.55, −206.58, −206.64, −206.69. Molecular weight for $C_{51}H_{50}FN_8O_{13}PS$ (M+H): calculated 1065.3018, found 1065.3014.

Compound 33: Compound 32 (32a top spot: 1 g, 0.94 mmol; 32b lower spot: 1 g, 0.94 mmol) was dried overnight under high vacuum and dissolved in dry ethyl acetate (32a: 13 ml; 32b: 12 ml). N,N-Diisopropylamine (32a: 409 µl, 304 mg, 2.35 mmol, 2.5 eq.; 32b: 409 µl, 304 mg, 2.35 mmol, 2.5 eq.) was added dropwise under rigorous stirring. Subsequently, 2-cyanoethyl N,N-diisopropylchlorophosphoramidite (4a: 424 µl, 450 mg, 1.9 mmol, 2 eq.; 32b: 424 µl, 450 mg, 1.9 mmol, 2 eq.) was added dropwise (over 1 minute), and the reaction mixture was stirred at room temperature for 1.5 hours. The reaction mixture was diluted with 200 ml EA, washed with 100 ml NaHCO$_3$ and 100 ml brine, dried over Na$_2$SO$_4$, and concentrated to dryness. The crude (white foam) was dissolved in 5 ml DCM and precipitated from 1 L cold n-hexane/diethyl ether (1:1) to yield 33a (top spot: 1.13 g, 95%) and 33b (lower spot: 1.08 g, 91%).

33a $^1$H NMR (500 MHz, acetonitrile-d$_3$) δ 9.35 (s, 2H), 8.57 (s, 1H), 8.26 (s, 1H), 8.02 (d, J=7.6 Hz, 2H), 7.65 (t, J=7.4 Hz, 1H), 7.55 (t, J=7.7 Hz, 2H), 7.52-7.46 (m, 1H), 7.44 (d, J=7.7 Hz, 2H), 7.35-7.26 (m, 6H), 7.25-7.20 (m, 1H), 6.84 (d, J=8.2 Hz, 4H), 6.17-6.12 (m, 1H), 5.85 (dd, J=19.6, 4.9 Hz, 1H), 5.60 (d, J=8.1 Hz, 1H), 5.49-5.41 (m, 1H), 5.26-5.10 (m, 1H), 4.95-4.89 (m, 1H), 4.62-4.51 (m, 1H), 4.49-4.15 (m, 6H), 3.89-3.77 (m, 2H), 3.76 (s, 6H), 3.70-3.61 (m, 2H), 3.50-3.45 (m, 1H), 3.43 (d, J=3.1 Hz, 3H), 3.42-3.36 (m, 1H), 2.79-2.72 (m, 2H), 2.70-2.63 (m, 2H), 1.21-1.15 (m, 12H). $^{13}$C NMR (126 MHz, cd$_3$cn) δ 163.94, 159.80, 152.98, 151.20, 151.16, 151.12, 145.82, 145.82, 143.78, 143.77, 142.02, 141.87, 136.67, 134.92, 133.68, 131.15, 131.12, 129.73, 129.25, 129.14, 128.93, 128.02, 125.89, 119.63, 114.16, 103.15, 103.07, 94.34, 93.80, 92.84, 92.27, 91.38, 91.28, 91.10, 90.99, 87.55, 87.36, 87.33, 83.62, 83.59, 83.55, 81.32, 81.29, 80.96, 80.91, 80.89, 80.84, 76.98, 76.95, 70.87, 70.77, 70.75, 70.62, 67.95, 67.91, 67.65, 67.60, 64.33, 64.29, 63.64, 59.96, 59.81, 59.77, 59.62, 59.42, 56.00, 44.36, 44.34, 44.26, 44.24, 25.18, 25.12, 25.02, 24.99, 24.97, 24.96, 24.93, 24.92, 21.14, 21.08, 21.07, 21.01, 20.20, 20.13. $^{31}$P NMR (202 MHz, cd$_3$cn) δ 152.06, 152.03, 68.66, 68.64. $^{19}$F NMR (376 MHz, cd$_3$cn) δ −198.90, −198.93, −198.95, −198.98, −199.01, −199.03, −199.04, −199.07, −199.09, −199.12, −199.15, −199.17, −199.55, −199.57, −199.60, −199.62, −199.65, −199.67, −199.69, −199.71, −199.74, −199.76, −199.79, −199.81. Molecular weight for $C_{60}H_{67}FN_{10}O_4P_2S$ (M+H): calculated 1265.4096, found 1265.4106.

33b $^1$H NMR (500 MHz, acetonitrile-d$_3$) δ 9.36 (s, 2H), 8.57 (s, 1H), 8.25 (s, 1H), 8.01 (d, J=7.5 Hz, 2H), 7.65 (t, J=7.4 Hz, 1H), 7.55 (t, J=7.7 Hz, 2H), 7.46-7.40 (m, 3H), 7.35-7.25 (m, 6H), 7.24-7.19 (m, 1H), 6.86-6.80 (m, 4H), 6.13-6.09 (m, 1H), 5.86-5.77 (m, 1H), 5.61-5.58 (m, 1H), 5.47-5.42 (m, 1H), 5.28-5.13 (m, 1H), 4.97-4.92 (m, 1H), 4.64-4.48 (m, 1H), 4.47-4.39 (m, 2H), 4.37-4.17 (m, 4H), 3.91-3.77 (m, 2H), 3.75 (s, 6H), 3.72-3.61 (m, 2H), 3.49-3.44 (m, 1H), 3.43 (s, 3H), 3.40-3.35 (m, 1H), 2.86-2.80 (m, 2H), 2.70-2.64 (m, 2H), 1.22-1.17 (m, 12H). $^{13}$C NMR (126 MHz, cd$_3$cn) δ 163.94, 159.78, 159.77, 152.99, 151.20, 151.16, 151.13, 145.86, 143.89, 142.34, 142.14, 136.66, 134.93, 133.67, 131.16, 131.12, 129.73, 129.25, 129.11, 128.93, 127.99, 119.61, 114.16, 103.19, 103.12, 94.42, 93.86, 93.84, 92.93, 92.36, 92.34, 91.77, 91.49, 87.53, 87.52, 87.43, 87.41, 83.73, 83.69, 83.65, 81.26, 81.23, 81.12, 81.09, 81.05, 81.02, 80.75, 80.70, 80.67, 80.63, 77.15, 77.12, 70.63, 70.58, 70.50, 70.45, 70.38, 70.32, 67.34, 67.31, 67.06, 67.03, 64.52, 64.48, 63.66, 61.04, 60.00, 59.85, 59.77, 59.61, 59.36, 55.99, 44.37, 44.34, 44.27, 44.24, 25.21, 25.15, 25.04, 25.01, 24.98, 24.95, 24.93, 21.22, 21.16, 21.10, 21.03, 20.25, 20.18. $^{31}$P NMR (202 MHz, cd$_3$cn) δ 151.97, 151.94, 68.75, 68.71. $^{19}$F NMR (376 MHz, cd$_3$cn) δ −197.89, −197.94, −197.97, −198.00, −198.02, −198.05, −198.08, −198.11, −198.16, −198.32, −198.34, −198.38, −198.40, −198.43, −198.45, −198.46, −198.48, −198.52, −198.54, −198.57, −198.59. Molecular weight for $C_{60}H_{67}FN_{10}O_{14}P_2S$ (M+H): calculated 1265.4096, found 1265.4065.

E-2. Synthesis of Fully Deprotected, Chirally Pure $A_{OMe}sU_F$

Scheme E-2. Synthesis of fully deprotected, chirally pure $A_{OMe}sU_F$ dinucleotide (asUf)

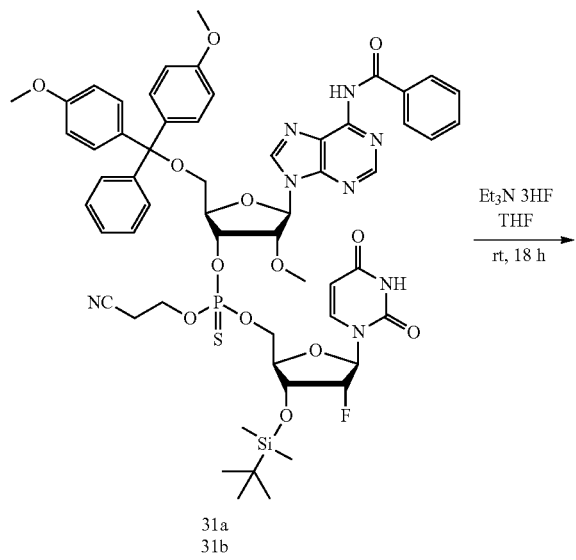

31a
31b 34a
34b

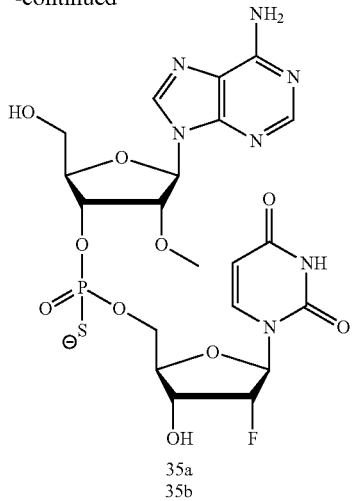

35a
35b

Compound 34: Compound 34 (34a top spot: Rf=0.14, 800 mg, 1.05 mmol; 34b lower spot: Rf=0.06, 400 mg, 0.53 mmol) was obtained during the TBDMS-deprotection reaction. In EtOAc: n-hexane (1:1+2.5% MeOH).

Compound 35: Compound 34 (34a top spot: 800 mg, 1.05 mmol; 34b lower spot: 400 mg, 0.53 mmol) was dissolved 12 ml methylamine (33 wt % solution in absolute ethanol) and stirred for 2 hours at room temperature. The reaction mixture was concentrated and purified by Combiflash column (24 g Gold column, 35 ml/min flow, ethyl acetate/MeOH (70:30) for 8 minutes, ethyl acetate/MeOH (60:40) for 5 minutes and ethyl acetate/MeOH (60:40) for 10 minutes) to yield 35a (502 mg, 79%) and 35b (282 mg, 88%). In ethyl acetate/MeOH (2:1), 35a Rf=0.25 and 35b Rf=0.16.

35a $^1$H NMR (500 MHz, deuterium oxide) δ 8.22 (s, 1H), 8.02 (s, 1H), 7.68 (d, J=8.1 Hz, 1H), 6.03 (d, J=3.5 Hz, 1H), 5.76 (d, J=17.3 Hz, 1H), 5.50 (d, J=8.1 Hz, 1H), 5.02-4.85 (m, 2H), 4.42 (t, J=3.9 Hz, 1H), 4.36-4.32 (m, 1H), 4.31-4.15 (m, 3H), 4.10-4.04 (m, 1H), 3.92-3.77 (m, 2H), 3.47 (s, 3H). $^{13}$C NMR (126 MHz, d$_2$o) δ 165.88, 155.54, 152.65, 150.98, 148.18, 141.02, 140.08, 119.18, 101.95, 94.31, 92.83, 88.59, 88.31, 86.85, 84.03, 83.99, 81.62, 81.59, 80.98, 80.90, 72.62, 72.58, 67.61, 67.48, 63.17, 63.12, 60.42, 58.16. $^{31}$P NMR (202 MHz, D$_2$O) δ 57.83. $^{19}$F NMR (376 MHz, D$_2$O) δ −203.49, −203.54, −203.55, −203.60, −203.63, −203.68, −203.69, −203.74. Molecular weight for $C_{20}H_{25}FN_7O_{10}PS$ (M+H): calculated 606.1184, found 606.1171.

35b $^1$H NMR (500 MHz, deuterium oxide) δ 8.19 (s, 1H), 8.04 (s, 1H), 7.67 (d, J=8.1 Hz, 1H), 5.99 (d, J=5.3 Hz, 1H), 5.83 (d, J=18.3 Hz, 1H), 5.57 (d, J=8.1 Hz, 1H), 5.02 (dd, J=52.4, 4.2 Hz, 1H), 4.93-4.87 (m, 1H), 4.45 (t, J=5.0 Hz, 1H), 4.41-4.37 (m, 1H), 4.36-4.27 (m, 1H), 4.25-4.08 (m, 3H), 3.84-3.72 (m, 2H), 3.40 (s, 3H). $^{13}$C NMR (126 MHz, d$_2$o) δ 165.90, 155.61, 152.59, 151.07, 148.35, 141.64, 140.44, 119.25, 102.05, 94.19, 92.72, 89.06, 88.78, 86.84, 84.66, 84.63, 81.55, 81.51, 81.08, 81.01, 72.83, 72.78, 67.83, 67.70, 63.91, 63.87, 60.95, 58.21. $^{31}$P NMR (202 MHz, D$_2$O) δ 56.63. $^{19}$F NMR (376 MHz, D$_2$O) δ −202.83, −202.88, −202.94, −202.97, −203.02, −203.08. Molecular weight for $C_{20}H_{25}FN_7O_{10}PS$ (M+H): calculated 606.1184, found 606.1183.

F-1. Synthesis of Chirally Pure 2'-OMe Adenosine-2'-OMe Adenosine Phosphorothioate Dinucleotide ($A_{OMe}sA_{OMe}$) (asa)
Scheme F-1. Synthesis of chirally pure 2'-OMe adenosine-2'-OMe adenosine phosphorothioate dinucleotide ($A_{OMe}sA_{OMe}$) phosphoramidite building block (asa)
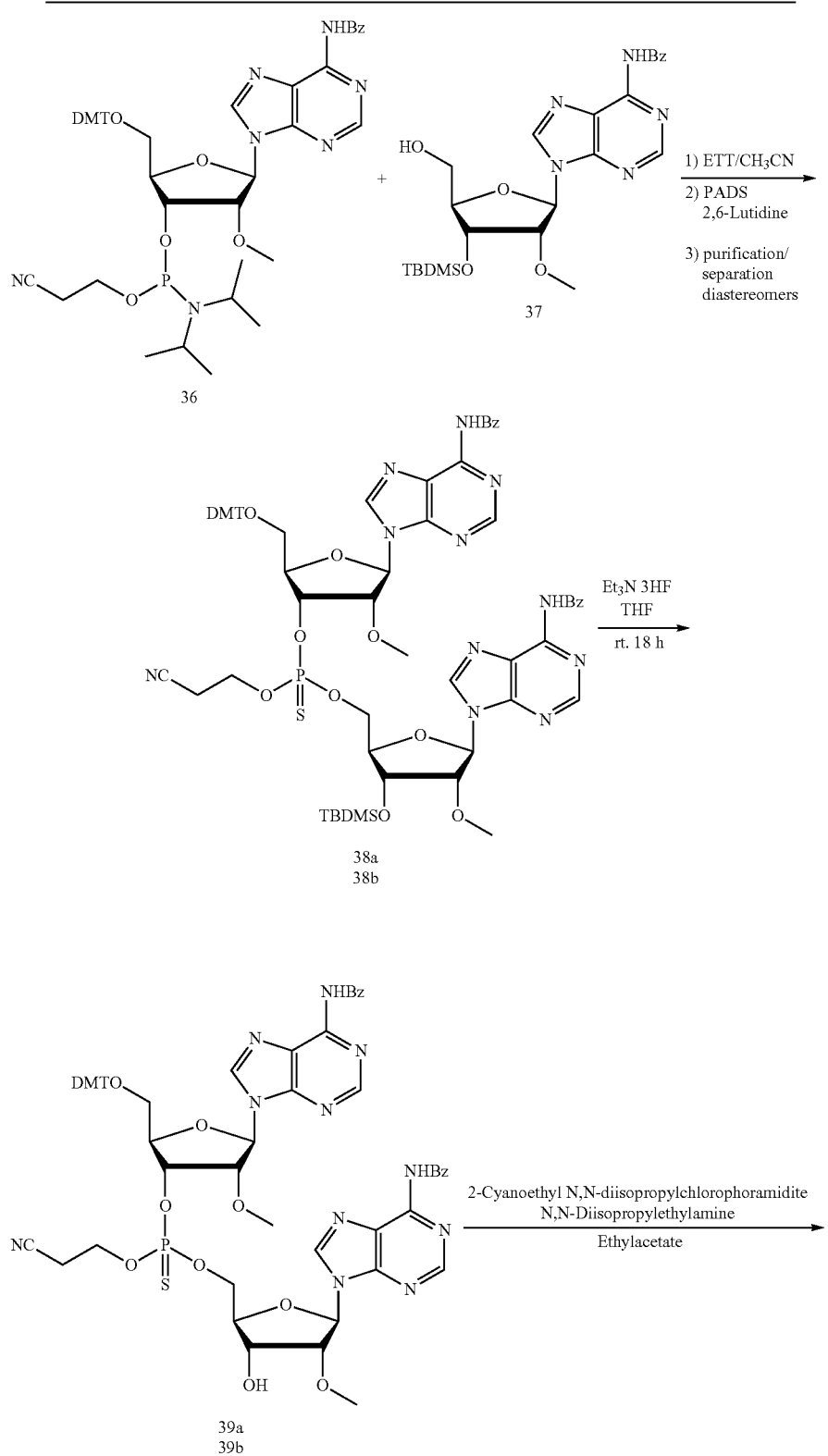

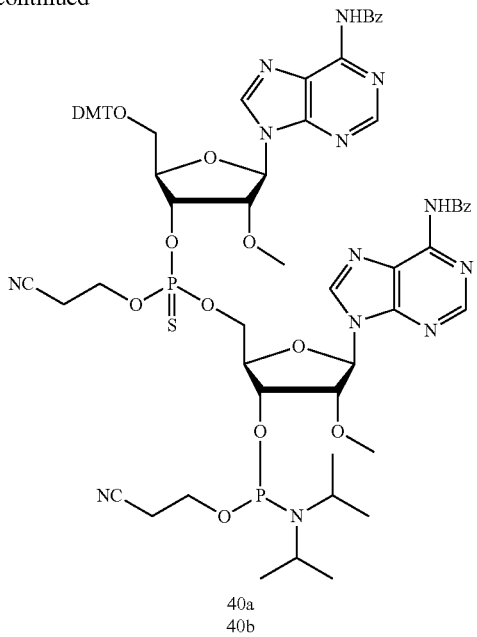

40a
40b

Compound 38: Compound 36 (13.05 g, 14.7 mmol) and compound 37 (7.7 g, 15.4 mmol, 1.05 eq.) were dried under high vacuum and dissolved in 110 ml dichloromethane (dry). To this solution was added 117 ml ETT (3.83 g, 29.4 mmol, 2 eq.), and the reaction mixture was stirred for 1.5 hours. PADS (6.35 g, 22.05 mmol, 1.5 eq.) and 2.52 ml 2.6-lutidine (2.36 g, 22.05 mmol, 1.5 eq.) were added, and the reaction mixture was stirred overnight. The reaction mixture was diluted with 1000 ml dichloromethane and washed twice with 400 ml $H_2O$. The organic layer was dried over anhydrous $Na_2SO_4$, and concentrated. The diastereomers were separated by CombiFlash column (crude 30 g, EtOAc: n-hexane (1:1+2.5% MeOH)) to yield 38a (top spot: 11.55 g, 60%) and 38b (lower spot: 6.81 g, 35%). In EtOAc: n-hexane (1:1+2.5% MeOH), 38a $R_f$=0.16, 38b $R_f$=0.11.

38a $^1$H NMR (500 MHz, DMSO-$d_6$) δ 11.24 (s, 1H), 11.23 (s, 1H), 8.75 (s, 1H), 8.69 (s, 1H), 8.62 (s, 1H), 8.57 (s, 1H), 8.03 (s, 4H), 7.70-7.58 (m, 2H), 7.59-7.47 (m, 4H), 7.44-7.33 (m, 2H), 7.29-7.20 (m, 7H), 6.88-6.80 (m, 4H), 6.19 (s, 2H), 5.44-5.30 (m, 1H), 5.04 (s, 1H), 4.72 (s, 1H), 4.62 (s, 1H), 4.54-4.46 (m, 1H), 4.43 (s, 1H), 4.37-4.28 (m, 1H), 4.27-4.10 (m, 3H), 3.70 (s, 6H), 3.34 (s, 4H), 3.31 (s, 4H), 2.89 (s, 2H), 0.91 (s, 9H), 0.15 (s, 6H). $^{13}$C NMR (126 MHz, DMSO) δ 165.59, 158.09, 151.93, 151.88, 151.73, 151.57, 150.64, 150.54, 144.51, 143.60, 143.21, 135.27, 135.19, 133.24, 133.21, 132.45, 132.41, 129.68, 128.47, 128.41, 127.75, 127.66, 126.71, 125.97, 125.89, 117.90, 113.13, 85.99, 85.87, 85.36, 82.85, 82.78, 82.20, 81.22, 78.93, 78.89, 75.85, 75.81, 70.22, 67.39, 67.35, 63.12, 63.09, 62.72, 58.07, 57.75, 54.97, 25.58, 18.83, 18.76, 17.74, −4.84, −4.97. $^{31}$P NMR (202 MHz, DMSO) δ 68.19. Molecular weight for $C_{66}H_{72}N_{11}O_{13}PSSi$ (M+Na): calculated 1340.4436, found 1340.4451.

38b $^1$H NMR (500 MHz, DMSO-$d_6$) δ 11.24 (s, 1H), 11.22 (s, 1H), 8.76 (s, 1H), 8.69 (s, 1H), 8.62 (s, 1H), 8.58 (s, 1H), 8.04 (d, J=6.4 Hz, 4H), 7.67-7.60 (m, 2H), 7.57-7.51 (m, 4H), 7.38 (d, J=6.7 Hz, 2H), 7.24 (d, J=7.2 Hz, 7H), 6.86-6.77 (m, 4H), 6.23-6.18 (m, 1H), 6.18 −6.14 (m, 1H), 5.44-5.33 (m, 1H), 5.05 (s, 1H), 4.77-4.70 (m, 1H), 4.62 (s, 1H), 4.43-4.28 (m, 3H), 4.28-4.16 (m, 3H), 3.69 (s, 6H), 3.35 (s, 7H), 3.32 (s, 1H), 2.94-2.88 (m, 2H), 0.91 (s, 9H), 0.15 (s, 6H). $^{13}$C NMR (126 MHz, DMSO) δ 165.58, 158.06, 151.87, 151.74, 151.55, 150.65, 150.54, 144.52, 143.74, 143.17, 135.26, 135.19, 133.26, 133.22, 132.44, 132.40, 129.67, 128.46, 128.41, 128.40, 127.70, 127.64, 126.65, 126.02, 125.86, 118.00, 113.09, 85.96, 85.82, 85.54, 82.80, 82.73, 82.24, 81.21, 78.89, 75.75, 70.08, 67.04, 63.36, 63.32, 62.60, 58.09, 57.76, 54.94, 25.59, 18.82, 18.75, 17.74, −4.84, −4.95. $^{31}$P NMR (202 MHz, DMSO) δ 68.32. Molecular weight for $C_{66}H_{72}N_{11}O_{13}PSSi$ (M+Na): calculated 1340.4436, found 1340.4429.

Compound 39: Compound 38 (38a top spot: 10.55 g, 8 mmol; 38b lower spot: 5.81 g, 4.4 mmol) was dissolved in dry THF (38a: 160 ml; 38b: 80 ml) and $Et_3N$ 3HF (38a: 15.6 ml, 96 mmol, 12 eq.; 38b: 8.6 ml, 53 mmol, 12 eq.) was added. The reaction mixture was stirred for 14 h. The reaction mixture was concentrated, co-evaporated three times with THF and purified by CombiFlash column (330 g Gold column, flow 150 ml/min, DCM to 5% MeOH in DCM) to yield 39a (top spot: 7.18 g, 74.8%) and 39b (lower spot: 2.74 g, 52%). In 5% MeOH in DCM, 39a: $R_f$=0.17, 39b: $R_f$=0.16.

39a $^1$H NMR (400 MHz, DMSO-$d_6$) δ 11.24 (s, 1H), 11.23 (s, 1H), 8.75 (s, 1H), 8.66 (s, 1H), 8.63 (s, 1H), 8.56 (s, 1H), 8.08-8.00 (m, 4H), 7.68-7.59 (m, 2H), 7.58-7.49 (m, 4H), 7.42-7.36 (m, 2H), 7.26 (dd, J=8.1, 5.2 Hz, 6H), 7.22-7.15 (m, 1H), 6.84 (dd, J=8.9, 2.9 Hz, 4H), 6.25-6.16 (m, 2H), 5.61-5.56 (m, 1H), 5.42-5.35 (m, 1H), 5.10-5.01 (m, 1H), 4.55-4.40 (m, 4H), 4.39-4.29 (m, 1H), 4.27-4.11 (m, 3H), 3.71 (s, 6H), 3.37 (s, 4H), 3.33 (s, 1H), 3.31 (s, 3H), 2.94-2.87 (m, 2H). $^{13}$C NMR (126 MHz, DMSO) δ 165.61, 165.59, 158.09, 151.96, 151.88, 151.81, 151.57, 150.64, 150.50, 144.53, 143.82, 142.87, 135.29, 135.21, 133.24, 133.21, 132.46, 132.41, 129.70, 128.47, 128.43, 128.41, 127.76, 127.67, 126.71, 126.04, 125.75, 117.99, 113.14, 85.86, 85.51, 82.73, 82.66, 82.22, 81.79, 78.84, 75.82, 68.76, 67.83, 63.08, 63.05, 62.67, 58.07, 57.73, 54.98, 18.81, 18.74. $^{31}$P NMR (162 MHz, DMSO) δ 68.18.

Molecular weight for $C_{60}H_{58}N_{11}O_{13}PS$ (M+Na): calculated 1226.3572, found 1226.3572.

39b $^1$H NMR (400 MHz, DMSO-d$_6$) δ 11.25 (s, 1H), 11.22 (s, 1H), 8.76 (s, 1H), 8.66 (s, 1H), 8.62 (s, 1H), 8.58 (s, 1H), 8.07-8.00 (m, 4H), 7.68-7.59 (m, 2H), 7.59-7.49 (m, 4H), 7.42-7.35 (m, 2H), 7.30-7.21 (m, 6H), 7.21-7.14 (m, 1H), 6.83 (dd, J=8.9, 2.9 Hz, 4H), 6.21 (d, J=4.6 Hz, 1H), 6.17 (d, J=6.7 Hz, 1H), 5.60 (d, J=5.3 Hz, 1H), 5.46-5.32 (m, 1H), 5.13-4.98 (m, 1H), 4.60-4.46 (m, 2H), 4.46-4.39 (m, 1H), 4.39-4.31 (m, 2H), 4.31-4.14 (m, 3H), 3.70 (s, 6H), 3.39 (s, 3H), 3.36 (s, 3H), 3.34-3.27 (m, 2H), 2.92 (t, J=5.8 Hz, 2H). $^{13}$C NMR (126 MHz, DMSO) δ 165.60, 158.06, 151.95, 151.86, 151.81, 151.57, 150.65, 150.51, 144.54, 143.82, 142.91, 135.29, 135.22, 133.26, 133.22, 132.46, 132.41, 129.69, 128.47, 128.43, 128.40, 127.74, 127.66, 126.67, 126.05, 125.77, 118.07, 113.12, 85.94, 85.93, 85.84, 85.60, 85.59, 82.75, 82.69, 82.20, 81.73, 78.83, 75.62, 68.69, 67.74, 63.30, 63.26, 62.57, 58.08, 57.75, 54.96, 18.79, 18.72. $^{31}$P NMR (162 MHz, DMSO) δ 68.27. Molecular weight for $C_{60}H_{58}N_{11}O_{13}PS$ (M+Na): calculated 1226.3572, found 1226.3562.

Compound 40: Compound 39 (39a top spot: 500 mg, 0.42 mmol; 39b lower spot: 500 g, 0.42 mmol) was dried overnight under high vacuum and dissolved in dry DCM (39a: 5 ml, 39b: 5 ml). N,N-Diisopropylamine (39a: 1.1 ml, 814 mg, 6.5 mmol, 2.5 eq.; 39b: 1.5 ml, 1.1 g, 8.4 mmol, 20 eq.) was added dropwise under rigorous stirring. Subsequently, 2-cyanoethyl N,N-diisopropylchlorophosphoramidite (39a: 1.1 ml, 1.2 g, 5.2 mmol, 12.5 eq.; 39b: 1.5 ml, 1.6 g, 6.8 mmol, 16 eq.) were added dropwise (over 1 minute), and the reaction mixture was stirred at room temperature for 1.5 hours. The reaction mixture was diluted with 200 ml DCM, washed with 100 ml NaHCO$_3$ and 100 ml brine, dried over Na$_2$SO$_4$, and concentrated to dryness. The crude (white foam) was dissolved in 5 ml DCM and purified by Combi-Flash column (DCM to 5% MeOH in DCM) to yield 40a (top spot: 371 mg, 63%) and 40b (lower spot: 324 mg, 55%).

40a $^1$H NMR (500 MHz, acetonitrile-d$_3$) δ 9.35 (s, 2H), 8.63 (s, 1H), 8.47 (s, 1H), 8.39-8.33 (m, 1H), 8.26 (s, 1H), 8.00-7.97 (m, 4H), 7.66-7.61 (m, 1H), 7.61-7.55 (m, 1H), 7.55-7.51 (m, 2H), 7.50-7.46 (m, 2H), 7.44-7.40 (m, 2H), 7.31-7.28 (m, 4H), 7.28-7.24 (m, 2H), 7.21-7.17 (m, 1H), 6.83-6.80 (m, 4H), 6.18-6.14 (m, 1H), 6.12-6.09 (m, 1H), 5.44-5.38 (m, 1H), 4.87-4.82 (m, 1H), 4.82-4.75 (m, 1H), 4.62-4.54 (m, 1H), 4.53-4.43 (m, 2H), 4.41-4.37 (m, 2H), 4.20-4.11 (m, 2H), 3.94-3.80 (m, 2H), 3.73 (s, 6H), 3.71-3.64 (m, 2H), 3.47 (s, 2H), 3.43-3.40 (m, 2H), 3.36 (s, 4H), 2.75-2.67 (m, 4H), 1.24-1.19 (m, 12H). $^{13}$C NMR (126 MHz, CD$_3$CN) δ 159.78, 152.89, 151.13, 151.10, 145.87, 144.08, 143.52, 143.40, 136.68, 134.94, 133.66, 133.59, 131.15, 131.12, 129.72, 129.68, 129.26, 129.23, 129.12, 128.91, 127.98, 125.99, 125.86, 114.15, 88.46, 88.04, 87.50, 87.44, 83.54, 83.18, 83.01, 81.16, 76.96, 72.38, 71.77, 71.76, 68.81, 68.56, 64.26, 63.61, 60.04, 59.89, 59.39, 59.22, 58.97, 56.00, 44.36, 44.29, 44.19, 25.19, 25.14, 25.00, 21.13, 21.08, 20.15, 20.08. $^{31}$P NMR (202 MHz, CD$_3$CN) δ 152.07, 151.35, 68.79, 68.75. Molecular weight for $C_{69}H_{75}N_{13}O_{14}P_2S$ (M+H): calculated 1404.4831, found 1404.4828.

40b $^1$H NMR (500 MHz, acetonitrile-d$_3$) δ 9.29 (s, 1H), 8.65 (d, J=1.7 Hz, 1H), 8.49 (s, 1H), 8.32-8.27 (m, 1H), 8.27-8.23 (m, 1H), 7.98 (d, J=7.3 Hz, 2H), 7.93 (d, J=7.5 Hz, 2H), 7.64 (t, J=7.4 Hz, 1H), 7.60-7.51 (m, 3H), 7.46 (t, J=7.7 Hz, 2H), 7.43-7.38 (m, 2H), 7.32-7.27 (m, 4H), 7.24 (t, J=7.7 Hz, 2H), 7.18 (t, J=7.3 Hz, 1H), 6.80 (dd, J=8.9, 2.4 Hz, 4H), 6.17-6.12 (m, 1H), 6.05-6.00 (m, 1H), 5.40-5.34 (m, 1H), 4.95-4.82 (m, 2H), 4.60 (dt, J=25.6, 4.5 Hz, 1H), 4.46-4.37 (m, 2H), 4.37-4.30 (m, 2H), 4.30-4.21 (m, 3H), 3.94-3.79 (m, 2H), 3.72 (s, 7H), 3.50 (s, 2H), 3.45 (s, 1H), 3.39-3.36 (m, 3H), 3.36-3.32 (m, 1H), 3.30-3.24 (m, 1H), 2.79 (q, J=6.1 Hz, 2H), 2.73-2.66 (m, 2H), 1.26-1.19 (m, 12H). $^{13}$C NMR (126 MHz, CD$_3$CN) δ 159.74, 152.89, 151.12, 145.90, 144.22, 144.17, 143.54, 143.40, 136.68, 134.95, 133.67, 133.56, 131.15, 131.10, 129.74, 129.65, 129.20, 129.09, 128.90, 127.94, 126.03, 126.01, 125.81, 125.74, 119.70, 114.13, 88.60, 88.58, 88.13, 87.48, 83.62, 83.11, 82.80, 82.69, 81.00, 77.11, 72.19, 72.06, 71.70, 71.56, 68.12, 68.10, 64.42, 64.39, 63.61, 60.05, 59.90, 59.53, 59.30, 59.06, 55.98, 44.35, 44.30, 44.25, 44.20, 25.21, 25.15, 25.12, 25.07, 25.01, 21.23, 21.16, 21.10, 20.19, 20.12. $^{31}$P NMR (202 MHz, CD$_3$CN) δ 151.85, 151.29, 68.84, 68.75. Molecular weight for $C_{69}H_{75}N_{13}O_{14}P_2S$ (M+H): calculated 1404.4831, found 1404.4813.

F-2. Synthesis of Fully Deprotected, Chirally Pure A$_{OMe}$sA$_{OMe}$ (asa)

Scheme F-2. Synthesis of fully deprotected, chirally pure A$_{OMe}$sA$_{OMe}$ dinucleotide (asa)

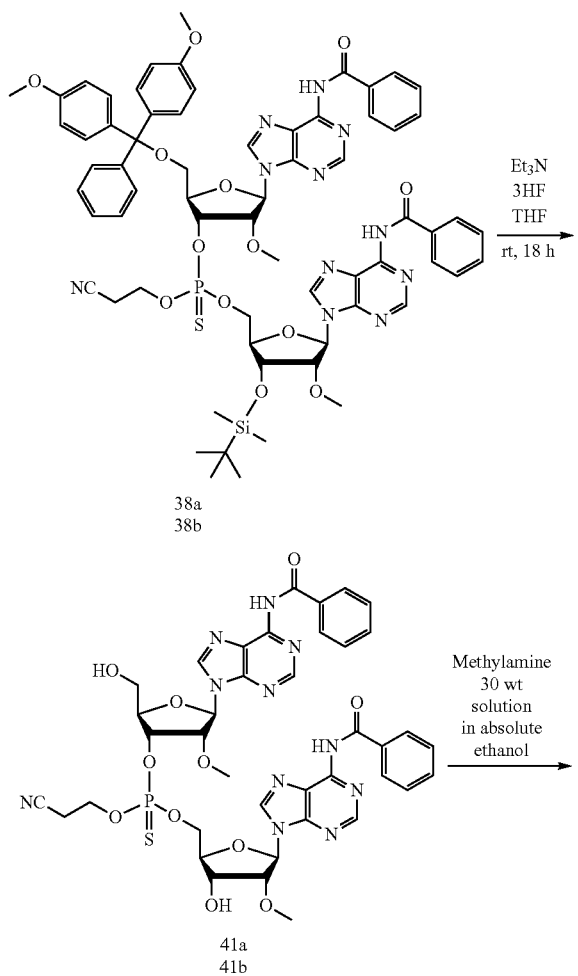

-continued

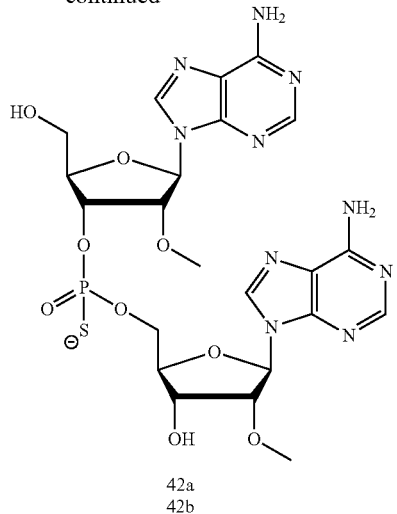

42a
42b

Compound 41: Compound 41 (41a top spot: 1.94 g, 2.2 mmol; 41b lower spot: 840 mg, 0.93 mmol) was obtained during the TBDMS-deprotection reaction. In 5% MeOH in DCM, 41a Rf=0.12 and 41b Rf=0.11.

41a $^1$H NMR (400 MHz, DMSO-d$_6$) δ 11.25 (s, 1H), 11.23 (s, 1H), 8.78 (s, 1H), 8.76 (s, 1H), 8.73 (s, 1H), 8.68 (s, 1H), 8.04 (d, J=7.5 Hz, 4H), 7.71-7.59 (m, 2H), 7.59-7.47 (m, 4H), 6.25-6.18 (m, 2H), 5.60 (d, J=4.9 Hz, 1H), 5.42 (t, J=5.6 Hz, 1H), 5.29 (dd, J=10.9, 4.8 Hz, 1H), 4.88-4.80 (m, 1H), 4.57-4.45 (m, 3H), 4.42-4.31 (m, 2H), 4.30-4.20 (m, 3H), 3.71-3.61 (m, 2H), 3.38 (s, 3H), 3.33 (s, 3H), 2.98 (t, J=5.9 Hz, 2H). $^{13}$C NMR (126 MHz, DMSO) δ 165.62, 152.11, 151.99, 151.83, 150.63, 150.51, 142.94, 133.25, 133.22, 132.47, 132.43, 128.48, 128.44, 128.42, 125.80, 125.75, 118.17, 85.88, 85.06, 84.71, 82.84, 82.77, 81.75, 80.52, 80.49, 76.42, 76.39, 68.73, 67.91, 67.86, 63.18, 63.15, 60.86, 58.03, 57.73, 54.88, 18.84, 18.77. $^{31}$P NMR (202 MHz, DMSO) δ 67.94. Molecular weight for C$_{39}$H$_{40}$N$_{11}$O$_{11}$PS (M+Na): calculated 924.2266, found 901.4.

41b $^1$H NMR (400 MHz, DMSO-d$_6$) δ 11.25 (s, 1H), 11.22 (s, 1H), 8.78 (s, 1H), 8.76 (s, 1H), 8.75 (s, 1H), 8.68 (s, 1H), 8.04 (dd, J=5.8, 3.9 Hz, 4H), 7.69-7.59 (m, 2H), 7.59-7.49 (m, 4H), 6.22 (d, J=4.0 Hz, 1H), 6.18 (d, J=7.2 Hz, 1H), 5.61 (d, J=4.9 Hz, 1H), 5.42 (t, J=5.7 Hz, 1H), 5.29 (ddd, J=10.9, 4.8, 1.9 Hz, 1H), 4.91-4.76 (m, 1H), 4.59-4.48 (m, 2H), 4.47-4.34 (m, 2H), 4.34-4.29 (m, 1H), 4.29-4.21 (m, 3H), 3.77-3.56 (m, 2H), 3.41 (s, 3H), 3.37 (s, 3H), 2.96 (t, J=5.9 Hz, 2H). $^{13}$C NMR (126 MHz, DMSO) δ 165.61, 152.11, 151.96, 151.83, 150.63, 150.51, 142.99, 142.93, 133.26, 133.22, 132.47, 132.42, 128.47, 128.44, 128.41, 125.80, 125.76, 118.13, 85.95, 85.09, 84.68, 82.76, 82.69, 81.70, 80.49, 76.32, 68.70, 67.85, 67.82, 63.28, 63.25, 60.81, 58.06, 57.78, 18.80, 18.73. $^{31}$P NMR (202 MHz, DMSO) δ 68.05. Molecular weight for C$_{39}$H$_{40}$N$_{11}$O$_{11}$PS (M+Na): calculated 924.2266, found 924.2268.

Compound 42: Compound 41 (41a top spot: 1.9 mg, 2 mmol; 41b lower spot: 840 mg, 0.9 mmol) was dissolved 12 ml methylamine (33 wt % solution in absolute ethanol) and stirred for 4 hours at room temperature. The reaction mixture was concentrated and purified by CombiFlash column (24 g Gold column, 35 ml/min flow, ethyl acetate/MeOH (70:30) for 8 minutes, ethyl acetate/MeOH (60:40) for 5 minutes) to yield 42a (1.2 g, 99%) and 42b (210 mg, 37%). In ethyl acetate/MeOH (2:1), 42a: Rf=0.13 and 42b: Rf=0.1.

42a $^1$H NMR (500 MHz, deuterium oxide) δ 8.41 (s, 1H), 8.22 (s, 1H), 8.11 (s, 1H), 7.92 (s, 1H), 6.04 (d, J=4.4 Hz, 1H), 5.99 (d, J=3.9 Hz, 1H), 5.05-4.99 (m, 1H), 4.63 (t, J=5.0 Hz, 1H), 4.42-4.35 (m, 3H), 4.31-4.19 (m, 3H), 3.98-3.85 (m, 2H), 3.52 (s, 3H), 3.49 (s, 3H). $^{13}$C NMR (126 MHz, D$_2$O) δ 157.75, 157.50, 155.31, 154.76, 150.78, 150.34, 142.44, 141.89, 121.29, 120.85, 89.31, 88.42, 86.39, 86.20, 86.01, 84.02, 75.23, 71.37, 67.00, 63.01, 60.98, 60.47. $^{31}$P NMR (202 MHz, D$_2$O) δ 57.51. Molecular weight for C$_{22}$H$_{29}$N$_{10}$O$_9$PS (M+H): calculated 641.1656, found 641.1668.

42b $^1$H NMR (500 MHz, deuterium oxide) δ 8.38 (s, 1H), 8.20 (s, 1H), 8.10 (s, 1H), 7.97 (s, 1H), 6.08 (d, J=4.6 Hz, 1H), 5.91 (d, J=5.4 Hz, 1H), 5.04-4.98 (m, 1H), 4.67 (t, J=4.7 Hz, 1H), 4.43 (t, J=5.0 Hz, 1H), 4.41-4.37 (m, 2H), 4.37-4.33 (m, 1H), 4.26-4.20 (m, 2H), 3.83-3.74 (m, 2H), 3.50 (s, 3H), 3.46 (s, 3H). $^{13}$C NMR (126 MHz, D2O) δ 157.74, 155.22, 154.74, 151.11, 150.55, 142.85, 141.96, 121.48, 120.97, 89.24, 88.19, 86.99, 86.26, 86.18, 85.74, 83.92, 75.42, 71.50, 67.87, 63.51, 60.91, 60.54. $^{31}$P NMR (202 MHz, D$_2$O) δ 56.27. Molecular weight for C$_{22}$H$_{29}$N$_{10}$O$_9$PS (M+H): calculated 641.1656, found 641.1655.

G-1. Synthesis of Chirally Pure 2'-OMe Guanosine-2'-OMe Adenosine Phosphorothioate Dinucleotide (G$_{OMe}$sA$_{OMe}$) (gsa)

Scheme G-1. Synthesis of chirally pure 2'-OMe guanosine-2'-OMe adenosine phosphorothioate dinucleotide (G$_{OMe}$sA$_{OMe}$) phosphoramidite building block (gsa)

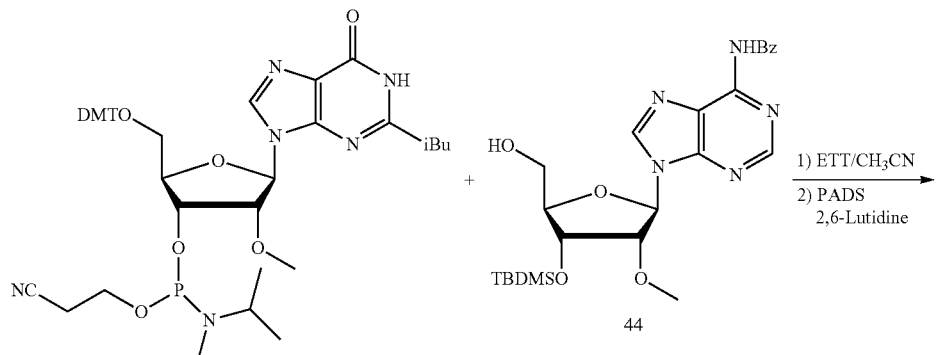

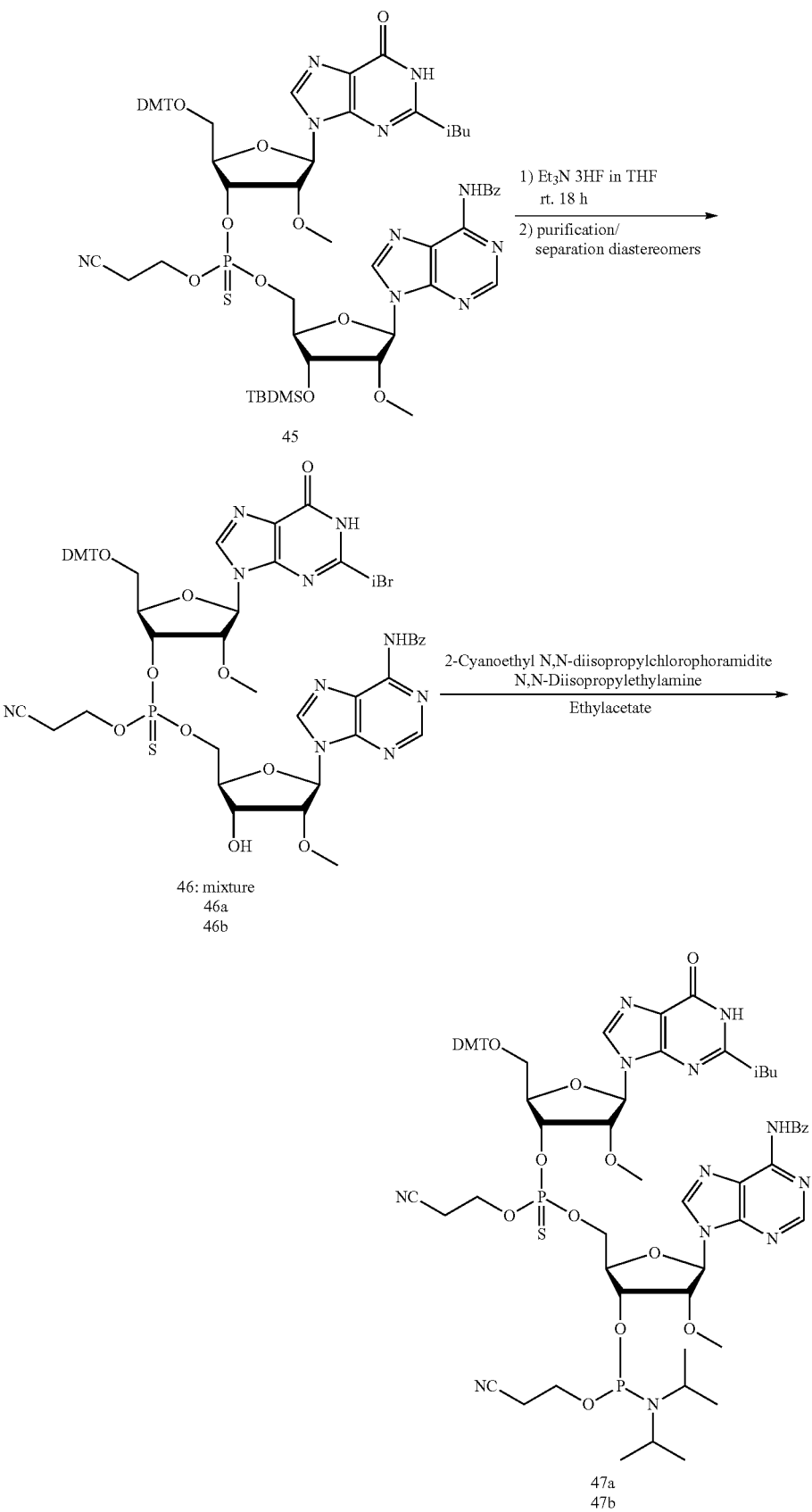

Compound 45: Compound 43 (13.1 g, 14.7 mmol) and compound 44 (5.6 g, 15.4 mmol, 1.05 eq.) were dried under high vacuum and dissolved in 110 ml dichloromethane (dry). To this solution was added 117 ml ETT (3.83 g, 29.4 mmol, 2 eq.), and the reaction mixture was stirred for 2 hours. PADS (6.35 g, 22.05 mmol, 1.5 eq.) and 2.52 ml 2.6-lutidine (2.36 g, 22.05 mmol, 1.5 eq.) were added, and the reaction mixture was stirred overnight. The reaction mixture was diluted with 1000 ml dichloromethane and washed twice with 400 ml H$_2$O. The organic layer was dried over anhydrous Na$_2$SO$_4$, and concentrated. The crude was purified by CombiFlash column (crude 30 g, EtOAc: n-Hexane (1:1+2.5% MeOH) to yield 45 (16.5 g, 86%). In EtOAc: n-Hexane (1:1+2.5% MeOH), 45 R$_f$=0.13.

45 $^1$H NMR (500 MHz, DMSO-d$_6$) δ 12.05 (s, 1H), 11.55 (s, 1H), 11.21 (d, J=10.6 Hz, 1H), 8.74 (d, J=13.1 Hz, 1H), 8.67 (d, J=6.5 Hz, 1H), 8.12 (d, J=3.0 Hz, 1H), 8.03 (d, J=7.6 Hz, 2H), 7.64 (t, J=7.4 Hz, 1H), 7.54 (t, J=7.7 Hz, 2H), 7.34 (d, J=7.6 Hz, 2H), 7.28-7.17 (m, 7H), 6.86-6.79 (m, 4H), 6.18 (t, J=5.5 Hz, 1H), 5.89 (d, J=7.6 Hz, 1H), 5.22-5.12 (m, 1H), 4.78-4.66 (m, 2H), 4.62-4.54 (m, 1H), 4.49-4.24 (m, 3H), 4.17 (dq, J=13.4, 8.0, 7.1 Hz, 3H), 3.72-3.69 (m, 6H), 3.36-3.34 (m, 4H), 3.31 (s, 3H), 3.26-3.18 (m, 1H), 2.93-2.83 (m, 2H), 2.75-2.64 (m, 1H), 1.13-1.05 (m, 6H), 0.93-0.83 (m, 9H), 0.12 (s, 6H). $^{13}$C NMR (126 MHz, DMSO) δ 179.96, 165.55, 158.10, 154.65, 151.82, 151.77, 151.69, 150.53, 148.98, 148.94, 148.36, 144.37, 143.21, 137.00, 136.89, 135.09, 133.21, 132.44, 129.69, 129.63, 128.44, 128.40, 127.77, 127.65, 126.76, 126.72, 125.87, 120.29, 120.27, 118.01, 117.98, 113.12, 86.12, 86.02, 85.93, 83.73, 83.49, 82.75, 82.46, 82.45, 81.20, 79.52, 76.13, 70.21, 70.01, 67.80, 67.20, 63.34, 63.19, 63.03, 59.69, 58.16, 58.10, 57.75, 54.96, 54.94, 34.76, 25.56, 25.54, 18.75, 18.70, 17.70, −4.84, −4.97, −5.03. $^{31}$P NMR (202 MHz, DMSO) δ 68.60, 68.33. Molecular weight for C$_{63}$H$_{74}$N$_{11}$O$_{14}$PSSi (M+H): calculated 1300.4723, found 1300.4712.

Compound 46: Compound 45 (16 g, 12.3 mmol) was dissolved in dry THF (140 ml), and Et$_3$N 3HF (15.1 ml, 92.4 mmol, 7.5 eq.) was added. The reaction mixture was stirred for 14 hours. The reaction mixture was concentrated, co-evaporated three times with THF and purified by Combi-Flash column (DCM to 5% MeOH in DCM to yield 46 (13.1 g, 90%). Diastereomers were not resolved. Diastereomers were separated on a Gilson RP-column (buffer A: 50 mM TEAA, buffer B: 20% A, 80% ACN; gradient 60 to 90% B over 30 minutes; 50 ml/min).

46a $^1$H NMR (500 MHz, DMSO-d$_6$) δ 12.06 (s, 1H), 11.58 (s, 1H), 11.20 (s, 1H), 8.74 (s, 1H), 8.64 (s, 1H), 8.11 (s, 1H), 8.02 (d, J=7.5 Hz, 2H), 7.63 (t, J=7.4 Hz, 1H), 7.53 (t, J=7.7 Hz, 2H), 7.34 (d, J=7.5 Hz, 2H), 7.28-7.16 (m, 8H), 6.86-6.80 (m, 4H), 6.19 (d, J=4.6 Hz, 1H), 5.89 (d, J=7.6 Hz, 1H), 5.58 (d, J=5.6 Hz, 1H), 5.18 (dd, J=10.0, 4.4 Hz, 1H), 4.76-4.69 (m, 1H), 4.52-4.43 (m, 2H), 4.35-4.26 (m, 3H), 4.22-4.14 (m, 3H), 3.70 (s, 6H), 3.38 (s, 3H), 3.35 (s, 3H), 3.34-3.32 (m, 1H), 3.24 (dd, J=10.5, 4.1 Hz, 1H), 2.88 (t, J=5.8 Hz, 2H), 2.74-2.66 (m, 1H), 1.10 (s, 3H), 1.09 (s, 3H). $^{13}$C NMR (126 MHz, DMSO) δ 180.01, 165.58, 158.12, 158.10, 154.68, 151.91, 151.81, 150.53, 149.00, 148.41, 144.42, 142.94, 136.93, 135.14, 135.13, 133.24, 132.45, 129.72, 129.67, 128.47, 128.41, 127.80, 127.68, 126.76, 125.78, 120.27, 118.09, 113.15, 85.99, 85.97, 83.64, 82.69, 82.62, 82.55, 81.72, 79.67, 79.63, 75.97, 75.94, 68.70, 67.90, 67.87, 63.32, 63.28, 63.14, 58.14, 57.78, 54.98, 54.96, 34.78, 18.77, 18.71. $^{31}$P NMR (202 MHz, DMSO) δ 67.27. Molecular weight for C$_7$H$_{60}$N$_{11}$O$_{14}$PS (M+H): calculated 1186.3858, found 1186.3893.

46b $^1$H NMR (500 MHz, DMSO-d$_6$) δ 12.04 (s, 1H), 11.54 (s, 1H), 11.19 (s, 1H), 8.72 (s, 1H), 8.62 (s, 1H), 8.10 (s, 1H), 8.03 (d, J=7.4 Hz, 2H), 7.63 (t, J=7.4 Hz, 1H), 7.53 (t, J=7.7 Hz, 2H), 7.34 (d, J=7.4 Hz, 2H), 7.26 (t, J=7.6 Hz, 2H), 7.23-7.17 (m, 5H), 6.86-6.79 (m, 4H), 6.18 (d, J=4.1 Hz, 1H), 5.91 (d, J=7.6 Hz, 1H), 5.56 (d, J=5.3 Hz, 1H), 5.17 (dd, J=10.1, 4.4 Hz, 1H), 4.76-4.69 (m, 1H), 4.49-4.38 (m, 3H), 4.35-4.26 (m, 2H), 4.23-4.09 (m, 3H), 3.71 (s, 6H), 3.38 (s, 3H), 3.36-3.32 (m, 1H), 3.29 (s, 3H), 3.22 (dd, J=10.5, 4.1 Hz, 1H), 2.91-2.86 (m, 2H), 2.74-2.66 (m, 1H), 1.09 (s, 3H), 1.08 (s, 3H). $^{13}$C NMR (126 MHz, DMSO) δ 179.98, 165.57, 158.12, 158.10, 154.67, 151.85, 151.77, 150.50, 148.96, 148.38, 144.39, 142.86, 136.93, 135.13, 135.09, 133.22, 132.45, 129.71, 129.66, 128.46, 128.41, 127.79, 127.67, 126.77, 125.74, 120.28, 118.06, 113.14, 85.97, 83.63, 82.60, 82.54, 81.80, 79.68, 79.64, 76.12, 76.08, 68.79, 68.20, 68.15, 63.20, 63.06, 63.02, 58.08, 57.79, 54.98, 54.97, 34.78, 18.81, 18.77, 18.75. $^{31}$P NMR (202 MHz, DMSO) δ 67.16. Molecular weight for C$_7$H$_{60}$N$_{11}$O$_{14}$PS (M+H): calculated 1186.3858, found 1186.3885.

Compound 47: Compound 46 (46a top spot: 630 mg, 0.53 mmol; 46b lower spot: 920 g, 0.78 mmol) was dried overnight under high vacuum, and dissolved in dry ethyl acetate (46a: 8 ml, 46b: 9 ml). N,N-Diisopropylamine (46a: 232 µl, 172 mg, 1.33 mmol, 2.5 eq.; 46b: 340 µl, 252 mg, 2 mmol, 2.5 eq.) was added dropwise under rigorous stirring. Subsequently, 2-cyanoethyl N,N-diisopropylchlorophosphoramidite (46a: 246 µl, 260 mg, 1.1 mmol, 2 eq.; 46b: 357 µl, 379 mg, 1.6 mmol, 2 eq.) was added dropwise (over 1 minute) and the reaction mixture was stirred at room temperature for 1.5 hours. The reaction mixture was diluted 200 ml ethyl acetate, washed with 100 ml NaHCO$_3$ and 100 ml brine, dried over Na$_2$SO$_4$, and concentrated to dryness. The crude (white foam) was dissolved in 5 ml DCM and precipitated from 1 L cold n-hexane/diethyl ether (1:1) to yield 47a (top spot: 689 mg, 94%) and 47b (lower spot: 1.07 g, 98%).

47a $^1$H NMR (500 MHz, acetonitrile-d$_3$) δ 8.70 (d, J=2.4 Hz, 1H), 8.33 (d, 1H), 7.91 (d, J=7.0 Hz, 2H), 7.82 (d, J=3.0 Hz, 1H), 7.60 (t, J=7.4 Hz, 1H), 7.47 (t, J=7.6 Hz, 2H), 7.41 (d, J=7.8 Hz, 2H), 7.30-7.24 (m, 6H), 7.23-7.18 (m, 1H), 6.83-6.77 (m, 4H), 6.17-6.10 (m, 1H), 5.80-5.73 (m, 1H), 5.28-5.21 (m, 1H), 4.93-4.85 (m, 1H), 4.73-4.63 (m, 2H), 4.43-4.19 (m, 7H), 3.97-3.75 (m, 2H), 3.74 (s, 6H), 3.73-3.65 (m, 3H), 3.52 (s, 1H), 3.47 (s, 2H), 3.41 (d, J=5.1 Hz, 3H), 3.36-3.29 (m, 1H), 3.29-3.22 (m, 1H), 2.83-2.76 (m, 2H), 2.73-2.67 (m, 2H), 2.56-2.47 (m, 1H), 1.26-1.20 (m, 12H), 1.14-1.03 (m, 7H). $^{13}$C NMR (126 MHz, cd$_3$cn) δ 180.83, 159.79, 159.77, 156.25, 152.92, 152.85, 152.74, 151.01, 149.77, 149.19, 149.18, 145.82, 145.81, 143.99, 143.86, 138.53, 138.50, 136.62, 136.53, 136.52, 134.61, 133.68, 131.18, 131.11, 131.04, 129.77, 129.66, 129.18, 129.11, 129.06, 128.93, 128.78, 128.02, 125.86, 125.79, 122.41, 122.39, 119.74, 119.71, 114.14, 114.01, 88.85, 88.40, 87.49, 86.22, 83.96, 83.93, 83.20, 83.11, 82.91, 82.89, 82.73, 82.69, 82.67, 82.62, 81.58, 81.55, 77.01, 76.97, 76.93, 72.05, 71.92, 71.59, 71.47, 68.24, 68.21, 67.94, 67.90, 64.44, 64.40, 64.16, 64.13, 60.02, 59.88, 59.50, 59.34, 59.30, 59.28, 59.06, 59.05, 55.97, 55.91, 48.19, 44.32, 44.26, 44.22, 44.16, 36.78, 25.19, 25.17, 25.14, 25.11, 25.05, 25.00, 24.99, 24.95, 21.21, 21.15, 21.10, 20.19, 20.13, 19.84, 19.27, 19.26, 19.19. $^{31}$P NMR (202 MHz, CD$_3$CN) δ 151.68, 151.17, 68.81, 68.70. Molecular weight for C$_{66}$H$_{77}$N$_{13}$O$_{15}$P$_2$S (M+H): calculated 1386.4936, found 1386.4935.

47b $^1$H NMR (500 MHz, acetonitrile-d$_3$) δ 8.75-8.70 (m, 1H), 8.40-8.34 (m, 1H), 8.00 (d, J=7.6 Hz, 2H), 7.84 (s, 1H), 7.63 (t, J=7.4 Hz, 1H), 7.52 (t, J=7.5 Hz, 2H), 7.41 (d, J=7.7 Hz, 2H), 7.31-7.26 (m, 6H), 7.23-7.18 (m, 1H), 6.85-6.80 (m, 4H), 6.18-6.14 (m, 1H), 5.89-5.85 (m, 1H), 5.36-5.27 (m, 1H), 4.84-4.76 (m, 1H), 4.67 (dt, J=20.5, 4.7 Hz, 1H), 4.63-4.58 (m, 1H), 4.54-4.37 (m, 3H), 4.36-4.30 (m, 1H), 4.18-4.01 (m, 2H), 3.94-3.76 (m, 2H), 3.74 (s, 6H), 3.73-3.65 (m, 3H), 3.49 (s, 1H), 3.44 (s, 2H), 3.36 (s, 4H), 3.35-3.29 (m, 2H), 2.73-2.64 (m, 4H), 2.58-2.51 (m, 1H), 1.25-1.20 (m, 12H), 1.09-1.04 (m, 7H). $^{13}$C NMR (126 MHz, cd$_3$cn) δ 180.97, 180.95, 159.81, 159.78, 156.30, 152.90, 152.79, 151.00, 149.55, 149.54, 149.19, 149.16, 145.73, 143.92, 143.79, 138.59, 138.54, 136.60, 136.54, 136.53, 134.67, 133.73, 131.13, 131.05, 129.72, 129.36, 129.22, 129.12, 128.93, 128.05, 125.91, 125.84, 122.44, 122.43, 119.74, 114.14, 113.99, 88.80, 88.40, 87.50, 87.49, 86.67, 86.65, 83.71, 83.64, 83.48, 83.43, 83.25, 83.21, 83.17, 83.13, 82.90, 82.88, 82.70, 82.66, 81.95, 81.92, 76.65, 72.45, 72.33, 71.81, 71.68, 68.92, 68.88, 68.69, 68.64, 64.21, 64.18, 63.87, 63.84, 60.03, 59.88, 59.28, 59.25, 58.99, 58.97, 55.98, 55.97, 48.18, 44.33, 44.26, 44.24, 44.16, 36.77, 25.15, 25.14, 25.10, 25.08, 25.04, 24.98, 24.92, 21.20, 21.15, 21.13, 21.07, 20.11, 20.04, 19.76, 19.45, 19.44, 19.10, 19.09. $^{31}$P NMR (202 MHz, cd$_3$cn) δ 152.00, 151.26, 68.81, 68.72. Molecular weight for C$_{66}$H$_{77}$N$_{13}$O$_{15}$P$_2$S (M+H): calculated 1386.4936, found 1386.4927.

G-2. Synthesis of Fully Deprotected, Chirally Pure G$_{OMe}$sA$_{OMe}$

Scheme G-2. Synthesis of fully deprotected, chirally pure G$_{OMe}$sA$_{OMe}$ dinucleotide (gsa)

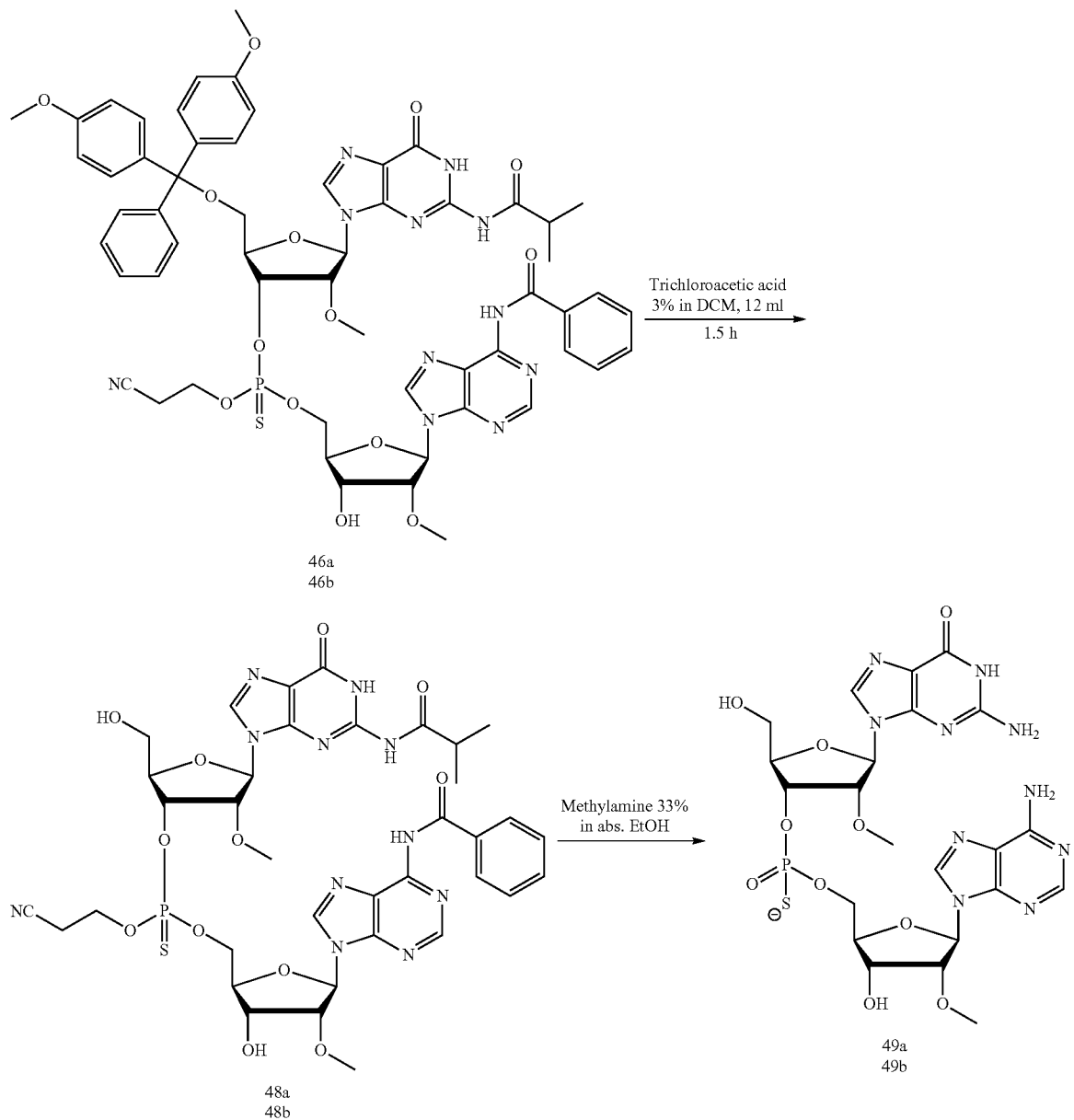

Compound 48: Compound 46 (46a top spot: 531 mg, 0.45 mmol; 46b lower spot: 517 mg, 0.43 mmol) was dissolved in 1.5 ml DCM, and 17 ml trichloroacetic acid (3% in DCM) were added. The reaction mixture was stirred at room temperature for 1.5 hours. The reaction mixture was concentrated and purified by CombiFlash column (40 g Gold column, 50 ml/min flow, DCM to 5% MeOH in DCM for 8 minutes, 5% MeOH in DCM for 15 minutes) to yield 48a (373 mg, 94%) and 48b (365 mg, 92%). In 10% MeOH in DCM, 48a Rf=0.39 and 48b Rf=0.39.

48a $^1$H NMR (400 MHz, DMSO-$d_6$) δ 12.07 (s, 1H), 11.67 (s, 1H), 11.22 (s, 1H), 8.77 (s, 1H), 8.67 (s, 1H), 8.30 (s, 1H), 8.03 (d, J=7.4 Hz, 2H), 7.64 (t, J=7.4 Hz, 1H), 7.54 (t, J=7.6 Hz, 2H), 6.20 (d, J=4.1 Hz, 1H), 5.91-5.85 (m, 1H), 5.61 (d, J=5.5 Hz, 1H), 5.37 (t, J=5.3 Hz, 1H), 5.19 (dd, J=10.5, 4.6 Hz, 1H), 4.61 (dt, J=7.7, 3.4 Hz, 1H), 4.54-4.46 (m, 2H), 4.37 (ddt, J=18.7, 11.1, 5.9 Hz, 2H), 4.27-4.15 (m, 4H), 3.59 (d, J=4.5 Hz, 2H), 3.40 (s, 3H), 3.32 (s, 3H), 2.93 (t, J=5.8 Hz, 2H), 2.77-2.67 (m, 1H), 1.10 (d, J=6.8 Hz, 6H). $^{13}$C NMR (126 MHz, DMSO) δ 180.06, 165.61, 164.38, 154.71, 151.92, 151.84, 150.52, 149.01, 148.45, 143.00, 137.10, 133.22, 132.46, 128.46, 128.43, 125.80, 119.97, 118.17, 86.00, 84.65, 84.64, 83.66, 82.71, 82.64, 81.70, 80.83, 80.79, 76.70, 76.66, 71.06, 68.70, 67.95, 67.91, 63.27, 63.24, 60.72, 58.01, 57.81, 34.76, 18.81, 18.77, 18.73. $^{31}$P NMR (202 MHz, DMSO) δ 68.30. Molecular weight for $C_{36}H_{42}N_{11}O_{12}PS$ (M+H): calculated 884.2551, found 884.2556.

48b $^1$H NMR (400 MHz, DMSO-$d_6$) δ 12.06 (s, 1H), 11.63 (s, 1H), 11.20 (s, 1H), 8.75 (s, 1H), 8.66 (s, 1H), 8.29 (s, 1H), 8.02 (d, J=7.3 Hz, 2H), 7.64 (t, J=7.4 Hz, 1H), 7.54 (t, J=7.6 Hz, 2H), 6.20 (d, J=4.1 Hz, 1H), 5.88 (d, J=7.9 Hz, 1H), 5.62-5.55 (m, 1H), 5.34 (t, J=5.2 Hz, 1H), 5.17 (dd, J=10.5, 4.6 Hz, 1H), 4.63-4.55 (m, 1H), 4.53-4.41 (m, 3H), 4.37-4.29 (m, 1H), 4.27-4.16 (m, 4H), 3.62-3.50 (m, 2H), 3.39 (s, 3H), 3.27 (s, 3H), 2.96 (t, J=5.8 Hz, 2H), 2.76-2.66 (m, 1H), 1.09 (d, J=6.7 Hz, 6H). $^{13}$C NMR (126 MHz, DMSO) δ 180.05, 165.59, 154.70, 151.89, 151.81, 150.51, 148.99, 148.43, 143.00, 137.08, 133.21, 132.47, 128.47, 128.43, 125.78, 119.96, 118.23, 86.01, 84.63, 83.65, 82.69, 82.62, 81.73, 80.88, 80.84, 76.72, 76.68, 68.78, 68.20, 68.16, 63.15, 63.12, 60.72, 57.94, 57.80, 34.76, 18.84, 18.80, 18.76. $^{31}$P NMR (202 MHz, DMSO) δ 68.19. Molecular weight for $C_{36}H_{42}N_{11}O_{12}PS$ (M+H): calculated 884.2551, found 884.2552.

Compound 49: Compound 48 (48a top spot: 358 mg, 0.41 mmol; 48b lower spot: 350 mg, 0.4 mmol) was dissolved 17 ml methylamine (33 wt % solution in absolute ethanol) and stirred for 3 hours at room temperature. The reaction mixture was concentrated and purified by CombiFlash column (24 g Gold column, 40 ml/min flow, ethyl acetate/MeOH (70:30) for 8 minutes, ethyl acetate/MeOH (60:40) for 5 minutes) to yield 49a (222 mg, 83%) and 49b (240 mg, 91%).

49a $^1$H NMR (400 MHz, deuterium oxide) δ 8.41 (s, 1H), 8.17 (s, 1H), 7.92 (s, 1H), 6.14 (d, J=4.9 Hz, 1H), 5.75 (d, J=5.1 Hz, 1H), 5.04-4.95 (m, 1H), 4.68 (t, J=4.8 Hz, 1H), 4.45-4.34 (m, 3H), 4.34-4.27 (m, 1H), 4.27-4.19 (m, 2H), 3.79 (d, J=3.1 Hz, 2H), 3.49 (d, J=8.3 Hz, 6H), 3.36 (s, 1H), 2.61 (s, 2H). $^{13}$C NMR (126 MHz, $d_2$o) δ 158.74, 155.56, 153.59, 153.01, 151.16, 148.88, 139.66, 137.71, 118.69, 116.69, 86.17, 85.81, 84.15, 84.12, 83.94, 83.86, 83.38, 81.37, 81.33, 72.76, 72.71, 69.11, 65.61, 65.56, 61.07, 58.55, 58.10. $^{31}$P NMR (202 MHz, d2o) δ 56.07. Molecular weight for $C_{22}H_{29}N_{10}O_{10}PS$ (M+H): calculated 657.1605, found 657.1580.

49b $^1$H NMR (400 MHz, deuterium oxide) δ 8.46 (s, 1H), 8.17 (s, 1H), 7.90 (s, 1H), 6.13 (d, J=4.4 Hz, 1H), 5.80 (d, J=3.2 Hz, 1H), 5.04 (dt, J=11.4, 5.6 Hz, 1H), 4.65 (t, J=4.9 Hz, 1H), 4.43-4.37 (m, 1H), 4.35-4.25 (m, 4H), 4.25-4.16 (m, 1H), 3.98-3.80 (m, 2H), 3.51 (d, J=9.7 Hz, 6H), 2.61 (s, 2H). $^{13}$C NMR (126 MHz, $d_2$o) δ 158.51, 155.51, 153.42, 153.00, 150.82, 148.59, 139.64, 137.36, 118.60, 116.59, 86.68, 86.08, 83.83, 83.71, 83.63, 83.57, 83.53, 81.43, 81.41, 72.79, 72.75, 69.08, 64.67, 64.61, 60.68, 58.63, 58.00. $^{31}$P NMR (202 MHz, $d_2$o) δ 57.53. Molecular weight for $C_{22}H_{29}N_{10}O_{10}PS$ (M+H): calculated 657.1605, found 657.1583.

H. Synthesis of Chirally Pure 2'-O-2-Methoxypropane Thymidine-2'-F Uridine Phosphorothioate Dinucleotide ($T_{OMeProp}sU_F$)

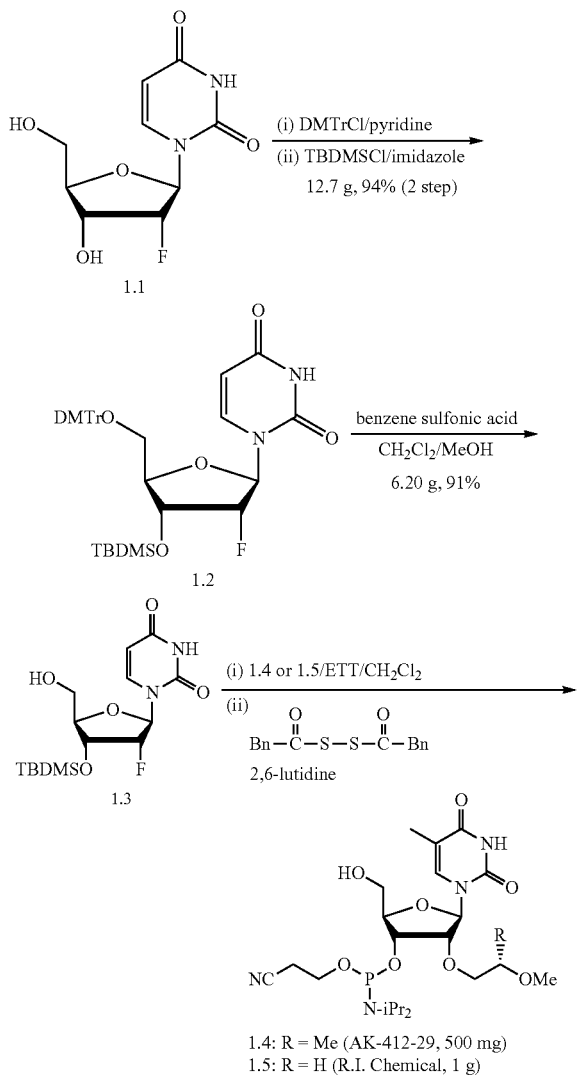

Scheme H-1.

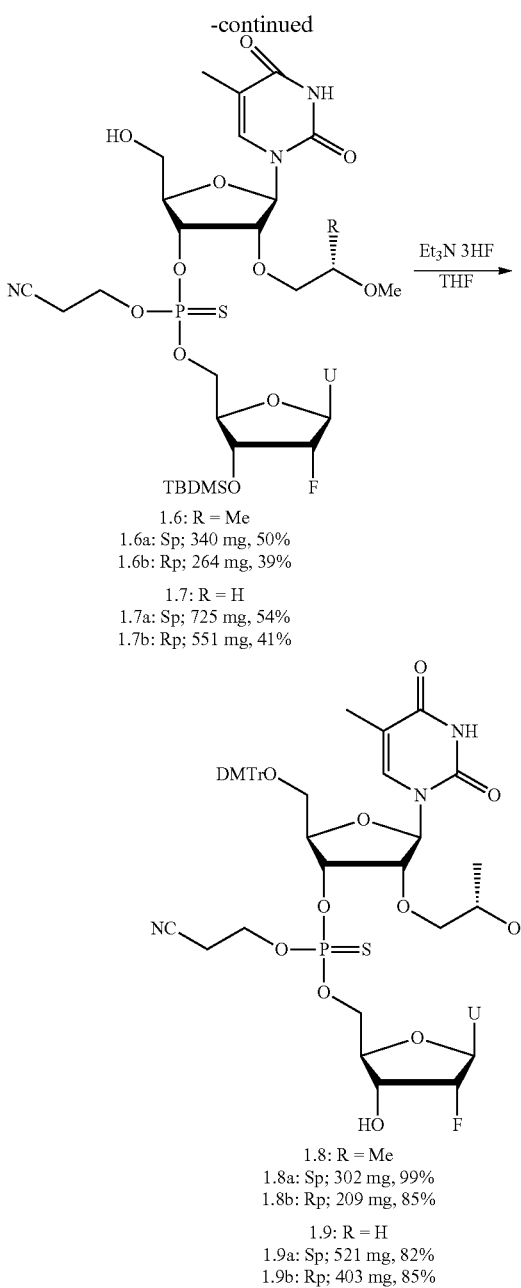

1.6: R = Me
1.6a: Sp; 340 mg, 50%
1.6b: Rp; 264 mg, 39%

1.7: R = H
1.7a: Sp; 725 mg, 54%
1.7b: Rp; 551 mg, 41%

1.8: R = Me
1.8a: Sp; 302 mg, 99%
1.8b: Rp; 209 mg, 85%

1.9: R = H
1.9a: Sp; 521 mg, 82%
1.9b: Rp; 403 mg, 85%

Compound 1.2: To a solution of 1.1 (5.0 g, 20.3 mmol, R.I. Chemicals, Inc.) in pyridine (50 ml), DMTrCl (7.57 g, 22.3 mmol) was added. The reaction mixture was stirred for 3 hours. Imidazole (3.46 g, 50.8 mmol) and TBDMSCl (3.67 g, 24.4 mmol) were added. The reaction mixture was stirred overnight. After removal of the solvent, the residue was extracted with $CH_2Cl_2$ and saturated $NaHCO_3$ (aq.), dried over anhydrous $Na_2SO_4$, and purified by silica gel column chromatography (hexane: EtOAc, 2:1, $R_f$=0.18) to yield 1.2 (12.7 g, 19.2 mmol, 94%).

1.2: $R_f$=0.18 (hexane: EtOAc, 2:1) $^1$H NMR (DMSO-d$_6$, 400 MHz) δ 11.46 (s, 1H), 7.87 (d, J=8.0 Hz, 1H), 7.22-7.38 (m, 9H), 6.87-6.90 (m, 4H), 5.89 (d, J=20.4 Hz, 1H), 5.32-5.34 (d, J=8.4 Hz, 1H), 5.12-5.27 (m, 1H), 4.51 (ddd, J=22.8 Hz, 8.8 Hz, 4.4 Hz, 1H), 3.96-3.98 (m, 1H), 3.73 (s, 6H), 3.43 (d, J=9.6 Hz, 1H), 3.15 (dd, J=11.0 Hz, 3.9 Hz, 1H), 0.74 (s, 9H), 0.034 (s, 3H), −0.059 (s, 3H). $^{13}$C NMR (DMSO-d$_6$, 100 MHz) δ 163.3, 158.2, 150.1, 144.4, 141.1, 135.0, 129.8, 127.7, 126.9, 113.2, 101.4, 93.5, 89.3, 88.9, 85.9, 81.0, 68.9, 68.7, 61.2, 55.1, 25.4, 17.6, −4.9, −5.5. $^{19}$F NMR (DMSO-d$_6$, 376 MHz) δ −202.39, −202.44, −202.50, −202.53, −202.59, −202.65. Molecular weight for $C_{36}H_{43}FN_2NaO_7Si$ (M+Na): calculated 685.27, found 685.3.

Compound 1.3: To a solution of 1.2 (12.5 g, 18.9 mmol) in $CH_2Cl_2$ (126 ml) and MeOH (54 ml), benzenesulfonic acid (8.95 g, 56.6 mmol) in $CH_2Cl_2$ (63 ml) and MeOH (27 ml) was added dropwise at −20° C. The mixture was stirred at the same temperature for 1 hour and quenched with 200 ml saturated aqueous $NaHCO_3$. The organic layer was separated, and the aqueous layer was extracted with $CH_2Cl_2$. The combined organic layer was dried over $Na_2SO_4$, filtered and concentrated. The crude was purified by silica gel column chromatography (hexane: EtOAc, 1:1, $R_f$=0.20) to yield 1.3 (6.20 g, 17.2 mmol, 91%).

1.3: $R_f$=0.20 (hexane: EtOAc). $^1$H NMR (DMSO-d$_6$, 400 MHz) δ 11.41 (s, 1H), 7.89 (d, J=8.0 Hz, 1H), 5.89 (dd, J=17.9 Hz, 1.9 Hz, 1H), 5.64 (d, J=8.0 Hz, 1H), 5.03-5.23 (m, 2H), 4.33 (ddd, J=18.9 Hz, 7.1 Hz, 4.5 Hz, 1H), 3.86-3.88 (m, 1H), 3.76 (d, J=12.0 Hz, 1H), 3.54 (d, J=12.0 Hz, 1H), 0.87 (s, 9H), 0.10 (s, 3H), 0.10 (s, 3H). $^{13}$C NMR (DMSO-d$_6$, 100 MHz) δ 163.2, 150.3, 140.6, 101.7, 93.5, 91.6, 87.6, 87.3, 83.4, 68.8, 68.6, 59.1, 25.6, 17.8, −4.9, −5.2. $^{19}$F NMR (DMSO-d$_6$, 376 MHz) δ −205.34, −205.38, −205.43, −205.48, −205.53, −205.57. Molecular weight for $C_{15}H_{26}FN_2O_5Si$ (M+H): calculated 361.16, found 361.2.

Compound 1.6: To a solution of 1.3 (227 mg, 0.630 mmol) and 1.4 (500 mg, 0.600 mmol) in $CH_2Cl_2$ (15 ml), 0.25 M ethylthio-1H-tetrazole in $CH_3CN$ (4.8 ml, 1.2 mmol, Glen Research) was added dropwise. The mixture was stirred at room temperature for 2 hours. Then phenylacetyl disulfide (270 mg, 0.893 mmol) and 2,6-lutidine (0.105 ml, 0.902 mmol) were added and the mixture was stirred overnight. Aqueous work-up and silica gel column chromatography yielded 1.6a (340 mg, 0.302 mmol, 50%) and 1.6b (264 mg, 0.235 mmol, 39%).

1.6a: S$_p$ isomer, $R_f$=0.47 (hexane: EtOAc, 1:4). $^1$H NMR (CD$_3$CN, 400 MHz) δ 9.29-9.31 (m, 2H), 7.27-7.79 (m, 9H), 6.91-6.93 (m, 4H), 6.01 (d, J=6.4 Hz, 1H), 5.87 (d, J=1.6 Hz, 0.5H), 5.82 (d, J=1.6 Hz, 0.5H), 5.65 (d, J=8.4 Hz, 1H), 5.22 (ddd, J=10.7 Hz, 5.1 Hz, 3.2 Hz, 1H), 5.13 (dd, J=4.7, 1.6 Hz, 0.5H), 5.00 (dd, J=4.7, 1.6 Hz, 0.5H), 4.47-4.53 (m, 2H), 4.13-4.38 (m, 6H), 3.80 (s, 6H), 3.67 (dd, J=11.0 Hz, 3.5 Hz, 1H), 3.38-3.58 (m, 4H), 3.24 (s, 3H), 2.71-2.75 (m, 2H), 1.47 (d, J=1.2 Hz, 3H), 1.07 (d, J=6.4 Hz, 3H), 0.94 (s, 9H), 0.17 (s, 3H), 0.15 (s, 3H). $^{13}$C NMR (CD$_3$CN, 100 MHz) δ 164.8, 164.3, 160.2, 152.0, 151.5, 151.1, 145.9, 142.3, 137.3, 136.6, 131.5, 129.4, 128.5, 125.2, 114.6, 112.2, 103.4, 94.7, 92.8, 91.4, 91.0, 88.4, 87.4, 83.5, 82.3, 82.2, 81.6, 77.7, 77.3, 77.2, 75.7, 70.8, 70.7, 68.1, 64.6, 64.2, 57.3, 56.3, 28.2, 26.4, 20.5, 20.4, 19.0, 16.4, 15.7, 12.6, −4.2, −4.4. $^{31}$P NMR (CD$_3$CN, 162 MHz) δ 67.17. $^{19}$F NMR (CD$_3$CN, 376 MHz) δ −203.34, −203.40, −203.45, −203.49, −203.54, −203.59. Molecular weight for $C_{53}H_{67}FN_5NaO_{15}PSSi$ (M+Na): calculated 1146.37, found 1146.3.

1.6b: R$_p$ isomer, $R_f$=0.27 (hexane: EtOAc, 1:4). $^1$H NMR (CD$_3$CN, 400 MHz) δ 9.33 (brs, 2H), 7.27-7.50 (m, 9H), 6.89-6.93 (m, 4H), 6.00 (d, J=6.6 Hz, 1H), 5.75 (dd, J=20.6, 1.3 Hz, 1H), 5.60 (d, J=8.0 Hz, 1H), 5.26 (ddd, J=10.7 Hz, 5.1 Hz, 2.9 Hz, 1H), 5.07 (ddd, J=53.3 Hz, 4.8 Hz, 1.3 Hz, 1H), 4.17-4.47 (m, 6H), 4.04-4.06 (m, 1H), 3.79 (s, 6H), 3.70 (dd, J=10.8 Hz, 3.2 Hz, 1H), 3.49-3.58 (m, 2H), 3.26-3.36 (m, 3H), 3.25 (s, 3H), 2.84 (t, J=5.9 Hz, 2H), 1.43

(s, 3H), 1.10 (d, J=6.2 Hz, 3H), 0.92 (s, 9H), 0.15 (s, 3H), 0.14 (s, 3H). $^{13}$C NMR (CD$_3$CN, 100 MHz) δ 164.8, 164.4, 160.2, 155.9, 152.1, 151.5, 145.9, 142.5, 137.5, 136.6, 136.5, 131.5, 131.5, 129.4, 129.4, 128.5, 125.2, 114.6, 112.3, 103.4, 94.7, 92.9, 91.9, 91.5, 88.4, 87.2, 83.6, 82.0, 81.9, 81.8, 77.6, 77.5, 75.7, 70.5, 70.3, 67.5, 64.8, 64.7, 64.1, 57.2, 56.3, 28.2, 26.4, 20.5, 19.0, 16.4, 15.7, 12.6, −4.2, −4.4. $^{31}$P NMR (CD$_3$CN, 162 MHz) δ 67.55. $^{19}$F NMR (CD$_3$CN, 376 MHz) δ −202.41, −202.47, −202.52, −202.56, −202.61, −202.67.

Compound 1.7: To a solution of 1.3 (462 mg, 1.28 mmol) and 1.5 (1.0 g, 1.22 mmol, R.I. Chemicals, Inc.) in CH$_2$Cl$_2$ (30 ml), 0.25 M ethylthio-1H-tetrazole in CH$_3$CN (9.76 ml, 2.44 mmol, Glen Research) was added dropwise. The mixture was stirred at room temperature for 2 h. Then phenylacetyl disulfide (533 mg, 1.83 mmol) and 2,6-lutidine (0.213 ml, 1.83 mmol) were added and the mixture was stirred overnight. Aqueous work-up and silica gel column chromatography yielded 1.7a (725 mg, 0.653 mmol, 54%) and 1.7b (551 mg, 0.496 mmol, 41%).

1.7a: S$_p$ isomer, R$_f$=0.28 (hexane:EtOAc, 1:4). $^1$H NMR (DMSO-d$_6$, 400 MHz) δ 11.55-11.35 (m, 2H), 7.69-7.54 (m, 1H), 7.46 (s, 1H), 7.19-7.43 (m, 10H), 6.89-6.91 (m, 4H), 5.91 (d, J=6.8 Hz, 1H), 5.85 (d, J=21.0 Hz, 1H), 5.62 (dd, J=8.0 Hz, 2.1 Hz, 1H), 5.14-5.29 (m, 2H), 4.06-4.49 (m, 8H), 3.74 (s, 6H), 3.71-3.72 (m, 2H), 3.31-3.46 (m, 3H), 3.17 (s, 3H), 2.86 (t, J=5.8 Hz, 2H), 1.38 (s, 3H), 0.88 (s, 9H), 0.12 (s, 3H), 0.11 (s, 3H). $^{13}$C NMR (DMSO-d$_6$, 100 MHz) δ 163.5, 163.2, 158.3, 154.0, 150.6, 150.2, 144.3, 141.4, 135.3, 135.2, 134.8, 129.8, 129.7, 128.0, 127.7, 127.0, 120.7, 118.0, 113.3, 110.2, 101.9, 92.8, 91.0, 89.5, 89.2, 86.4, 85.6, 81.6, 80.3, 79.0, 76.2, 71.7, 69.8, 69.2, 69.1, 66.7, 63.1, 63.0, 58.3, 55.1, 26.5, 25.5, 18.9, 18.8, 17.7, 14.9, 11.6, −4.9, −5.2. $^{31}$P NMR (DMSO-d$_6$, 162 MHz) δ 71.96. $^{19}$F NMR (DMSO-d$_6$, 376 MHz) δ −202.51, −202.57, −202.62, −202.65, −202.71, −202.76. Molecular weight for C$_{52}$H$_{65}$FN$_5$NaO$_{15}$PSSi (M+Na): calculated 1132.36, found 1132.2.

1.7b: R$_p$ isomer, R$_f$=0.10 (hexane: EtOAc, 1:4). $^1$H NMR (DMSO-d$_6$, 400 MHz) δ 11.53-11.33 (m, 2H), 7.57 (d, J=8.1 Hz, 1H), 7.48 (s, 1H), 7.23-7.40 (m, 10H), 6.88-6.90 (m, 4H), 5.89 (d, J=6.4 Hz, 1H), 5.83 (d, J=19.9 Hz, 1H), 5.60 (dd, J=8.1 Hz, 2.1 Hz, 1H), 5.11-5.26 (m, 2H), 3.97-4.45 (m, 8H), 3.73 (s, 6H), 3.70-3.77 (m, 2H), 3.21-3.49 (m, 3H), 3.20 (s, 3H), 2.95 (t, J=5.8 Hz, 2H), 1.38 (s, 3H), 0.85 (s, 9H), 0.10 (s, 3H), 0.090 (s, 3H). $^{13}$C NMR (DMSO-d$_6$, 100 MHz) δ 163.6, 163.2, 158.3, 150.5, 150.1, 144.3, 141.2, 135.4, 135.1, 134.8, 129.8, 128.0, 127.7, 127.0, 118.2, 113.3, 110.1, 101.9, 92.9, 91.1, 89.4, 89.1, 86.4, 85.9, 81.6, 80.2, 80.1, 79.1, 75.8, 71.6, 69.8, 69.0, 68.8, 66.1, 63.4, 63.3, 62.7, 58.3, 55.1, 30.2, 26.5, 25.5, 20.8, 18.9, 18.8, 18.6, 17.7, 15.0, 13.6, 11.6, −4.9, −5.2. $^{31}$P NMR (DMSO-d$_6$, 162 MHz) δ 72.24. $^{19}$F NMR (DMSO-d$_6$, 376 MHz) δ −202.50, −202.56, −202.61, −202.65, −202.70, −202.76. Molecular weight for C$_2$H$_{65}$FN$_5$NaO$_{15}$PSSi (M+Na): calculated 1132.36, found 1132.2.

Compound 1.8a: To a solution of compound 1.6a (340 mg, 0.302 mmol) in THF (7 ml), triethylamine trihydrofluoride (0.176 ml, 3.26 mmol) was added. The mixture was stirred overnight then concentrated. Purification by silica gel column chromatography (5% MeOH in CH$_2$Cl$_2$, R$_f$=0.22) yielded 1.8a (302 mg, 0.299 mmol, 99%).

1.8a: S$_p$ isomer, R$_f$=0.22 5% (MeOH in DCM). $^1$H NMR (CD$_3$CN, 400 MHz) δ 9.10 (s, 2H), 7.24-7.49 (m, 11H), 6.88-6.90 (m, 4H), 5.97 (d, J=6.8 Hz, 1H), 5.74-5.88 (m, 1H), 5.60 (d, J=8.1 Hz, 1H), 5.17 (ddd, J=10.5 Hz, 4.9 Hz, 2.6 Hz, 1H), 5.04 (dd, J=52.5 Hz, 4.0 Hz, 1H), 4.11-4.51 (m, 5H), 3.87 (d, J=7.1 Hz, 1H), 3.77 (s, 6H), 3.68-3.71 (m, 1H), 3.32-3.51 (m, 4H), 3.21 (s, 3H), 2.72 (td, J=5.5 Hz, 3.1 Hz, 2H), 1.42 (s, 3H), 1.04 (d, J=6.1 Hz, 3H). $^{13}$C NMR (CD$_3$CN, 100 MHz) δ 164.8, 164.3, 160.3, 152.1, 151.5, 145.9, 142.0, 137.3, 136.7, 136.6, 131.5, 129.5, 128.6, 114.7, 112.4, 103.3, 95.6, 93.7, 91.0, 90.7, 88.5, 87.1, 83.7, 82.0, 81.9, 77.6, 75.8, 69.9, 69.7, 68.4, 64.6, 64.5, 64.3, 57.2, 56.4, 20.5, 20.4, 16.4, 12.6. $^{31}$P NMR (CD$_3$CN, 162 MHz) δ 72.66. $^{19}$F NMR (376 MHz, CD$_3$CN) δ −204.02, −204.08, −204.13, −204.16, −204.22, −204.27.

Compound 1.8b: To a solution of compound 1.6b (273 mg, 0.243 mmol) in THF (6 ml), triethylamine trihydrofluoride (0.142 ml, 2.62 mmol) was added. The mixture was stirred overnight then concentrated. Purification by silica gel column chromatography (5% MeOH in CH$_2$Cl$_2$, R$_f$=0.21) yielded 1.8b (209 mg, 0.207 mmol, 85%).

1.8b: R$_p$ isomer, R$_f$=0.21 (5% MeOH in CH$_2$Cl$_2$). $^1$H NMR (CD$_3$CN, 400 MHz) δ 9.12 (s, 2H), 7.24-7.46 (m, 11H), 6.87-6.90 (m, 4H), 5.97 (d, J=6.6 Hz, 1H), 5.74 (d, J=19.3 Hz, 1H), 5.57 (d, J=8.1 Hz, 1H), 5.22 (ddd, J=10.7 Hz, 5.1 Hz, 2.9 Hz, 1H), 5.03 (dd, J=53.1 Hz, 4.7 Hz, 1H), 4.43 (t, J=5.3 Hz, 1H), 4.19-4.36 (m, 3H), 4.04 (s, 1H), 3.77 (s, 6H), 3.66-3.70 (m, 2H), 3.41-3.56 (m, 2H), 3.27-3.39 (m, 2H), 3.23 (s, 3H), 2.82 (t, J=5.9 Hz, 2H), 1.41 (s, 3H), 1.07 (d, J=6.1 Hz, 3H). $^{13}$C NMR (CD$_3$CN, 100 MHz) δ 164.8, 164.3, 160.3, 152.1, 151.5, 146.0, 142.3, 137.3, 136.7, 136.6, 131.5, 129.5, 128.5, 114.7, 112.4, 103.3, 95.5, 93.6, 91.5, 91.2, 88.4, 87.3, 83.6, 81.8, 81.7, 77.6, 77.5, 77.4, 75.8, 69.8, 69.7, 68.1, 68.0, 64.8, 64.7, 64.2, 57.2, 56.4, 20.5, 16.4, 12.6. $^{31}$P NMR (CD$_3$CN, 162 MHz) δ 72.86. $^{19}$F NMR (376 MHz, CD$_3$CN) δ −203.18, −203.24, −203.29, −203.32, −203.38, −203.43.

Compound 1.9a: To a solution of compound 1.7a (705 mg, 0.635 mmol) in THF (14 ml), triethylamine trihydrofluoride (0.412 ml, 7.62 mmol) was added. The mixture was stirred overnight then concentrated. Purification by silica gel column chromatography (5% MeOH in CH$_2$Cl$_2$, R$_f$=0.26) yielded 1.9a (521 mg, 0.523 mmol, 82%).

1.9a: S$_p$ isomer, R$_f$=0.26 (5% MeOH in CH$_2$Cl$_2$). $^1$H NMR (CD$_3$CN, 400 MHz) δ 9.32 (s, 2H), 7.24-7.53 (m, 11H), 6.88-6.90 (m, 4H), 5.97 (d, J=6.8 Hz, 1H), 5.84 (d, J=19.2 Hz, 1H), 5.63 (d, J=8.1 Hz, 1H), 5.22 (ddd, J=10.4 Hz, 4.9 Hz, 2.5 Hz, 1H), 5.04 (dd, J=53.0 Hz, 4.5 Hz, 1H), 4.08-4.55 (m, 8H), 3.94 (s, 1H), 3.77 (s, 6H), 3.72-3.83 (m, 2H), 3.48-3.51 (m, 2H), 3.40 (dd, J=11.0 Hz, 2.8 Hz, 1H), 3.33 (dd, J=11.0 Hz, 2.7 Hz, 1H), 3.24 (s, 3H), 2.72 (td, J=5.6 Hz, 2.5 Hz, 2H), 1.40 (s, 3H). $^{13}$C NMR (CD$_3$CN, 100 MHz) δ 174.4, 164.8, 164.3, 160.2, 152.1, 151.5, 145.9, 141.8, 137.3, 136.6, 136.5, 131.5, 129.4, 125.1, 114.6, 112.4, 103.2, 95.6, 93.7, 90.8, 90.5, 88.4, 87.1, 83.6, 83.5, 81.9, 81.8, 81.5, 81.4, 77.9, 73.4, 71.8, 69.7, 69.5, 68.1, 64.5, 64.4, 64.2, 59.6, 56.3, 20.5, 20.4, 12.6. $^{19}$F NMR (376 MHz, CD$_3$CN) δ −204.24, −204.30, −204.35, −204.39, −204.44, −204.50. Molecular weight for C$_{43}$H$_{47}$FN$_4$O$_{15}$PS (M-CH$_2$CH$_2$CN): calculated 941.25, found 941.2.

Compound 1.9b: To a solution of compound 1.7b (530 mg, 0.477 mmol) in THF (10 ml), triethylamine trihydrofluoride (0.309 ml, 5.72 mmol) was added. The mixture was stirred overnight then concentrated. Purification by silica gel column chromatography (5% MeOH in CH$_2$Cl$_2$, R$_f$=0.21) yielded 1.9b (403 mg, 0.405 mmol, 85%).

1.9b: R$_p$ isomer, R$_f$=0.21 (5% MeOH in CH$_2$Cl$_2$). $^1$H NMR (CD$_3$CN, 400 MHz) □ 9.30 (s, 2H), 7.22-7.48 (m, 11H), 6.88-6.90 (m, 4H), 5.96 (d, J=6.5 Hz, 1H), 5.70-5.80 (m, 1H), 5.58 (d, J=8.1 Hz, 1H), 5.26 (ddd, J=10.7 Hz, 5.1 Hz, 3.0 Hz, 1H), 5.04 (dd, J=52.8 Hz, 4.2 Hz, 1H), 4.40 (t, J=5.4 Hz, 1H), 4.23-4.34 (m, 6H), 4.00-4.08 (m, 1H), 3.78-3.80 (m, 3H), 3.77 (s, 6H), 3.45-3.57 (m, 2H), 3.36 (dd, J=11.0 Hz, 2.9 Hz, 1H), 3.30 (dd, J=11.0 Hz, 2.6 Hz, 1H), 3.26 (s, 3H), 2.82 (t, J=5.9 Hz, 2H), 1.40 (s, 3H). $^{13}$C NMR (CD$_3$CN, 100 MHz) δ 164.8, 164.3, 160.2, 152.1, 151.4, 145.9, 142.2, 137.3, 136.6, 136.5, 131.5, 129.4, 125.1, 114.6, 112.3, 103.3, 95.5, 93.6, 91.4, 91.1, 88.3, 87.3, 83.5, 81.7, 81.4, 77.6, 77.5, 73.4, 71.7, 69.7, 69.5, 68.0, 67.9, 64.7, 64.1, 59.6, 56.3, 20.5, 20.4, 12.5. $^{31}$P NMR (CD$_3$CN, 162 MHz) δ 72.76. $^{19}$F NMR (376 MHz, CD$_3$CN) δ −203.21, −203.27, −203.32, −203.36, −203.41, −203.47. Molecular weight for C$_{43}$H$_{47}$FN$_4$O$_{15}$PS (M−CH$_2$CH$_2$CN): calculated 941.25, found 941.2.

Scheme H-2.

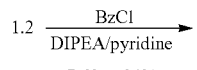

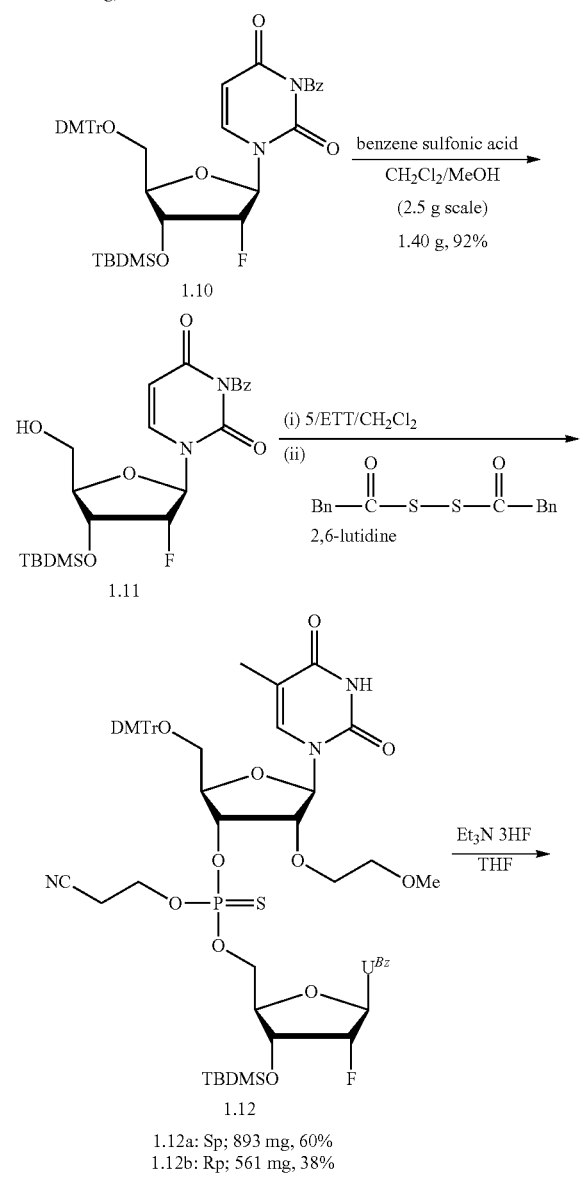

1.12a: Sp; 893 mg, 60%
1.12b: Rp; 561 mg, 38%

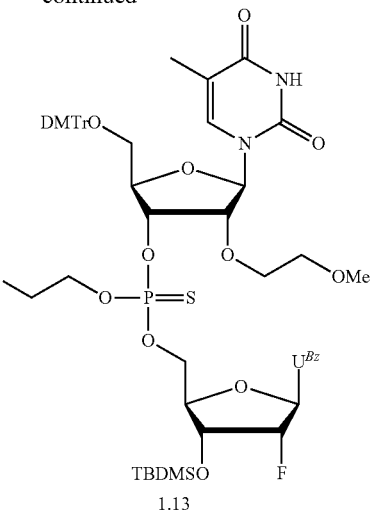

1.13a: Sp; 698 mg, 88%
1.13b: Rp; 456 mg, 93%

Compound 1.10: To a solution of 1.2 (7.91 g, 11.9 mmol) in pyridine (40 ml) and DIPEA (10.4 ml, 59.5 mmol), BzCl (2.21 ml, 19.0 mmol) was added at 0° C. The reaction mixture was stirred for 14 hours at room temperature. After removal of the solvents, the residue was extracted with CH$_2$Cl$_2$ and saturated NaHCO$_3$ (aq.), dried over anhydrous Na$_2$SO$_4$, and purified by silica gel column chromatography (hexane: EtOAc, 2:1; R$_f$=0.39) to yield 1.10 (7.68 g, 10.0 mmol, 84%). 1.10: R$_f$=0.39 (hexane: EtOAc, 2:1). $^1$H NMR (400 MHz, DMSO-d$_6$) δ 8.09 (d, J=8.2 Hz, 1H), 8.00-8.06 (m, 2H), 7.76 (t, J=7.4 Hz, 1H), 7.55 (t, J=7.7 Hz, 2H), 7.15-7.44 (m, 9H), 6.88-6.91 (m, 4H), 5.94 (d, J=20.0 Hz, 1H), 5.56 (d, J=8.0 Hz, 1H), 5.23 (dd, J=53.4 Hz, 4.4 Hz, 1H), 4.52 (ddd, J=23.3 Hz, 9.1 Hz, 4.4 Hz, 1H), 3.92-4.09 (m, 1H), 3.74 (s, 6H), 3.47 (d, J=10.3 Hz, 1H), 3.20 (dd, J=11.1 Hz, 3.6 Hz, 1H), 0.74 (s, 9H), 0.046 (s, 3H), −0.052 (s, 3H). $^{13}$C NMR (101 MHz, DMSO-d$_6$) δ 169.3, 161.9, 158.2, 149.6, 148.7, 144.3, 141.8, 135.6, 135.1, 134.9, 131.0, 130.5, 129.8, 129.4, 127.9, 127.7, 126.9, 123.9, 113.4, 100.9, 93.4, 91.6, 89.5, 89.2, 85.9, 81.2, 68.6, 68.4, 61.0, 55.1, 25.4, 17.5, −4.8, −5.4. $^{19}$F NMR (376 MHz, DMSO-d$_6$) δ −202.92 (brs). Molecular weight for C$_{43}$H$_{47}$FN$_2$NaO$_8$Si (M+Na): calculated 789.30, found 789.2.

Compound 1.11: To a solution of 1.10 (2.50 g, 3.26 mmol) in CH$_2$Cl$_2$ (21 ml) and MeOH (9 ml), benzenesulfonic acid (1.55 g, 9.78 mmol) in CH$_2$Cl$_2$ (12 ml) and MeOH (5 ml) was added dropwise at −20° C. The mixture was stirred at the same temperature for 1 hour and quenched with 50 ml saturated NaHCO$_3$ (aq.). The organic layer was separated, and the aqueous layer was extracted with CH$_2$Cl$_2$. The combined organic layer was dried over Na$_2$SO$_4$, filtered and concentrated. The crude was purified by silica gel column chromatography (hexane: EtOAc, 1:1; R$_f$=0.21) to yield 1.11 (1.40 g, 3.01 mmol, 92%).

1.11: R$_f$=0.21 (hexane:EtOAc, 1:1). $^1$H NMR (400 MHz, DMSO-d$_6$) δ 8.14 (d, J=8.2 Hz, 1H), 8.03 (d, J=7.4 Hz, 2H), 7.80 (t, J=7.4 Hz, 1H), 7.61 (t, J=7.8 Hz, 2H), 5.90-5.96 (m, 2H), 5.34 (t, J=4.7 Hz, 1H), 5.09-5.23 (m, 1H), 4.38 (ddd, J=20.3 Hz, 7.6 Hz, 4.4 Hz, 1H), 3.92 (d, J=7.5 Hz, 1H), 3.81-3.95 (m, 1H), 3.58 (ddd, J=12.4 Hz, 4.8 Hz, 3.0 Hz, 1H), 0.88 (s, 9H), 0.122 (s, 3H), 0.115 (s, 3H). $^{13}$C NMR (100 MHz, DMSO-d$_6$) δ 169.40, 161.9, 148.9, 141.3, 135.6, 131.1, 130.5, 129.5, 101.2, 93.6, 91.8, 88.1, 87.8, 83.6, 68.5, 68.3, 58.7, 25.5, 17.7, −4.9, −5.1. $^{19}$F NMR (376 MHz, DMSO-d$_6$) δ −204.99, −205.04, −205.10, −205.14, −205.19, −205.23.

Compound 1.12: To a solution of 1.11 (595 mg, 1.28 mmol) and 1.5 (1.00 g, 1.22 mmol) in CH$_2$Cl$_2$ (30 ml), 0.25 M ethylthio-1H-tetrazole in CH$_3$CN (9.76 ml, 2.44 mmol, Glen Research) was added dropwise. The mixture was stirred at room temperature for 1 hour. Then phenylacetyl disulfide (533 mg, 1.83 mmol) and 2,6-lutidine (0.213 ml, 1.83 mmol) were added, and the mixture was stirred overnight. Aqueous work-up and silica gel column chromatography yielded 1.12a (893 mg, 0.735 mmol, 60%) and 1.12b (561 mg, 0.462 mmol, 38%).

1.12a: S$_p$ isomer, R$_f$=0.71 (hexane:EtOAc, 1:4). $^1$H NMR (400 MHz, CD$_3$CN) δ 9.10 (s, 1H), 7.98-8.00 (m, 2H), 7.24-7.72 (m, 14H), 6.88-6.90 (m, 4H), 5.99 (d, J=6.6 Hz, 1H), 5.90 (dd, J=18.5 Hz, 1.1 Hz, 1H), 5.84 (d, J=8.2 Hz, 1H), 5.27 (ddd, J=10.8 Hz, 5.1 Hz, 2.9 Hz, 1H), 4.99-5.13 (m, 1H), 4.56 (ddd, J=11.6 Hz, 6.6 Hz, 1.8 Hz, 1H), 4.47 (t, J=5.6 Hz, 1H), 4.27-4.35 (m, 3H), 4.12-4.18 (m, 3H), 3.78-3.80 (m, 2H), 3.77 (s, 6H), 3.48-3.52 (m, 2H), 3.40 (dd, J=10.9 Hz, 3.0 Hz, 1H), 3.33 (dd, J=11.0 Hz, 2.7 Hz, 1H), 3.24 (s, 3H), 2.70 (dd, J=9.3 Hz, 5.6 Hz, 2H), 1.41 (s, 3H), 0.91 (s, 9H), 0.14 (s, 3H), 0.13 (s, 3H). $^{13}$C NMR (100 MHz, CD$_3$CN) δ 225.9, 170.7, 164.8, 163.5, 160.3, 152.0, 150.6, 145.9, 142.3, 136.7, 136.6, 132.7, 131.7, 131.5, 130.8, 129.4, 125.2, 118.7, 114.6, 112.3, 103.2, 94.7, 92.9, 91.2, 90.8, 88.4, 87.5, 83.6, 82.5, 82.4, 81.4, 81.3, 77.9, 73.5, 71.7, 70.6, 70.4, 67.7, 64.6, 64.3, 59.7, 56.34, 28.2, 26.4, 20.5, 20.4, 19.0, 15.7, 12.6, −4.2, −4.4. $^{31}$P NMR (CD$_3$CN, 162 MHz) δ 72.57. $^{19}$F NMR (CD$_3$CN, 376 MHz) δ −204.23, −204.28, −204.33, −204.37, −204.42, −204.48. Molecular weight for C$_{59}$H$_{69}$FN$_5$NaO$_{16}$PSSi (M+Na): calculated 1236.38, found 1236.3.

1.12b: R$_p$ isomer, R$_f$=0.40 (hexane: EtOAc, 1:4). $^1$H NMR (400 MHz, CD$_3$CN) δ 9.11 (s, 1H), 7.97-7.99 (m, 2H), 7.24-7.65 (m, 14H), 6.88-6.90 (m, 4H), 6.00 (d, J=6.4 Hz, 1H), 5.82-5.89 (m, 2H), 5.31 (ddd, J=10.9 Hz, 5.0 Hz, 3.1 Hz, 1H), 5.02 (dd, J=52.7 Hz, 4.5 Hz, 1H), 4.43 (t, J=5.7 Hz, 1H), 4.22-4.34 (m, 6H), 4.07-4.09 (m, 1H), 3.80 (t, J=4.2 Hz, 2H), 3.76 (s, 6H), 3.46-3.57 (m, 2H), 3.40 (dd, J=11.0 Hz, 2.8 Hz, 1H), 3.34 (dd, J=10.9 Hz, 2.6 Hz, 1H), 3.26 (s, 3H), 2.82 (t, J=5.9 Hz, 2H), 1.39 (s, 3H), 0.89 (s, 9H), 0.13 (s, 3H), 0.11 (s, 3H). $^{13}$C NMR (100 MHz, CD$_3$CN) δ 170.7, 164.8, 163.5 160.3, 151.9, 150.6, 145.9, 142.0, 137.4, 136.8, 136.5, 132.7, 131.7, 131.6, 131.5, 130.8, 129.4, 125.2, 119.0, 118.7, 114.6, 112.3, 111.1, 103.2, 94.8, 92.9, 91.1, 90.7, 88.4, 87.5, 83.6, 82.3, 82.2, 81.5, 81.4, 77.8, 73.4, 71.8, 70.3, 70.1, 67.2, 64.9, 64.8, 64.1, 59.6, 56.3, 26.4, 20.6, 20.5, 19.0, 12.6, −4.2, −4.4. $^{31}$P NMR (CD$_3$CN, 162 MHz) δ 73.05. $^{19}$F NMR (CD$_3$CN, 376 MHz) δ −203.94, −203.99, −204.05, −204.08, −204.13, −204.19. Molecular weight for C$_9$H$_{69}$FN$_5$NaO$_{16}$PSSi (M+Na): calculated 1236.38, found 1236.3.

Compound 1.13a: To a solution of compound 1.12a (875 mg, 0.721 mmol) in THF (15 ml), triethylamine trihydrofluoride (0.468 ml, 8.65 mmol) was added. The mixture was stirred overnight then concentrated. Purification by silica gel column chromatography (5% MeOH in CH$_2$Cl$_2$, R$_f$=0.46) yielded 1.13a (698 mg, 0.635 mmol, 88%). 1.13a: S$_p$ isomer, R$_f$=0.46 (5% MeOH in CH$_2$Cl$_2$). $^1$H NMR (400 MHz, CD$_3$CN) δ 9.22 (s, 1H), 7.98-8.00 (m, 2H), 7.81 (d, J=8.3 Hz, 1H), 7.25-7.57 (m, 13H), 6.89-6.91 (m, 4H), 6.00 (d, J=7.2 Hz, 1H), 5.89 (d, J=17.8 Hz, 1H), 5.83 (d, J=8.3 Hz, 1H), 5.21 (ddd, J=9.6 Hz, 4.7 Hz, 2.0 Hz, 1H), 5.10 (dd, J=52.7 Hz, 4.2 Hz, 1H), 4.53 (ddd, J=11.7 Hz, 6.1 Hz, 1.8 Hz, 1H), 4.33-4.44 (m, 4H), 4.12-4.22 (m, 3H), 3.82-3.86 (m, 2H), 3.77 (s, 6H), 3.49 (t, J=4.3 Hz, 2H), 3.43 (dd, J=11.0 Hz, 2.9 Hz, 1H), 3.35 (dd, J=11.0 Hz, 2.9 Hz, 1H), 3.23 (s, 3H), 2.73 (dt, J=9.2 Hz, 4.7 Hz, 2H), 1.41 (s, 3H). $^{13}$C NMR (100 MHz, CD$_3$CN) δ 225.4, 170.5, 164.4, 163.3, 159.9, 151.8, 150.2, 145.6, 141.6, 136.5, 136.2, 136.1, 132.5, 131.4, 131.2, 130.5, 129.1, 124.8, 114.3, 112.2, 102.5, 95.4, 93.6, 90.5, 90.2, 88.2, 86.4, 83.4, 83.3, 81.7, 81.6, 81.2, 78.1, 72.9, 71.6, 68.9, 68.8, 67.3, 64.1, 59.3, 56.0, 20.2, 20.1, 12.2. $^{31}$P NMR (CD$_3$CN, 162 MHz) δ 72.42. $^{19}$F NMR (376 MHz, CD$_3$CN) δ −205.08, −205.13, −205.18, −205.21, −205.27, −205.32.

Compound 1.13b: To a solution of compound 1.12b (541 mg, 0.446 mmol) in THF (10 ml), triethylamine trihydrofluoride (0.289 ml, 5.35 mmol) was added. The mixture was stirred overnight then concentrated. Purification by silica gel column chromatography (5% MeOH in CH$_2$Cl$_2$, R$_f$=0.38) yielded 1.13b (456 mg, 0.415 mmol, 93%). 1.13b: R$_p$ isomer, R$_f$=0.38 (5% MeOH in CH$_2$Cl$_2$). $^1$H NMR (400 MHz, CD$_3$CN) δ 9.17 (s, 1H), 7.98 (d, J=7.3 Hz, 2H), 7.65 (d, J=8.3 Hz, 1H), 7.24-7.66 (m, 13H), 6.88-6.90 (m, 4H), 5.99 (d, J=6.5 Hz, 1H), 5.81-5.88 (m, 2H), 5.29 (ddd, J=10.8 Hz, 5.0 Hz, 3.0 Hz, 1H), 5.05 (dd, J=52.5 Hz, 4.3 Hz, 1H), 4.43 (t, J=5.4 Hz, 1H), 4.09-4.35 (m, 7H), 3.79-3.82 (m, 2H), 3.76 (s, 6H), 3.48-3.59 (m, 2H), 3.40 (dd, J=11.0 Hz, 2.9 Hz, 1H), 3.34 (dd, J=11.0 Hz, 2.7 Hz, 1H), 3.26 (s, 3H), 2.83 (t, J=5.9 Hz, 2H), 1.40 (s, 3H). $^{13}$C NMR (100 MHz, CD$_3$CN) δ 170.3, 164.4, 163.1, 159.9, 151.6, 150.2, 145.6, 141.6, 136.6, 136.5, 136.2, 132.4, 131.4, 131.2, 130.5, 129.1, 124.8, 114.3, 112.0, 102.8, 95.2, 93.4, 90.6, 90.2, 88.1, 87.1, 83.3, 83.2, 81.6, 81.5, 81.1, 77.4, 77.3, 73.1, 71.4, 69.2, 69.0, 67.4, 67.3, 64.5, 63.8, 59.3, 56.0, 20.2, 20.1, 12.2. $^{31}$P NMR (CD$_3$CN, 162 MHz) δ 72.89. $^{19}$F NMR (376 MHz, CD$_3$CN) δ −204.52, −204.57, −204.58, −204.63, −204.66, −204.71, −204.77.

Scheme H-3.

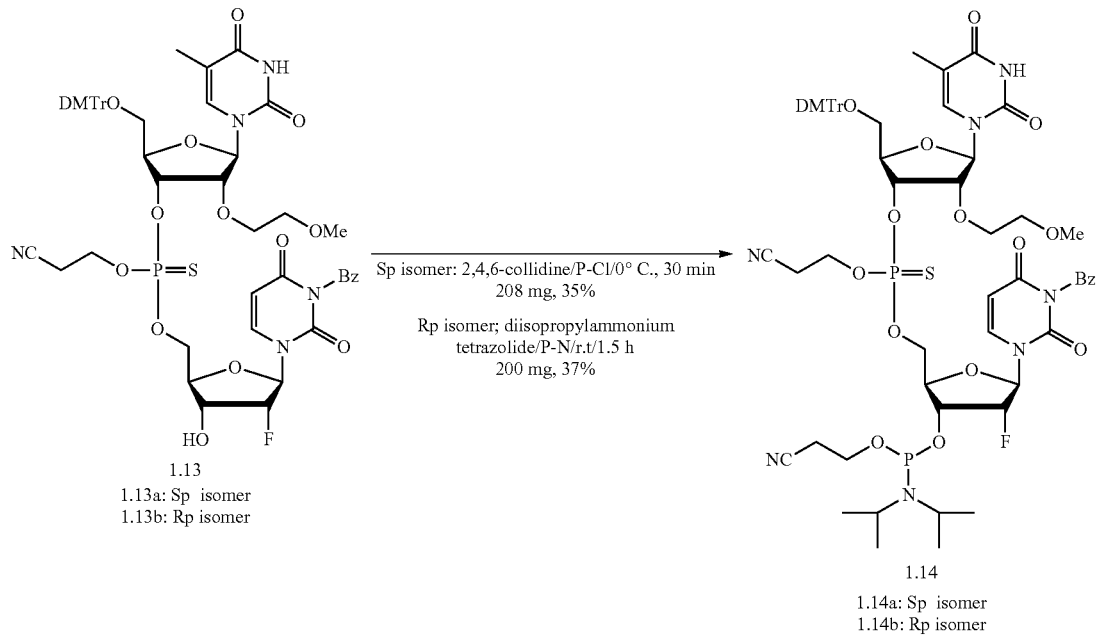

1.13
1.13a: Sp isomer
1.13b: Rp isomer

Sp isomer: 2,4,6-collidine/P-Cl/0° C., 30 min
208 mg, 35%

Rp isomer; diisopropylammonium
tetrazolide/P-N/r.t/1.5 h
200 mg, 37%

1.14
1.14a: Sp isomer
1.14b: Rp isomer

Compound 1.14a (S$_p$ isomer): To a solution of compound 1.13a (500 mg, 0.455 mmol) in CH$_2$Cl$_2$ (5 ml), 2,4,6-collidine (0.241 ml, 1.82 mmol) and 2-cyanoethyl N,N-diisopropylchlorophosphoramidite (0.152 ml, 0.683 mmol) were added at 0° C. The reaction mixture was stirred for 30 minutes at 0° C. The reaction mixture was diluted with CH$_2$Cl$_2$ (50 ml) and washed with 2% NaHCO$_3$ (aq. 20 ml). The organic layer was separated and dried over anhydrous Na$_2$SO$_4$. The filtrate was concentrated and the resulting crude material was purified by silica gel column chromatography (CH$_2$Cl$_2$:EtOAc, 1:1; R$_f$=0.43) to yield 1.14a (208 mg, 0.160 mmol, 35%).

1.14a: S$_p$ isomer, R$_f$=0.43 (CH$_2$Cl$_2$:EtOAc, 1:1). $^1$H NMR (400 MHz, CD$_3$CN) δ 9.08 (s, 1H), 7.24-7.77 (m, 16H), 6.88-6.90 (m, 4H), 5.82-5.99 (m, 3H), 5.13-5.31 (m, 2H), 4.09-4.67 (m, 8H), 3.31-3.87 (m, 16H), 3.24 (s, 3H), 2.64-2.86 (m, 4H), 1.41 (s, 3H), 1.15-1.28 (m, 12H). $^{13}$C NMR (100 MHz, CD$_3$CN) δ 225.3, 225.2, 170.6, 164.7, 163.5, 160.2, 152.0, 151.1, 150.6, 145.9, 142.5, 142.3, 136.9, 136.6, 132.7, 131.7, 131.5, 130.8, 129.4, 128.5, 125.1, 120.1, 118.7, 114.6, 112.3, 103.3, 103.2, 94.9, 92.4, 91.6, 91.2, 88.4, 87.5, 83.6, 81.7, 81.4, 77.8, 73.6, 73.5, 71.7, 71.0, 70.9, 70.7, 67.8, 67.5, 65.2, 64.6, 64.5, 64.3, 60.3, 60.1, 60.0, 59.8, 59.7, 56.3, 48.7, 44.7, 44.5, 25.5, 25.4, 25.3, 25.2, 25.19, 25.2, 23.1, 21.7, 21.5, 21.4, 20.5, 20.4, 14.4, 12.6, 2.3, 2.1, 1.9, 1.7, 1.5, 1.3, 1.1. $^{31}$P NMR (CD$_3$CN, 162 MHz) δ 156.40, 156.36, 156.28, 72.67. $^{19}$F NMR (376 MHz, CD$_3$CN) δ -201.75, -201.87, -202.37, -202.52.

Compound 1.14b (R$_p$ isomer): To a solution of compound 1.13b (400 mg, 0.418 mmol) in CH$_3$CN (5 ml), diisopropylethylammonium tetrazolide (142 mg, 0.836 mmol, ChemGenes Corp.) and 2-cyanoethyl N,N,N',N'-tetraisopropylphosphordiamidite (0.200 ml, 0.628 mmol) were added. The reaction mixture was stirred for 2 hours at room temperature. The reaction mixture was diluted with 50 ml EtOAc and washed with 2% NaHCO$_3$ (aq. 20 ml). The organic layer was separated, and dried over anhydrous Na$_2$SO$_4$. The filtrate was concentrated and the resulting crude material was purified by silica gel column chromatography (CH$_2$Cl$_2$: EtOAc, 1:1; R$_f$=0.23) to yield 1.14b (200 mg, 0.154 mmol, 37%). 1.14b: R$_p$ isomer, R$_f$=0.23 (CH$_2$Cl$_2$: EtOAc, 1:1). $^1$H NMR (400 MHz, CD$_3$CN) δ 8.99 (s, 1H), 7.24-7.99 (m, 16H), 6.88-6.90 (m, 4H), 5.99 (dd, J=6.5 Hz, 3.0 Hz, 1H), 5.87 (dd, J=18.9 Hz, 8.5 Hz, 1H), 5.81 (dd, J=8.2 Hz, 1.5 Hz, 1H), 5.10-5.34 (m, 2H), 4.00-4.45 (m, 8H), 3.32-3.84 (m, 16H), 3.26 (s, 3H), 2.62-2.84 (m, 4H), 1.38 (s, 3H), 1.13-1.24 (m, 12H). $^{31}$P NMR (CD$_3$CN, 162 MHz) δ 156.37, 156.32, 156.13, 156.08, 72.91, 72.84.

I. Synthesis of Chiral OAP Monomers

I-1. Synthesis of Chirally Pure 5'-O-(DMTr)-2'-F-Adenosine (N6-Bz)-(Sp) Phosphoramidite Scheme I-1: Synthesis of chirally pure 5'-O-(DMTr)-2'-F-adenosine (N6-Bz)-(Sp) phosphoramidite

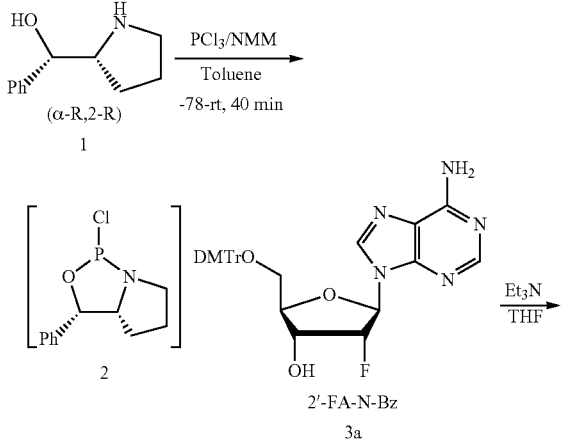

153

-continued

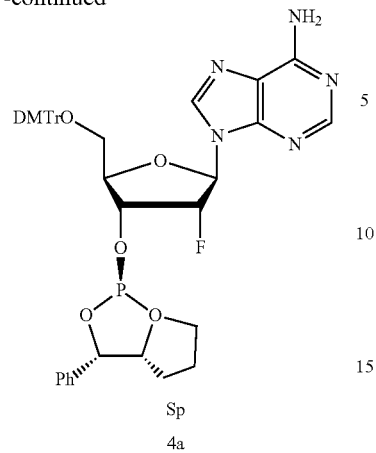

Sp
4a

Compound 4a: To a heat-oven dried 100 mL RBF, added a solution of compound 1 ((S)-phenyl ((R)-pyrrolidin-2-yl) methanol, (2 g, 11.28 mmol, 1.0 equiv.) in anhydrous toluene (15 mL). N-methylmorpholine (2.48 mL, 22.57 mmol, 2 eq.) was added to the solution, and the resulting solution was added dropwise to a stirred solution of PCl₃ (0.935 mL, 10.72 mmol, 0.95 eq.) in anhydrous toluene (10 mL) via cannula at −78° C. under argon. The mixture was then allowed to warm to room temperature and stirred for 40 minutes. The resulting solution was added dropwise via cannula to a stirred solution compound 3a (2.68 g, 3.948 mmol, 0.35 eq.) in anhydrous THF (40 mL) with trimethylamine (7.86 mL, 56.4 mmol, 5 eq.) at −78° C. under argon. The reaction mixture was then stirred at room temperature for 3 hours. TLC plate was neutralized with 1% TEA in hexane solution. TLC was eluted with 92%:5%:3% (EtOAc: ACN:TEA). The reaction mixture was quenched with saturated NaHCO₃ aqueous solution and extracted with ethyl acetate. The combined organic solution was dried over anhydrous Na₂SO₄, filtered, and concentrated to light yellow foam. Purification was conducted via ISCO column chromatography with 125 filtration silica gel column eluted with 100% of 92%:5%:3% (EtOAc:ACN:TEA), to yield a white foam product (1.21 g, 35%).

$^1$H NMR (500 MHz, chloroform-d) δ 9.07 (s, 1H), 8.80 (s, 1H), 8.31 (s, 1H), 8.06-8.00 (m, 2H), 7.65-7.58 (m, 1H), 7.53 (t, J=7.6 Hz, 3H), 7.42-7.36 (m, 3H), 7.36-7.16 (m, 16H), 6.83-6.74 (m, 5H), 6.31 (dd, J=17.2, 1.7 Hz, 1H), 5.88 (d, J=6.4 Hz, 1H), 5.32-5.20 (m, 2H), 4.39 (dd, J=7.1, 3.7 Hz, 1H), 3.94 (dq, J=9.0, 6.3 Hz, 1H), 3.77 (d, J=1.4 Hz, 8H), 3.67-3.53 (m, 3H), 3.40 (dd, J=11.1, 3.4 Hz, 1H), 3.21 (tt, J=10.6, 6.6 Hz, 1H), 1.20 (dq, J=11.7, 5.7 Hz, 2H), 0.96 (dq, J=12.6, 8.9 Hz, 1H). $^{31}$P NMR (202 MHz, chloroform-d) δ 155.91, 155.88.

I-2. Synthesis of Chirally Pure 5'-O-(DMTr)-2'-F-Adenosine (N6-Bz)-(Rp) Phosphoramidite Scheme I-2: Synthesis of chirally pure 5'-O-(DMTr)-2'-F-adenosine (N6-Bz)-(Rp) phosphoramidite.

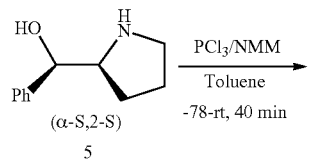

154

-continued

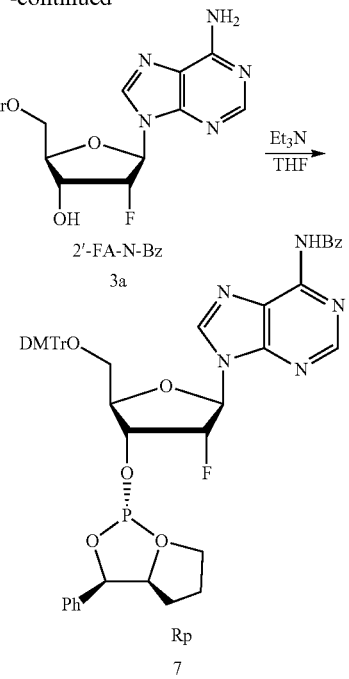

Compound 7: 5'-O-(DMTr)-2'-F-adenosine (N-Bz)-(R) phosphoramidite was obtained by starting the synthesis from (R)-phenyl ((S)-pyrrolidin-2-yl) (compound 5) through an intermediate compound 5'-O-(DMTr)-2'-F-adenosine (N-Bz), in a manner similar to the synthesis of compound 4a, as illustrated above in Section I-1.

$^1$H NMR (400 MHz, chloroform-d) δ 9.06 (s, 1H), 8.79 (s, 1H), 8.22 (s, 1H), 8.06-7.99 (m, 2H), 7.66-7.48 (m, 3H), 7.42-7.11 (m, 14H), 6.83-6.68 (m, 4H), 6.31 (dd, J=16.9, 2.2 Hz, 1H), 5.85 (t, J=4.8 Hz, 1H), 4.37 (dt, J=7.0, 3.4 Hz, 1H), 3.98 (dq, J=8.6, 6.2 Hz, 1H), 3.74 (d, J=1.7 Hz, 6H), 3.63-3.51 (m, 2H), 3.40 (dd, J=11.0, 4.1 Hz, 1H), 3.18-3.05 (m, 1H), 2.04 (s, 2H), 1.63 (d, J=8.6 Hz, 2H), 1.26-1.14 (m, 1H), 0.96 (dq, J=12.6, 8.7 Hz, 1H). P NMR (202 MHz, chloroform-d) δ 155.80, 155.76.

I-3. Synthesis of Chirally Pure 5'-O-(DMTr)-2'-OMe-Cytidine (N4-Acetyl)-(Sp) Phosphoramidite

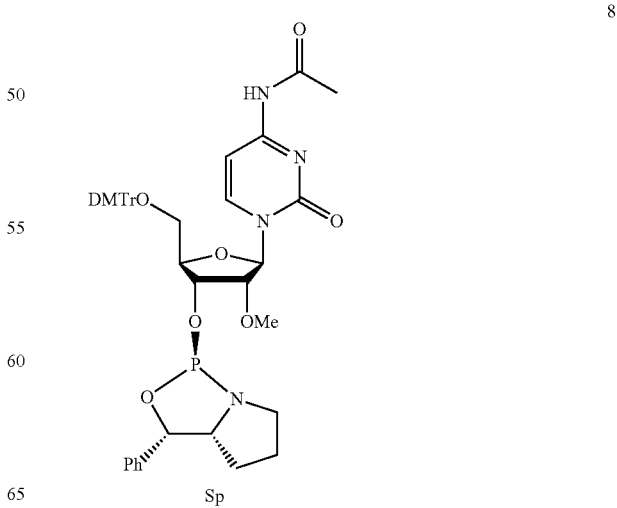

Sp

Compound 8 was obtained by starting the synthesis from (S)-phenyl ((R)-pyrrolidin-2-yl)methanol (compound 1) through an intermediate compound 5'-O-(DMTr)-2'-OMe-cytidine (N-acetyl) in a manner similar to the synthesis of compound 4a, as illustrated above in I-1.

¹H NMR (500 MHz, chloroform-d) δ 8.97 (s, 1H), 8.66 (d, J=7.4 Hz, 1H), 7.45-7.39 (m, 2H), 7.34 (q, J=2.9 Hz, 5H), 7.32-7.23 (m, 9H), 7.03 (d, J=7.5 Hz, 1H), 6.90-6.82 (m, 4H), 5.94 (s, 1H), 5.89 (d, J=6.2 Hz, 1H), 4.73 (ddd, J=9.5, 7.4, 4.8 Hz, 1H), 4.31 (dt, J=9.7, 2.2 Hz, 1H), 3.87 (dq, J=9.2, 6.4 Hz, 2H), 3.81 (d, J=3.0 Hz, 8H), 3.66-3.49 (m, 7H), 2.21 (s, 3H), 1.67 (s, 4H), 1.16 (dtd, J=12.5, 6.2, 3.7 Hz, 2H), 0.96 (dq, J=12.5, 9.2 Hz, 1H). ³¹P NMR (202 MHz, chloroform-d) δ 158.17, 154.18.

I-4. Synthesis of Chirally Pure 5'-O-(DMTr)-2'-OMe-Cytidine (N4-Acetyl)-(Rp) Phosphoramidite

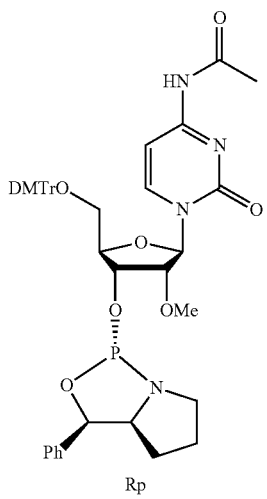

9

Rp

Compound 9 was obtained by starting the synthesis from (R)-phenyl ((S)-pyrrolidin-2-yl) methanol (compound 5) through an intermediate compound 5'-O-(DMTr)-2'-OMe-cytidine (N-acetyl), in a manner similar to the synthesis of compound 4a, as illustrated above in I-1.

¹H NMR (400 MHz, chloroform-d) δ 9.28 (s, 1H), 8.55 (d, J=7.5 Hz, 1H), 7.42-7.16 (m, 16H), 6.96 (d, J=7.5 Hz, 1H), 6.91-6.73 (m, 4H), 6.01 (s, 1H), 5.76 (d, J=6.4 Hz, 1H), 4.73 (ddd, J=9.2, 7.7, 4.7 Hz, 1H), 4.31 (dt, J=9.3, 2.3 Hz, 1H), 3.99-3.86 (m, 2H), 3.86-3.68 (m, 9H), 3.67-3.50 (m, 4H), 3.17 (tdd, J=10.5, 7.7, 5.8 Hz, 1H), 2.23 (s, 3H), 2.04 (s, 2H), 1.66-1.56 (m, 2H), 1.23-1.14 (m, 1H). ³¹P NMR (202 MHz, chloroform-d) δ 157.63.

I-5. Synthesis of Chirally Pure 5'-O-(DMTr)-2'-F-Adenosine (N6-DMF)-(Sp) Phosphoramidite Scheme I-5: Synthesis of chirally pure 5'-O-(DMTr)-2'-F-adenosine (N-DMF)-(S) phosphoramidite.

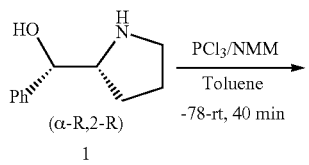

(α-R,2-R)
1

PCl₃/NMM
Toluene
-78-rt, 40 min

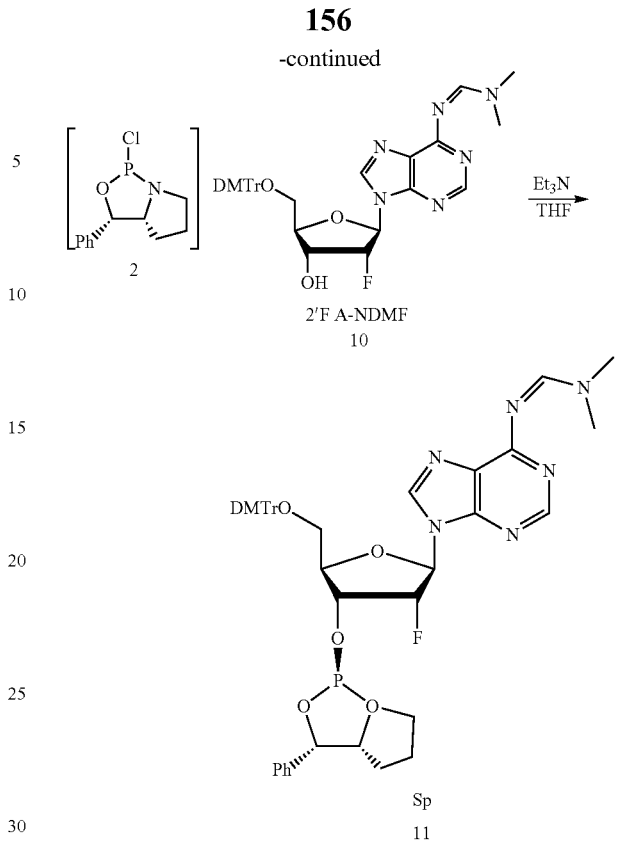

2'F A-NDMF
10

Sp
11

Compound 11: To a heat-oven dried 200 mL RBF, added a solution of compound 1 ((S)-phenyl ((R)-pyrrolidin-2-yl) methanol, 3 g, 16.93 mmol, 1.0 equiv.) in anhydrous toluene (25 mL). N-methylmorpholine (3.72 mL, 33.85 mmol, 2 eq.) was added to the solution, and the resulting solution was added dropwise to a stirred solution of PCl₃ (1.403 mL, 16.08 mmol, 0.95 eq.) in anhydrous toluene (15 mL) via cannula at −78° C. under argon. The mixture was then allowed to warm to room temperature and stirred for 40 minutes. The resulting solution was added dropwise via cannula to a stirred solution 5'-O-(DMTr)-2'-F-adenosine (N-DMF) compound 10 (3.71 g, 5.93 mmol, 0.35 eq.) in anhydrous THF (60 mL) with trimethylamine (11.8 mL, 84.65 mmol, 5 eq.) at 78° C. under argon. The reaction mixture was then stirred at room temperature for 3 hours. TLC plate was neutralized with 1% TEA in hexane solution. TLC was eluted with 92%:5%:3% (EtOAc:ACN:TEA). The reaction mixture was quenched with saturated NaHCO₃ aqueous solution and extracted with ethyl acetate. The combined organic solution was dried over anhydrous Na₂SO₄, filtered, and concentrated to a light yellow foam. Purification was conducted via ISCO column chromatography with 125 filtration silica gel column eluted with 100% of 92%:5%:3% (EtOAc:ACN:TEA) to yield a white foam product (3.43 g, 69.3%).

¹H NMR (400 MHz, chloroform-d) δ 8.96 (s, 1H), 8.53 (s, 1H), 8.15 (s, 1H), 7.43-7.12 (m, 15H), 6.80-6.70 (m, 4H), 6.26 (dd, J=18.3, 1.7 Hz, 1H), 5.89 (d, J=6.4 Hz, 1H), 5.30 (dtd, J=16.3, 8.2, 4.5 Hz, 1H), 4.34 (dd, J=7.7, 3.3 Hz, 1H), 3.95 (dq, J=8.9, 6.3 Hz, 1H), 3.76 (d, J=1.3 Hz, 6H), 3.65-3.51 (m, 2H), 3.35 (dd, J=11.0, 3.5 Hz, 1H), 3.26 (s, 3H), 3.21 (s, 4H), 2.04 (s, 1H), 1.18 (dt, J=11.6, 5.9 Hz, 1H), 0.95 (dq, J=12.5, 8.9 Hz, 1H). ³¹P NMR (202 MHz, chloroform-d) δ 154.97, 154.94.

I-6. Synthesis of Chirally Pure 5'-O-(DMTr)-2'-F-Adenosine (N6-DMF)-(Rp) Phosphoramidite

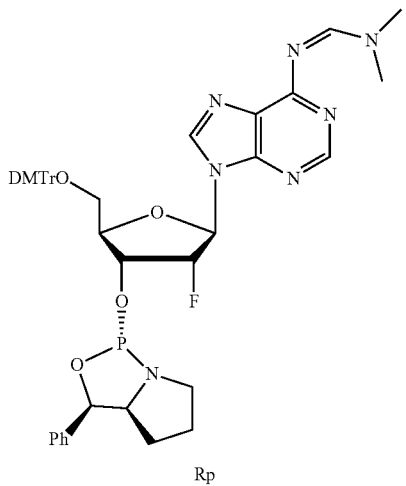

12

Rp

Compound 12 was obtained by starting the synthesis from (R)-phenyl ((S)-pyrrolidin-2-yl) methanol (compound 5) through an intermediate compound 5'-O-(DMTr)-2'-F-adenosine (N-DMF), in a manner similar to the synthesis of compound 11, as illustrated above in I-5.

$^1$H NMR (400 MHz, chloroform-d) δ 8.94 (s, 1H), 8.08 (s, 1H), 7.40-7.33 (m, 3H), 7.33-7.19 (m, 1OH), 7.19-7.09 (m, 3H), 6.76-6.67 (m, 4H), 6.26 (dd, J=18.1, 2.1 Hz, 1H), 5.83 (dd, J=20.8, 5.5 Hz, 2H), 5.37-5.22 (m, 1H), 4.33 (dt, J=7.2, 3.5 Hz, 1H), 3.99 (dq, J=8.7, 6.2 Hz, 1H), 3.73 (s, 6H), 3.61-3.48 (m, 2H), 3.36 (dd, J=10.9, 4.2 Hz, 1H), 3.26 (s, 3H), 3.21 (s, 3H), 3.14-3.01 (m, 1H), 2.04 (s, 1H), 1.59 (q, J=7.3 Hz, 2H), 1.18 (dt, J=12.0, 6.1 Hz, 1H). P NMR (202 MHz, chloroform-d) δ 154.69, 154.64.

I-7. Synthesis of Chirally Pure 5'-O-(DMTr)-2'-OMe-Guanosine (N2-DMF)-(Sp) Phosphoramidite

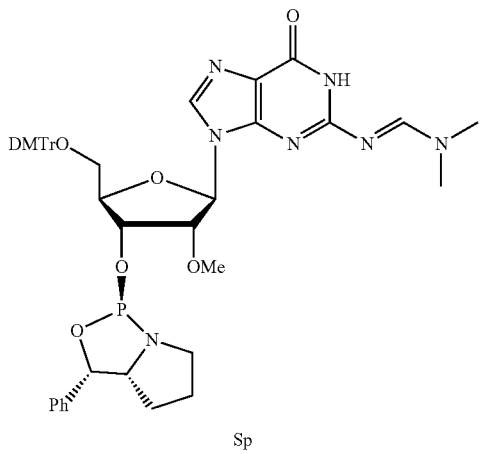

13

Sp

Compound 13 was obtained by starting the synthesis from (S)-phenyl ((R)-pyrrolidin-2-yl)methanol (compound 1) through an intermediate compound 5'-O-(DMTr)-2'-OMe-guanosine(N-DMF), in a manner similar to the synthesis of compound 11, as illustrated above in I-5.

$^1$H NMR (400 MHz, chloroform-d) δ 8.61 (s, 1H), 7.80 (s, 1H), 7.47-7.39 (m, 2H), 7.38-7.17 (m, 11H), 6.86-6.77 (m, 3H), 6.08 (d, J=5.2 Hz, 1H), 5.79 (d, J=6.3 Hz, 1H), 4.93 (dt, J=9.9, 4.9 Hz, 1H), 4.36-4.23 (m, 2H), 3.88 (dq, J=8.6, 6.2 Hz, 1H), 3.78 (d, J=2.0 Hz, 5H), 3.64-3.45 (m, 2H), 3.42-3.31 (m, 3H), 3.23-3.04 (m, 6H), 2.04 (s, 1H), 1.30-1.16 (m, 2H), 0.97 (dq, J=12.5, 8.7 Hz, 1H). $^{31}$P NMR (202 MHz, chloroform-d) δ 155.52.

I-8. Synthesis of Chirally Pure 5'-O-(DMTr)-2'-OMe-Guanosine (N2-DMF)-(Rp) Phosphoramidite

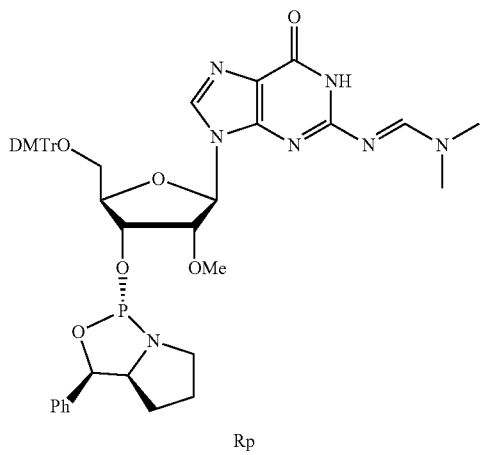

14

Rp

Compound 14 was obtained by starting the synthesis from (R)-phenyl ((S)-pyrrolidin-2-yl) methanol (compound 5) through an intermediate compound 5'-O-(DMTr)-2'-OMe-guanosine (N-DMF), in a manner similar to the synthesis of compound 11, as illustrated above in I-5.

$^1$H NMR (400 MHz, chloroform-d) δ 8.62 (s, 1H), 7.75 (s, 1H), 7.44-7.14 (m, 15H), 6.81-6.70 (m, 4H), 6.11 (d, J=5.9 Hz, 1H), 5.74 (d, J=6.4 Hz, 1H), 4.83 (ddd, J=9.6, 5.2, 3.9 Hz, 1H), 4.35-4.25 (m, 2H), 3.97-3.72 (m, 7H), 3.58 (ddt, J=14.0, 10.4, 7.2 Hz, 1H), 3.48 (s, 3H), 3.45-3.30 (m, 2H), 3.23-3.05 (m, 7H), 2.04 (s, 1H), 1.21-1.10 (m, 1H), 0.94 (dq, J=12.6, 8.8 Hz, 1H). $^{31}$P NMR (202 MHz, chloroform-d) δ 157.32.

I-9. Synthesis of Chirally Pure 5'-O-(DMTr)-2'-OMe-Cytidine(N4-DMF)-(Rp) Phosphoramidite

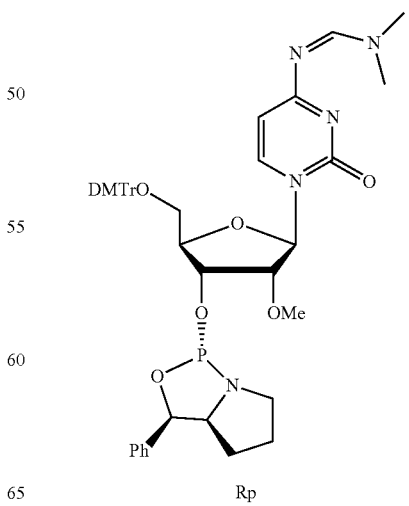

15

Rp

Compound 15 was obtained by starting the synthesis from (R)-phenyl ((S)-pyrrolidin-2-yl) methanol (compound 5) through an intermediate compound 5'-O-(DMTr)-2'-OMe-cytidine (N-DMF), in a manner similar to the synthesis of compound 11, as illustrated above in I-5.

¹H NMR (400 MHz, chloroform-d) δ 8.81 (s, 1H), 8.21 (d, J=7.2 Hz, 1H), 7.43-7.13 (m, 16H), 6.81-6.69 (m, 4H), 5.72 (dd, J=24.6, 6.8 Hz, 2H), 4.74 (td, J=8.5, 4.9 Hz, 1H), 4.28 (dt, J=9.0, 2.4 Hz, 1H), 3.99-3.85 (m, 2H), 3.72 (d, J=6.9 Hz, 6H), 3.70-3.52 (m, 6H), 3.13 (d, J=13.7 Hz, 7H), 1.17 (dt, J=12.4, 6.3 Hz, 1H), 0.95 (dq, J=12.5, 8.7 Hz, 1H). P NMR (202 MHz, chloroform-d) δ 157.40.

I-10. Synthesis of Chirally Pure 5'-O-(DMTr)-2'-OMe-Cytidine(N4-DMF)-(Sp) Phosphoramidite

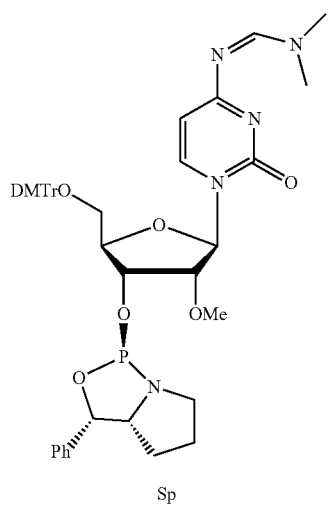

Compound 16 was obtained by starting the synthesis from (S)-phenyl ((R)-pyrrolidin-2-yl) methanol (compound 1) through an intermediate compound 5'-O-(DMTr)-2'-OMe-cytidine (N-DMF), in a manner similar to the synthesis of compound 11, as illustrated above in I-5.

¹H NMR (500 MHz, acetonitrile-d₃) δ 8.66 (s, 1H), 8.08 (d, J=7.2 Hz, 1H), 7.49-7.42 (m, 2H), 7.38-7.27 (m, 9H), 7.27-7.21 (m, 2H), 6.89-6.81 (m, 4H), 5.86 (d, J=1.8 Hz, 1H), 5.78 (d, J=6.4 Hz, 1H), 5.63 (d, J=7.2 Hz, 1H), 4.78 (td, J=8.5, 5.0 Hz, 1H), 4.13 (dt, J=8.3, 2.7 Hz, 1H), 3.91-3.83 (m, 2H), 3.75 (s, 6H), 3.61-3.44 (m, 5H), 3.38 (dd, J=11.2, 3.1 Hz, 1H), 3.14 (s, 3H), 3.13-3.02 (m, 4H), 1.97 (s, 1H), 1.65-1.54 (m, 2H). ³¹P NMR (202 MHz, acetonitrile-d₃) δ 153.90.

I-11. Synthesis of Chirally Pure 5'-O-(DMTr)-2'-OMe-Adenosine (N6-DMF)-(Sp) Phosphoramidite

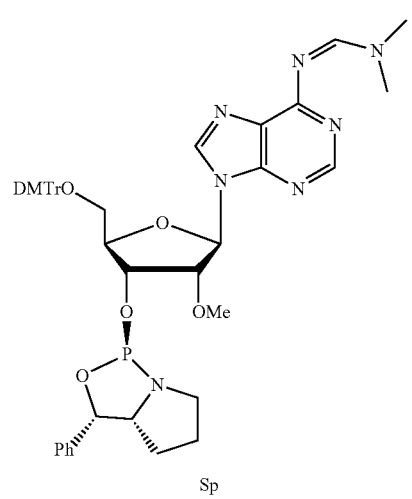

Compound 17 was obtained by starting the synthesis from (S)-phenyl ((R)-pyrrolidin-2-yl) methanol (compound 1) through an intermediate compound 5'-O-(DMTr)-2'-OMe-adenosine (N-DMF), in a manner similar to the synthesis of compound 11, as illustrated above in I-5.

¹H NMR (500 MHz, acetonitrile-d₃) δ 8.90 (s, 1H), 7.40-7.14 (m, 17H), 6.79-6.72 (m, 5H), 6.05 (d, J=4.0 Hz, 1H), 5.79 (d, J=6.5 Hz, 1H), 5.18 (dt, J=9.7, 5.4 Hz, 1H), 4.74 (dd, J=5.0, 4.0 Hz, 1H), 4.19 (dt, J=5.8, 3.7 Hz, 1H), 4.02-3.91 (m, 1H), 3.73 (d, J=2.1 Hz, 7H), 3.56 (dddd, J=13.5, 10.4, 8.0, 6.0 Hz, 1H), 3.42 (s, 4H), 3.23-3.02 (m, 9H). ³¹P NMR (202 MHz, acetonitrile-d₃) δ 150.80.

I-12. Synthesis of Chirally Pure 5'-O-(DMTr)-2'-OMe-Adenosine (N6-DMF)-(Rp) Phosphoramidite

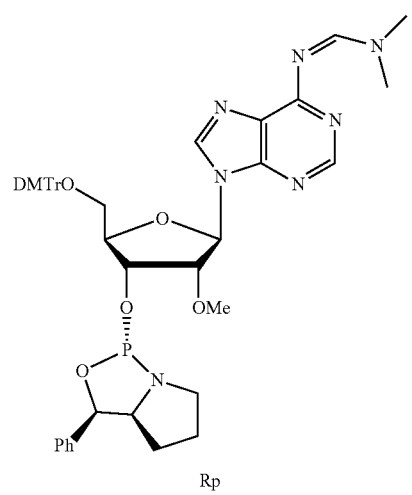

Compound 18 was obtained by starting the synthesis from (R)-phenyl ((S)-pyrrolidin-2-yl) methanol (compound 5) through an intermediate compound 5'-O-(DMTr)-2'-OMe-adenosine (N-DMF), in a similar manner to compound 11, as illustrated above in I-5.

$^1$H NMR (500 MHz, acetonitrile-d$_3$) δ 8.89 (s, 1H), 8.40 (s, 1H), 8.12 (s, 1H), 7.44-7.32 (m, 5H), 7.32-7.13 (m, 11H), 6.80-6.72 (m, 4H), 6.05 (d, J=4.5 Hz, 1H), 5.89 (d, J=6.5 Hz, 1H), 5.15 (dt, J=10.0, 5.1 Hz, 1H), 4.70 (t, J=4.8 Hz, 1H), 4.25-4.16 (m, 1H), 3.93 (dq, J=8.1, 6.2 Hz, 1H), 3.71 (d, J=1.1 Hz, 6H), 3.55-3.39 (m, 6H), 3.29 (dd, J=10.7, 4.8 Hz, 1H), 3.15 (d, J=3.1 Hz, 6H), 2.94 (tdd, J=10.4, 8.0, 5.7 Hz, 1H). $^{31}$P NMR (202 MHz, acetonitrile-d$_3$) δ 153.21.

I-13. Synthesis of Chirally Pure 5'-O-(DMTr)-2'F-Cytidine (N4-DMF)-(Sp) Phosphoramidite

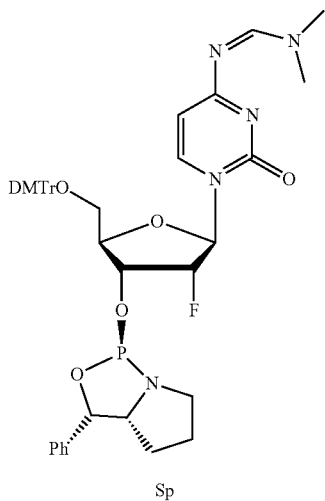

19

Sp

Compound 19 was obtained by starting the synthesis from (S)-phenyl ((R)-pyrrolidin-2-yl) methanol (compound 1) through an intermediate compound 5'-O-(DMTr)-2'-F-cytidine (N-DMF), in a manner similar to the synthesis of compound 11, as illustrated above in I-5.

$^1$H NMR (500 MHz, acetonitrile-d$_3$) δ 8.68 (s, 1H), 7.98 (d, J=7.2 Hz, 1H), 7.49-7.41 (m, 2H), 7.38-7.28 (m, 8H), 7.28-7.19 (m, 5H), 6.87-6.80 (m, 4H), 5.87 (d, J=19.5 Hz, 1H), 5.81 (d, J=6.5 Hz, 1H), 5.68 (d, J=7.2 Hz, 1H), 5.19 (d, J=4.4 Hz, 1H), 4.94 (dtd, J=23.6, 8.9, 4.3 Hz, 1H), 4.17 (dt, J=9.2, 2.7 Hz, 1H), 3.89 (dq, J=8.6, 6.2 Hz, 1H), 3.75 (s, 6H), 3.60-3.48 (m, 2H), 3.37 (dd, J=11.2, 3.3 Hz, 1H), 3.14 (s, 3H), 3.12-3.02 (m, 4H), 2.10 (s, 1H), 1.69-1.53 (m, 2H). $^{31}$P NMR (202 MHz, acetonitrile-d$_3$) δ 153.74, 153.72

I-14. Synthesis of Chirally Pure 5'-O-(DMTr)-2'F-Cytidine (N4-DMF)-(Rp) Phosphoramidite

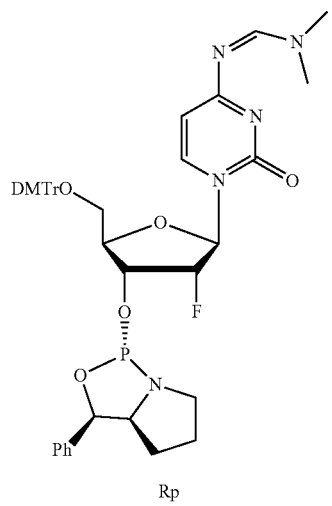

20

Rp

Compound 20 can be obtained by starting the synthesis from (R)-phenyl ((S)-pyrrolidin-2-yl) methanol (compound 5) through an intermediate compound 5'-O-(DMTr)-2'-F-cytidine (N-DMF), in a manner similar to the synthesis of compound 11, as illustrated above in I-5.

I-15. Synthesis of Chirally Pure 5'-O-(DMTr)-2'F-Guanosine (N2-DMF)-(Rp) Phosphoramidite

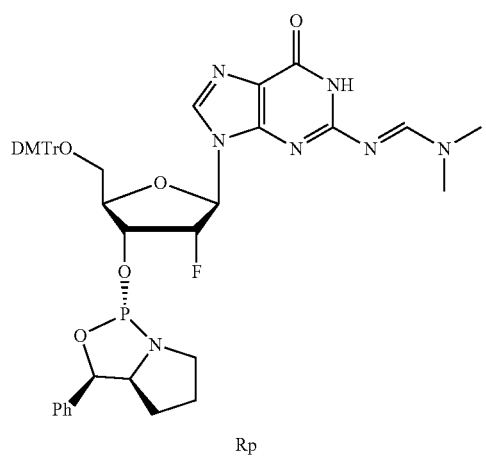

21

Rp

Compound 21 can be obtained by starting the synthesis from (R)-phenyl ((S)-pyrrolidin-2-yl) methanol (compound 5) through an intermediate compound 5'-O-(DMTr)-2'-F-guanosine (N-DMF), in a manner similar to the synthesis of compound 11, as illustrated above in I-5.

I-16. Synthesis of Chirally Pure 5'-O-(DMTr)-2'F-Guanosine (N2-DMF)-(Sp) Phosphoramidite

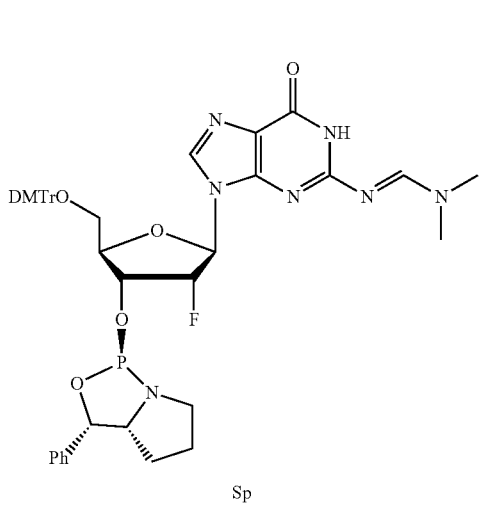

Sp

Compound 22 can be obtained by starting the synthesis from (S)-phenyl ((R)-pyrrolidin-2-yl) methanol (compound 1) through an intermediate compound 5'-O-(DMTr)-2'-F-guanosine (N2-DMF), in a manner similar to the synthesis of compound 11, as illustrated above in I-5.

I-17. Synthesis of Chirally Pure 5'-O-(DMTr)-2'F-Uridine-(Rp) Phosphoramidite

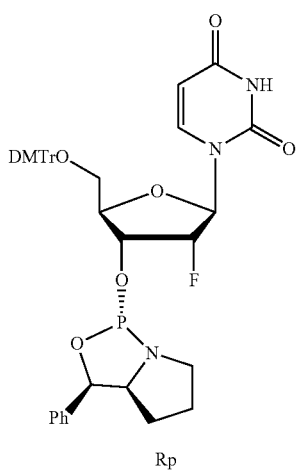

Rp

Compound 23 was obtained by starting the synthesis from (R)-phenyl ((S)-pyrrolidin-2-yl) methanol (compound 5) through an intermediate compound 5'-O-(DMTr)-2'-F-uridine, in a manner similar to the synthesis of compound 11, as illustrated above in I-5.

I-18. Synthesis of Chirally Pure 5'-O-(DMTr)-2'F-Uridine-(Sp) Phosphoramidite

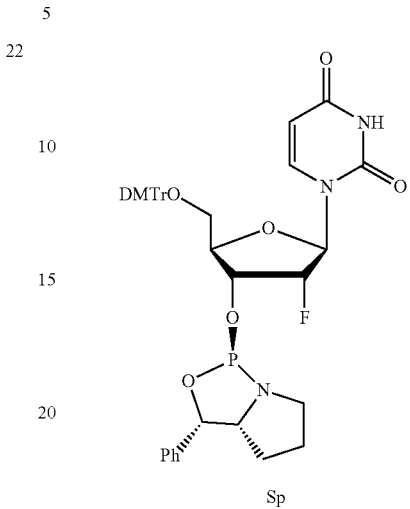

Sp

Compound 23 was obtained by starting the synthesis from (S)-phenyl ((R)-pyrrolidin-2-yl) methanol (compound 1) through an intermediate compound 5'-O-(DMTr)-2'-F-uridine, in a manner similar to the synthesis of compound 11, as illustrated above in I-5.

I-19. Synthesis of Chirally Pure 5'-O-(DMTr)-2'OMe-Uridine-(Rp) Phosphoramidite

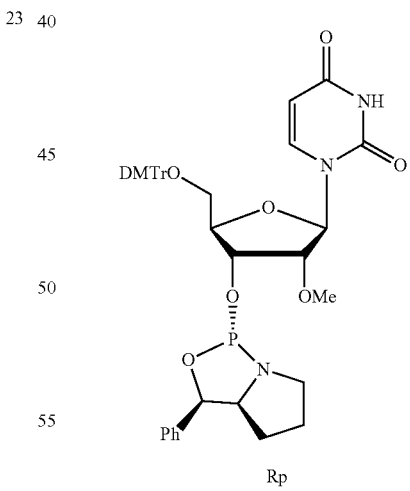

Rp

Compound 25 was obtained by starting the synthesis from (R)-phenyl ((S)-pyrrolidin-2-yl) methanol (compound 5) through an intermediate compound 5'-O-(DMTr)-2'-OMe-uridine, in a manner similar to the synthesis of compound 11, as illustrated above in I-5.

I-20. Synthesis of Chirally Pure 5'-O-(DMTr)-2'OMe-Uridine-(Sp) Phosphoramidite

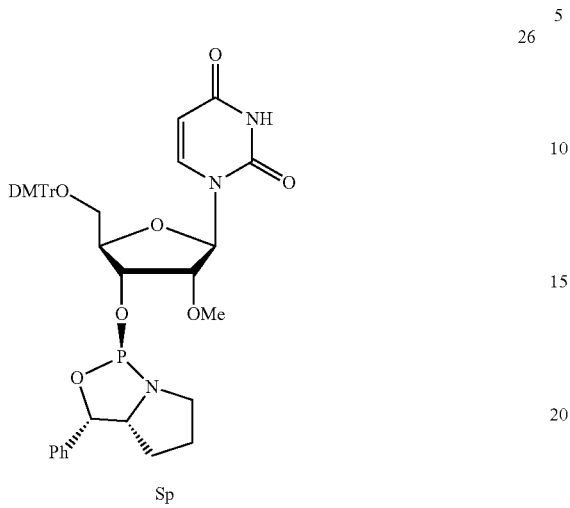

Compound 26 was obtained by starting the synthesis from (S)-phenyl ((R)-pyrrolidin-2-yl) methanol (compound 1) through an intermediate compound 5'-O-(DMTr)-2'-OMe-uridine (N-DMF), in a manner similar to the synthesis of compound 11, as illustrated above in I-5.

J. Assignment of Phosphorothioate (PS) Stereochemistry in Dinucleotides Snake Venom Phosphodiesterase (SVPDE) Assay A 1 mg/mL solution in $H_2O$ (nuclease free) of each chirally pure fully deprotected phosphorothioate dinucleotide was prepared, incubated with snake venom phosphodiesterase (SVPDE) for 48 hours at 37° C. and analyzed on RP-HPLC. For each sample, an individual control was prepared (Enzyme was replaced by $H_2O$). The experimental conditions for SVPDE and control experiment are shown in Table 5.

TABLE 5

Experimental condition for SVPDE and control experiment

| Sample preparation for SVPDE experiment | | | Sample preparation for control | | |
|---|---|---|---|---|---|
| amount | compound | concentration | amount | compound | concentration |
| 20 µL | dinucleotide | 1 mg/mL | 20 µL | dinucleotide | 1 mg/mL |
| 60 µL | Buffer (Tris/MgCl$_2$) | 50 mM Tris-HCl pH 7.2, 10 mM MgCl$_2$ | 60 µL | Buffer (Tris/MgCl$_2$) | 50 mM Tris-HCl pH 7.2, 10 mM MgCl$_2$ |
| 15 µL | ddH$_2$O | | 20 µL | ddH$_2$O | |
| 5 µL | SVPDE | 125 u/mL, 5 µl = 6.25 u | — | — | — |

RP-HPLC conditions. xBridge C18, 3.5 um, 4.6×150 mm column, Buffer B=acetonitrile, A=ddH$_2$O, gradient 3-30% B in 6 minutes, flow 1.2 mL/min or gradient 3-15% B in 6 minutes.

Snake venom phosphodiesterase assay with TLC top spot diastereomer results are shown in FIGS. 10-16.

Snake venom phosphodiesterase assay with TLC lower spot diastereomer results are shown in FIGS. 17-23.

Phosphodiesterease II (PDII) Assay

A 1 mg/mL solution in $H_2O$ (nuclease free) of each chirally pure phosphorothioate dinucleotide was prepared, incubated with Phosphodiesterease II (PDII) for 48 hours (and 5 days) at 37° C. and analyzed on RP-HPLC. For each sample an individual control was prepared (Enzyme was replaced by $H_2O$). The experimental conditions for SVPDE and control experiment are shown in Table 6.

TABLE 6

Experimental condition for PDII and control experiment

| Sample preparation for PDII experiment | | | Sample preparation for control | | |
|---|---|---|---|---|---|
| amount | compound | concentration | amount | compound | concentration |
| 20 µL | dinucleotide | 1 mg/mL | 20 µL | dinucleotide | 1 mg/mL |
| 60 µL | Buffer (Potassium Phosphate/MgCl$_2$) | 50 mM PotPhos pH 6.5, 10 mM MgCl$_2$ | 60 µL | Buffer (Potassium Phosphate/MgCl$_2$) | 50 mM PotPhos pH 6.5, 10 mM MgCl$_2$ |
| — | ddH$_2$O | — | 20 µL | ddH$_2$O | — |
| 20 µL | PDII | 25 U/mL, 20 µL = 500 mU | — | PDII | — |

RP-HPLC conditions: xBridge C18, 3.5 um, 4.6×150 mm column, Buffer B=acetonitrile, A=ddH$_2$O, gradient 3-30% B in 6 minutes, flow 1.2 mL/min or gradient 3-15% B in 6 minutes.

Phosphodiesterase II assay with TLC top spot diastereomer results are shown in FIGS. 24-33.

Phosphodiesterase II assay with TLC lower spot diastereomer results are shown in FIGS. 34-43.

K. Assignment of PS Stereochemistry in Chirally Pure PS Oligonucleotides Using Chirally Pure PS Dinucleotides Methods of Assignment of Stereochemical Configurations for Synthesized Isomers.

To predict stereochemistry of the stereopure oligonucleotides that were synthesized using the chirally pure PS dinucleotide phosphoramidite building blocks, the same methods described in "Methods of assignment of stereochemical configurations for purified isomers" (see Section L. below) were employed. Because these compounds were not synthesized as isomer mixtures, the oligonucleotide contained one (sense strand) or two (antisense strand) chirally pure stereocenters. $^{31}$P-NMR was used to analytically determine whether only the R$_p$ or S$_p$ isomer was present in the final purified compounds, or whether a mixture of the R$_p$ and S$_p$ isomers were present. Ion-exchange analysis was used to confirm retention time differences between the R$_p$ and S$_p$ isomers. To do this, compounds containing different configurations at one positon (but the same configuration at the opposite end, if antisense) were mixed in a set ratio (for instance, 75:25) to determine which isomer eluted faster. This was performed with the 5'-DMT-on (DMT: dimethoxytrityl protection group) and DMT-off for the 5' end isomers, to visualize the "flip" described in the above "Methods of assignment of stereochemical configurations for purified isomers" section.

Incubation of the antisense strands with the 3' exonuclease snake venom phosphodiesterase (SVPD), which preferentially degrades R$_p$ isomers, was used to provide further evidence of 3' end R$_p$ or S$_p$ assignment. The 5' exonuclease phosphodiesterase II was used when the phosphothioate linkage (PS) was in combination with a 2'-F modified nucleotide. Table 7 shows all compounds that were identified in this manner.

TABLE 7

Compounds synthesized using the chirally pure dimers.

| Oligo ID | Oligonucleotide Sequence (5'-3') | Target | S/AS | Chiral "Spot" Used |
|---|---|---|---|---|
| A-153864 | (AfRs)aCfaGfuGfuUfCfUfuGfcUfcUfaUfaAfL96 | mrTTR | S | 5' end: top spot |
| A-153865 | (AfSs)aCfaGfuGfuUfCfUfuGfcUfcUfaUfaAfL96 | mrTTR | S | 5' end: lower spot |
| A-152476 | (aRs)aCfaGfuGfuUfCfUfuGfcUfcUfaUfaAfL96 | mrTTR | S | 5' end: top spot |
| A-152477 | (aSs)aCfaGfuGfuUfCfUfuGfcUfcUfaUfaAfL96 | mrTTR | S | 5' end: lower spot |
| A-152478 | (uRs)UfaUfaGfaGfcAfagaAfcAfcUfgUfu(uRs)u | mrTTR | AS | 5' end: top spot<br>3' end: top spot |
| A-152480 | (uRs)UfaUfaGfaGfcAfagaAfcAfcUfgUfu(uSs)u | mrTTR | AS | 5' end: top spot<br>3' end: lower spot |
| A-152479 | (uSs)UfaUfaGfaGfcAfagaAfcAfcUfgUfu(uRs)u | mrTTR | AS | 5' end: lower spot<br>3' end: top spot |
| A-152481 | (uSs)UfaUfaGfaGfcAfagaAfcAfcUfgUfu(uSs)u | mrTTR | AS | 5' end: lower spot<br>3' end: lower spot |
| A-156820 | (gSs)aCfaAfaAfuAfAfCfuCfaCfuAfuAfaUfL96 | C5 | S | 5' end: top spot |
| A-156821 | (gRs)aCfaAfaAfuAfAfCfuCfaCfuAfuAfaUfL96 | C5 | S | 5' end: lower spot |
| A-156822 | (aRs)UfuAfuAfgUfgAfguuAfuUfuUfgUfc(aRs)a | C5 | AS | 5' end: top spot<br>3' end: top spot |

TABLE 7-continued

Compounds synthesized using the chirally pure dimers.

| Oligo ID | Oligonucleotide Sequence (5'-3') | Target | S/AS | Chiral "Spot" Used |
|---|---|---|---|---|
| A-156823 | (aRs)UfuAfuAfgUfgAfguuAfuUfuUfgUfc(aSs)a | C5 | AS | 5' end: top spot<br>3' end: lower spot |
| A-156824 | (aSs)UfuAfuAfgUfgAfguuAfuUfuUfgUfc(aRs)a | C5 | AS | 5' end: lower spot<br>3' end: top spot |
| A-156825 | (aSs)UfuAfuAfgUfgAfguuAfuUfuUfgUfc(aSs)a | C5 | AS | 5' end: lower spot<br>3' end: lower spot |

Lower case letters represent 2'-OMe modified RNA residues. Capital letters followed by "f" represent 2'-F modified RNA residues. A nucleotide followed by "Rs" or "Ss" and enclosed in parentheses indicates an $R_p$ or $S_p$ phosphorothioate isomer. "L96" indicates a GalNAc moiety.

Discussions of "top spot" and "lower spot" can be found in Sections A1-H, describing the synthesis and separation of the phosphoramidite dimers into their chiral counterparts. In all cases in Table 7, the top spot was found to correspond to the $R_p$ isomer and the lower spot corresponded to the $S_p$ isomer, except in the case of the "(gsa)" dimer separation. The "(gsa)" dimer was separated by reverse phase, while all others were separated by normal phase.

Identification of mrTTR Isomers Synthesized Using Chiral Pure Dimers.

Table 8 summarizes the methods used to predict the configurations of the mrTTR isomers used in this example.

TABLE 8

Determining 5'-end and 3'-end configurations

| Compound | Strand | Predicted 5'-end Configuration | Methods Used | Predicted 3'-end Configuration | Methods Used |
|---|---|---|---|---|---|
| A-153864 | Sense | $R_p$ top spot | DMT-off IEX (fast)<br>DMT-on IEX (slow) | N/A | N/A |
| A-153865 | Sense | $S_p$ lower spot | DMT-off IEX (slow)<br>DMT-on IEX (fast) | N/A | N/A |
| A-152476 | Sense | $R_p$ top spot | DMT-off IEX (fast)<br>DMT-on IEX (slow) | N/A | N/A |
| A-152477 | Sense | $S_p$ lower spot | DMT-off IEX (slow)<br>DMT-on IEX (fast) | N/A | N/A |
| A-152478 | Antisense | $R_p$ top spot | DMT-on IEX (slow) | $R_p$ top spot | SVPD assay |
| A-152479 | Antisense | $S_p$ lower spot | DMT-on IEX (fast) | $R_p$ top spot | SVPD assay |
| A-152480 | Antisense | $R_p$ top spot | DMT-on IEX (slow) | $S_p$ lower spot | SVPD assay |
| A-152481 | Antisense | $S_p$ lower spot | DMT-on IEX (fast) | $S_p$ lower spot | SVPD assay |

For these analyses, all crude oligonucleotide concentrations were determined based on UV absorbance at 260 nm, mixed at the ratios indicated, and diluted to approximately 3 OD/mL with water. Injection volumes were 30 µL, and samples were separated over Dionex DNAPac PA200 ion-exchange analytical column, 4 mm×250 mm (ThermoFisher Cat #063000) at 45° C. column temperature. Buffer A was 20 mM sodium phosphate, 15% acetonitrile, pH 11; and Buffer B also contained 1 M sodium bromide. A gradient of 31% to 57% over 16 minutes at a flow rate of 1 mL/min was used to analyze all samples.

Figure 44:
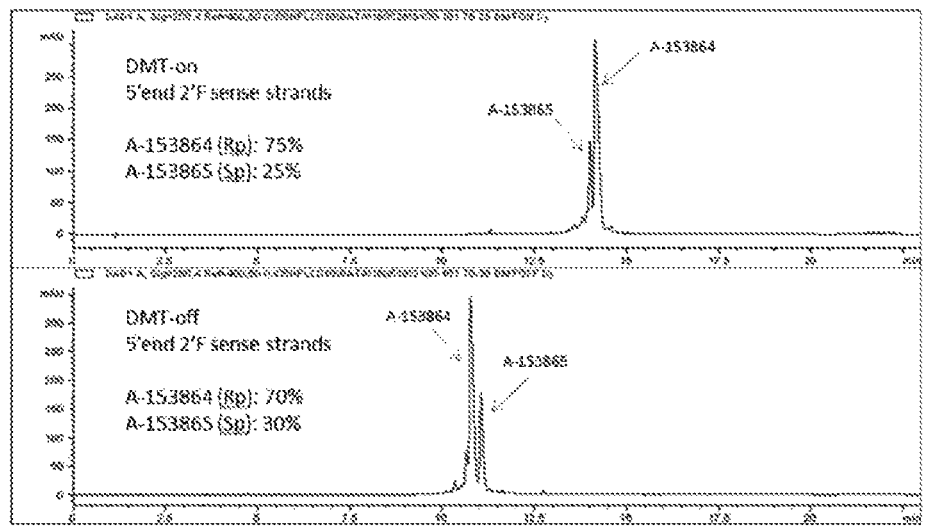
FIG. 44. Isomer elution profiles for the 2'-F sense strand during the ion-exchange separation. The $R_p$ isomer eluted later than the $S_p$ isomer with DMT-on (top) and earlier than the Sp once DMT was removed (bottom).
Figure 45:
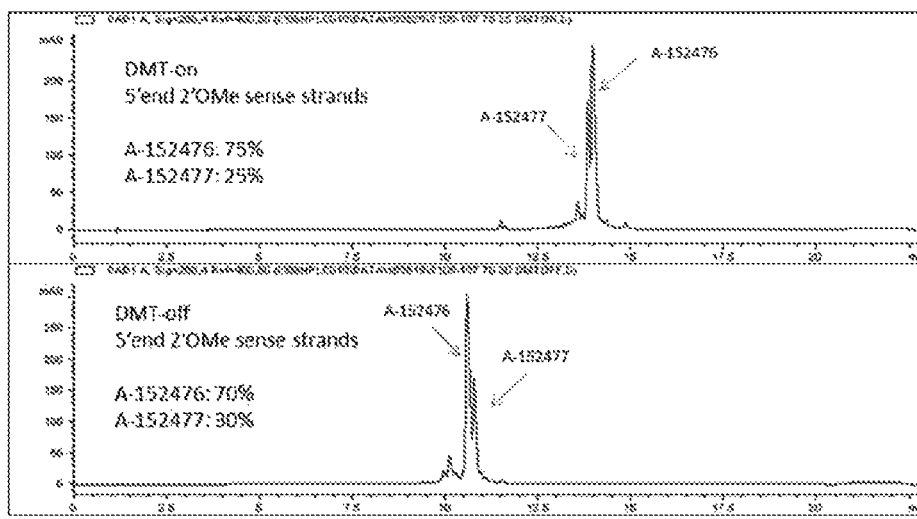
FIG. 45. Isomer elution profiles for the 2'-OMe sense strand during the ion-exchange separation. The $R_p$ isomer eluted later than the $S_p$ isomer with DMT-on (top) and earlier once DMT was removed (bottom).

The 5'-end isomers in all sense strands showed good separation with the 5'-DMT-on as well as with the 5'-DMT-off. The "flip" in elution time during an ion-exchange analysis (IEX) can be observed for isomers of all sense strands (FIG. 45) when the crude compounds are mixed in the ratios shown in FIGS. 44-45.

Figure 46:
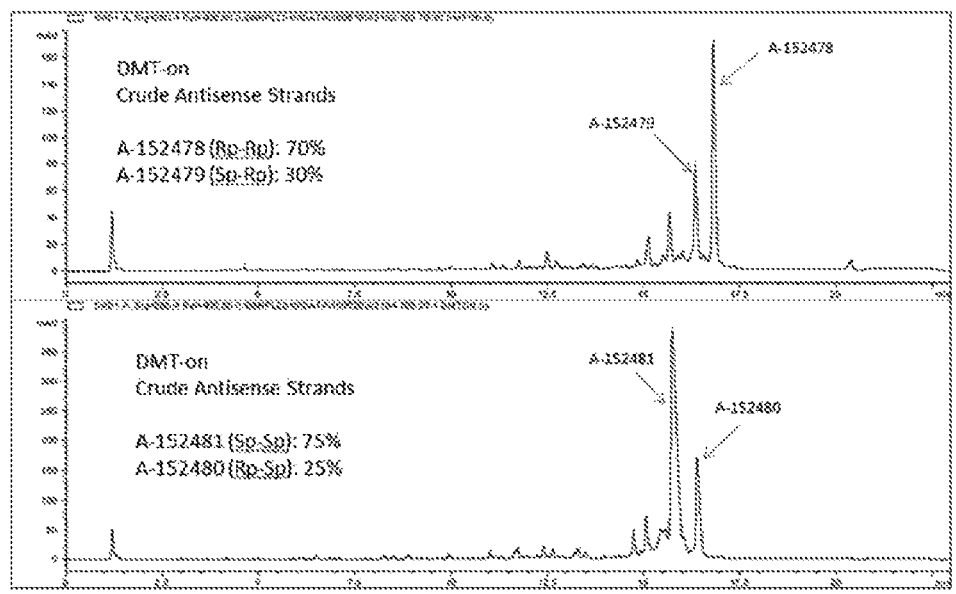
FIG. 46. The results of the ion-exchange analysis of the mixtures of the crude DMT-on antisense strands that differed only in 5'-end configuration. The 3'-end configuration of both mixed compounds was either $R_p$ (top) or $S_p$ (bottom). The isomer that eluted first was designated to be $S_p$.
Figure 47:
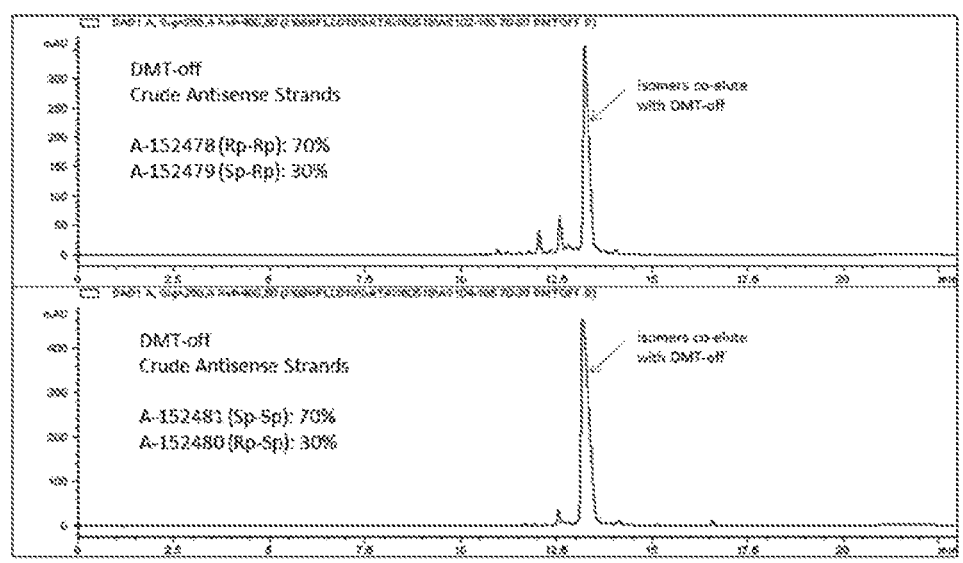
FIG. 47. The results of the ion-exchange analysis of the mixtures of the crude DMT-off antisense strands that differed only in 5'-end configuration. The 3'-end configuration of both mixed compounds was either $R_p$ (top) or $S_p$ (bottom). The isomers co-eluted under these conditions.

The 5'-end isomers in all antisense strands showed good separation with the 5'-DMT-on only. The oligonucleotide with the PS in the $S_p$ configuration was determined to elute earlier (fast) than the $R_p$ configuration (slow) with the 5'-DMT-on (FIGS. 46-47).

Figure 48:
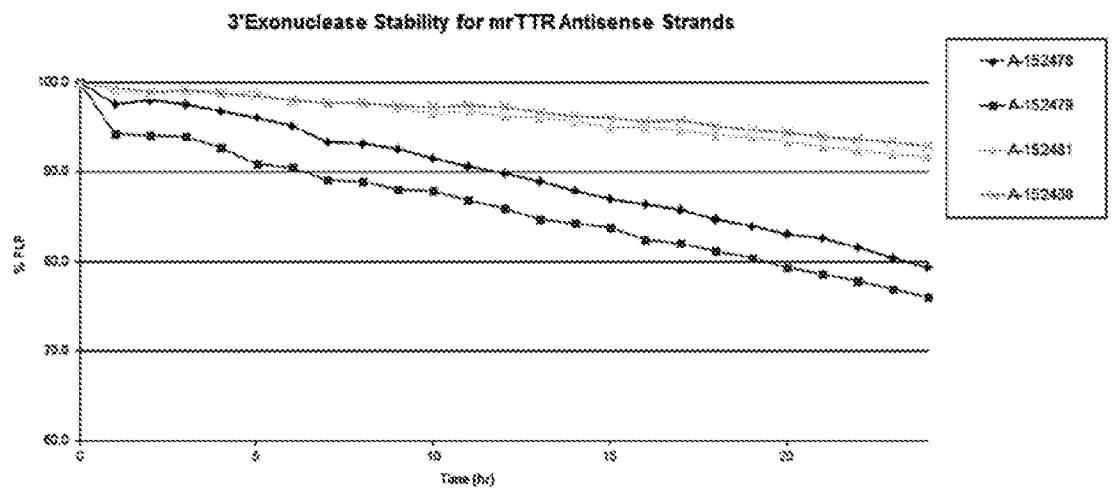
FIG. 48. SVPD degradation profiles of indicated oligonucleotides.

The four antisense strand isomers were incubated with SVPD to assess the stability of the 3'-end diastereomers, and sampled and analyzed automatically every hour as described in the assay protocol, "3' Exonuclease SVPD Stability Assay" (see Section O. below). The SVPD degradation results are shown in FIG. 48. FIG. 48 illustrates that A-152478 and A-152479 were found to be less stable than A-152481 and A-152480. Accordingly, A-152478 and A-152479 were determined to have the $R_p$ configuration at the 3'-end.

Identification of Isomers Used for C5 siRNAs Synthesized Using Chirally Pure Dinucleotides Table 9 summarizes the methods used to determine the configurations of the C5 isomers that were synthesized using the chirally pure dinucleotide phosphoramidites.

TABLE 9

Determination of the 5'-end and 3'-end configurations.

| Compound | Strand | Determined 5'-end Configuration | Methods Used | Determined 3'-end Configuration | Methods Used |
|---|---|---|---|---|---|
| A-156820 | Sense | $S_p$ top spot | $^{31}$P-NMR DMT-off IEX (slow) | N/A | N/A |
| A-156821 | Sense | $R_p$ lower spot | $^{31}$P-NMR DMT-off IEX (fast) | N/A | N/A |
| A-156822 | Antisense | $R_p$ top spot | $^{31}$P-NMR | $R_p$ top spot | $^{31}$P-NMR DMT-off IEX (fast) |
| A-156823 | Antisense | $R_p$ top spot | $^{31}$P-NMR | $S_p$ lower spot | $^{31}$P-NMR DMT-off IEX (slow) |
| A-156824 | Antisense | $S_p$ lower spot | $^{31}$P-NMR | $R_p$ top spot | $^{31}$P-NMR DMT-off IEX (fast) |
| A-156825 | Antisense | $S_p$ lower spot | $^{31}$P-NMR | $S_p$ lower spot | $^{31}$P-NMR DMT-off IEX (slow) |

A-156820 and A-156821 are the sense strands synthesized with the (gsa) dimer. This is the only instance found where compound with the higher Rf value (top spot) did not correspond to the $R_p$ configuration.

Figure 49:
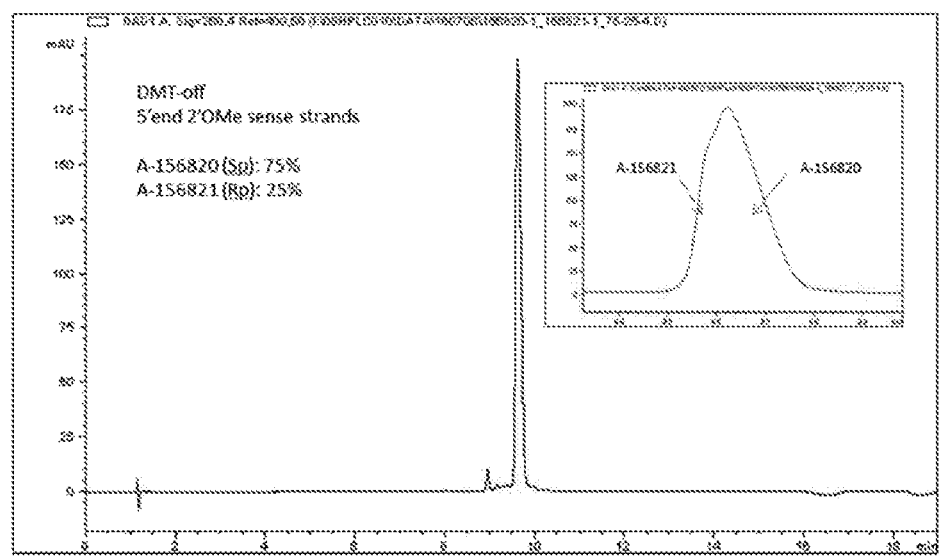
FIG. 49. The results of the ion-exchange analysis of A-156820 and A-156821. Isomer elution for the purified C5 2'OMe sense strands during the ion-exchange analysis after mixing in the aforementioned ratios.

The oligonucleotides designed to target the C5 mRNA made with the chirally pure dinucleotides were synthesized with DMT-off for the ion-exchange purification. DMT-off ion-exchange analysis was performed to confirm the 5'-end sense strand diastereomers and the 3'-end antisense diastereomers. The 5'-end diastereomers of the antisense strand did not separate by the ion-exchange analysis without the presence of 5'-DMT. As shown in FIG. 49, the determined 5'-end $R_p$ isomer of the sense strand eluted earlier with DMT-off, as compared to the $S_p$ isomer, although the difference was slight.

Figure 50:
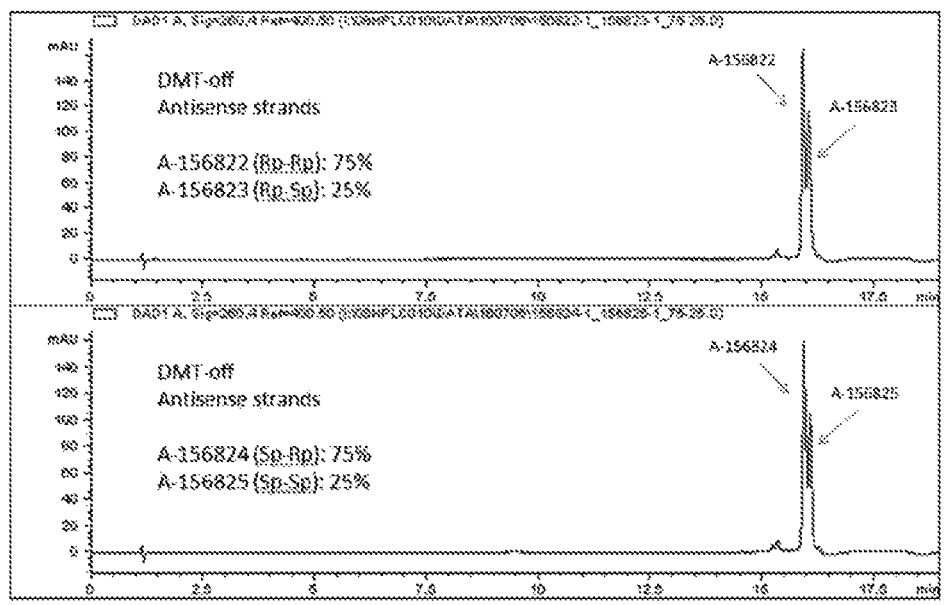
FIG. 50. The results of the ion-exchange analysis of the mixtures of the purified DMT-off antisense strands that differ only in 3'-end configuration. The 5'-end configurations were $R_p$ (top) or $S_p$ (bottom). The isomer that eluted first was designated to be the $R_p$.

The 3'-end isomers of the antisense strand (A-156822 and A-156823, A-156824 and A-156825, as shown in FIG. 50) were resolved during the ion-exchange separation. Isomers on the 3'-end were unaffected by the presence of DMT on the 5'-end of a sequence. The 3'-end $R_p$ isomer always eluted first during the ion-exchange analysis regardless of whether DMT was present on the 5'-end. DMT-off oligonucleotides differing only in 3'-end configuration were analyzed by the ion-exchange analysis using a 75:25 ratio. In these chromatograms, the gradient was 30% to 50% buffer B over 12 minutes; all other parameters of sample preparation and analysis were as described above.

Figure 51:
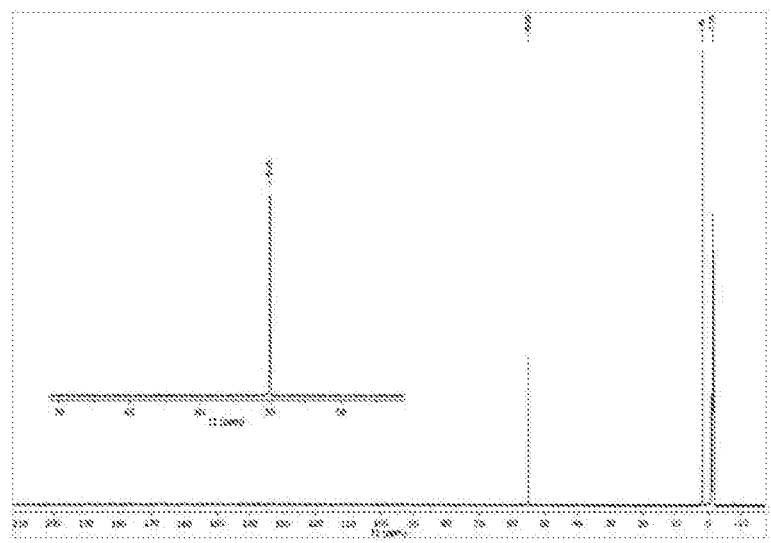
FIG. 51. $^{31}$P-NMR of sense strand A-156820 showing resonance peak at 55.05 ppm, determined to be $S_p$.
Figure 52:
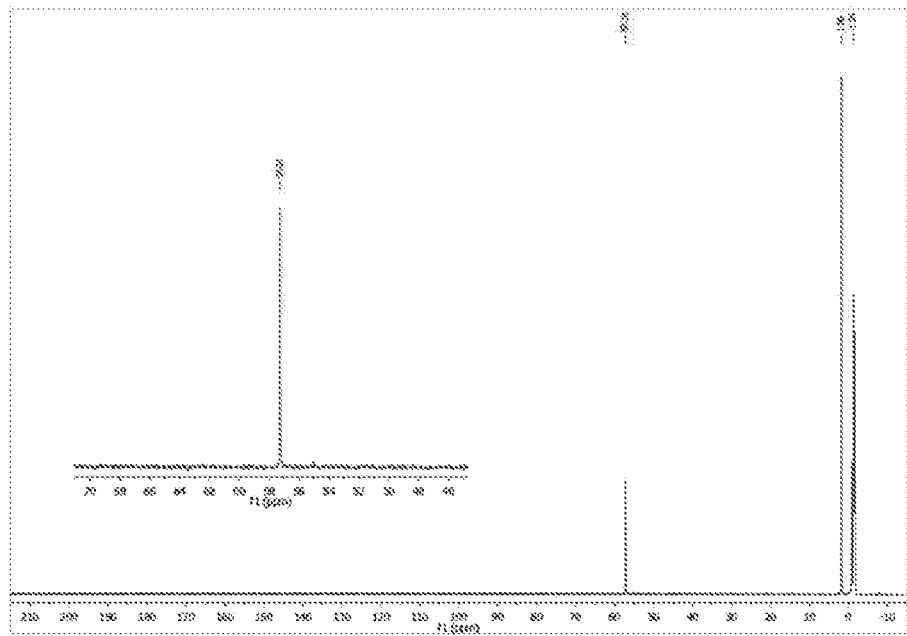
FIG. 52. $^{31}$P-NMR of sense strand A-156821 showing resonance peak at 57.28 ppm, determined to be Rp.

After the isomers for each sequence were purified, desalted, and lyophilized, each isomer was submitted for a $^{31}$P-NMR analysis by dissolving the lyophilized compound to 10 mg/mL in deuterium oxide. The resulting $^{31}$P-NMR spectra are shown in FIGS. 51-52. FIGS. 51-52 show that the 2'-OMe sense strand with Rp configuration were downfield shifted (57.28 ppm) relative to the Sp configuration (55.05 ppm).

Figure 53:
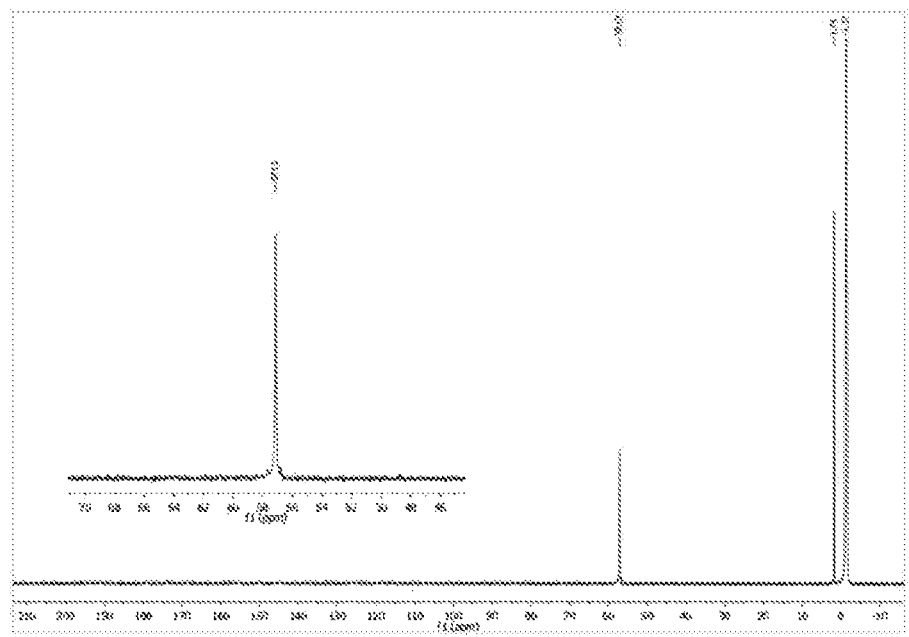
FIG. 53. $^{31}$P-NMR of antisense strand A-156822. A-156822, determined to be $R_p$-$R_p$.
Figure 54:
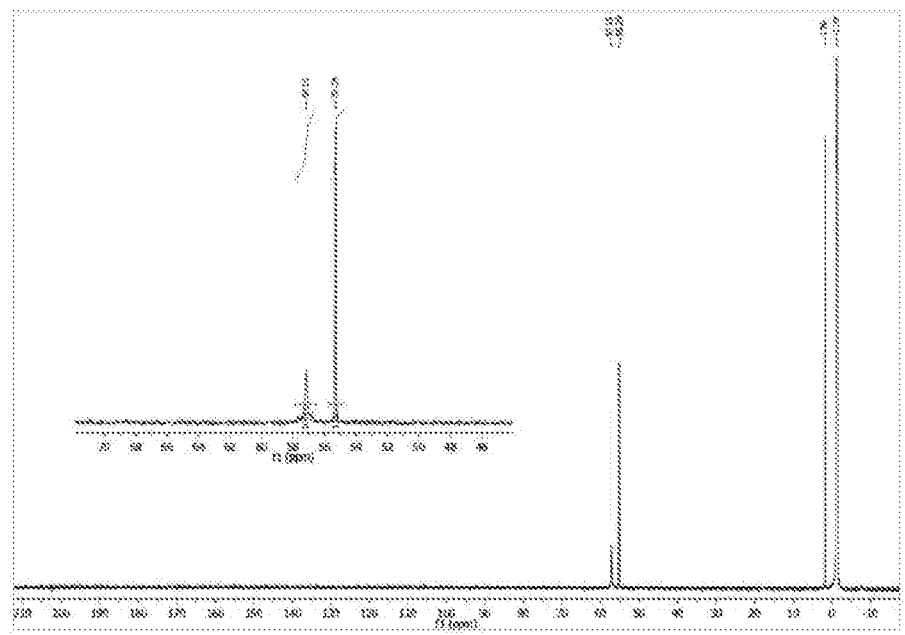
FIG. 54. $^{31}$P-NMR of antisense strand A-156823, determined to be $R_p$-$S_p$.
Figure 55:
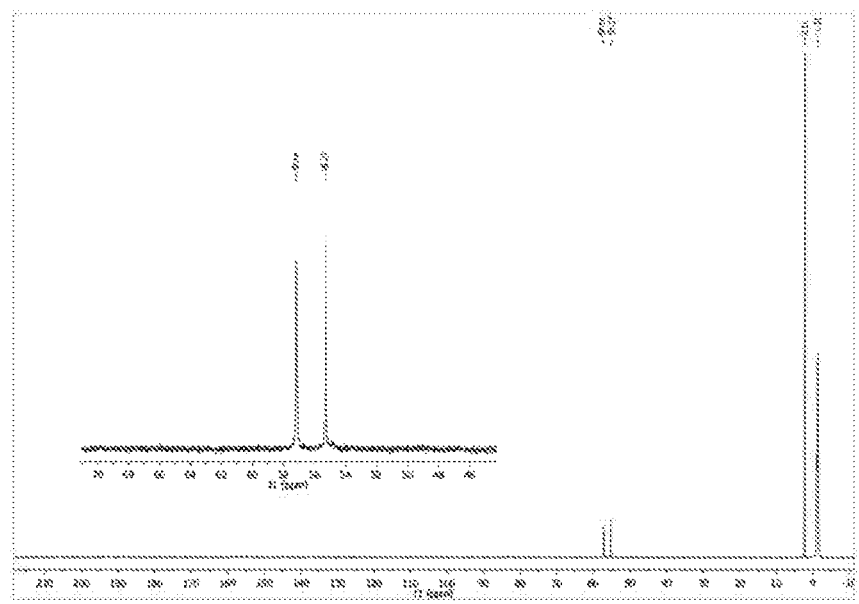
FIG. 55. $^{31}$P-NMR of antisense strand A-156824, determined to be $S_p$-$R_p$.
Figure 56:
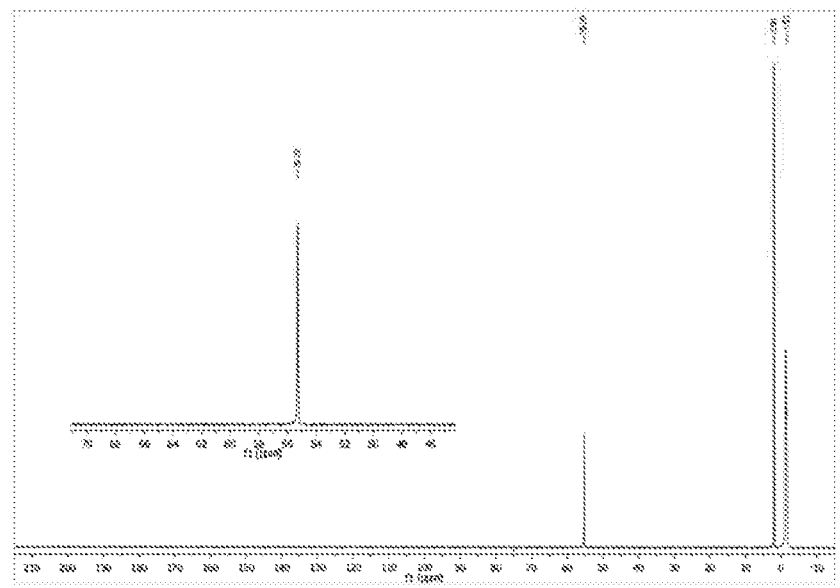
FIG. 56. $^{31}$P-NMR of antisense strand A-156825, determined to be $S_p$-$S_p$.

FIG. 53 shows the $^{31}$P-NMR spectra of the antisense strand A-156822 having a resonance peak at 57.13 ppm, corresponding to the $R_p$ isomers only. FIG. 54 shows the $^{31}$P-NMR spectra of the antisense strand A-156823 having resonance peaks at 57.15 ppm and 55.29 ppm, corresponding to the $R_p$ and $S_p$ isomers, respectively. FIG. 55 shows the $^{31}$P-NMR spectra of the antisense strand A-156824 having resonance peaks at 57.16 ppm and 55.27 ppm, corresponding to the $R_p$ and $S_p$ isomers, respectively. FIG. 56 shows the $^{31}$P-NMR spectra of the antisense strand A-156825 having a single resonance peak at 55.27 ppm, corresponding to the $S_p$ isomers only.

L. Oligonucleotide Synthesis

General Oligonucleotide Synthesis and Analysis Oligonucleotides were synthesized on a Bioautomation Mermade 12 Synthesizer using commercially available RNA amidites, 5'-O-(4,4'-dimethoxytrityl)-2'-deoxy-2'-fluoro-, and 5'-O-(4, 4'-dimethoxytrityl)-2'-O-methyl-3'-O-(2-cyanoethyl-N,N-diisopropyl) phosphoramidite monomers of uridine, 4-N-acetylcytidine, 6-N-benzoyladenosine, and 2-N-isobutyrylguanosine. Standard solid-phase oligonucleotide synthesis protocols were used. The GalNAc ligand was covalently linked to the 3' end of the sense (S) strand of the siRNA by a phosphodiester linkage between the pyrrolidine scaffold as described (see Nair et al., "Multivalent N-acetylgalactosamine-conjugated siRNA localizes in hepatocytes and elicits robust RNAi-mediated gene silencing," J. Am. Chem. Soc. 136:16958-61 (2014); Parmar et al., "5'-(E)-Vinylphosphonate: a stable phosphate mimic can improve the RNAi activity of siRNA-GalNAc conjugates," Chem Bio Chem. 17:985-89 (2016), which are incorporated herein by reference in their entirety). Phosphorothioate linkages were introduced by oxidation of phosphite utilizing 0.1 M 3-((N, N-dimethyl-aminomethylidene)amino)-3H-1,2,4-dithiazole-5-thione (DDTT) in pyridine. If phosphorothioate isomers were to be separated post-synthesis, the final dimethoxytrityl protecting group was not removed after synthesis was completed.

The deprotection procedures utilized were suitable for 2'-F and 2'-OMe modified oligonucleotides. After synthesis, the support was treated on column with 0.5 M piperidine in acetonitrile (ACN) for 15 minutes. The column was washed with ACN and treated again with 0.5 M piperadine in ACN for an additional 15 minutes, then washed again with ACN. The support was dried on-column under vacuum, and then added to a sealable container and heated at 60° C. in aqueous ammonium hydroxide (28-30%) for 2-3 hours. The deprotection procedure was completed by shaking overnight at 30° C. The oligonucleotide was then filtered to remove the support with 5× volume of water and analyzed by LC-MS and ion-exchange analysis to determine the quality of the crude as described in Nair et al. and Parmar et al. provided above.

The column size for the ion-exchange HPLC purification depended on scale (total OD load). TSKgel Super Q-5PW (20) anion exchange resin from Tosoh Corporation was used for purification. Purification buffer A consisted of 20 mM sodium phosphate (pH 8.5), 15% ACN, and Buffer B was 20 mM sodium phosphate (pH 8.5), 15% ACN, 1M sodium bromide. A gradient of 15% to 45% in about 20 column volumes was sufficient, unless isomer separation post-synthesis was performed. The gradient start time was adjusted depending on the retention time of the full-length product in the ion-exchange analysis of the crude. Fractions were analyzed by the ion-exchange analysis using the Dionex DNAPac PA200 ion-exchange analytical column, 4 mm×250 mm (ThermoFisher Cat #063000) at room temperature. Buffer A was 20 mM sodium phosphate (pH 12), 15% acetonitrile, Buffer B was 20 mM sodium phosphate (pH 12), 15% acetonitrile, 1M sodium bromide. A gradient of 30% to 50% over 12 minutes at a flow rate of 1 ml/min was used to analyze the fractions.

The fractions with greater than 85% purity were pooled, dried, dissolved in water, and desalted over size exclusion columns (GE Healthcare) at a flow rate of 10 ml/min. The desalted final product was dried, resuspended in water, filtered through 0.2 μm polyethersulfone filters, and quantified analysis of absorbance at 260 nm. Samples approximately 1 OD/ml were assessed by LC-MS and ion-exchange analysis. The oligonucleotides were then frozen and lyophilized, followed by annealing of equimolar amounts of complementary strands to provide the desired siRNA duplexes by heating to 90° C. and slow cooling. The siRNA samples were analyzed by mass spectrometry and capillary gel electrophoresis and for endotoxin and osmolality as described in Nair et al. and Parmar et al. provided above.

General Oligonucleotide Synthesis Using Dinucleotide Building Blocks

The dinucleotide phosphoramidite building blocks were manually coupled to support or to the elongating oligonucleotide. The dinucleotide phosphoramidites were prepared as 0.15 M solutions in dry acetonitrile. The activator 5-(ethylthio)-1H-tetrazole (0.25 M solution in dry acetonitrile) was used. A single 15-minute coupling time was used.

Figure 57:
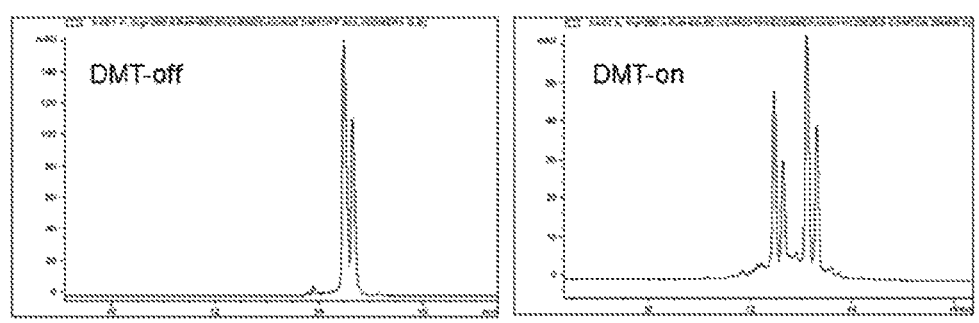
FIG. 57. The results of the ion-exchange separation of DMT-off (left) and DMT-on (right) A-122625.

M. Separation/Assignment of Stereochemistry of PS Diastereomers in Oligonucleotides (Approach Purification of Antisense Strand A-122625 into Four Diastereomers Oligonucleotide A-122625 (5'DMT-asUfuAfuAfgUfgAfguuAfuUfuUfgUfcasa-3') containing two phosphorothioate linkages, one on the 5' end and one on the 3' end, was separated into four diastereomers. Samples were diluted to approximately 0.03 mg/ml with water and 30 was injected onto a Dionex DNAPac PA200 ion-exchange analytical column, 4 mm×250 mm (ThermoFisher) at 30° C. column temperature. Buffer A was 20 mM sodium phosphate, 15% acetonitrile, pH 11 and Buffer B was identical with additional 1M sodium bromide. A gradient of 40% to 68% over 16 minutes at a flow rate of 1 mL/min was used to analyze the DMT-on samples. A gradient of 31% to 57% over 16 minutes was used to analyze DMT-off samples (see FIG. 57). The column temperature was maintained at 30° C. Baseline separation of all four diastereomers of DMT-on A-122625 was obtained by an ion-exchange HPLC. After the DMT removal, only the 3' end isomers were resolved.

Figure 58:
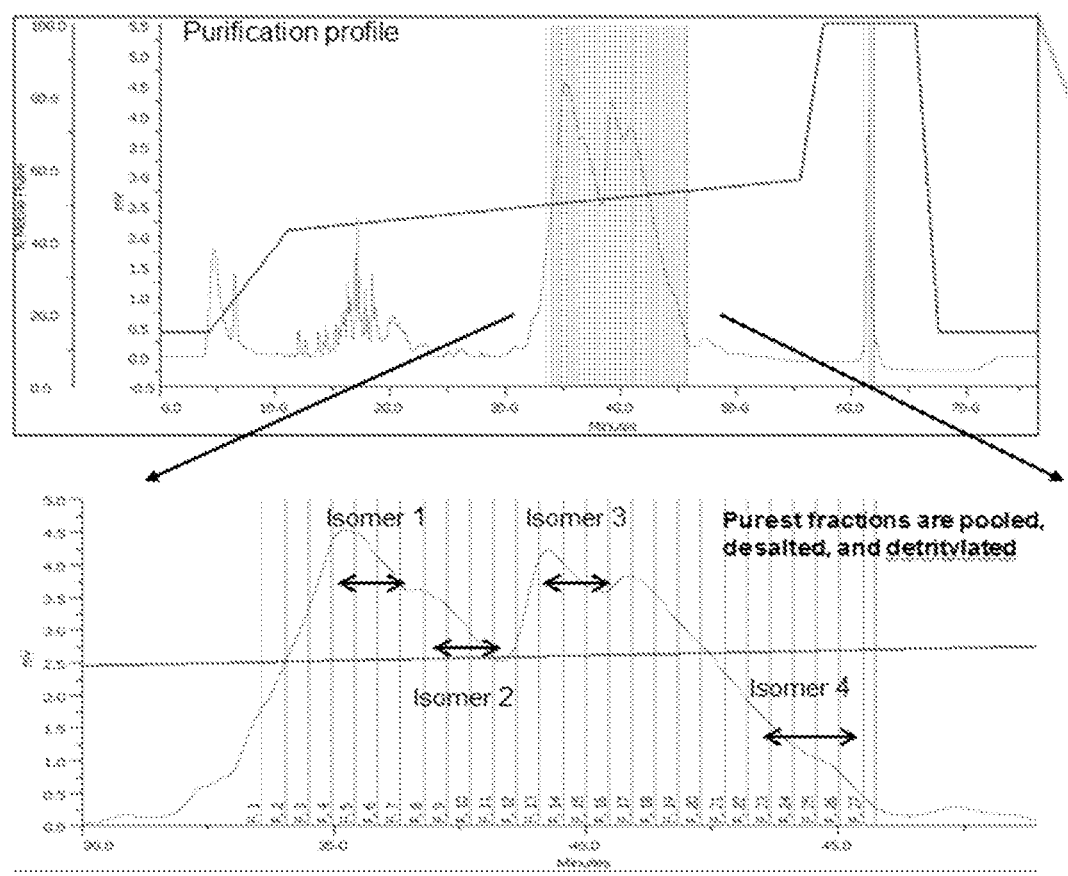
FIG. 58. The results of the anion-exchange purification of isomers from the crude isomer mixture.

This above analytical method was scaled up to achieve the isomer separation at the preparatory scale. An anion-exchange Dionex DNAPak PA200 (22 mm×250 mm) preparatory column (ThermoFisher) was used, and Buffers A and B were identical to the analytical buffers described above. The gradient was 42% to 57% Buffer B in 45 minutes at a flow rate of 12 ml/min, corresponding to 5.7 column volumes, and column temperature was maintained at 40° C. To achieve good separation, a small amount of crude material (~3.2 mg) was loaded per run. To obtain isomer purities of ≥85%, the fractions were combined to create "enriched" isomer pools and re-purified. The purest regions for each of the four isomers were pooled across runs; a total of 50 runs were performed in this manner. Because the method was reproducible, these regions were pooled without analysis of the fractions from every run. Two to four 5.5 mL fractions were pooled for each isomer per run, with the retention time between 35-36.5 minutes for isomer 1, 37-38 minutes for isomer 2, 39-40.5 minutes for isomer 3, and 43.5-45.5 minutes for isomer 4. The purification profile of the four isomers is shown in FIG. 58, which shows the pooled regions for each isomer.

Figure 59:
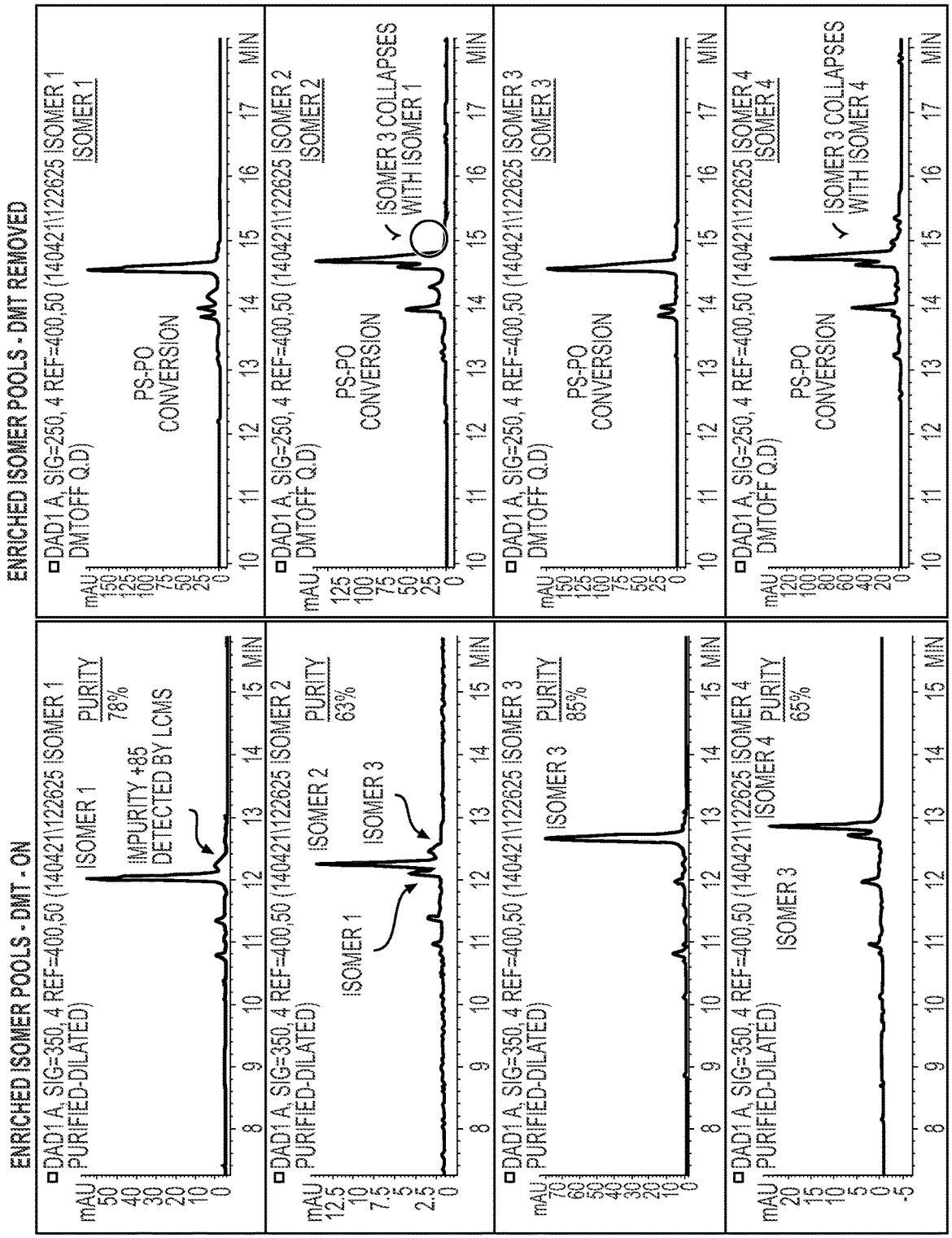
FIG. 59. Fraction pools analyzed before and after DMT removal (right and left columns, respectively) by the ion-exchange chromatography.
Figure 60:
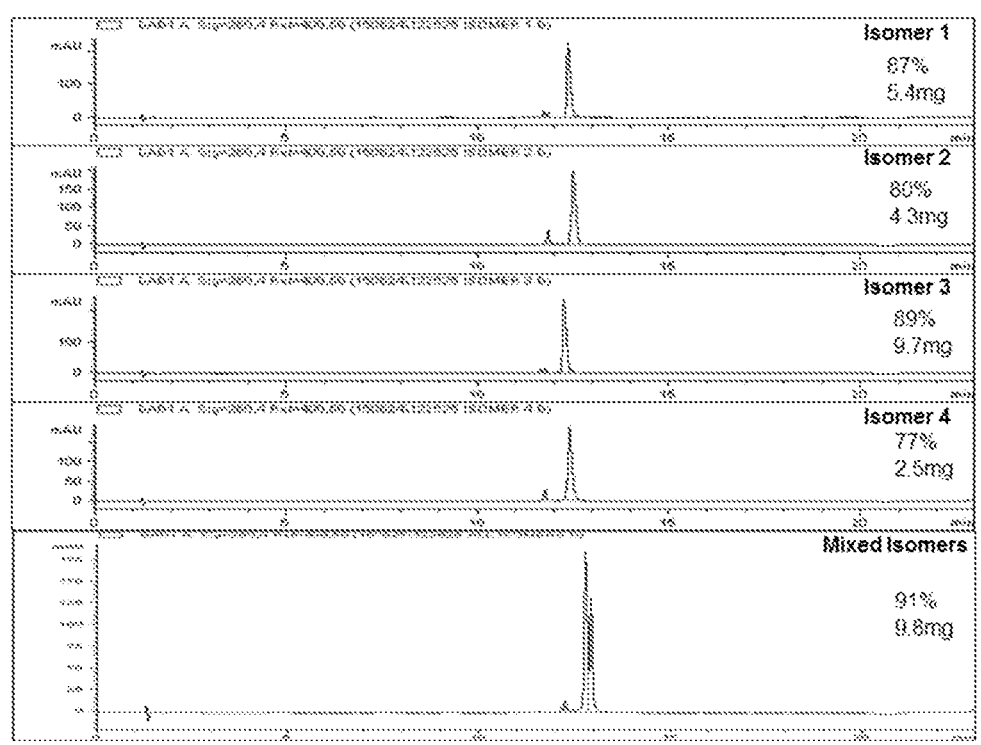
FIG. 60. IEX analysis of isomers of A-122625.

The four isomer pools were dried down, desalted over size exclusion columns (GE Healthcare) at a flow rate of 10 ml/min, dried down again, and detritylated by adding 5 ml of 20% acetic acid at room temperature for 10 minutes. The incubation time was minimal to avoid PS to PO conversion. Each pool was then neutralized by adding 18 mL of a saturated sodium bicarbonate solution. Samples were dried, dissolved in water, and desalted again by size exclusion. Each isomer pool was re-purified to eliminate the remaining impurities. To determine the chiral purity, an ion-exchange analysis was performed using the Dionex DNAPac PA200 column (4 mm×250 mm) at a flow rate of 1 mL/min. Analytical gradients for the DMT-on sample was 40% to 68% Buffer B in 16 minutes. For the DMT-off sample, the gradient was 31% to 57% Buffer B in 16 minutes. Peak area integration at 260 nm was used to determine the chiral purity. A reverse phase LC-MS analysis was used to detect the mass impurities. The column used was Waters XBridge (C8 2.5 μm, 2.1 mm×50 mm; PN 186003101). Buffer A was 200 mM hexafluoroisopropanol and 16 mM triethylamine in water. Buffer B was 100% methanol. All reagents were LC-MS grade. The gradient was 0% to 40% methanol in 9.6 minutes at a flow rate 0.7 mL/min. The ion-exchange chromatograms of the enriched isomer pools are shown in FIG. 59, and final purities of isomers 1, 2, 3, and 4 are shown in FIG. 60.

A compound containing the isomer mixture at standard synthesis ratios was also needed. This compound was synthesized DMT-off and purified by ion-exchange chromatography using 20 mM sodium phosphate, 15% acetonitrile, pH 8.5 for buffer A; Buffer B also contained 1 M sodium bromide. The purification was performed on the Waters 2-AP column packed with TSKgel Super Q-5PW (20) anion exchange resin from Tosoh Corporation. A gradient of 17% to 42% Buffer B over 150 minutes at a flow rate of 10 ml/min was employed. The fractions were analyzed via pH 11 IEX, and the fractions of >85% purity were pooled. This pool was dried, resuspended in water, and desalted by size exclusion chromatography as described above.

Purification of A-141381 and A-141382 into Two Diastereomers.

Two GalNAc-conjugated sense strands, A-141381 and A-141382, were synthesized, each with one PS on the 5'end. As shown in Table 10, A-141381 contained 2'F-G on the 5' end, and A-141382 contained 2'OMe-G on the 5' end. Purification was performed with DMT-on, which allowed for efficient separation of the 5' end phosphorothioate isomers.

TABLE 10

Sequences of the sense strands for duplexing with A-122625.

| Strand ID | Sequence (5'-3') |
|---|---|
| A-141381 | GfsaCfaAfaAfuAfAfCfuCfaCfuAfuAfaUfL96 |
| A-141382 | gsaCfaAfaAfuAfAfCfuCfaCfuAfuAfaUfL96 |

Figure 61:
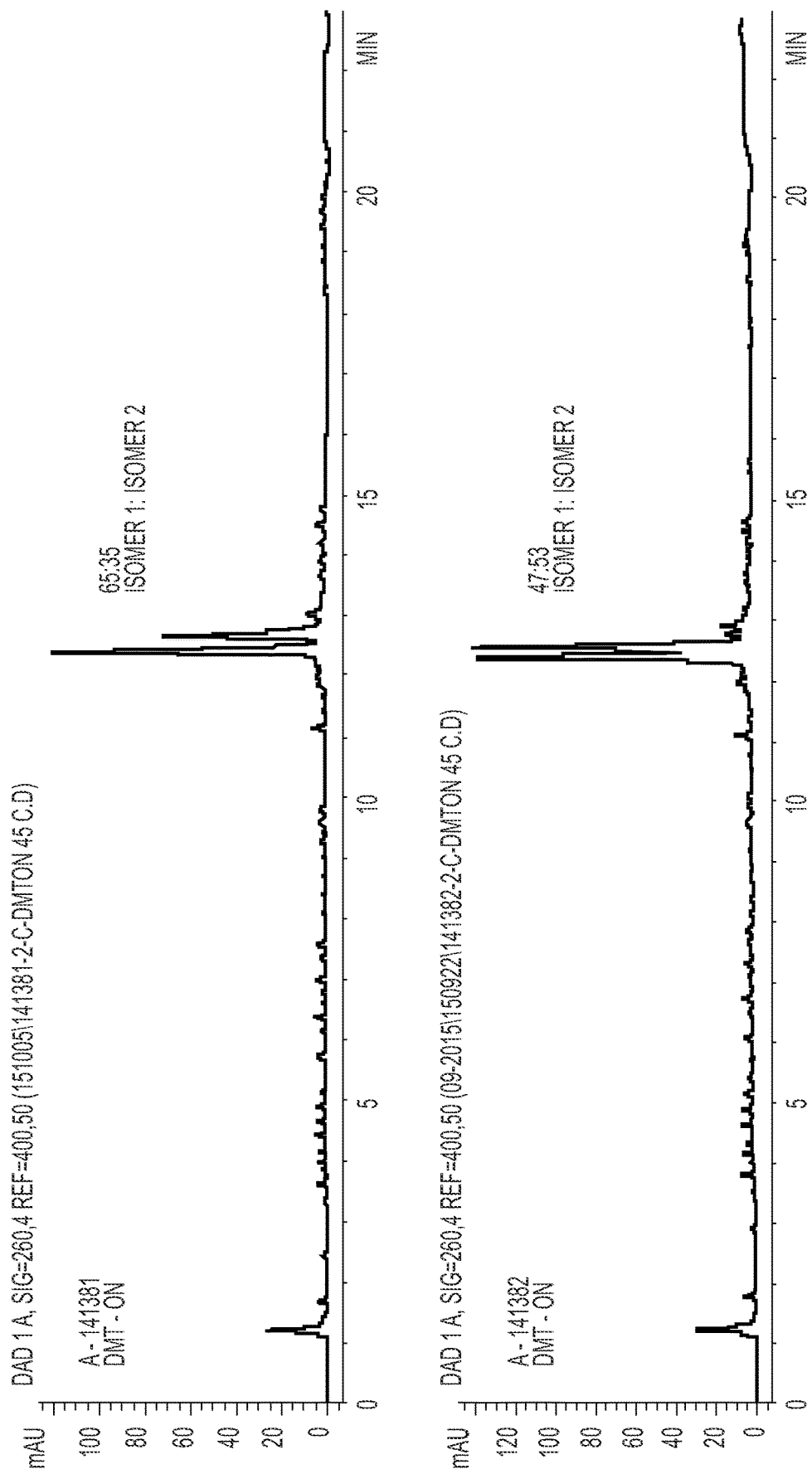
FIG. 61. The ion-exchange chromatograms of DMT-on crude A-141381 and A-141382.

The samples were diluted to approximately 0.03 mg/mL with water and 30 µl of each sample was injected onto a Dionex DNAPac PA200 ion-exchange analytical column (4 mm×250 mm; ThermoFisher). Buffer A was 20 mM sodium phosphate (pH 11,) 15% acetonitrile, and Buffer B was 20 mM sodium phosphate (pH 11,) 15% acetonitrile, 1M sodium bromide. A gradient of 31% to 57% Buffer B over 16 minute at a flow rate of 1 ml/min was used to analyze these samples. The column temperature was maintained at 45° C. The isomer separation was baseline (or near baseline) as shown in FIG. 61.

Figure 62:
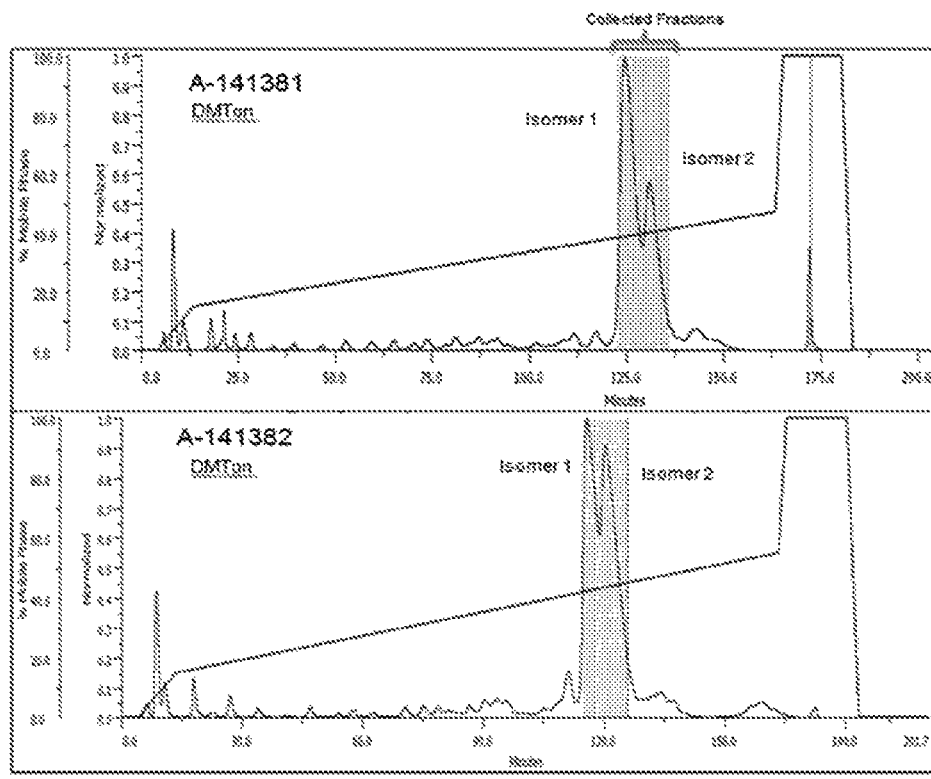
FIG. 62. The results of the chromatograms showing the separation of the PS isomers of A-141381 and A-141382.

A different anion exchange resin was used to purify these compounds into their respective isomers (Source 30Q, GE Healthcare). This resin was manually packed into a 2 cm diameter glass column (Waters Corporation, AP-2 Glass Column, 20 mm×300 mm). Buffer A was 20 mM sodium phosphate (pH 11), 15% acetonitrile, and Buffer B was 20 mM sodium phosphate (pH 11), 15% acetonitrile, 1 M sodium bromide. The gradient used was 15% to 55% Buffer B in 150 minutes at a flow rate of 10 mL/min. This gradient is equivalent to approximately 21 column volumes. Temperature of the column was 65° C. Three to five runs were performed for each compound, with approximately 800 OD/run. This procedure resulted in adequate amounts of each isomer at >85% purity. The purification profile of the isomers is shown in FIG. 62. The fractions were analyzed by pH 11 IEX and the fractions>85% pure for each isomer were combined.

Figure 63:
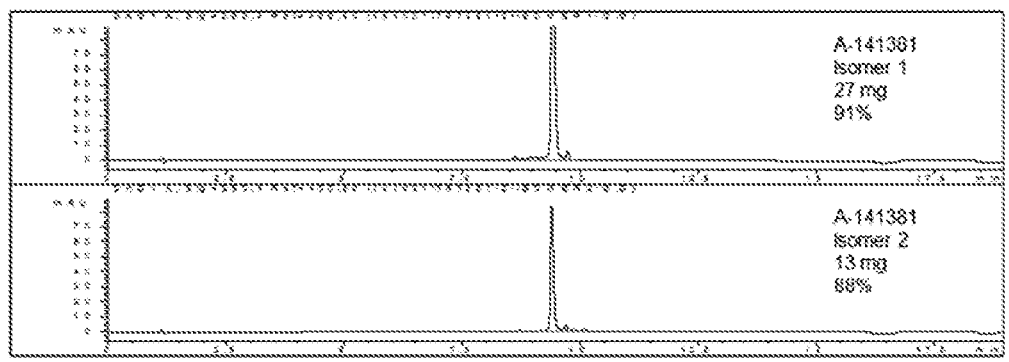
FIG. 63. Final purities of isomers for sense strands A-141381, by pH 11 anion exchange analysis (31-57% in 16 minutes, 1 mL/min, using a Dionex DNAPac PA200 4 mm×250 mm column).
Figure 64:
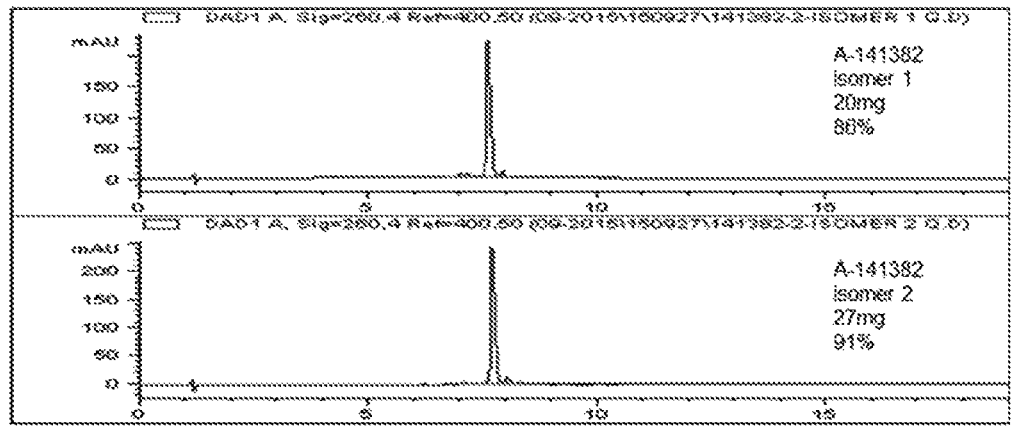
FIG. 64. Analysis of A-141382, by pH 11 IEX (31-57% in 16 minutes, 1 mL/min, using a Dionex DNAPac PA200 4 mm×250 mm column).

The resulting DMT-on pools for the four isomers were dried, resuspended in water, and desalted over size exclusion columns (GE Healthcare) at a flow rate of 10 mL/min, dried again, and detritylated by adding 5 mL of 20% acetic acid at room temperature for 10 minutes. Each pool was then neutralized by adding 18 mL of a saturated sodium bicarbonate solution. These solutions were dried, and oligonucleotides were again desalted by size exclusion. The pH 11 IEX chromatograms in FIG. 63 and FIG. 64 show the purities of the sense strand isomers. A difference in the column temperature may have accounted for the difference in the retention time between A-141381 (FIG. 63, 45° C.) and A-141382 (FIG. 64, 30° C.).

Methods of Assignment of Stereochemical Configurations for Purified Isomers.

To predict the stereochemistry, several methods were employed. One tool used was the synthesis ratios of the $R_p$ isomer vs. the $S_p$ isomer, which depend on the size and nature of the 2'-modification of the amidites being coupled. These coupling reactions can be mimicked through the synthesis of a PS dinucleotide in order to represent the diastereoisomer ratio generated during a given coupling step in the oligonucleotide synthesis. During synthesis, these ratios are not significantly affected by the scale of synthesis or the position within an oligonucleotide sequence, as long as the protecting groups on the phosphate (cyanoethyl) and activator type (0.5 M ETT) are constant.

The synthesis ratios of the $R_p$ isomer vs. the $S_p$ isomer were determined for all possible 2'-F and 2'-OMe (cyanoethyl-protected) dinucleotides using 0.5 M ETT as the activator. The diastereomer ratios for the 2'-F and 2'-OMe dinucleotides are shown in Table 11. The ratios were based on $^{31}$P-NMR spectra and are presented as Downfield Diastereomer ($R_p$)/Upfield Diastereomer ($S_p$).

TABLE 11

The diastereomer ratios for the 2'-F and 2'-OMe dinucleotides.

| Dimer Matrix 5' Nucleotide | 3' Nucleotide | 2'-OMe U | 2'-OMe C | 2'-OMe G | 2'-OMe A | 2'-F U | 2'-F G | 2'-F A | 2'-F C |
|---|---|---|---|---|---|---|---|---|---|
| | 2'-F U | usUf (59/41) | csUf (49/51) | gsUf (53/47) | asUf (60/40) | UfsUf (51/49) | GfsUf (36/64) | AfsUf (54/46) | CfsUf (53/47) |
| | 2'-F G | usGf (55/45) | csGf (50/50) | gsGf (53/47) | asGf (60/40) | UfsGf (47/53) | GfsGf (32/68) | AfsGf (52/48) | CfsGf (45/55) |
| | 2'-F A | usAf (62/38) | csAf (51/49) | gsAf (58/42) | asAf (59/41) | UfsAf (50/50) | GfsAf (34/66) | AfsAf (53/47) | CfsAf (48/52) |
| | 2'-F C | usCf (64/36) | csCf (53/47) | gsCf (63/37) | asCf (61/39) | UfsCf (46/54) | GfsCf (39/61) | AfsCf (52/48) | CfsCf (50/50) |
| | 2'-OMe U | usu (66/34) | csu (61/39) | gsu (61/39) | asu (69/31) | Ufsu (56/44) | Gfsu (36/64) | Afsu (61/39) | Cfsu (54/46) |
| | 2'-OMe C | usc (70/30) | csc (60/40) | gsc (64/36) | asc (65/35) | Ufsc (54/46) | Gfsc (40/60) | Afsc (59/41) | Cfsc (54/46) |
| | 2'-OMe G | usg (56/44) | csg (50/50) | gsg (52/48) | asg (57/43) | Ufsg (46/54) | Gfsg (28/72) | Afsg (53/47) | Cfsg (46/54) |

TABLE 11-continued

The diastereomer ratios for the 2'-F and 2'-OMe dinucleotides.

| Dimer Matrix 5' Nucleotide | 3' Nucleotide | 2'-OMe U | 2'-OMe C | 2'-OMe G | 2'-OMe A | 2'-F U | 2'-F G | 2'-F A | 2'-F C |
|---|---|---|---|---|---|---|---|---|---|
| 2'-OMe A | | usa (65/35) | csa (55/45) | gsa (53/47) | asa (66/34) | Ufsa (50/50) | Gfsa (30/70) | Afsa (53/47) | Cfsa (49/51) |

The dinucleotides listed in Table 11 were synthesized at 40 μM scale on universal support on an ABI synthesizer. Ammonia was used for cleavage from the solid support and deptrotection and was removed post-deprotection by evaporation (centrifuge under vacuum), and the resulting material was frozen and lyophilized. Samples were prepared for the $^{31}$P-NMR analysis by dissolving 5 mg lyophilized product in 500 μL of deuterium oxide. The $^{31}$P-NMR analysis was used for two reasons. First, the isomers are resolved in the 55-60 ppm range; not all the isomers for all the dinucleotides were observed to split in the ion-exchange analysis or reverse phase HPLC analysis. Second, for fully deprotected dinucleotides, the $R_p$ isomer was downfield shifted (farther from 0 ppm, $\delta^{31}$PP, relative to the calibration standard) compared to the $S_p$ isomer which was upfield shifted (farther from 0 ppm, $\delta^{31}$PP, relative to the calibration standard).

The $^{31}$P-NMR analysis was also used as an analytical method to determine whether only the $R_p$ or $S_p$ isomer was present in the final purified oligonucleotides, versus a mixture of the $R_p$ and $S_p$ isomers.

Another method used to identify the isomers was HPLC ion-exchange analysis, in which the $R_p$ isomer was determined to elute earlier than the $S_p$ isomer. The $R_p$ isomer eluted first, with the following exception: when the phosphorothioate linkage was on the 5'-end, and the DMT protecting group was left on, the $S_p$ isomer eluted before the $R_p$ isomer. This observation helped confirm the isomer configuration on the 5' end, as described in the identification of isomers using synthesis Approach 2.

A complementary method used to identify the purified isomers, particularly on the 3' end, was through the analysis of degradation by exonucleases. The $S_p$ isomer was more stable against snake venom phosphodiesterase (SVPD), a 3' exonuclease, than the Rp isomer.

Additionally, the $R_p$ isomer was more stable against phosphodiesterase II, a 5' exonuclease (PDII), than the $S_p$ isomer. However, in some cases where the PS bond was in combination with a 2'-OMe modification, there was little or no difference in the degradation rate of the $R_p$ and $S_p$ isomers for SVPD and/or Phosphodiesterase II.

A-122625 Diastereomer Identification

A-122625 contains two PS linkages, one on the 3'-end and one on the 5'-end of the sequence, resulting in four distinct stereoisomers. After removal of the 5'-DMT protecting group, only the 3'-end isomers separated by the anion exchange HPLC analysis. This was confirmed by the synthesis and analysis of A-122628 which has a single PS linkage at the 5' end. As shown in Table 12, A-122628 has the same sequence as A-122625, except without the PS linkage on the 3'end. Only one peak was observed in the ion-exchange HPLC analysis of A-122628, confirming that the splitting observed came from the 3'end isomers.

TABLE 12

Sequences synthesized having two PS linkages

| Strand ID | Sequence (5'-3') | Location of PS | Number of Peaks |
|---|---|---|---|
| A-122625 | asUfuAfuAfgUfgAfguuAfuUfuUfgUfcasa | 5' and 3' ends | 2 |
| A-122628 | asUfuAfuAfgUfgAfguuAfuiffuUfgUfcaa | 5' end only | 1 |

The diastereomer ratio from the $^{31}$P-NMR analysis for the 3'-end (asa) dimer of A-122625 is 66:34 ($R_p$:$S_p$) based on data shown in Table 11.

Figure 65:
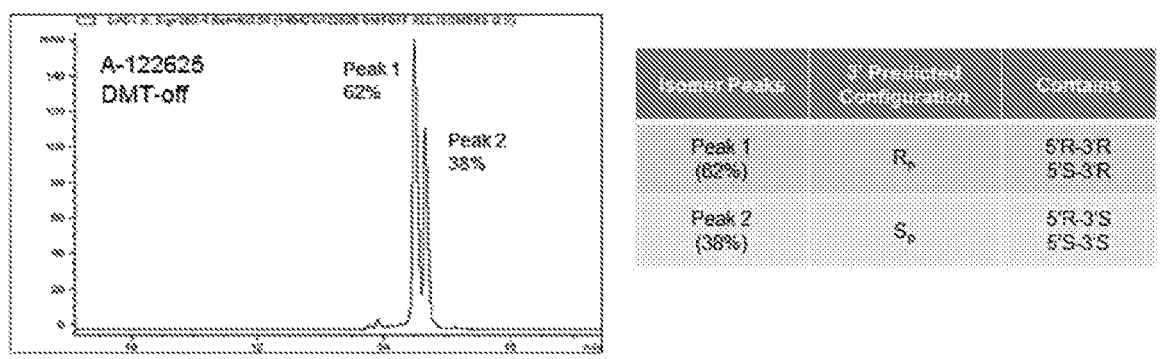
FIG. 65. The results of the ion-exchange analysis for DMT-off A-122625.

After the compound was synthesized the ratio for A-122625 was 62:38 by the ion-exchange HPLC analysis (FIG. 65). Isomers corresponding to the PS linkage at the 3'-end were resolved, irrespective of the configuration at the 5'end.

Figure 66:
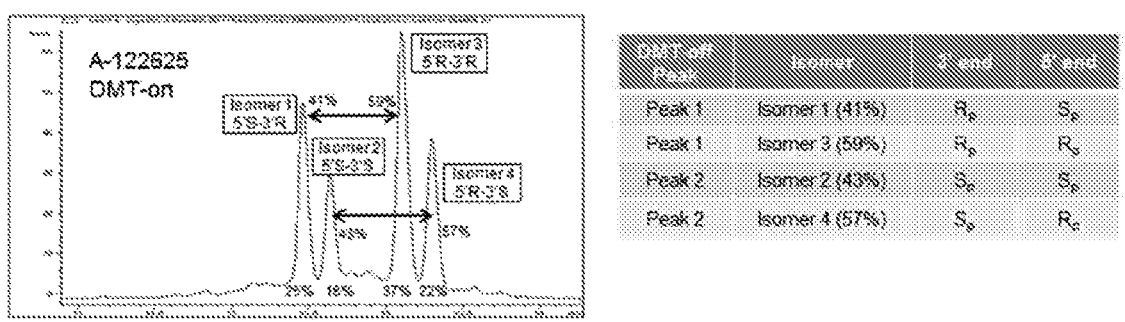
FIG. 66. The results of the ion-exchange analysis for DMT-on A-122625 showing peak resolution of the four diastereomers of A-122625.

When analyzing A-122625, with 5'-DMT on, the 5'-end PS isomers as well as 3'end PS isomers were resolved by ion-exchange HPLC (FIG. 66). The diastereomer ratios of 59:41 and 57:43 ($R_p$:$S_p$) for A-122625 observed in FIG. 66 were similar to the ratio of 60:40 ($R_p$:$S_p$; asUf in Table 11). Additionally, if the four main peaks are integrated by UV area with the total equaling 100%, isomers 1 and 3 (the 3'-$R_p$ isomers) made up 62% of the total. Isomers 2 and 4 (the 3'-$S_p$ isomers) made up 38%. This corresponds to the $R_p$:$S_p$ ratio (62:38) observed in the DMT-off A-122625 (FIG. 65).

Figure 67:
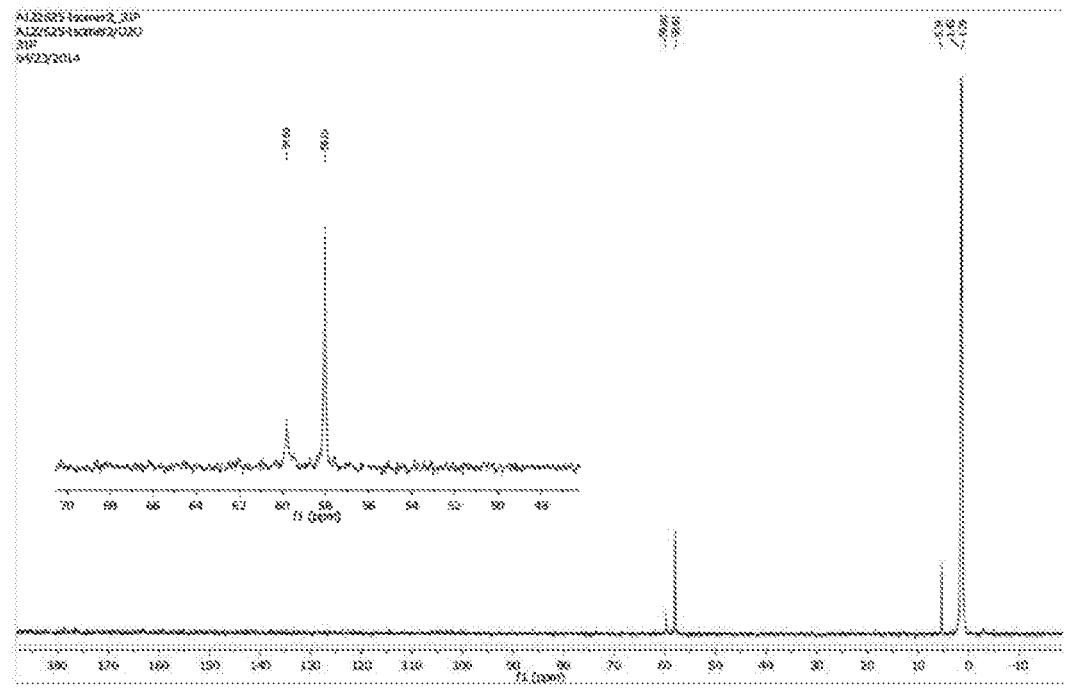
FIG. 67. The $^{31}$P-NMR spectra of Isomer 2 (5'S-3'S).
Figure 68:
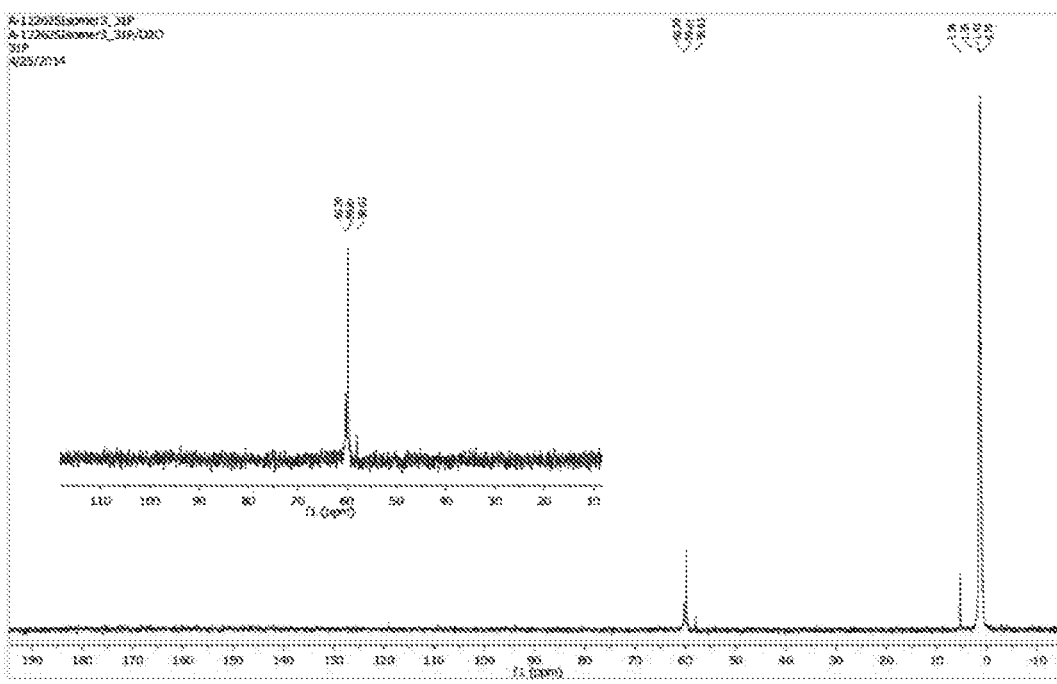
FIG. 68. The $^{31}$P-NMR spectra of Isomer 3 (5'R-3'R).
Figure 69:
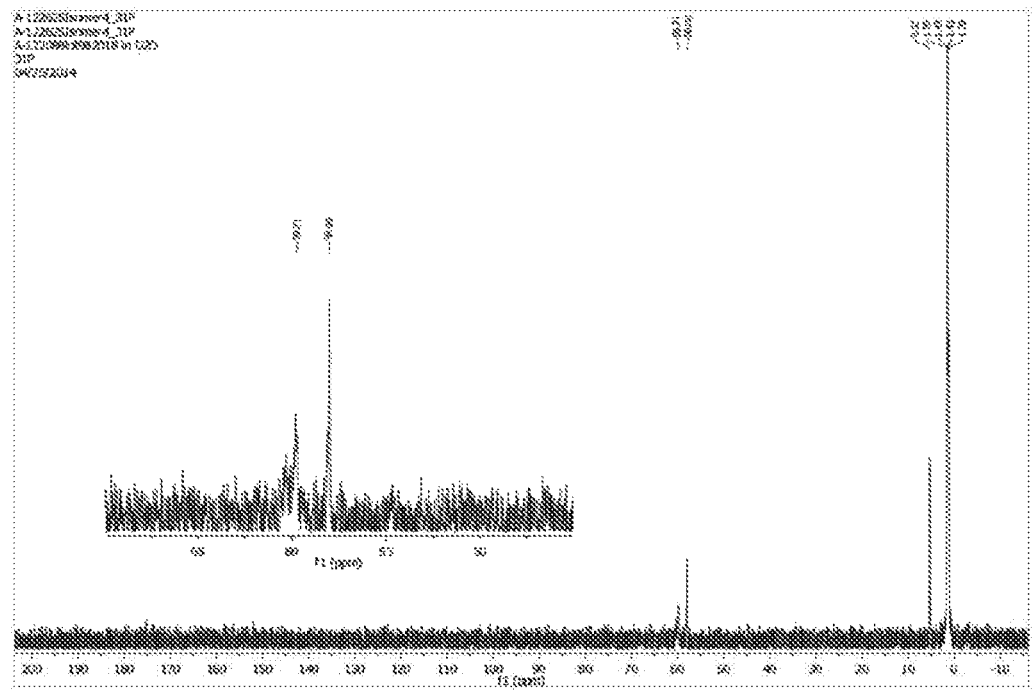
FIG. 69. The $^{31}$P-NMR spectra of Isomer 4 (5'R-3'S).

Once the four isomers of A-122625 were obtained in reasonable purity and adequate amounts, the compounds were analyzed by the $^{31}$P-NMR analysis to confirm the isomer identity assignments. Compounds were prepared by dissolving lyophilized oligonucleotide in 550 μL of deuterium oxide at the concentrations of 10 mg/mL. Isomer 4 (5'R-3'S) was analyzed at the concentration of 4.4 mg/mL. The $^{31}$P-NMR analyses for isomers 2, 3 and 4 as well as the isomer mixture are shown in FIGS. 67-70. As shown in FIG. 67, the major peak at 58.01 ppm for Isomer 2 (5'S-3'S) was upfield shifted relative to the peak at 59.80 ppm which may be due to the presence of minor amounts of Isomer 1 (5'S-3'R) and/or Isomer 3 (5'R-3'R). The peaks of the $R_p$ isomers in the $^{31}$P-NMR spectra for Isomer 3 (5'R-3'R) were observed at 60.30 and 59.81 ppm; the peaks for the $S_p$ isomer were not detected at 58.03 ppm (FIG. 68). The peak characteristics for both $R_p$ (59.71 ppm) and $S_p$ (58.00 ppm) were visible in the $^{31}$P-NMR spectra for Isomer 4 (5'R-3'S) (FIG. 69).

Figure 70:
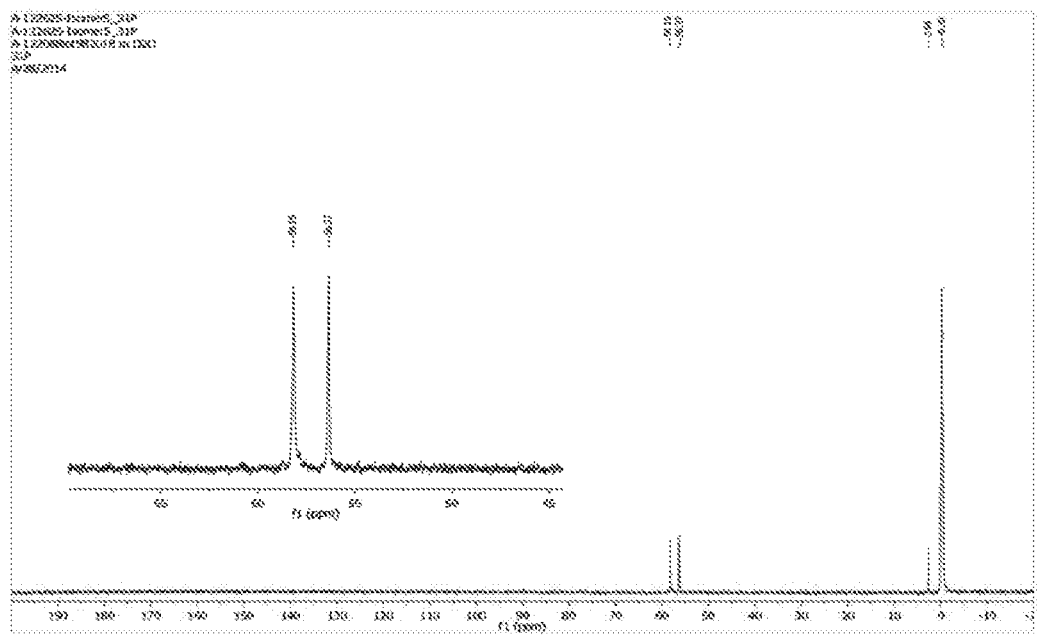
FIG. 70. The $^{31}$P-NMR spectra of mixture containing all four isomers.

The peaks at 58.18 ppm and 56.37 ppm in the $^{31}$P-NMR spectra for mixture containing all four isomers were due to $R_p$ and $S_p$ isomers, respectively (FIG. 70). Integrating the area under the peaks, the $R_p$:$S_p$ ratio was approximately 1.4:1.0, consistent with the synthesis ratios.

Figure 71:
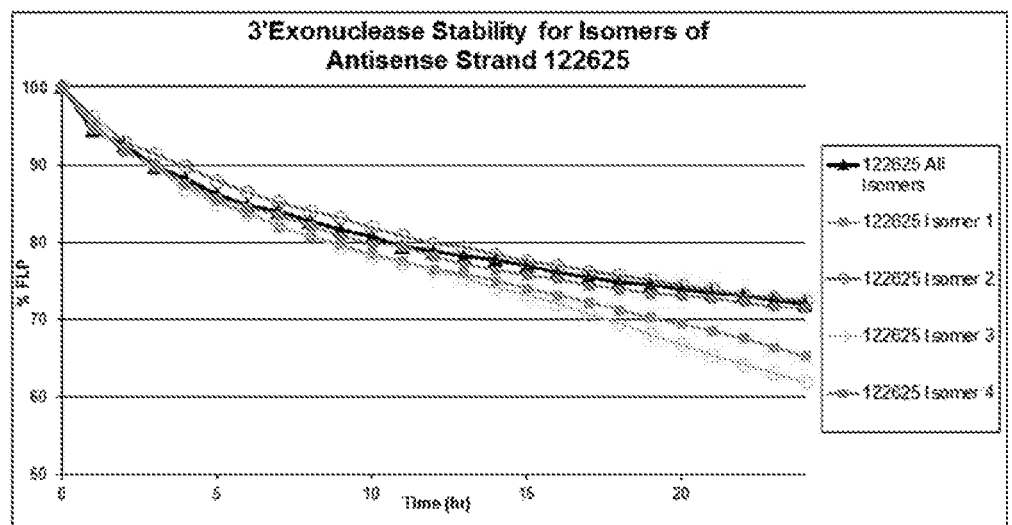
FIG. 71. Full length A-122615 as a function of time in the presence of SVPD.

The 3'-end configurations were further analyzed with the samples incubated with SVPD assay. The analysis of the A-122625 isomers and mixture are shown in FIG. 71. The half-lives of each isomer and the mixture are listed in Table 13.

TABLE 13

Half-life of each isomer, and the mixture of A-122625 isomers in the presence of SVPD.

| Isomer | Predicted Configuration | Calculated Half-Life (hrs) |
| --- | --- | --- |
| Isomer 1 | 5'S-3'R | 44.6 |
| Isomer 2 | 5'S-3'S | 56.7 |
| Isomer 3 | 5'R-3'R | 39.2 |
| Isomer 4 | 5'R-3'S | 56.4 |
| All Isomers | Mixed | 58.6 |

The results in FIG. 71 and Table 13 illustrate that the samples containing a phosphorothioate in combination with 2'-OMe (in this case, the 3'-end is 2'-OMe-A in combination with the PS linkage) showed difference in stability between the $R_p$ and $S_p$ isomers when incubated with SVPD.

A-141381 and A-141382 Diastereomer Identification

The above methods were employed to identify each of the two isomers that were separated for both sense strands A-141381 and A-141382 (sequences are shown in Table 10). Both sequences contain a single PS linkage at the 5' end. A-141381 has a 2'-F-G (Gf) at the 5' end and A-141382 has a 2'-OMe-G (g) at the 5' end.

Figure 72:
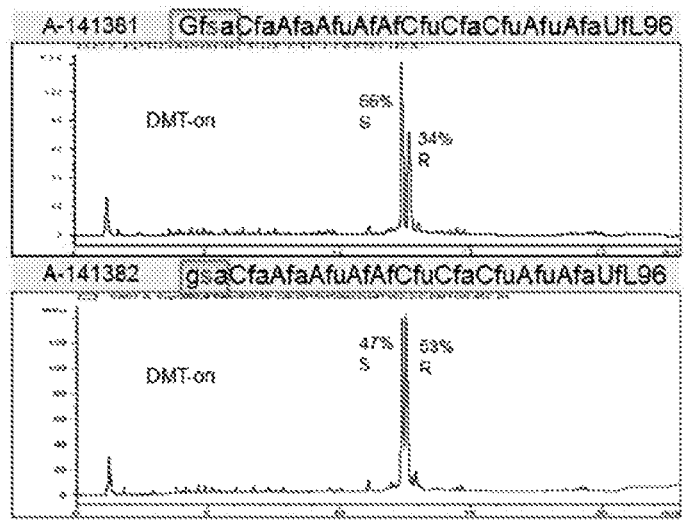
FIG. 72. The results of the ion-exchange chromatography of DMT-on A-141381 and A-141382.

For A-141381, with (Gfsa) on the 5' end, the synthesis ratio is 30:70 ($R_p$:$S_p$, Table 11), and the ratio obtained by peak integration on the ion-exchange chromatogram of the crude compound was 34:66 ($R_p$:$S_p$), as shown in FIG. 72. For A-141382, with (gsa) on the 5' end, the synthesis ratio is 53:47 ($R_p$:$S_p$, Table 11), and the ratio found experimentally was 53:47 ($R_p$:$S_p$), as shown in FIG. 72.

Figure 77:
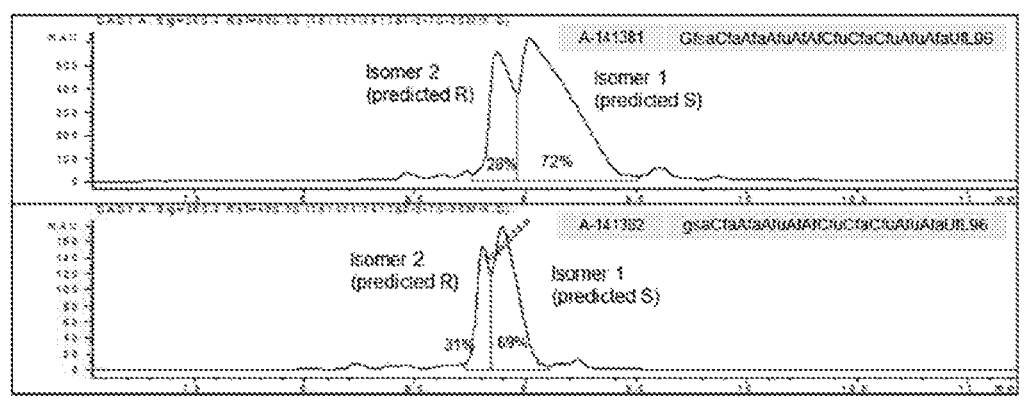
FIG. 77. The results of the ion-exchange chromatography for DMT-off A-141381 and A-141382.

The faster migrating of the two peaks in each of the chromatograms shown in FIG. 72 was determined to be $S_p$ and the second peak was determined to be $R_p$ (5'-DMT on), which matched the synthesis ratios of the dinucleotides in Table 11. Once the 5'-DMT group was removed from the final product, the $S_p$ isomer eluted with a longer retention time (slow eluting isomer). As shown in FIG. 77, the presence of DMT causes a "flip" in the elution of 5' end $R_p$ vs. $S_p$ isomers relative to the elution of DMT-on products.

Figure 73:
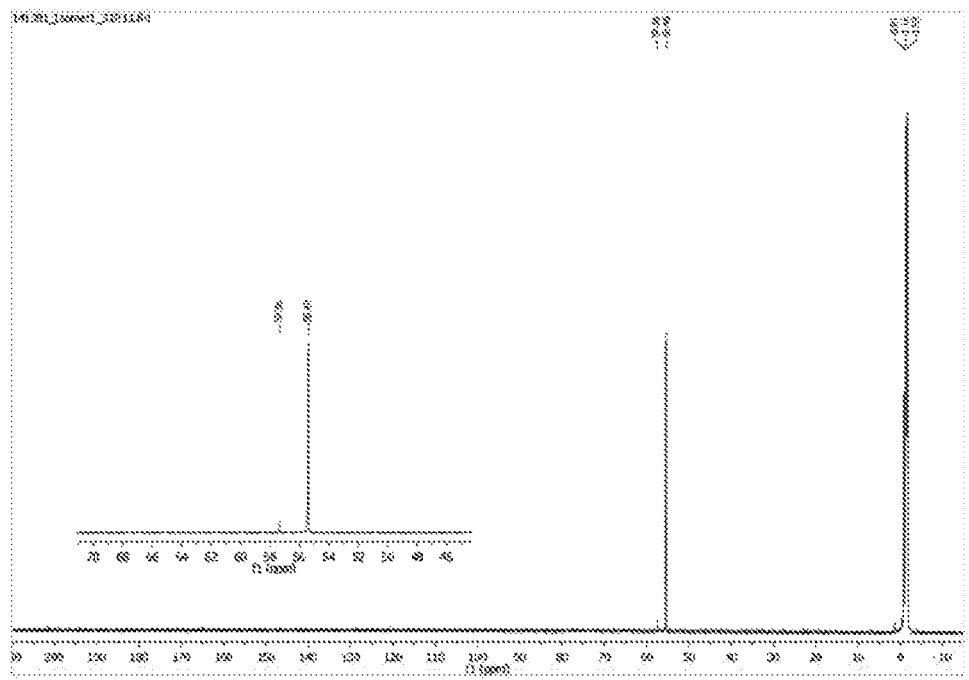
FIG. 73. The results of the $^{31}$P-NMR spectra of isomers of A-141381. Isomer 1 ($S_p$).
Figure 74:
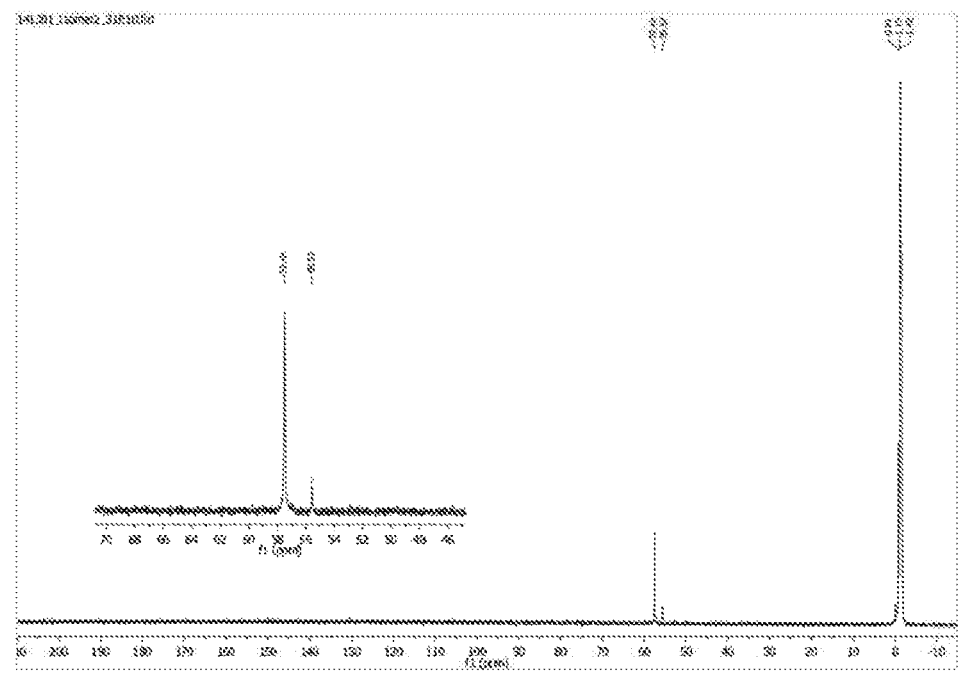
FIG. 74. The results of the $^{31}$P-NMR spectra of isomers of A-141381. Isomer 2 ($R_p$).
Figure 75:
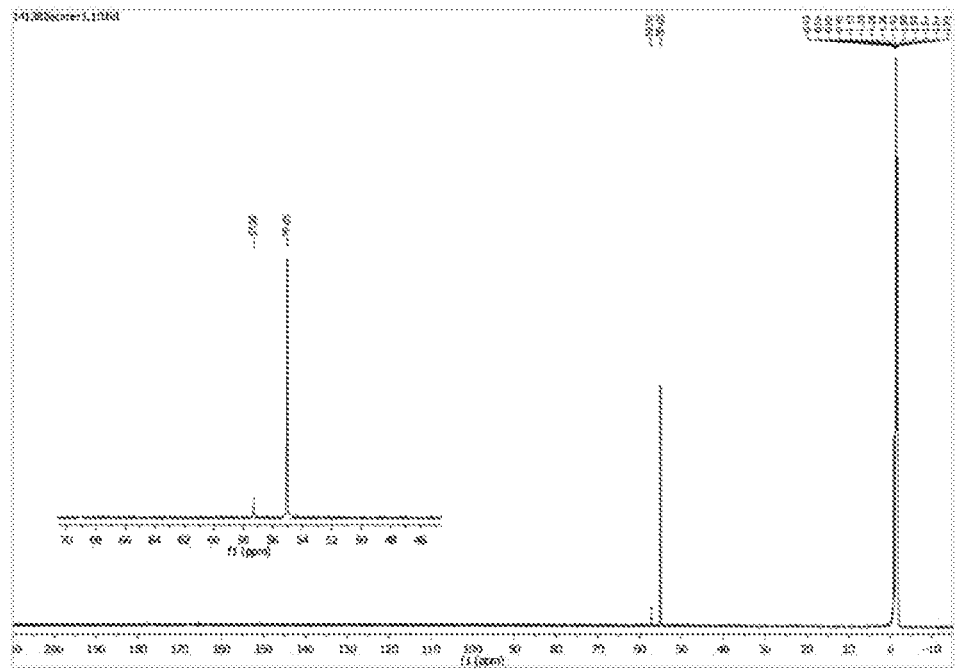
FIG. 75. $^{31}$P-NMR spectra of isomers of A-141382. Isomer 1 ($S_p$).
Figure 76:
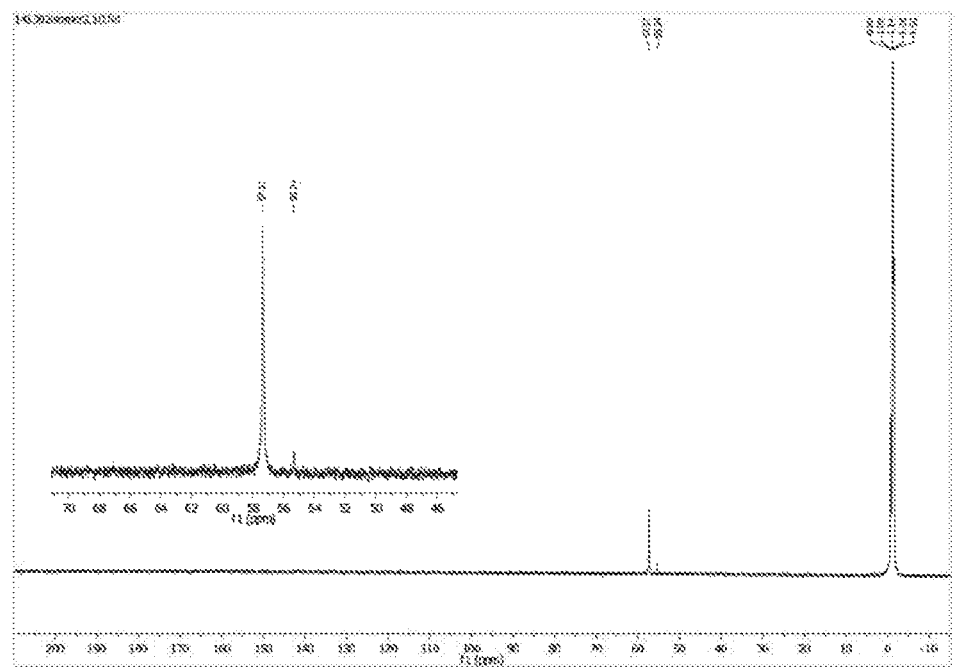
FIG. 76. $^{31}$P-NMR spectra of isomers of A-141382. Isomer 2 ($R_p$).

Once the isomers for each sequence were purified and DMT removed, each isomer was submitted for $^{31}$P-NMR analysis as 10 mg/mL solutions in deuterium oxide. The resulting P-NMR spectra are shown in FIGS. 73-76. For of A-141381, the $^{31}$P-NMR spectra for Isomer 1 ($S_p$) shows the main resonance peak at 55.40 ppm, upfield shifted relative to the impurity $R_p$ isomer at 57.36 ppm (FIG. 73). The $^{31}$P-NMR spectra for Isomer 2 ($R_p$) shows the main resonance peak at 57.48 ppm, downfield shifted relative to the impurity $S_p$ isomer at 55.57 ppm (FIG. 74). For A-141382, Isomer 1 ($S_p$) has a main resonance peak at 55.05 ppm, upfield shifted relative to the impurity (the $R_p$ isomer) at 57.30 ppm (FIG. 75). Isomer 2 ($R_p$) has a main resonance peak at 57.37 ppm, downfield shifted relative to the impurity (the $S_p$ isomer) at 55.34 ppm (FIG. 76).

Oligonucleotide Synthesis Using Oxazaphospholidine (OAP) Monomers (Approach 3)

A third approach using bicyclic oxazaphospholidine (OAP) monomers was utilized for all compounds containing consecutive chiral linkages. A modified synthesis cycle was optimized and used, following the parameters described by Wan et al., "Synthesis, biophysical properties, and biological activity of second generation antisense oligonucleotides containing chiral phosphorothioate linkages," *Nucleic Acids Research* 42(22): 13456-68 (2014), which is incorporated herein by reference in its entirety. Two separate cycles were needed, one for the chiral PS couplings at either the 5' or 3' end of the oligonucleotide using the modified cycle and another for the internal stretch of PO nucleotide couplings using standard solid phase oligonucleotide synthesis protocols.

After synthesis and characterization, OAP monomers were prepared at 0.2 M in acetonitrile:toluene 1:1 (v:v) and used immediately on an ABI 394 automated synthesizer. For the chiral PS cycle using the OAP monomers, 1 M 4,5-dicyanoimidazole with 0.1 M N-methylimidazole in acetonitrile was used as the activator. To increase coupling efficiency, a "double coupling" (two applications of OAP and activator; 7.5-minute contact time each) was used. After coupling, a 2-minute exposure to Cap A reagent containing acetic anhydride/pyridine/THF (Glen Research) was performed first (see Iwamoto et al., "Control of Phosphorothioate Stereochemistry Substantially Increases the Efficacy of Antisense Oligonucleotides," *Nature Biotechnology* 35(9): 845-851 (2017), which is incorporated herein by reference in its entirety). After this, Cap A and Cap B containing 10% N-methylimidazole in THF (Glen Research) were sent together to the column. To sulfurize the chiral phosphite triester post coupling, the sulfurization agent 0.1 M 3-((N, N-dimethyl-aminomethylidene)amino)-3H-1,2,4-dithiazole-5-thione (DDTT) in pyridine was utilized. To ensure sufficient sulfurization, four passes of DDTT were employed with 7.5-minute contact time for each pass. Standard deblocking reagent (3% dichloroacetic acid in dichloromethane) was used for detritylation. After the completion of the synthesis, the final DMT protecting group was removed and the column containing the solid support oligonucleotide was exposed to 1 M piperidine in dry acetonitrile three times, 10 minutes each (see O'Shea et al., "An efficient deprotection method for 5'-[O,O-bis(pivaloyloxymethyl)]-€-vinylphosphonate containing oligonucleotides," *Tetrahedron* 74(42): 6182-6186 (2018), which is incorporated herein by reference in its entirety). The solid support was washed with ACN, dried, and suspended in aqueous ammonia (28-30 wt. %) and heated at 60° C. for 8-10 hours.

In the case of oligonucleotides containing 5'[O,O-bis (pivaloyloxymethyl)]-(E)-vinylphosphonate, deprotection was performed using 5% (v/v) diethylamine in ammonia according to O'Shea et al. "An efficient deprotection method for 5'-[O,O-bis(pivaloyloxymethyl)]-(E)-vinylphosphonate containing oligonucleotides," *Tetrahedron* 74(42): 6182-6186 (2018), which is incorporated herein by reference in its entirety.

N. In Vitro Experiment

Transfection

Primary Mouse Hepatocytes (PMH) were transfected with siRNA to test for silencing efficiency, siRNA (5 μl) at indicated concentrations was mixed with 4.9 μl of Opti- MEM and 0.1 µl of Lipofectamine RNAiMax (Invitrogen, Carlsbad Calif. cat #13778-150) per well of a 384-well plate and incubated at room temperature. After 15 minutes, 40 µl of William's E Medium (Life Tech) or EMEM medium (ATCC) containing approximately $5 \times 10^3$ cells were added to the wells. Cells were incubated for 24 hours prior to RNA purification.

Freeuptake

Free uptake experiments were carried out in PMH. SiRNA (5 µl at indicated concentration) was mixed with 5 µl Opti-MEM per well of a 384-well plate. After 15 minutes, 40 µl of William's E Medium (Life Tech) or EMEM medium (ATCC) containing approximately $5 \times 10^3$ cells were then added to the siRNA mixture. Cells were incubated for 24 hours prior to the RNA purification.

Total RNA Isolation Using DYNABEADS mRNA Isolation Kit:

RNA was isolated using an automated protocol on a BioTek-EL406 platform using DYNABEADs (Invitrogen, cat #61012). Briefly, 50 µl of Lysis/Binding Buffer and 25 µl of lysis buffer containing 3 µl of magnetic beads were added to each well. The plates were incubated on an electromagnetic shaker for 10 minutes at room temperature, and then magnetic beads were captured and the supernatant was removed. The bead-bound RNA was then washed twice with 150 µl/well of Buffer A and once with 150 µl/well Buffer B. The beads were then washed with 150 µl Elution Buffer, re-captured, and supernatant collected.

cDNA Synthesis Using ABI High-Capacity cDNA Reverse Transcription Kit cDNA synthesis was performed using an ABI kit Cat #4368813. To the wells of a 384-well plate containing RNA isolated using DYNABEADS was added 10 µl of a master mix containing 1 µl 10× Buffer, 0.4 µl 25×dNTPs, 1 µl 10× random primers, 0.5 µl reverse transcriptase, 0.5 µl RNase inhibitor and 6.6 µl of $H_2O$. The plates were sealed, mixed, and incubated on an electromagnetic shaker for 10 minutes at room temperature, followed by 2 hours at 37° C.

Real Time PCR

To each well of a 384-well plates (Roche Cat #04887301001) containing cDNA (2 µl) was added to a master mix containing 0.5 µl of mouse GAPDH TaqMan Probe (4352339E), 0.5 µl C5 mouse probe (Mm00439275_ml), or the appropriate target probe, and 5 µl Lightcycler 480 probe master mix. A real-time PCR was done in a LightCycler 480 Real Time PCR system (Roche). Each siRNA concentration was analyzed in duplicates. To calculate relative fold change, the real time data were analyzed using the ΔΔCt method and normalized to assays performed with cells transfected with a non-targeting control siRNA.

O. RISC Loading Experiment

Quantification of Whole Liver and Ago2-Associated siRNA Levels

Mice were sacrificed on day 7 post-dose, and livers were snap frozen in liquid nitrogen and ground into powder for further analysis. Total siRNA liver levels were measured by reconstituting liver powder at 10 mg/ml in PBS containing 0.25% Triton-X 100. The tissue suspension was further ground with 5-mm steel grinding balls at 50 cycles/s for 5 minutes in a tissue homogenizer (Qiagen TissueLyser LT) at 4° C. Homogenized samples were then heated at 95° C. for 5 minutes, briefly vortexed, and allowed to rest on ice for 5 minutes. Samples were then centrifuged at 21,000×g for 5 minutes at 4° C. The siRNA-containing supernatants were transferred to new tubes. The siRNA sense and guide strand levels were quantified by stem loop reverse transcription followed by Taqman PCR (SL-RT QPCR) based on a previously published method (see Chen, "Real-time quantification of microRNAs by stem-loop RT-PCR," *Nucleic Acids Research* 33: e179 (2005); Pei et al., "Quantitative evaluation of siRNA delivery in vivo," *RNA* 16: 2553-63 (2010), both of which are incorporated herein by reference in their entirety).

Ago2-bound siRNA from mouse liver was quantified by preparing liver powder lysates at 100 mg/ml in lysis buffer (50 mM Tris-HCl, pH 7.5, 150 mM NaCl, 2 mM EDTA, 0.5% Triton-X 100) supplemented with freshly added protease inhibitors (Sigma-Aldrich, P8340) at 1:100 dilution and 1 mM PMSF (Life Technologies). Total liver lysate (10 mg) was used for each Ago2 immunoprecipitation (IP) and control IP. Anti-Ago2 antibody was purchased from Wako Chemicals (Clone No.: 2D4). Control mouse IgG was from Santa Cruz Biotechnology (sc-2025). Protein G Dynabeads (Life Technologies) were used to precipitate antibodies. Ago2-associated siRNAs were eluted by heating (50 µL PBS, 0.25% Triton; 95° C., 5 minutes) and quantified by SL-RT QPCR as described by Chen and Pei et al., provided above.

In Vitro Quantification of Human Ago2-Associated siRNAs

Ago2-bound siRNA was quantified in HEK293 cell lysates overexpressing FLAG-HA-tagged human Ago2 (see Pei et al., provided above). HEK293 lysates were prepared by incubating cells at room temperature for 30 minutes in lysis buffer (100 mM KCl, 20 mM HEPES pH 7.5, 0.5 mM TCEP, 0.05% NP-40) with gentle rocking. Lysates were cleared by centrifugation (25,000×g, 20 minutes, 4° C.), and supernatant aliquots were frozen on dry ice before storage at −80° C. Each 70 µl in vitro loading reaction contained 30 mM HEPES (pH 7.5), 100 mM NaCl, 5 mM $MgCl_2$, 1 mM DTT, 0.03 mg/ml creatine kinase, 25 mM creatine phosphate, 1 U/µl Superase-In nuclease inhibitor, 1 mM ATP, 0.2 mM GTP, 35 µL HEK293 cell lysate, and 7 µL of 200 nM siRNA duplex (1.4 pmol total). Loading reactions were incubated at 37° C. for 4 hours. Following incubation, reactions were cleaned using 430 µL of 20 mg/ml QAE 50 anion exchange resin (GE Healthcare), rotating for 15 minutes at 4° C. Samples were passed through a cellulose acetate filter column to remove the QAE resin prior to addition of 60 µL of Protein G Dynabeads (Life Technologies), 3 µl of anti-HA antibody (Cell Signaling, 3724S), and 600 µl of lysis buffer supplemented with freshly added protease inhibitors (Sigma-Aldrich, P8340) at 1:100 dilution and 1 mM PMSF (Life Technologies). After overnight incubation (immunoprecipitation) at 4° C., Ago2-associated siRNAs were eluted by heating (50 µL PBS, 0.25% Triton; 95° C., 5 minutes) and quantified by SL-RT QPCR as described by Chen and Pei et al., provided above.

P. 3'/5'Exo Nuclease Assay

3' Exonuclease SVPD Stability Assay

Modified oligonucleotide was added at 0.1 mg/ml to a solution of 50 mM Tris-HCl (pH7.2) (Lonza Cat No. 51236) and 10 mM $MgCl_2$ (Ambion P/N AM9530G). Snake Venom Phosphodiesterase (SVPD) (Worthington Cat #LS003926) was added to the mixture at 750 mU/ml. Immediately after addition of enzyme, sample was injected onto a Dionex DNAPac PA200 column (4 mm×250 mm) at 30° C. and run at a flow rate of 1 ml/min with a gradient of 40-55% Buffer B over 7.5 minutes. Buffer A was 20 mM sodium phosphate, 15% acetonitrile, pH11; Buffer B also contained 1M sodium bromide (pH11). Aliquots were analyzed every hour for 24 hours. The area under the peak corresponding to full-length oligonucleotide was normalized to the area from the 0 h time point (first injection). First-order decay kinetics were assumed in calculation of half-lives. A control sequence, $dT_{19}sdT$ (where dT is deoxythymidine) was analyzed each day, and half-lives were reported relative to half-life of control sequence. Enzyme was prepared as a stock of 1000 mU/ml aliquoted into 1 ml tubes and stored at −20° C. A new aliquot was used each week.

5' Exonuclease, Phosphodiesterase II Stability Assay

Modified oligonucleotide was added at 0.1 mg/ml to a solution of 50 mM sodium acetate (pH 6.5) (Sigma Cat. S8750-1 kg) and 10 mM $MgCl_2$ (Ambion P/N AM9530G). Phosphodiesterase II from bovine spleen (Worthington Cat #LS003602) was added to the mixture at 500 mU/ml. Immediately after addition of enzyme, sample was injected onto a Dionex DNAPac PA200 column (4 mm×250 mm) run at a flow rate of 1 ml/min with a gradient of 37-52% Buffer B over 7.5 minutes. Buffer A was 20 mM sodium phosphate, 15% acetonitrile, pH11; Buffer B also contained 1M sodium bromide. Aliquots were analyzed every hour for 24 hours. The area under the peak corresponding to full-length oligonucleotide was normalized to the area from the 0 h time point (first injection). First-order decay kinetics were assumed in calculation of half-lives. A control sequence, $dTsdT_{19}$, was analyzed each day, and half-lives were reported relative to half-life of control sequence. Enzyme was prepared as a stock of 2000 mU/ml aliquoted into 1 ml tubes and stored at −20° C. A new aliquot was used each week.

Q. In Vivo Experiments

Animals:

All procedures using mice were conducted by certified laboratory personnel using protocols consistent with local, state, and federal regulations. Experimental protocols were approved by the Institutional Animal Care and Use Committee, the Association for Assessment and Accreditation of Laboratory Animal Care International (accreditation number: 001345), and the office of Laboratory Animal Welfare (accreditation number: #A4517-01). When deciding on sample numbers for animal studies, we determined the final number required to be one that would allow for confidence in the resulting data set utilizing the least number of animals, as required in accordance with IACUC guidelines. All animals were acclimated in-house for 48 h prior to study start. Female C57BL/6 mice approximately 8 weeks of age were obtained from Charles River Laboratories and randomly assigned to each group. All animals were treated in accordance with IACUC protocols. Animals were dosed subcutaneously at 10 µl/kg with siRNA duplex or with PBS saline control. The siRNAs were diluted into phosphate buffered saline (Gibco). All dosing solutions were stored at 4° C. until time of injection. Animals were sacrificed at either 5 or 7 days post dose. Livers were harvested and snap frozen for analysis.

Monkeys:

Males Cynomolgus monkey (non-naïve) were used in the studies. The body weight at the dose administration of each animals was 2 to 5 kg or greater and the age at the dose administration was young adult/adult.

Dose Administration. Animals in all groups were fasted overnight (approximately 12-18 hours) prior to the dose administration through approximately 4 hours postdose. The test article was administered to all animals on Day 1 by subcutaneous injection. The subcutaneous dose was administered by syringe and needle in the mid scapular region. The volume of the test article to be administered to each animal was calculated based on the body weight collected on the day of the dose administration. Dose formulations for all groups were prepared at appropriate concentrations to meet the dosage level requirements by mixing the siRNA test article stock solutions in 1× phosphate-buffered saline (PBS).

Plasma for pharmacokinetics (PK). Blood (approximately 1 mL) was collected from each animal at approximately 0.25, 1, 4, 8, and 24 hours postdose. Blood was collected by venipuncture of the femoral vein (or from a saphenous vein if necessary) into tubes containing K2EDTA anticoagulant and processed to plasma. Blood samples were mixed gently and placed on wet ice (crushed) or in chilled cryoracks until centrifugation. The samples were centrifuged for approximately 10 minutes in a refrigerated centrifuge (approximately 4° C.) at approximately 2700 rpm. Levels of the test article for each PK timepoint were assessed using RT-qPCR.

Plasma for pharmacodynamics (PD). Blood (approximately 1 mL) was collected from each animal on Days −6, −3, 1 (predose), 4, 8, 15, 22, 29, 36, 43, 57, 71, 85, 99, 113, 127, 141, 155, and 169, respectively. Blood was collected by venipuncture of the femoral vein (or from a saphenous vein if necessary) into tubes containing K2EDTA anticoagulant and processed to plasma. Blood samples were mixed gently and placed on wet ice (crushed) or in chilled cryoracks until centrifugation. The samples were centrifuged for approximately 10 minutes in a refrigerated centrifuge (approximately 4° C.) at approximately 2700 rpm. Circulating protein levels for PD were analyzed by using the appropriate ELISA kits Liver biopsy (Laparoscopic). Liver biopsy samples were collected from 1 animal/group/time point at approximately 24 and 168 hours postdose (Days 2 and 8, respectively), for a total of 1 non-terminal biopsy/animal for two animals/group.

Gene Expression Analysis (RT-gPCR):

RNA isolation using the QIAzol reagent (Qiagen) was performed by adding the reagent either to growing cells immediately following a PBS (lx) wash, or to cell pellets collected after a PBS wash and snap frozen and stored at −80° C. Alternatively, RNA was isolated from samples using the Qiagen RNAeasy kit following the manufacturer's instructions. RNA concentrations were determined using a Nanodrop spectrophotometer (ThermoFisher Scientific). The RNA concentrations were adjusted to 25 ng/µl. cDNA was made from 250 ng RNA using reverse transcription kit from Applied Biosystems (catalog number 4368814). All probes for RNA quantification were acquired from Life Technologies utilizing their Taqman gene expression system with dual labeled probes which allowed for analysis of gene expression. Target gene expression was normalized to the GAPDH ubiquitous control in each well utilizing a dual label system. Cp values were measured using a Light Cycler 480 (Roche). The following formula was used to determine relative gene expression: $2^{-(C_tTarget)}/2^{-(C_tControl)}$. Taqman probe catalogue numbers: Mouse C5 (Mm00439275_ml), Mouse GAPDH 4352339E, Mouse TTR (Mm00443267_m1).

Serum Collection:

Blood was collected utilizing the retro-orbital eye bleed procedure 24 hours post the final dose in accordance with the IACUC approved protocol. The sample was collected in Becton Dickinson (BD) serum separator tubes (Fisher Scientific Cat #BD365967). Serum samples were kept at room temperature for 1 hour and then spun in a micro-centrifuge at 22×g at room temperature for 10 minutes. Serum was transferred to 1.5 ml micro-centrifuge tubes for storage at −80° C. Serum collected for the analysis of circulating C5 was kept at room temperature for 15 minutes and then immediately transferred to 4° C. prior to spinning in a micro-centrifuge at 22×g at room temperature for 10 minutes.

Circulating Serum Transthyretin Levels

Serum samples were diluted 1:4000 and assayed using a commercially available kit from ALPCO specific for detection of mouse prealbumin (catalog number 41-PALMS-E01). Protein concentrations (μg/ml) were determined by comparison to a purified TTR standard prepared in-house and the manufacturer's instructions were followed.

Circulating C5 Levels

An ELISA assay was developed to specifically detect circulating mouse C5 levels. The primary antibody was goat-anti-human C5 (Complement Technologies #A220), and the secondary antibody was bovine anti-goat IgG-HRP (Jackson ImmunoResearch 805-035-180), which had minimal cross-reactivity to other species. Antibodies were used 0.8 mg/ml. The assay was developed using a TMB substrate kit, and the reaction was stopped using sulfuric acid prior to measurement. The serum samples were diluted 1 to 5,000 for analysis.

Circulating Angptl3 Levels

An ELISA human angiopoietin-like 3 Quantikine ELISA Kit (R&D Systems Cat #DANL30) was used following the manufacturer's protocol.

Circulating Factor 12 Levels

An ELISA human coagulation Factor XII total antigen ELISA Kit (Molecular Innovations Cat #HFXIIKT-TOT) was used following the manufacturer's protocol.

Circulating Angiotensinogen Levels

An ELISA Human Total Angiotensinogen Assay Kit (IBL Cat #27412) was used following the manufacturer's protocol.

Coprecipitation of RNA with Argonaute (from NHP Livers)

Argonaute proteins were isolated from non-human primate liver lysates using Ago-APP (Argonaute protein Affinity Purification by Peptides) (modified from Hauptmann et al., "Peptide-Based Isolation of Argonaute Protein Complexes Using Ago-APP" in Tamas Dalmay, "MicroRNA Detection and Target Identification: Methods and Protocols, Methods in Molecular Biology," vol. 1580 (Springer 2017), which is incorporated herein by reference in its entirety). Ago-APP relies on a peptide derived from the human protein TNRC6B, which contains several GW (glycine, tryptophan) repeats that are known to bind to two tryptophan-binding pockets on the PIWI domain of argonaute proteins across species. The peptide was further modified to include a GST tag to enable purification from bacteria, and a FLAG tag to enable argonaute pulldowns by magnetic beads coated with anti-FLAG antibodies. Following the incubation of sample lysates with the APP peptide and magnetic beads, a magnet was used to secure the beads while the remaining lysate was removed and discarded. The beads were washed several times to remove nonspecific background interactions. Argonaute-loaded siRNA was eluted by boiling the sample and collecting the eluate for siRNA quantification by RT-qPCR.

Example 3. Determination of Metabolic Stability of Chirally Pure PS Isomers in Mice, Rat, and NHP Oligonucleotides containing chirally pure PS linkages were prepared using the protocols in Examples 1-2 (Approaches 1, 2, and 3). Metabolic stability of chirally-modified internucleotide linkage(s) containing siRNA duplexes were evaluated.

The mrTTR sequences and configuration motifs for the PS chirally-modified siRNA agents are shown in Tables 14-19.

TABLE 14

The sequences and configuration motifs for the chirally-modified duplex

| Duplex | Oligo ID# | S/AS | Sequence (5'-3') | Configuration Motif |
|---|---|---|---|---|
| AD-218596.1 R/4PS mix | 184839 128003 | S AS | (aRs)acaguGfuUfCfUfugcucuauaaL96 usUfsauaGfaGfCfaagaAfcAfcuguususu | R-L96 mix-mix—mix-mix |
| AD-218597.1 S/4PS mix | 184840 128003 | S AS | (aSs)acaguGfuUfCfUfugcucuauaaL96 usUfsauaGfaGfCfaagaAfcAfcuguususu | S—-L96 mix-mix—mix-mix |
| AD-218594.1 mix/4PS mix | 184837 128003 | S AS | asacaguGfuUfCfUfugcucuauaaL96 usUfsauaGfaGfCfaagaAfcAfcuguususu | mix-L96 mix-mix—mix-mix |
| AD-218598.1 2PS/2PS-1PS(S) | 128009 401927 | S AS | asascaguGfuUfCfUfugcucuauaaL96 usUfsauaGfaGfCfaagaAfcAfcuguus(uSs)u | mix-mix—L96 S-mix—mix-mix |
| AD-218599.1 2PS/2PS-1PS(R) | 128049 401926 | S AS | asascaguGfuUfCfUfugcucuauaaL96 usUfsauaGfaGfCfaagaAfcAfcuguus(uRs)u | mix-mix—L96 R-mix—mix-mix |

Figure 95:
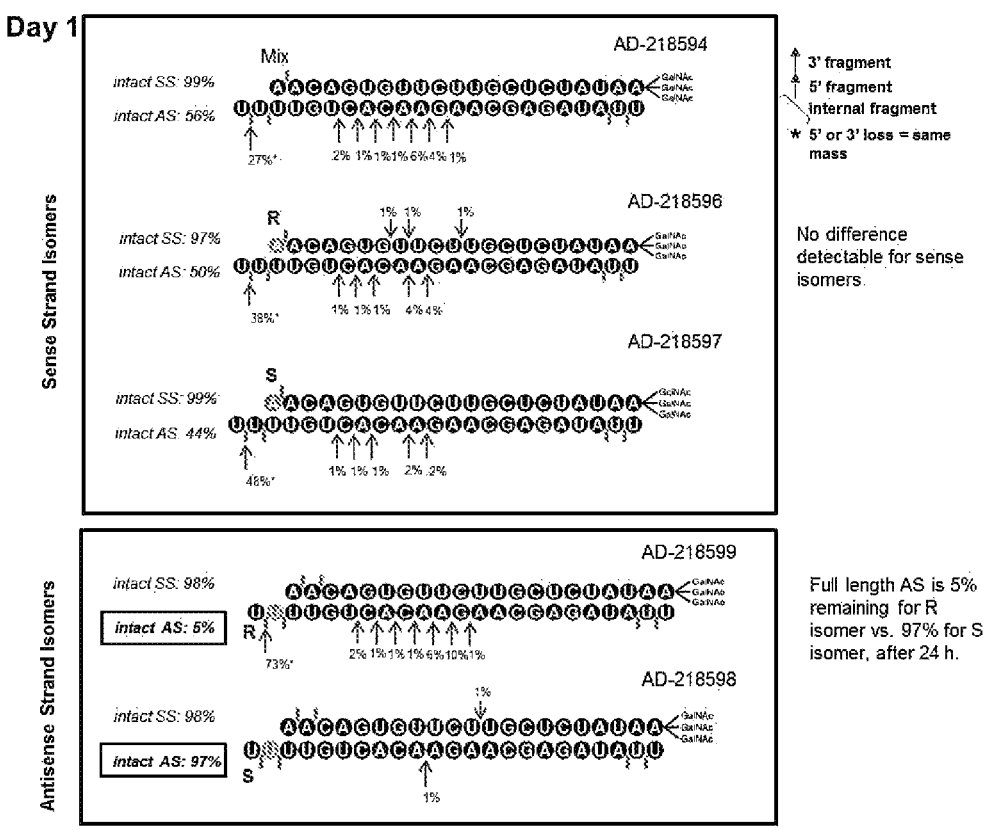
FIG. 95. Day 1 in vivo metabolic stability profiles of sense and antisense strands of m/rTTR siRNA-GalNAc conjugates in female rat.
Figure 96:
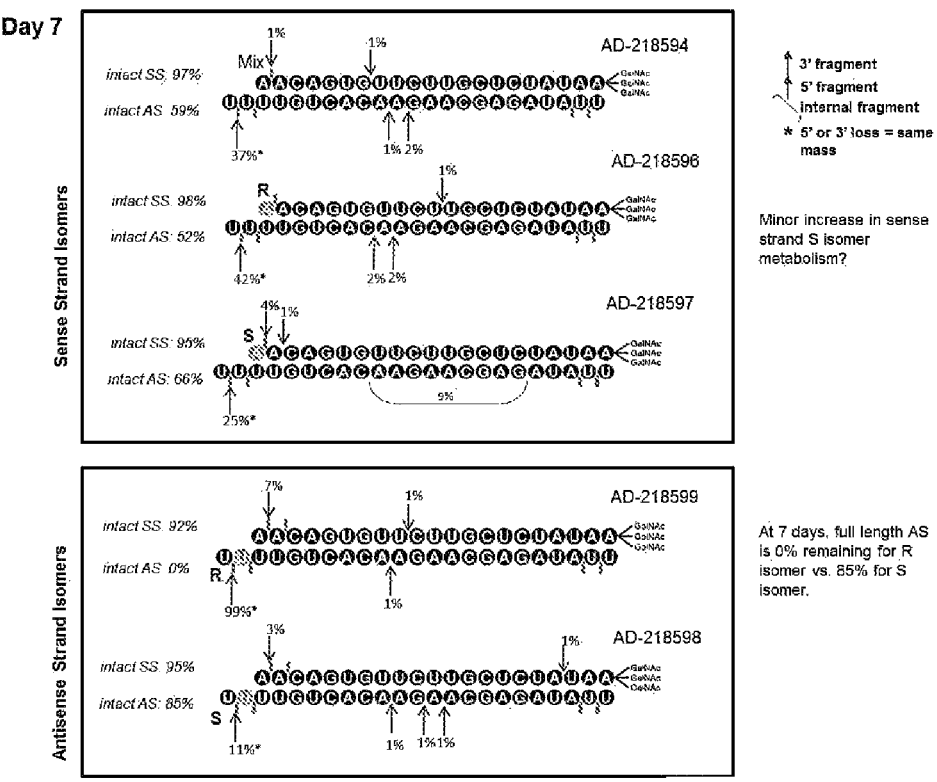
FIG. 96. Day 7 in vivo metabolic stability profiles of sense and antisense strands of m/rTTR siRNA-GalNAc conjugates in female rat.
Figure 97:
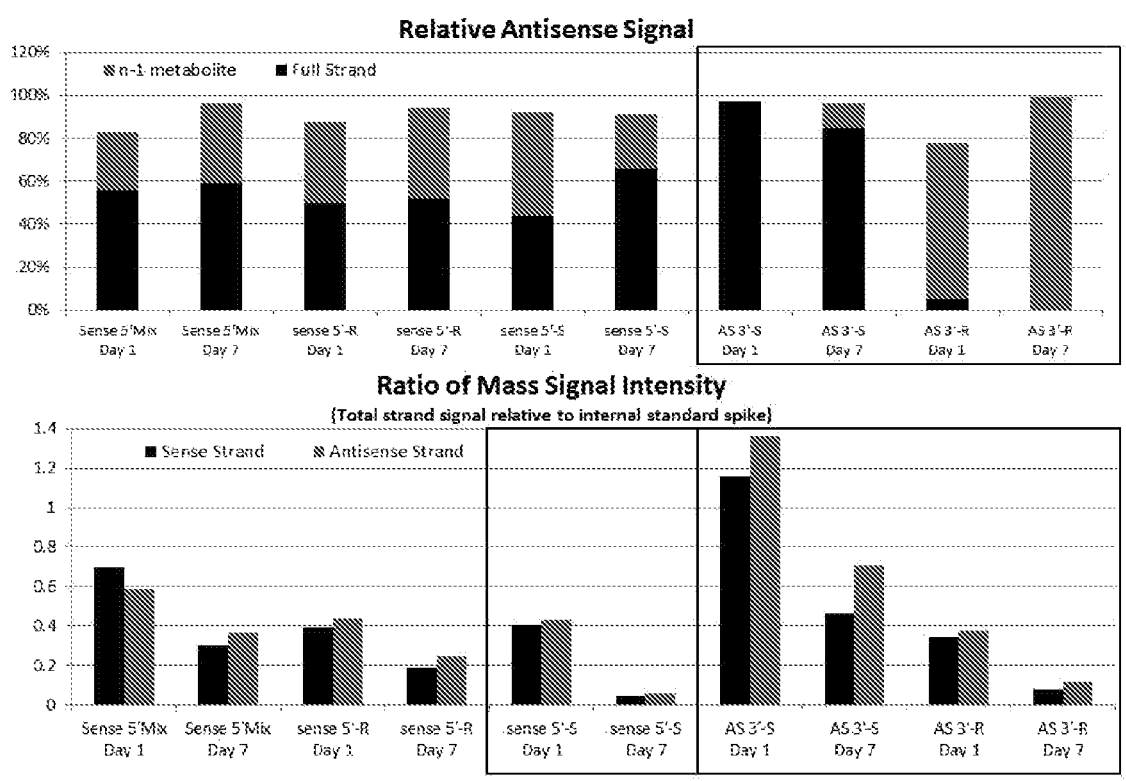
FIG. 97. Days 1 and 7 relative in vivo metabolic stability profiles of sense and antisense strands of m/rTTR siRNA-GalNAc conjugates in female rat.

Exemplary m/rTTR siRNA and its chiral PS siRNA versions were dosed subcutaneously in female rats (n=3) at a single dose of 10 mg/kg. Animals were sacrificed on Days 1 and 7 after dose. Livers were harvested, homogenized, nucleic acids were extracted and analyzed via LC-MS. The results of the relative in vivo metabolic stability profiles of sense and antisense strands of the m/rTTR siRNA-GalNAc conjugates in female rat at Day 1 and Day 7 are shown in FIGS. 95-97. These results indicate that stereochemically pure PS linkages showed a strong impact on exonuclease degradation of modified siRNA.

TABLE 15

The sequences and configuration motifs for the mrTTR PS chirally-modified siRINAs used in a rat in vivo study, where animals were dosed at 0.375 mg/kg and sacrificed at day 7.

| Duplex | Oligo ID# | S/AS | Sequence (5'-3') | Configuration Motif |
|---|---|---|---|---|
| AD-64228 25 6PS Mixture | 128009 128003 | S AS | asascaguGfuUfCfUfugcucuauaaL96 usUfsauaGfaGfCfaagaAfcAfcuguususu | mix-mix—L96 mix-mix—mix-mix |
| AD-157695.1 R/R-S Control | 184839 184841 | S AS | (aRs)acaguGfuUfCfUfugcucuauaaL96 (uRs)UfauaGfaGfCfaagaAfcAfcuguu(uSs)u | R—L96 S—R |
| AD-157697.1 R/R-RS | 184839 250030 | S AS | (aRs)acaguGfuUfCfUfugcucuauaaL96 (uRs)UfauaGfaGfCfaagaAfcAfcugu(uRs)(uSs)u | R—L96 S—R—R |
| AD-157698.1 R/R-SS | 184839 250031 | S AS | (aRs)acaguGfuUfCfUfugcucuauaaL96 (uRs)UfauaGfaGfCfaagaAfcAfcugu(uSs)(uSs)u | R—L96 S—S—R |
| AD-157701.1 R/RR-SS | 184839 184842 | S AS | (aRs)acaguGfuUfCfUfugcucuauaaL96 (uRs)(UfRs)auaGfaGfCfaagaAfcAfcugu(uSs)(uSs)u | R—L96 S—S—R—R |

Endpoint analysis: RISC loading and whole liver exposure. The labels R and S on the figure denote Rp and Sp configuration of the linkage phosphorus atom and mix denotes racemic.

Figure 85:
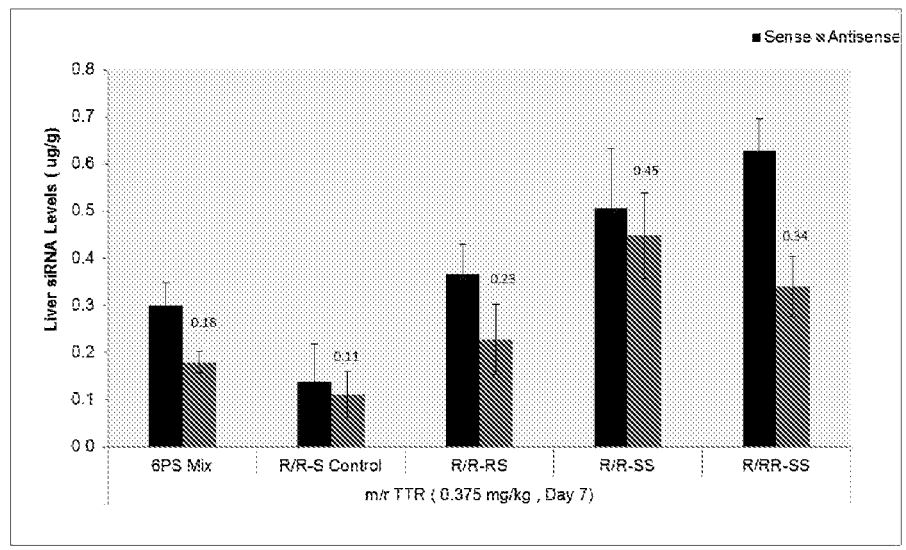
FIG. 85. Whole liver levels of siRNA duplexes with chiral PS isomers. The labels R and S on the figure denote Rp and Sp configuration of the linkage phosphorus atom; mix denotes racemic.
Figure 86:
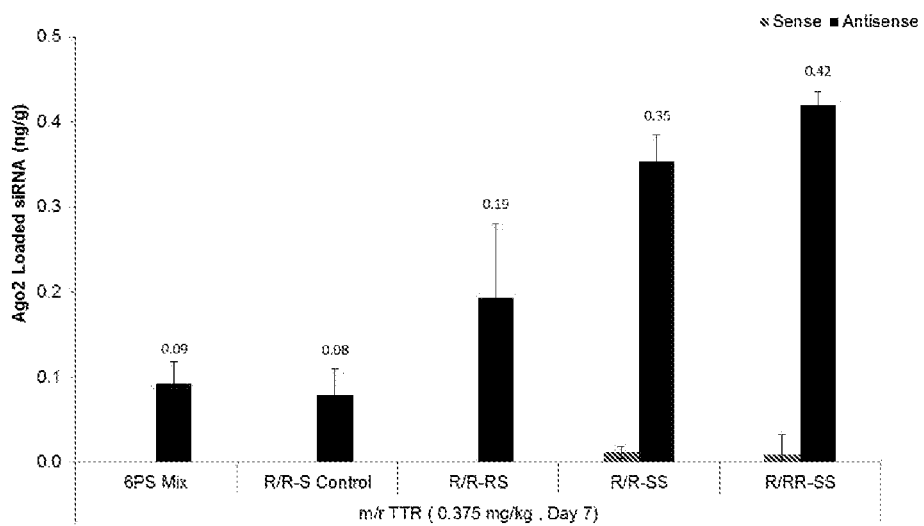
FIG. 86. Ago2 levels of siRNA duplexes with chiral PS isomers. The labels R and S on the figure denote Rp and Sp configuration of the linkage phosphorus atom; mix denotes racemic.
Figure 87:
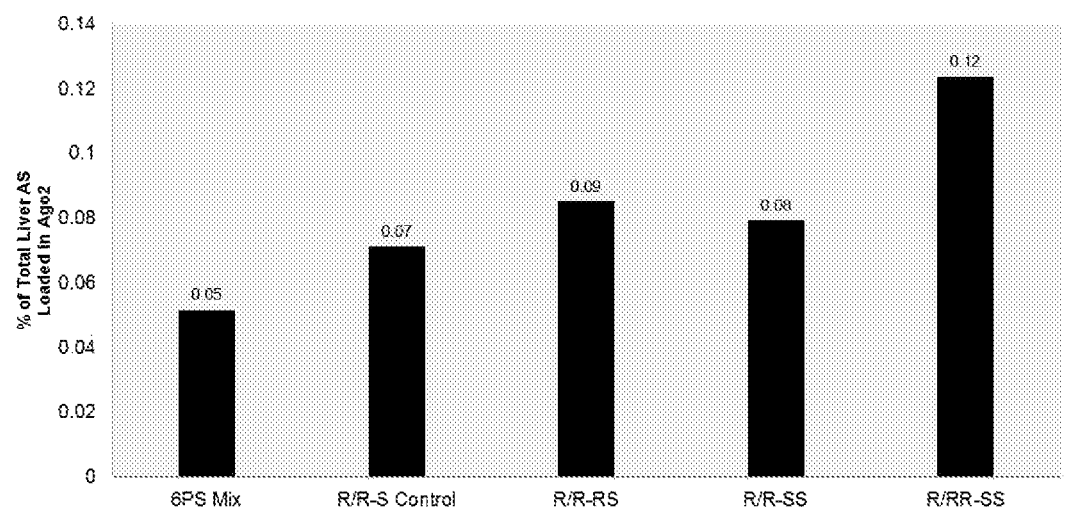
FIG. 87. Percent of total liver level of antisense strand loaded in Ago2. Rp/RpRp-SpSp may be exhibiting better loading or increased residence time in Ago2. The labels R and S on the figure denote Rp and Sp configuration of the linkage phosphorus atom; mix denotes racemic.
Figure 88:
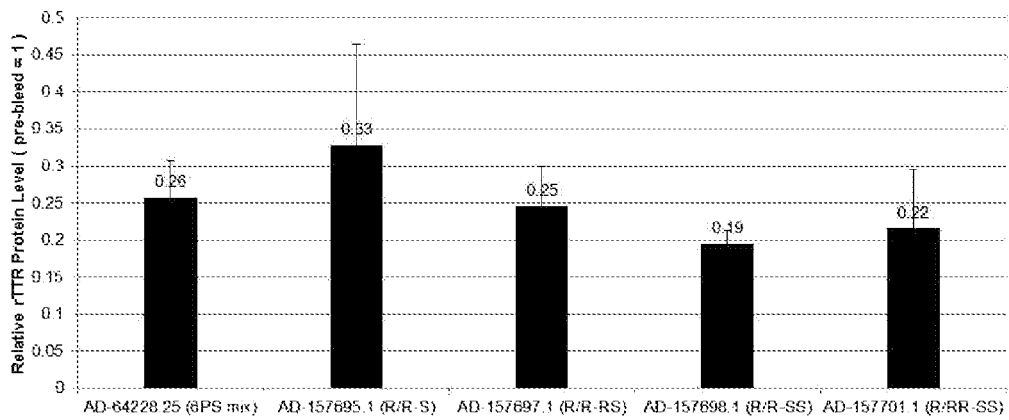
FIG. 88. Gene expression at day 7 to complement liver level and Ago2 loading analysis. Rp-SpSp and RpRp-SpSp antisense strands are quite similar, more potent than Rp-Sp and slightly better than Rp-RpSp, At day 7 Rp-SpSp and RpRp-SpSp have similar efficacy, but may behave differently in terms of duration. The labels R and S on the figure denote Rp and Sp configuration of the linkage phosphorus atom; mix denotes racemic.
Figure 89:
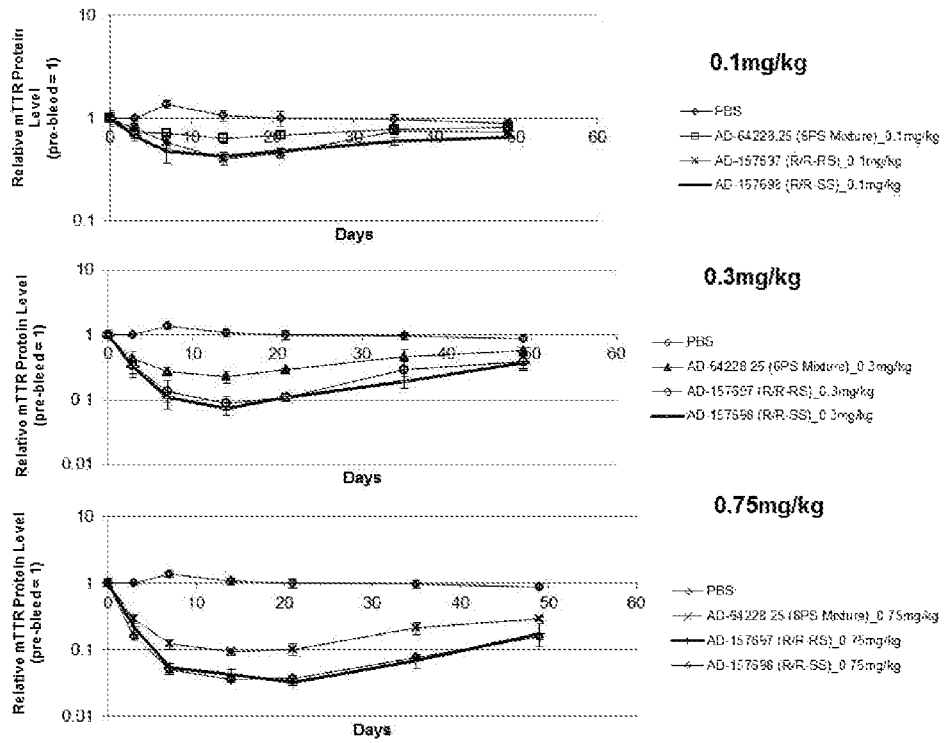
FIG. 89. In vivo mouse dose response study to day 49. Rp/Rp-RpSp and Rp/Rp-SpSp designs were behaving nearly identically across the dose groups in mice (both are better compared to 6PS mix). In rat, benefit was limited to Rp/Rp-SpSp design (or any design with 3'end SpSp configuration). The labels R and S on the figure denote Rp and Sp configuration of the linkage phosphorus atom; mixture denotes racemic.

The whole liver levels of siRNA duplexes at Day 7 are shown in FIG. 85. The total Ago2-levels of the siRNA are shown in FIG. 86, and the total Ago2 percentages of the whole liver levels are shown in FIG. 87. The knockdown at Day 7 (rTTR protein level) is shown in FIG. 88. Additionally, a dose-response in vivo duration study was performed in mouse, comparing AD-157697 (R/R-RS) and AD-157698 (R/R-SS) to AD-64228 (6PS mixture) in ascending doses of 0.1, 0.3, and 0.75 mg/kg. The results are shown in FIG. 89.

TABLE 16

The configuration motifs for the PS chirally-modified siRNAs used in the m/rTTR rat duration study, which were dosed at 0.35 mg/kg.

| Duplex | Motif | | |
|---|---|---|---|
| 6PS Mixture AD-64228 | mix-mix mix-mix | ——— ——— | L96 mix-mix |
| 4PS Best Isomer Combination | R S-S | ——— ——— | L96 R |
| 4PS 1PS mix at 5'end Sense only | mix S-S | ——— ——— | L96 R |

TABLE 16-continued

The configuration motifs for the PS chirally-modified siRNAs used in the m/rTTR rat duration study, which were dosed at 0.35 mg/kg.

| Duplex | Motif | | |
|---|---|---|---|
| 5PS Additional isomer on 3'AS (with double overhang) | R S-S-S R S-S-R | ——— ——— ——— ——— | L96 R L96 R |
| 3PS 3'N-1 AS strand with S only (single overhang) | R S | ——— ——— | L96 R |
| 4PS 1PS mix at 5'end Sense and AS | mix S-S | ——— ——— | L96 mix |
| 6PS 2PS MIX at 5'end Sense and AS | mix-mix S-S | ——— ——— | L96 mix-mix |

The labels R and S on the figure denote Rp and Sp configuration of the linkage phosphorus atom and mix denotes racemic.

Figure 90:
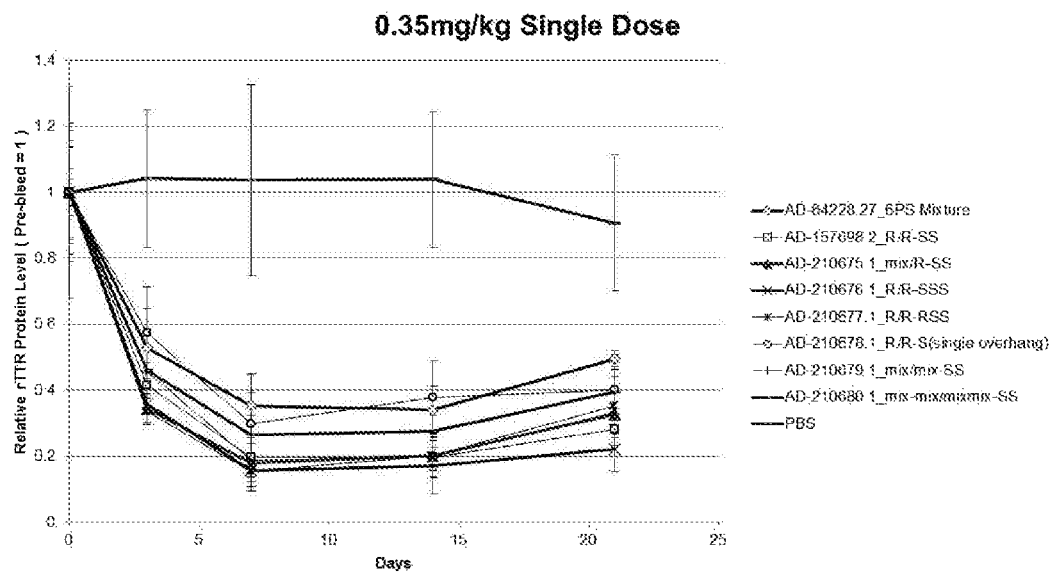
FIG. 90. m/rTTR follow up duration study in rat—data to day 21. The labels R and S on the figure denote Rp and Sp configuration of the linkage phosphorus atom; mixture denotes racemic.
Figure 91:
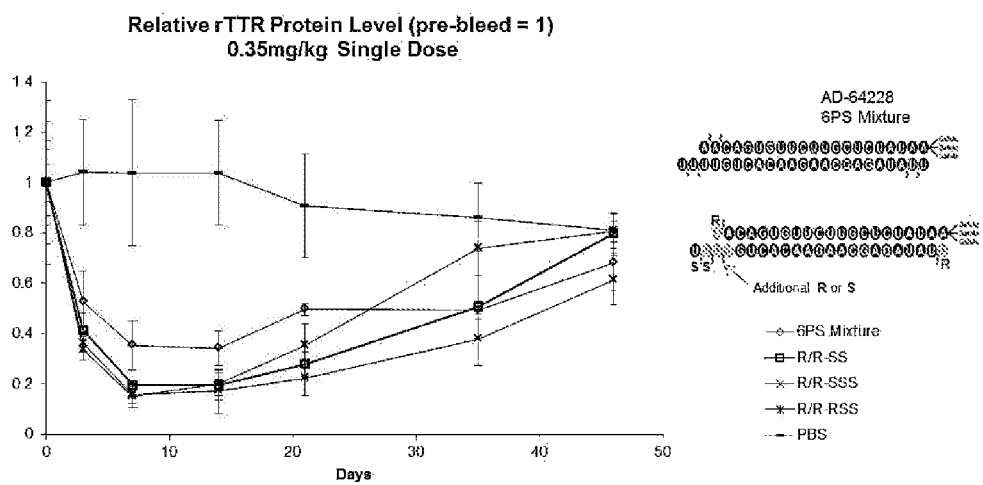
FIG. 91. m/rTTR Duration study—3'end-SSS and —RSS isomers. Small potency boost for both 3'end-SSS and -RSS relative to 3'end SS; improved duration with additional S isomer at this position, consistent with known 3'exonuclease preference.
Figure 92:
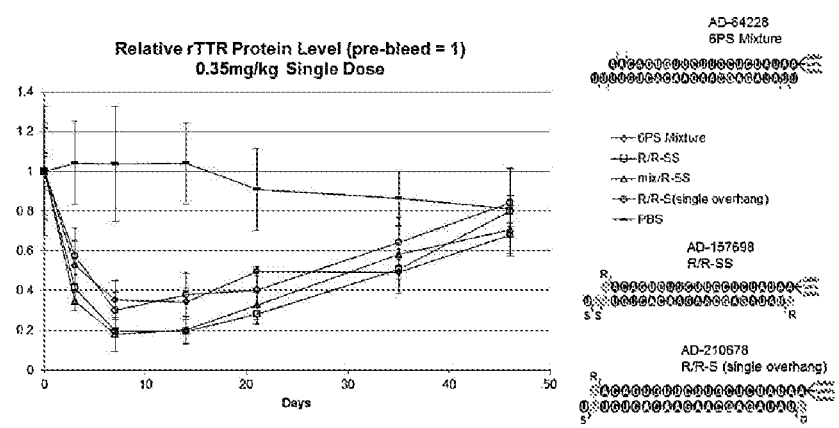
FIG. 92. m/rTTR Duration study results for sense strand mixture and single overhang. Mix/R-SS is equipotent to R/R-SS. R/R-S (single overhang) has identical potency to 6PS mix (and the R/R-S double overhang); consistent with metabolic stability finding: 3'end SS double overhang is stable in vivo and adds a significant potency boost.
Figure 93:
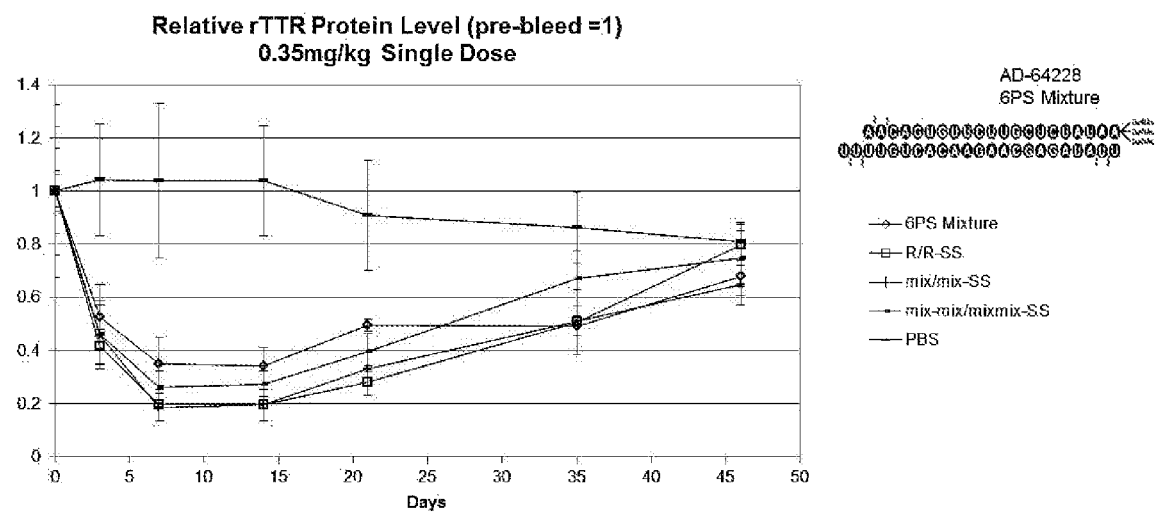
FIG. 93. m/rTTR Results for 1PS and 2PS mixtures on 5'end S/AS. Mix/Mix-SS has efficacy similar to R/R-SS; 5'end 2PS mixture duplex is less potent, closer to 6PS mix FIG. 94. Isomers of PS show characteristic RISC loading in hAgo2. Sense strand loading is lower than usually seen with assay control AD-57727.3PS, 4PS and 5PS mixture duplexes—loading is too low. The Rp-SpSp antisense configuration is clearly the optimal configuration for hAGO2 loading, consistent with in vivo data. The Rp-RpSp antisense showed significantly reduced loading compared to Rp-SpSp. Addition of a third isomer on the 3'end of the antisense (whether Rp or Sp) reduced loading. The labels R and S on the figure denote Rp and Sp configuration of the linkage phosphorus atom; mix/mixture denotes racemic.

FIG. 90 shows the follow-up in vivo activity duration study of all the m/rTTR siRNAs in rat to Day 21. FIGS. 91-93 show the follow-up in vivo activity duration study of all the m/rTTR siRNAs in rat to Day 46, with each figure comparing a different set of siRNA duplexes to the 6PS mixture (AD-64228).

TABLE 17

The sequences and configuration motifs for the PS chirally-modified siRNAs used in the m/rTTR in vitro hAGO2 RISC loading study.

| Duplex | Oligo ID# | S/AS | Sequence (5'-3') | Configuration Motif |
|---|---|---|---|---|
| AD-157694.1 3PS Mixture | 184837 184838 | S AS | asacaguGfuUfCfUfugcucuauaaL96 usUfauaGfaGfCfaagaAfcAfcuguuusu | mix—L96 mix—mix |
| AD-210977.1 4PS Mixture | 184837 380480 | S AS | asacaguGfuUfCfUfugcucuauaaL96 usUfauaGfaGfCfaagaAfcAfcuguususu | mix—L96 mix-mix—mix |
| AD-210975.1 5PS Mixture | 184837 380481 | S AS | asacaguGfuUfCfUfugcucuauaaL96 usUfauaGfaGfCfaagaAfcAfcugusususu | mix—L96 mix-mix-mix—mix |
| AD-210976.1 mix/R-S | 184837 184841 | S AS | asacaguGfuUfCfUfugcucuauaaL96 (uRs)UfauaGfaGfCfaagaAfcAfcuguu(uSs)u | mix—L96 S—R |

TABLE 17-continued

The sequences and configuration motifs for the PS chirally-modified siRNAs used in the m/rTTR in vitro hAGO2 RISC loading study.

| Duplex | Oligo ID# | S/AS | Sequence (5'-3') | Configuration Motif |
|---|---|---|---|---|
| AD-210675.2 mix/R-SS | 184837 250031 | S AS | asacaguGfuUfCfUfugcucuauaaL96 (uRs)UfaUaGfaGfCfaagaAfcAfcugu(uSs)(uSs)u | mix—L96 S-S-R |
| AD-210978.1 mix/R-SSS | 184837 380483 | S AS | asacaguGfuUfCfUfugcucuauaaL96 (uRs)UfauaGfaGfCfaagaAfcAfcug(uSs)(uSs)(uSs)u | mix—L96 S-S-S-R |
| AD-210979.1 mix/S-SS | 184837 380482 | S AS | asacaguGfuUfCfUfugcucuauaaL96 (uSs)UfauaGfaGfCfaagaAfcAfcugu(uSs)(uSs)u | mix—L96 S-S-S |
| AD-210980.1 mix/R-RS | 184837 250030 | S AS | asacaguGfuUfCfUfugcucuauaaL96 (uRs)UfauaGfaGfCfaagaAfcAfcugu(uRs)(uSs)u | mix—L96 S-R-R |
| AD-210981.1 mix/R-RRS | 184837 380485 | S AS | asacaguGfuUfCfUfugcucuauaaL96 (uRs)UfauaGfaGfCfaagaAfcAfcug(uRs)(uRs)(uSs)u | mix—L96 S-R-R-R |
| AD-210735.1 mix/R-RSS | 184837 380484 | S AS | asacaguGfuUfCfUfugcucuauaaL96 (uRs)UfauaGfaGfCfaagaAfcAfcug(uRs)(uSs)(uSs)u | mix—L96 S-S-R-R |

The labels R and S on the figure denote Rp and Sp configuration of the linkage phosphorus atom; mix denotes racemic.

Figure 94:
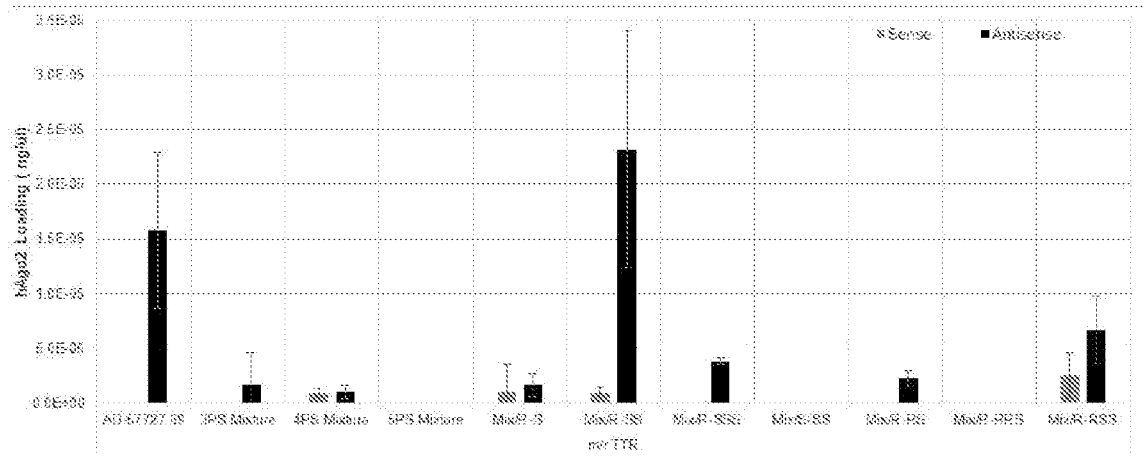

The hAgo2 loading levels for these siRNA duplexes are shown in FIG. 94.

TABLE 18

The sequences and configuration motifs for the PS chirally-modified duplexes used in free uptake and transfection in vitro studies in Primary Mouse Hepatocytes.

| Duplex | Oligo ID # | S/AS | Sequence (5/-3') | Configuration Motif |
|---|---|---|---|---|
| AD-64228.25 6PS Mixture | 128009 128003 | S AS | asascaguGfuUfCfUfugcucuauaaL96 usUfsauaGfaGfCfaagaAfcAfcuguususu | mix-mix—L96 mix-mix—mix-mix |
| AD-157694.1 3PS Mixture | 184837 184838 | S AS | asacaguGfuUfCfUfugcucuauaaL96 usUfauaGfaGfCfaagaAfcAfcuguuusu | mix—L96 mix—mix |
| AD-157695.1 R/R-S Control | 184839 184841 | S AS | (aRs)acaguGfuUfCfUfugcucuauaaL96 (uRs)UfauaGfaGfCfaagaAfcAfcuguu(uSs)u | —L96 S— |
| AD-157696.1 S/R-S Control | 184840 184841 | S AS | (aSs)acaguGfuUfCfUfugcucuauaaL96 (uRs)UfauaGfaGfCfaagaAfcAfcuguu(uSs)u | S—L96 S— |
| AD-157697.1 R/R-RS | 184839 250030 | S AS | (aRs)acaguGfuUfCfUfugcucuauaaL96 (uRs)UfauaGfaGfCfaagaAfcAfcugu(uRs)(uSs)u | —L96 S— |
| AD-157698.1 R/R-SS | 184839 250031 | S AS | (aRs)acaguGfuUfCfUfugcucuauaaL96 (uRs)UfauaGfaGfCfaagaAfcAfcugu(uSs)(uSs)u | —L96 S-S— |
| AD-157699.1 R/RR-S | 184839 250032 | S AS | (aRs)acaguGfuUfCfUfugcucuauaaL96 (uRs)(UfRs)auaGfaGfCfaagaAfcAfcuguu(uSs)u | —L96 S— |
| AD-157700.1 R/RS-S | 184839 250033 | S AS | (aRs)acaguGfuUfCfUfugcucuauaaL96 (uRs)(UfSs)auaGfaGfCfaagaAfcAfcuguu(uSs)u | —L96 S—S |
| AD-157701.1 R/RR-SS | 184839 184842 | S AS | (aRs)acaguGfuUfUfugcucuauaaL96 (uRs)(UfRs)auaGfaGfCfaagaAfcAfcugu(uSs)(uSs)u | —L96 S-S— |
| AD-157702.1 mix-mix/RR-SS | 128009 184842 | S AS | asascaguGfuUfCfUfugcucuauaaL96 (uRs)(UfRs)auaGfaGfCfaagaAfcAfcugu(uSs)(uSs)u | mix-mix—L96 S-S— |
| AD-74959.2 No PS control | 150198 150199 | S AS | aacaguGfuUfCfUfugcucuauaaL96 uUfauaGfaGfCfaagaAfcAfcuguuuu | —L96 — |

Figure 78:
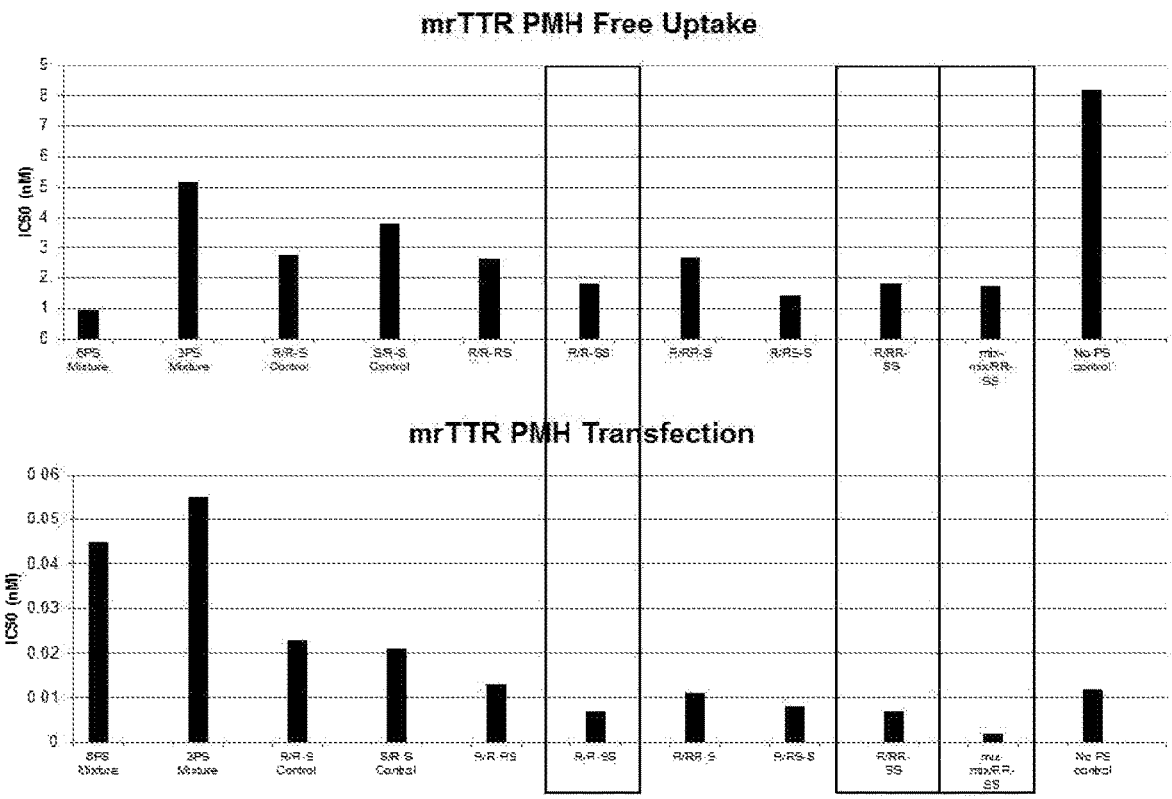
FIG. 78. mrTTR ELF In Vitro IC50—Freeuptake and Transfection. Compounds with SpSp on 3'end show the best activity, consistent with in vivo findings. The labels R and S on the figure denote Rp and Sp configuration of the linkage phosphorus atom; denotes racemic.
Figure 79:
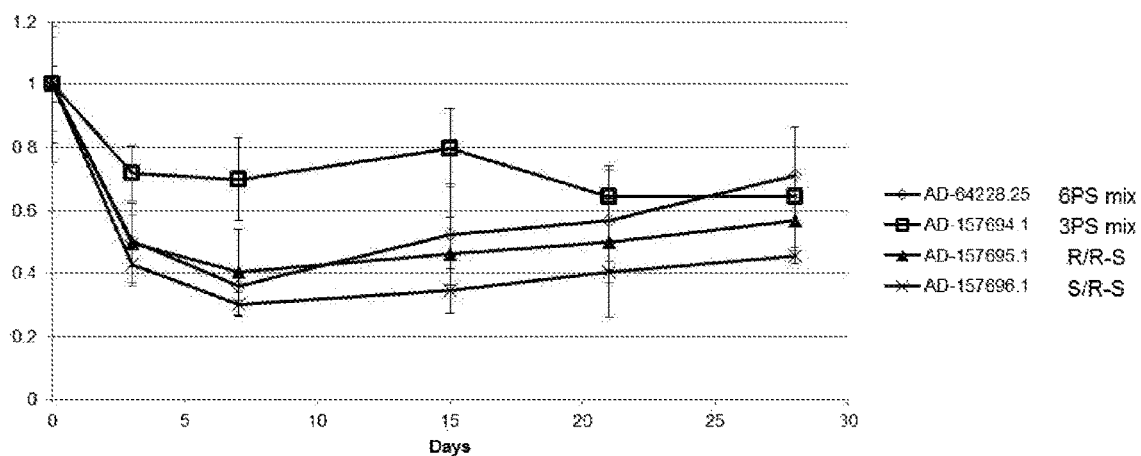
FIG. 79. Efficacy and duration for m/rTTR ELF 3PS chiral pure controls. Rp/Rp-Sp and Sp/Rp-Sp were as active as the 6PS mix and both have better duration. Sp/Rp-Sp is outperforming Rp/Rp-Sp. The labels R and S on the figure denote Rp and Sp configuration of the linkage phosphorus atom; mix denotes racemic.
Figure 80:
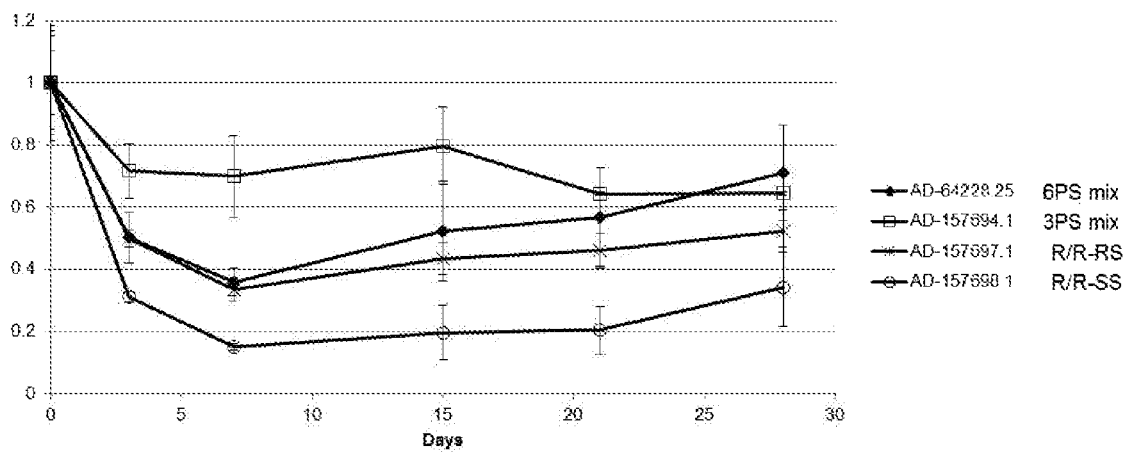
FIG. 80. Efficacy and duration for compounds with additional chiral PS at internal 3'end AS position. The chiral pure 4PS with a 3'SpSp chirality is considerably more active than the 6PS mix and the Rp/Rp-Sp chiral pure control. Additional Rp configuration at internal 3'AS position produced no improvement over Rp/Rp-Sp. The labels R and S on the figure denote Rp and Sp configuration of the linkage phosphorus atom; mix denotes racemic.
Figure 81:
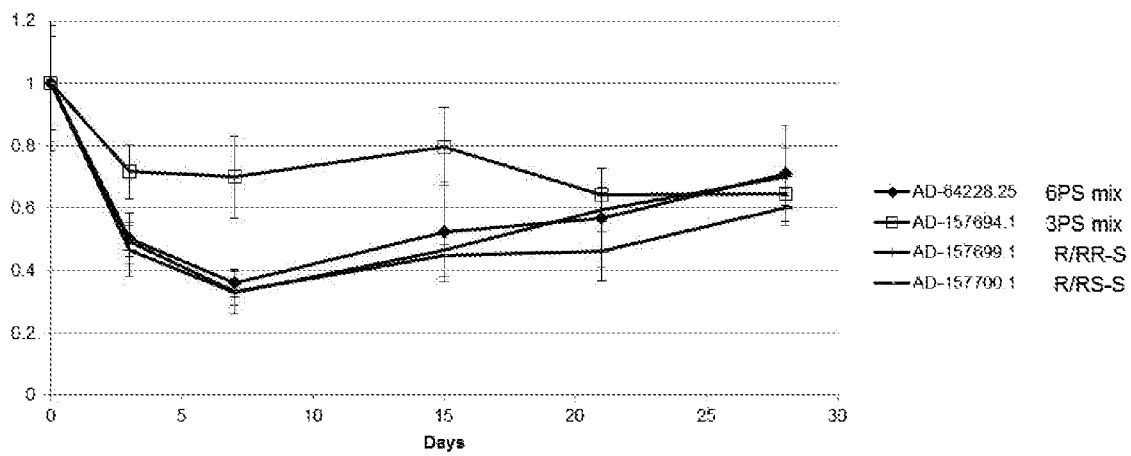
FIG. 81. Efficacy and duration of compounds with additional chiral PS at internal 5'end AS position. The chiral pure 4PS with a 5'RpRp or RpSp chirality doesn't improve activity over the 6PS mix (or the Rp/Rp-Sp chiral pure control). The labels R and S on the figure denote Rp and Sp configuration of the linkage phosphorus atom; mix denotes racemic.
Figure 82:
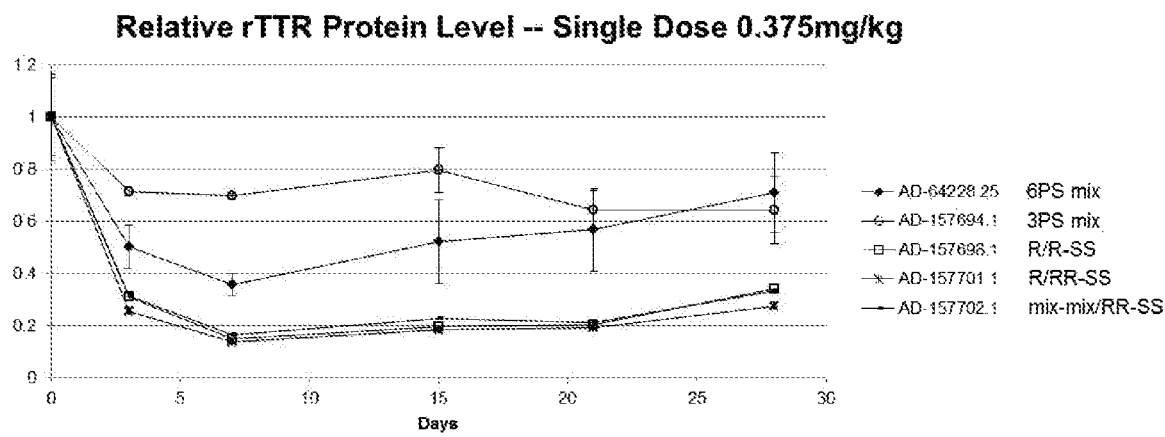
FIG. 82. Efficacy and duration for m/rTTR ELF 5PS and 6PS chiral pure in rats. The chiral pure 4PS Rp/Rp-SpSp was as active as the 5PS Rp/RpRp-SpSp. The chiral pure 5PS Rp/RpRp-SpSp was as active as the 6PS mix-mix/RpRp-SpSp. The labels R and S on the figure denote Rp and Sp configuration of the linkage phosphorus atom; mix denotes racemic.
Figure 83:
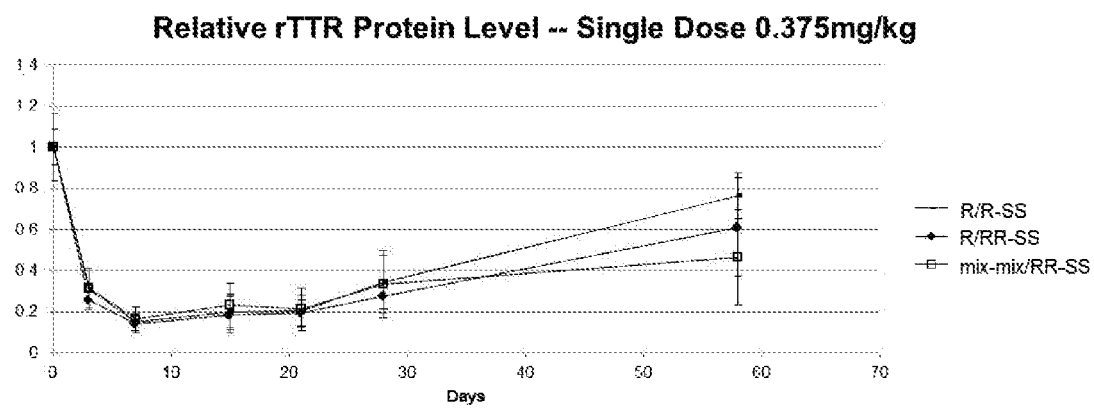
FIG. 83. Additional 5'end internal PS (on sense and antisense) show improved duration. Sp isomer at internal 5'end of AS maintained potency and improved duration similarly to Rp. The labels R and S on the figure denote Rp and Sp configuration of the linkage phosphorus atom; mix denotes racemic.
Figure 84:
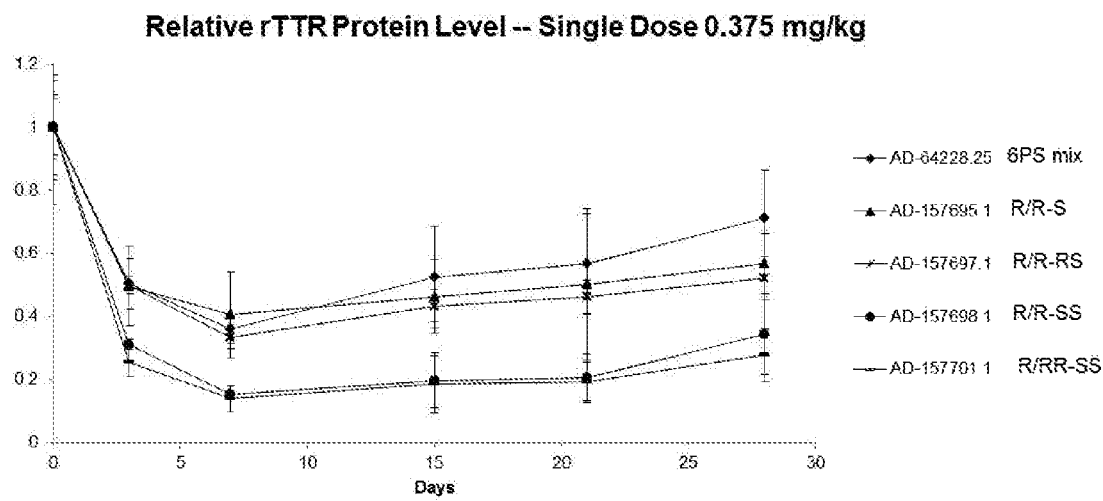
FIG. 84. Efficacy and duration for m/rTTR ELF 4PS and 5PS chiral pure in rats. Both chiral pure compounds with 3'end SpSp are considerably more active than the 6PS mix, the Rp/Rp-Sp chiral pure control, and the 4PS Rp/Rp-RpSp. The labels R and S on the figure denote Rp and Sp configuration of the linkage phosphorus atom; mix denotes racemic.

The labels R and S on the figure denote Rp and Sp configuration of the linkage phosphorus atom; mix denotes racemic. The in vitro IC50 values for these siRNA duplexes are shown in FIG. 78.

Figure 99A:
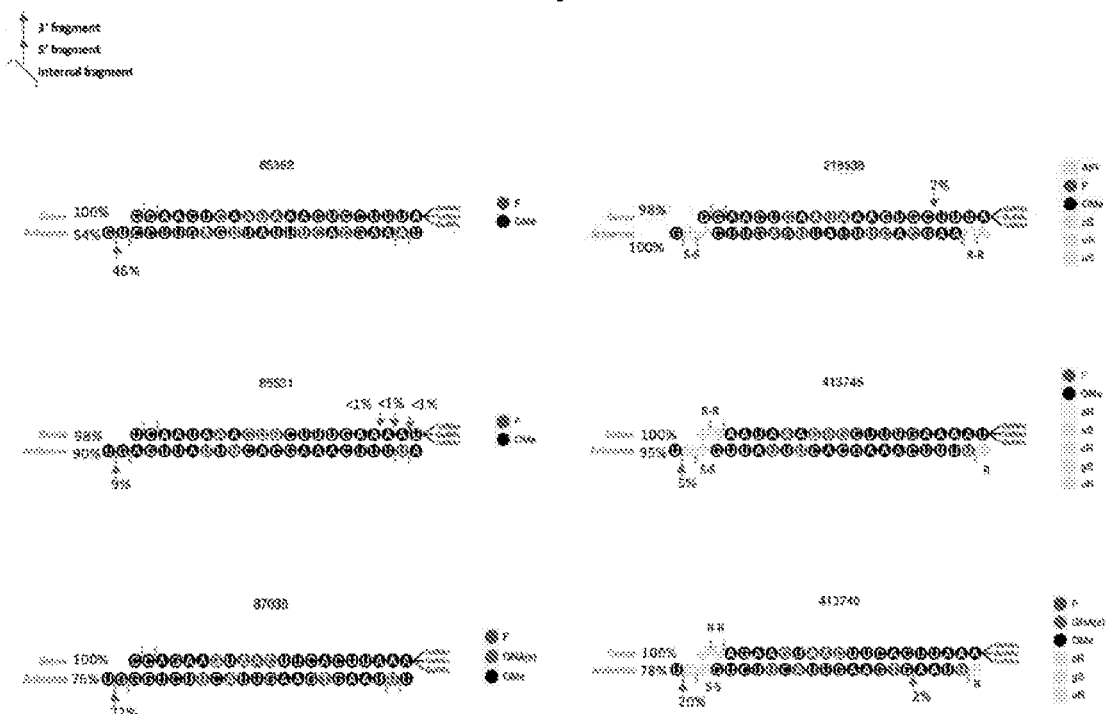
FIG. 99. Day 1 (FIG. 99A) and Day 7 (FIG. 99B) relative in vivo metabolic stability profiles of sense and antisense strands of the F12 and Angtpl3 (ANG) siRNAs and their chiral PS siRNA versions in mice (n=1) at a single dose of 10 mg/kg, analyzed via LC-MS.
Figure 99B:
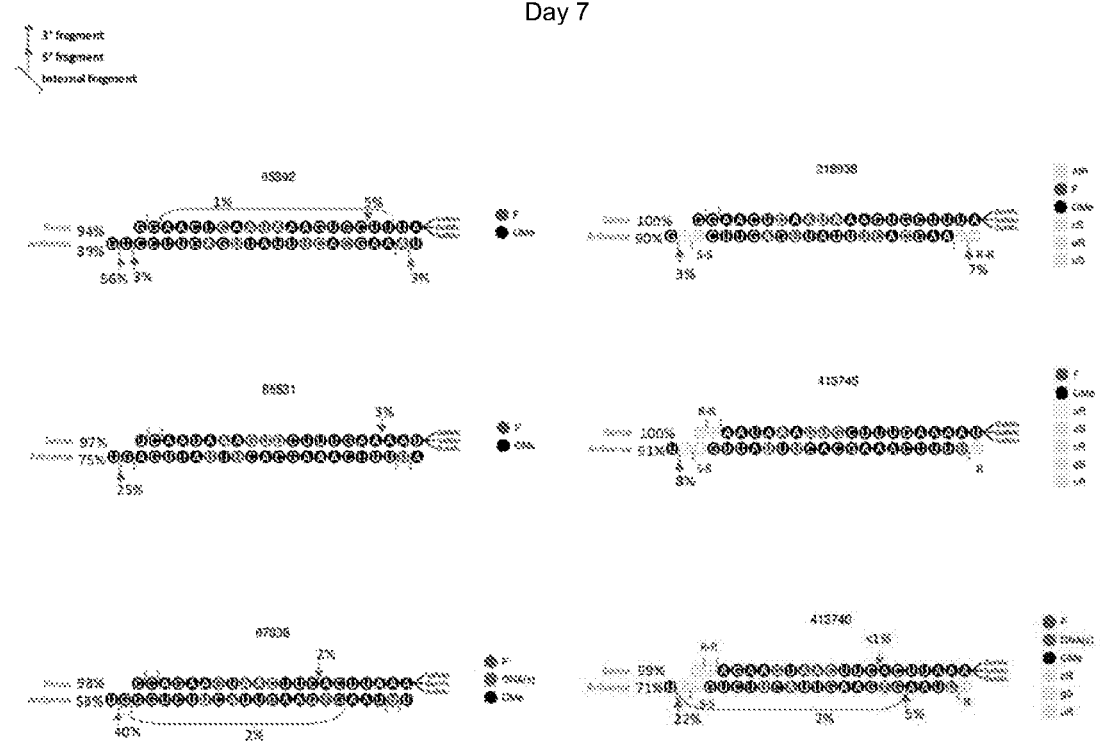

LC-MS. The results of the relative in vivo metabolic stability profiles of sense and antisense strands of the F12 siRNA and its chiral PS siRNA versions in mice at Day 1 and Day 7 are shown in FIGS. 99A-99B. These results indicate that

TABLE 19

The sequences and configuration motifs for the PS chirally-modified siRNAs used in the m/rTTR duration study in rat: dosed at 0.375 mg/kg.

| Duplex | Oligo ID # | S/AS | Sequence (5'-3') | Configuration Motif |
|---|---|---|---|---|
| AD-64228.25 | 128009 | S | asascaguGfuUfCfUfugcucuauaaL96 | mix-mix L96 |
| 6PS Mixture | 128003 | AS | usUfsauaGfaGfCfaagaAfcAfcuguususu | mix-mix mix-mix |
| AD-157694.1 | 184837 | S | asacaguGfuUfCfUfugcucuauaaL96 | mix L96 |
| 3PS Mixture | 184838 | AS | usUfauaGfaGfCfaagaAfcAfcuguuusu | mix mix |
| AD-157695.1 | 184839 | S | (aRs)acaguGfuUfCfUfugcucuauaaL96 | R L96 |
| R/R-S Control | 184841 | AS | (uRs)UfauaGfaGfCfaagaAfcAfcuguu(uSs)u | S R |
| AD-157696.1 | 184840 | S | (aSs)acaguGfuUfCfUfugcucuauaaL96 | S L96 |
| S/R-S Control | 184841 | AS | (uRs)UfauaGfaGfCfaagaAfcAgcuguu(uSs)u | S R |
| AD-157697.1 | 184839 | S | (aRs)acaguGfuUfCfUfugcucuauaaL96 | R L96 |
| R/R-RS | 250030 | AS | (uRs)UfauaGfaGfCfaagaAfcAfcugu(uRs)(uSs)u | S-R R |
| AD-157698.1 | 184839 | S | (aRs)acaguGfuUfCfUfugcucuauaaL96 | R L96 |
| R/R-SS | 250031 | AS | (uRs)UfauaGfaGfCfaagaAfcAfcugu(uSs)(uSs)u | S-S R |
| AD-157699.1 | 184839 | S | (aRs)acaguGfuUfCfUfugcucuauaaL96 | R L96 |
| R/RR-S | 250032 | AS | (uRs)(UfRs)auaGfaGfCfaagaAfcAfcuguu(uSs)u | S R-R |
| AD-157700.1 | 184839 | S | (aRs)acaguGfuUfCfUfugcucuauaaL96 | R L96 |
| R/RS-S | 250033 | AS | (uRs)(UfSs)auaGfaGfCfaagaAfcAfcuguu(uSs)u | S S-R |
| AD-157701.1 | 184839 | S | (aRs)acaguGfuUfCfUfugcucuauaaL96 | R L96 |
| R/RR-SS | 184842 | AS | (uRs)(UfRs)auaGfaGfCfaagaAfcAfcugu(uSs)(uSs)u | S-S R-R |
| AD-157702.1 | 128009 | S | asascaguGfuUfCfUfugcucuauaaL96 | mix-mix L96 |
| mix-mix/RR-SS | 184842 | AS | (uRs)(UfRs)auaGfaGfCfaagaAfcAgcugu(uSs)(uSs)u | S-S R-R |

FIGS. 79-84 show the results of the in vivo activity for various groupings of these compounds in rat. All figures show the activity to Day 28, except FIG. 83, which shows the the activity data to Day 58 for the three most potent compounds.

Rp and Sp Isomers affected in vivo stability of the site-specific chirally-modified internucleotide-containing siRNAs. The Sp isomer on the 3'-end of the antisense strand added stability to the m/rTTR duplex whereas the Rp isomer on the 3'-end of the antisense strand added liability to the m/rTTR duplex. Fixed isomers on the 5'-end of the sense strand did not improve stability over the parent; a minor increase in the metabolism of the S-isomer on the sense strand was observed (see FIG. 96).

Figure 98A:
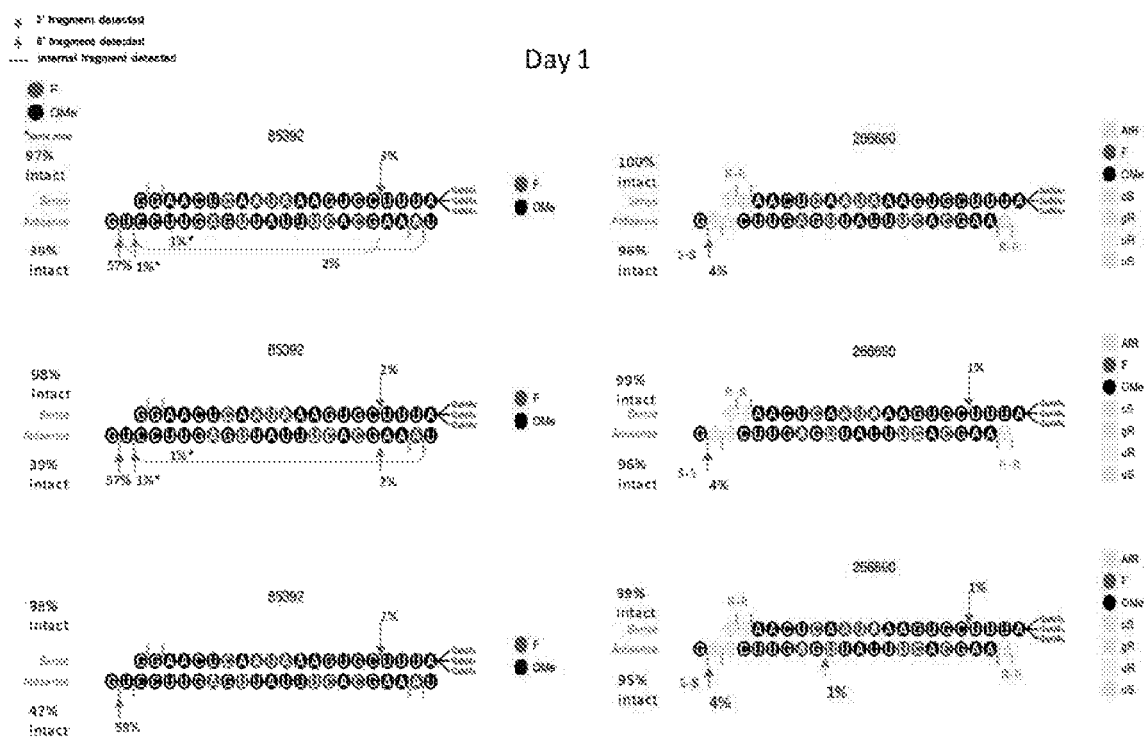
FIG. 98. Day 1 (FIG. 98A) and Day 4 (FIG. 98B) relative in vivo metabolic stability profiles of sense and antisense strands of the F12 siRNA and its chiral PS siRNA versions in female rats (n=3) at a single dose of 10 mg/kg, analyzed via the strand signal intensity relative to internal standard (IS) measured by LC-MS (FIG. 98C).
Figure 98B:
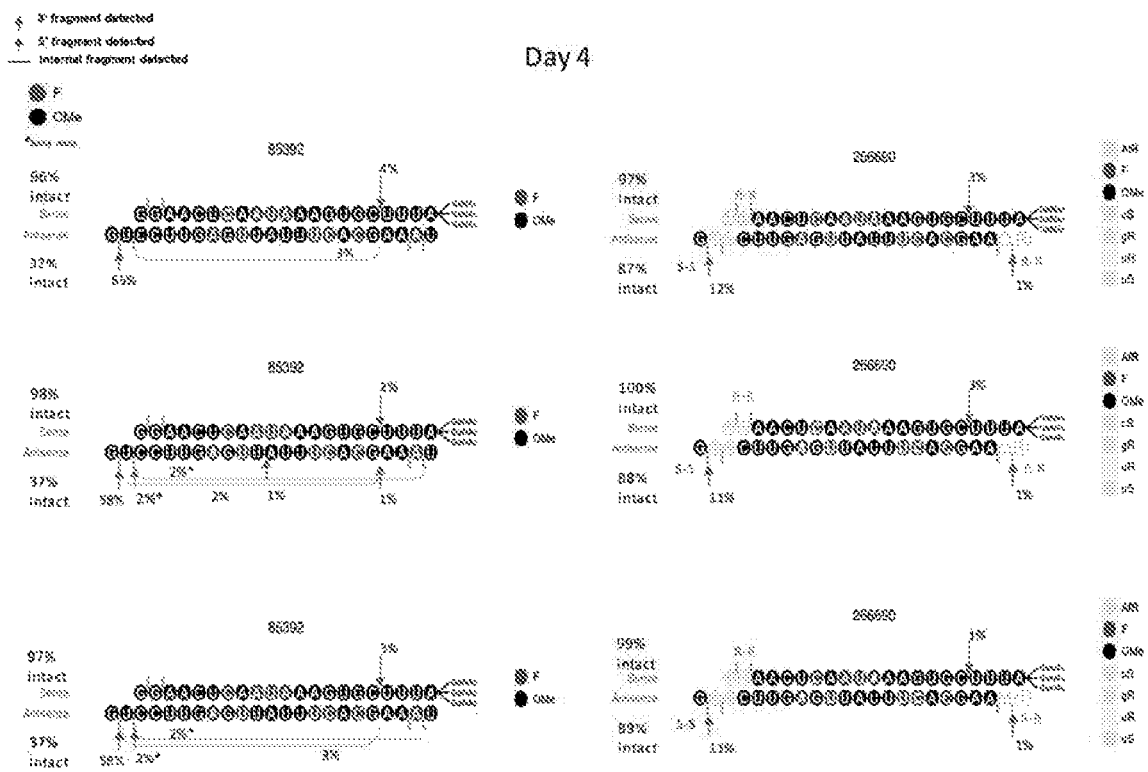
Figure 98C:
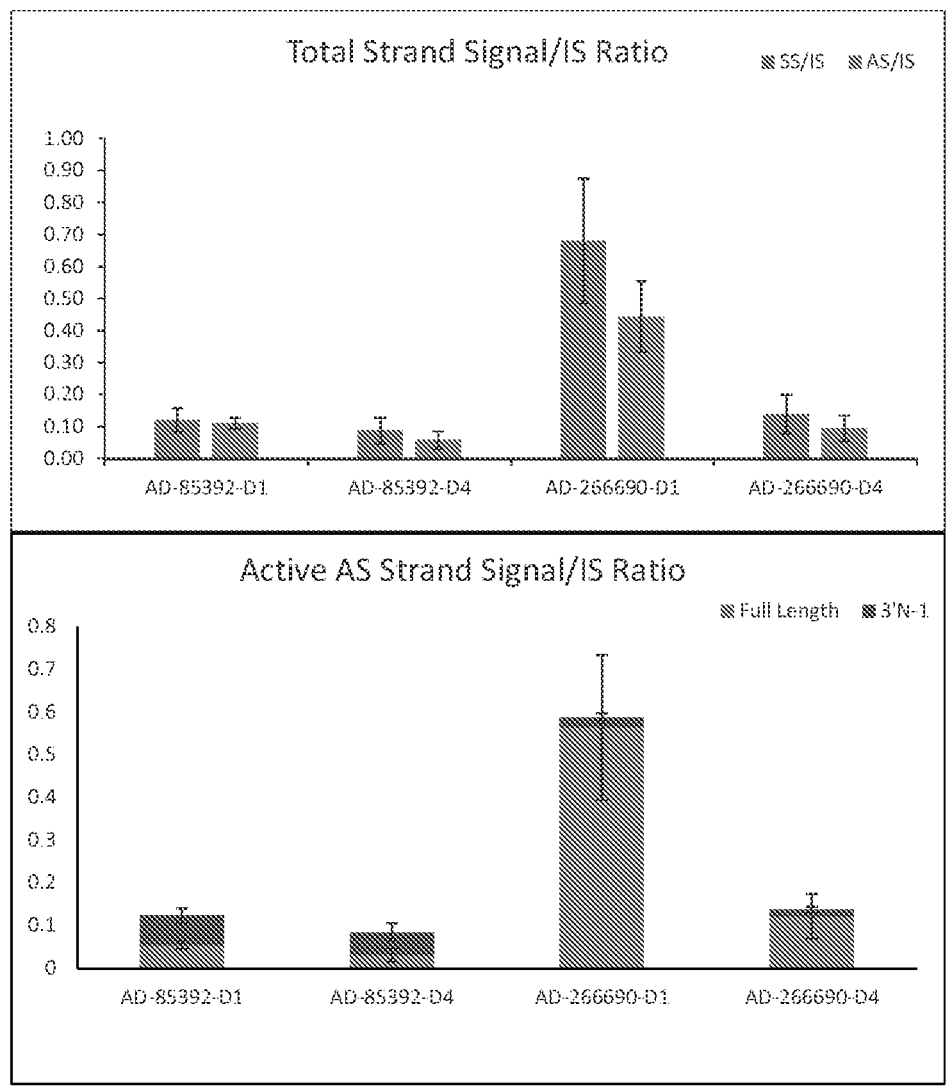

Exemplary F12 siRNA and its chiral PS siRNA versions were dosed subcutaneously in female rats (n=3) at a single dose of 10 mg/kg. Animals were sacrificed on Days 1 and 4 after dose. Livers were harvested, homogenized, nucleic acids were extracted and analyzed via LC-MS. The results of the relative in vivo metabolic stability profiles of sense and antisense strands of the F12 siRNA and its chiral PS siRNA versions in female rat at Day 1 and Day 4 are shown in FIGS. 98A-98C. These results indicate that stereochemically pure PS linkages showed a strong impact on the exonuclease degradation of the modified siRNA.

Exemplary F12 and Angtp13 (ANG) siRNAs and their chiral PS siRNA versions were dosed subcutaneously in mice (n=1) at a single dose of 10 mg/kg. Animals were sacrificed on Day 1 or 7 after dose. Livers were harvested, homogenized, nucleic acids were extracted and analyzed via stereochemically pure PS linkages showed an impact on the exonuclease degradation of the modified siRNA.

Figure 100:
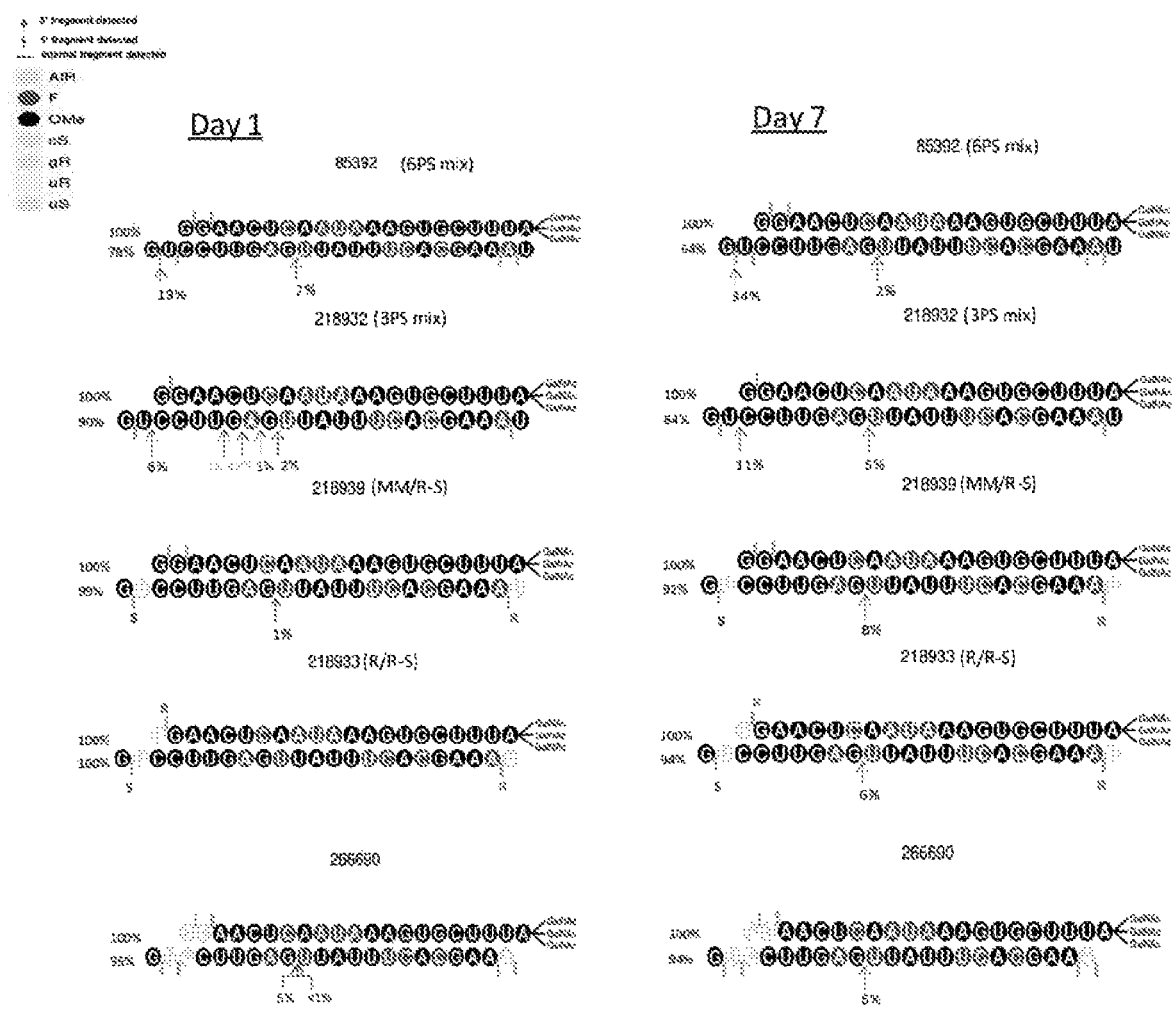
FIG. 100. Day 1 and Day 7 relative in vivo metabolic stability profiles of sense and antisense strands of the F12 siRNA and its chiral PS siRNA versions in NHP (n=1) at a single dose of 1 mg/kg, analyzed via LC-MS.

Exemplary F12 siRNA and its chiral PS siRNA versions were dosed subcutaneously in NHP (n=1) at a single dose of 1 mg/kg. Liver biopsies were taken on Day 1 or Day 7 after dose. Liver biopsies were processed, homogenized, and nucleic acids were extracted and analyzed via LC-MS. The results of the relative in vivo metabolic stability profiles of sense and antisense strands of the F12 siRNA and its chiral PS siRNA versions in NHP at Days 1 and 7 are shown in FIG. 100. These results indicate that stereochemically pure PS linkages showed an impact on the exonuclease degradation of the modified siRNA.

Figure 101A:
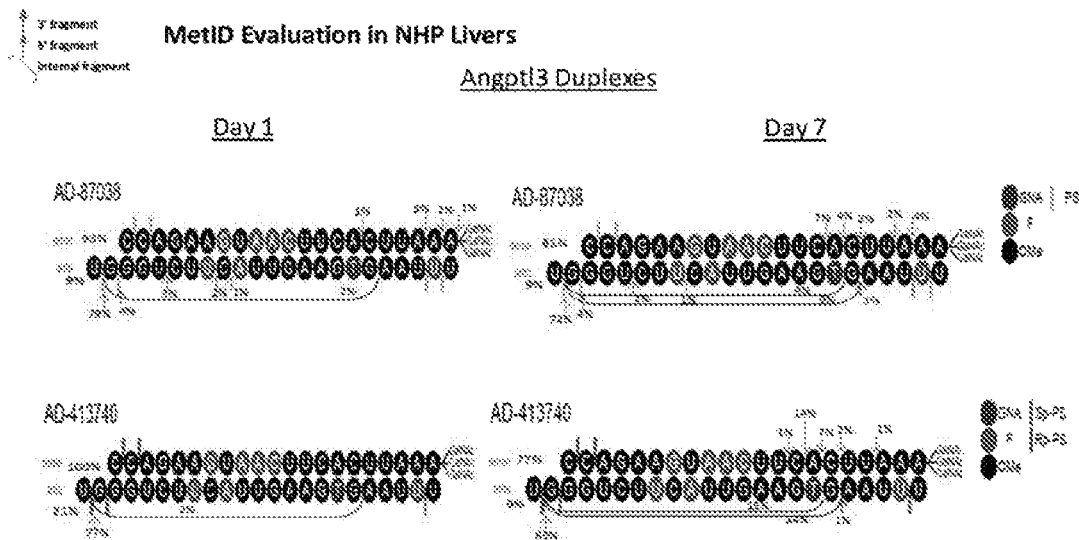
FIG. 101. Day 1 and Day 7 relative in vivo metabolic stability profiles of sense and antisense strands of the Angptl3 (ANG) and its chiral PS siRNA versions in NHP (n=1) at a single dose of 3 mg/kg (FIG. 101A), analyzed via LC-MS (FIG. 101B).
Figure 101B:
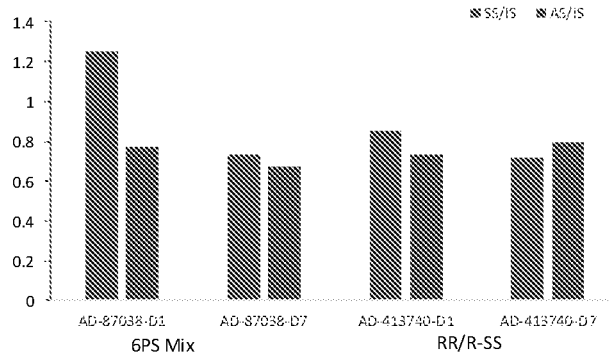
Figure 101B:
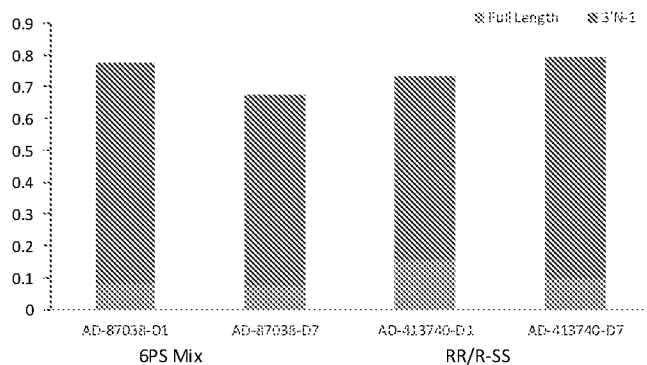

Exemplary Angptl3 (ANG) siRNA and its chiral PS siRNA versions were dosed subcutaneously in NHP (n=1) at a single dose of 3 mg/kg. Liver biopsies were taken on Day 1 or Day 7 after dose. Liver biopsies were processed, homogenized, and nucleic acids were extracted and analyzed via LC-MS. The results of the relative in vivo metabolic stability profiles of sense and antisense strands of the ANG siRNA and its chiral PS siRNA versions in NHP at Days 1 and 7 are shown in FIGS. 101A-101B. These results indicate that stereochemically pure PS linkages showed no impact on the exonuclease degradation of the modified siRNA.

Figure 103A:
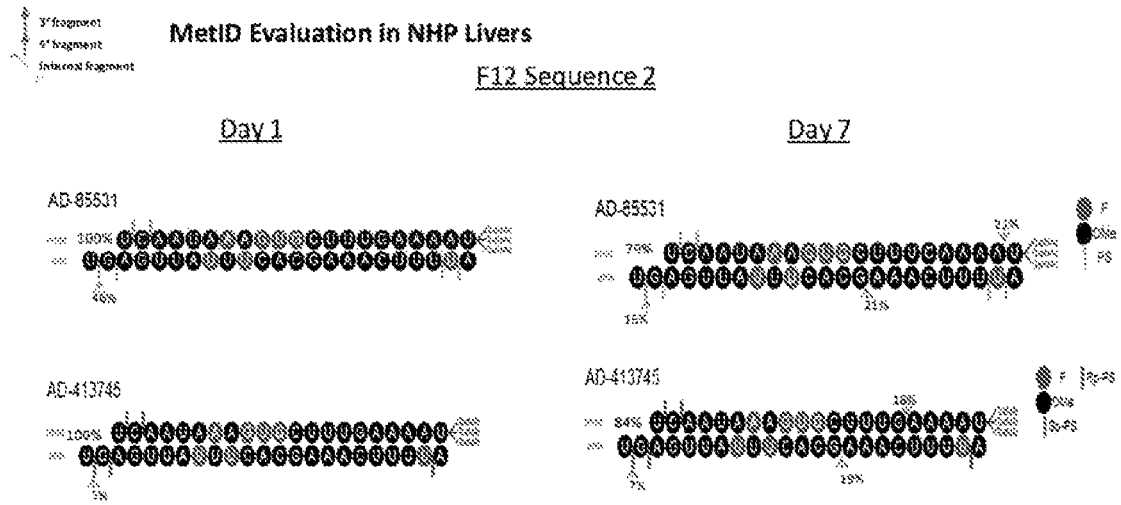
FIG. 103. Day 1 and Day 7 relative in vivo metabolic stability profiles of sense and antisense strands of the F12 Sequence 2 and its chiral PS siRNA versions in NHP (n=1) at a single dose of 1 mg/kg (FIG. 103A), analyzed via LC-MS (FIG. 103B).
Figure 103B:
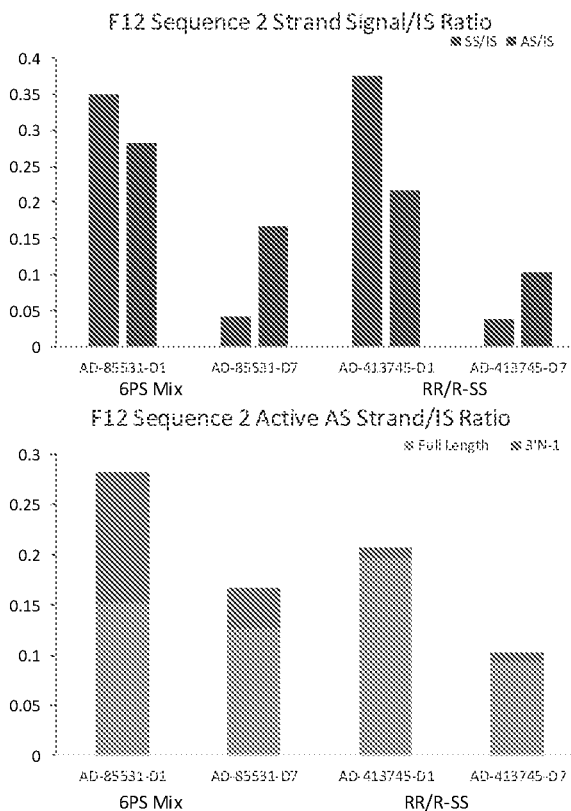

Exemplary F12 Sequence 2 siRNA and its chiral PS siRNA versions were dosed subcutaneously in NHP (n=1) at a single dose of 1 mg/kg. Liver biopsies were taken on Day 1 or Day 7 after dose. Liver biopsies were processed, homogenized, and nucleic acids were extracted and analyzed via LC-MS. The results of the relative in vivo metabolic stability profiles of sense and antisense strands of the F12 Sequence 2 siRNA and its chiral PS siRNA versions in NHP at Days 1 and 7 are shown in FIGS. 103A-103B. These results indicate that stereochemically pure PS linkages showed an impact on the exonuclease degradation of the modified siRNA.

Figure 102A:
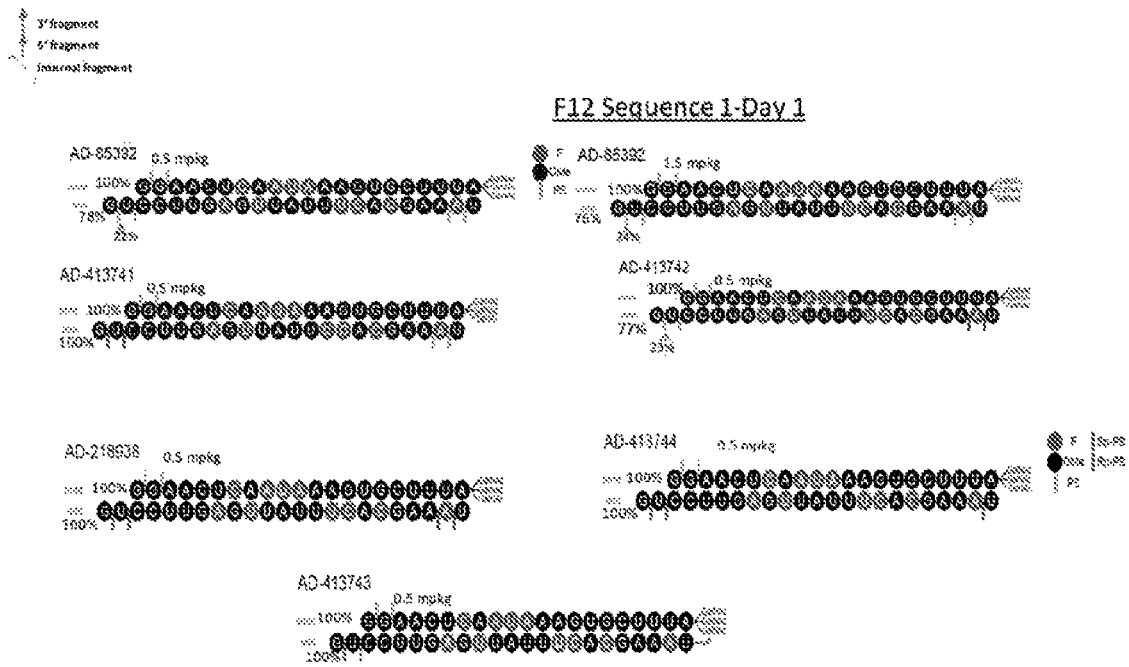
FIG. 102. Day 1 (FIG. 102A) and Day 7 (FIG. 102B) relative in vivo metabolic stability profiles of sense and antisense strands of the F12 Sequence 1 and its chiral PS siRNA versions in NHP (n=1) at a single dose of 1.5 or 0.5 mg/kg, analyzed via LC-MS (FIG. 102C).
Figure 102B:
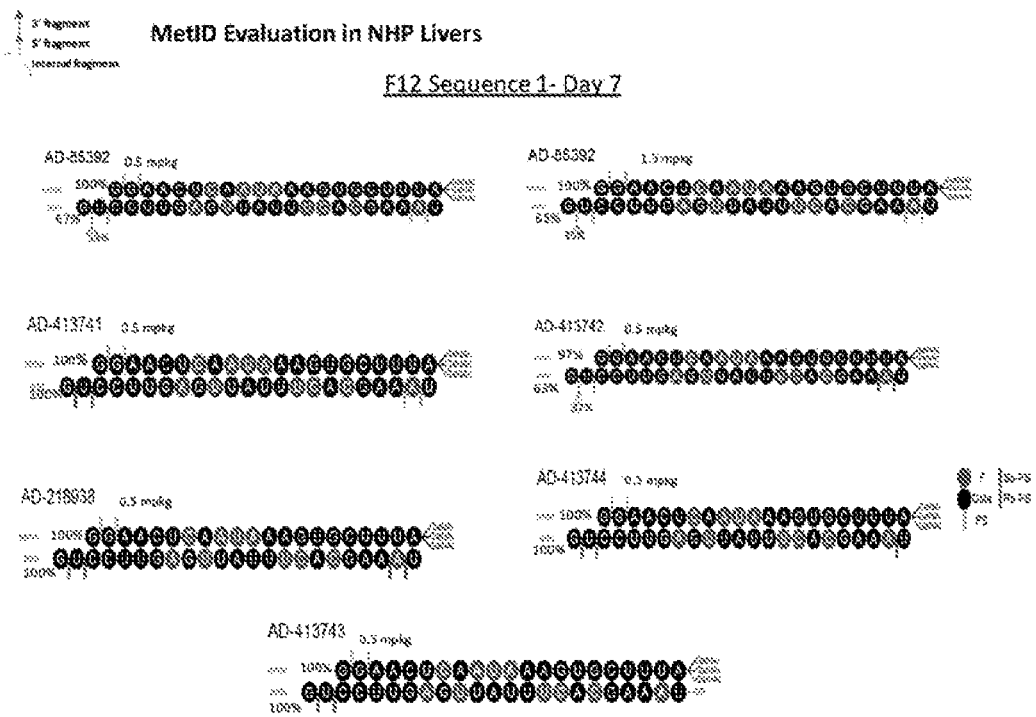
Figure 102C:
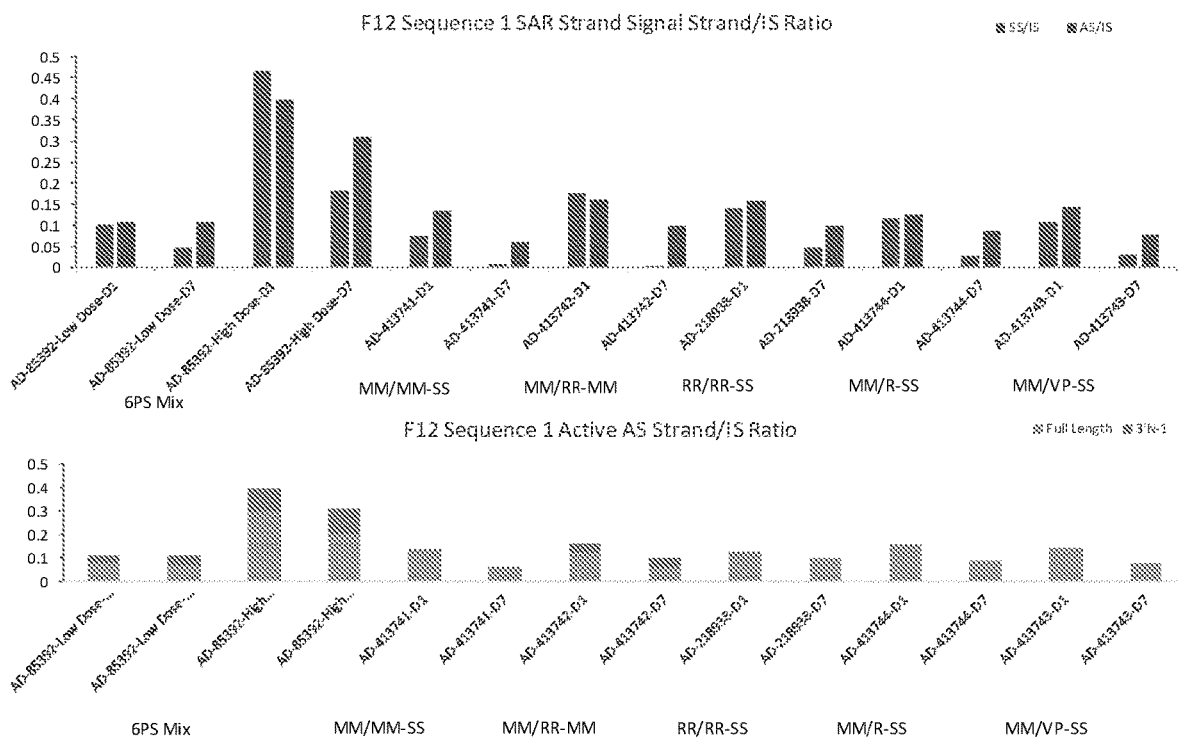

Exemplary F12 Sequence 1 siRNA and its chiral PS siRNA versions were dosed subcutaneously in NHP (n=1) at a single dose of 1.5 or 0.5 mg/kg. Liver biopsies were taken on Days 1 or 7 after dose. Liver biopsies were processed, homogenized, and nucleic acids were extracted and analyzed via LC-MS. The results of the relative in vivo metabolic stability profiles of sense and antisense strands of the F12 Sequence 1 and its chiral PS siRNA versions in NHP at Days 1 and 7 are shown in FIGS. 102A-102C. These results indicate that stereochemically pure PS linkages showed an impact on the exonuclease degradation of the modified siRNA.

Figures 104C, 105A:
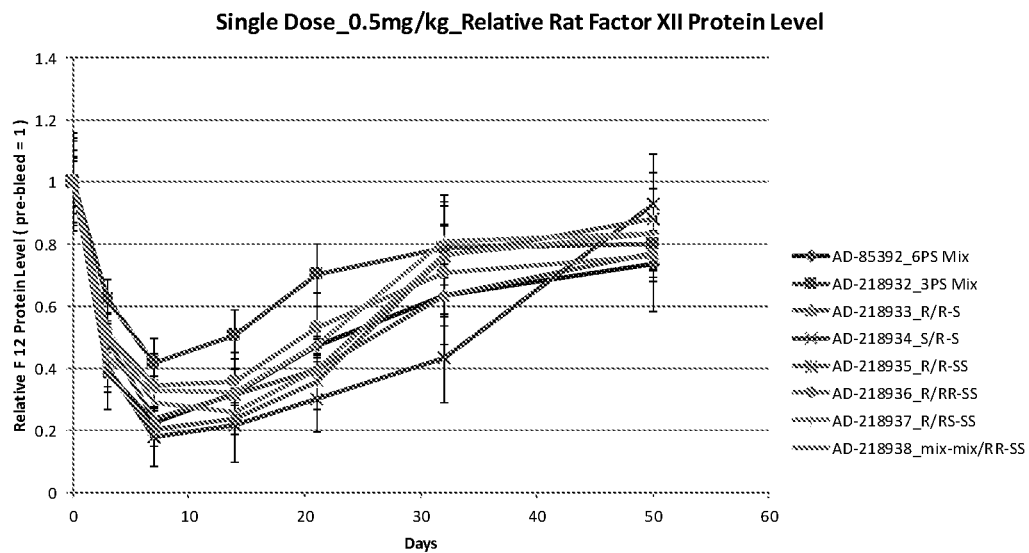
FIG. 104C shows the results of the F12 ELF duration study to Day 50.
FIG. 105A shows the study design for the duration study, including the configuration motifs for the F12 PS chirally-modified siRNAs used, dosage used, and the durations of the study.

Example 4. Evaluation of the Potency of Chirally Pure PS Isomers In Vitro and in Mice, Rat, and NHP Duration Study of Exemplary F12 siRNA and its Chiral PS siRNA Versions in Rats Exemplary F12 ELF siRNA and its chiral PS siRNA versions were studied for duration study in rats, and the results are shown in FIGS. 104A-104C. FIG. 104A shows the study design for the duration study, including the configuration motifs for the chirally-modified siRNAs used, animals and dosage used, and the durations of the study. FIG. 104B lists the F12 ELF isomers used for the duration study in rats. FIG. 104C shows the results of the F12 ELF duration study to Day 50.

Duration Study of Exemplary F12 ELF siRNA and its Sense Strand Chiral PS Isomers in Rats Exemplary F12 ELF siRNA and its sense strand chiral PS isomers were studied for in vivo relative protein expression levels in rats to Day 28, and the results are shown in FIGS. 105A-105C. FIG. 105A shows the study design for the duration study, including the configuration motifs for the chirally-modified siRNAs used, animals and dosage used, and the durations of the study. FIG. 105B lists the F12 ELF sense strand isomers used for the duration study in rats. FIG. 105C shows the results of the F12 ELF sense strand isomers duration study to Day 28.

Figures 106C, 107A:
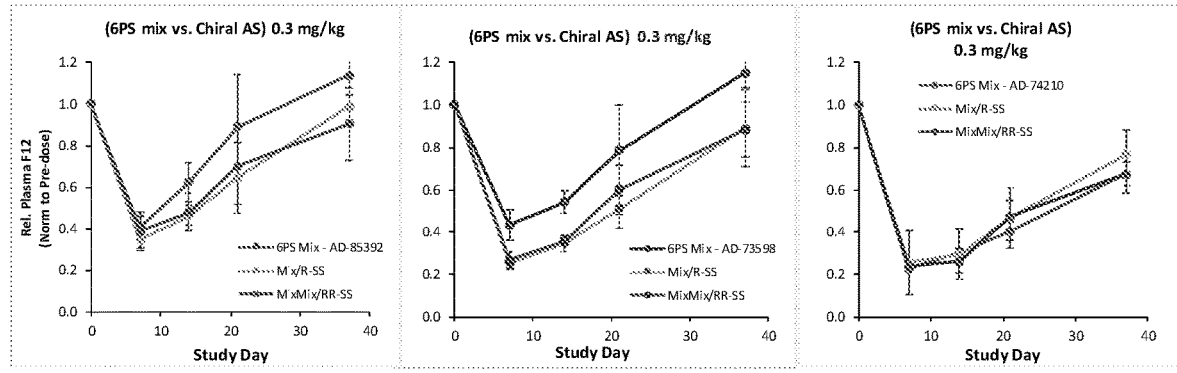
FIG. 106C shows the results of the F12 ELF relative plasma expression levels to Day 35.
FIG. 107A lists the sequences and configuration motifs for the F12 ELF chirally-modified siRNA used.

In Vivio Mouse Study of Exemplary F12 ELF siRNA and its Chiral PS siRNA Versions Exemplary F12 ELF siRNA and its chiral PS siRNA versions were studied for in vivo relative plasma expression levels in mice to Day 35, and the results are shown in FIGS. 106A-106C. FIG. 106A shows the study design, including the sequence variables and configuration motifs for the chirally-modified siRNAs used, dosage used, and the durations of the study. FIG. 106B lists the F12 ELF isomers used. FIG. 106C shows the results of the F12 ELF relative plasma expression levels to Day 35.

Figure 107B:
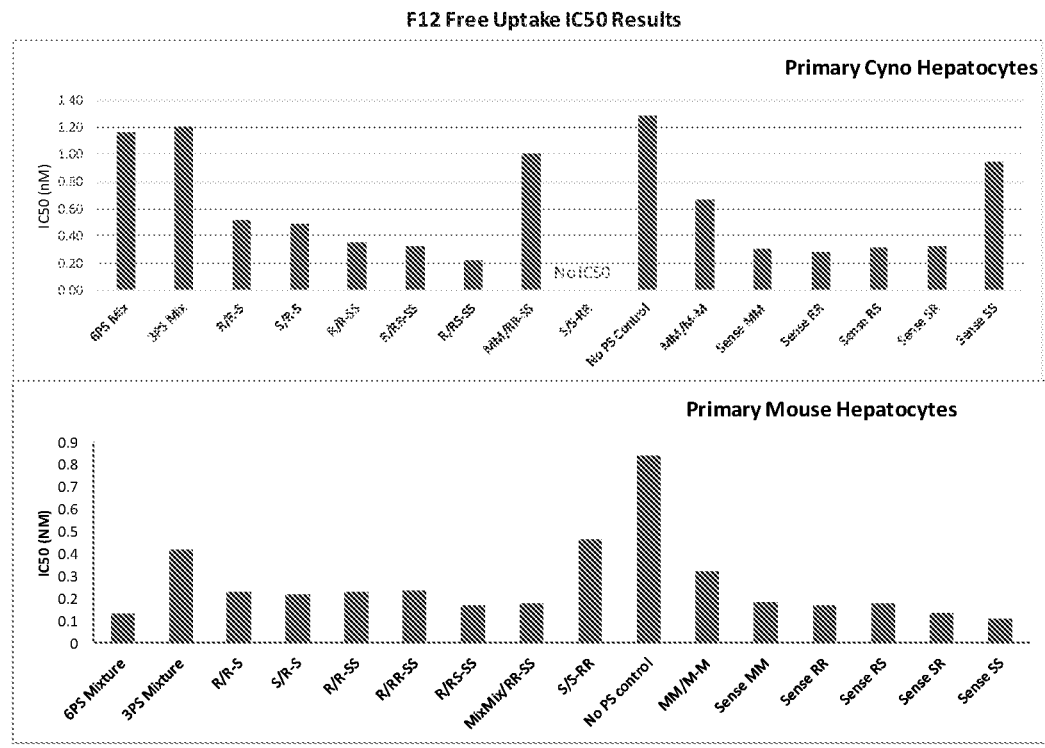
FIG. 107B shows the in vitro free uptake IC50 results in primary mice and cyno hepatocytes.
Figure 107C:
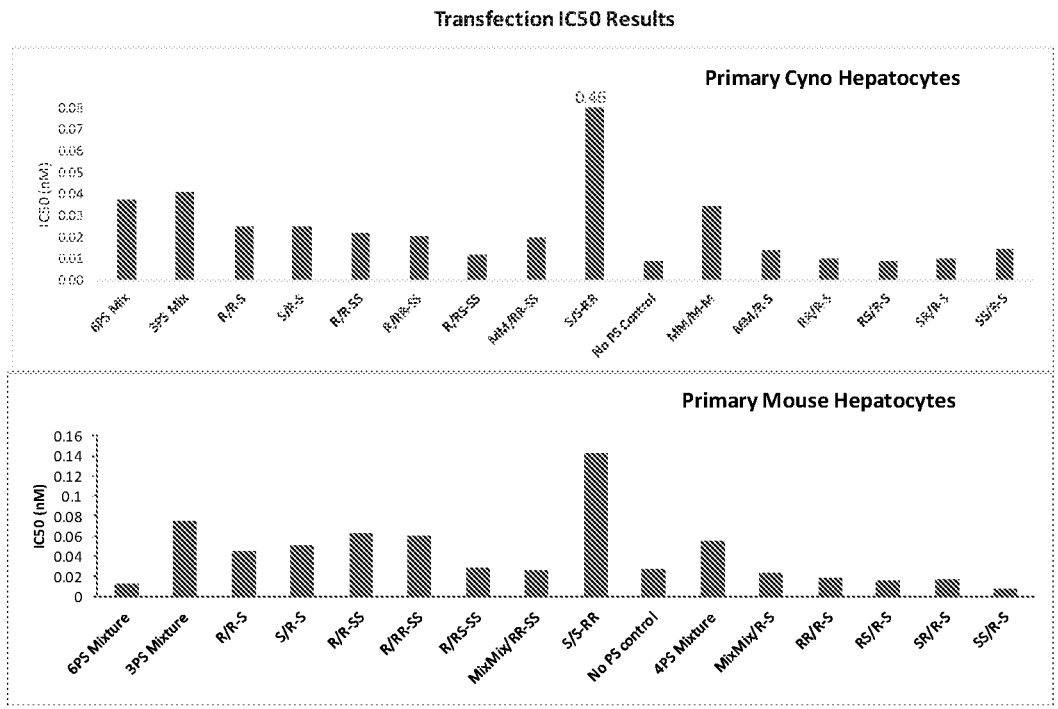
FIG. 107C shows the in vitro transfection IC50 results in primary mice and cyno hepatocytes.

In Vitro Free Uptake and Transfection IC50 Results of F12 ELF siRNA and its Chiral PS siRNA Versions Exemplary F12 ELF siRNA and its chiral PS siRNA versions were studied for in vitro free uptake IC50 and in vitro transfection IC50 in primary mice hepatocytes and primary cyno hepatocytes, and the results are shown in FIGS. 107A-107C. FIG. 107A lists the sequences and configuration motifs for the chirally-modified siRNAs used. FIG. 107B shows the in vitro free uptake IC50 results in primary mice and cyno hepatocytes. FIG. 107C shows the in vitro transfection IC50 results in primary mice and cyno hepatocytes.

Evaluation of F12 ELF siRNA and its Chiral PS siRNA Versions in NHP.

Figures 108A, 108B:
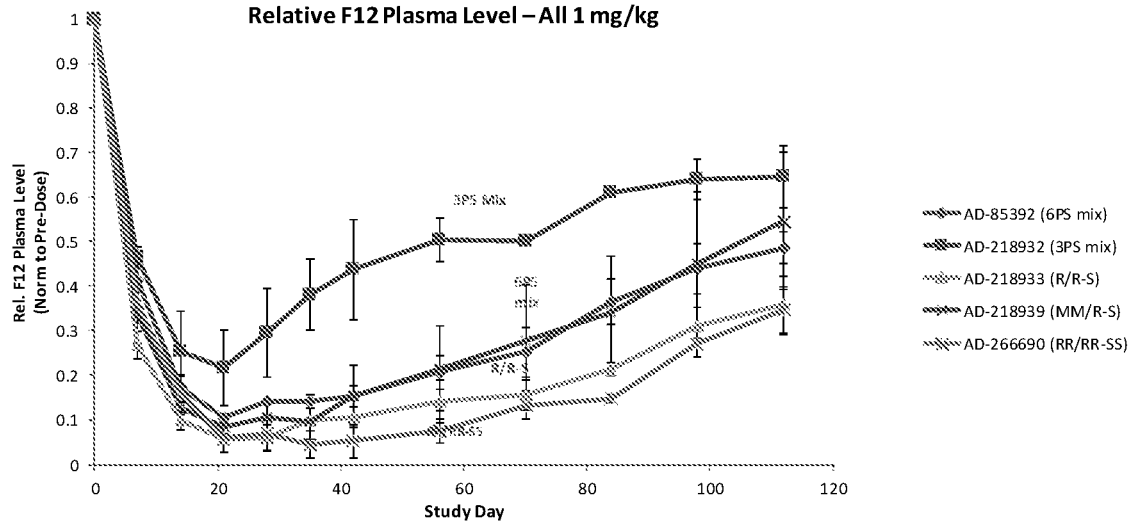
FIG. 108A lists the dosage, sequences, and configuration motifs for the F12 ELF chirally-modified siRNA used.
FIG. 108B shows the plasma pharmacodynamics (PD) results (relative plasma levels of the F12 ELF siRNA and its chiral PS siRNA versions) in NHP.
Figure 108C:
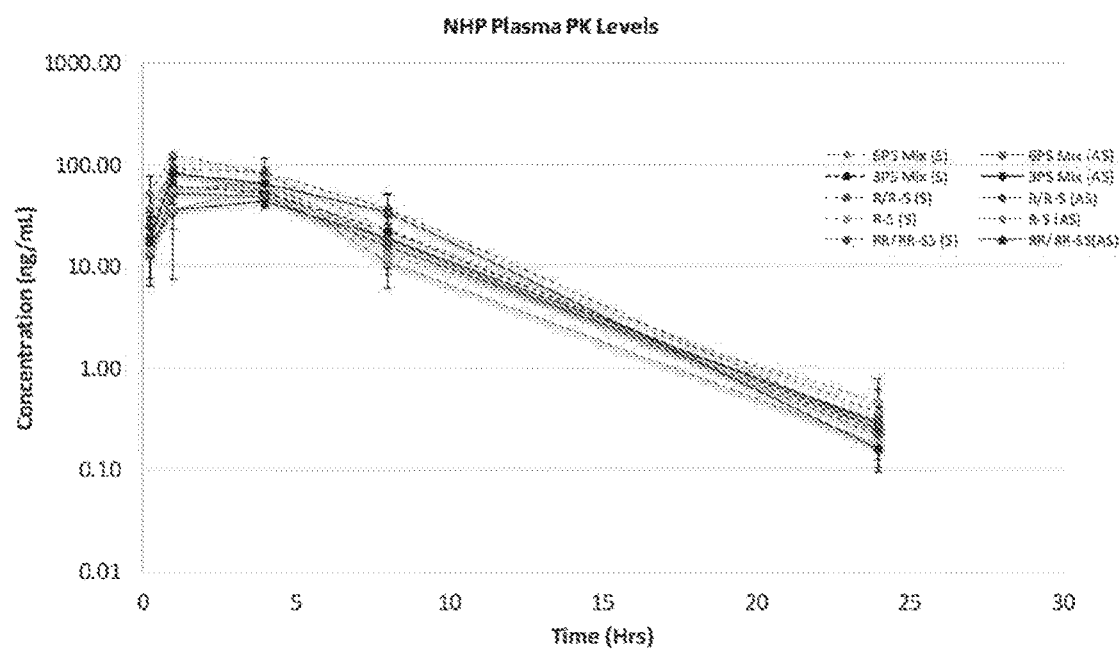
FIG. 108C shows the plasma pharmacokinetics (PK) results in NHP.
Figure 108D:
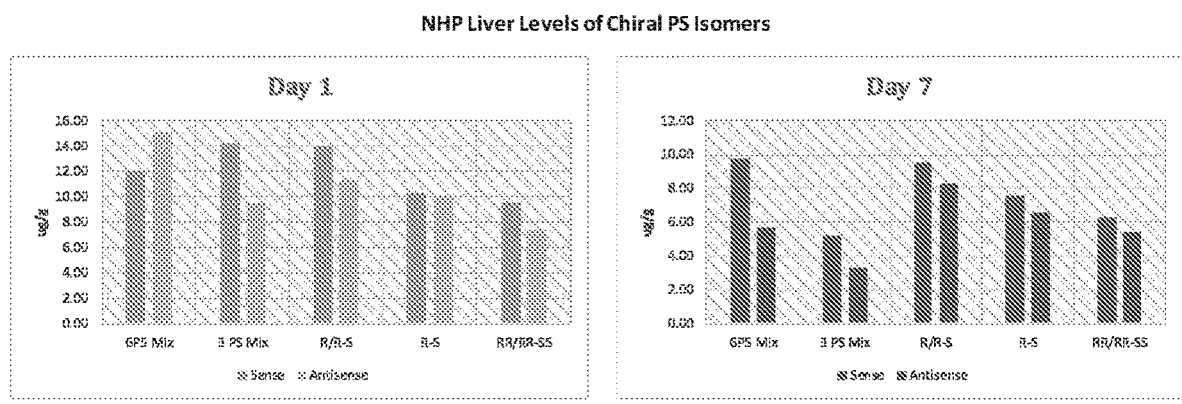
FIG. 108D shows the liver levels of the F12 ELF siRNA and its chiral PS siRNA versions in NHP.
Figures 108E, 109A:
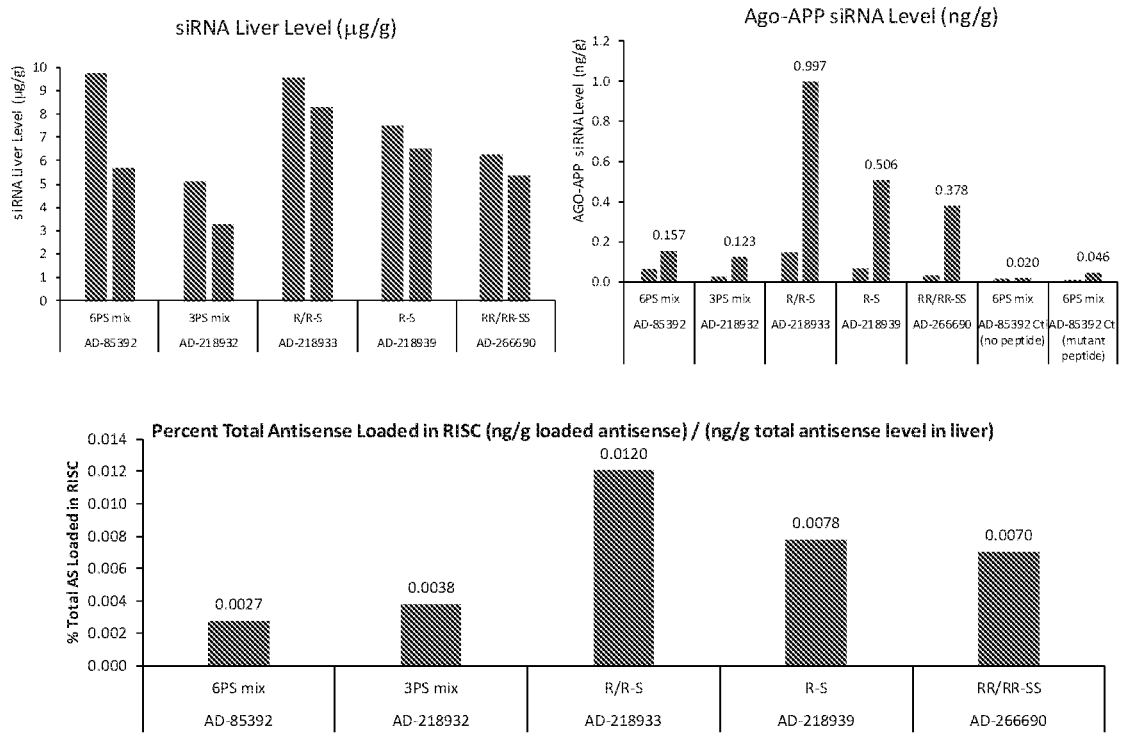
FIG. 108E shows the results of the argonaute protein affinity purification by peptides (Ago-APP) in NHP and the antisense loaded in RISC in liver.
FIG. 109A lists the sequences and configuration motifs for the chirally-modified siRNAs used.

Exemplary F12 ELF siRNA and its chiral PS siRNA versions were studied for plasma PD, plasma PK, liver levels in NHP, and ago affinity purification by peptides and percent total antisense loaded in RISC in liver. The results are shown in FIGS. 108A-108E. FIG. 108A lists the dosage, sequences, and configuration motifs for the chirally-modified siRNAs used. FIG. 108B shows the plasma pharmacodynamics (PD) results (relative plasma levels of the F12 ELF siRNA and its chiral PS siRNA versions) in NHP. FIG. 108C shows the plasma pharmacokinetics (PK) results in NHP. FIG. 108D shows the liver levels of the F12 ELF siRNA and its chiral PS siRNA versions in NHP. FIG. 108E shows the results of the argonaute protein affinity purification by peptides (Ago-APP) in NHP and the antisense loaded in RISC in liver.

Figures 109B, 110A:
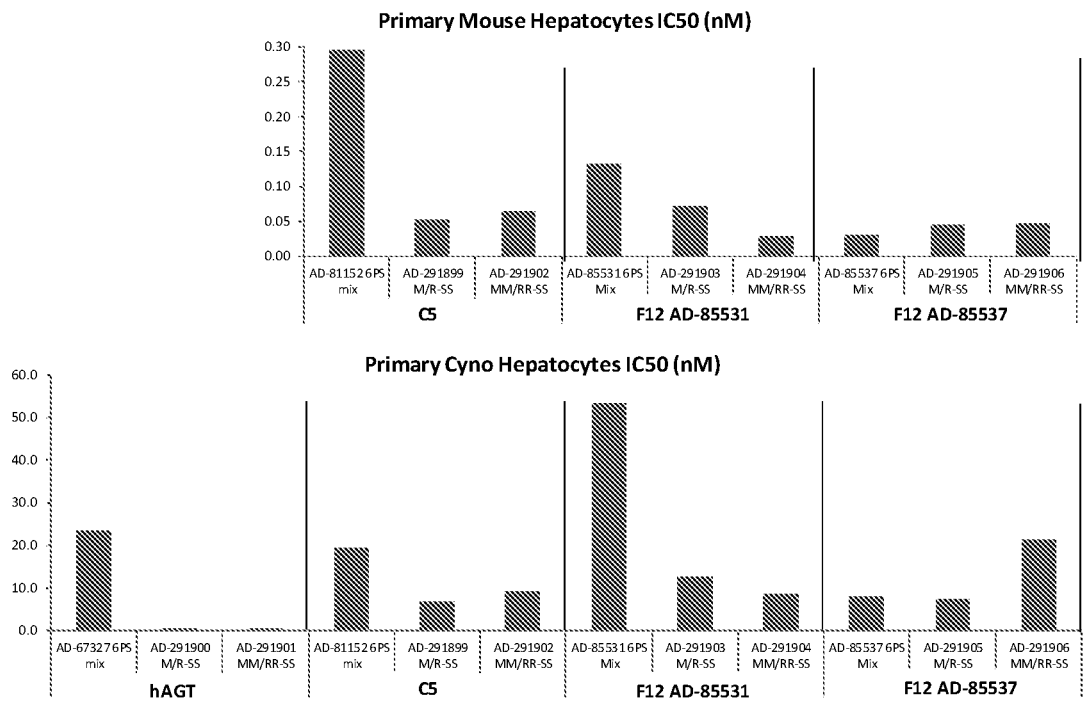
FIG. 109B shows the in vitro free uptake IC50 results in primary mice and cyno hepatocytes.
FIG. 110A shows the study design, including the configuration motifs for the chirally-modified siRNAs used, dosage used, and the durations of the study.

In Vitro Free Uptake IC50 Results of C5, F12, and hAGT siRNAs and their Chiral PS siRNA Versions Exemplary C5, F12, hAGT siRNAs and their chiral PS siRNA versions were studied for in vitro free uptake IC50 in primary mice hepatocytes and primary cyno hepatocytes, and the results are shown in FIGS. 109A-109B. FIG. 109A lists the sequences and configuration motifs for the chirally-modified siRNAs used. FIG. 109B shows the in vitro free uptake IC50 results in primary mice and cyno hepatocytes.

Figures 110B, 110C:
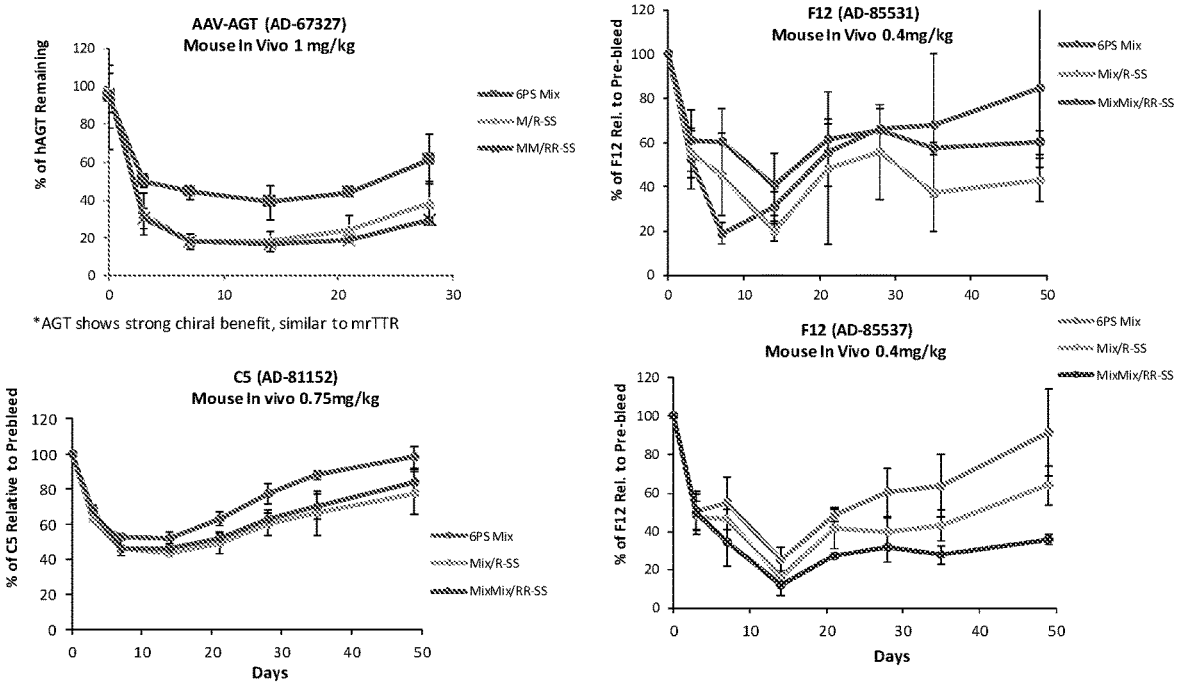
FIG. 110B lists all the sequences used.
FIG. 110C shows the results of the relative expression levels to Day 28 or Day 48.

In Vivio Mouse Study of Exemplary C5, F12, and hAGT siRNAs and their Chiral PS siRNA Versions Exemplary C5, F12, and hAGT siRNAs and their chiral PS siRNA versions were studied for in vivo relative expression levels in mice to Day 28 or Day 48, and the results are shown in FIGS. 110A-110C. FIG. 110A shows the study design, including the configuration motifs for the chirally-modified siRNAs used, dosage used, and the durations of the study. FIG. 110B lists all the sequences used. FIG. 110C shows the results of the relative expression levels to Day 28 or Day 48.

Evaluation of F12 ELF siRNA and its Chiral PS siRNA Versions in NHP.

Figure 111C:
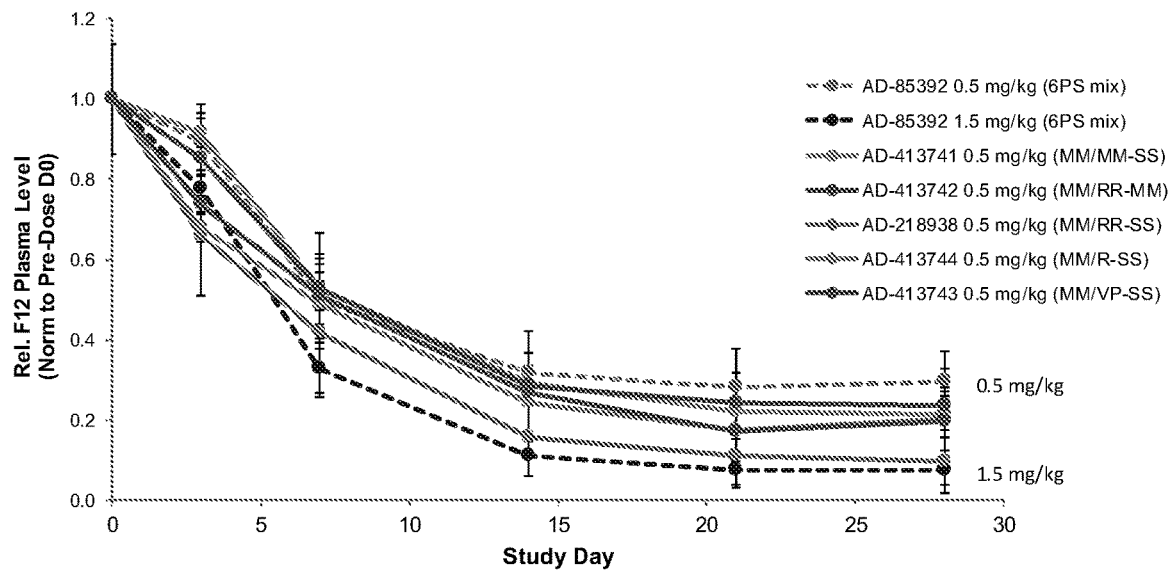
FIG. 111C shows the plasma pharmacodynamics (PD) results (relative plasma levels) of F12 Sequence 1 siRNA and its chiral PS siRNA versions in NHP.
Figure 111D:
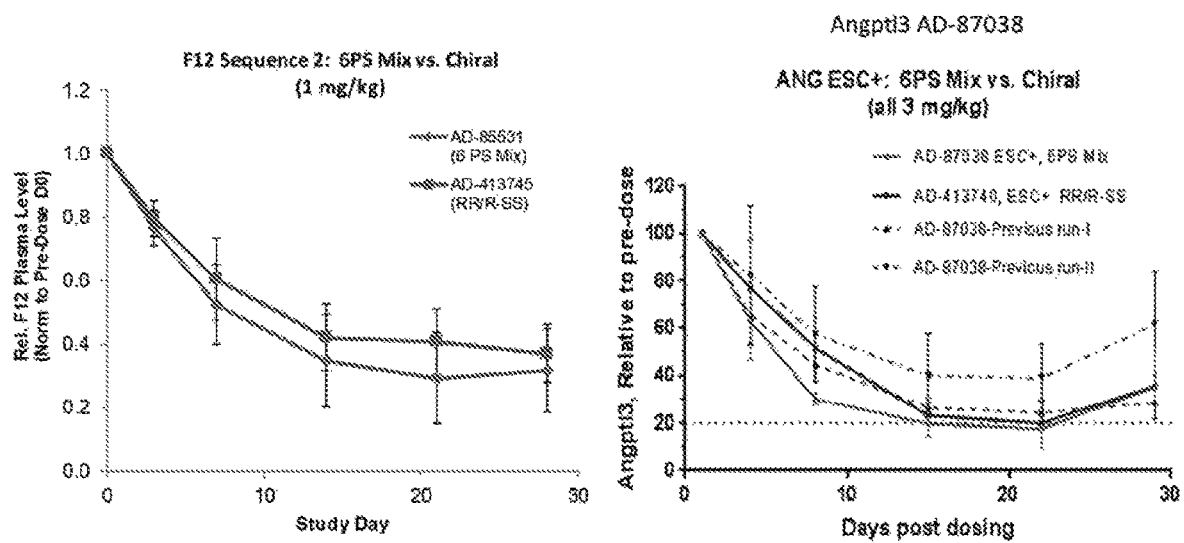
FIG. 111D shows the plasma pharmacodynamics (PD) results (relative plasma levels) of F12 Sequence 2 and Angptl3 (ANG) siRNAs and their chiral PS siRNA versions in NHP.

Exemplary F12 and Angptl3 (ANG) siRNA and their chiral PS siRNA versions were studied for plasma PD in NHP, and the results are shown in FIGS. 111A-111D. FIG. 111A lists the configuration motifs for the chirally-modified siRNAs used and the animal and dosage used. FIG. 111B lists all the sequences used. FIG. 111C shows the plasma pharmacodynamics (PD) results (relative plasma levels) of F12 Sequence 1 siRNA and its chiral PS siRNA versions in NHP. FIG. 111D shows the plasma pharmacodynamics (PD) results (relative plasma levels) of F12 Sequence 2 and Angptl3 (ANG) siRNAs and their chiral PS siRNA versions in NHP.

All of the U.S. patents, U.S. patent application publications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A chirally-modified double-stranded RNA (dsRNA) agent capable of inhibiting the expression of a target gene, said chirally-modified dsRNA agent comprising a sense strand and an antisense strand, each strand having 14 to 40 nucleotides,
wherein:
the sense strand comprises one or more terminal, chirally-modified internucleotide linkages at the 5' end;
the antisense strand comprises one or more terminal, chirally-modified internucleotide linkages at the 5' end and one or more terminal, chirally-modified internucleotide linkages at the 3' end;
each terminal, chirally-modified internucleotide linkage is a phosphorothioate linkage;
a terminal, chiral modification occurs at the first internucleotide linkage at the 3' end of the antisense strand, and the linkage phosphorus atom is in Sp configuration; and
a terminal, chiral modification occurs at the first internucleotide linkage at the 5' end of the antisense strand, and the linkage phosphorus atom is in Rp configuration.

2. The chirally-modified dsRNA agent of claim 1, wherein the chiral purity with respect to the chiral linkage phosphorus atom for each terminal, chirally-modified internucleotide linkage is at least 50%.

3. The chirally-modified dsRNA agent of claim 1, wherein a terminal, chiral modification occurs at the first internucleotide linkage at the 5' end of the sense strand, and the linkage phosphorus atom is in either Rp configuration or Sp configuration.

4. The chirally-modified dsRNA agent of claim 1, wherein the chirally-modified dsRNA agent comprises:
a terminal, chiral modification occurring at the first internucleotide linkage at the 3' end of the antisense strand, having the linkage phosphorus atom in Sp configuration,
a terminal, chiral modification occurring at the first internucleotide linkage at the 5' end of the antisense strand, having the linkage phosphorus atom in Rp configuration, and
a terminal, chiral modification occurring at the first internucleotide linkage at the 5' end of the sense strand, having the linkage phosphorus atom in either Rp configuration or Sp configuration.

5. The chirally-modified dsRNA agent of claim 1, wherein the chirally-modified dsRNA agent comprises four or more terminal, chirally-modified internucleotide linkages.

6. The chirally-modified dsRNA agent of claim 5, wherein the chirally-modified dsRNA agent comprises:
a terminal, chiral modification occurring at the first and second internucleotide linkages at the 3' end of the antisense strand, having the linkage phosphorus atom in Sp configuration,
a terminal, chiral modification occurring at the first internucleotide linkage at the 5' end of the antisense strand, having the linkage phosphorus atom in Rp configuration, and
a terminal, chiral modification occurring at the first internucleotide linkage at the 5' end of the sense strand, having the linkage phosphorus atom in either Rp or Sp configuration.

7. The chirally-modified dsRNA agent of claim 1, wherein the chirally-modified dsRNA agent comprises five or more terminal, chirally-modified internucleotide linkages.

8. The chirally-modified dsRNA agent of claim 7, wherein the chirally-modified dsRNA agent comprises:
a terminal, chiral modification occurring at the first, second and third internucleotide linkages at the 3' end of the antisense strand, having the linkage phosphorus atom in Sp configuration,
a terminal, chiral modification occurring at the first internucleotide linkage at the 5' end of the antisense strand, having the linkage phosphorus atom in Rp configuration, and
a terminal, chiral modification occurring at the first internucleotide linkage at the 5' end of the sense strand, having the linkage phosphorus atom in either Rp or Sp configuration.

9. The chirally-modified dsRNA agent of claim 7, wherein the chirally-modified dsRNA agent comprises:
a terminal, chiral modification occurring at the first, and second internucleotide linkages at the 3' end of the antisense strand, having the linkage phosphorus atom in Sp configuration,
a terminal, chiral modification occurring at the third internucleotide linkages at the 3' end of the antisense strand, having the linkage phosphorus atom in Rp configuration,
a terminal, chiral modification occurring at the first internucleotide linkage at the 5' end of the antisense strand, having the linkage phosphorus atom in Rp configuration, and
a terminal, chiral modification occurring at the first internucleotide linkage at the 5' end of the sense strand, having the linkage phosphorus atom in either Rp or Sp configuration.

10. The chirally-modified dsRNA agent of claim 7, wherein the chirally-modified dsRNA agent comprises:
a terminal, chiral modification occurring at the first, and second internucleotide linkages at the 3' end of the antisense strand, having the linkage phosphorus atom in Sp configuration,
a terminal, chiral modification occurring at the first, and second internucleotide linkages at the 5' end of the antisense strand, having the linkage phosphorus atom in Rp configuration, and
a terminal, chiral modification occurring at the first internucleotide linkage at the 5' end of the sense strand, having the linkage phosphorus atom in either Rp or Sp configuration.

11. The chirally-modified dsRNA agent of claim 1, wherein the chirally-modified dsRNA agent comprises six or more terminal, chirally-modified internucleotide linkages.

12. The chirally-modified dsRNA agent of claim 1, wherein the chirally-modified dsRNA agent comprises eight or more terminal, chirally-modified internucleotide linkages.

13. The chirally-modified dsRNA agent of claim 1, wherein each nucleotide of a dinucleotide connected by the terminal, chirally-modified internucleotide linkage is independently modified with a modification selected from the group consisting of acyclic nucleotides, LNA, HNA, CeNA, 2'-O-methoxyalkyl, 2' O-methyl, 2'-O-allyl, 2'-C-allyl, 2'-deoxy, 2'-fluoro, 2'-O-N-methylacetamido (2' O NMA), 2'-O-dimethylaminoethoxyethyl (2'-O-DMAEOE), 2'-O-aminopropyl (2' O AP), and 2'-ara F.

14. The chirally-modified dsRNA agent of claim 1, wherein each of the sense and antisense strands is independently modified with a modification selected from the group consisting of acyclic nucleotides, LNA, HNA, CeNA, 2' O-methoxyalkyl, 2' O-methyl, 2'-O-allyl, 2'-C-allyl, 2'-deoxy, 2'-fluoro, 2'-O-N-methylacetamido (2'-O-NMA), 2'-O-dimethylaminoethoxyethyl (2'-O-DMAEOE), 2' O aminopropyl (2'-O-AP), and 2'-ara-F.

15. The chirally-modified dsRNA agent of claim 1, wherein each of the sense and antisense strands has 15-30 nucleotides.

16. The chirally-modified dsRNA agent of claim 15, wherein the sense strand has 19-22 nucleotides, and the antisense strand has 19-25 nucleotides.

17. The chirally-modified dsRNA agent of claim 1, further comprising at least one ASGPR ligand.

18. The chirally-modified dsRNA agent of claim 17, wherein the ASGPR ligand is attached to the 3' end of the sense strand or antisense strand.

19. The chirally-modified dsRNA agent of claim 17, wherein the ASGPR ligand is attached through one or more cleavable linkers.

20. The chirally-modified dsRNA agent of claim 17, wherein the ASGPR ligand is one or more GalNAc derivatives attached through a bivalent or trivalent branched linker.

21. The chirally-modified dsRNA agent of claim 20, wherein the ASGPR ligand is:

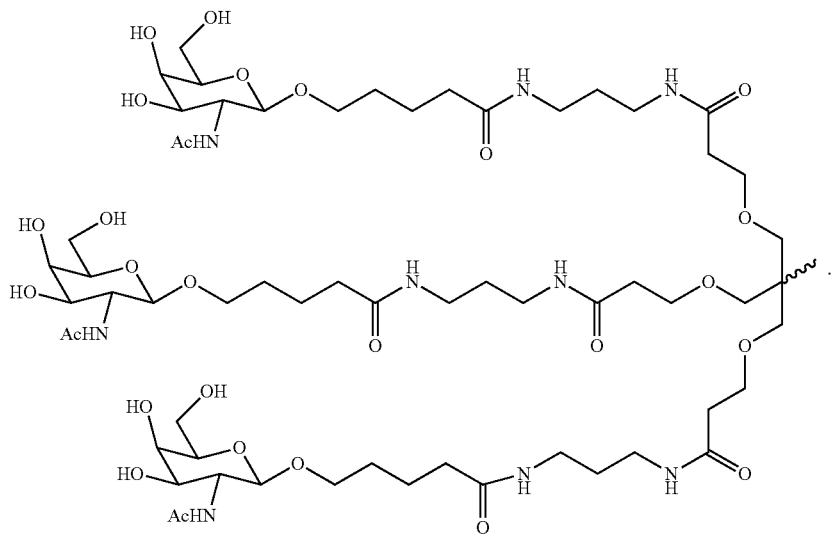 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

22. A pharmaceutical composition comprising the chirally-modified dsRNA agent of claim 1 and a pharmaceutically acceptable carrier or excipient.

23. A method for inhibiting the expression of a target gene comprising the step of administering the chirally-modified dsRNA agent of claim 1 in an amount sufficient to inhibit expression of the target gene.

24. The method of claim 23, wherein the chirally-modified dsRNA agent is administered through subcutaneous or intravenous administration.

* * * * *